US011692180B2

(12) United States Patent
Ferreira

(10) Patent No.: US 11,692,180 B2
(45) Date of Patent: Jul. 4, 2023

(54) ENGINEERED ARYL SULFATE-DEPENDENT ENZYMES

(71) Applicant: OPTIMVIA, LLC, Batavia, OH (US)

(72) Inventor: Tarsis Gesteira Ferreira, Pearland, TX (US)

(73) Assignee: OPTIMVIA, LLC, Batavia, OH (US)

( * ) Notice: Subject to any disclaimer, the term of this patent is extended or adjusted under 35 U.S.C. 154(b) by 0 days.

(21) Appl. No.: 17/376,341

(22) Filed: Jul. 15, 2021

(65) Prior Publication Data

US 2022/0042062 A1 Feb. 10, 2022

Related U.S. Application Data

(63) Continuation-in-part of application No. PCT/US2020/013677, filed on Jan. 15, 2020.

(60) Provisional application No. 62/853,261, filed on May 28, 2019, provisional application No. 62/808,074, filed on Feb. 20, 2019, provisional application No. 62/797,466, filed on Jan. 28, 2019, provisional application No. 62/792,440, filed on Jan. 15, 2019.

(51) Int. Cl.
*C12N 9/10* (2006.01)
*C12N 15/63* (2006.01)
*C12P 19/64* (2006.01)

(52) U.S. Cl.
CPC ............... *C12N 9/13* (2013.01); *C12N 15/63* (2013.01); *C12P 19/64* (2013.01); *C12Y 208/02008* (2013.01)

(58) Field of Classification Search
CPC .... C12N 9/13; C12P 19/64; C12Y 208/02008
See application file for complete search history.

(56) References Cited

U.S. PATENT DOCUMENTS

| | | | |
|---|---|---|---|
| 4,554,101 A | 11/1985 | Hopp | |
| 5,541,095 A | 7/1996 | Hirschberg et al. | |
| 5,817,487 A | 10/1998 | Kobayashi et al. | |
| 5,834,282 A | 11/1998 | Habuchi et al. | |
| 5,919,673 A | 7/1999 | Wong et al. | |
| 6,255,088 B1 | 7/2001 | Wong et al. | |
| 6,569,998 B2 | 5/2003 | Cummings et al. | |
| 6,861,254 B1 * | 3/2005 | Rosenberg .............. | C12N 9/13 435/325 |
| 6,992,183 B2 | 1/2006 | Oreste et al. | |
| 7,307,159 B2 | 12/2007 | Deangelis | |
| 7,655,445 B2 | 2/2010 | Rosenberg et al. | |
| 7,741,091 B2 | 6/2010 | Deangelis et al. | |
| 8,088,604 B2 | 1/2012 | Deangelis et al. | |
| 8,450,297 B2 | 5/2013 | Rosenberg et al. | |
| 8,580,290 B2 | 11/2013 | Deangelis | |
| 8,771,995 B2 | 7/2014 | Liu et al. | |
| 8,809,300 B2 | 8/2014 | Zhao et al. | |
| 8,815,529 B2 | 8/2014 | Wu | |
| 8,980,608 B2 | 3/2015 | Deangelis et al. | |
| 9,629,914 B2 | 4/2017 | Deangelis | |
| 9,951,149 B2 | 4/2018 | Liu et al. | |
| 2004/0147469 A1 | 7/2004 | Grimpe et al. | |
| 2005/0255562 A1 | 11/2005 | Rosenberg et al. | |
| 2006/0154894 A1 | 7/2006 | Berry et al. | |
| 2007/0020243 A1 | 1/2007 | Sengupta et al. | |
| 2008/0207895 A1 | 8/2008 | Rosenberg et al. | |
| 2009/0035787 A1 | 2/2009 | Liu et al. | |
| 2009/0197308 A1 | 8/2009 | Liu et al. | |
| 2010/0048638 A1 | 2/2010 | Crawford et al. | |
| 2013/0296540 A1 | 11/2013 | Xu et al. | |
| 2014/0349962 A1 | 11/2014 | Rosenberg et al. | |
| 2016/0122446 A1 | 5/2016 | Liu et al. | |
| 2017/0190803 A1 | 7/2017 | Deangelis | |

(Continued)

FOREIGN PATENT DOCUMENTS

| | | |
|---|---|---|
| EP | 3399044 | 11/2018 |
| WO | 2012116048 | 8/2012 |
| WO | 2017144671 | 8/2017 |

(Continued)

OTHER PUBLICATIONS

Kaysser et al. A New Arylsulfate Sulfotransferase Involved in Liponucleoside Antibiotic Biosynthesis in Streptomycetes. The Journal of Biological Chemistry (2010), 285(17), p. 12684-12694. (Year: 2010).*

Xu et al. Mutational Study of Heparan Sulfate 2-O-Sulfotransferase and Chondroitin Sulfate 2-O-Sulfotransferase. The Journal of Biological Chemistry (2007), 282(11), 8356-8367. (Year: 2007).*

P. Stothard. The Sequence Manipulation Suite: JavaScript Programs for Analyzing and Formatting Protein and DNA Sequences. Biotechniques (2000), 28(6), 1102-1103. (Year: 2000).*

Gesteira et al., "Structural basis of oligosaccharide processing by glycosaminoglycan sulfotransferases", Jun. 6, 2018, Glycobiology, 28(11): p. 885-897 (13 pages).

Non-final Office Action dated Jan. 27, 2022 in copending U.S. Appl. No. 17/376,322, filed Jul. 15, 2021 (17 pages).

(Continued)

*Primary Examiner* — Sean C. Barron
(74) *Attorney, Agent, or Firm* — Daniel H. Lajiness; Daniel F. Nesbitt; Nesbitt IP LLC

(57) ABSTRACT

The present invention provides several non-naturally occurring sulfotransferase enzymes that have been engineered to react with aryl sulfate compounds as sulfo group donors, instead of the natural substrate 3'-phosphoadenosine 5'-phosphosulfate (PAPS), and with heparosan-based polysaccharides, particularly heparan sulfate, as sulfo group acceptors. Each of the engineered sulfotransferase enzymes have a biological activity characterized by the position within the heparosan-based polysaccharide that receives the sulfo group, including glucosaminyl N-sulfotransferase activity, hexuronyl 2-O sulfotransferase activity, glucosaminyl 6-O sulfotransferase activity, or glucosaminyl 3-O sulfotransferase activity. Methods of using the engineered sulfotransferases to produce sulfated heparosan-based polysaccharides, including polysaccharides having anticoagulant activity, are also provided.

9 Claims, 70 Drawing Sheets

Specification includes a Sequence Listing.

(56) References Cited

U.S. PATENT DOCUMENTS

| | | | |
|---|---|---|---|
| 2017/0226543 A1 | 8/2017 | Jendresen et al. | |
| 2019/0225998 A1 | 7/2019 | Douaisi et al. | |

FOREIGN PATENT DOCUMENTS

| | | |
|---|---|---|
| WO | 2018048973 | 3/2018 |
| WO | 2018135027 | 7/2018 |
| WO | 2018165656 | 9/2018 |
| WO | 2019050051 | 3/2019 |

OTHER PUBLICATIONS

Non-final Office action dated Feb. 7, 2022 in copending U.S. Appl. No. 17/376,332, filed Jul. 15, 2021 (19 pages).
Notice of Allowance dated Feb. 11, 2022 in copending U.S. Appl. No. 17/376,335, filed Jul. 15, 2021 (11 pages).
Gilbert, "The Reactions of Sulfur Trioxide, and of Its Adducts, With Organic Compounds", Nov. 6, 1961, Allied Chemical Corporation, p. 549-589 (41 pages).
Lloyd et al., "Preparation of [$^{35}$S] Sulphamate Derivatives for Studies on Heparin Degrading Enzymes of Mammalian Origin", 1971, Biochemical Pharmacology 20: p. 637-648 (12 pages).
Shively et al., "Formation of Anhydrosugars in the Chemical Depolymerization of Heparin", 1976, Biochemistry 15(18): p. 3932-3942 (11 pages).
Kyte et al., "A simple method for displaying the hydropathic character of a protein", May 5, 1982, J. Mol. Biol. 157(1): p. 105-132 (28 pages).
Bienkowski et al., "Structural Characterization of the Oligosaccharides Formed by Depolymerization of Heparin with Nitrous Acid", Jan. 10, 1985, J. Biol. Chem. 260(1): p. 356-365 (10 pages).
Harding et al., "Molecular Weight Determination of Polysaccharides", 1991, Advances in Carbohydrate Analysis 1: p. 63-144 (82 pages).
Mulloy et al., "N.m.r. and molecular-modelling studies of the solution conformation of heparin", 1993, Biochem. J. 293: p. 849-858 (10 pages).
Komatsu et al., "A P-loop-related Motif (GxxGxxK) Highly Conserved in Sulfotransferases Is Required for Binding the Activated Sulfate Donor", Nov. 14, 1994, Biochem. Biophys. Res. Comm. 204(3): p. 1178-1185 (abstract only).
Marsolais et al., "Identification of Amino Acid Residues Critical for Catalysis and Cosubstrate Binding in the Flavonol 3-Sulfotransferase", Dec. 22, 1995, J. Biol. Chem. 270(51): p. 30458-30463 (6 pgs).
Nadkarni et al., "Preparation and biological activity of N-sulfonated chondroitin and dermatan sulfate derivatives", 1996, Carbohydrate Research 290: p. 87-96 (10 pages).
Recksiek et al., "Sulfatases, Trapping of the Sulfated Enzyme Intermediate by Substituting the Active Site Formylglycine", Mar. 13, 1998, J. Biol. Chem. 273(11): p. 6096-6103 (8 pages).
Desai et al, "Mechanism of Heparin Activation of Antithrombin", Mar. 27, 1998, J. Biol. Chem. 273(13): p. 7478-7487 (10 pages).
Sueyoshi et al., "A role of Lys614 in the sulfotransferase activity of human heparan sulfate N-deacetylase/N-sulfotransferase", Aug. 21, 1998, FEBS Letters 433: p. 211-214 (4 pages).
Uhlhorn-Dierks et al., "How Does Nature Cleave Sulfuric Acid Esters? A Novel Posttranslational Modification of Sulfatases", Oct. 2, 1998, Agnew. Chem. Int. Ed. 37(18): p. 2453-2455 (abstract only).
Linhardt et al., "Production and Chemical Processing of Low Molecular Weight Heparins", 1999, Seminars in Thrombosis and Hemostasis 25(3): p. 5-16 (12 pages).
Kariya et al., "Preparation of completely 6-O-desulfated heparin and its ability to enhance activity of basic fibroblast growth factor", Aug. 25, 2000, J. Biol. Chem 275(34): p. 25949-25958 (10 pages).
Burkart et al., "Regeneration of PAPS forthe enzymatic synthesis of sulfated oligosaccharides", Sep. 8, 2000, J Org Chem. 8;65(18): p. 5565-5574 (10 pages).

Hirsh et al., "Mechanism of Action and Pharmacology of Unfractionated Heparin", 2001, Arterioscler. Thromb. Vasc. Biol. 21: p. 1094-1096 (3 pages).
Rong et al., "Substrate Specificity of the Heparan Sulfate Hexuronic Acid 2-O-Sulfotransferase", 2001, Biochemistry 40: p. 5548-5555 (8 pages).
Negishi et al., "Structure and Function of Sulfotransferases", May 24, 2001, Arch. Biochem. Biophys. 390(2): p. 149-157 (9 pages).
Pedersen et al., "Crystal Structure of the Human Estrogen Sulfotransferase-PAPS Complex", May 17, 2002, J. Biol. Chem. 277(20): p. 17928-17932 (5 pages).
Kuberan et al., "Chemoenzymatic synthesis of classical and non-classical anticoagulant heparan sulfate polysaccharides", Dec. 26, 2003, J. Biol. Chem. 278(52): p. 52613-52621 (9 pages).
Hanson et al., "Sulfatases: Structure, Mechanism, Biological Activity, Inhibition, and Synthetic Utility", 2004, Angew. Chem. Int. Ed. 43: p. 5736-5763 (28 pages).
Edavettal et al., "Crystal structure and mutational analysis of heparan sulfate 3-O-sulfotransferase isoform 1", Jun. 11, 2004, J. Biol. Chem. 24(11): p. 25789-25797 (9 pages).
Li et al., "Structure of the antithrombin-thrombin-heparin ternary complex reveals the antithrombotic mechanism of heparin", Sep. 2004, Nature Struct. Mol. Biol. 11(9): p. 857-862 (6 pages).
Holmborn et al., "Heparan sulfate synthesized by mouse embryonic stem cells deficient in NDST1 and NDST2 is 6-O-sulfated but contains no N-sulfate groups", Oct. 8, 2004, J. Biol. Chem. 279(41): p. 42355-42358 (4 pages).
Ledin et al., "Heparan Sulfate Structure in Mice with Genetically Modified Heparan Sulfate Production", Oct. 8, 2004, J. Biol. Chem. 279(41): p. 42732-42741 (10 pages).
Rath et al., "Sulfotransferase structural biology and inhibitor discovery", Dec. 23, 2004, Drug Discovery Today 9(23): p. 1003-1011 (9 pages).
Whitelock et al., "Heparan Sulfate: a Complex Polymer Charged with Biological Activity", 2005, Chem. Rev. 105(7): p. 2745-2764 (20 pages).
Chen et al., "Enzymatic Redesigning of Biologically Active Heparan Sulfate", Dec. 30, 2005, J. Biol. Chem. 280(52): p. 42817-42825 (9 pages).
Linhardt et al., "Enzymatic Synthesis of Glycosaminoglycan Heparin", Jul. 2007, Semin. Thromb. Hemost. 33(5): p. 453-465 (author manuscript, 24 pages).
Zhang et al., "Solution Structures of Chemoenzymatically Synthesized Heparin and Its Precursors", 2008, J. Am. Chem. Soc. 130: p. 12998-13007 (10 pages).
Xu et al., "Engineering Sulfotransferases to Modify Heparan Sulfate", Mar. 2008, Nat. Chem. Biol. 4(3): p. 200-202 (author manuscript, 8 pages).
Gray et al., "Heparin and low-molecular-weight heparin", May 2008, Thromb. Haemost. 99: p. 807-818 (12 pages).
Malojcic et al., "A structural and biochemical basis for PAPS-independent sulfuryl transfer by aryl sulfotransferase from uropathogenic *Escherichia coli*", Dec. 9, 2008, PNAS 105(49): p. 19217-19222 (6 pages).
Peterson et al., "Design of biologically active heparan sulfate and heparin using an enzyme-based approach", Feb. 27, 2009, the Royal Society of Chemistry—Nat. Prod. Rev. 26: p. 610-627 (18 pages).
Rudd et al., "The potential for circular dichroism as an additional facile and sensitive method of monitoring low-molecular-weight heparins and heparinoids", May 11, 2009, Thromb. Haemost. 102: p. 874-878 (5 pages).
Kaysser et al., "A New Arylsulfate Sulfotransferase Involved in Liponucleoside Antibiotic Biosynthesis in Streptomycetes", Apr. 23, 2010, J. Biol. Chem. 285(17): p. 12864-12694 (11 pages).
Wang et al., "*E. coli* K5 fermentation and the Preparation of Heparosan, a Bioengineered Heparin Precursor", Dec. 15, 2010, Biotechnol Bioeng. 107(6): p. 964-973 (author manuscript, 19 pages).
Ly et al., "Analysis of *E. coli* K5 capsular polysaccharide Heparosan", Apr. 21, 2010, Anal. Bioanal. Chem. 399: p. 737-745 (9 pages).
Keire et al., "Characterization of currently marketed heparin products: key tests for quality assurance", Aug. 1, 2010, Anal. Bioanal. Chem. 399: p. 581-591 (11 pages).

(56) References Cited

OTHER PUBLICATIONS

Malojcic et al., "The PAPS-independent Aryl Sulfotransferase and the Alternative Disulfide Bond Formation System in Pathogenic Bacteria", Aug. 31, 2010, Antioxidants & Redox Signaling 13(8): p. 1247-1259 (13 pages).
Sheng et al., "The dominating role of N-deacetylase/N-sulfotransferase 1 in forming domain structures in heparan sulfate", Jun. 3, 2011, J. Biol.Chem. 286(22): p. 19768-19776 (9 pages).
Wang et al., "Control of the heparosan N-deacetylation leads to an improved bioengineered heparin", Jul. 2011, Appl. Microbiol. Biotechnol. 91(1): p. 91-99 (author manuscript, 19 pages).
Xu et al., "Chemoenzymatic Synthesis of Homogeneous Ultralow Molecular Weight Heparins", Oct. 28, 2011, Science 334 (6055): p. 498-501 (4 pages).
Linhardt et al., "Synthetic heparin", Feb. 8, 2012, Current Opinion in Pharmacology 12: p. 217-219 (3 pages).
Zhang et al., "Metabolic engineering of *Escherichia coli* BL21 for biosynthesis of heparosan, a bioengineered heparin precursor", Jul. 8, 2012, Metabolic Engineering 14: p. 521-527 (7 pages).
Kreuger et al., "Heparan Sulfate Biosynthesis: Regulation and Variability", Sep. 2012, J. Histochem. Cytochem. 60(12): p. 898-907 (10 pages).
Cumpstey, "Chemical Modification of Polysaccharides", 2013, Hindawi Publishing Corporation—ISRN Organic Chemistry, Article ID 417672 (27 pages).
Lindahl et al., "Pathophysiology of heparan sulphate: many diseases, few drugs", 2013, J. Intern. Med. 273: 555-571 (17 pages).
Gesteira et al., "Insights into the N-sulfation mechanism: molecular dynamics simulations of the N-sulfotransferase domain of NDST1 and mutants", Aug. 5, 2013, PLoS One 8(8): e70880 (12 pages).
Garcia-Suarez et al., "Multiple alterations of heparan sulphate in cancer", May 2013, OA Cancer 1(1):1 (7 pages).
Fu et al., "Structural Characterization of Pharmaceutical Heparins Prepared from Different Animal Tissues", May 2013, J. Pharm. Sci. 102(5) (author manuscript, 19 pages).
Chen et al., "Tailor design and synthesis of heparan sulfate (HS) oligosaccharide analogs using sequential one-pot multienzyme (OPME) systems", Nov. 4, 2013, Angew. Chem. Int. Ed. Engl. 52(45): p. 11852-11856 (author manuscript, 12 pages).
Taniguchi et al, "Handbook of Glycosyltransferases and Related Genes", $2^{nd}$ ed., 2014, Section X—Sulfotransferases, Chapters 86-103 (218 pages).
Sterner et al., "Assays for determining heparan sulfate and heparin O-sulfotransferase activity and specificity", Jan. 2014, Anal Bioanal Chem. 406(2): p. 525-536 (author manuscript, 27 pages).
Liu et al., "Chemoenzymatic synthesis of heparan sulfate and heparin", Jun. 2014, Royal Society of Chemistry, Nat. Prod. Rep., 31: p. 1676-1685 (10 pages).
Mulloy et al., "USP compendial methods for analysis of heparin: chromatographic determination of molecular weight distributions for heparin sodium", Jun. 24, 2014, Anal. Bioanal. Chem. 406: p. 4815-4823 (9 pages).
Santos et al., "Structural and functional analyses of bovine and porcine intestinal heparins confirm they are different drugs", Nov. 2014, Drug Discovery Today 19(11): p. 1801-1807 (7 pages).
Bhaskar et al., "Combinatorial one-pot chemoenzymatic synthesis of heparin", Nov. 7, 2014, Carbohydrate Polymers 122: p. 399-407 (9 pages).
Deangelis, "Heparosan, a promising 'naturally good' polymeric conjugating vehicle for delivery of injectable therapeutics", 2015, Expert Opin. Drug Deliv. 12(3): p. 349-352 (4 pages).
Joice et al., "Glycosaminoglycans: Chemistry and Biology—Chapter 2: Enzymatic Synthesis of Heparan Sulfate and Heparin", 2015, Springer Science + Business Media, p. 11-19 (9 pages).
Pimpao et al., "Phenolic sulfates as new and highly abundant metabolites in human plasma after ingestion of a mixed berry fruit puree", Jan. 9, 2015, Br. J. Nutr. 113: p. 454-463 (10 pgs).
Baik et al., "Optimization of bioprocess conditions improves production of a CHO cell-derived, bioengineered heparin", Jun. 3, 2015, Biotechnol. J. 10: p. 1067-1081 (15 pages).

Dou et al., "Role of Deacetylase Activity of N-Deacetylase/N-Sulfotransferase 1 in Forming N-Sulfated Domain in Heparan Sulfate", Jun. 24, 2015, J. Biol. Chem. 290(33): p. 20427-20437 (11 pages).
Sulfita et al., "Heparin and related polysaccharides: synthesis using recombinant enzymes and metabolic engineering", Jul. 29, 2015, Appl. Microbiol. Biotechnol. 99: p. 7465-7479 (15 pages).
Keire et al., "Diversifying the Global Heparin Supply Chain: Reintroduction of Bovine Heparin in the United States?", Nov. 2, 2015, PharmTech, http://www.pharmtech.com/diversifying-global-heparin-supply-chain-reintroduction-bovine-heparin-united-states (7 pages).
Ange et al., "Analysis of Heparins Derived From Bovine Tissues and Comparison to Porcine Intestinal Heparins", 2016, Clin. Appl. Thrombosis/Hemostasis 22(6): p. 520-527 (8 pages).
Yates et al., "Recent innovations in the structural analysis of heparin", 2016, International Journal of Cardiology 212S1: p. S5-S9 (5 pages).
Szajek et al., "The US regulatory and pharmacopeia response to the global heparin contamination crisis", Jun. 9, 2016, Nature Biotechnology 34(6): p. 625-630 (6 pages).
Deligny et al., "NDST2 (N-Deacetylase/N-Sulfotransferase-2) Enzyme Regulates Heparan Sulfate Chain Length", Jul. 7, 2016, J. Biol. Chem. 291(36): p. 18600-18607 (8 pages).
Tovar et al., "Structural and haemostatic features of pharmaceutical heparins from different animal sources: challenges to define thresholds separating distinct drugs", Oct. 18, 2016, Nature Scientific Reports 6:35619 (12 pages).
Li et al., "Enzymatic Synthesis of Homogeneous Chondroitin Sulfate Oligosaccharides", 2017, Angew. Chem. Int. Ed. 56: p. 11784-11787 (4 pages).
Wang et al., "Sulfated Cyclocarya paliurus polysaccharides markedly attenuates inflammation and oxidative damage in lipopolysaccharide-treated macrophage cells and mice", Jan. 17, 2017, Nature Scientific Reports 7:40402 (12 pages).
Xu et al., "Structure Based Substrate Specificity Analysis of Heparan Sulfate 6-O-Sulfotransferases", Jan. 20, 2017, ACS Chem. Biol. 12(1): p. 73-82 (author manuscript, 18 pages).
Vaidyanathan et al., "Engineered heparins as new anticoagulant drugs", Mar. 2017, Bioengineering & Translational Medicine 2(1): p. 17-30 (accepted preprint version, 45 pages).
Bertini et al., "Molecular Weights of Bovine and Porcine Heparin Samples: Comparison of Chromatographic Methods and Results of a Collaborative Survey", Jul. 19, 2017, Molecules 22(1214) (10 pages).
Meneghetti et al., "Insights into the role of 3-O-sulfotransferase in heparan sulfate biosynthesis", Aug. 16, 2017, Org. Biomol. Chem. 15: p. 6792-6799 (author manuscript, 16 pages).
Stancanelli et al., "Recognition and Conformational Properties of an Alternative Antithrombin Binding Sequence Obtained by Chemoenzymatic Synthesis", 2018, ChemBioChem 19: p. 1178-1188 (11 pages).
Islam et al., "A robust protocol for directed aryl sulfotransferase evolution towards the carbohydrate building block GlcNAc", May 2018, Biotech. & Bioeng. 115(5): p. 1106-1115 (accepted preprint version, 34 pages).
Islam et al., "KnowVolution Campaign of an Aryl Sulfotransferase Increases Activity toward Cellobiose", 2018, Chem. Eur. J. 24: p. 17117-17124 (8 pages).
Sulfita, Matt, "Chemoenzymatic Synthesis of Heparan Sulfates, and Investigations of Their Role in Cell Signaling, Human Health and Disease", May 2018, Rensselaer Polytechnic Institute, Department of Biology (161 pages).
Cimini et al., "Microbial production and metabolic engineering of chondroitin and chondroitin sulfate", Oct. 4, 2018, Portland Press—Emerging Topics in Life Sciences (13 pages).
Vessella et al., "Development of Semisynthetic, Regioselective Pathways for Accessing the Missing Sulfation Patterns of Chondroitin Sulfate", Jun. 24, 2019, Biomacromolecules 20: p. 3021-3030 (10 pages).
International Search Report and Written Opinion dated Apr. 20, 2020 in corresponding International Application No. PCT/US2020/013677 filed Jan. 15, 2020 (13 pages).

(56) References Cited

OTHER PUBLICATIONS

International Search Report and Written Opinion dated Nov. 4, 2020 in related International Application No. PCT/US2020/041404 filed Jul. 9, 2020 (12 pages).
International Preliminary Report on Patentability (Chapter I) dated Jun. 16, 2021 in corresponding International Application No. PCT/US2020/013677 filed Jan. 15, 2020 (8 pages).
U.S. Appl. No. 17/376,322, filed Jul. 15, 2021, Ferreira.
U.S. Appl. No. 17/376,332, filed Jul. 15, 2021, Ferreira.
U.S. Appl. No. 17/376,335, filed Jul. 15, 2021, Ferreira.
U.S. Appl. No. 17/376,354, filed Jul. 15, 2021, Gesteira et al..
Notice of Allowance dated Mar. 4, 2022 in copending U.S. Appl. No. 17/376,335, filed Jul. 15, 2021 (11 pages).
Non-final Office action dated Apr. 20, 2022 in copending U.S. Appl. No. 17/376,354, filed Jul. 15, 2021 (13 pages).
Xu et al., Mutational Study of Heparan Sulfate 2-O-Sulfotransferase and Chondroitin Sulfate 2-O Sulfotransferase, the Journal of Biological Chemistry (2007), 282(11), 8356-8367 (12 pages).
Bethea et al., Redirecting the substrate specificity of heparan sulfate 2-O-sulfotransferase by structurally guided mutagenesis, PNAS, Dec. 2, 2008, vol. 105, No. 48, pp. 18724-18729 (6 pages).
Li et al., Using Engineered 2-O-Sulfotransferase to Determine the Activity of Heparan Sulfate C5-epimerase and Its Mutants, the Journal of Bio Chem, Apr. 9, 2010, vol. 285, No. 15, pp. 11106-11113 (8 pages).
Thieker et al, Downstream Products are Potent Inhibitors of the Heparan Sulfate 2-O-Sulfotransferase, Scientific Reports, 2018, 8:11832, pp. 1-13 (13 pages).

* cited by examiner

Reaction

Transition State

Products

Figure 6C

Reaction

Transition State

Products

Reaction

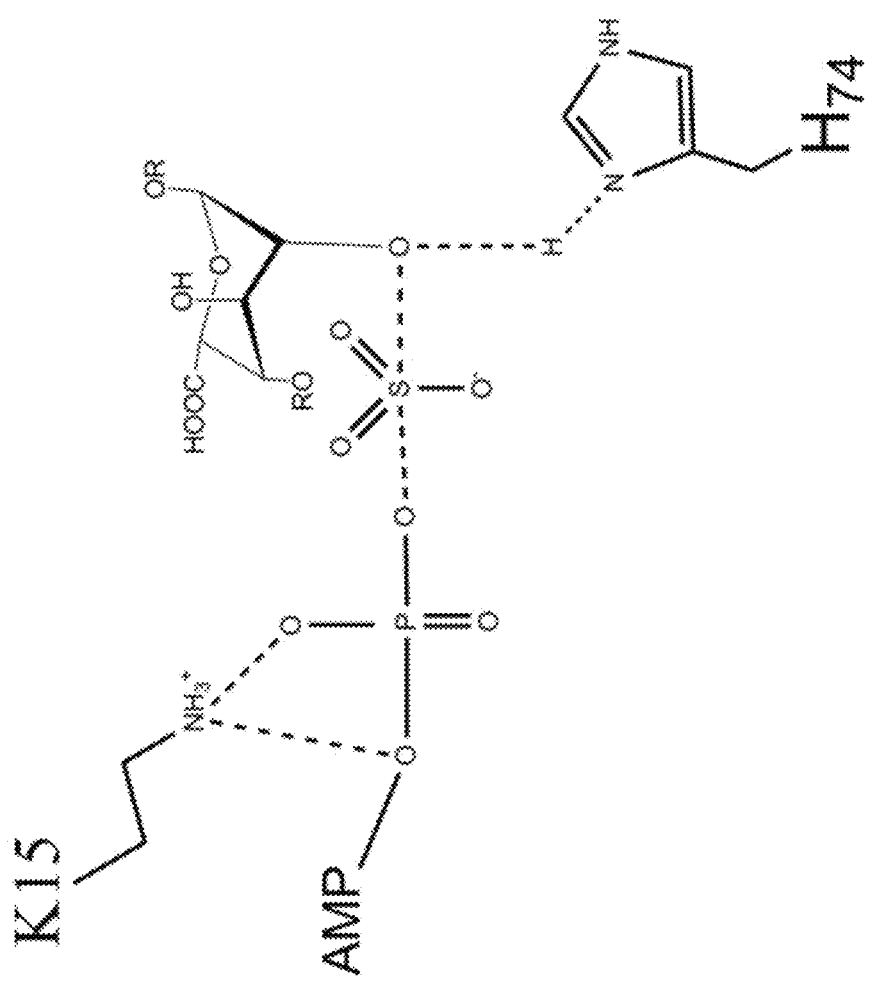

Products

Reaction

Transition State

Products

| SEQ ID NO | | | | |
|---|---|---|---|---|
| 206 | sp\|O14792\|HS3S1_HUMAN | 100% | GVAPNGSA | QQLPQTI IIGVRKGGTRALLEMLSLHP |
| 207 | sp\|H9ZG39\|H9ZG39_MACMU | 98% | GAAPNGSA | QQLPQTI IIGVRKGGTRALLEMLSLHP |
| 208 | tr\|D2HWC3\|D2HWC3_AILME | 95% | ..PNGSA | QQLPQTI IIGVRKGGTRALLEMLSLHP |
| 209 | tr\|F6VH42\|F6VH42_HORSE | 93% | GAAPNGSA | QQLPQTI IIGVRKGGTRALLEMLSLHP |
| 210 | tr\|I3LHH5\|I3LHH5_PIG | 91% | SAAPNGSV | QQLPQTI IIGVRKGGTRALLEMLSLHP |
| 211 | tr\|Q0VCB5\|Q0VCB5_BOVIN | 90% | GAAPNGSA | QQLPQTI IIGVRKGGTRALLEMLSLHP |
| 212 | sp\|Q9ESG5\|HS3S1_RAT | 87% | GAATNGSI | QQLPQTI IIGVRKGGTRALLEMLSLHP |
| 213 | sp\|O35310\|HS3S1_MOUSE | 83% | GTASNGST | QQLPQTI IIGVRKGGTRALLEMLSLHP |
| 214 | tr\|E1C4I5\|E1C4I5_CHICK | 79% | NIHSNGS | CRQLPQTI IIGVRKGGTRALLEMLSLHP |
| 215 | tr\|H9GAC0\|H9GAC0_ANOCA | 76% | WIHFNET | LRQLPQTI LIGVRKGGTRALLEMLSLHS |
| 216 | tr\|I3KYG4\|I3KYG4_ORENI | 70% | TSHPNGT | LQQLPHI IIGVRKGGTRALLEMLSLHP |
| 217 | tr\|K4FTU4\|K4FTU4_CALMI | 68% | LVFPNGTS | QRLPQTI IIGVRKGGTRALLEMLSLHP |
| 218 | tr\|A0A3B4C5Z8\|A0A3B4C5Z8_PYGNA | 62% | RMLQNGT. | RHLPDII IIGVRKGGTRALLEMLSLHS |
| 219 | tr\|T1E5H6\|T1E5H6_CROHD | 56% | QVRFFGTS | RQIPQTI IIGVRKGGTRALLEMLDVHP |
| 220 | sp\|Q8IZT8\|HS3S5_HUMAN | 53% | QVRLHDLV | QQLPKAI IIGVRKGGTRALLEMLNLHP |

Figure 26A

| SEQ ID NO | β3 → | | | | | α2 | | | | | α3 | | | | | β4 → | | | β5 → | | | η1 | | | | α4 | | | |
|---|---|---|---|---|---|---|---|---|---|---|---|---|---|---|---|---|---|---|---|---|---|---|---|---|---|---|---|---|---|
| 206 | D V A A A E N E V H F F D W E E H Y S H G L G W Y L S Q M P F S W P H Q L T V E K T P A Y F T S P K V P E R V Y S M N P |
| 207 | D V A A A E N E V H F F D W E E H Y G H G L G W Y L S Q M P F S W P H Q L T V E K T P A Y F T S P K V P E R V H S M N P |
| 208 | D V A A A E N E V H F F D W E E H Y S Q G L G W Y L S Q M P F S S P H Q L T V E K T P A Y F T S P K V P E R V H S M N P |
| 209 | D V A A A E N E V H F F D W E E H Y S Q G L G W Y L S Q M P F S A P H Q L T V E K T P A Y F T S P K V P E R V H G M N P |
| 210 | D V A A A E N E V H F F D W E E H Y S Q G L G W Y L S Q M P F S A P H Q L T V E K T P A Y F T S P K V P E R V H G M N P |
| 211 | D V A A A E N E V H F F D W E E H Y S Q G L G W Y L S Q M P F S S P H Q L T V E K T P A Y F T S P K V P E R V H S M N P |
| 212 | D V A A A E N E V H F F D W E E H Y S Q G L G W Y L S Q M P F S S P H Q L T V E K T P A Y F T S P K V P E R V H S M N P |
| 213 | D V A A A E N E V H F F D W E D H Y R N G L G W Y I N Q M P F S Y P D I H Q L T V E K T P A Y F T S P K V P E R I H S M N P |
| 214 | D I A A A E S E V H F F D W E E H Y G K G L G W Y I N Q M P L S D I H Q L T V E K T P A Y F T S P K V P E R V Y K M N Q |
| 215 | D I A A A E S E V H F F D W E E H Y G Q G L G W Y L S Q M P Y A F P D L T V E K T P A Y F T S P K V P E R V H Q M N T |
| 216 | S V A A A Q N E V H F F D W E S H Y F Q R G L P W Y G K Q M P L S Y P R Q L T V E K T P A Y F T S P K V P E R I H N M N K |
| 217 | D V T A A E N E V H F F D W E E N Y A K G L Q W Y A S Q M P S A Q P G L T V E K T P A Y F T S E V P E R V F H M N P |
| 218 | S I T S A E N E V H F F D W E S H Y Q Q G L T W Y A S Q M P S A Q P G L T V E K T P A Y F T C A K V P E R V F H M N P |
| 219 | N I V V A A I E V H F F D W D E N Y V K G I D W Y R S L M P F S Y E N Q I T I E K T P G Y F T S P Q A P E R I H D M N S |
| 220 | A V V K A S Q E I H F F D N D E N Y G K G I E W Y R K K M P F S Y P Q I T I E K S P A Y F I T E E V P E R I Y K M N S |

| SEQ ID NO | Sequence |
|---|---|
| 206 | LHESKGRAHPQVDPKLLNKLHEYFHEPNKKFELVGRTFDWH |
| 207 | LHESKGRAHPQVDPKLLNKLHEYFHEPNKKFELVGRTFDWH |
| 208 | LHESKGRAHPQVDPRLLNKLHEYFHEPNKKFELVGRTFDWH |
| 209 | LHESKGRAHPQIDPKLLNKLHEYFHEPNKKFELVGRTFDWH |
| 210 | LHESKGRAHPQVDPKLLNKLHEYFHEPNKKFELVGRTFDWH |
| 211 | LHESKGRAHPQVDPKLLNKLHEYFHEPNKKFKLVGRTFDWH |
| 212 | LHESKGRAHPQVDPKLLNKLHEYFHEPNKKFKLVGRTFDWH |
| 213 | LHESKGRAHPQVDPKLLDKLHEYFREPNKKFELVGRTFDWH |
| 214 | LHESKGRAHPQVDPKLLDKLHEYFHEPNKKFELVGRTFDWH |
| 215 | LHESKGRAHPQVDTRLLEKLHKYFYEPCEPNQKFELVGRTFDWH |
| 216 | LHESKGRAHPKVDPHLLHILYQFFHEPNKKFELVGRTFDWH |
| 217 | LHDSKGRTHPQVDSTVLNKLHEFESEPNRKFETVGRTFIWK |
| 218 | LHSSKGRTHPQVSPEILQKLRDYFHKPHNEKFELVGRTFDWH |
| 219 | LHESKGRPHPVVNSTVLEQLYSYFREHNEKFYRMINHSFDWH |
| 220 | LAGSKGRIHPEVDPSVITKLRKFFHPFNQKFYQITGRTLNWP |

Figure 26F

SEQUENCE LISTING

<160> NUMBER OF SEQ ID NOS: 300

<210> SEQ ID NO 1
<211> LENGTH: 309
<212> TYPE: PRT
<213> ORGANISM: Artificial Sequence
<220> FEATURE:
<223> OTHER INFORMATION: Engineered glucosaminyl N-sulfotransferase
      mutant_sulfatase 1

<400> SEQUENCE: 1

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His Lys Thr Gly His Thr Ala Leu Tyr
        35                  40                  45

Leu Phe Leu Gly Met His Pro Asp Leu Ser Ser Asn Tyr Pro Ser Ser
    50                  55                  60

Thr Thr Gly Glu Ser Ile Gly Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Ala His Gly Gly Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205

Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Lys Ser Lys Gly Arg Lys Tyr Pro Glu Met Asp Leu Asp Ser Arg
            260                 265                 270

Ala Phe Leu Lys Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Asp
    290                 295                 300

Leu Gln Asn Thr Arg
305

<210> SEQ ID NO 2
<211> LENGTH: 927
<212> TYPE: DNA
<213> ORGANISM: Artificial Sequence
<220> FEATURE:

<223> OTHER INFORMATION: Polynucleotide sequence encoding for engineered
glucosaminyl N-sulfotransferase mutant_sulfatase 1

<400> SEQUENCE: 2

```
atgagcgaag agaaggaccc tttgtggcag gacccgtgcg aagataagcg ccacaaagac    60
atctggtcga agaaaaagac gtgcgaccgt ttccctaaac ttttaattat cggtccgcat   120
aagacagggc atacagcact ttatttattt ttggggatgc acccggattt gtcctcgaac   180
tatccctcgt ctacgaccgg ggagagcatt ggcttcttca atggacacaa ctatcataag   240
ggaattgact ggtatatgga attcttccct atcccagca atactacctc agatttctac    300
ttcgaagcgc acgggggta tttttgatagc gaggtcgccc cacgtcgcgc tgccgcattg   360
cttcccaagg caaaggtgct tactattttg attaaccctg cagaccgtgc ttactcctgg   420
tatcaacacc aacgtgcgca cgatgatcct gtggcgttga atacacatt tcacgaagta    480
attactgcgg atctgatgc gtctagcaaa ttgcgtgcct acagaaccg ctgccttgtt     540
ccaggttggt acgccacgca cattgagcgt tggctgtctg cgtatcacgc taaccagatt   600
cttgtattag acggaaaatt gctgcgtaca gagcccgcta aggtgatgga tatggtgcaa   660
aagttccttg gtgtaacgaa caccattgat tatcataaaa cgttggcttt tgaccctaaa   720
aagggatttt ggtgccagtt acttgaagga gggaagacaa agtgtctggg aagagcaaa    780
gggcgtaaat acccagaaat ggatttagat agtcgcgcat tccttaaaga ttactatcgc   840
gatcataaca tcgaattatc gaagctttta tacaaaatgg ccagacatt gccaacgtgg    900
ctgcgtgaag acttgcagaa cacacgc                                        927
```

<210> SEQ ID NO 3
<211> LENGTH: 309
<212> TYPE: PRT
<213> ORGANISM: Artificial Sequence
<220> FEATURE:
<223> OTHER INFORMATION: Engineered glucosaminyl N-sulfotransferase
mutant_sulfatase 2

<400> SEQUENCE: 3

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Gln Lys Thr Gly Ala Trp Ala Leu Tyr
        35                  40                  45

His Phe Leu Gly Met His Pro Asp Leu Ser Ser Asn Tyr Pro Ser Ser
    50                  55                  60

Glu Ser His Ala Arg Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Met Ala Asn Tyr Phe Ser Glu Val
                100                 105                 110

Ala Pro Arg Arg Ala Ala Ala Leu Leu Pro Lys Ala Lys Val Leu Thr
            115                 120                 125

Ile Leu Ile Asn Pro Ala Asp Arg Ala Tyr Ser Trp Tyr Gln His Gln
        130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
```

```
                165                 170                 175
Arg Cys Leu Val Pro Gly Trp Tyr Ala Thr His Ile Glu Arg Trp Leu
                180                 185                 190

Ser Ala Tyr His Ala Asn Gln Ile Leu Val Leu Asp Gly Lys Leu Leu
                195                 200                 205

Arg Thr Glu Pro Ala Lys Val Met Asp Met Val Gln Lys Phe Leu Gly
            210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

His Lys Arg Ala Gly Arg Lys Tyr Pro Glu Met Asp Leu Asp Ser Arg
            260                 265                 270

Ala Phe Leu Lys Asp Tyr Tyr Arg Asp His Asn Ile Glu Leu Ser Lys
                275                 280                 285

Leu Leu Tyr Lys Met Gly Gln Thr Leu Pro Thr Trp Leu Arg Glu Asp
                290                 295                 300

Leu Gln Asn Thr Arg
305
```

```
<210> SEQ ID NO 4
<211> LENGTH: 927
<212> TYPE: DNA
<213> ORGANISM: Artificial Sequence
<220> FEATURE:
<223> OTHER INFORMATION: Polynucleotide sequence encoding for engineered
      glucosaminyl N-sulfotransferase mutant_sulfatase 2

<400> SEQUENCE: 4
atgagcgaag agaaggaccc tttgtggcag gacccgtgcg aggacaagcg ccacaaggac      60
atttggagta aggaaaagac atgcgaccgc ttcccgaaat tattgattat tggtccgcag     120
aaaactgggg catgggcatt gtaccacttc ttaggtatgc acccagactt atcgtctaac     180
tatccatcct ccgaaagtca tgctcgcatc caattcttca acggtcataa ctatcataag     240
ggtattgact ggtacatgga gttttttccc atccccagta ataccactag tgactttttac     300 tttgagatgt cggcaaacta cttttgacagc gaggttgctc cgcgtcgtgc ggcagcgctt     360
ctgccgaaag ccaaggtatt aactattttg atcaacccag cagatcgtgc gtatagttgg     420
taccagcacc aacgcgccca tgatgatcct gtcgctctta agtacacctt ccatgaagta     480 attacgcgg gcagcgatgc ttcgtctaaa cttcgtgcgt tgcagaatcg ctgcctggtt     540
cccgggtggt acgcgaccca cattgagcgc tggctttccg catatcatgc caatcaaatc     600
ttggtattgg acgaaagct tctgcgcacc gagcctgcga aagtgatgga catggtacag     660
aagttcttag gagttacaaa tacgatcgat tatcacaaga cccttgcttt tgaccctaaa     720
aaaggattct ggtgccaact tttggaggga ggtaagacta gtgccttca taaacgcgca     780 gggcgcaaat atcccgagat ggacttagat tcacgcgcgt tccttaaaga ttactatcgt     840
gatcataata tcgagttaag caaacttctg tataagatgg gacagacact gcctacatgg     900
ctgcgtgaag acttgcagaa cacacgc                                        927
```

```
<210> SEQ ID NO 5
<211> LENGTH: 309
<212> TYPE: PRT
<213> ORGANISM: Artificial Sequence
<220> FEATURE:
<223> OTHER INFORMATION: Engineered glucosaminyl N-sulfotransferase
``` mutant_sulfotransferase 1

<400> SEQUENCE: 5

```
Met Ser Glu Glu Lys Asp Pro Leu Trp Gln Asp Pro Cys Glu Asp Lys
1               5                   10                  15
Arg His Lys Asp Ile Trp Ser Lys Glu Lys Thr Cys Asp Arg Phe Pro
            20                  25                  30
Lys Leu Leu Ile Ile Gly Pro Gln Lys Thr Gly Ala Trp Ala Leu Tyr
        35                  40                  45
His Phe Leu Gly Met His Pro Asp Leu Ser Ser Asn Tyr Pro Ser Ser
    50                  55                  60
Glu Thr His Gly Ser Ile Gln Phe Phe Asn Gly His Asn Tyr His Lys
65                  70                  75                  80
Gly Ile Asp Trp Tyr Met Glu Phe Phe Pro Ile Pro Ser Asn Thr Thr
                85                  90                  95
Ser Asp Phe Tyr Phe Glu Lys Ser Ala Asn Tyr Phe Asp Ser Glu Val
            100                 105                 110
Ala Pro Arg Arg Ala Ala Ala Leu Leu Pro Lys Ala Lys Val Leu Thr
        115                 120                 125
Ile Leu Ile Asn Pro Ala Asp Arg Ala Tyr Ser Trp Tyr Gln His Gln
    130                 135                 140
Arg Ala His Asp Asp Pro Val Ala Leu Lys Tyr Thr Phe His Glu Val
145                 150                 155                 160
Ile Thr Ala Gly Ser Asp Ala Ser Ser Lys Leu Arg Ala Leu Gln Asn
                165                 170                 175
Arg Cys Leu Val Pro Gly Trp Tyr Ala Thr His Ile Glu Arg Trp Leu
            180                 185                 190
Ser Ala Tyr His Ala Asn Gln Ile Leu Val Leu Asp Gly Lys Leu Leu
        195                 200                 205
Arg Thr Glu Pro Ala Lys Val Met Asp Met Val Gln Lys Phe Leu Gly
    210                 215                 220
Val Thr Asn Thr Ile Asp Tyr His Lys Thr Leu Ala Phe Asp Pro Lys
225                 230                 235                 240
Lys Gly Phe Trp Cys Gln Leu Leu Glu Gly Gly Lys Thr Lys Cys Leu
                245                 250                 255
Gly Lys Ser His Gly Arg Lys Tyr Pro Glu Met Asp Leu Asp Ser Arg
            260                 265                 270
Ala Phe Leu Lys Asp Tyr Tyr Arg Asp His Asn Ile Glu Leu Ser Lys
        275                 280                 285
Leu Leu Tyr Lys Met Gly Gln Thr Leu Pro Thr Trp Leu Arg Glu Asp
    290                 295                 300
Leu Gln Asn Thr Arg
305
```

<210> SEQ ID NO 6
<211> LENGTH: 927
<212> TYPE: DNA
<213> ORGANISM: Artificial Sequence
<220> FEATURE:
<223> OTHER INFORMATION: Polynucleotide sequence encoding for engineered glucosaminyl N-sulfotransferase mutant_sulfotransferase 1

<400> SEQUENCE: 6

```
atgagcgaag agaaggaccc tttgtggcag gacccgtgcg aggacaaacg ccacaaagac      60
atttggtcga aggagaaaac ctgtgaccgc ttccctaagt tgcttattat tggtccgcaa     120
```

-continued

```
aagaccggcg cctgggcgct ttaccatttc ctgggtatgc atcccgatct tagttccaac    180
tacccgtcga gtgaaacaca tggcagtatc caattcttta atggacataa ctaccataag    240
ggcatcgact ggtatatgga attttcccc attccctcaa ataccacttc tgacttttat     300
ttcgagaaat cagcgaatta ttttgacagt gaggtagcgc ctcgccgcgc agcagcattg    360
ttgcccaaag caaaagtgct gactattctt atcaatccag ctgaccgcgc atattcttgg    420
tatcagcacc agcgcgccca cgacgacccg gtggcgctga atacacatt ccatgaagtg     480 attactgctg gaagcgatgc gtcgtctaag ttgcgtgctc tgcagaaccg ctgtttggta    540
cctggctggt atgctacgca cattgaacgt tggctgtccg catatcacgc gaaccagatc    600 ctggtttag atggtaaatt acttcgcacg gagccagcta aagtcatgga catggtacaa     660
aagttcctgg gggtaacgaa taccattgat tatcataaga ctttggcttt cgaccccaag    720
aagggatttt ggtgccagtt attggagggg ggcaagacga agtgcttagg caaatcgcat    780
gggcgcaagt acccggagat ggatttggac tcacgcgcct ttcttaagga ctactaccgc    840
gaccacaaca ttgaattgag taaattatta tacaaaatgg ggcaaactct tccgacttgg    900
ttgcgtgaag acttgcagaa cacacgc                                       927
```

<210> SEQ ID NO 7
<211> LENGTH: 309
<212> TYPE: PRT
<213> ORGANISM: Artificial Sequence
<220> FEATURE:
<223> OTHER INFORMATION: Engineered glucosaminyl N-sulfotransferase mutant_sulfotransferase 2

<400> SEQUENCE: 7

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Ser Lys Thr Gly Ala Phe Leu Leu Thr
        35                  40                  45

His Phe Leu Gly Met His Pro Asp Leu Ser Ser Asn Tyr Pro Ser Ser
    50                  55                  60

Glu Thr Gly His Ser Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Thr Ser Ser Asn Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205

Arg Thr Glu Pro Ala Lys Val Met Asp Met Val Gln Lys Phe Leu Gly
```

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys His
            245                 250                 255

Gly Lys Arg Trp Gly Arg Lys Tyr Pro Glu Met Asp Leu Asp Ser Arg
        260                 265                 270

Ala Phe Leu Lys Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Asp
        290                 295                 300

Leu Gln Asn Thr Arg
305

<210> SEQ ID NO 8
<211> LENGTH: 927
<212> TYPE: DNA
<213> ORGANISM: Artificial Sequence
<220> FEATURE:
<223> OTHER INFORMATION: Polynucleotide sequence encoding for engineered
      glucosaminyl N-sulfotransferase mutant_sulfotransferase 2

<400> SEQUENCE: 8
atgagcgaag agaaggaccc tttgtggcag gacccgtgcg aggacaaacg ccataaggac      60
atctggtcga agagaagac ttgtgaccgt tttccaaaat tacttattat cggtccttca     120
aagaccggcg ctttcctttt aacccacttt ttggggatgc atccagacct tagttcaaat     180
taccttcgt ctgagactgg gcattccatt caattcttca acgggcacaa ttatcacaag     240
ggtattgact ggtacatgga attttttccg attccgagca atacaacttc cgattttttac     300
tttgaaacct catccaatta ttttgattcc gaagtcgctc cacgccgcgc cgctgctttg     360
ttgccaaaag ctaaggtttt gactattctg atcaacccgg ctgaccgcgc ctattcatgg     420
taccaacacc agcgtgctca tgatgaccca gtggctttga gtatacgtt ccatgaggtc     480
attacagcgg gcagcgacgc aagctccaaa cttcgcgcat tgcaaaaccg ctgccttgtg     540
cccggttggt acgcgacaca cattgaacgc tggctgtccg cttaccacgc caaccaaatt     600
ttagttttag atgggaaatt acttcgtacc gaacctgcca aggtcatgga catggtgcag     660
aaatttttgg gagtcactaa cactatcgac taccacaaaa cattggcatt cgatccaaaa     720
aaggggtttt ggtgccagct tttagaaggg ggcaagacga gtgtcacgg gaagcgttgg     780
gggcgtaagt atccagagat ggatcttgat agccgcgctt tcttaaaaga ttattaccgt     840
gaccacaaca ttgagcttag caaactgctt tacaagatgg gtcagacact tccgacatgg     900
ctgcgtgaag acttgcagaa cacacgc                                        927

<210> SEQ ID NO 9
<211> LENGTH: 309
<212> TYPE: PRT
<213> ORGANISM: Artificial Sequence
<220> FEATURE:
<223> OTHER INFORMATION: Engineered glucosaminyl N-sulfotransferase
      mutant_sulfotransferase 3

<400> SEQUENCE: 9

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His Gly Thr Gly His Ala Leu Tyr
        35                     40                          45

Leu Phe Leu Gly Met His Pro Asp Leu Ser Ser Asn Tyr Pro Ser Ser
50                      55                    60

Glu Thr Gly Glu Glu Ile Gln Phe Phe Asn Gly His Asn Tyr His Lys
65                      70                    75                    80

Gly Ile Asp Trp Tyr Met Glu Phe Phe Pro Ile Pro Ser Asn Thr Thr
                85                        90                    95

Ser Asp Phe Tyr Phe Glu Lys Ser Ala Asn Tyr Phe Asp Ser Glu Val
                100                   105                   110

Ala Pro Arg Arg Ala Ala Ala Leu Leu Pro Lys Ala Lys Val Leu Thr
                115                   120                   125

Ile Leu Ile Asn Pro Ala Asp Arg Ala Tyr Ser Trp Tyr Gln Ala Gln
    130                   135                   140

Arg Ala His Asp Asp Pro Val Ala Leu Lys Tyr Thr Phe His Glu Val
145                     150                   155                 160

Ile Thr Ala Gly Ser Asp Ala Ser Ser Lys Leu Arg Ala Leu Gln Asn
                165                   170                   175

Arg Cys Leu Val Pro Gly Trp Tyr Ala Thr His Ile Glu Arg Trp Leu
            180                   185                   190

Ser Ala Tyr His Ala Asn Gln Ile Leu Val Leu Asp Gly Lys Leu Leu
        195                   200                   205

Arg Thr Glu Pro Ala Lys Val Met Asp Met Val Gln Lys Phe Leu Gly
    210                   215                   220

Val Thr Asn Thr Ile Asp Tyr His Lys Thr Leu Ala Phe Asp Pro Lys
225                     230                   235                 240

Lys Gly Phe Trp Cys Gln Leu Leu Glu Gly Gly Lys Thr Lys Cys Gly
                245                   250                   255

Gly Lys His Leu Gly Arg Lys Tyr Pro Glu Met Asp Leu Asp Ser Arg
            260                   265                   270

Ala Phe Leu Lys Asp Tyr Tyr Arg Asp His Asn Ile Glu Leu Ser Lys
        275                   280                   285

Leu Leu Tyr Lys Met Gly Gln Thr Leu Pro Thr Trp Leu Arg Glu Asp
    290                   295                   300

Leu Gln Asn Thr Arg
305

<210> SEQ ID NO 10
<211> LENGTH: 927
<212> TYPE: DNA
<213> ORGANISM: Artificial Sequence
<220> FEATURE:
<223> OTHER INFORMATION: Polynucleotide sequence encoding for engineered
     glucosaminyl N-sulfotransferase mutant_sulfotransferase 3

<400> SEQUENCE: 10
atgagcgaag agaaggaccc tttgtggcag gacccgtgcg aagataagcg tcacaaggac    60
atctggtcaa agagaaaac ttgcgaccgc tttccgaaat tgttaattat tggaccacat   120
ggcaccgggg gtcacgcact ttacttattc ttgggaatgc acccagatct gagctccaac   180
taccccagct ctgaaaccgg cgaagaaatc caatttttca acgggcacaa ttatcataaa   240
ggcattgatt ggtatatgga attcttcccc atcccgtcta atactaccag cgatttctat   300
tttgaaaaaa gtgcgaacta cttcgactcg gaggtggcac ccgtcgtgc tgcggcctta   360 ctgccaaagg ccaaggtttt aaccatcttg attaatccgg ctgaccgtgc ttattcctgg   420

```
taccaggctc aacgcgcaca tgacgacccc gttgcgctta aatatacatt ccacgaggtc    480
attactgcgg gctctgatgc ttcttcgaaa cttcgtgcgc tgcaaaatcg ttgtttagtg    540
ccgggttggt acgccacgca catcgagcgt tggcttagtg cctaccatgc gaatcaaatc    600
cttgtcttgg atgggaagct tttgcgtact gaaccggcca aggtcatgga catggtccag    660
aagtttctgg gtgttaccaa cactattgat taccataaga ctttagcctt cgatccgaag    720
aaaggcttct ggtgtcaatt acttgagggt ggtaagacca agtgcggagg aaaacatctt    780
gggcgcaaat accccgaaat ggacttagat agccgtgcct ttctgaaaga ttactaccgc    840
gaccataata tcgagcttag caaattattg tacaaaatgg ccaaaccttg ccgacgtgg    900 ctgcgtgaag acttgcagaa cacacgc                                        927
```

<210> SEQ ID NO 11
<211> LENGTH: 309
<212> TYPE: PRT
<213> ORGANISM: Artificial Sequence
<220> FEATURE:
<223> OTHER INFORMATION: Engineered glucosaminyl N-sulfotransferase
mutant_sulfotransferase 4

<400> SEQUENCE: 11

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His Gly Thr Gly Gly His Ala Leu Tyr
        35                  40                  45

Leu Phe Leu Gly Met His Pro Asp Leu Ser Ser Asn Tyr Pro Ser Ser
    50                  55                  60

Glu Thr Phe Leu Ser Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu His Ser Gly Asn Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Arg Ala Tyr Val Trp Gln
    130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205

Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Lys Ser Leu Gly Ser Lys Tyr Pro Glu Met Asp Leu Asp Ser Arg
```

260                 265                 270
Ala Phe Leu Lys Asp Tyr Tyr Arg Asp His Asn Ile Glu Leu Ser Lys
            275                 280                 285

Leu Leu Tyr Lys Met Gly Gln Thr Leu Pro Thr Trp Leu Arg Glu Asp
        290                 295                 300

Leu Gln Asn Thr Arg
305

<210> SEQ ID NO 12
<211> LENGTH: 927
<212> TYPE: DNA
<213> ORGANISM: Artificial Sequence
<220> FEATURE:
<223> OTHER INFORMATION: Polynucleotide sequence encoding for engineered
      glucosaminyl N-sulfotransferase mutant_sulfotransferase 4

<400> SEQUENCE: 12
atgagcgaag agaaggaccc tttgtggcag gacccgtgcg aagataagcg ccacaaggac     60
atctggagca aggagaaaac ttgcgaccgc tttccaaagt tgctgattat tgggcctcac    120
ggcacgggcg ccacgcgct gtacctgttt cttggcatgc acccggacct ttccagcaat     180
tatcctagta gtgagacatt tttgagtatc aatttttta acggacataa ctatcacaaa     240
ggtatcgatt ggtacatgga attcttccca attccgtcta atacgacatc tgactttat    300 ttcgagcatt cggggaatta ctttgattcc gaggtagccc cacgccgtgc cgccgctctt    360
ttgcccaagg cgaaagtctt gactattctt attaatcccg cagaccgtgc ctaccgcgcg    420
tatgtatggc aacgcgcaca cgatgaccca gtcgcattga aatatacatt ccatgaggtg    480
attaccgcgg gtagtgacgc ttctagcaag ttacgtgctc ttcagaatcg ctgccttgtc    540
ccaggttggt atgccacaca catcgaacgt tggctgtccg cctaccatgc taatcagatt    600
cttgtgctgg atggtaaatt gttgcgtaca gagcctgcca agttatggaa tatggtgcaa    660 aaattttttgg gtgttacgaa tactattgat taccataaga cacttgcatt tgacccgaaa    720
aaaggtttct ggtgccaatt gttggagggt ggcaagacta agtgcttagg taagagtctt    780
ggttcgaagt accccgaaat ggatttagac tcgcgcgctt tcttgaagga ctattatcgt    840
gaccacaata tcgaactttc taaacttttta tataagatgg ccaaacact tcccacgtgg    900 ctgcgtgaag acttgcagaa cacacgc                                       927

<210> SEQ ID NO 13
<211> LENGTH: 309
<212> TYPE: PRT
<213> ORGANISM: Artificial Sequence
<220> FEATURE:
<223> OTHER INFORMATION: Engineered glucosaminyl N-sulfotransferase
      mutant_sulfotransferase 5

<400> SEQUENCE: 13

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His Lys Thr Gly Val His Ala Leu Tyr
        35                  40                  45

Leu Phe Leu Gly Met His Pro Asp Leu Ser Ser Asn Tyr Pro Ser Ser
    50                  55                  60

Glu Thr Gly Asn His Ile Gly Phe Phe Gly Gly His Asn Tyr His Lys
65                  70                  75                  80

Gly Ile Asp Trp Tyr Met Glu Phe Phe Pro Ile Pro Ser Asn Thr Thr
            85                  90                  95

Ser Asp Phe Tyr Phe Glu Lys Ser Ala Trp Tyr Phe Asp Ser Glu Val
           100                 105                 110

Ala Pro Arg Arg Ala Ala Ala Leu Leu Pro Lys Ala Lys Val Leu Thr
           115                 120                 125

Ile Leu Ile Asn Pro Ala Asp Arg Ala Tyr Ser Trp Tyr Gln His Gln
130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
            195                 200                 205

Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Lys Ser Val Gly Arg Lys Tyr Pro Glu Met Asp Leu Asp Ser Arg
            260                 265                 270

Ala Phe Leu Lys Asp Tyr Tyr Arg Asp His Asn Ile Glu Leu Ser Lys
            275                 280                 285

Leu Leu Tyr Lys Met Gly Gln Thr Leu Pro Thr Trp Leu Arg Glu Asp
    290                 295                 300

Leu Gln Asn Thr Arg
305

<210> SEQ ID NO 14
<211> LENGTH: 927
<212> TYPE: DNA
<213> ORGANISM: Artificial Sequence
<220> FEATURE:
<223> OTHER INFORMATION: Polynucleotide sequence encoding for engineered
      glucosaminyl N-sulfotransferase mutant_sulfotransferase 5

<400> SEQUENCE: 14
atgagcgaag agaaggaccc tttgtggcag gacccgtgcg aagataagcg tcataaagac    60
atttggagta agagaagac  ttgtgatcgt ttccccaagt tactgatcat cggcccacat   120
aagacaggag tacatgcatt gtacttgttt ttgggaatgc atccggacct gtcttcaaat   180
taccccagtt cagagacagg caatcacatc ggcttcttcg gaggacataa ctaccacaaa   240
ggcatcgatt ggtacatgga attctttcct atccctctca atactacctc agatttttac   300
ttcgagaaaa gtgcttggta cttttgactcc gaagttgctc ctcgtcgcgc agcagcatta   360
cttccaaagg cgaaagttct gactattttg atcaaccctg cggatcgcgc ctacagctgg   420
tatcaacacc agcgcgccca cgatgatcct gtcgcattga aatacacctt tcatgaagtt   480
atcaccgctg gctccgatgc gtctagcaaa ttgcgtgcat tacagaatcg ttgccttgtg   540
ccaggatggt acgctaccca tattgagcgc tggctgagtg catatcacgc gaatcagatt   600
ctggtgttag atggaaagct gctgcgtact gaaccggcca agtaatggga catggttcaa   660

-continued

```
aagttcctgg gggtgacgaa cacaattgat taccataaga ctcttgcatt tgatcctaag    720
aaaggctttt ggtgtcaact tttagagggg gggaagacca agtgcttagg gaagagcgtg    780
ggacgcaagt accccgaaat ggacttagat agccgtgctt tcttgaagga ttattatcgc    840
gaccacaaca ttgaactttc taaactgtta tacaagatgg ccagacact gccgacctgg     900 ctgcgtgaag acttgcagaa cacacgc                                        927
```

<210> SEQ ID NO 15
<211> LENGTH: 309
<212> TYPE: PRT
<213> ORGANISM: Artificial Sequence
<220> FEATURE:
<223> OTHER INFORMATION: Engineered glucosaminyl N-sulfotransferase mutant_sulfotransferase 6

<400> SEQUENCE: 15

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Ala Lys Thr Gly Ala Trp Leu Leu His
        35                  40                  45

His Phe Leu Gly Met His Pro Asp Leu Ser Ser Asn Tyr Pro Ser Ser
    50                  55                  60

Glu Thr His Ser Ser Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Thr Ser Ala Asn Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205

Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Ala
                245                 250                 255

His Lys Gly Leu Gly Arg Lys Tyr Pro Glu Met Asp Leu Asp Ser Arg
            260                 265                 270

Ala Phe Leu Lys Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Asp
    290                 295                 300

Leu Gln Asn Thr Arg
305
```

<210> SEQ ID NO 16
<211> LENGTH: 927
<212> TYPE: DNA
<213> ORGANISM: Artificial Sequence
<220> FEATURE:
<223> OTHER INFORMATION: Polynucleotide sequence encoding for engineered
glucosaminyl N-sulfotransferase mutant_sulfotransferase 6

<400> SEQUENCE: 16

```
atgagcgaag agaaggaccc tttgtggcag gacccgtgcg aagataagcg tcacaaggat      60
atttggtcca agaaaagac ctgcgatcgc tttcccaagc tgttaatcat cggcccggcc     120
aaaacaggcg cctggctttt gcatcatttc ctgggcatgc atcccgactt gtcgagtaac    180
tatccgtcgt ccgaaactca ctcctctatt caattcttca atgggcataa ttatcacaag    240
ggtatcgact ggtacatgga gttctttcca atccctagta atacaaccag tgattttat    300
tttgagacta gcgctaacta ctttgattca gaggtggcac cgcgtcgtgc ggcggcgctg    360
ttgccgaagg cgaaagtttt aactatcttg atcaatccgg cagatcgtgc gtacagctgg    420
taccaacatc aacgtgctca cgatgacccg gtggccctga atataccctt ccacgaggtc    480
attacagccg aagtgacgc ttccagtaaa ttgcgcgcgt acaaaatcg ttgtctggtc     540
cctgggtggt acgcaacgca cattgaacgc tggttatcgg cataccacgc aaatcagatc    600
cttgtgcttg acggaaagtt attgcgtact gaaccggcca aggtgatgga tatggtacag    660
aaattccttg gcgtcaccaa tacgatcgac tatcacaaga cgcttgcctt cgaccccaag    720
aaggggtttt ggtgccaact tttagagggt ggtaagacaa agtgtgctca taaggggtta    780
ggccgcaagt accctgaaat ggatctggac tcgcgcgctt ttttgaaaga ctattatcgc    840
gatcacaata ttgagttgag caagttgctg tataaaatgg acagacact gccgacctgg    900
ctgcgtgaag acttgcagaa cacacgc                                         927
```

<210> SEQ ID NO 17
<211> LENGTH: 309
<212> TYPE: PRT
<213> ORGANISM: Artificial Sequence
<220> FEATURE:
<223> OTHER INFORMATION: Engineered glucosaminyl N-sulfotransferase
mutant_variable
<220> FEATURE:
<221> NAME/KEY: MISC_FEATURE
<222> LOCATION: (40)..(40)
<223> OTHER INFORMATION: Xaa is glutamine, histidine, serine, or alanine
<220> FEATURE:
<221> NAME/KEY: MISC_FEATURE
<222> LOCATION: (41)..(41)
<223> OTHER INFORMATION: Xaa is lysine or glycine
<220> FEATURE:
<221> NAME/KEY: MISC_FEATURE
<222> LOCATION: (44)..(44)
<223> OTHER INFORMATION: Xaa is alanine, histidine, glycine, or valine
<220> FEATURE:
<221> NAME/KEY: MISC_FEATURE
<222> LOCATION: (45)..(45)
<223> OTHER INFORMATION: Xaa is threonine, tryptophan, histidine, or
phenylalanine
<220> FEATURE:
<221> NAME/KEY: MISC_FEATURE
<222> LOCATION: (46)..(46)
<223> OTHER INFORMATION: Xaa is alanine or leucine
<220> FEATURE:
<221> NAME/KEY: MISC_FEATURE
<222> LOCATION: (48)..(48)
<223> OTHER INFORMATION: Xaa is tyrosine, threonine, or histidine
<220> FEATURE:

```
<221> NAME/KEY: MISC_FEATURE
<222> LOCATION: (49)..(49)
<223> OTHER INFORMATION: Xaa is leucine or histidine
<220> FEATURE:
<221> NAME/KEY: MISC_FEATURE
<222> LOCATION: (65)..(65)
<223> OTHER INFORMATION: Xaa is glutamic acid or threonine
<220> FEATURE:
<221> NAME/KEY: MISC_FEATURE
<222> LOCATION: (66)..(66)
<223> OTHER INFORMATION: Xaa is threonine or serine
<220> FEATURE:
<221> NAME/KEY: MISC_FEATURE
<222> LOCATION: (67)..(67)
<223> OTHER INFORMATION: Xaa is phenylalanine, glycine, or histidine
<220> FEATURE:
<221> NAME/KEY: MISC_FEATURE
<222> LOCATION: (68)..(68)
<223> OTHER INFORMATION: Xaa is glutamic acid, histidine, alanine,
      leucine, glycine, asparagine, or serine
<220> FEATURE:
<221> NAME/KEY: MISC_FEATURE
<222> LOCATION: (69)..(69)
<223> OTHER INFORMATION: Xaa is glutamic acid, serine, arginine, or
      histidine
<220> FEATURE:
<221> NAME/KEY: MISC_FEATURE
<222> LOCATION: (71)..(71)
<223> OTHER INFORMATION: Xaa is glutamine or glycine
<220> FEATURE:
<221> NAME/KEY: MISC_FEATURE
<222> LOCATION: (74)..(74)
<223> OTHER INFORMATION: Xaa is asparagine or glycine
<220> FEATURE:
<221> NAME/KEY: MISC_FEATURE
<222> LOCATION: (103)..(103)
<223> OTHER INFORMATION: Xaa is lysine, alanine, methionine, histidine,
      or threonine
<220> FEATURE:
<221> NAME/KEY: MISC_FEATURE
<222> LOCATION: (104)..(104)
<223> OTHER INFORMATION: Xaa is serine or histidine
<220> FEATURE:
<221> NAME/KEY: MISC_FEATURE
<222> LOCATION: (105)..(105)
<223> OTHER INFORMATION: Xaa is alanine, serine, or glycine
<220> FEATURE:
<221> NAME/KEY: MISC_FEATURE
<222> LOCATION: (106)..(106)
<223> OTHER INFORMATION: Xaa is asparagine, glycine, or tryptophan
<220> FEATURE:
<221> NAME/KEY: MISC_FEATURE
<222> LOCATION: (139)..(139)
<223> OTHER INFORMATION: Xaa is serine or arginine
<220> FEATURE:
<221> NAME/KEY: MISC_FEATURE
<222> LOCATION: (140)..(140)
<223> OTHER INFORMATION: Xaa is tryptophan or alanine
<220> FEATURE:
<221> NAME/KEY: MISC_FEATURE
<222> LOCATION: (142)..(142)
<223> OTHER INFORMATION: Xaa is glutamine or valine
<220> FEATURE:
<221> NAME/KEY: MISC_FEATURE
<222> LOCATION: (143)..(143)
<223> OTHER INFORMATION: Xaa is histidine, alanine, or tryptophan
<220> FEATURE:
<221> NAME/KEY: MISC_FEATURE
<222> LOCATION: (256)..(256)
<223> OTHER INFORMATION: Xaa is leucine, histidine, glycine, or alanine
<220> FEATURE:
<221> NAME/KEY: MISC_FEATURE
<222> LOCATION: (257)..(257)
<223> OTHER INFORMATION: Xaa is glycine or histidine
<220> FEATURE:
<221> NAME/KEY: MISC_FEATURE
<222> LOCATION: (259)..(259)
<223> OTHER INFORMATION: Xaa is serine, arginine, histidine, or glycine
<220> FEATURE:
```

<220> FEATURE:
<221> NAME/KEY: MISC_FEATURE
<222> LOCATION: (260)..(260)
<223> OTHER INFORMATION: Xaa is lysine, alanine, histidine, tryptophan, or leucine
<220> FEATURE:
<221> NAME/KEY: MISC_FEATURE
<222> LOCATION: (262)..(262)
<223> OTHER INFORMATION: Xaa is arginine or serine

<400> SEQUENCE: 17

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Xaa Xaa Thr Gly Xaa Xaa Xaa Leu Xaa
        35                  40                  45

Xaa Phe Leu Gly Met His Pro Asp Leu Ser Ser Asn Tyr Pro Ser Ser
50                  55                  60

Xaa Xaa Xaa Xaa Ile Xaa Phe Phe Xaa Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Xaa Xaa Xaa Tyr Phe Asp Ser Glu Val
            100                 105                 110

Ala Pro Arg Arg Ala Ala Ala Leu Leu Pro Lys Ala Lys Val Leu Thr
            115                 120                 125

Ile Leu Ile Asn Pro Ala Asp Arg Ala Tyr Xaa Xaa Tyr Xaa Xaa Gln
130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
            195                 200                 205

Arg Thr Glu Pro Ala Lys Val Met Asp Met Val Gln Lys Phe Leu Gly
210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Xaa
            245                 250                 255

Xaa Lys Xaa Xaa Gly Xaa Lys Tyr Pro Glu Met Asp Leu Asp Ser Arg
            260                 265                 270

Ala Phe Leu Lys Asp Tyr Tyr Arg Asp His Asn Ile Glu Leu Ser Lys
            275                 280                 285

Leu Leu Tyr Lys Met Gly Gln Thr Leu Pro Thr Trp Leu Arg Glu Asp
            290                 295                 300

Leu Gln Asn Thr Arg
305
```

<210> SEQ ID NO 18
<211> LENGTH: 309
<212> TYPE: PRT
<213> ORGANISM: Artificial Sequence
<220> FEATURE:
<223> OTHER INFORMATION: Engineered glucosaminyl N-sulfotransferase mutant_sulfotransferase 7

```
<220> FEATURE:
<221> NAME/KEY: MISC_FEATURE
<222> LOCATION: (40)..(40)
<223> OTHER INFORMATION: Xaa is glutamine, serine, or alanine
<220> FEATURE:
<221> NAME/KEY: MISC_FEATURE
<222> LOCATION: (45)..(45)
<223> OTHER INFORMATION: Xaa is tryptophan or phenylalanine
<220> FEATURE:
<221> NAME/KEY: MISC_FEATURE
<222> LOCATION: (46)..(46)
<223> OTHER INFORMATION: Xaa is alanine or leucine
<220> FEATURE:
<221> NAME/KEY: MISC_FEATURE
<222> LOCATION: (48)..(48)
<223> OTHER INFORMATION: Xaa is tyrosine, threonine, or histidine
<220> FEATURE:
<221> NAME/KEY: MISC_FEATURE
<222> LOCATION: (67)..(67)
<223> OTHER INFORMATION: Xaa is histidine or glycine
<220> FEATURE:
<221> NAME/KEY: MISC_FEATURE
<222> LOCATION: (68)..(68)
<223> OTHER INFORMATION: Xaa is glycine, histidine, or serine
<220> FEATURE:
<221> NAME/KEY: MISC_FEATURE
<222> LOCATION: (103)..(103)
<223> OTHER INFORMATION: Xaa is lysine or threonine
<220> FEATURE:
<221> NAME/KEY: MISC_FEATURE
<222> LOCATION: (105)..(105)
<223> OTHER INFORMATION: Xaa is alanine or serine
<220> FEATURE:
<221> NAME/KEY: MISC_FEATURE
<222> LOCATION: (256)..(256)
<223> OTHER INFORMATION: Xaa is leucine, histidine, or alanine
<220> FEATURE:
<221> NAME/KEY: MISC_FEATURE
<222> LOCATION: (257)..(257)
<223> OTHER INFORMATION: Xaa is glycine or histidine
<220> FEATURE:
<221> NAME/KEY: MISC_FEATURE
<222> LOCATION: (259)..(259)
<223> OTHER INFORMATION: Xaa is serine, arginine, or glycine
<220> FEATURE:
<221> NAME/KEY: MISC_FEATURE
<222> LOCATION: (260)..(260)
<223> OTHER INFORMATION: Xaa is histidine, tryptophan, or leucine

<400> SEQUENCE: 18

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
                20                  25                  30

Lys Leu Leu Ile Ile Gly Pro Xaa Lys Thr Gly Ala Xaa Xaa Leu Xaa
            35                  40                  45

His Phe Leu Gly Met His Pro Asp Leu Ser Ser Asn Tyr Pro Ser Ser
        50                  55                  60

Glu Thr Xaa Xaa Ser Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Xaa Ser Xaa Asn Tyr Phe Asp Ser Glu Val
                100                 105                 110

Ala Pro Arg Arg Ala Ala Ala Leu Leu Pro Lys Ala Lys Val Leu Thr
            115                 120                 125

Ile Leu Ile Asn Pro Ala Asp Arg Ala Tyr Ser Trp Tyr Gln His Gln
        130                 135                 140

Arg Ala His Asp Asp Pro Val Ala Leu Lys Tyr Thr Phe His Glu Val
```

```
                145                 150                 155                 160
Ile Thr Ala Gly Ser Asp Ala Ser Ser Lys Leu Arg Ala Leu Gln Asn
            165                 170                 175

Arg Cys Leu Val Pro Gly Trp Tyr Ala Thr His Ile Glu Arg Trp Leu
        180                 185                 190

Ser Ala Tyr His Ala Asn Gln Ile Leu Val Leu Asp Gly Lys Leu Leu
    195                 200                 205

Arg Thr Glu Pro Ala Lys Val Met Asp Met Val Gln Lys Phe Leu Gly
210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Xaa
                245                 250                 255

Xaa Lys Xaa Xaa Gly Arg Lys Tyr Pro Glu Met Asp Leu Asp Ser Arg
            260                 265                 270

Ala Phe Leu Lys Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Asp
    290                 295                 300

Leu Gln Asn Thr Arg
305

<210> SEQ ID NO 19
<211> LENGTH: 309
<212> TYPE: PRT
<213> ORGANISM: Artificial Sequence
<220> FEATURE:
<223> OTHER INFORMATION: Engineered glucosaminyl N-sulfotransferase
      mutant_sulfotransferase 8
<220> FEATURE:
<221> NAME/KEY: MISC_FEATURE
<222> LOCATION: (41)..(41)
<223> OTHER INFORMATION: Xaa is glycine or lysine
<220> FEATURE:
<221> NAME/KEY: MISC_FEATURE
<222> LOCATION: (44)..(44)
<223> OTHER INFORMATION: Xaa is glycine or valine
<220> FEATURE:
<221> NAME/KEY: MISC_FEATURE
<222> LOCATION: (67)..(67)
<223> OTHER INFORMATION: Xaa is glycine or phenylalanine
<220> FEATURE:
<221> NAME/KEY: MISC_FEATURE
<222> LOCATION: (68)..(68)
<223> OTHER INFORMATION: Xaa is glutamic acid, leucine, or asparagine
<220> FEATURE:
<221> NAME/KEY: MISC_FEATURE
<222> LOCATION: (69)..(69)
<223> OTHER INFORMATION: Xaa is glutamic acid, serine, or histidine
<220> FEATURE:
<221> NAME/KEY: MISC_FEATURE
<222> LOCATION: (71)..(71)
<223> OTHER INFORMATION: Xaa is glutamine or glycine
<220> FEATURE:
<221> NAME/KEY: MISC_FEATURE
<222> LOCATION: (74)..(74)
<223> OTHER INFORMATION: Xaa is asparagine or glycine
<220> FEATURE:
<221> NAME/KEY: MISC_FEATURE
<222> LOCATION: (103)..(103)
<223> OTHER INFORMATION: Xaa is lysine or histidine
<220> FEATURE:
<221> NAME/KEY: MISC_FEATURE
<222> LOCATION: (105)..(105)
<223> OTHER INFORMATION: Xaa is alanine or glycine
<220> FEATURE:
<221> NAME/KEY: MISC_FEATURE
<222> LOCATION: (106)..(106)
```

```
<223> OTHER INFORMATION: Xaa is asparagine or tryptophan
<220> FEATURE:
<221> NAME/KEY: MISC_FEATURE
<222> LOCATION: (139)..(139)
<223> OTHER INFORMATION: Xaa is serine or arginine
<220> FEATURE:
<221> NAME/KEY: MISC_FEATURE
<222> LOCATION: (140)..(140)
<223> OTHER INFORMATION: Xaa is tryptophan or alanine
<220> FEATURE:
<221> NAME/KEY: MISC_FEATURE
<222> LOCATION: (142)..(142)
<223> OTHER INFORMATION: Xaa is glutamine or valine
<220> FEATURE:
<221> NAME/KEY: MISC_FEATURE
<222> LOCATION: (143)..(143)
<223> OTHER INFORMATION: Xaa is histidine, alanine, or tryptophan
<220> FEATURE:
<221> NAME/KEY: MISC_FEATURE
<222> LOCATION: (256)..(256)
<223> OTHER INFORMATION: Xaa is leucine or glycine
<220> FEATURE:
<221> NAME/KEY: MISC_FEATURE
<222> LOCATION: (259)..(259)
<223> OTHER INFORMATION: Xaa is serine or histidine
<220> FEATURE:
<221> NAME/KEY: MISC_FEATURE
<222> LOCATION: (260)..(260)
<223> OTHER INFORMATION: Xaa is leucine or valine
<220> FEATURE:
<221> NAME/KEY: MISC_FEATURE
<222> LOCATION: (262)..(262)
<223> OTHER INFORMATION: Xaa is arginine or serine

<400> SEQUENCE: 19

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His Xaa Thr Gly Xaa His Ala Leu Tyr
        35                  40                  45

Leu Phe Leu Gly Met His Pro Asp Leu Ser Ser Asn Tyr Pro Ser Ser
    50                  55                  60

Glu Thr Xaa Xaa Xaa Ile Xaa Phe Phe Xaa Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Xaa Ser Xaa Xaa Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Xaa Xaa Tyr Xaa Xaa Gln
    130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205

Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
```

```
                225                 230                 235                 240
        Lys Gly Phe Trp Cys Gln Leu Leu Glu Gly Gly Lys Thr Lys Cys Xaa
                            245                 250                 255

Gly Lys Xaa Xaa Gly Xaa Lys Tyr Pro Glu Met Asp Leu Asp Ser Arg
                        260                 265                 270

Ala Phe Leu Lys Asp Tyr Tyr Arg Asp His Asn Ile Glu Leu Ser Lys
                        275                 280                 285

Leu Leu Tyr Lys Met Gly Gln Thr Leu Pro Thr Trp Leu Arg Glu Asp
                        290                 295                 300

Leu Gln Asn Thr Arg
        305

<210> SEQ ID NO 20
<211> LENGTH: 309
<212> TYPE: PRT
<213> ORGANISM: Artificial Sequence
<220> FEATURE:
<223> OTHER INFORMATION: Engineered glucosaminyl N-sulfotransferase
      mutant_sulfotransferase 9

<400> SEQUENCE: 20

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
                20                  25                  30

Lys Leu Leu Ile Ile Gly Pro Gln Lys Thr Gly Ala Trp Ala Leu Tyr
            35                  40                  45

His Phe Leu Gly Leu His Pro Asp Leu Ser Ser Asn Tyr Pro Ser Ser
        50                  55                  60

Glu Thr His Gly Ser Ile Gln Phe Phe Asn Gly His Asn Tyr His Lys
65                  70                  75                  80

Gly Ile Asp Trp Tyr Met Asp Phe Phe Pro Ile Pro Ser Asn Thr Thr
                85                  90                  95

Ser Asp Phe Tyr Phe Glu Lys Ser Ala Asn Tyr Phe Asp Ser Asp Val
                100                 105                 110

Ala Pro Arg Arg Ala Ala Ala Leu Leu Pro Lys Ala Lys Val Leu Thr
            115                 120                 125

Ile Leu Ile Asn Pro Ala Asp Arg Ala Tyr Ser Trp Tyr Gln His Gln
        130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
                180                 185                 190

Gly Ala Phe His Ala Asn Gln Ile Leu Val Leu Asp Gly Lys Leu Leu
            195                 200                 205

Arg Thr Glu Pro Ala Arg Val Met Asp Thr Val Gln Lys Phe Leu Gly
        210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Arg Ser His Gly Arg Lys Tyr Pro Asp Met Asp Pro Asp Ser Arg
                260                 265                 270
```

Ala Phe Leu Arg Asp Tyr Tyr Arg Asp His Asn Ile Glu Leu Ser Lys
275 280 285

Leu Leu Tyr Lys Met Gly Gln Thr Leu Pro Thr Trp Leu Arg Glu Glu
290 295 300

Leu Gln Asn Thr Arg
305

<210> SEQ ID NO 21
<211> LENGTH: 309
<212> TYPE: PRT
<213> ORGANISM: Artificial Sequence
<220> FEATURE:
<223> OTHER INFORMATION: Engineered glucosaminyl N-sulfotransferase
      mutant_sulfotransferase 10

<400> SEQUENCE: 21

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Ser Lys Thr Gly Ala Phe Leu Leu Thr
        35                  40                  45

His Phe Leu Gly Leu His Pro Asp Leu Ser Ser Asn Tyr Pro Ser Ser
    50                  55                  60

Glu Thr Gly His Ser Ile Gln Phe Phe Asn Gly His Asn Tyr His Lys
65                  70                  75                  80

Gly Ile Asp Trp Tyr Met Asp Phe Phe Pro Ile Pro Ser Asn Thr Thr
                85                  90                  95

Ser Asp Phe Tyr Phe Glu Thr Ser Ser Asn Tyr Phe Asp Ser Asp Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
            180                 185                 190

Gly Ala Phe His Ala Asn Gln Ile Leu Val Leu Asp Gly Lys Leu Leu
        195                 200                 205

Arg Thr Glu Pro Ala Arg Val Met Asp Thr Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys His
                245                 250                 255

Gly Arg Arg Trp Gly Arg Lys Tyr Pro Asp Met Asp Pro Asp Ser Arg
            260                 265                 270

Ala Phe Leu Arg Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Glu
    290                 295                 300

Leu Gln Asn Thr Arg
305

<210> SEQ ID NO 22
<211> LENGTH: 309
<212> TYPE: PRT
<213> ORGANISM: Artificial Sequence
<220> FEATURE:
<223> OTHER INFORMATION: Engineered glucosaminyl N-sulfotransferase mutant_sulfotransferase 11

<400> SEQUENCE: 22

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His His Thr Gly Gly His Ala Leu Tyr
        35                  40                  45

Leu Phe Leu Gly Leu His Pro Asp Leu Ser Ser Asn Tyr Pro Ser Ser
    50                  55                  60

Glu Thr Gly Glu Glu Ile Gln Phe Phe Asn Gly His Asn Tyr His Lys
65                  70                  75                  80

Gly Ile Asp Trp Tyr Met Asp Phe Phe Pro Ile Pro Ser Asn Thr Thr
                85                  90                  95

Ser Asp Phe Tyr Phe Glu Lys Ser Ala Asn Tyr Phe Asp Ser Asp Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln Ala Gln
    130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
            180                 185                 190

Gly Ala Phe His Ala Asn Gln Ile Leu Val Leu Asp Gly Lys Leu Leu
        195                 200                 205

Arg Thr Glu Pro Ala Arg Val Met Asp Thr Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Gly
                245                 250                 255

Gly Arg His Leu Gly Arg Lys Tyr Pro Asp Met Asp Pro Asp Ser Arg
            260                 265                 270

Ala Phe Leu Arg Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Glu
    290                 295                 300

Leu Gln Asn Thr Arg
305
```

<210> SEQ ID NO 23
<211> LENGTH: 309
<212> TYPE: PRT
<213> ORGANISM: Artificial Sequence
<220> FEATURE:
<223> OTHER INFORMATION: Engineered glucosaminyl N-sulfotransferase mutant_sulfotransferase 12

<400> SEQUENCE: 23

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His Gly Thr Gly Gly His Ala Leu Tyr
        35                  40                  45

Leu Phe Leu Gly Leu His Pro Asp Leu Ser Ser Asn Tyr Pro Ser Ser
    50                  55                  60

Glu Thr Phe Leu Ser Ile Gln Phe Phe Asn Gly His Asn Tyr His Lys
65                  70                  75                  80

Gly Ile Asp Trp Tyr Met Asp Phe Phe Pro Ile Pro Ser Asn Thr Thr
                85                  90                  95

Ser Asp Phe Tyr Phe Glu His Ser Gly Asn Tyr Phe Asp Ser Asp Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Arg Ala Tyr Val Trp Gln
    130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
            180                 185                 190

Gly Ala Phe His Ala Asn Gln Ile Leu Val Leu Asp Gly Lys Leu Leu
        195                 200                 205

Arg Thr Glu Pro Ala Arg Val Met Asp Thr Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Arg Ser Leu Gly Ser Lys Tyr Pro Asp Met Asp Pro Asp Ser Arg
            260                 265                 270

Ala Phe Leu Arg Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Glu
    290                 295                 300

Leu Gln Asn Thr Arg
305

<210> SEQ ID NO 24
<211> LENGTH: 309
<212> TYPE: PRT
<213> ORGANISM: Artificial Sequence
<220> FEATURE:
<223> OTHER INFORMATION: Engineered glucosaminyl N-sulfotransferase
      mutant_sulfotransferase 13

<400> SEQUENCE: 24

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro

```
            20                  25                  30
Lys Leu Leu Ile Ile Gly Pro His Lys Thr Gly Val His Ala Leu Tyr
            35                  40                  45

Leu Phe Leu Gly Leu His Pro Asp Leu Ser Ser Asn Tyr Pro Ser Ser
            50                  55                  60

Glu Thr Gly Asn His Ile Gly Phe Phe Gly His Asn Tyr His Lys
65                  70                  75                  80

Gly Ile Asp Trp Tyr Met Asp Phe Phe Pro Ile Pro Ser Asn Thr Thr
                    85                  90                  95

Ser Asp Phe Tyr Phe Glu Lys Ser Ala Trp Tyr Phe Asp Ser Asp Val
                    100                 105                 110

Ala Pro Arg Arg Ala Ala Leu Leu Pro Lys Ala Lys Val Leu Thr
                115                 120                 125

Ile Leu Ile Asn Pro Ala Asp Arg Ala Tyr Ser Trp Tyr Gln His Gln
            130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
                180                 185                 190

Gly Ala Phe His Ala Asn Gln Ile Leu Val Leu Asp Gly Lys Leu Leu
                195                 200                 205

Arg Thr Glu Pro Ala Arg Val Met Asp Thr Val Gln Lys Phe Leu Gly
                210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Lys Thr Lys Cys Leu
                245                 250                 255

Gly Arg Ser Val Gly Arg Lys Tyr Pro Asp Met Asp Pro Asp Ser Arg
                260                 265                 270

Ala Phe Leu Arg Asp Tyr Tyr Arg Asp His Asn Ile Glu Leu Ser Lys
                275                 280                 285

Leu Leu Tyr Lys Met Gly Gln Thr Leu Pro Thr Trp Leu Arg Glu Glu
            290                 295                 300

Leu Gln Asn Thr Arg
305

<210> SEQ ID NO 25
<211> LENGTH: 309
<212> TYPE: PRT
<213> ORGANISM: Artificial Sequence
<220> FEATURE:
<223> OTHER INFORMATION: Engineered glucosaminyl N-sulfotransferase
      mutant_sulfotransferase 14

<400> SEQUENCE: 25

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Ala Lys Thr Gly Ala Trp Leu Leu His
            35                  40                  45

His Phe Leu Gly Leu His Pro Asp Leu Ser Ser Asn Tyr Pro Ser Ser
            50                  55                  60
```

Glu Thr His Ser Ser Ile Gln Phe Phe Asn Gly His Asn Tyr His Lys
65                  70                  75                  80

Gly Ile Asp Trp Tyr Met Asp Phe Phe Pro Ile Pro Ser Asn Thr Thr
            85                  90                  95

Ser Asp Phe Tyr Phe Glu Thr Ser Ala Asn Tyr Phe Asp Ser Asp Val
            100                 105                 110

Ala Pro Arg Arg Ala Ala Ala Leu Leu Pro Lys Ala Lys Val Leu Thr
            115                 120                 125

Ile Leu Ile Asn Pro Ala Asp Arg Ala Tyr Ser Trp Tyr Gln His Gln
            130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
            165                 170                 175

Arg Cys Leu Val Pro Gly Trp Tyr Ala Thr His Leu Glu Arg Trp Leu
            180                 185                 190

Gly Ala Phe His Ala Asn Gln Ile Leu Val Leu Asp Gly Lys Leu Leu
            195                 200                 205

Arg Thr Glu Pro Ala Arg Val Met Asp Thr Val Gln Lys Phe Leu Gly
210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Ala
            245                 250                 255

His Arg Gly Leu Gly Arg Lys Tyr Pro Asp Met Asp Pro Asp Ser Arg
            260                 265                 270

Ala Phe Leu Arg Asp Tyr Tyr Arg Asp His Asn Ile Glu Leu Ser Lys
            275                 280                 285

Leu Leu Tyr Lys Met Gly Gln Thr Leu Pro Thr Trp Leu Arg Glu Glu
            290                 295                 300

Leu Gln Asn Thr Arg
305

<210> SEQ ID NO 26
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 1

<400> SEQUENCE: 26
atggatgagg aagacgacgt cgtgattatt tataaccatg tacataagac tgccagccat      60
tcattcacga atatcgcgta cgatctttgc gctaaaaacc gttatcatgt tttacatatt     120
aataccacca aaaacaatcc ggtgatgtca ttgcaggatc aggtgcgttt cgtaaagaat     180
gtcacctcat ggaaagagat gaagccaggg ttttatcatg gcacgttag ttatttggat      240 tttgctaagt ttggtgtaaa aagaagcc atctacatca atgtcattcg tgatcccatt       300
gaacgcttgg tctcctatta ctactttttg cgctttggcg acgactaccg ccccggatta    360
cgccgccgca agcaggggga caagaaaact tttgacgaat gcgtcgctgc cggtggtagc    420
gactgcgccc cggagaaatt atggcttcaa attccctttt tctgcggcca ttcttcggaa    480
tgctggaacg taggtagtcg ctgggctctt gaacaggcaa aatataatct tatcaacgaa    540
tactttcttg tcggagttac cgaggagttg gaggacttta ttatgcttct ggaggctgcg    600

```
ctgccgcgtt ttttcgtgg tgcgaccgag ctgtatcgta caggtaaaaa aagtcatctt    660
cgtaaaacga cggaaaagaa gctgccaact aaggaaacaa tcgcgaaact gcaacagagt    720
gaaatctgga aaatggaaaa tgaattctat gagtttgccc tggagcaatt ccaattcgtt    780
cgcgcccatg ccgtacgtga aggacggc gaattatata tccttgcaca aaacttcttc    840
tatgagaaga tctatcctaa gtctaactaa                                    870
```

<210> SEQ ID NO 27
<211> LENGTH: 289
<212> TYPE: PRT
<213> ORGANISM: Artificial Sequence
<220> FEATURE:
<223> OTHER INFORMATION: Engineered hexuronyl 2-O sulfotransferase mutant_sulfat
<211> LENGTH: 870
<212> TYPE: DNA
<213> ORGANISM: Artificial Sequence
<220> FEATURE:
<223> OTHER INFORMATION: Polynucleotide sequence encoding for engineered hexuronyl 2-O sulfotransferase mutant_sulfatase 2

<400> SEQUENCE: 28

```
atggatgagg aagacgacgt cgtgattatt tataaccgtg taccgaccac tgcccatacg    60
tcattcacga atatcgcgta cgatctttgc gctaaaaacc gttatcatgt tttacatatt   120
aataccacca aaaacaatcc ggtgatgtca ttgcaggatc aggtgcgttt cgtaaagaat   180
gtcacctcat ggaaagagat gaagccaggg ttttatcatg ggcacgttag ttatttggat   240
tttgctaagt ttggtgtaaa gaagaagccc atctacatca atgtcattcg tgatcccatt   300
gaacgcttgg tctcctatta ctaccatttg cgctttggcg acgactaccg ccccggatta   360
cgccgccgca agcaggggga caagaaaact tttgacgaat gcgtcgctgc cggtggtagc   420
gactgcgccc cggagaaatt atggcttcaa attccctttt tctgcggcca ttcttcggaa   480
tgctggaacg taggtagtcg ctgggctctt gaacaggcaa atataatct tatcaacgaa   540
tactttcttg tcggagttac cgaggagttg gaggacttta ttatgcttct ggaggctgcg   600
ctgccgcgtt ttttcgtgg tgcgaccgag ctgtatcgta caggtaaaaa aagtcatctt   660
cgtaaaacga cggaaaagaa gctgccaact aaggaaacaa tcgcgaaact gcaacgagt   720
gaaatctgga aatggaaaa tgaattctat gagtttgccc tggagcaatt ccaattcgtt   780
cgcgcccatg ccgtacgtga aaggacggc gaattatata tccttgcaca aaacttcttc   840
tatgagaaga tctatcctaa gtctaactaa                                    870
```

<210> SEQ ID NO 29
<211> LENGTH: 289
<212> TYPE: PRT
<213> ORGANISM: Artificial Sequence
<220> FEATURE:
<223> OTHER INFORMATION: Engineered hexuronyl 2-O sulfotransferase mutant_sulfatase 2

<400> SEQUENCE: 29

```
Met Asp Glu Glu Asp Asp Val Val Ile Ile Tyr Asn Arg Val Pro Thr
  1               5                  10                  15
Thr Ala His Thr Ser Phe Thr Asn Ile Ala Tyr Asp Leu Cys Ala Lys
             20                  25                  30
Asn Arg Tyr His Val Leu His Ile Asn Thr Thr Lys Asn Asn Pro Val
         35                  40                  45
Met Ser Leu Gln Asp Gln Val Arg Phe Val Lys Asn Val

```
Cys Trp Asn Val Gly Ser Arg Trp Ala Leu Glu Gln Ala Lys Tyr Asn
            165                 170                 175

Leu Ile Asn Glu Tyr Phe Leu Val Gly Val Thr Glu Leu Glu Asp
        180                 185                 190

Phe Ile Met Leu Leu Glu Ala Ala Leu Pro Arg Phe Phe Arg Gly Ala
        195                 200                 205

Thr Glu Leu Tyr Arg Thr Gly Lys Lys Ser His Leu Arg Lys Thr Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270

Tyr Ile Leu Ala Gln Asn Phe Phe Tyr Glu Lys Ile Tyr Pro Lys Ser
        275                 280                 285

Asn

<210> SEQ ID NO 30
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 3

<400> SEQUENCE: 30
atggatgagg aagacgacgt cgtgattatt tataaccgtg tacataccac tgccagcacg      60
tcattcacga atatcgcgta cgatctttgc gctaaaaacc gttatcatgt tttacatatt     120
aataccacca aaaacaatcc ggtgatgtca ttgcaggatc aggtgcgttt cgtaaagaat     180
gtcacctcat ggaaagagat gaagccaggg ttttatcatg ggcacgttag ttatttggat     240
tttgctaagt ttggtgtaaa gaagaagccc atctacatca atgtcattcg tgatcccatt     300
gaacgcttgg tctcctatta ctacttttg cgctttggcg acgactaccg ccccggatta     360
cgccgccgca agcaggggga caagaaaact tttgacgaat gcgtcgctgc cggtggtagc     420
gactgcgccc cggagaaatt atggcttcaa attcccttt tctgcggcca ttcttcggaa     480
tgctggaacg taggtagtcg ctgggctctt gaacaggcaa aatataatct tatcaacgaa     540
tactttcttg tcggagttac cgaggagttg gaggacttta ttatgcttct ggaggctgcg     600
ctgccgcgtt ttttcgtgg tgcgaccgag ctgtatcgta caggtaaaaa aagtcatctt     660
cgtaaaacga cggaaaagaa gctgccaact aaggaaacaa tcgcgaaact gcaacagagt     720
gaaatctgga aaatggaaaa tgaattctat gagtttgccc tggagcaatt ccaattcgtt     780
cgcgcccatg ccgtacgtga aaggacggc gaattatata tccttgcaca aaacttcttc     840
tatgagaaga tctatcctaa gtctaactaa                                      870

<210> SEQ ID NO 31
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 3

<400> SEQUENCE: 31
```

```
Met Asp Glu Glu Asp Val Val Ile Ile Tyr Asn Arg Val His Thr
1               5                   10                  15

Thr Ala Ser Thr Ser Phe Thr Asn Ile Ala Tyr Asp Leu Cys Ala Lys
            20                  25                  30

Asn Arg Tyr His Val Leu His Ile Asn Thr Thr Lys Asn Asn Pro Val
                35                  40                  45

Met Ser Leu Gln Asp Gln Val Arg Phe Val Lys Asn Val Thr Ser Trp
50                  55                  60

Lys Glu Met Lys Pro Gly Phe Tyr His Gly Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Phe Leu Arg Phe
                100                 105                 110

Gly Asp Tyr Arg Pro Gly Leu Arg Arg Lys Gln Gly Asp Lys
                115                 120                 125

Lys Thr Phe Asp Glu Cys Val Ala Ala Gly Ser Asp Cys Ala Pro
130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
                180                 185                 190

Phe Ile Met Leu Leu Glu Ala Ala Leu Pro Arg Phe Phe Arg Gly Ala
                195                 200                 205

Thr Glu Leu Tyr Arg Thr Gly Lys Lys Ser His Leu Arg Lys Thr Thr
210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
                260                 265                 270

Tyr Ile Leu Ala Gln Asn Phe Phe Tyr Glu Lys Ile Tyr Pro Lys Ser
                275                 280                 285

Asn
```

<210> SEQ ID NO 32
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 4

<400> SEQUENCE: 32

```
atggatgagg aagacgacgt cgtgattatt tataaccgtg taccgaccac tgcccataac      60
tcattcacga atatcgcgta cgatctttgc gctaaaaacc gttatcatgt tttacatatt     120
aataccacca aaaacaatcc ggtgatgtca ttgcaggatc aggtgcgttt cgtaaagaat     180
gtcacctcat ggaaagagat gaagccaggg ttttatcatg gcacgttag ttatttggat     240 tttgctaagt ttggtgtaaa gaagaagccc atctacatca atgtcattcg tgatcccatt     300
gaacgcttgg tctcctatta ctaccatttg cgctttggcg acgactaccg ccccggatta     360
```

-continued

```
cgccgccgca agcagggga caagaaaact tttgacgaat gcgtcgctgc cggtggtagc    420
gactgcgccc cggagaaatt atggcttcaa attccctttt tctgcggcca ttcttcggaa    480
tgctggaacg taggtagtcg ctgggctctt gaacaggcaa atataatct tatcaacgaa     540 tactttcttg tcggagttac cgaggagttg gaggacttta ttatgcttct ggaggctgcg    600
ctgccgcgtt ttttcgtgg tgcgaccgag ctgtatcgta caggtaaaaa aagtcatctt     660
cgtaaaacga cggaaaagaa gctgccaact aaggaaacaa tcgcgaaact gcaacagagt    720
gaaatctgga aaatggaaaa tgaattctat gagtttgccc tggagcaatt ccaattcgtt    780
cgcgcccatg ccgtacgtga aaggacggc gaattatata tccttgcaca aacttcttc     840 tatgagaaga tctatcctaa gtctaactaa                                     870
```

<210> SEQ ID NO 33
<211> LENGTH: 289
<212> TYPE: PRT
<213> ORGANISM: Artificial Sequence
<220> FEATURE:
<223> OTHER INFORMATION: Engineered hexuronyl 2-O sulfotransferase mutant_sulfatase 4

<400> SEQUENCE: 33

```
Met Asp Glu Glu Asp Asp Val Val Ile Ile Tyr Asn Arg Val Pro Thr
1               5                   10                  15

Thr Ala His Asn Ser Phe Thr Asn Ile Ala Tyr Asp Leu Cys Ala Lys
            20                  25                  30

Asn Arg Tyr His Val Leu His Ile Asn Thr Thr Lys Asn Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly His Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr His Leu Arg Phe
            100                 105                 110

Gly Asp Asp Tyr Arg Pro Gly Leu Arg Arg Lys Gln Gly Asp Lys
        115                 120                 125

Lys Thr Phe Asp Glu Cys Val Ala Ala Gly Gly Ser Asp Cys Ala Pro
130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
        195                 200                 205

Thr Glu Leu Tyr Arg Thr Gly Lys Lys Ser His Leu Arg Lys Thr Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270
```

Tyr Ile Leu Ala Gln Asn Phe Phe Tyr Glu Lys Ile Tyr Pro Lys Ser
            275                 280                 285

Asn

<210> SEQ ID NO 34
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 5

<400> SEQUENCE: 34
atggatgagg aagacgacgt cgtgattatt tataaccgtg taccgaacac tgccagcacg      60
tcattcacga atatcgcgta cgatctttgc gctaaaaacc gttatcatgt tttacatatt     120
aataccacca aaaacaatcc ggtgatgtca ttgcaggatc aggtgcgttt cgtaaagaat     180
gtcacctcat ggaaagagat gaagccaggg ttttatcatg gcacgttag ttatttggat      240 tttgctaagt ttggtgtaaa gaagaagccc atctacatca atgtcattcg tgatcccatt     300
gaacgcttgg tccattatta ctaccatttg cgctttggcg acgactaccg ccccggatta    360
cgccgccgca agcaggggga caagaaaact tttgacgaat gcgtcgctgc cggtggtagc    420
gactgcgccc cggagaaatt atggcttcaa attcccttt tctgcggcca ttcttcggaa     480
tgctggaacg taggtagtcg ctgggctctt gaacaggcaa aatataatct tatcaacgaa    540
tactttcttg tcggagttac cgaggagttg gaggacttta ttatgcttct ggaggctgcg    600
ctgccgcgtt ttttcgtgg tgcgaccgag ctgtatcgta caggtaaaaa aagtcatctt     660
cgtaaaacga cggaaaagaa gctgccaact aaggaaacaa tcgcgaaact gcaacagagt    720
gaaatctgga aaatggaaaa tgaattctat gagtttgccc tggagcaatt ccaattcgtt    780
cgcgcccatg ccgtacgtga aaggacggc gaattatata tccttgcaca aaacttcttc     840
tatgagaaga tctatcctaa gtctaactaa                                     870

<210> SEQ ID NO 35
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 5

<400> SEQUENCE: 35

Met Asp Glu Glu Asp Asp Val Val Ile Ile Tyr Asn Arg Val Pro Asn
1               5                   10                  15

Thr Ala Ser Thr Ser Phe Thr Asn Ile Ala Tyr Asp Leu Cys Ala Lys
            20                  25                  30

Asn Arg Tyr His Val Leu His Ile Asn Thr Thr Lys Asn Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly His Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val His Tyr Tyr His Leu Arg Phe
            100                 105                 110

```
Gly Asp Asp Tyr Arg Pro Gly Leu Arg Arg Arg Lys Gln Gly Asp Lys
            115                 120                 125
Lys Thr Phe Asp Glu Cys Val Ala Ala Gly Gly Ser Asp Cys Ala Pro
    130                 135                 140
Glu Lys Leu Trp Leu Gln Ile Pro Phe Phe Cys Gly His Ser Ser Glu
145                 150                 155                 160
Cys Trp Asn Val Gly Ser Arg Trp Ala Leu Glu Gln Ala Lys Tyr Asn
                165                 170                 175
Leu Ile Asn Glu Tyr Phe Leu Val Gly Val Thr Glu Glu Leu Glu Asp
            180                 185                 190
Phe Ile Met Leu Leu Glu Ala Ala Leu Pro Arg Phe Phe Arg Gly Ala
        195                 200                 205
Thr Glu Leu Tyr Arg Thr Gly Lys Lys Ser His Leu Arg Lys Thr Thr
    210                 215                 220
Glu Lys Lys Leu Pro Thr Lys Glu Thr Ile Ala Lys Leu Gln Gln Ser
225                 230                 235                 240
Glu Ile Trp Lys Met Glu Asn Glu Phe Tyr Glu Phe Ala Leu Glu Gln
                245                 250                 255
Phe Gln Phe Val Arg Ala His Ala Val Arg Glu Lys Asp Gly Glu Leu
            260                 265                 270
Tyr Ile Leu Ala Gln Asn Phe Phe Tyr Glu Lys Ile Tyr Pro Lys Ser
        275                 280                 285
Asn

<210> SEQ ID NO 36
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 6

<400> SEQUENCE: 36
atggatgagg aagacgacgt cgtaatcatc tacaaccgcg tcccgcacac agccagccac      60
tccttcacca atattgcgta tgatctgtgc gctaagaacc gttaccatgt gttgcacatt     120
accactacga agcgtaaccc cgtaatgtca cttcaagatc aagttcgctt cgttaagaac     180
gtgcatctt ggaaggagat gaagccagga ttctatcatg gggaagttag ctacttggac      240
tttgccaagt tcggtgtaaa gaaaaaacca atctacatca atgttattcg tgatcccatc     300
gaacgcttag tgtcttacta ttatgcccct cgctttggag cgaccgtcg cccgggcttt      360
cgtatgcgca agcaaggga caagaagacc ttcgacagt gtgtagccgc gggtgggtct      420
gactgtgcgc cggaaaagtt atggttacaa attccatttt tctgtggtca ctcgtcagag     480
tgctggaatg ttggttcgcg ctgggcgctg gagcaagcga atataacttt gattaatgaa     540
tactttttag tagggtgac agaggagttg gaggactta ttatgcttct tgaggctgcg      600
ttacctcgct ttttccgcgg tgcgactgag ttgtatcgta ccggtaaaaa atctcatctg     660
cataaaacaa ctgaaaagaa gctgccaacg aaagagacga ttgctaaact tcagcagagt     720
gagatctgga aaatggaaaa tgagttctac gagtttgcct tggagcaatt ccaattcgtg     780
cgtgcccatg ccgttcgtga aaaggatggt gaattataca tcttggcaca gaatttcttc     840
tatgagaaaa tttatcctaa gtctaactaa                                      870

<210> SEQ ID NO 37
<211> LENGTH: 289
```

```
<212> TYPE: PRT
<213> ORGANISM: Artificial Sequence
<220> FEATURE:
<223> OTHER INFORMATION: Engineered hexuronyl 2-O sulfotransferase
      mutant_sulfatase 6

<400> SEQUENCE: 37
```

Met Asp Glu Glu Asp Asp Val Val Ile Ile Tyr Asn Arg Val Pro His
1               5                   10                  15

Thr Ala Ser His Ser Phe Thr Asn Ile Ala Tyr Asp Leu Cys Ala Lys
            20                  25                  30

Asn Arg Tyr His Val Leu His Ile Thr Thr Thr Lys Arg Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Ala Leu Arg Phe
                100                 105                 110

Gly Gly Asp Arg Arg Pro Gly Leu Arg Met Arg Lys Gln Gly Asp Lys
            115                 120                 125

Lys Thr Phe Asp Glu Cys Val Ala Ala Gly Ser Asp Cys Ala Pro
130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
        195                 200                 205

Thr Glu Leu Tyr Arg Thr Gly Lys Lys Ser His Leu His Lys Thr Thr
210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270

Tyr Ile Leu Ala Gln Asn Phe Phe Tyr Glu Lys Ile Tyr Pro Lys Ser
        275                 280                 285

Asn

```
<210> SEQ ID NO 38
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 7

<400> SEQUENCE: 38
atggatgagg aagacgacgt cgtaatcatc tacaaccgcg tcccgcacac agccgagcac    60
tccttcacca atattgcgta tgatctgtgc gctaagaacc gttaccatgt gttgcacatt   120
```

```
accactacga agcgtaaccc cgtaatgtca cttcaagatc aagttcgctt cgttaagaac    180
gtgacatctt ggaaggagat gaagccagga ttctatcatg gggaagttag ctacttggac    240
tttgccaagt tcggtgtaaa gaaaaaacca atctacatca atgttattcg tgatcccatc    300
gaacgcttag tgtcttacta ttatgccctt cgctttggag cgaccgtcg cccggggctt     360 cgtatgcgca agcaagggga caagaagacc ttcgacgagt gtgtagccgc gggtgggtct    420
gactgtgcgc cggaaaagtt atggttacaa attccatttt tctgtggtca ctcgtcagag    480
tgctggaatg ttggttcgcg ctgggcgctg gagcaagcga atataacttg gattaatgaa    540 tacttttag taggggtgac agaggagttg gaggacttta ttatgcttct tgaggctgcg     600
ttacctcgct ttttccgcgg tgcgactgag ttgtatcgta ccggtaaaaa atctcatctg    660
cataaaacaa ctgaaaagaa gctgccaacg aaagagacga ttgctaaact tcagcagagt    720
gagatctgga aaatggaaaa tgagttctac gagtttgcct tggagcaatt ccaattcgtg    780
cgtgcccatg ccgttcgtga aaaggatggt gaattataca tcttggcaca gaatttcttc    840
tatgagaaaa tttatcctaa gtctaactaa                                     870
```

<210> SEQ ID NO 39
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 7

<400> SEQUENCE: 39

```
Met Asp Glu Glu Asp Asp Val Val Ile Ile Tyr Asn Arg Val Pro His
1               5                   10                  15

Thr Ala Glu His Ser Phe Thr Asn Ile Ala Tyr Asp Leu Cys Ala Lys
            20                  25                  30

Asn Arg Tyr His Val Leu His Ile Thr Thr Thr Lys Arg Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly Glu Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Ala Leu Arg Phe
                100                 105                 110

Gly Gly Asp Arg Arg Pro Gly Leu Arg Met Arg Lys Gln Gly Asp Lys
            115                 120                 125

Lys Thr Phe Asp Glu Cys Val Ala Ala Gly Ser Asp Cys Ala Pro
    130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
        195                 200                 205

Thr Glu Leu Tyr Arg Thr Gly Lys Lys Ser His Leu His Lys Thr Thr
    210                 215                 220
```

```
Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
            245                 250                 255

Phe Gln Phe Val Arg Ala His Ala Val Arg Glu Lys Asp Gly Glu Leu
        260                 265                 270

Tyr Ile Leu Ala Gln Asn Phe Phe Tyr Glu Lys Ile Tyr Pro Lys Ser
    275                 280                 285

Asn

<210> SEQ ID NO 40
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 8

<400> SEQUENCE: 40
atggatgagg aagacgacgt cgtgatcatc tacaaccgtg ttcctcacac ggcttcgcac      60
tctttcacga atatcgctta cgacttatgt gccaagaatc gttatcatgt gttacacatc    120
actaccacca aaaacaaccc cgtcatgtcg ttacaggacc aagtgcgttt cgtgaaaaac    180
gttacatcct ggaaggagat gaaacccggt ttctatcatg gaatggtctc ttacctggat    240
tttgctaaat tggtgtgaa aaaaaaaccc atttatatta acgtcatccg cgatccaatc     300
gagcgtttgg tttcttatta ttatgcctta cgtttcggga gtgatcgccg tcccggattg    360
cgtatgcgta acagggaga caagaaaact ttcgatgaat gtgttgccgc cggaggttcc     420
gactgtgcac cggaaaaact gtggcttcag atccctttct tttgtggtca cagttcagaa    480
tgttggaacg tcgggtcacg ttgggcgctt gaacaggcca agtacaatct tatcaacgag    540 tatttctgg taggggtgac tgaagagctg gaggacttta ttatgcttct tgaagcggca     600
ttgccacgct ttttcgtgg cgcgactgaa ttatatcgta caggaaagaa atcgcacttg     660
cacaagacta cagaaaaaaa actgcctact aaggagacga ttgctaagtt gcaacaatca    720
gaaatttgga agatggaaaa cgaattctac gagttcgcat tagaacagtt tcaattcgta    780
cgcgctcacg ctgtgcgtga aaagacggg gaactgtaca ttttggccca aaatttttc     840 tatgagaaaa tttatcctaa gtctaactaa                                     870

<210> SEQ ID NO 41
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 8

<400> SEQUENCE: 41

Met Asp Glu Glu Asp Asp Val Val Ile Ile Tyr Asn Arg Val Pro His
1               5                   10                  15

Thr Ala Ser His Ser Phe Thr Asn Ile Ala Tyr Asp Leu Cys

```
                65                  70                  75                  80
Phe Ala Lys Phe Gly Val Lys Lys Pro Ile Tyr Ile Asn Val Ile
                    85                  90                  95

Arg Asp Pro Ile Glu Arg Leu Val Ser Tyr Tyr Ala Leu Arg Phe
                    100                 105                 110

Gly Ser Asp Arg Arg Pro Gly Leu Arg Met Arg Lys Gln Gly Asp Lys
                    115                 120                 125

Lys Thr Phe Asp Glu Cys Val Ala Ala Gly Ser Asp Cys Ala Pro
    130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
                180                 185                 190

Phe Ile Met Leu Leu Glu Ala Ala Leu Pro Arg Phe Phe Arg Gly Ala
                195                 200                 205

Thr Glu Leu Tyr Arg Thr Gly Lys Lys Ser His Leu His Lys Thr Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
                260                 265                 270

Tyr Ile Leu Ala Gln Asn Phe Phe Tyr Glu Lys Ile Tyr Pro Lys Ser
                275                 280                 285

Asn

<210> SEQ ID NO 42
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 9

<400> SEQUENCE: 42
atggatgagg aagacgacgt cgtaattatc tacaatcgcg tgccacacac ggcatcccat    60
tcattcacca acattgcgta cgatttgtgt gcaaaaaacc gttatcatgt cttacacatc   120
aacactacaa aaaacaatcc cgtaatgagt ctgcaagatc aggtccgttt tgtcaaaaat   180
gtaacctcgt ggaaggagat gaagccgggc ttctatcacg ggatggtcag ctaccttgac   240
tttgctaaat ttggggtaaa gaaaaaacct atctatatca atgtgattcg tgatcctatc   300
gaacgccttg taagttatta ctacgctctt cgtttcgggg cagatcgccg tcccggactt   360
cgcatgcgca agcaggggga taagaagaca tttgacgagt gcgtcgcggc gggtggatct   420
gattgtgccc ctgagaaact gtggttgcaa attccattct tttgtgggca cagcagtgag   480
tgctggaatg tgggatctcg ttgggctctg aacaggcca agtacaacct tattaatgag   540
tacttcttag taggagtcac ggaagagctt gaagacttca ttatgttact ggaagcagcc   600
ttgcctcgtt ttttccgcgg tgcaacggag ctgtaccgca cagggaaaaa atcccatctt   660
cataagacca cagagaaaaa actgccgacg aaggagacga ttgcgaaact gcaacaaagt   720
gaaatctgga agatggagaa tgaattttat gagtttgctt tggagcaatt tcaattcgtc   780
```
cgtgcgcatg cggtccgtga aaaggacggt gaattgtata tcttggctca aaacttttc      840 tatgagaaaa tttatcctaa gtctaactaa                                      870

<210> SEQ ID NO 43
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 9

<400> SEQUENCE: 43

Met Asp Glu Glu Asp Asp Val Val Ile Ile Tyr Asn Arg Val Pro His
1               5                   10                  15

Thr Ala Ser His Ser Phe Thr Asn Ile Ala Tyr Asp Leu Cys Ala Lys
            20                  25                  30

Asn Arg Tyr His Val Leu His Ile Asn Thr Thr Lys Asn Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly Met Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Ala Leu Arg Phe
            100                 105                 110

Gly Ala Asp Arg Arg Pro Gly Leu Arg Met Arg Lys Gln Gly Asp Lys
            115                 120                 125

Lys Thr Phe Asp Glu Cys Val Ala Ala Gly Gly Ser Asp Cys Ala Pro
    130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
        195                 200                 205

Thr Glu Leu Tyr Arg Thr Gly Lys Lys Ser His Leu His Lys Thr Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270

Tyr Ile Leu Ala Gln Asn Phe Phe Tyr Glu Lys Ile Tyr Pro Lys Ser
        275                 280                 285

Asn

<210> SEQ ID NO 44
<211> LENGTH: 870
<212> TYPE: DNA
<213> ORGANISM: Artificial Sequence
<220> FEATURE:
<223> OTHER INFORMATION: Polynucleotide sequence encoding for engineered hexuronyl 2-O sulfotransferase mutant_sulfatase 10

<400> SEQUENCE: 44

```
atggatgagg aagacgacgt cgtaatcatc tacaaccgcg tcccgcacac agccagccac      60
tccttcacca atattgcgta tgatctgtgc gctaagaacc gttaccatgt gttgcacatt     120
accactacga agcgtaaccc cgtaatgtca cttcaagatc aagttcgctt cgttaagaac     180
gtgacatctt ggaaggagat gaagccagga ttctatcatg gggaagttag ctacttggac     240
tttgccaagt tcggtgtaaa gaaaaaacca atctacatca atgttattcg tgatcccatc     300
gaacgcttag tgtcttacta ttatgcccct cgctttggag ccgaccgtcg cccggggctt     360
cgtatgcgca agcaagggga caagaagacc ttcgacgagt gtgtagccgc gggtgggtct     420
gactgtgcgc cggaaaagtt atggttacaa attccatttt tctgtggtca ctcgtcagag     480
tgctggaatg ttggttcgcg ctgggcgctg gagcaagcga aatataactt gattaatgaa     540
tacttttag taggggtgac agaggagttg gaggacttta ttatgcttct tgaggctgcg     600
ttacctcgct ttttccgcgg tgcgactgag ttgtatcgta ccggtaaaaa atctcatctg     660
cataaaacaa ctgaaaagaa gctgccaacg aaagagacga ttgctaaact tcagcagagt     720
gagatctgga aaatggaaaa tgagttctac gagtttgcct tggagcaatt ccaattcgtg     780
cgtgcccatg ccgttcgtga aaaggatggt gaattataca tcttggcaca gaatttcttc     840
tatgagaaaa tttatcctaa gtctaactaa                                      870
```

<210> SEQ ID NO 45
<211> LENGTH: 289
<212> TYPE: PRT
<213> ORGANISM: Artificial Sequence
<220> FEATURE:
<223> OTHER INFORMATION: Engineered hexuronyl 2-O sulfotransferase mutant_sulfatase 10

<400> SEQUENCE: 45

```
Met Asp Glu Glu Asp Asp Val Val Ile Ile Tyr Asn Arg Val Pro His
 1               5                  10                  15

Thr Ala Ser His Ser Phe Thr Asn Ile Ala Tyr Asp Leu Cys Ala Lys
            20                  25                  30

Asn Arg Tyr His Val Leu His Ile Thr Thr Thr Lys Arg Asn Pro Val
        35                  40                  45

Met Ser Leu G

```
            180                 185                 190
Phe Ile Met Leu Leu Glu Ala Ala Leu Pro Arg Phe Phe Arg Gly Ala
            195                 200                 205

Thr Glu Leu Tyr Arg Thr Gly Lys Lys Ser His Leu His Lys Thr Thr
        210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270

Tyr Ile Leu Ala Gln Asn Phe Phe Tyr Glu Lys Ile Tyr Pro Lys Ser
        275                 280                 285

Asn
```

```
<210> SEQ ID NO 46
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 11

<400> SEQUENCE: 46
atggatgagg aagacgacgt cgtaattatc tacaatcgcg taccgcatac tgcaagccac      60
agctttacta acatcgccta tgatttgtgt gcgaagaacc gctatcatgt actgcatatt     120
acgacgacca agaataatcc tgtaatgtcc ttacaggacc aagttcgctt cgttaaaaac     180
gtaacttcgt ggaaagagat gaagccaggg ttttaccacg gaatggtcag ctacttagat     240
ttcgcaaagt tcggtgtgaa gaaaaagccc atctatatca atgtcatccg cgaccctatc     300
gaacgtctgg tatcttacta ttatgcgctt cgcttcggcg gtgatcgccg tcctggttta     360
cgtatgcgta agcaaggaga taagaaaacc ttcgacgaat gtgtcgcggc cggggggcagt     420 gactgtgccc cggagaagtt atggttacag atcccatttt tttgtggaca cagttccgaa     480
tgttggaacg tgggtagtcg ttgggcatta gagcaagcca agtacaactt aatcaatgaa     540
tatttcttgg taggtgtaac tgaggagctg gaagacttta ttatgttact gaagctgcg      600 ctgccccgtt tctttcgtgg tgcgacggag ttataccgta cagggaagaa gagccactta     660
cataagacaa ctgagaaaaa gttacccacg aaagaaacaa tcgctaaatt acaacaaagt     720
gagatttgga gatggaaaa cgaattttat gagttcgcat tagaacagtt tcaattcgtg     780
cgtgcgcatg cggtccgcga gaaggacggt gaactttaca ttcttgcaca gaacttcttc     840
tatgagaaaa tttatcctaa gtctaactaa                                      870
```

```
<210> SEQ ID NO 47
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 11

<400> SEQUENCE: 47

Met Asp Glu Glu Asp Asp Val Val Ile Ile Tyr Asn Arg Val Pro His
1               5                   10                  15

Thr Ala Ser His Ser Phe Thr Asn Ile Ala Tyr Asp Leu Cys Ala Lys
            20                  25                  30
```

```
Asn Arg Tyr His Val Leu His Ile Thr Thr Thr Lys Asn Asn Pro Val
         35                  40                  45

Met Ser Leu Gln Asp Gln Val Arg Phe Val Lys Asn Val Thr Ser Trp
 50                  55                  60

Lys Glu Met Lys Pro Gly Phe Tyr His Gly Met Val Ser Tyr Leu Asp
 65                  70                  75                  80

Phe Ala Lys Phe Gly Val Lys Lys Pro Ile Tyr Ile Asn Val Ile
                 85                  90                  95

Arg Asp Pro Ile Glu Arg Leu Val Ser Tyr Tyr Ala Leu Arg Phe
                100                 105                 110

Gly Gly Asp Arg Arg Pro Gly Leu Arg Met Arg Lys Gln Gly Asp Lys
                115                 120                 125

Lys Thr Phe Asp Glu Cys Val Ala Ala Gly Gly Ser Asp Cys Ala Pro
130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
                180                 185                 190

Phe Ile Met Leu Leu Glu Ala Ala Leu Pro Arg Phe Phe Arg Gly Ala
                195                 200                 205

Thr Glu Leu Tyr Arg Thr Gly Lys Lys Ser His Leu His Lys Thr Thr
                210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
                260                 265                 270

Tyr Ile Leu Ala Gln Asn Phe Phe Tyr Glu Lys Ile Tyr Pro Lys Ser
                275                 280                 285

Asn
```

<210> SEQ ID NO 48
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 12

<400> SEQUENCE: 48

```
atggatgagg aagacgacgt cgtaattatc tacaaccgcg tccatcgtac tgcgtctcac      60
agctttacta acattgccta cgacttatgc gcaaagaatc gttaccacgt tttgcatatc     120
aacacgacca agggtaatcc ggtaatgtca ttgcaagatc aggtgcgttt cgtaaaaaac     180
gtcacgagct ggaaagaaat gaagccggga ttttaccacg ggacagtcag ctaccttgat     240
tttgcaaaat tcggagtcaa aaaaaaaccc atttacatta acgtgatccg cgatccaatt     300
gaacgtcttg tctcgtacta ttatttctta cgtttcggga cgacctgcg tccgggtttg      360 cgtcgtcgca aacaaggaga caagaagaca tttgacgaat gtgtagcagc agggggctct     420
gactgcgccc cggaaaaatt gtggttacag atcccgttct tttgtggaca tagttccgag     480
tgctggaatg taggctcccg ttgggcgtta gaacaggcaa aatacaatct gattaacgag     540
```

```
tacttttag taggcgtgac cgaggagtta gaagatttta ttatgctgtt agaggcggcg      600
ctgccgcgtt ttttccgtgg agccacggaa ttgtatcgta ccggaaagaa atctcacctt      660
cacaagacta cagaaaaaaa attaccaact aaagagacaa tcgcaaagtt gcagcagtcg      720
gagatctgga agatggaaaa tgagttttat gaattcgcat tagaacagtt ccaattcgtt      780
cgtgcgcacg cagtacgcga aaaggacggg gagctttaca tcctggctca gaattttttc      840
tatgagaaaa tttatcctaa gtctaactaa                                       870
```

```
<210> SEQ ID NO 49
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 12

<400> SEQUENCE: 49
```

Met Asp Glu Glu Asp Val Val Ile Ile Tyr Asn Arg Val His Arg
1               5                   10                  15

Thr Ala Ser His Ser Phe Thr Asn Ile Ala Tyr Asp Leu Cys Ala Lys
            20                  25                  30

Asn Arg Tyr His Val Leu His Ile Asn Thr Thr Lys Gly Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly Thr Val Ser Tyr Leu Asp
65              70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Phe Leu Arg Phe
            100                 105                 110

Gly Asn Asp Leu Arg Pro Gly Leu Arg Arg Lys Gln Gly Asp Lys
        115                 120                 125

Lys Thr Phe Asp Glu Cys Val Ala Ala Gly Gly Ser Asp Cys Ala Pro
    130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
        195                 200                 205

Thr Glu Leu Tyr Arg Thr Gly Lys Lys Ser His Leu His Lys Thr Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270

Tyr Ile Leu Ala Gln Asn Phe Phe Tyr Glu Lys Ile Tyr Pro Lys Ser
        275                 280                 285

Asn

<210> SEQ ID NO 50
<211> LENGTH: 870
<212> TYPE: DNA
<213> ORGANISM: Artificial Sequence
<220> FEATURE:
<223> OTHER INFORMATION: Polynucleotide sequence encoding for engineered hexuronyl 2-O sulfotransferase mutant_sulfatase 13

<400> SEQUENCE: 50

```
atggatgagg aagacgacgt cgtaattatc tacaaccgcg tccatcgtac tgcgtctcac        60
agctttacta acattgccta cgacttatgc gcaaagaatc gttaccacgt tttgcatatc       120
aacacgacca agggtaatcc ggtaatgtca ttgcaagatc aggtgcgttt cgtaaaaaac       180
gtcacgagct ggaaagaaat gaagccggga ttttaccacg ggccagtcag ctaccttgat       240
tttgcaaaat tcggagtcaa aaaaaaaccc atttacatta acgtgatccg cgatccaatt       300
gaacgtcttg tctcgtacta ttatttctta cgtttcggga gcgacctgcg tccgggtttg       360
cgtcagcgca acaaggaga caagaagaca tttgacgaat gtgtagcagc aggggggctct       420
gactgcgccc cggaaaaatt gtggttacag atcccgttct tttgtggaca tagttccgag       480
tgctggaatg taggctcccg ttgggcgtta gaacaggcaa aatacaatct gattaacgag       540
tacttttttag taggcgtgac cgaggagtta gaagatttta ttatgctgtt agaggcggcg       600
ctgccgcgtt ttttccgtgg agccacggaa ttgtatcgta ccggaaagaa atctcacctt       660
cacaagacta cagaaaaaaa attaccaact aaagagacaa tcgcaaagtt gcagcagtcg       720
gagatctgga agatggaaaa tgagtttat gaattcgcat tagaacagtt ccaattcgtt       780
cgtgcgcacg cagtacgcga aaaggacggg gagctttaca tcctggctca gaattttttc       840
tatgagaaaa tttatcctaa gtctaactaa                                        870
```

<210> SEQ ID NO 51
<211> LENGTH: 289
<212> TYPE: PRT
<213> ORGANISM: Artificial Sequence
<220> FEATURE:
<223> OTHER INFORMATION: Engineered hexuronyl 2-O sulfotransferase mutant_sulfatase 13

<400> SEQUENCE: 51

```
Met Asp Glu Glu Asp Asp Val Val Ile Ile Tyr Asn Arg Val His Arg
1               5                   10                  15

Thr Ala Ser His Ser Phe Thr Asn Ile Ala Tyr Asp Leu Cys Ala L

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
        195                 200                 205

Thr Glu Leu Tyr Arg Thr Gly Lys Lys Ser His Leu His Lys Thr Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270

Tyr Ile Leu Ala Gln Asn Phe Phe Tyr Glu Lys Ile Tyr Pro Lys Ser
        275                 280                 285

Asn

<210> SEQ ID NO 52
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 14

<400> SEQUENCE: 52

```
atggatgagg aagacgacgt cgtgattatc tataaccgcg tgcatcgtac ggcttcacat       60
tcgttcacaa atattgcgta cgacctttgt gctaagaatc gctatcacgt cttacacatc      120
aacaccacca aaggcaatcc tgtcatgtct cttcaagatc aagtacgttt cgtgaagaac      180
gtgacatcat ggaaggagat gaagccgggg ttctaccatg ggccggtaag ttacttggat      240
ttcgctaaat ttggggttaa aaaaaagcct atctacatta atgttattcg tgaccctatc      300
gaacgtttgg tttcctatta ttacttcctt cgctttggaa atgatcgccg tcctggtttg      360
cgtcaacgca gcagggcga taaaaaaaca tttgacgaat gcgtagctgc cggcggctcc       420
gactgtgcgc cagaaaagct gtggttacag atcccatttt tctgtggaca ctcctcggag      480
tgttggaacg tggggtcgcg ttgggcatta gaacaggcca atacaatttt aatcaacgaa      540
tatttcctgg ttggcgtcac ggaggaactg gaagatttca ttatgctttt agaagctgcg      600
ttaccacgct tctttcgcgg cgctaccgag ttataccgta ccggaaagaa gtctcatctg      660
cacaagacga cggaaaagaa gcttcccact aaagaaacta ttgctaaatt acagcagagt      720
gaaatctgga aaatggaaaa tgagttctac gagttcgcgt tggaacagtt tcaattcgtt      780
cgtgcccatg ccgttcgcga aaaggatggc gaattgtata ttcttgccca gaacttcttc      840
tatgagaaaa tttatcctaa gtctaactaa                                       870
```

<210> SEQ ID NO 53
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 14

<400> SEQUENCE: 53

Met Asp Glu Glu Asp Val Val Ile Ile Tyr Asn Arg Val His Arg
1               5                   10                  15

Thr Ala Ser His Ser Phe Thr Asn Ile Ala Tyr Asp Leu Cys Ala Lys
            20                  25                  30

Asn Arg Tyr His Val Leu His Ile Asn Thr Thr Lys Gly Asn Pro Val
            35                  40                  45

Met Ser Leu Gln Asp Gln Val Arg Phe Val Lys Asn Val Thr Ser Trp
50                  55                  60

Lys Glu Met Lys Pro Gly Phe Tyr His Gly Pro Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Phe Leu Arg Phe
                100                 105                 110

Gly Asn Asp Arg Arg Pro Gly Leu Arg Gln Arg Lys Gln Gly Asp Lys
                115                 120                 125

Lys Thr Phe Asp Glu Cys Val Ala Ala Gly Ser Asp Cys Ala Pro
130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
                180                 185                 190

Phe Ile Met Leu Leu Glu Ala Ala Leu Pro Arg Phe Phe Arg Gly Ala
                195                 200                 205

Thr Glu Leu Tyr Arg Thr Gly Lys Lys Ser His Leu His Lys Thr Thr
                210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
                260                 265                 270

Tyr Ile Leu Ala Gln Asn Phe Phe Tyr Glu Lys Ile Tyr Pro Lys Ser
                275                 280                 285

Asn

<210> SEQ ID NO 54
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 15

<400> SEQUENCE: 54
atggatgagg aagacgacgt cgtgattatt tataaccgtg tgcctcacac tgcttcgacc    60
tcatttacaa acattgctta cgatctttgt gctaagaatc gttaccacgt cctgcatatt   120
aacacgacaa aaaataaccc tgtaatgtct cttcaagatc aagtccgctt cgtgaaaaat   180
gtgacgagtt ggaaagaaat gaagccggga ttttatcacg gcccgtgtc ataccttgac   240 ttcgctaaat ttggggttaa gaaaaaacct atctatatca atgtgatccg tgatcccatc   300

```
gaacgccttg tttcatatta ttatgcatta cgttttggtt cagattatcg cccaggcctt    360
cgcatgcgta agcaagggga caagaagaca ttcgatgagt gcgttgcggc gggggggatca   420 gattgtgcac cagagaagct gtggttgcaa atcccgttct tctgcggaca cagctccgaa    480
tgttggaatg tcgggtcacg ttgggcgctt gaacaggcta agtacaatct gattaacgag    540 tacttttag tcggtgttac ggaggagttg gaagacttca ttatgctgct ggaggctgcg     600
ctgccccgct tcttccgcgg cgccaccgag ttgtaccgta caggaaagaa gtcccattta    660
cacaagcata ctgagaaaaa gttgcccact aaggaaacca ttgctaagtt gcaacagtcg    720
gaaatttgga aaatggagaa cgagttctac gaatttgcat tagaacagtt ccaatttgtt    780
cgtgcccatg ccgtacgtga aaggacggc gaattatata tccttgcaca aaacttcttc     840
tatgagaaga tctatcctaa gtctaactaa                                     870
```

<210> SEQ ID NO 55
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 15

<400> SEQUENCE: 55

```
Met Asp Glu Glu Asp Asp Val Val Ile Ile Tyr Asn Arg Val Pro His
1               5                   10                  15

Thr Ala Ser Thr Ser Phe Thr Asn Ile Ala Tyr Asp Leu Cys Ala Lys
            20                  25                  30

Asn Arg Tyr His Val Leu His Ile Asn Thr Thr Lys Asn Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly Pro Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Ala Leu Arg Phe
                100                 105                 110

Gly Ser Asp Tyr Arg Pro Gly Leu Arg Met Arg Lys Gln Gly Asp Lys
            115                 120                 125

Lys Thr Phe Asp Glu Cys Val Ala Ala Gly Ser Asp Cys Ala Pro
    130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Arg Gly Ala
        195                 200                 205

Thr Glu Leu Tyr Arg Thr Gly Lys Lys Ser His Leu His Lys His Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255
```

-continued

Phe Gln Phe Val Arg Ala His Ala Val Arg Glu Lys Asp Gly Glu Leu
                260                 265                 270

Tyr Ile Leu Ala Gln Asn Phe Phe Tyr Glu Lys Ile Tyr Pro Lys Ser
            275                 280                 285

Asn

<210> SEQ ID NO 56
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 16

<400> SEQUENCE: 56
atggatgagg aagacgacgt cgtgattatt tataaccgtg tgcctcacac tgcttcgacc      60
tcatttacaa acattgctta cgatctttgt gctaagaatc gttaccacgt cctgcatatt    120
aacacgacaa aaataaaccc tgtaatgtct cttcaagatc aagtccgctt cgtgaaaaat    180
gtgacgagtt ggaaagaaat gaagccggga ttttatcacg gaacgtgtc atacctgac     240 ttcgctaaat ttggggttaa gaaaaaacct atctatatca atgtgatccg tgatcccatc    300
gaacgccttg tttcatatta ttatgcatta cgttttggtt cagattatcg cccaggcctt    360
cgcatgcgta agcaaggga caagaagaca ttcgatgagt gcgttgcggc gggggatca     420 gattgtgcac cagagaagct gtggttgcaa atcccgttct tctgcggaca cagctccgaa    480
tgttggaatg tcgggtcacg ttgggcgctt gaacaggcta agtacaatct gattaacgag    540 tacttttag tcggtgttac ggaggagttg gaagacttca ttatgctgct ggaggctgcg    600
ctgccccgct tcttccgcgg cgccaccgag ttgtaccgta caggaaagaa gtcccattta    660
cacaagcata ctgagaaaaa gttgcccact aaggaaacca ttgctaagtt gcaacagtcg    720
gaaatttgga aaatggagaa cgagttctac gaatttgcat tagaacagtt ccaatttgtt    780
cgtgcccatg ccgtacgtga aaggacggc gaattatata tccttgcaca aaacttcttc      840
tatgagaaga tctatcctaa gtctaactaa                                      870

<210> SEQ ID NO 57
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 16

<400> SEQUENCE: 57

Met Asp Glu Glu Asp Asp Val Val Ile Ile Tyr Asn Arg Val Pro His
1               5                   10                  15

Thr Ala Ser Thr Ser Phe Thr Asn Ile Ala Tyr Asp Leu Cys Ala Lys
            20                  25                  30

Asn Arg Tyr His Val Leu His Ile Asn Thr Thr Lys Asn Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly Asn Val Ser Tyr Leu Asp
65                  70                  75                  80

Phe Ala Lys Phe Gly Val Lys Lys Lys Pro Ile Tyr Ile Asn Val Ile
                85                  90                  95

Arg Asp Pro Ile Glu Arg Leu Val Ser Tyr Tyr Ala Leu Arg Phe
            100                 105                 110

Gly Ser Asp Tyr Arg Pro Gly Leu Arg Met Arg Lys Gln Gly Asp Lys
        115                 120                 125

Lys Thr Phe Asp Glu Cys Val Ala Ala Gly Gly Ser Asp Cys Ala Pro
    130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
            195                 200                 205

Thr Glu Leu Tyr Arg Thr Gly Lys Lys Ser His Leu His Lys His Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270

Tyr Ile Leu Ala Gln Asn Phe Phe Tyr Glu Lys Ile Tyr Pro Lys Ser
            275                 280                 285

Asn

<210> SEQ ID NO 58
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 17

<400> SEQUENCE: 58
atggatgagg aagacgacgt cgtgattatt tataaccatg ttcataagac tgcttcgcat       60
tcattcacta acatcgctta tgatttatgt gcaagaaacc gttatcacgt tcttcacatc      120
accacgacaa agggtaatcc ggtaatgtca ctgcaggacc aggttcgttt cgtcaaaaat      180
gtaacttcgt ggaaagagat gaagccgggg ttctaccacg gccccgtgtc ttatcttgac      240
ttcgcgaaat tcggagttaa aaaaaaacca atctacatca acgtgatccg cgatcctatc      300
gaacgtcttg tatcttatta ctattttta cgcttcgggg atgactaccg ccctgggctt      360
cgtcgtcgca agcagggcga caagaaaacg ttcgacgagt gcgtcgccgc cggaggctcg      420
gactgtgctc cggagaaaat tgtggttgca attcccttt tctgtggaca ctcgtctgag      480
tgctggaacg taggatcacg ctgggcatta gaacaagcga agtataactt gattaacgag      540
tatttcctgg tcggcgtaac tgaagaactg gaggatttca ttatgcttct ggaagccgcg      600
ctgccccgtt ttttccgtgg ggccactgag ctttaccgca caggaaagaa gtctcacctt      660
cgtaaaacga ctgagaaaaa gcttcccacc aaggagacta cgcaaaaact caacaatca      720 gaaatttgga gatggaaaa tgagttctac gagttcgcct ggaacagtt ccagttcgtc      780 cgtgcccatg ccgtacgtga aaggacggc gaattatata tccttgcaca aaacttcttc      840
tatgagaaga tctatcctaa gtctaactaa                                        870

-continued

```
<210> SEQ ID NO 59
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 17

<400> SEQUENCE: 59
```

Met Asp Glu Glu Asp Val Val Ile Ile Tyr Asn His Val His Lys
1               5                   10                  15

Thr Ala Ser His Ser Phe Thr Asn Ile Ala Tyr Asp Leu Cys Ala Lys
            20                  25                  30

Asn Arg Tyr His Val Leu His Ile Thr Thr Thr Lys Gly Asn Pro Val
            35                  40                  45

Met Ser Leu Gln Asp Gln Val Arg Phe Val Lys Asn Val Thr Ser Trp
        50                  55                  60

Lys Glu Met Lys Pro Gly Phe Tyr His Gly Pro Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Tyr Phe Leu Arg Phe
            100                 105                 110

Gly Asp Asp Tyr Arg Pro Gly Leu Arg Arg Arg Lys Gln Gly Asp Lys
            115                 120                 125

Lys Thr Phe Asp Glu Cys Val Ala Ala Gly Gly Ser Asp Cys Ala Pro
        130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
        195                 200                 205

Thr Glu Leu Tyr Arg Thr Gly Lys Lys Ser His Leu Arg Lys Thr Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270

Tyr Ile Leu Ala Gln Asn Phe Phe Tyr Glu Lys Ile Tyr Pro Lys Ser
        275                 280                 285

Asn

```
<210> SEQ ID NO 60
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_sulfatase 18

<400> SEQUENCE: 60
```
atggatgagg aagacgacgt cgtgattatt tataaccatg ttcataagac tgcttcgcat      60

```
tcattcacta acatcgctta tgatttatgt gcaaagaacc gttatcacgt tcttcacatc    120
accacgacaa agaataatcc ggtaatgtca ctgcaggacc aggttcgttt cgtcaaaaat    180
gtaacttcgt ggaaagagat gaagccgggg ttctaccacg gccccgtgtc ttatcttgac    240
ttcgcgaaat tcggagttaa aaaaaaacca atctacatca acgtgatccg cgatcctatc    300
gaacgtcttg tatcttatta ctatttttta cgcttcgggg atgactaccg ccctgggctt    360
cgtcgtcgca agcagggcga caagaaaacg ttcgacgagt gcgtcgccgc cggaggctcg    420
gactgtgctc cggagaaatt gtggttgcag attcccttt tctgtggaca ctcgtctgag    480
tgctggaacg taggatcacg ctgggcatta gaacaagcga agtataactt gattaacgag    540
tatttcctgg tcggcgtaac tgaagaactg gaggatttca ttatgcttct ggaagccgcg    600
ctgccccgtt ttttccgtgg ggccactgag ctttaccgca caggaaagaa gtctcacctt    660
cgtaaaacga ctgagaaaaa gcttcccacc aaggagacta tcgcaaaact tcaacaatca    720
gaaatttgga agatggaaaa tgagttctac gagttcgcct tggaacagtt ccagttcgtc    780
cgtgcccatg ccgtacgtga aaggacggc gaattatata tccttgcaca aaacttcttc    840
tatgagaaga tctatcctaa gtctaactaa                                     870
```

<210> SEQ ID NO 61
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfatase 18

<400> SEQUENCE: 61

```
Met Asp Glu Glu Asp Val Val Ile Ile Tyr Asn His Val His Lys
1               5                  10                  15

Thr Ala Ser His Ser Phe Thr Asn Ile Ala Tyr Asp Leu Cys Ala Lys
            20                  25                  30

Asn Arg Tyr His Val Leu His Ile Thr Thr Thr Lys Asn Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly Pro Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Phe Leu Arg Phe
            100                 105                 110

Gly Asp Asp Tyr Arg Pro Gly Leu Arg Arg Lys Gln Gly Asp Lys
        115                 120                 125

Lys Thr Phe Asp Glu Cys Val Ala Ala Gly Ser Asp Cys Ala Pro
    130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
        195                 200                 205
```

```
Thr Glu Leu Tyr Arg Thr Gly Lys Lys Ser His Leu Arg Lys Thr Thr
    210                 215                 220
Glu Lys Lys Leu Pro Thr Lys Glu Thr Ile Ala Lys Leu Gln Gln Ser
225                 230                 235                 240
Glu Ile Trp Lys Met Glu Asn Glu Phe Tyr Glu Phe Ala Leu Glu Gln
                245                 250                 255
Phe Gln Phe Val Arg Ala His Ala Val Arg Glu Lys Asp Gly Glu Leu
            260                 265                 270
Tyr Ile Leu Ala Gln Asn Phe Phe Tyr Glu Lys Ile Tyr Pro Lys Ser
        275                 280                 285
Asn
```

<210> SEQ ID NO 62
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_ sulfotransferase 1

<400> SEQUENCE: 62

```
atggatgagg aagacgacgt cgtgattatt tataaccgtg taccgcatac tgccagcacg      60
tcattcacga atatcgcgta cgatctttgc gctaaaaacc gttatcatgt tttacatatt     120
aataccacca aaaacaatcc ggtgatgtca ttgcaggatc aggtgcgttt cgtaaagaat     180
gtcacctcat ggaaagagat gaagccaggg ttttatcatg ggcacgttag ttatttggat     240
tttgctaagt ttggtgtaaa gaagaagccc atctacatca atgtcattcg tgatcccatt     300
gaacgcttgg tctcctatta ctaccatttg cgctttggcg acgactaccg ccccggatta     360
cgccgccgca agcaggggga caagaaaact tttgacgaat gcgtcgctgc cggtggtagc     420
gactgcgccc cggagaaatt atggcttcaa attcccttt tctgcggcca ttcttcggaa      480
tgctggaacg taggtagtcg ctgggctctt gaacaggcaa aatataatct tatcaacgaa     540
tactttcttg tcggagttac cgaggagttg gaggacttta ttatgcttct ggaggctgcg     600
ctgccgcgtt ttttcgtgg tgcgaccgag ctgtatcgta caggtaaaaa aagtcatctt      660
cataaaacga cggaaaagaa gctgccaact aaggaaacaa tcgcgaaact gcaacagagt     720
gaaatctgga aaatggaaaa tgaattctat gagtttgccc tggagcaatt ccaattcgtt     780
cgcgcccatg ccgtacgtga aaggacggc gaattatata tccttgcaca aaacttcttc      840
tatgagaaga tctatcctaa gtctaactaa                                      870
```

<210> SEQ ID NO 63
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfotransferase
      1

<400> SEQUENCE: 63

```
Met Asp Glu Glu Asp Asp Val Val Ile Ile Tyr Asn Arg Val Pro His
1               5                   10                  15
Thr Ala Ser Thr Ser Phe Thr Asn Ile Ala Tyr Asp Leu Cys Ala Lys
            20                  25                  30
Asn Arg Tyr His Val Leu His Ile Asn Thr Thr Lys Asn Asn Pro Val
        35                  40                  45
```

Met Ser Leu Gln Asp Gln Val Arg Phe Val Lys Asn Val Thr Ser Trp
     50                  55                  60
Lys Glu Met Lys Pro Gly Phe Tyr His Gly His Val Ser Tyr Leu Asp
 65                  70                  75                  80
Phe Ala Lys Phe Gly Val Lys Lys Pro Ile Tyr Ile Asn Val Ile
                 85                  90                  95
Arg Asp Pro Ile Glu Arg Leu Val Ser Tyr Tyr His Leu Arg Phe
                100                 105                 110
Gly Asp Asp Tyr Arg Pro Gly Leu Arg Arg Lys Gln Gly Asp Lys
                115                 120                 125
Lys Thr Phe Asp Glu Cys Val Ala Ala Gly Ser Asp Cys Ala Pro
            130                 135                 140
Glu Lys Leu Trp Leu Gln Ile Pro Phe Phe Cys Gly His Ser Ser Glu
145                 150                 155                 160
Cys Trp Asn Val Gly Ser Arg Trp Ala Leu Glu Gln Ala Lys Tyr Asn
                165                 170                 175
Leu Ile Asn Glu Tyr Phe Leu Val Gly Val Thr Glu Glu Leu Glu Asp
            180                 185                 190
Phe Ile Met Leu Leu Glu Ala Ala Leu Pro Arg Phe Phe Arg Gly Ala
        195                 200                 205
Thr Glu Leu Tyr Arg Thr Gly Lys Lys Ser His Leu His Lys Thr Thr
210                 215                 220
Glu Lys Lys Leu Pro Thr Lys Glu Thr Ile Ala Lys Leu Gln Gln Ser
225                 230                 235                 240
Glu Ile Trp Lys Met Glu Asn Glu Phe Tyr Glu Phe Ala Leu Glu Gln
                245                 250                 255
Phe Gln Phe Val Arg Ala His Ala Val Arg Glu Lys Asp Gly Glu Leu
            260                 265                 270
Tyr Ile Leu Ala Gln Asn Phe Phe Tyr Glu Lys Ile Tyr Pro Lys Ser
        275                 280                 285
Asn

<210> SEQ ID NO 64
<211> LENGTH: 870
<212> TYPE: DNA
<213> ORGANISM: Artificial Sequence
<220> FEATURE:
<223> OTHER INFORMATION: Polynucleotide sequence encoding for engineered
      hexuronyl 2-O sulfotransferase mutant_ sulfotransferase 2

<400> SEQUENCE: 64
atggatgagg aagacgacgt cgtaattatt tacaatcgtg tacaccgtac agcctcgcat     60 tctttttacta acattgctta tgatctgtgc gcaaaaaacc gttaccacgt gttgcacatc    120
aatactacta agggtaatcc cgttatgagc ctgcaagacc aggtgcgctt tgttaagaat    180
gttacctcct ggaaagagat gaaacctggc ttctatcacg gacctgtatc ctacttggac    240
ttcgctaaat ttggcgtaaa gaaaaaacct atttacatca atgtgatccg tgaccctatc    300
gaacgtctgg tatcgtatta ttatttcctg cgcttcggat cggataagcg tccaggtttg    360
cgcatgcgta agcagggga taaaaaaacg tttgacgaat gcgtggcggc tggtgggagc    420
gactgtgcgc cggaaaagtt atggttgcaa atcccgtttt tctgtgggca tagctctgaa    480
tgttggaatg ttggctcgcg ctgggcgctt gagcaagcta aatacaacct gatcaatgag    540
tacttcttag tcggagtaac tgaggaatta gaggacttca ttatgttgct tgaggctgct    600
ttaccacgct tcttccgcgg tgcgacagaa ttgtaccgca ccggaaaaaa gagccactta    660

```
cacaagacca cagaaaagaa attaccgacc aaagaaacta tcgccaagtt acaacaaagt    720
gagatttgga aaatggaaaa cgaattctat gaattcgcgt tggaacaatt tcaattcgtg    780
cgtgctcacg cagtacgcga aaggacggg gagctttata ttttggccca aaacttttc     840 tatgagaaaa tttatcctaa gtctaactaa                                    870

<210> SEQ ID NO 65
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfotransferase 2

<400> SEQUENCE: 65
```

Met Asp Glu Glu Asp Asp Val Val Ile Ile Tyr Asn Arg Val His Arg
1               5                   10                  15

Thr Ala Ser His Ser Phe Thr Asn Ile Ala Tyr Asp Leu Cys Ala Lys
            20                  25                  30

Asn Arg Tyr His Val Leu His Ile Asn Thr Thr Lys Gly Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly Pro Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Tyr Phe Leu Arg Phe
            100                 105                 110

Gly Ser Asp Lys Arg Pro Gly Leu Arg Met Arg Lys Gln Gly Asp Lys
        115                 120                 125

Lys Thr Phe Asp Glu Cys Val Ala Ala Gly Gly Ser Asp Cys Ala Pro
    130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
        195                 200                 205

Thr Glu Leu Tyr Arg Thr Gly Lys Lys Ser His Leu His Lys Thr Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270

Tyr Ile Leu Ala Gln Asn Phe Phe Tyr Glu Lys Ile Tyr Pro Lys Ser
        275                 280                 285

Asn

```
<210> SEQ ID NO 66
<211> LENGTH: 289
```

```
<212> TYPE: PRT
<213> ORGANISM: Artificial Sequence
<220> FEATURE:
<223> OTHER INFORMATION: Engineered hexuronyl 2-O sulfotransferase
      mutant_variable
<220> FEATURE:
<221> NAME/KEY: MISC_FEATURE
<222> LOCATION: (13)..(13)
<223> OTHER INFORMATION: Xaa is arginine or histidine
<220> FEATURE:
<221> NAME/KEY: MISC_FEATURE
<222> LOCATION: (15)..(15)
<223> OTHER INFORMATION: Xaa is histidine or proline
<220> FEATURE:
<221> NAME/KEY: MISC_FEATURE
<222> LOCATION: (16)..(16)
<223> OTHER INFORMATION: Xaa is lysine, histidine, threonine, arginine,
      or asparagine
<220> FEATURE:
<221> NAME/KEY: MISC_FEATURE
<222> LOCATION: (19)..(19)
<223> OTHER INFORMATION: Xaa is histidine, glutamic acid, or serine
<220> FEATURE:
<221> NAME/KEY: MISC_FEATURE
<222> LOCATION: (20)..(20)
<223> OTHER INFORMATION: Xaa is histidine, threonine, or asparagine
<220> FEATURE:
<221> NAME/KEY: MISC_FEATURE
<222> LOCATION: (41)..(41)
<223> OTHER INFORMATION: Xaa is threonine or asparagine
<220> FEATURE:
<221> NAME/KEY: MISC_FEATURE
<222> LOCATION: (45)..(45)
<223> OTHER INFORMATION: Xaa is arginine, glycine, or asparagine
<220> FEATURE:
<221> NAME/KEY: MISC_FEATURE
<222> LOCATION: (75)..(75)
<223> OTHER INFORMATION: Xaa is histidine, glutamic acid, methionine,
      proline, threonine, or asparagine
<220> FEATURE:
<221> NAME/KEY: MISC_FEATURE
<222> LOCATION: (105)..(105)
<223> OTHER INFORMATION: Xaa is histidine or serine
<220> FEATURE:
<221> NAME/KEY: MISC_FEATURE
<222> LOCATION: (109)..(109)
<223> OTHER INFORMATION: Xaa is histidine, alanine, or phenylalanine
<220> FEATURE:
<221> NAME/KEY: MISC_FEATURE
<222> LOCATION: (114)..(114)
<223> OTHER INFORMATION: Xaa is aspartic acid, glycine, serine, alanine,
      or asparagine
<220> FEATURE:
<221> NAME/KEY: MISC_FEATURE
<222> LOCATION: (116)..(116)
<223> OTHER INFORMATION: Xaa is tyrosine, arginine, or leucine
<220> FEATURE:
<221> NAME/KEY: MISC_FEATURE
<222> LOCATION: (122)..(122)
<223> OTHER INFORMATION: Xaa is methionine, arginine, or glutamine
<220> FEATURE:
<221> NAME/KEY: MISC_FEATURE
<222> LOCATION: (221)..(221)
<223> OTHER INFORMATION: Xaa is arginine or histidine
<220> FEATURE:
<221> NAME/KEY: MISC_FEATURE
<222> LOCATION: (223)..(223)
<223> OTHER INFORMATION: Xaa is threonine or histidine

<400> SEQUENCE: 66

Met Asp Glu Glu Asp Asp Val Val Ile Ile Tyr Asn Xaa Val Xaa Xaa
1               5                   10                  15

Thr Ala Xaa Xaa Ser Phe Thr Asn Ile Ala Tyr Asp Leu Cys Ala Lys
            20                  25                  30

Asn Arg Tyr His Val Leu His Ile Xaa Thr Thr Lys Xaa Asn Pro Val
        35                  40                  45
```

-continued

Met Ser Leu Gln Asp Gln Val Arg Phe Val Lys Asn Val Thr Ser Trp
    50                  55                  60
Lys Glu Met Lys Pro Gly Phe Tyr His Gly Xaa Val Ser Tyr Leu Asp
65                  70                  75                  80
Phe Ala Lys Phe Gly Val Lys Lys Pro Ile Tyr Ile Asn Val Ile
                85                  90                  95
Arg Asp Pro Ile Glu Arg Leu Val Xaa Tyr Tyr Xaa Leu Arg Phe
            100                 105                 110
Gly Xaa Asp Xaa Arg Pro Gly Leu Arg Xaa Arg Lys Gln Gly Asp Lys
            115                 120                 125
Lys Thr Phe Asp Glu Cys Val Ala Ala Gly Gly Ser Asp Cys Ala Pro
    130                 135                 140
Glu Lys Leu Trp Leu Gln Ile Pro Phe Phe Cys Gly His Ser Ser Glu
145                 150                 155                 160
Cys Trp Asn Val Gly Ser Arg Trp Ala Leu Glu Gln Ala Lys Tyr Asn
                165                 170                 175
Leu Ile Asn Glu Tyr Phe Leu Val Gly Val Thr Glu Leu Glu Asp
            180                 185                 190
Phe Ile Met Leu Leu Glu Ala Ala Leu Pro Arg Phe Phe Arg Gly Ala
    195                 200                 205
Thr Glu Leu Tyr Arg Thr Gly Lys Lys Ser His Leu Xaa Lys Xaa Thr
    210                 215                 220
Glu Lys Lys Leu Pro Thr Lys Glu Thr Ile Ala Lys Leu Gln Gln Ser
225                 230                 235                 240
Glu Ile Trp Lys Met Glu Asn Glu Phe Tyr Glu Phe Ala Leu Glu Gln
                245                 250                 255
Phe Gln Phe Val Arg Ala His Ala Val Arg Glu Lys Asp Gly Glu Leu
            260                 265                 270
Tyr Ile Leu Ala Gln Asn Phe Phe Tyr Glu Lys Ile Tyr Pro Lys Ser
            275                 280                 285
Asn

<210> SEQ ID NO 67
<211> LENGTH: 617
<212> TYPE: PRT
<213> ORGANISM: homo sapiens

<400> SEQUENCE: 67

Met Arg Cys Leu Ala Ala Arg Val Asn Tyr Lys Thr Leu Ile Ile Ile
1               5                   10                  15
Cys Ala Leu Phe Thr Leu Val Thr Val Leu Leu Trp Asn Lys Cys Ser
                20                  25                  30
Ser Asp Lys Ala Ile Gln Phe Pro Arg Arg Ser Ser Gly Phe Arg
            35                  40                  45
Val Asp Gly Phe Glu Lys Arg Ala Ala Ala Ser Glu Ser Asn Asn Tyr
    50                  55                  60
Met Asn His Val Ala Lys Gln Gln Ser Glu Glu Ala Phe Pro Gln Glu
65                  70                  75                  80
Gln Gln Lys Ala Pro Pro Val Val Gly Gly Phe Asn Ser Asn Val Gly
                85                  90                  95
Ser Lys Val Leu Gly Leu Lys Tyr Glu Glu Ile Asp Cys Leu Ile Asn
            100                 105                 110
Asp Glu His Thr Ile Lys Gly Arg Arg Glu Gly Asn Glu Val Phe Leu
            115                 120                 125

-continued

```
Pro Phe Thr Trp Val Glu Lys Tyr Phe Asp Val Tyr Gly Lys Val Val
    130                 135                 140

Gln Tyr Asp Gly Tyr Asp Arg Phe Glu Phe Ser His Ser Tyr Ser Lys
145                 150                 155                 160

Val Tyr Ala Gln Arg Ala Pro Tyr His Pro Asp Gly Val Phe Met Ser
                165                 170                 175

Phe Glu Gly Tyr Asn Val Glu Val Arg Asp Arg Val Lys Cys Ile Ser
                180                 185                 190

Gly Val Glu Gly Val Pro Leu Ser Thr Gln Trp Gly Pro Gln Gly Tyr
            195                 200                 205

Phe Tyr Pro Ile Gln Ile Ala Gln Tyr Gly Leu Ser His Tyr Ser Lys
    210                 215                 220

Asn Leu Thr Glu Lys Pro Pro His Ile Glu Val Tyr Glu Thr Ala Glu
225                 230                 235                 240

Asp Arg Asp Lys Asn Lys Pro Asn Asp Trp Thr Val Pro Lys Gly Cys
                245                 250                 255

Phe Met Ala Asn Val Ala Asp Lys Ser Arg Phe Thr Asn Val Lys Gln
                260                 265                 270

Phe Ile Ala Pro Glu Thr Ser Glu Gly Val Ser Leu Gln Leu Gly Asn
    275                 280                 285

Thr Lys Asp Phe Ile Ile Ser Phe Asp Leu Lys Phe Leu Thr Asn Gly
    290                 295                 300

Ser Val Ser Val Val Leu Glu Thr Thr Glu Lys Asn Gln Leu Phe Thr
305                 310                 315                 320

Ile His Tyr Val Ser Asn Ala Gln Leu Ile Ala Phe Lys Glu Arg Asp
                325                 330                 335

Ile Tyr Tyr Gly Ile Gly Pro Arg Thr Ser Trp Ser Thr Val Thr Arg
                340                 345                 350

Asp Leu Val Thr Asp Leu Arg Lys Gly Val Gly Leu Ser Asn Thr Lys
            355                 360                 365

Ala Val Lys Pro Thr Lys Ile Met Pro Lys Lys Val Val Arg Leu Ile
    370                 375                 380

Ala Lys Gly Lys Gly Phe Leu Asp Asn Ile Thr Ile Ser Thr Thr Ala
385                 390                 395                 400

His Met Ala Ala Phe Phe Ala Ala Ser Asp Trp Leu Val Arg Asn Gln
                405                 410                 415

Asp Glu Lys Gly Gly Trp Pro Ile Met Val Thr Arg Lys Leu Gly Glu
                420                 425                 430

Gly Phe Lys Ser Leu Glu Pro Gly Trp Tyr Ser Ala Met Ala Gln Gly
            435                 440                 445

Gln Ala Ile Ser Thr Leu Val Arg Ala Tyr Leu Leu Thr Lys Asp His
    450                 455                 460

Ile Phe Leu Asn Ser Ala Leu Arg Ala Thr Ala Pro Tyr Lys Phe Leu
465                 470                 475                 480

Ser Glu Gln His Gly Val Lys Ala Val Phe Met Asn Lys His Asp Trp
                485                 490                 495

Tyr Glu Glu Tyr Pro Thr Thr Pro Ser Ser Phe Val Leu Asn Gly Phe
                500                 505                 510

Met Tyr Ser Leu Ile Gly Leu Tyr Asp Leu Lys Glu Thr Ala Gly Glu
            515                 520                 525

Lys Leu Gly Lys Glu Ala Arg Ser Leu Tyr Glu Arg Gly Met Glu Ser
530                 535                 540
```

```
Leu Lys Ala Met Leu Pro Leu Tyr Asp Thr Gly Ser Gly Thr Ile Tyr
545                 550                 555                 560

Asp Leu Arg His Phe Met Leu Gly Ile Ala Pro Asn Leu Ala Arg Trp
            565                 570                 575

Asp Tyr His Thr Thr His Ile Asn Gln Leu Gln Leu Leu Ser Thr Ile
            580                 585                 590

Asp Glu Ser Pro Val Phe Lys Glu Phe Val Lys Arg Trp Lys Ser Tyr
            595                 600                 605

Leu Lys Gly Ser Arg Ala Lys His Asn
610                 615

<210> SEQ ID NO 68
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfotransferase 3

<400> SEQUENCE: 68

Met Asp Glu Glu Asp Met Val Ile Ile Tyr Asn Arg Val Pro His
1               5                   10                  15

Thr Ala Ser Thr Ser Phe Thr Asn Ile Ala Tyr Asp Leu Cys Ala Lys
                20                  25                  30

Asn Lys Tyr His Val Leu His Ile Asn Thr Thr Lys Asn Asn Pro Val
            35                  40                  45

Met Ser Leu Gln Asp Gln Val Arg Phe Val Lys Asn Ile Thr Ser Trp
50                  55                  60

Lys Glu Met Lys Pro Gly Phe Tyr His Gly His Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Tyr His Leu Arg Phe
            100                 105                 110

Gly Asp Asp Tyr Arg Pro Gly Leu Arg Arg Arg Lys Gln Gly Asp Lys
            115                 120                 125

Lys Thr Phe Asp Glu Cys Val Ala Glu Gly Gly Ser Asp Cys Ala Pro
130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Met Asp Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
            195                 200                 205

Thr Glu Leu Tyr Arg Thr Gly Lys Lys Ser His Leu His Lys Thr Thr
            210                 215                 220

Glu Lys Lys Leu Pro Thr Lys Gln Thr Ile Ala Lys Leu Gln Gln Ser
225                 230                 235                 240

Asp Ile Trp Lys Met Glu Asn Glu Phe Tyr Glu Phe Ala Leu Glu Gln
                245                 250                 255

Phe Gln Phe Ile Arg Ala His Ala Val Arg Glu Lys Asp Gly Asp Leu
            260                 265                 270

Tyr Ile Leu Ala Gln Asn Phe Phe Tyr Glu Lys Ile Tyr Pro Lys Ser
            275                 280                 285
```

Asn

<210> SEQ ID NO 69
<211> LENGTH: 289
<212> TYPE: PRT
<213> ORGANISM: Artificial Sequence
<220> FEATURE:
<223> OTHER INFORMATION: Engineered hexuronyl 2-O sulfotransferase
      mutant_sulfotransferase 4

<400> SEQUENCE: 69

| Met | Asp | Glu | Glu | Asp | Met | Val | Ile | Ile | Tyr | Asn | Arg | Val | His | Arg |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Thr | Ala | Ser | His | Ser | Phe | Thr | Asn | Ile | Ala | Tyr | Asp | Leu | Cys | Ala | Lys |
|     |     |     | 20  |     |     |     |     | 25  |     |     |     |     | 30  |     |     |

| Asn | Lys | Tyr | His | Val | Leu | His | Ile | Asn | Thr | Thr | Lys | Gly | Asn | Pro | Val |
|     |     | 35  |     |     |     |     | 40  |     |     |     |     | 45  |     |     |     |

| Met | Ser | Leu | Gln | Asp | Gln | Val | Arg | Phe | Val | Lys | Asn | Ile | Thr | Ser | Trp |
| 50  |     |     |     |     | 55  |     |     |     |     | 60  |     |     |     |     |     |

| Lys | Glu | Met | Lys | Pro | Gly | Phe | Tyr | His | Gly | Pro | Val | Ser | Tyr | Leu | Asp |
| 65  |     |     |     |     | 70  |     |     |     |     | 75  |     |     |     |     | 80  |

| Phe | Ala | Lys | Phe | Gly | Val | Lys | Lys | Pro | Ile | Tyr | Ile | Asn | Val | Ile |
|     |     |     |     | 85  |     |     |     |     | 90  |     |     |     |     | 95  |

| Arg | Asp | Pro | Ile | Glu | Arg | Leu | Val | Ser | Tyr | Tyr | Phe | Leu | Arg | Phe |
|     |     |     |     | 100 |     |     |     |     | 105 |     |     |     | 110 |     |

| Gly | Ser | Asp | Lys | Arg | Pro | Gly | Leu | Arg | Met | Arg | Lys | Gln | Gly | Asp | Lys |
|     |     |     | 115 |     |     |     |     | 120 |     |     |     |     | 125 |     |     |

| Lys | Thr | Phe | Asp | Glu | Cys | Val | Ala | Glu | Gly | Gly | Ser | Asp | Cys | Ala | Pro |
| 130 |     |     |     |     | 135 |     |     |     |     | 140 |     |     |     |     |     |

| Glu | Lys | Leu | Trp | Leu | Gln | Ile | Pro | Phe | Phe | Cys | Gly | His | Ser | Ser | Glu |
| 145 |     |     |     |     | 150 |     |     |     |     | 155 |     |     |     |     | 160 |

| Cys | Trp | Asn | Val | Gly | Ser | Arg | Trp | Ala | Met | Asp | Gln | Ala | Lys | Tyr | Asn |
|     |     |     |     | 165 |     |     |     |     | 170 |     |     |     |     | 175 |     |

| Leu | Ile | Asn | Glu | Tyr | Phe | Leu | Val | Gly | Val | Thr | Glu | Glu | Leu | Glu | Asp |
|     |     |     |     | 180 |     |     |     |     | 185 |     |     |     | 190 |     |     |

| Phe | Ile | Met | Leu | Leu | Glu | Ala | Ala | Leu | Pro | Arg | Phe | Arg | Gly | Ala |
|     |     |     | 195 |     |     |     |     | 200 |     |     |     |     | 205 |     |

| Thr | Glu | Leu | Tyr | Arg | Thr | Gly | Lys | Lys | Ser | His | Leu | His | Lys | Thr | Thr |
|     | 210 |     |     |     |     | 215 |     |     |     |     | 220 |     |     |     |     |

| Glu | Lys | Lys | Leu | Pro | Thr | Lys | Gln | Thr | Ile | Ala | Lys | Leu | Gln | Gln | Ser |
| 225 |     |     |     |     | 230 |     |     |     |     | 235 |     |     |     |     | 240 |

| Asp | Ile | Trp | Lys | Met | Glu | Asn | Glu | Phe | Tyr | Glu | Phe | Ala | Leu | Glu | Gln |
|     |     |     |     | 245 |     |     |     |     | 250 |     |     |     |     | 255 |     |

| Phe | Gln | Phe | Ile | Arg | Ala | His | Ala | Val | Arg | Glu | Lys | Asp | Gly | Asp | Leu |
|     |     |     |     | 260 |     |     |     |     | 265 |     |     |     | 270 |     |     |

| Tyr | Ile | Leu | Ala | Gln | Asn | Phe | Phe | Tyr | Glu | Lys | Ile | Tyr | Pro | Lys | Ser |
|     |     |     | 275 |     |     |     |     | 280 |     |     |     |     | 285 |     |     |

Asn

<210> SEQ ID NO 70
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 1

<400> SEQUENCE: 70

Met Lys Tyr Tyr Phe Pro Val Arg Glu Leu Glu Arg Ser Leu Arg Phe
1               5                   10                  15
Asp Met Lys Gly Asp Asp Val Ile Val Phe Leu His Ile Gln Lys Thr
            20                  25                  30
His Gly Thr Thr Phe Gly Arg His Leu Val Gln Asn Val Arg Leu Glu
        35                  40                  45
Val Pro Cys Asp Cys Arg Pro Gly Gln Lys Lys Cys Thr Cys Tyr Arg
    50                  55                  60
Pro Asn Arg Arg Glu Thr Trp Leu Phe Ser Arg Phe Ser Thr Gly Trp
65                  70                  75                  80
Ser Cys Gly Leu His Ala Asp Trp Thr Glu Leu Thr Asn Cys Val Pro
                85                  90                  95
Gly Val Leu Asp Arg Arg Asp Pro Ala Gly Leu Arg Ser Pro Arg Lys
            100                 105                 110
Phe Tyr Tyr Ile Thr Leu Leu His Leu Pro Val His Arg Tyr Leu Ser
        115                 120                 125
Glu Trp Arg His Val Gln Arg Gly Ala Thr Trp Lys Thr Ser Leu His
    130                 135                 140
Met Cys Asp Gly Arg Thr Pro Thr Pro Glu Glu Leu Pro Pro Cys Tyr
145                 150                 155                 160
Glu Gly Thr Asp Trp Ser Gly Cys Thr Leu Gln Glu Phe Met Asp Cys
                165                 170                 175
Pro Tyr Asn Leu Ala Asn Asn Arg Gln Val Arg Met Leu Ala Asp Leu
            180                 185                 190
Ser Leu Val Gly Cys Tyr Asn Leu Ser Phe Ile Pro Glu Ser Lys Arg
        195                 200                 205
Ala Gln Leu Leu Leu Glu Ser Ala Lys Lys Asn Leu Arg Gly Met Ala
    210                 215                 220
Phe Phe Gly Leu Ala Trp Phe Gly Arg Lys Thr Gln Tyr Leu Phe Glu
225                 230                 235                 240
Arg Thr Phe Asn Leu Lys Phe Ile Arg Pro Phe Met Gln Val Lys Ser
                245                 250                 255
Ser Arg Ala Ser Gly Val Glu Val Asp Glu Asp Thr Ile Arg His Ile
            260                 265                 270
Glu Glu Leu Asn Asp Leu Asp Met Gln Leu Tyr Asp Tyr Ala Lys Asp
        275                 280                 285
Leu Phe Gln Gln Arg Tyr Gln Tyr Lys Arg Gln Leu Glu Arg Arg Glu
    290                 295                 300
Gln Arg Leu Arg Asn Arg Glu Glu
305                 310

<210> SEQ ID NO 71
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 1

<400> SEQUENCE: 71
atgaagtact attttccggt ccgcgaattg gagcgctctc tgcgtttcga catgaaaggg      60
gatgacgtta ttgtattttt gcatatccag aagacgcacg ggacaacatt tggacgccat     120
ttagtgcaga acgtccgctt ggaagtacca tgcgattgtc gcccaggtca gaaaaaatgc     180

```
acatgttatc gcccaaaccg tcgtgaaact tggctgttca gccgcttttc taccggatgg    240
tcatgcggcc ttcatgcaga ctggacggaa ttgaccaatt gtgtcccagg agtcttggac    300
cgtcgtgacc cggcgggctt gcgtagccct cgtaaattct attatattac tttgttacac    360
ttacctgttc accgctactt gtccgagtgg cgtcatgtcc agcgcggtgc aacatggaaa    420
acctccctgc acatgtgtga cggtcgtacc ccgacaccgg aggaattacc tccgtgctac    480
gagggaaccg attggagtgg ttgcacccct caagagttca tggactgtcc gtacaattta    540
gctaacaacc gccaagtccg tatgcttgct gacttaagtc tggtcggttg ttacaacctg    600
agctttattc ccgaatcgaa acgtgctcaa ctgcttctgg agtctgccaa aaagaatctg    660
cgtggaatgg ccttcttcgg cttggcttgg ttcggtcgca agacgcaata tttatttgaa    720 cgcacccttta acttgaaatt tatccgcccg ttcatgcagg taaagagtag tcgtgctagt    780
ggcgttgagg ttgacgagga tacgattcgt catatcgaag aattgaatga cttagacatg    840
cagctgtatg actacgccaa agacctgttc cagcagcgct accagtacaa acgtcagttg    900
gagcgccgcg agcagcgttt acgcaatcgt gaggaataa                          939
```

<210> SEQ ID NO 72
<211> LENGTH: 295
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 2

<400> SEQUENCE: 72

```
Met Lys Gly Asp Asp Val Ile Val Phe Leu His Ile Gly His Thr Gly
1               5                   10                  15

Gly Thr Thr Phe Gly Arg His Leu Val Gln Asn Val Arg Leu Glu Val
            20                  25                  30

Pro Cys Asp Cys Arg Pro Gly Gln Lys Lys Cys Thr Cys Tyr Arg Pro
        35                  40                  45

Asn Arg Arg Glu Thr Trp Leu Phe Ser Arg Phe Ser Thr Gly Trp Ser
    50                  55                  60

Cys Gly Thr Asn Ala Asp Trp Thr Glu Leu Thr Asn Cys Val Pro Gly
65                  70                  75                  80

Val Leu Asp Arg Arg Asp Pro Ala Gly Leu Arg Ser Pro Arg Lys Phe
                85                  90                  95

Tyr Tyr Ile Thr Leu Leu Arg Asp Pro Val Ser Arg Tyr Leu Ser Ala
            100                 105                 110

Trp Arg His His Gln Arg Gly Gly Ser Asn Lys Thr Ser Leu His Met
        115                 120                 125

Cys Asp Gly Arg Thr Pro Thr Pro Glu Glu Leu Pro Pro Cys Tyr Glu
    130                 135                 140

Gly Thr Asp Trp Ser Gly Cys Thr Leu Gln Glu Phe Met Asp Cys Pro
145                 150                 155                 160

Tyr Asn Leu Gly Asn Asn Arg Gln Val Arg Met Leu Ala Asp Leu Ser
                165                 170                 175

Leu Val Gly Cys Tyr Asn Leu Ser Phe Ile Pro Glu Ser Lys Arg Ala
            180                 185                 190

Gln Leu Leu Leu Glu Ser Ala Lys Lys Asn Leu Arg Gly Met Ala Phe
        195                 200                 205

Phe Gly Leu Thr Glu Phe Gln Arg Lys Thr Gln Tyr Leu Phe Glu Arg
    210                 215                 220
```

```
Thr Phe Asn Leu Lys Phe Ile Arg Pro Phe Met Gln Tyr Asn Ser Thr
225                 230                 235                 240

Arg Ala Gly Gly Val Glu Val Asp Glu Asp Thr Ile Arg His Ile Glu
            245                 250                 255

Glu Leu Asn Asp Leu Asp Met Gln Leu Tyr Asp Tyr Ala Lys Asp Leu
            260                 265                 270

Phe Gln Gln Arg Tyr Gln Tyr Lys Arg Gln Leu Glu Arg Arg Glu Gln
            275                 280                 285

Arg Leu Arg Asn Arg Glu Glu
    290                 295
```

<210> SEQ ID NO 73
<211> LENGTH: 888
<212> TYPE: DNA
<213> ORGANISM: Artificial Sequence
<220> FEATURE:
<223> OTHER INFORMATION: Polynucleotide sequence encoding for engineered glucosaminyl 6-O sulfotransferase mutant_sulfatase 2

<400> SEQUENCE: 73

```
atgaaaggcg acgacgtcat tgtattcctg catattggtc atacaggcgg aactacgttc    60
ggacgtcact tagttcaaaa tgtgcgtctg gaggtaccct gtgattgtcg tccaggacag   120
aaaaagtgca cttgttaccg ccctaatcgc cgtgagacgt ggctgttttc tcgttttagc   180
acaggctgga gttgcggcac gaacgccgac tggaccgagc ttacgaattg cgtaccaggt   240
gttttagatc gtcgtgatcc tgccggactt cgctccccgc gtaagtttta ctacatcacg   300
ttgcttcgcg acccagttag ccgctatttg agcgcttggc gtcaccatca acgcggggcc   360
tccaacaaga cttctttgca catgtgcgac gggcgcacgc cgacaccaga agaacttccg   420
ccgtgttatg aagggacgga ctggtctggt tgtaccctct aagagttcat ggattgcccg   480
tacaatctgg gcaataatcg tcaagtacgc atgttagcag accttagcct gtagggtgc    540
tacaatttga gctttatccc tgagagtaaa cgtgctcagc tttttattaga gtccgccaaa   600
aagaatttac gtggtatggc atttttcgga ttgaccgagt tccagcgcaa acccaatac    660
ttattcgaac gcacgtttaa cttgaaattc attcgtcctt tcatgcaata taattctacc   720
cgcgcggggg gcgtagaggt ggatgaggat acgatccgcc atatcgagga gcttaacgat   780
ttggacatgc agttatacga ctacgcgaaa gacttatttc aacaacgcta tcagtacaag   840
cgtcagcttg aacgccgcga gcagcgttta cgcaatcgtg aggaataa              888
```

<210> SEQ ID NO 74
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase mutant_sulfatase 3

<400> SEQUENCE: 74

```
Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Ser His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60
```

```
Pro Asn Arg Arg Glu Thr Trp Leu Phe Ser Arg Phe Ser Thr Gly Trp
 65                 70                  75                  80

Ser Cys Gly Thr Arg Ala Asp Trp Thr Glu Leu Thr Asn Cys Val Pro
             85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Ser
        115                 120                 125

Ala Trp Arg His His Gln Arg Gly Gly Thr Asn Lys Thr Ser Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Gly Ser Lys Arg
        195                 200                 205

Ala Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Arg Glu
    290                 295                 300

Gln Arg Leu Arg Asn Arg Glu Glu
305                 310
```

<210> SEQ ID NO 75
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 3

<400> SEQUENCE: 75

```
atgaagtact attttccggt ccgcgaattg gagcgcagcc ttcgcttcga catgaaaggt    60
gatgatgtca tcgtattcct tcacatttca cacacaggcg gtactacttt cgggcgtcat   120
cttgtccaga atgttcgctt agaggtacca tgcgattgtc gtcccggaca aaagaaatgt   180
acttgctatc gtccgaaccg ccgtgaaaca tggcttttca gccgtttctc accggatgg    240
tcatgtggca ctcgcgcaga ttggacggaa ctgacaaatt gcgttccagg cgttttggac   300
cgtcgtgacc cggccggtct tcgttcgcct cgtaagtttt attatatcac ccttttgcgc   360
gatcccgtgt cgcgttatct gagtgcttgg cgccaccacc aacgtggtgg taccaacaag   420
acatcactgc acatgtgtga tggtcgtact ccaacgcccg aagagctgcc cccttgctat   480
gaaggtacag attggtcggg gtgtactctt caggagttca tggactgtcc ctataatctg   540
gctaataatc gccaggtgcg tatgctggca gaccttagtc tggtcggttg ttacaacctg   600
```

```
agtttcatcc cgaaagtaa gcgtgcacaa ctgctttggg aaagcgccaa aaagaacctt    660
cgcggaatgg cttttttcgg tttgaccgaa tttcagcgca agactcagta cctgtttgag    720
cgtacattca acttaaagtt tattcgtccg tttatgcaat acaattccac acgcgcagga    780
ggtgtagagg ttgacgaaga cacaatccgt cacattgaag aattaaatga cttagatatg    840
cagctttacg attatgctaa agacctgttc cagcaacgtt atcagtacaa acgtcaactt    900
gaacgccgcg agcagcgttt acgcaatcgt gaggaataa                           939
```

<210> SEQ ID NO 76
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase mutant_sulfatase 4

<400> SEQUENCE: 76

```
Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Ala His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
50                  55                  60

Pro Asn Arg Arg Glu Thr Trp Leu Phe Ser Arg Phe Ser Thr Gly Trp
65                  70                  75                  80

Ser Cys Gly Thr Arg Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Ser
        115                 120                 125

His Trp Arg His Met Gln Arg Gly Ala Asn Asn Ser Thr Gly Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Gly Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Arg Glu
    290                 295                 300
```

Gln Arg Leu Arg Asn Arg Glu Glu
305                 310

<210> SEQ ID NO 77
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 4

<400> SEQUENCE: 77
atgaagtact attttccggt ccgcgaattg gagcgctcct tacgtttcga tatgaaaggc      60
gacgacgtca ttgttttttct tcacattgct catacgggag gtacgacctt tggacgccat    120
ttagtgcaaa atgtccgttt agaggtaccc tgtgattgcc gtccaggtca aaagaaatgt    180
acgtgctatc gtcctaatcg tcgtgagact tggcttttta gccgtttctc cactggatgg    240
tcctgcggaa ctcgtgcgga ttggactgag ttaactaatt gtgtaccggg ggtgttggac    300
cgtcgtgacc ctgccggcct gcgtagtccg cgcaaatttt attacattac gttgcttcgc    360
gaccctgtga gccgctacct gtcccattgg cgtcacatgc aacgtggcgc aaacaactct    420
acaggcttgc acatgtgcga cggtcgtact ccaacgcctg aagaattgcc accatgttac    480
gagggcactg actggagtgg ctgcacttta caggaattta tggattgccc ctataatctg    540
ggtaataatc gtcaggtgcg tatgctggcg gatctgtcgt ggtaggatg ttacaacctt    600 tcgtttatcc ctgaatcaaa acgcgcgcag ctttttacttg agtcggcgaa aaagaattta    660
cgcggtatgg cctttttttgg gcttaccgag ttccagcgca agacacagta tttgtttgag    720
cgcacgttca acttaaaatt tattcgcccc tttatgcaat acaattctac acgcgccggt    780
ggagtggagg ttgatgagga tacgatccgc cacatcgagg aactgaatga cctggacatg    840
caattatacg attatgcgaa agatctttttt cagcaacgct accaatacaa acgccaactt    900
gaacgccgcg agcagcgttt acgcaatcgt gaggaataa                            939

<210> SEQ ID NO 78
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 5

<400> SEQUENCE: 78

Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Thr Gln Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

```
Phe Tyr Tyr Ile Thr Leu Leu Arg Asp Pro Val Ser Arg Tyr Leu Ser
            115                 120                 125

Ala Trp Arg His His Gln Arg Gly Gly Thr Asn Lys Thr Ser Leu His
130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Glu
    290                 295                 300

Gln Arg Leu Arg Asn Arg Glu Glu
305                 310
```

<210> SEQ ID NO 79
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 5

<400> SEQUENCE: 79

```
atgaagtact attttccggt ccgcgaattg gagcgctcct tacgtttcga catgaaaggc      60
gacgatgtaa tcgtgttcct tcatattggg cacaccgggg gcaccacatt tggccgccat     120
ctggtccaaa acgtccgttt agaggttccg tgtgactgcc gtcccggtca gaaaaaatgc     180
acctgctatc gccctaaccg ccgtgaaacc tggttgttct ctcgcttttc tactggctgg     240
tcgtgcggga cccaggctga ctggaccgag ttgacaaatt gcgtgcccgg tgttcttgat     300
cgtcgcgacc ctgcaggctt acgttcacca cgtaagtttt actacatcac gcttcttcgt     360
gatcccgtca gccgctatct tagtgcatgg cgtcatcacc aacgtggggg tactaacaaa     420
acttcattgc acatgtgcga cgggcgcacc cctacgccag aagaacttcc cccatgttat     480
gaagggacag attggagtgg ctgcacccctt caggagttta tggactgtcc gtataattta     540
gcaaataacc gtcaagtgcg tatgttagcg gatcttagtc tggtggggtg ttacaatttg     600
tcctttatcc ctgagagtaa gcgtgcccag ttgttgttgg agagtgcgaa gaaaaacttg     660
cgtgggatgg cgttcttcgg tctgactgaa tttcaacgta aaacgcagta tttgttcgaa     720
cgcactttca atttaaagtt tatccgtccc tttatgcagt acaatagcac gcgtgcaggc     780
ggcgtagaag tggatgagga caccattcgc catatcgaag aattaaacga tctggacatg     840
cagttatacg actatgctaa ggacttgttt cagcagcgct accaatataa acgccaactt     900
```
gaacgccgcg agcagcgttt acgcaatcgt gaggaataa         939

```
<210> SEQ ID NO 80
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 6

<400> SEQUENCE: 80
```

Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Ser His Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Ser
        115                 120                 125

Ala Trp Arg His His Gln Arg Gly Pro Ala Asn Thr Thr Gly Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Arg Glu
    290                 295                 300

Gln Arg Leu Arg Asn Arg Glu Glu
305                 310

```
<210> SEQ ID NO 81
<211> LENGTH: 939
<212> TYPE: DNA
<213> ORGANISM: Artificial Sequence
```

<220> FEATURE:
<223> OTHER INFORMATION: Polynucleotide sequence encoding for engineered
     glucosaminyl 6-O sulfotransferase mutant_sulfatase 6

<400> SEQUENCE: 81

```
atgaagtact attttccggt ccgcgaattg gagcgctcac ttcgcttcga catgaaggga    60
gacgatgtaa tcgtcttcct tcacatcggg catacaggcg ggacgacttt cgggcgtcat   120
ttggtacaaa acgtacgttt agaggttccc tgtgattgcc gccctggaca aaagaaatgt   180
acctgctacc gcccgaaccg tcgtgaaaca tggttgttta gtcgcttctc gactggatgg   240
tcgtgcggct cccatgctga ttggacggag cttaccaatt gtgtgccagg tgtattagac   300
cgtcgtgacc cagcagggct gcgtagccca cgcaaattct attatattac attgcttcgc   360
gaccccgtgt cacgttatct gagcgcctgg cgtcaccatc aacgtggtcc tgcaaacacg   420
actggacttc acatgtgtga tggccgtacc cccacacccg aagagctgcc accgtgttac   480
gagggcacgg actggtctgg ctgtactctg caagaattta tggactgccc ctataattta   540
gctaacaacc gccaagtccg tatgctggct gacctgagct tggttggttg ctataatctt   600
agttttatcc cagaaagtaa acgcgcacaa ctgttattag aatctgcaaa gaaaaactta   660
cgcgggatgg cattttttgg cttgaccgaa tttcaacgca agacacaata ccttttcgaa   720
cgcaccttta atcttaaatt catccgtccc ttcatgcagt acaatagtac tcgtgcgggg   780
ggtgtcgaag tcgacgaaga tacgattcgc cacatcgaag aactgaacga cctggacatg   840
caattatacg attatgctaa agacttattt caacaacgtt accaatacaa gcgtcaactt   900
gaacgccgcg agcagcgttt acgcaatcgt gaggaataa                          939
```

<210> SEQ ID NO 82
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
     mutant_sulfatase 7

<400> SEQUENCE: 82

```
Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Thr Arg Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Ser
        115                 120                 125

Ala Trp Arg His His Gln Arg Gly Gly Thr Asn Lys Thr Ser Leu His
    130                 135                 140

Met Cys Asp Gly Arg Thr Pro Thr Pro Glu Glu Leu Pro Pro Cys Tyr
145                 150                 155                 160
```

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Arg Glu
    290                 295                 300

Gln Arg Leu Arg Asn Arg Glu Glu
305                 310

<210> SEQ ID NO 83
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 7

<400> SEQUENCE: 83
atgaagtact attttccggt ccgcgaattg gagcgtagct acgcttcga catgaaaggt      60 gacgatgtga ttgtcttcct gcacatcggt cataccgggg gtacaacgtt cggtcgccac    120
ttagtccaaa atgttcgctt ggaggttcct tgcgattgtc gtccagggca gaagaaatgt    180
acatgttacc gtcccaaccg tcgtgagact tggttattta gtcgcttttc gactggctgg    240
tcctgcggca cgcgcgcaga ttggactgaa ctgacaaatt gtgtaccagg agtgttggat    300
cgtcgtgatc ccgccggatt acgctctccg cgtaagttct attacattac tttgctgcgc    360
gatccagtgt cacgctattt gtcggcatgg cgtcatcacc agcgtggcgg tacgaacaag    420
acgtccttgc acatgtgtga tggacgcact cccaccccgg aggagctgcc cccatgctac    480
gaagggactg attggagtgg tgtatacatta caggaattta tggactgccc gtacaacctt    540
gccaataacc gccaagtacg catgctggca gatttgagcc tggtcggttg ctataaccct    600
tcttttatcc cagaatctaa agcgtgctcaa cttttattgg agagtgcgaa gaagaattta    660
cgcggaatgg ccttttttgg cctgacagaa ttccaacgca aacccaata tttattcgag     720 cgcacgttta acttgaagtt cattcgtcct ttcatgcaat ataatagcac acgtgccggg    780
ggagtcgagg tcgacgaaga tactattcgt catattgaag agctgaatga tcttgacatg    840
caactttacg attacgccaa ggatttgttt caacagcgct accaatacaa gcgtcaactt    900
gaacgccgcg agcagcgttt acgcaatcgt gaggaataa                           939

<210> SEQ ID NO 84
<211> LENGTH: 312
<212> TYPE: PRT
<213> ORGANISM: Artificial Sequence
<220> FEATURE:

<223> OTHER INFORMATION: Engineered glucosaminyl 6-O sulfotransferase
       mutant_sulfatase 8

<400> SEQUENCE: 84

Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Ser His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Thr Asn Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Ser
        115                 120                 125

Ala Trp Arg His His Gln Arg Gly Gly Asn Lys Thr Ser Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Arg Glu
    290                 295                 300

Gln Arg Leu Arg Asn Arg Glu Glu
305                 310

<210> SEQ ID NO 85
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 8

<400> SEQUENCE: 85
atgaagtact attttccggt ccgcgaattg gagcgctcat tgcgtttcga tatgaagggc       60
gacgacgtga tcgtgttttt acacatctcc cacactggag gcaccacttt tggccgtcat      120

```
ttggttcaga atgtacgtct ggaggtacca tgtgactgtc gtcctggaca aaaaaaatgc      180
acttgttatc gcccgaaccg tcgtgaaact tggctgttct ctcgcttttc aaccggatgg      240
tcgtgtggga caaatgcgga ctggacagag cttacaaatt gtgttccgg cgtgttggac       300 cgtcgcgatc ctgcgggatt gcgttcgccg cgcaagttct actacattac cttactgcgc      360
gatccggtat cccgttacct gtcagcctgg cgccatcacc agcgtggcgg cggaaataaa      420
acgtcgttac acatgtgcga tggtcgtacg ccaacacccg aggaattgcc tccatgttat      480
gagggcacgg actggtccgg ctgcacactt caagagttta tggactgccc atataattta      540
gcaaataatc gccaagttcg catgttggct gacttgagcc ttgtcggctg ttacaattta      600
tcattcattc ccgaatcgaa gcgtgctcag ctgctgcttg aaagtgcaaa gaaaaatttg      660
cgtggcatgg cgtttttgg tttaacggaa tttcaacgta aaacacaata tttgttcgag        720
cgtacgttta accttaaatt catccgcccc ttcatgcagt ataattcaac acgcgctggt      780
ggagtggagt tgatgaaga cacaattcgt catattgagg agcttaacga cttagatatg       840
cagttgtatg attacgcaaa ggatttattc caacagcgtt atcagtacaa gcgtcagctt      900
gaacgccgcg agcagcgttt acgcaatcgt gaggaataa                              939

<210> SEQ ID NO 86
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 9

<400> SEQUENCE: 86

Met Lys Tyr Tyr Phe Pro Val Arg Glu Leu Glu Arg Ser Leu Arg Phe
1               5                   10                  15

Asp Met Lys Gly Asp Asp Val Ile Val Phe Leu Gly Ile Ala His Thr
            20                  25                  30

Gly Gly Ala Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Gly
65                  70                  75                  80

Ser Cys Gly Ala Asn Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Ser
        115                 120                 125

Met Trp Arg His His Gln Arg Gly Ala Thr His Lys Thr Ser Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205
```

Ala Gln Leu Leu Leu Glu Ser Ala Lys Lys Asn Leu Arg Gly Met Ala
        210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Arg Glu
290                 295                 300

Gln Arg Leu Arg Asn Arg Glu Glu
305                 310

<210> SEQ ID NO 87
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 9

<400> SEQUENCE: 87
atgaagtact attttccggt ccgcgaattg gagcgctcat tgcgttttga tatgaaagga      60
gacgacgtca tcgtattttt gggcattgcc catacgggag gcgcgacatt cggacgccac    120
ctggtccaaa acgttcgcct ggaagttccc tgtgactgtc gcccaggtca agaagtgt      180 acgtgctatc gccccaaccg ccgtgagacg tggcttttt cgcgtttctc cactggtggc    240
tcctgtgggg caaatgccga ctggactgag ttgacaaatt gcgtgccagg tgttctggat    300
cgccgcgacc ccgccggact tcgctcacca cgtaagtttt attacatcac tttgttgcgc    360
gacccagtgt cccgttacct gtctatgtgg cgtcaccatc agcgtggtgc gacacataaa    420
acgtcgctgc acatgtgcga tggacgcacg ccgactccag aggagttgcc tccatgctac    480
gagggcacgg attggagcgg ctgcactttg caagagttta tggattgccc ttataatttg    540
gcgaacaacc gtcaagtgcg tatgttagct gatttgagtt tagttggctg ctacaatctt    600
tcctttattc ccgaatcaaa acgcgctcag ctgctgttgg agagtgcgaa gaagaacctt    660
cgcgggatgg cattttttgg ccttacagag tttcaacgca agactcagta tttgtttgag    720
cgtacgttca atttgaaatt catccgtcct tttatgcagt ataatagcac ccgcgccggc    780
ggcgttgaag tagatgagga cactattcgt cacattgaag agcttaatga tctggacatg    840
cagttatatg actatgcaaa agatttattt caacagcgct atcagtacaa acgtcaactt    900
gaacgccgcg agcagcgttt acgcaatcgt gaggaataa                           939

<210> SEQ ID NO 88
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 10

<400> SEQUENCE: 88

Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gly His Thr

```
                      20                  25                  30
Gly Gly Thr Thr Phe Gly Arg His Leu Val Gln Asn Val Arg Leu Glu
                  35                  40                  45
Val Pro Cys Asp Cys Arg Pro Gly Gln Lys Lys Cys Thr Cys Tyr Arg
 50                  55                  60
Pro Asn Arg Arg Glu Thr Trp Leu Phe Ser Arg Phe Ser Thr Gly Trp
 65                  70                  75                  80
Ser Cys Gly Thr Arg Ala Asp Trp Thr Glu Leu Thr Asn Cys Val Pro
                  85                  90                  95
Gly Val Leu Asp Arg Arg Asp Pro Ala Gly Leu Arg Ser Pro Arg Lys
                 100                 105                 110
Phe Tyr Tyr Ile Thr Leu Leu Arg Asp Pro Val Ser Arg Tyr Leu Ser
                 115                 120                 125
Ala Trp Arg His His Gln Arg Gly Ala Ser Asn Ser Thr Ser Leu His
                 130                 135                 140
Met Cys Asp Gly Arg Thr Pro Thr Pro Glu Glu Leu Pro Pro Cys Tyr
145                 150                 155                 160
Glu Gly Thr Asp Trp Ser Gly Cys Thr Leu Gln Glu Phe Met Asp Cys
                 165                 170                 175
Pro Tyr Asn Leu Gly Asn Asn Arg Gln Val Arg Met Leu Ala Asp Leu
                 180                 185                 190
Ser Leu Val Gly Cys Tyr Asn Leu Ser Phe Ile Pro Glu Ser Lys Arg
                 195                 200                 205
Ala Gln Leu Leu Leu Glu Ser Ala Lys Lys Asn Leu Arg Gly Met Ala
                 210                 215                 220
Phe Phe Gly Leu Thr Glu Phe Gln Arg Lys Thr Gln Tyr Leu Phe Glu
225                 230                 235                 240
Arg Thr Phe Asn Leu Lys Phe Ile Arg Pro Phe Met Gln Tyr Asn Ser
                 245                 250                 255
Thr Arg Ala Gly Gly Val Glu Val Asp Glu Asp Thr Ile Arg His Ile
                 260                 265                 270
Glu Glu Leu Asn Asp Leu Asp Met Gln Leu Tyr Asp Tyr Ala Lys Asp
                 275                 280                 285
Leu Phe Gln Gln Arg Tyr Gln Tyr Lys Arg Gln Leu Glu Arg Arg Glu
                 290                 295                 300
Gln Arg Leu Arg Asn Arg Glu Glu
305                 310

<210> SEQ ID NO 89
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 10

<400> SEQUENCE: 89
atgaagtact attttccggt ccgcgaatta gagcgctcat tgcgttttga catgaagggg      60
gatgacgtta ttgtgttcct tcatatcggc cacacaggcg ggactacgtt cggtcgccat     120
cttgtgcaga atgtccgttt ggaggtacct tgtgactgcc gtccggggca gaaaaaatgt     180
acctgctatc gcccaaatcg ccgtgaaacg tggttattct ctcgttttag tactggatgg     240
tcgtgtggaa cccgcgctga ctggacagag cttacaaact gcgtaccagg cgtgctggac     300
cgccgtgacc ctgcgggtct tcgtagtccc cgcaagttct attatattac tcttcttcgt     360
```

```
gatccagtaa gccgttatct gagtgcttgg cgccatcacc aacgcggtgc ttcaaattcc      420
acaagccttc acatgtgcga tgggcgtact ccgaccccgg aagagcttcc gccctgttac      480
gaaggtacag attggtccgg ttgtacgctg caggaattta tggactgtcc atacaactta      540
ggcaacaatc gccaggtacg catgcttgcg gatctgagtc tggtcggttg ctacaacttg      600
tcttttatcc agaatctaa acgcgcccaa ttactgttag aaagtgcgaa gaagaaccttt     660 cgtggcatgg ccttctttgg acttacggag ttccagcgta agactcaata cctgttcgag      720
cgtacattta atcttaaatt cattcgtcca ttcatgcaat ataattctac gcgcgcaggc      780
ggcgtggagg tcgatgaaga tacgatccgt catatcgagg aactgaatga tctggacatg      840
cagttatatg actacgcgaa agaccttttc caacagcgct accaatacaa gcgtcaatta      900
gagcgccgtg agcagcgttt acgcaatcgt gaggaataa                             939
```

<210> SEQ ID NO 90
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase mutant_sulfatase 11

<400> SEQUENCE: 90

```
Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gln Lys Thr
            20                  25                  30

His Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Leu His Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu His His Pro Val His Arg Tyr Leu Ser
        115                 120                 125

Glu Trp Arg His Val Gln Arg Gly Ala Thr Trp Lys Thr Ser Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Ala Trp Phe Gly Arg Lys Thr Gln Tyr Leu Phe Glu
225                 230                 235                 240

Arg Thr Phe Asn Leu Lys Phe Ile Arg Pro Phe Met Gln Val Lys Ser
                245                 250                 255
```

```
Ser Arg Ala Ser Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Arg Glu
    290                 295                 300

Gln Arg Leu Arg Asn Arg Glu Glu
305                 310

<210> SEQ ID NO 91
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 11

<400> SEQUENCE: 91
atgaagtact attttccggt ccgcgaattg gagcgctcat tgcgttttga tatgaaaggt    60
gacgacgtaa ttgtgtttct tcatattcag aagacccatg gcacaacatt tggtcgccat   120
cttgtgcaaa atgtgcgttt agaggtgccg tgtgactgcc gtccaggtca aaagaaatgc   180
acctgctatc gtccaaatcg tcgcgaaacg tggcttttct cccgtttcag cacgggttgg   240
tcctgcggct acatgcgga ctggactgaa ctgacaaact gtgtgccagg agtgcttgat   300
cgccgcgatc cagcggggct tcgctcgccg cgcaagtttt actatatcac ccttctgcac   360
catccggtac accgctattt gagcgagtgg cgtcacgtcc agcgcgggc aacgtggaag   420 accagtttac acatgtgcga cggacgtacc cctacacccg aagagcttcc gccatgctat   480
gaagggacgg attggagtgg ctgtacgtta caggagttca tggattgtcc ctataatctg   540
gccaataatc gtcaagtgcg tatgttagcc gacctttcac tggttggttg ctataactta   600
tcattcattc cggagtctaa acgcgctcag cttttgcttg aatctgccaa aaagaatctt   660
cgtgggatgg ctttctttgg tttagcctgg tttgggcgca aaactcaata cttattcgag   720
cgtactttta atttgaaatt tattcgtccc tttatgcaag ttaagagtag ccgtgcatct   780
ggagtagagg tagacgaaga cactattcgt cacatcgagg agcttaatga tttggatatg   840
cagctgtacg attatgctaa agacttgttc aacagcgttt atcagtataa gcgtcagctt   900
gaacgccgcg agcagcgttt acgcaatcgt gaggaataa                          939

<210> SEQ ID NO 92
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 12

<400> SEQUENCE: 92

Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gln Lys Thr
            20                  25                  30

His Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
```

```
                65                  70                  75                  80
Ser Cys Gly Leu His Ala Asp Trp Thr Glu Leu Thr Asn Cys Val Pro
                        85                  90                  95

Gly Val Leu Asp Arg Arg Asp Pro Ala Gly Leu Arg Ser Pro Arg Lys
                100                 105                 110

Phe Tyr Tyr Ile Thr Leu Leu His Pro Val His Arg Tyr Leu Ser
            115                 120                 125

Glu Trp Arg His Val Gln Arg Gly Ala Thr Trp Lys Thr Ser Leu His
        130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Gly Trp Phe Gly Arg Lys Thr Gln Tyr Leu Phe Glu
225                 230                 235                 240

Arg Thr Phe Asn Leu Lys Phe Ile Arg Pro Phe Met Gln Val Lys Ser
                245                 250                 255

Asn Arg Ala Ser Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Glu
    290                 295                 300

Gln Arg Leu Arg Asn Arg Glu Glu
305                 310

<210> SEQ ID NO 93
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 12

<400> SEQUENCE: 93
atgaagtact attttccggt ccgcgaattg gagcgctcat tgcgtttcga catgaaaggt     60
gatgacgtaa tcgtatttct gcatatccaa aagacacatg cacaactttt ggacgccat   120 ctggtccaga acgtccgtct ggaggttccg tgtgactgtc gtcccggtca aagaaatgc    180 acatgctacc gtccaaatcg ccgtgagaca tggctttttt cccgctttag cacgggctgg   240
agctgcggct tacatgctga ctggaccgag cttactaact gtgtccccgg ggtccttgac   300
cgccgtgatc ctgctgggtt gcgctcacct cgcaaatttt attatatcac cttattgcac   360
catccagttc accgttactt gtcggaatgg cgtcacgtcc agcgtggagc gacttggaaa   420
acgtctcttc acatgtgtga tggccgtaca cccacgcccg aagagcttcc gccatgctat   480
gaaggcactg attggtcagg gtgcaccctt caagaattca tggattgccc atacaactta   540
gccaacaatc gccaggttcg tatgttagcg gatttgtcgt tagtaggttg ctacaatctg   600
tcttttattc ccgaatcgaa gcgcgctcaa ctgttgttag agtccgcgaa gaaaaatttg   660
```

```
cgtggtatgg cgttttttgg cttgggatgg tttgggcgta agactcagta tcttttcgaa    720 cgtacttttta atcttaagtt tattcgcccc ttcatgcaag ttaagtcaaa ccgcgcctca    780
ggcgtagagg tagatgaaga cacgattcgt cacatcgaag agcttaatga cttagatatg    840
caactttatg actatgccaa agatttattt cagcagcgtt accaatacaa acgtcagctt    900
gaacgccgcg agcagcgttt acgcaatcgt gaggaataa                            939
```

```
<210> SEQ ID NO 94
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 13

<400> SEQUENCE: 94
```

Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gln Lys Thr
            20                  25                  30

His Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
50                  55                  60

Pro Asn Arg Arg Glu Thr Trp Leu Phe Ser Arg Phe Ser Thr Gly Trp
65                  70                  75                  80

Ser Cys Gly Leu His Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu His Lys Pro Val His Arg Tyr Leu Ser
        115                 120                 125

Glu Trp Arg His Val Gln Arg Gly Ala Thr Trp Lys Thr Ser Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Gly Trp Phe Gly Arg Lys Thr Gln Tyr Leu Phe Glu
225                 230                 235                 240

Arg Thr Phe Asn Leu Lys Phe Ile Arg Pro Phe Met Gln Val Lys Ser
                245                 250                 255

Ser Arg Ala Ser Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Arg Glu
    290                 295                 300

```
Gln Arg Leu Arg Asn Arg Glu Glu
305                 310
```

<210> SEQ ID NO 95
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 13

<400> SEQUENCE: 95

```
atgaagtact attttccggt ccgcgaattg gagcgctcat tgcgttttga tatgaagggt     60
gatgatgtta ttgttttttct gcacatccaa aagacacacg ggacaacctt cggacgccac   120
ttggtgcaga acgttcgcct ggaagtacca tgcgattgtc gtcccgggca aaagaaatgc   180
acctgttacc gtcccaatcg tcgtgagacg tggttattta gccgtttttc caccgggtgg   240
agctgtggac ttcacgcaga ctggacagag ttaaccaact gtgtaccgg tgttttggac    300
cgccgcgacc cagcggggct gcgttctcca cgtaaattct actatattac acttctgcat   360
aagcccgtac accgttatct gagtgaatgg cgtcacgtcc agcgcggggc gacctggaag   420
acgagcctgc acatgtgcga tggtcgtacg cccactcctg aagaattacc tccctgttat   480
gagggaactg actggtcagg gtgtacatta caggagttta tggactgtcc ctataatctt   540
gctaataatc gtcaagttcg catgcttgct gacttatcat tggtggggtg ctataattta   600
tcgttcattc ctgaaagcaa acgcgcccaa ttgcttcttg agtcggctaa gaagaactta   660
cgcggtatgg ctttctttgg tttgggctgg tttggacgta aaactcaata tttgttcgag   720
cgtacccttta acttaaagtt tatccgcccct tttatgcagg ttaaatccag ccgcgcatcg   780
ggagtagaag tcgatgagga tacgattcgc catatcgaag aattgaacga tctggacatg   840
caactttatg actacgctaa agatttattc caacaacgct atcagtataa acgccagctt   900
gaacgccgcg agcagcgttt acgcaatcgt gaggaataa                         939
```

<210> SEQ ID NO 96
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 14

<400> SEQUENCE: 96

```
Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gln Lys Thr
            20                  25                  30

His Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Leu His Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu His Asp Pro Val His Arg Tyr Leu Ser
```

```
            115                 120                 125
Glu Trp Arg His Val Gln Arg Gly Ala Thr Trp Lys Thr Ser Leu His
        130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Gly Arg Phe Gln Arg Lys Thr Gln Tyr Leu Phe Glu
225                 230                 235                 240

Arg Thr Phe Asn Leu Lys Phe Ile Arg Pro Phe Met Val Thr Asn Ser
                245                 250                 255

Ser Arg Ala Ser Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Arg Glu
    290                 295                 300

Gln Arg Leu Arg Asn Arg Glu Glu
305                 310
```

<210> SEQ ID NO 97
<211> LENGTH: 939
<212> TYPE: DNA
<213> ORGANISM: Artificial Sequence
<220> FEATURE:
<223> OTHER INFORMATION: Polynucleotide sequence encoding for engineered glucosaminyl 6-O sulfotransferase mutant_sulfatase 14

<400> SEQUENCE: 97

```
atgaagtact attttccggt ccgcgaattg gagcgctcat tgcgtttcga tatgaaaggg      60
gatgatgtta ttgtgttcct gcatattcaa aaaacgcatg cactacatt tggtcgtcat     120
ttagttcaga atgtgcgttt agaagtgccg tgtgactgtc gccctgggca gaaaaagtgc    180
acctgttacc gccctaatcg ccgtgagacg tggttgttca gtcgcttctc tactggctgg    240
tcgtgcggcc ttcatgccga ctggactgag cttacaaatt gcgttccagg tgtattagat    300
cgccgcgatc ccgctgggct gcgctcccca cgcaagtttt attatatcac tcttttacac    360
gatccagttc atcgttatct ttcagaatgg cgccacgtgc aacgcgggc gacgtggaaa     420
acgtctcttc acatgtgcga cggtcgcact cccacgcctg aagaattgcc gcctgctat     480
gaaggaacag attggagcgg ttgcacgtta caagaattca tggattgccc ctataactta    540
gctaacaacc gtcaagtacg tatgcttgcc gacctgtccc ttgtagggtg ctacaatttg    600
tcctttattc ccgagtcaaa gcgcgctcaa cttttgttgg aaagtgcaaa aaaaaacctg    660
cgtggaatgg ctttcttcgg actgggtcgt tttcaacgta agacgcagta tttattcgag    720
cgcacgttca atttgaaatt catccgcccg tttatggtca ctaattcatc ccgcgcgagc    780
ggggtcgagg tggacgagga tactatccgc catatcgaag agcttaacga cttggatatg    840
cagttgtacg attatgccaa agatcttttt caacagcgct accaatacaa gcgtcagctt    900
```
gaacgccgcg agcagcgttt acgcaatcgt gaggaataa                    939

<210> SEQ ID NO 98
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 15

<400> SEQUENCE: 98

```
Met Lys Tyr Tyr Phe Pro Val Arg Glu Leu Glu Arg Ser Leu Arg Phe
1               5                   10                  15

Asp Met Lys Gly Asp Val Ile Val Phe Leu His Ile Ala His Thr
            20                  25                  30

Gly Gly Thr Thr Phe Gly Arg His Leu Val Gln Asn Val Arg Leu Glu
            35                  40                  45

Val Pro Cys Asp Cys Arg Pro Gly Gln Lys Lys Cys Thr Cys Tyr Arg
50                  55                  60

Pro Asn Arg Arg Glu Thr Trp Leu Phe Ser Arg Phe Ser Thr Gly Gly
65                  70                  75                  80

Ser Cys Gly Ala Ala Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Ser
            115                 120                 125

Met Trp Arg His His Gln Arg Gly Ala Thr His Lys Thr Ser Leu His
130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
            195                 200                 205

Ala Gln Leu Leu Leu Glu Ser Ala Lys Lys Asn Leu Arg Gly Met Ala
210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
            275                 280                 285

Leu Phe Gln Gln Arg Tyr Gln Tyr Lys Arg Gln Leu Glu Arg Glu
290                 295                 300

Gln Arg Leu Arg Asn Arg Glu Glu
305                 310
```

<210> SEQ ID NO 99
<211> LENGTH: 939
<212> TYPE: DNA
<213> ORGANISM: Artificial Sequence
<220> FEATURE:

<223> OTHER INFORMATION: Polynucleotide sequence encoding for engineered
      glucosaminyl 6-O sulfotransferase mutant_sulfatase 15

<400> SEQUENCE: 99

```
atgaagtact attttccggt ccgcgaattg gagcgctcat tgcgttttga tatgaagggg      60
gatgacgtga tcgttttttct tcatattgct catactggtg gcacgacatt cggtcgccat    120
ttggtccaga acgtccgtct tgaggtgcca tgcgattgcc gtcctggcca agaagaagtgc    180
acgtgttatc gtccgaaccg ccgtgagact tggttgttta gtcgcttttc aactggcggt    240
tcgtgcggcg ccgcagcgga ttggacagaa ttaaccaatt gtgtacccgg tgttttagat    300
cgtcgcgatc cagcgggatt acgttcgccc cgtaagttct attatattac tctgttacgc    360
gatccagtct cacgctatct gtcgatgtgg cgccatcatc aacgtggggc tactcataag    420
acttcgttac acatgtgtga cggccgtact ccgaccccgg aagaacttcc accctgctac    480
gaaggcaccg actggtctgg atgtacgctg caggaattta tggattgtcc gtacaacttg    540
gctaacaacc gtcaagtgcg tatgttggct gatctttcat tagtcggatg ctacaacttg    600
tcgttcatcc agaaagcaa acgtgcacag cttctgcttg agtccgccaa gaaaaatttg    660
cgtggtatgg ccttctttgg attgacagag ttccagcgca aaacgcagta tcttttcgag    720
cgtaccttca acctgaaatt tatccgcccg ttcatgcaat acaattccac tcgcgcaggg    780
ggtgttgaag tagacgagga tacgattcgt catatcgagg aattgaatga cctggatatg    840
cagctgtatg actacgcgaa agatttgttc cagcagcgct accagtacaa acgtcagctt    900
gaacgccgcg agcagcgttt acgcaatcgt gaggaataa                           939
```

<210> SEQ ID NO 100
<211> LENGTH: 295
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 16

<400> SEQUENCE: 100

```
Met Lys Gly Asp Asp Val Ile Val Phe Leu His Ile Gly His Thr Gly
1               5                   10                  15

Gly Thr Thr Phe Gly Arg His Leu Val Gln Asn Val Arg Leu Glu Val
                20                  25                  30

Pro Cys Asp Cys Arg Pro Gly Gln Lys Lys Cys Thr Cys Tyr Arg Pro
            35                  40                  45

Asn Arg Arg Glu Thr Trp Leu Phe Ser Arg Phe Ser Thr Gly Trp Ser
        50                  55                  60

Cys Gly Thr Arg Ala Asp Trp Thr Glu Leu Thr Asn Cys Val Pro Gly
65                  70                  75                  80

Val Leu Asp Arg Arg Asp Pro Ala Gly Leu Arg Ser Pro Arg Lys Phe
                85                  90                  95

Tyr Tyr Ile Thr Leu Leu Arg Asp Pro Val Ser Arg Tyr Leu Ser Ala
            100                 105                 110

Trp Arg His His Gln Arg Gly Ala Thr Gly Lys Thr Ser Leu His Met
        115                 120                 125

Cys Asp Gly Arg Thr Pro Thr Pro Glu Glu Leu Pro Pro Cys Tyr Glu
    130                 135                 140

Gly Thr Asp Trp Ser Gly Cys Thr Leu Gln Glu Phe Met Asp Cys Pro
145                 150                 155                 160

Tyr Asn Leu Ala Asn Asn Arg Gln Val Arg Met Leu Ala Asp Leu Ser
```

```
                165                 170                 175
Leu Val Gly Cys Tyr Asn Leu Ser Phe Ile Pro Glu Ser Lys Arg Ala
            180                 185                 190

Gln Leu Leu Leu Glu Ser Ala Lys Lys Asn Leu Arg Gly Met Ala Phe
        195                 200                 205

Phe Gly Leu Thr Glu Phe Gln Arg Lys Thr Gln Tyr Leu Phe Glu Arg
    210                 215                 220

Thr Phe Asn Leu Lys Phe Ile Arg Pro Phe Met Gln Tyr Asn Ser Thr
225                 230                 235                 240

Arg Ala Gly Gly Val Glu Val Asp Glu Asp Thr Ile Arg His Ile Glu
                245                 250                 255

Glu Leu Asn Asp Leu Asp Met Gln Leu Tyr Asp Tyr Ala Lys Asp Leu
            260                 265                 270

Phe Gln Gln Arg Tyr Gln Tyr Lys Arg Gln Leu Glu Arg Glu Gln
        275                 280                 285

Arg Leu Arg Asn Arg Glu Glu
    290                 295

<210> SEQ ID NO 101
<211> LENGTH: 888
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 16

<400> SEQUENCE: 101
atgaaaggtg atgatgtgat cgttttttg catatcgggc acacaggggg gactaccttc      60
gggcgtcatc tggtgcagaa cgtacgcctt gaggtaccat gtgattgtcg ccccgggcaa    120
aaaaagtgca cttgttatcg ccctaaccgt cgtgaaactt ggttattttc ccgcttttcg    180
acagggtgga gttgtggtac acgcgctgac tggacagagt tgaccaactg cgtcccaggg    240
gtacttgacc gtcgtgaccc tgctggactg cgcagcccac gtaagttcta ctacattacg    300
ttactgcgtg atcctgtatc acgttacctg tctgcctggc gccatcacca gcgcggagcg    360
acagggaaga catctctgca catgtgtgac ggacgtactc cgacgccaga agagttaccc    420
ccgtgctatg aaggtactga ttggtcgggg tgcaccctgc aagaattcat ggactgcccg    480
tacaacctgg ctaacaaccg tcaagtgcgt atgttagcgg acctgagttt ggtgggatgc    540
tacaatctga gctttatccc tgagtctaag cgcgcacagt tactgcttga tcggcgaaa     600 aagaatctgc gtggcatggc gttcttcggg ctgacggaat tcagcgtaa acacaatac      660 cttttttgagc gcacgtttaa cttgaagttt attcgcccgt ttatgcagta caactccacc   720
cgcgcagggg gcgtcgaggt cgatgaagat acaattcgcc atattgagga gttgaacgat   780
cttgatatgc aattatacga ttacgctaaa gacttgtttc aacagcgcta tcaatacaaa   840
cgtcagttgg aacgccgcga gcagcgttta cgcaatcgtg aggaataa                 888

<210> SEQ ID NO 102
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfatase 17

<400> SEQUENCE: 102

Met Arg Tyr Asn Phe Ser Arg Gly Asp Leu Leu Arg Lys Val Asp Phe
```

```
  1               5                  10                 15
Asp Ile Lys Gly Asp Asp Leu Ile Val Phe Leu His Ile Gln Lys Thr
                 20                  25                 30
His Gly Thr Gln Phe Gly Arg His Leu Val Arg Asn Ile Gln Leu Glu
                 35                  40                 45
Gln Pro Cys Glu Cys Arg Val Gly Gln Lys Lys Cys Thr Cys His Arg
 50                  55                  60
Pro Gly Lys Arg Glu Thr Trp Leu Phe Ser Arg Phe Ser Thr Gly Trp
 65                  70                  75                 80
Ser Cys Gly Leu His Ala Asp Trp Thr Glu Leu Thr Ser Cys Val Pro
                 85                  90                 95
Ala Val Val Asp Gly Lys Arg Asp Ala Arg Leu Arg Pro Ser Arg Asn
                 100                 105                110
Phe His Tyr Ile Thr Ile Leu Arg Asp Pro Val His Arg Tyr Leu His
                 115                 120                125
Glu Trp Arg His Val Gln Arg Gly Ala Thr Trp Lys Ala Ser Leu His
                 130                 135                140
Val Cys Asp Gly Arg Pro Pro Thr Ser Glu Glu Leu Pro Ser Cys Tyr
145                  150                 155                160
Thr Gly Asp Asp Trp Ser Gly Cys Pro Leu Lys Glu Phe Met Asp Cys
                 165                 170                175
Pro Tyr Asn Leu Ala Asn Asn Arg Gln Val Arg Met Leu Ser Asp Leu
                 180                 185                190
Thr Leu Val Gly Cys Tyr Asn Leu Ser Val Met Pro Glu Lys Gln Arg
                 195                 200                205
Asn Lys Val Leu Leu Glu Ser Ala Lys Ser Asn Leu Lys His Met Ala
                 210                 215                220
Phe Phe Gly Leu Gly Glu Phe Gln Arg Lys Thr Gln Tyr Leu Phe Glu
225                  230                 235                240
Lys Thr Phe Asn Met Asn Phe Ile Ser Pro Phe Thr Gln Thr Asn Thr
                 245                 250                255
Ser Arg Ala Ser Ser Val Glu Ile Asn Glu Glu Ile Gln Lys Arg Ile
                 260                 265                270
Glu Gly Leu Asn Phe Leu Asp Met Glu Leu Tyr Ser Tyr Ala Lys Asp
                 275                 280                285
Leu Phe Leu Gln Arg Tyr Gln Phe Met Arg Gln Lys Glu His Gln Asp
                 290                 295                300
Ala Arg Arg Lys Arg Gln Glu Gln
305                  310
```

<210> SEQ ID NO 103
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfatase 17

<400> SEQUENCE: 103

```
atgcgctata acttcagtcg tggggacctt ttacgtaaag tggatttcga tatcaaagga      60
gacgatctta ttgtgttctt acatattcaa aaaacacatg gcacgcagtt cgggcgtcac     120
ttagtccgta acatccagct tgaacagccg tgtgagtgcc gtgtgggaca aaaaaaatgc     180
acttgccacc gcccaggaaa acgcgagacc tggctgtttt cgcgcttttc tactggttgg     240
tcttgcggat acatgctga ttggacagag ttgacgtcat gcgttccggc agttgtagat     300
```

```
ggaaaacgcg atgctcgcct gcgcccgtcg cgtaatttcc attacattac gatcctgcgt    360
gatccagttc accgttacct tcatgagtgg cgccatgtac agcgcggtgc tacgtggaag    420
gcatcgttgc acgtatgtga tggccgtccc ccaacatcgg aggagctgcc ctcatgttat    480
actggcgatg actggtctgg ctgccccctg aaggagttta tggattgtcc ctacaacctg    540
gccaataacc gtcaggttcg tatgttgtca gatttaacat tagtaggttg ttacaatctg    600
tcagtaatgc cagaaaagca acgtaataag gtgctgctgg aaagtgctaa gtcaaactta    660
aagcacatgg ccttctttgg ccttggagaa tttcagcgta aaacacaata cttgtttgag    720
aagacgttta atatgaactt tatctccccc tttacgcaga ctaacacctc ccgtgcttca    780
tctgtagaaa tcaatgagga aattcaaaag cgcattgagg gattgaactt tttagatatg    840
gagttatatt cttacgcaaa ggatttgttc ttgcagcgtt atcaatttat gcgtcaaaaa    900
gaacatcaag acgcacgtcg taagcgtcag gagcagtaa                           939
```

<210> SEQ ID NO 104
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 1

<400> SEQUENCE: 104

```
Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Thr Asn Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Gly
        115                 120                 125

Gly Trp Arg His His Gln Arg Gly Gly Thr Asn Lys Thr Ser Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240
```

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
        260                 265                 270

Glu Glu Leu Asn Asp Leu Asp Met Gln Leu Tyr Asp Tyr Ala Lys Asp
    275                 280                 285

Leu Phe Gln Gln Arg Tyr Gln Tyr Lys Arg Gln Leu Glu Arg Arg Glu
290                 295                 300

Gln Arg Leu Arg Asn Arg Glu Glu
305                 310

<210> SEQ ID NO 105
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfotransferase 1

<400> SEQUENCE: 105
atgaagtact attttccggt ccgcgaattg gagcgctcac tgcgttttga tatgaagggt      60
gacgatgtga ttgtattcct tcatattggg catacaggcg ggacgacttt tggacgtcat     120
ttagtccaga acgttcgtct ggaggtaccc tgtgattgcc gcccgggtca aaaaaaatgc     180
acgtgttacc gcccaaatcg ccgtgagacc tggttgttct ctcgcttttc cacaggctgg     240
tcttgcggaa ctaacgccga ctggacagag cttaccaact gtgtcccagg ggtattggac     300
cgccgtgatc cagctgggtt cgctcgcca cgtaaatttt actatattac cctgctgcgc     360
gatcctgtct cccgctacct ggggggctgg cgccaccatc agcgtggcgg cacaaataaa     420
acatcgttgc acatgtgtga tgggcgcacg ccaacacccg aagagcttcc cccgtgctat     480
gagggaacgg actggagtgg atgtacttta caggaattta tggactgtcc ctacaatttg     540
gcaaacaatc gtcaagtccg catgcttgcg gatcttagtt tggtcggctg ttacaacttg     600
agctttattc ccgaaagtaa gcgcgcacaa cttttattag agagtgccaa gaagaacttg     660
cgtggaatgg cattctttgg attgaccgaa tttcagcgta aaacgcagta tttgttttgaa    720 cgtacattca acctgaaatt tatccgcccg tttatgcagt ataacagtac gcgcgcgggg     780
ggcgtggaag tggacgagga cacgattcgc cacattgagg aattgaatga ccttgatatg     840
caattgtacg actacgccaa agatctttc cagcaacgtt atcaatacaa gcgccagctt      900
gaacgccgcg agcagcgttt acgcaatcgt gaggaataa                            939

<210> SEQ ID NO 106
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 2

<400> SEQUENCE: 106

Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg

```
                50              55              60
Pro Asn Arg Arg Glu Thr Trp Leu Phe Ser Arg Phe Ser Thr Gly Trp
 65                  70                  75                  80

Ser Cys Gly Thr Arg Ala Asp Trp Thr Glu Leu Thr Asn Cys Val Pro
                 85                  90                  95

Gly Val Leu Asp Arg Arg Asp Pro Ala Gly Leu Arg Ser Pro Arg Lys
                100                 105                 110

Phe Tyr Tyr Ile Thr Leu Leu Arg Asp Pro Val Ser Arg Tyr Leu Ser
            115                 120                 125

His Trp Arg His Thr Gln Arg Gly Gly Ala Asn Lys Thr Gly Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Gly Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
            195                 200                 205

Ala Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
                260                 265                 270

Glu Glu Leu Asn Asp Leu Asp Met Gln Leu Tyr Asp Tyr Ala Lys Asp
            275                 280                 285

Leu Phe Gln Gln Arg Tyr Gln Tyr Lys Arg Gln Leu Glu Arg Arg Glu
    290                 295                 300

Gln Arg Leu Arg Asn Arg Glu Glu
305                 310
```

<210> SEQ ID NO 107
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfotransferase 2

<400> SEQUENCE: 107

```
atgaagtact attttccggt ccgcgaattg gagcgctcat tgcgtttcga tatgaagggt      60
gatgatgtca tcgtcttcct tcacattggt cacactggtg aaccaccctt tggacgtcat     120
cttgtgcaaa acgtacgttt agaggtccct tgcgattgtc gtccgggtca aaaaaaatgt     180
acttgctatc gtcctaatcg tcgtgaaacg tggcttttca gtcgttttag tacggggtgg     240
tcatgcggta cccgcgcaga ctggacggag ttaaccaact gcgtacctgg ggtgttggat     300
cgccgcgatc cggcaggttt acgctcccca cgtaaattct attatattac cctgttacgt     360
gacccagtca gtcgctattt gtctcactgg cgtcacacac aacgtggcgg cgcgaacaag     420
accggactgc acatgtgtga cgggcgtact cctacaccag aggaattacc ccatgctat     480 gagggaactg actggtcggg atgtacactg caggagttca tggactgccc atacaatctg     540
```

```
gggaataatc gccaagtccg tatgttggcg gatttaagcc ttgtcggatg ctataatttg    600
tcattcattc cagaatcaaa acgcgcgcaa cttcttcttg agtcagccaa gaaaaatttg    660
cgcggaatgg cattttcgg gttgacagaa tttcagcgca aaacacaata tctgttcgag     720
cgcacattca atttaaaatt tattcgtcct ttcatgcaat acaactctac acgtgcagga    780
ggagtcgaag tggacgagga cacaattcgc cacatcgagg aattaaatga tctggatatg    840
cagttgtatg actatgcaaa agatctgttt cagcaacgct atcaatacaa gcgtcagttg    900
gaacgccgcg agcagcgttt acgcaatcgt gaggaataa                            939
```

<210> SEQ ID NO 108
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 3

<400> SEQUENCE: 108

```
Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Ser His Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Ser
        115                 120                 125

Gly Trp Arg His His Gln Arg Gly Gly Ala Asn Lys Thr Ser Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Gly Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285
```

Leu Phe Gln Gln Arg Tyr Gln Tyr Lys Arg Gln Leu Glu Arg Arg Glu
            290                 295                 300

Gln Arg Leu Arg Asn Arg Glu Glu
305                 310

<210> SEQ ID NO 109
<211> LENGTH: 939
<212> TYPE: DNA
<213> ORGANISM: Artificial Sequence
<220> FEATURE:
<223> OTHER INFORMATION: Polynucleotide sequence encoding for engineered
      glucosaminyl 6-O sulfotransferase mutant_sulfotransferase 3

<400> SEQUENCE: 109

```
atgaagtact attttccggt ccgcgaattg gagcgctcat tgcgtttcga catgaaagga      60
gacgacgtca ttgtattttt acatattggc cacaccggtg gcacgacttt tggccgtcac    120
ttagtccaaa acgtacgctt agaggtgcct tgcgactgtc gtccagggca aagaaatgc     180 acctgctatc gccccaaccg ccgtgaaaca tggttgttta gtcgctttag taccggttgg    240
agctgtggct ctcatgctga ttggactgaa ctgacgaatt gtgtccccgg agtattggat    300
cgccgtgatc ctgctggttt acgctcacct gcaaattct attatattac gttacttcgt     360
gatcccgtta gccgttatct tagtgggtgg cgtcaccatc aacgcggagg ggctaataag    420
acgagcctgc acatgtgtga cggacgtacg ccaaccccg aggaactgcc gccctgttac     480
gaggggacgg actggtctgg ctgtacatta caagagtta tggattgccc atataacctg     540
ggtaacaatc gccaagtccg tatgttggcg gatctttcgc tggtgggatg ttataattta    600
agttttatcc cggagagcaa gcgtgcacag ttgctgcttg aatcagcgaa gaagaaccttc   660 cgcggaatgg cattttttcgg tttaacggag tttcaacgta agactcagta cctttttcgag  720 cgtaccttca acttgaaatt tatccgtccc ttcatgcagt acaactccac ccgcgctggt    780
ggagttgaag tcgacgagga taccatccgc cacattgaag aacttaatga cttagatatg    840
caattgtacg actatgctaa ggacttattc cagcaacgtt atcagtacaa cgccaattg     900 gaacgccgcg agcagcgttt acgcaatcgt gaggaataa                          939
```

<210> SEQ ID NO 110
<211> LENGTH: 295
<212> TYPE: PRT
<213> ORGANISM: Artificial Sequence
<220> FEATURE:
<223> OTHER INFORMATION: Engineered glucosaminyl 6-O sulfotransferase
      mutant_variable 1
<220> FEATURE:
<221> NAME/KEY: MISC_FEATURE
<222> LOCATION: (11)..(11)
<223> OTHER INFORMATION: Xaa is glycine or histidine
<220> FEATURE:
<221> NAME/KEY: MISC_FEATURE
<222> LOCATION: (13)..(13)
<223> OTHER INFORMATION: Xaa is glycine, alanine, serine, or glutamine
<220> FEATURE:
<221> NAME/KEY: MISC_FEATURE
<222> LOCATION: (14)..(14)
<223> OTHER INFORMATION: Xaa is histidine or lysine
<220> FEATURE:
<221> NAME/KEY: MISC_FEATURE
<222> LOCATION: (16)..(16)
<223> OTHER INFORMATION: Xaa is histidine or glycine
<220> FEATURE:
<221> NAME/KEY: MISC_FEATURE
<222> LOCATION: (18)..(18)
<223> OTHER INFORMATION: Xaa is alanine or threonine
<220> FEATURE:
<221> NAME/KEY: MISC_FEATURE

```
<222> LOCATION: (63)..(63)
<223> OTHER INFORMATION: Xaa is glycine or tryptophan
<220> FEATURE:
<221> NAME/KEY: MISC_FEATURE
<222> LOCATION: (67)..(67)
<223> OTHER INFORMATION: Xaa is threonine, serine, leucine, or alanine
<220> FEATURE:
<221> NAME/KEY: MISC_FEATURE
<222> LOCATION: (68)..(68)
<223> OTHER INFORMATION: Xaa is asparagine, arginine, glutamine,
      histidine, or alanine
<220> FEATURE:
<221> NAME/KEY: MISC_FEATURE
<222> LOCATION: (103)..(103)
<223> OTHER INFORMATION: Xaa is histidine or arginine
<220> FEATURE:
<221> NAME/KEY: MISC_FEATURE
<222> LOCATION: (104)..(104)
<223> OTHER INFORMATION: Xaa is histidine, lysine, leucine, or aspartic
      acid
<220> FEATURE:
<221> NAME/KEY: MISC_FEATURE
<222> LOCATION: (107)..(107)
<223> OTHER INFORMATION: Xaa is histidine or serine
<220> FEATURE:
<221> NAME/KEY: MISC_FEATURE
<222> LOCATION: (111)..(111)
<223> OTHER INFORMATION: Xaa is glycine or serine
<220> FEATURE:
<221> NAME/KEY: MISC_FEATURE
<222> LOCATION: (112)..(112)
<223> OTHER INFORMATION: Xaa is alanine, histidine, glutamic acid,
      methionine, or glycine
<220> FEATURE:
<221> NAME/KEY: MISC_FEATURE
<222> LOCATION: (116)..(116)
<223> OTHER INFORMATION: Xaa is histidine, methionine, valine, or
      threonine
<220> FEATURE:
<221> NAME/KEY: MISC_FEATURE
<222> LOCATION: (120)..(120)
<223> OTHER INFORMATION: Xaa is glycine, alanine, or proline
<220> FEATURE:
<221> NAME/KEY: MISC_FEATURE
<222> LOCATION: (121)..(121)
<223> OTHER INFORMATION: Xaa is serine, threonine, asparagine, or
      alanine
<220> FEATURE:
<221> NAME/KEY: MISC_FEATURE
<222> LOCATION: (122)..(122)
<223> OTHER INFORMATION: Xaa is asparagine, tryptophan, histidine, or
      glycine
<220> FEATURE:
<221> NAME/KEY: MISC_FEATURE
<222> LOCATION: (123)..(123)
<223> OTHER INFORMATION: Xaa is serine, lysine, or threonine
<220> FEATURE:
<221> NAME/KEY: MISC_FEATURE
<222> LOCATION: (125)..(125)
<223> OTHER INFORMATION: Xaa is glycine or serine
<220> FEATURE:
<221> NAME/KEY: MISC_FEATURE
<222> LOCATION: (164)..(164)
<223> OTHER INFORMATION: Xaa is glycine or alanine
<220> FEATURE:
<221> NAME/KEY: MISC_FEATURE
<222> LOCATION: (212)..(212)
<223> OTHER INFORMATION: Xaa is alanine, glycine, or threonine
<220> FEATURE:
<221> NAME/KEY: MISC_FEATURE
<222> LOCATION: (213)..(213)
<223> OTHER INFORMATION: Xaa is valine, arginine, or glutamic acid
<220> FEATURE:
<221> NAME/KEY: MISC_FEATURE
<222> LOCATION: (215)..(215)
<223> OTHER INFORMATION: Xaa is glycine or glutamine
<220> FEATURE:
<221> NAME/KEY: MISC_FEATURE
<222> LOCATION: (236)..(236)
```

<223> OTHER INFORMATION: Xaa is valine or glutamine
<220> FEATURE:
<221> NAME/KEY: MISC_FEATURE
<222> LOCATION: (237)..(237)
<223> OTHER INFORMATION: Xaa is valine, threonine, or tyrosine
<220> FEATURE:
<221> NAME/KEY: MISC_FEATURE
<222> LOCATION: (238)..(238)
<223> OTHER INFORMATION: Xaa is lysine or asparagine
<220> FEATURE:
<221> NAME/KEY: MISC_FEATURE
<222> LOCATION: (240)..(240)
<223> OTHER INFORMATION: Xaa is serine, asparagine, or threonine
<220> FEATURE:
<221> NAME/KEY: MISC_FEATURE
<222> LOCATION: (243)..(243)
<223> OTHER INFORMATION: Xaa is serine or glycine

<400> SEQUENCE: 110

Met Lys Gly Asp Asp Val Ile Val Phe Leu Xaa Ile Xaa Xaa Thr Xaa
1               5                   10                  15

Gly Xaa Thr Phe Gly Arg His Leu Val Gln Asn Val Arg Leu Glu Val
            20                  25                  30

Pro Cys Asp Cys Arg Pro Gly Gln Lys Lys Cys Thr Cys Tyr Arg Pro
        35                  40                  45

Asn Arg Arg Glu Thr Trp Leu Phe Ser Arg Phe Ser Thr Gly Xaa Ser
    50                  55                  60

Cys Gly Xaa Xaa Ala Asp Trp Thr Glu Leu Thr Asn Cys Val Pro Gly
65                  70                  75                  80

Val Leu Asp Arg Arg Asp Pro Ala Gly Leu Arg Ser Pro Arg Lys Phe
                85                  90                  95

Tyr Tyr Ile Thr Leu Leu Xaa Xaa Pro Val Xaa Arg Tyr Leu Xaa Xaa
            100                 105                 110

Trp Arg His Xaa Gln Arg Gly Xaa Xaa Xaa Thr Xaa Leu His Met
        115                 120                 125

Cys Asp Gly Arg Thr Pro Thr Pro Glu Glu Leu Pro Pro Cys Tyr Glu
130                 135                 140

Gly Thr Asp Trp Ser Gly Cys Thr Leu Gln Glu Phe Met Asp Cys Pro
145                 150                 155                 160

Tyr Asn Leu Xaa Asn Asn Arg Gln Val Arg Met Leu Ala Asp Leu Ser
                165                 170                 175

Leu Val Gly Cys Tyr Asn Leu Ser Phe Ile Pro Glu Ser Lys Arg Ala
            180                 185                 190

Gln Leu Leu Leu Glu Ser Ala Lys Lys Asn Leu Arg Gly Met Ala Phe
        195                 200                 205

Phe Gly Leu Xaa Xaa Phe Xaa Arg Lys Thr Gln Tyr Leu Phe Glu Arg
    210                 215                 220

Thr Phe Asn Leu Lys Phe Ile Arg Pro Phe Met Xaa Xaa Xaa Ser Xaa
225                 230                 235                 240

Arg Ala Xaa Gly Val Glu Val Asp Glu Asp Thr Ile Arg His Ile Glu
                245                 250                 255

Glu Leu Asn Asp Leu Asp Met Gln Leu Tyr Asp Tyr Ala Lys Asp Leu
            260                 265                 270

Phe Gln Gln Arg Tyr Gln Tyr Lys Arg Gln Leu Glu Arg Glu Gln
        275                 280                 285

Arg Leu Arg Asn Arg Glu Glu
    290                 295

<210> SEQ ID NO 111

```
<211> LENGTH: 411
<212> TYPE: PRT
<213> ORGANISM: Artificial Sequence
<220> FEATURE:
<223> OTHER INFORMATION: Engineered glucosaminyl 6-O sulfotransferase
      mutant_variable 2
<220> FEATURE:
<221> NAME/KEY: MISC_FEATURE
<222> LOCATION: (93)..(93)
<223> OTHER INFORMATION: Xaa is glycine or histidine
<220> FEATURE:
<221> NAME/KEY: MISC_FEATURE
<222> LOCATION: (95)..(95)
<223> OTHER INFORMATION: Xaa is glycine, serine, alanine, or glutamine
<220> FEATURE:
<221> NAME/KEY: MISC_FEATURE
<222> LOCATION: (96)..(96)
<223> OTHER INFORMATION: Xaa is histidine or lysine
<220> FEATURE:
<221> NAME/KEY: MISC_FEATURE
<222> LOCATION: (98)..(98)
<223> OTHER INFORMATION: Xaa is histidine or glycine
<220> FEATURE:
<221> NAME/KEY: MISC_FEATURE
<222> LOCATION: (100)..(100)
<223> OTHER INFORMATION: Xaa is alanine or threonine
<220> FEATURE:
<221> NAME/KEY: MISC_FEATURE
<222> LOCATION: (145)..(145)
<223> OTHER INFORMATION: Xaa is glycine or tryptophan
<220> FEATURE:
<221> NAME/KEY: MISC_FEATURE
<222> LOCATION: (149)..(149)
<223> OTHER INFORMATION: Xaa is threonine, serine, leucine, or alanine
<220> FEATURE:
<221> NAME/KEY: MISC_FEATURE
<222> LOCATION: (150)..(150)
<223> OTHER INFORMATION: Xaa is asparagine, arginine, glutamine,
      histidine, or alanine
<220> FEATURE:
<221> NAME/KEY: MISC_FEATURE
<222> LOCATION: (185)..(185)
<223> OTHER INFORMATION: Xaa is histidine or arginine
<220> FEATURE:
<221> NAME/KEY: MISC_FEATURE
<222> LOCATION: (186)..(186)
<223> OTHER INFORMATION: Xaa is histidine, lysine, leucine, or aspartic
      acid
<220> FEATURE:
<221> NAME/KEY: MISC_FEATURE
<222> LOCATION: (189)..(189)
<223> OTHER INFORMATION: Xaa is histidine or serine
<220> FEATURE:
<221> NAME/KEY: MISC_FEATURE
<222> LOCATION: (193)..(193)
<223> OTHER INFORMATION: Xaa is glycine or serine
<220> FEATURE:
<221> NAME/KEY: MISC_FEATURE
<222> LOCATION: (194)..(194)
<223> OTHER INFORMATION: Xaa is alanine, histidine, glutamic acid,
      methionine, or glycine
<220> FEATURE:
<221> NAME/KEY: MISC_FEATURE
<222> LOCATION: (198)..(198)
<223> OTHER INFORMATION: Xaa is histidine, methionine, valine, or
      threonine
<220> FEATURE:
<221> NAME/KEY: MISC_FEATURE
<222> LOCATION: (202)..(202)
<223> OTHER INFORMATION: Xaa is glycine, alanine, pr proline
<220> FEATURE:
<221> NAME/KEY: MISC_FEATURE
<222> LOCATION: (203)..(203)
<223> OTHER INFORMATION: Xaa is serine, threonine, asparagine, or
      alanine
<220> FEATURE:
<221> NAME/KEY: MISC_FEATURE
<222> LOCATION: (204)..(204)
<223> OTHER INFORMATION: Xaa is asparagine, tryptophan, histidine, or
```

```
        glycine
<220> FEATURE:
<221> NAME/KEY: MISC_FEATURE
<222> LOCATION: (205)..(205)
<223> OTHER INFORMATION: Xaa is serine, lysine, or threonine
<220> FEATURE:
<221> NAME/KEY: MISC_FEATURE
<222> LOCATION: (207)..(207)
<223> OTHER INFORMATION: Xaa is glycine or serine
<220> FEATURE:
<221> NAME/KEY: MISC_FEATURE
<222> LOCATION: (246)..(246)
<223> OTHER INFORMATION: Xaa is glycine or alanine
<220> FEATURE:
<221> NAME/KEY: MISC_FEATURE
<222> LOCATION: (294)..(294)
<223> OTHER INFORMATION: Xaa is alanine, glycine, or threonine
<220> FEATURE:
<221> NAME/KEY: MISC_FEATURE
<222> LOCATION: (295)..(295)
<223> OTHER INFORMATION: Xaa is tryptophan, arginine, or glutamic acid
<220> FEATURE:
<221> NAME/KEY: MISC_FEATURE
<222> LOCATION: (297)..(297)
<223> OTHER INFORMATION: Xaa is glycine or glutamine
<220> FEATURE:
<221> NAME/KEY: MISC_FEATURE
<222> LOCATION: (318)..(318)
<223> OTHER INFORMATION: Xaa is valine or glutamine
<220> FEATURE:
<221> NAME/KEY: MISC_FEATURE
<222> LOCATION: (319)..(319)
<223> OTHER INFORMATION: Xaa is valine, threonine, or tyrosine
<220> FEATURE:
<221> NAME/KEY: MISC_FEATURE
<222> LOCATION: (320)..(320)
<223> OTHER INFORMATION: Xaa is lysine or asparagine
<220> FEATURE:
<221> NAME/KEY: MISC_FEATURE
<222> LOCATION: (322)..(322)
<223> OTHER INFORMATION: Xaa is serine, asparagine, or threonine
<220> FEATURE:
<221> NAME/KEY: MISC_FEATURE
<222> LOCATION: (325)..(325)
<223> OTHER INFORMATION: Xaa is serine or glycine

<400> SEQUENCE: 111

Met Arg Arg Arg Arg Ala Gly Gly Arg Thr Met Val Glu Arg Ala Ser
1               5                   10                  15

Lys Phe Val Leu Val Val Ala Gly Ser Ala Cys Phe Met Leu Ile Leu
            20                  25                  30

Tyr Gln Tyr Ala Gly Pro Gly Leu Ser Leu Gly Ala Pro Gly Gly Arg
        35                  40                  45

Val Pro Pro Asp Asp Leu Asp Leu Phe Pro Thr Pro Asp Pro His Tyr
    50                  55                  60

Glu Lys Lys Tyr Tyr Phe Pro Val Arg Glu Leu Glu Arg Ser Leu Arg
65                  70                  75                  80

Phe Asp Met Lys Gly Asp Val Ile Val Phe Leu Xaa Ile Xaa Xaa
                85                  90                  95

Thr Xaa Gly Xaa Thr Phe Gly Arg His Leu Val Gln Asn Val Arg Leu
            100                 105                 110

Glu Val Pro Cys Asp Cys Arg Pro Gly Gln Lys Lys Cys Thr Cys Tyr
            115                 120                 125

Arg Pro Asn Arg Arg Glu Thr Trp Leu Phe Ser Arg Phe Ser Thr Gly
        130                 135                 140

Xaa Ser Cys Gly Xaa Xaa Ala Asp Trp Thr Glu Leu Thr Asn Cys Val
145                 150                 155                 160

Pro Gly Val Leu Asp Arg Arg Asp Pro Ala Gly Leu Arg Ser Pro Arg
```

```
                165                 170                 175
Lys Phe Tyr Tyr Ile Thr Leu Leu Xaa Xaa Pro Val Xaa Arg Tyr Leu
            180                 185                 190

Xaa Xaa Trp Arg His Xaa Gln Arg Gly Xaa Xaa Xaa Thr Xaa Leu
        195                 200                 205

His Met Cys Asp Gly Arg Thr Pro Thr Pro Glu Glu Leu Pro Pro Cys
    210                 215                 220

Tyr Glu Gly Thr Asp Trp Ser Gly Cys Thr Leu Gln Glu Phe Met Asp
225                 230                 235                 240

Cys Pro Tyr Asn Leu Xaa Asn Asn Arg Gln Val Arg Met Leu Ala Asp
                245                 250                 255

Leu Ser Leu Val Gly Cys Tyr Asn Leu Ser Phe Ile Pro Glu Ser Lys
                260                 265                 270

Arg Ala Gln Leu Leu Glu Ser Ala Lys Lys Asn Leu Arg Gly Met
            275                 280                 285

Ala Phe Phe Gly Leu Xaa Xaa Phe Xaa Arg Lys Thr Gln Tyr Leu Phe
    290                 295                 300

Glu Arg Thr Phe Asn Leu Lys Phe Ile Arg Pro Phe Met Xaa Xaa Xaa
305                 310                 315                 320

Ser Xaa Arg Ala Xaa Gly Val Glu Val Asp Glu Asp Thr Ile Arg His
                325                 330                 335

Ile Glu Glu Leu Asn Asp Leu Asp Met Gln Leu Tyr Asp Tyr Ala Lys
                340                 345                 350

Asp Leu Phe Gln Gln Arg Tyr Gln Tyr Lys Arg Gln Leu Glu Arg Arg
            355                 360                 365

Glu Gln Arg Leu Arg Asn Arg Glu Glu Arg Leu Leu His Arg Ser Lys
        370                 375                 380

Glu Ala Leu Pro Arg Glu Asp Pro Glu Glu Pro Gly Arg Val Pro Thr
385                 390                 395                 400

Glu Asp Tyr Met Ser His Ile Ile Glu Lys Trp
                405                 410

<210> SEQ ID NO 112
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 4
<220> FEATURE:
<221> NAME/KEY: MISC_FEATURE
<222> LOCATION: (84)..(84)
<223> OTHER INFORMATION: Xaa is threonine or serine
<220> FEATURE:
<221> NAME/KEY: MISC_FEATURE
<222> LOCATION: (85)..(85)
<223> OTHER INFORMATION: Xaa is asparagine, arginine, or histidine
<220> FEATURE:
<221> NAME/KEY: MISC_FEATURE
<222> LOCATION: (128)..(128)
<223> OTHER INFORMATION: Xaa is glycine or serine
<220> FEATURE:
<221> NAME/KEY: MISC_FEATURE
<222> LOCATION: (129)..(129)
<223> OTHER INFORMATION: Xaa is glycine or histidine
<220> FEATURE:
<221> NAME/KEY: MISC_FEATURE
<222> LOCATION: (133)..(133)
<223> OTHER INFORMATION: Xaa is histidine or threonine
<220> FEATURE:
<221> NAME/KEY: MISC_FEATURE
<222> LOCATION: (138)..(138)
<223> OTHER INFORMATION: Xaa is alanine or threonine
```

```
<220> FEATURE:
<221> NAME/KEY: MISC_FEATURE
<222> LOCATION: (142)..(142)
<223> OTHER INFORMATION: Xaa is glycine or serine
<220> FEATURE:
<221> NAME/KEY: MISC_FEATURE
<222> LOCATION: (181)..(181)
<223> OTHER INFORMATION: Xaa is glycine or alanine

<400> SEQUENCE: 112
```

| | | | | | | | | | | | | | | |
|---|---|---|---|---|---|---|---|---|---|---|---|---|---|---|
|Met|Lys|Tyr|Tyr|Phe|Pro|Val|Arg|Glu|Leu|Glu|Arg|Ser|Leu|Arg|Phe|
|1| | | |5| | | | |10| | | | |15| |

| | | | | | | | | | | | | | | | |
|---|---|---|---|---|---|---|---|---|---|---|---|---|---|---|---|
|Asp|Met|Lys|Gly|Asp|Asp|Val|Ile|Val|Phe|Leu|His|Ile|Gly|His|Thr|
| | | |20| | | | |25| | | | |30| | |

|Gly|Gly|Thr|Thr|Phe|Gly|Arg|His|Leu|Val|Gln|Asn|Val|Arg|Leu|Glu|
|---|---|---|---|---|---|---|---|---|---|---|---|---|---|---|---|
| | |35| | | | |40| | | | |45| | | |

|Val|Pro|Cys|Asp|Cys|Arg|Pro|Gly|Gln|Lys|Lys|Cys|Thr|Cys|Tyr|Arg|
|---|---|---|---|---|---|---|---|---|---|---|---|---|---|---|---|
|50| | | | |55| | | | |60| | | | | |

|Pro|Asn|Arg|Arg|Glu|Thr|Trp|Leu|Phe|Ser|Arg|Phe|Ser|Thr|Gly|Trp|
|---|---|---|---|---|---|---|---|---|---|---|---|---|---|---|---|
|65| | | | |70| | | | |75| | | | |80|

|Ser|Cys|Gly|Xaa|Xaa|Ala|Asp|Trp|Thr|Glu|Leu|Thr|Asn|Cys|Val|Pro|
|---|---|---|---|---|---|---|---|---|---|---|---|---|---|---|---|
| | | | |85| | | | |90| | | | |95| |

|Gly|Val|Leu|Asp|Arg|Arg|Asp|Pro|Ala|Gly|Leu|Arg|Ser|Pro|Arg|Lys|
|---|---|---|---|---|---|---|---|---|---|---|---|---|---|---|---|
| | | |100| | | | |105| | | | |110| | |

|Phe|Tyr|Tyr|Ile|Thr|Leu|Leu|Arg|Asp|Pro|Val|Ser|Arg|Tyr|Leu|Xaa|
|---|---|---|---|---|---|---|---|---|---|---|---|---|---|---|---|
| | |115| | | | |120| | | | |125| | | |

|Xaa|Trp|Arg|His|Xaa|Gln|Arg|Gly|Gly|Xaa|Asn|Lys|Thr|Xaa|Leu|His|
|---|---|---|---|---|---|---|---|---|---|---|---|---|---|---|---|
|130| | | | |135| | | | |140| | | | | |

|Met|Cys|Asp|Gly|Arg|Thr|Pro|Thr|Pro|Glu|Glu|Leu|Pro|Pro|Cys|Tyr|
|---|---|---|---|---|---|---|---|---|---|---|---|---|---|---|---|
|145| | | | |150| | | | |155| | | | |160|

|Glu|Gly|Thr|Asp|Trp|Ser|Gly|Cys|Thr|Leu|Gln|Glu|Phe|Met|Asp|Cys|
|---|---|---|---|---|---|---|---|---|---|---|---|---|---|---|---|
| | | | |165| | | | |170| | | | |175| |

|Pro|Tyr|Asn|Leu|Xaa|Asn|Asn|Arg|Gln|Val|Arg|Met|Leu|Ala|Asp|Leu|
|---|---|---|---|---|---|---|---|---|---|---|---|---|---|---|---|
| | | |180| | | | |185| | | | |190| | |

|Ser|Leu|Val|Gly|Cys|Tyr|Asn|Leu|Ser|Phe|Ile|Pro|Glu|Ser|Lys|Arg|
|---|---|---|---|---|---|---|---|---|---|---|---|---|---|---|---|
| | |195| | | | |200| | | | |205| | | |

|Ala|Gln|Leu|Leu|Leu|Glu|Ser|Ala|Lys|Lys|Asn|Leu|Arg|Gly|Met|Ala|
|---|---|---|---|---|---|---|---|---|---|---|---|---|---|---|---|
|210| | | | |215| | | | |220| | | | | |

|Phe|Phe|Gly|Leu|Thr|Glu|Phe|Gln|Arg|Lys|Thr|Gln|Tyr|Leu|Phe|Glu|
|---|---|---|---|---|---|---|---|---|---|---|---|---|---|---|---|
|225| | | | |230| | | | |235| | | | |240|

|Arg|Thr|Phe|Asn|Leu|Lys|Phe|Ile|Arg|Pro|Phe|Met|Gln|Tyr|Asn|Ser|
|---|---|---|---|---|---|---|---|---|---|---|---|---|---|---|---|
| | | | |245| | | | |250| | | | |255| |

|Thr|Arg|Ala|Gly|Gly|Val|Glu|Val|Asp|Glu|Asp|Thr|Ile|Arg|His|Ile|
|---|---|---|---|---|---|---|---|---|---|---|---|---|---|---|---|
| | | |260| | | | |265| | | | |270| | |

|Glu|Glu|Leu|Asn|Asp|Leu|Asp|Met|Gln|Leu|Tyr|Asp|Tyr|Ala|Lys|Asp|
|---|---|---|---|---|---|---|---|---|---|---|---|---|---|---|---|
| | |275| | | | |280| | | | |285| | | |

|Leu|Phe|Gln|Gln|Arg|Tyr|Gln|Tyr|Lys|Arg|Gly|Leu|Glu|Arg|Arg|Glu|
|---|---|---|---|---|---|---|---|---|---|---|---|---|---|---|---|
| |290| | | | |295| | | | |300| | | | |

|Gln|Arg|Leu|Arg|Asn|Arg|Glu|Glu|
|---|---|---|---|---|---|---|---|
|305| | | | |310| | |

```
<210> SEQ ID NO 113
<211> LENGTH: 411
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 5
```

-continued

```
<220> FEATURE:
<221> NAME/KEY: MISC_FEATURE
<222> LOCATION: (149)..(149)
<223> OTHER INFORMATION: Xaa is threonine or serine
<220> FEATURE:
<221> NAME/KEY: MISC_FEATURE
<222> LOCATION: (150)..(150)
<223> OTHER INFORMATION: Xaa is asparagine, arginine, or histidine
<220> FEATURE:
<221> NAME/KEY: MISC_FEATURE
<222> LOCATION: (193)..(193)
<223> OTHER INFORMATION: Xaa is glycine or serine
<220> FEATURE:
<221> NAME/KEY: MISC_FEATURE
<222> LOCATION: (194)..(194)
<223> OTHER INFORMATION: Xaa is glycine or histidine
<220> FEATURE:
<221> NAME/KEY: MISC_FEATURE
<222> LOCATION: (198)..(198)
<223> OTHER INFORMATION: Xaa is histidine or threonine
<220> FEATURE:
<221> NAME/KEY: MISC_FEATURE
<222> LOCATION: (203)..(203)
<223> OTHER INFORMATION: Xaa is alanine or threonine
<220> FEATURE:
<221> NAME/KEY: MISC_FEATURE
<222> LOCATION: (207)..(207)
<223> OTHER INFORMATION: Xaa is glycine or serine
<220> FEATURE:
<221> NAME/KEY: MISC_FEATURE
<222> LOCATION: (246)..(246)
<223> OTHER INFORMATION: Xaa is glycine or alanine

<400> SEQUENCE: 113

Met Arg Arg Arg Arg Ala Gly Gly Arg Thr Met Val Glu Arg Ala Ser
1               5                   10                  15

Lys Phe Val Leu Val Ala Gly Ser Ala Cys Phe Met Leu Ile Leu
            20                  25                  30

Tyr Gln Tyr Ala Gly Pro Gly Leu Ser Leu Gly Ala Pro Gly Gly Arg
        35                  40                  45

Val Pro Pro Asp Asp Leu Asp Leu Phe Pro Thr Pro Asp Pro His Tyr
50                  55                  60

Glu Lys Lys Tyr Tyr Phe Pro Val Arg Glu Leu Glu Arg Ser Leu Arg
65                  70                  75                  80

Phe Asp Met Lys Gly Asp Asp Val Ile Val Phe Leu His Ile Gly His
                85                  90                  95

Thr Gly Gly Thr Thr Phe Gly Arg His Leu Val Gln Asn Val Arg Leu
            100                 105                 110

Glu Val Pro Cys Asp Cys Arg Pro Gly Gln Lys Lys Cys Thr Cys Tyr
        115                 120                 125

Arg Pro Asn Arg Arg Glu Thr Trp Leu Phe Ser Arg Phe Ser Thr Gly
130                 135                 140

Trp Ser Cys Gly Xaa Xaa Ala Asp Trp Thr Glu Leu Thr Asn Cys Val
145                 150                 155                 160

Pro Gly Val Leu Asp Arg Arg Asp Pro Ala Gly Leu Arg Ser Pro Arg
                165                 170                 175

Lys Phe Tyr Tyr Ile Thr Leu Leu Arg Asp Pro Val Ser Arg Tyr Leu
            180                 185                 190

Xaa Xaa Trp Arg His Xaa Gln Arg Gly Gly Xaa Asn Lys Thr Xaa Leu
        195                 200                 205

His Met Cys Asp Gly Arg Thr Pro Thr Pro Glu Glu Leu Pro Pro Cys
    210                 215                 220

Tyr Glu Gly Thr Asp Trp Ser Gly Cys Thr Leu Gln Glu Phe Met Asp
225                 230                 235                 240
```

```
Cys Pro Tyr Asn Leu Xaa Asn Asn Arg Gln Val Arg Met Leu Ala Asp
                245                 250                 255

Leu Ser Leu Val Gly Cys Tyr Asn Leu Ser Phe Ile Pro Glu Ser Lys
            260                 265                 270

Arg Ala Gln Leu Leu Glu Ser Ala Lys Lys Asn Leu Arg Gly Met
        275                 280                 285

Ala Phe Phe Gly Leu Thr Glu Phe Gln Arg Lys Thr Gln Tyr Leu Phe
    290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Asp Glu Asp Thr Ile Arg His
                325                 330                 335

Ile Glu Glu Leu Asn Asp Leu Asp Met Gln Leu Tyr Asp Tyr Ala Lys
                340                 345                 350

Asp Leu Phe Gln Gln Arg Tyr Gln Tyr Lys Arg Gln Leu Glu Arg Arg
            355                 360                 365

Glu Gln Arg Leu Arg Asn Arg Glu Arg Leu Leu His Arg Ser Lys
        370                 375                 380

Glu Ala Leu Pro Arg Glu Asp Pro Glu Pro Gly Arg Val Pro Thr
385                 390                 395                 400

Glu Asp Tyr Met Ser His Ile Ile Glu Lys Trp
                405                 410

<210> SEQ ID NO 114
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 6

<400> SEQUENCE: 114

Met Lys Tyr Tyr Phe Pro Val Arg Glu Leu Glu Arg Ser Leu His Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Thr Asn Ala Asp Trp Thr Glu Leu Thr Asn Cys Val Pro
                85                  90                  95

Gly Val Leu Asp Arg Arg Asp Pro Ala Ala Leu Arg Thr Pro Arg Lys
            100                 105                 110

Phe Tyr Tyr Ile Thr Leu Leu Arg Asp Pro Val Ser Arg Tyr Leu Gly
        115                 120                 125

Gly Trp Arg His His Gln Arg Gly Gly Thr Asn Lys Thr Ser Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Ala Asn Asn Arg Gln Val Arg Met Leu Ala Asp Leu
```

```
            180                 185                 190
Ser Leu Val Gly Cys Tyr Asn Leu Ser Phe Ile Pro Glu Gly Lys Arg
        195                 200                 205

Ser Gln Leu Leu Leu Glu Ser Ala Lys Lys Asn Leu Arg Gly Met Ala
        210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Gly Glu Asp Thr Ile Arg Arg Ile
            260                 265                 270

Glu Glu Leu Asn Asp Leu Asp Met Gln Leu Tyr Asp Tyr Ala Arg Asp
        275                 280                 285

Leu Phe Gln Gln Arg Tyr Gln Tyr Lys Arg Gln Leu Glu Arg Arg Gln
        290                 295                 300

Gln Arg Leu Arg Ser Arg Glu Glu
305                 310

<210> SEQ ID NO 115
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 7

<400> SEQUENCE: 115

Met Lys Tyr Tyr Phe Pro Val Arg Glu Leu Glu Arg Ser Leu His Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Thr Arg Ala Asp Trp Thr Glu Leu Thr Asn Cys Val Pro
                85                  90                  95

Gly Val Leu Asp Arg Arg Asp Pro Ala Ala Leu Arg Thr Pro Arg Lys
            100                 105                 110

Phe Tyr Tyr Ile Thr Leu Leu Arg Asp Pro Val Ser Arg Tyr Leu Ser
        115                 120                 125

His Trp Arg His Thr Gln Arg Gly Gly Ala Asn Lys Thr Gly Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Gly Asn Asn Arg Gln Val Arg Met Leu Ala Asp Leu
            180                 185                 190

Ser Leu Val Gly Cys Tyr Asn Leu Ser Phe Ile Pro Glu Gly Lys Arg
        195                 200                 205

Ser Gln Leu Leu Leu Glu Ser Ala Lys Lys Asn Leu Arg Gly Met Ala
    210                 215                 220
```

```
Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Gly Glu Asp Thr Ile Arg Arg Ile
            260                 265                 270

Glu Glu Leu Asn Asp Leu Asp Met Gln Leu Tyr Asp Tyr Ala Arg Asp
        275                 280                 285

Leu Phe Gln Gln Arg Tyr Gln Tyr Lys Arg Gln Leu Glu Arg Arg Gln
        290                 295                 300

Gln Arg Leu Arg Ser Arg Glu Glu
305                 310
```

<210> SEQ ID NO 116
<211> LENGTH: 312
<212> TYPE: PRT
<213> ORGANISM: Artificial Sequence
<220> FEATURE:
<223> OTHER INFORMATION: Engineered glucosaminyl 6-O sulfotransferase mutant_sulfotransferase 8

<400> SEQUENCE: 116

```
Met Lys Tyr Tyr Phe Pro Val Arg Glu Leu Glu Arg Ser Leu His Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
50                  55                  60

Pro Asn Arg Arg Glu Thr Trp Leu Phe Ser Arg Phe Ser Thr Gly Trp
65                  70                  75                  80

Ser Cys Gly Ser His Ala Asp Trp Thr Glu Leu Thr Asn Cys Val Pro
                85                  90                  95

Gly Val Leu Asp Arg Arg Asp Pro Ala Ala Leu Arg Thr Pro Arg Lys
            100                 105                 110

Phe Tyr Tyr Ile Thr Leu Leu Arg Asp Pro Val Ser Arg Tyr Leu Ser
        115                 120                 125

Gly Trp Arg His His Gln Arg Gly Gly Ala Asn Lys Thr Ser Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Gly Asn Asn Arg Gln Val Arg Met Leu Ala Asp Leu
            180                 185                 190

Ser Leu Val Gly Cys Tyr Asn Leu Ser Phe Ile Pro Glu Gly Lys Arg
        195                 200                 205

Ser Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Gly Glu Asp Thr Ile Arg Arg Ile
            260                 265                 270
```

```
Glu Glu Leu Asn Asp Leu Asp Met Gln Leu Tyr Asp Tyr Ala Arg Asp
            275                 280                 285

Leu Phe Gln Gln Arg Tyr Gln Tyr Lys Arg Gln Leu Glu Arg Arg Gln
    290                 295                 300

Gln Arg Leu Arg Ser Arg Glu Glu
305                 310
```

<210> SEQ ID NO 117
<211> LENGTH: 411
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 9

<400> SEQUENCE: 117

```
Met Arg Arg Arg Arg Ala Gly Ser Arg Thr Met Val Glu Arg Ala Ser
1               5                   10                  15

Lys Phe Val Leu Val Ala Gly Ser Ala Cys Phe Met Leu Ile Leu
            20                  25                  30

Tyr Gln Tyr Ala Gly Pro Gly Leu Ser Leu Gly Ala Pro Gly Gly Arg
            35                  40                  45

Ala Pro Pro Asp Asp Leu Asp Leu Phe Pro Thr Pro Asp Pro His Tyr
 50                  55                  60

Glu Lys Lys Tyr Tyr Phe Pro Val Arg Glu Leu Arg Ser Leu His
65                  70                  75                  80

Phe Asp Met Lys Gly Asp Asp Val Ile Val Phe Leu His Ile Gly His
                85                  90                  95

Thr Gly Gly Thr Thr Phe Gly Arg His Leu Val Gln Asn Val Arg Leu
            100                 105                 110

Glu Val Pro Cys Asp Cys Arg Pro Gly Gln Lys Lys Cys Thr Cys Tyr
            115                 120                 125

Arg Pro Asn Arg Arg Glu Thr Trp Leu Phe Ser Arg Phe Ser Thr Gly
    130                 135                 140

Trp Ser Cys Gly Thr Asn Ala Asp Trp Thr Glu Leu Thr Asn Cys Val
145                 150                 155                 160

Pro Gly Val Leu Asp Arg Arg Asp Pro Ala Ala Leu Arg Thr Pro Arg
                165                 170                 175

Lys Phe Tyr Tyr Ile Thr Leu Leu Arg Asp Pro Val Ser Arg Tyr Leu
            180                 185                 190

Gly Gly Trp Arg His His Gln Arg Gly Gly Thr Asn Lys Thr Ser Leu
        195                 200                 205

His Met Cys Asp Gly Arg Thr Pro Thr Pro Glu Glu Leu Pro Pro Cys
    210                 215                 220

Tyr Glu Gly Thr Asp Trp Ser Gly Cys Thr Leu Gln Glu Phe Met Asp
225                 230                 235                 240

Cys Pro Tyr Asn Leu Ala Asn Asn Arg Gln Val Arg Met Leu Ala Asp
                245                 250                 255

Leu Ser Leu Val Gly Cys Tyr Asn Leu Ser Phe Ile Pro Glu Gly Lys
            260                 265                 270

Arg Ser Gln Leu Leu Glu Ser Ala Lys Lys Asn Leu Arg Gly Met
        275                 280                 285

Ala Phe Phe Gly Leu Thr Glu Phe Gln Arg Lys Thr Gln Tyr Leu Phe
    290                 295                 300

Glu Arg Thr Phe Asn Leu Lys Phe Ile Arg Pro Phe Met Gln Tyr Asn
```

```
305                 310                 315                 320
Ser Thr Arg Ala Gly Gly Val Glu Val Gly Glu Asp Thr Ile Arg Arg
                325                 330                 335

Ile Glu Glu Leu Asn Asp Leu Asp Met Gln Leu Tyr Asp Tyr Ala Arg
                340                 345                 350

Asp Leu Phe Gln Gln Arg Tyr Gln Tyr Lys Arg Gln Leu Glu Arg Arg
                355                 360                 365

Gln Gln Arg Leu Arg Ser Arg Glu Glu Arg Leu Leu His Arg Ala Lys
            370                 375                 380

Glu Ala Pro Pro Arg Gly Asp Thr Glu Pro Gly Arg Val Pro Thr
385                 390                 395                 400

Glu Asp Tyr Met Ser His Ile Ile Glu Lys Trp
                405                 410

<210> SEQ ID NO 118
<211> LENGTH: 411
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 10

<400> SEQUENCE: 118

Met Arg Arg Arg Arg Ala Gly Ser Arg Thr Met Val Glu Arg Ala Ser
1               5                   10                  15

Lys Phe Val Leu Val Val Ala Gly Ser Ala Cys Phe Met Leu Ile Leu
            20                  25                  30

Tyr Gln Tyr Ala Gly Pro Gly Leu Ser Leu Gly Ala Pro Gly Gly Arg
        35                  40                  45

Ala Pro Pro Asp Asp Leu Asp Leu Phe Pro Thr Pro Asp Pro His Tyr
    50                  55                  60

Glu Lys Lys Tyr Tyr Phe Pro Val Arg Glu Leu Glu Arg Ser Leu His
65                  70                  75                  80

Phe Asp Met Lys Gly Asp Asp Val Ile Val Phe Leu His Ile Gly His
                85                  90                  95

Thr Gly Gly Thr Thr Phe Gly Arg His Leu Val Gln Asn Val Arg Leu
                100                 105                 110

Glu Val Pro Cys Asp Cys Arg Pro Gly Gln Lys Lys Cys Thr Cys Tyr
            115                 120                 125

Arg Pro Asn Arg Arg Glu Thr Trp Leu Phe Ser Arg Phe Ser Thr Gly
        130                 135                 140

Trp Ser Cys Gly Thr Arg Ala Asp Trp Thr Glu Leu Thr Asn Cys Val
145                 150                 155                 160

Pro Gly Val Leu Asp Arg Asp Pro Ala Ala Leu Arg Thr Pro Arg
                165                 170                 175

Lys Phe Tyr Tyr Ile Thr Leu Leu Arg Asp Pro Val Ser Arg Tyr Leu
                180                 185                 190

Ser His Trp Arg His Thr Gln Arg Gly Gly Ala Asn Lys Thr Gly Leu
            195                 200                 205

His Met Cys Asp Gly Arg Thr Pro Thr Pro Glu Glu Leu Pro Pro Cys
        210                 215                 220

Tyr Glu Gly Thr Asp Trp Ser Gly Cys Thr Leu Gln Glu Phe Met Asp
225                 230                 235                 240

Cys Pro Tyr Asn Leu Gly Asn Asn Arg Gln Val Arg Met Leu Ala Asp
                245                 250                 255
```

-continued

```
Leu Ser Leu Val Gly Cys Tyr Asn Leu Ser Phe Ile Pro Glu Gly Lys
            260                 265                 270

Arg Ser Gln Leu Leu Leu Glu Ser Ala Lys Lys Asn Leu Arg Gly Met
        275                 280                 285

Ala Phe Phe Gly Leu Thr Glu Phe Gln Arg Lys Thr Gln Tyr Leu Phe
    290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Gly Asp Thr Ile Arg Arg
            325                 330                 335

Ile Glu Glu Leu Asn Asp Leu Asp Met Gln Leu Tyr Asp Tyr Ala Arg
            340                 345                 350

Asp Leu Phe Gln Gln Arg Tyr Gln Tyr Lys Arg Gln Leu Glu Arg Arg
            355                 360                 365

Gln Gln Arg Leu Arg Ser Arg Glu Glu Arg Leu Leu His Arg Ala Lys
        370                 375                 380

Glu Ala Pro Pro Arg Gly Asp Thr Glu Glu Pro Gly Arg Val Pro Thr
385                 390                 395                 400

Glu Asp Tyr Met Ser His Ile Ile Glu Lys Trp
                405                 410
```

<210> SEQ ID NO 119
<211> LENGTH: 411
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 11

<400> SEQUENCE: 119

```
Met Arg Arg Arg Arg Ala Gly Ser Arg Thr Met Val Glu Arg Ala Ser
1               5                   10                  15

Lys Phe Val Leu Val Val Ala Gly Ser Ala Cys Phe Met Leu Ile Leu
            20                  25                  30

Tyr Gln Tyr Ala Gly Pro Gly Leu Ser Leu Gly Ala Pro Gly Gly Arg
        35                  40                  45

Ala Pro Pro Asp Asp Leu Asp Leu Phe Pro Thr Pro Asp Pro His Tyr
    50                  55                  60

Glu Lys Lys Tyr Tyr Phe Pro Val Arg Glu Leu Glu Arg Ser Leu His
65                  70                  75                  80

Phe Asp Met Lys Gly Asp Val Ile Val Phe Leu His Ile Gly His
                85                  90                  95

Thr Gly Gly Thr Thr Phe Gly Arg His Leu Val Gln Asn Val Arg Leu
            100                 105                 110

Glu Val Pro Cys Asp Cys Arg Pro Gly Gln Lys Lys Cys Thr Cys Tyr
        115                 120                 125

Arg Pro Asn Arg Arg Glu Thr Trp Leu Phe Ser Arg Phe Ser Thr Gly
    130                 135                 140

Trp Ser Cys Gly Ser His Ala Asp Trp Thr Glu Leu Thr Asn Cys Val
145                 150                 155                 160

Pro Gly Val Leu Asp Arg Arg Asp Pro Ala Ala Leu Arg Thr Pro Arg
                165                 170                 175

Lys Phe Tyr Tyr Ile Thr Leu Leu Arg Asp Pro Val Ser Arg Tyr Leu
            180                 185                 190

Ser Gly Trp Arg His His Gln Arg Gly Gly Ala Asn Lys Thr Ser Leu
        195                 200                 205
```

```
His Met Cys Asp Gly Arg Thr Pro Thr Pro Glu Glu Leu Pro Pro Cys
    210                 215                 220

Tyr Glu Gly Thr Asp Trp Ser Gly Cys Thr Leu Gln Glu Phe Met Asp
225                 230                 235                 240

Cys Pro Tyr Asn Leu Gly Asn Asn Arg Gln Val Arg Met Leu Ala Asp
            245                 250                 255

Leu Ser Leu Val Gly Cys Tyr Asn Leu Ser Phe Ile Pro Glu Gly Lys
            260                 265                 270

Arg Ser Gln Leu Leu Leu Glu Ser Ala Lys Lys Asn Leu Arg Gly Met
            275                 280                 285

Ala Phe Phe Gly Leu Thr Glu Phe Gln Arg Lys Thr Gln Tyr Leu Phe
            290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Gly Glu Asp Thr Ile Arg Arg
            325                 330                 335

Ile Glu Glu Leu Asn Asp Leu Asp Met Gln Leu Tyr Asp Tyr Ala Arg
            340                 345                 350

Asp Leu Phe Gln Gln Arg Tyr Gln Tyr Lys Arg Gln Leu Glu Arg Arg
            355                 360                 365

Gln Gln Arg Leu Arg Ser Arg Glu Arg Leu Leu His Arg Ala Lys
            370                 375                 380

Glu Ala Pro Pro Arg Gly Asp Thr Glu Glu Pro Gly Arg Val Pro Thr
385                 390                 395                 400

Glu Asp Tyr Met Ser His Ile Ile Glu Lys Trp
            405                 410
```

<210> SEQ ID NO 120
<211> LENGTH: 470
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 12

<400> SEQUENCE: 120

```
Met Asp Glu Arg Phe Asn Lys Trp Leu Leu Thr Pro Val Leu Thr Leu
1               5                   10                  15

Leu Phe Val Val Ile Met Tyr Gln Tyr Val Ser Pro Ser Cys Thr Ser
                20                  25                  30

Ser Cys Thr Asn Phe Gly Glu Gln Leu Arg Ser Gly Glu Ala Arg Pro
            35                  40                  45

Pro Ala Val Pro Ser Pro Ala Arg Arg Ala Gln Ala Pro Leu Asp Glu
        50                  55                  60

Trp Glu Arg Arg Pro Gln Leu Pro Pro Pro Arg Gly Pro Pro Glu
65                  70                  75                  80

Gly Ser Arg Gly Val Ala Ala Pro Glu Asp Glu Asp Glu Asp Pro Gly
                85                  90                  95

Asp Pro Glu Glu Glu Glu Glu Glu Glu Glu Pro Asp Pro Glu
            100                 105                 110

Ala Pro Glu Asn Gly Ser Leu Pro Arg Phe Val Pro Arg Phe Asn Phe
        115                 120                 125

Thr Leu Lys Asp Leu Thr Arg Phe Val Asp Phe Asn Ile Lys Gly Arg
130                 135                 140

Asp Val Ile Val Phe Leu His Ile Gly His Thr Gly Gly Thr Thr Phe
```

```
            145                 150                 155                 160
    Gly Arg His Leu Val Lys Asn Ile Arg Leu Glu Gln Pro Cys Ser Cys
                    165                 170                 175

Lys Ala Gly Gln Lys Lys Cys Thr Cys His Arg Pro Gly Lys Lys Glu
                    180                 185                 190

Thr Trp Leu Phe Ser Arg Phe Ser Thr Gly Trp Ser Cys Gly Thr Asn
                    195                 200                 205

Ala Asp Trp Thr Glu Leu Thr Asn Cys Val Pro Ala Ile Met Glu Lys
                    210                 215                 220

Lys Asp Cys Pro Arg Asn His Ser His Thr Arg Asn Phe Tyr Tyr Ile
    225                 230                 235                 240

Thr Met Leu Arg Asp Pro Val Ser Arg Tyr Leu Gly Gly Trp Lys His
                    245                 250                 255

His Gln Arg Gly Gly Thr Asn Lys Thr Ser Leu His Met Cys Asp Gly
                    260                 265                 270

Arg Ser Pro Thr Pro Asp Glu Leu Pro Thr Cys Tyr Pro Gly Asp Asp
                    275                 280                 285

Trp Ser Gly Val Ser Leu Arg Glu Phe Met Asp Cys Ser Tyr Asn Leu
                    290                 295                 300

Ala Asn Asn Arg Gln Val Arg Met Leu Ala Asp Leu Ser Leu Val Gly
    305                 310                 315                 320

Cys Tyr Asn Leu Thr Phe Met Asn Glu Ser Glu Arg Asn Thr Ile Leu
                    325                 330                 335

Leu Gln Ser Ala Lys Asn Asn Leu Lys Asn Met Ala Phe Phe Gly Leu
                    340                 345                 350

Thr Glu Phe Gln Arg Lys Thr Gln Phe Leu Phe Glu Arg Thr Phe Asn
                    355                 360                 365

Leu Lys Phe Ile Ser Pro Phe Thr Gln Val Asn Ile Thr Arg Ala Ser
                    370                 375                 380

Asn Val Asp Ile Asn Asp Gly Ala Arg Gln His Ile Glu Glu Leu Asn
    385                 390                 395                 400

Phe Leu Asp Met Gln Leu Tyr Glu Tyr Ala Lys Asp Leu Phe Gln Gln
                    405                 410                 415

Arg Tyr His His Thr Lys Gln Leu Glu His Gln Arg Asp Arg Gln Lys
                    420                 425                 430

Arg Arg Glu Glu Arg Arg Leu Gln Arg Glu His Arg Ala His Arg Trp
                    435                 440                 445

Pro Lys Glu Asp Arg Ala Met Glu Gly Thr Val Thr Glu Asp Tyr Asn
    450                 455                 460

Ser Gln Val Val Arg Trp
    465                 470

<210> SEQ ID NO 121
<211> LENGTH: 470
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 13

<400> SEQUENCE: 121

Met Asp Glu Arg Phe Asn Lys Trp Leu Leu Thr Pro Val Leu Thr Leu
1               5                   10                  15

Leu Phe Val Val Ile Met Tyr Gln Tyr Val Ser Pro Ser Cys Thr Ser
                20                  25                  30
```

Ser Cys Thr Asn Phe Gly Glu Gln Leu Arg Ser Gly Glu Ala Arg Pro
             35                  40                  45

Pro Ala Val Pro Ser Pro Ala Arg Arg Ala Gln Ala Pro Leu Asp Glu
 50                  55                  60

Trp Glu Arg Arg Pro Gln Leu Pro Pro Pro Arg Gly Pro Pro Glu
 65                  70                  75                  80

Gly Ser Arg Gly Val Ala Ala Pro Glu Asp Glu Asp Glu Asp Pro Gly
                 85                  90                  95

Asp Pro Glu Glu Glu Glu Glu Glu Glu Glu Pro Asp Pro Glu
             100                 105                 110

Ala Pro Glu Asn Gly Ser Leu Pro Arg Phe Val Pro Arg Phe Asn Phe
             115                 120                 125

Thr Leu Lys Asp Leu Thr Arg Phe Val Asp Phe Asn Ile Lys Gly Arg
130                 135                 140

Asp Val Ile Val Phe Leu His Ile Gly His Thr Gly Gly Thr Thr Phe
145                 150                 155                 160

Gly Arg His Leu Val Lys Asn Ile Arg Leu Glu Gln Pro Cys Ser Cys
                 165                 170                 175

Lys Ala Gly Gln Lys Lys Cys Thr Cys His Arg Pro Gly Lys Lys Glu
             180                 185                 190

Thr Trp Leu Phe Ser Arg Phe Ser Thr Gly Trp Ser Cys Gly Thr Arg
             195                 200                 205

Ala Asp Trp Thr Glu Leu Thr Asn Cys Val Pro Ala Ile Met Glu Lys
             210                 215                 220

Lys Asp Cys Pro Arg Asn His Ser His Thr Arg Asn Phe Tyr Tyr Ile
225                 230                 235                 240

Thr Met Leu Arg Asp Pro Val Ser Arg Tyr Leu Ser His Trp Lys His
                 245                 250                 255

Thr Gln Arg Gly Gly Ala Asn Lys Thr Gly Leu His Met Cys Asp Gly
             260                 265                 270

Arg Ser Pro Thr Pro Asp Glu Leu Pro Thr Cys Tyr Pro Gly Asp Asp
             275                 280                 285

Trp Ser Gly Val Ser Leu Arg Glu Phe Met Asp Cys Ser Tyr Asn Leu
             290                 295                 300

Gly Asn Asn Arg Gln Val Arg Met Leu Ala Asp Leu Ser Leu Val Gly
305                 310                 315                 320

Cys Tyr Asn Leu Thr Phe Met Asn Glu Ser Glu Arg Asn Thr Ile Leu
                 325                 330                 335

Leu Gln Ser Ala Lys Asn Asn Leu Lys Asn Met Ala Phe Phe Gly Leu
             340                 345                 350

Thr Glu Phe Gln Arg Lys Thr Gln Phe Leu Phe Glu Arg Thr Phe Asn
             355                 360                 365

Leu Lys Phe Ile Ser Pro Phe Thr Gln Phe Asn Ile Thr Arg Ala Ser
370                 375                 380

Asn Val Asp Ile Asn Asp Gly Ala Arg Gln His Ile Glu Glu Leu Asn
385                 390                 395                 400

Phe Leu Asp Met Gln Leu Tyr Glu Tyr Ala Lys Asp Leu Phe Gln Gln
                 405                 410                 415

Arg Tyr His His Thr Lys Gln Leu Glu His Gln Arg Asp Arg Gln Lys
                 420                 425                 430

Arg Arg Glu Glu Arg Arg Leu Gln Arg Glu His Arg Ala His Arg Trp
             435                 440                 445

Pro Lys Glu Asp Arg Ala Met Glu Gly Thr Val Thr Glu Asp Tyr Asn

-continued

```
                450                 455                 460
Ser Gln Val Val Arg Trp
465                 470

<210> SEQ ID NO 122
<211> LENGTH: 470
<212> TYPE: PRT
<213> ORGANISM: Artificial Sequence
<220> FEATURE:
<223> OTHER INFORMATION: Engineered glucosaminyl 6-O sulfotransferase
      mutant_sulfotransferase 14

<400> SEQUENCE: 122

Met Asp Glu Arg Phe Asn Lys Trp Leu Leu Thr Pro Val Leu Thr Leu
1               5                   10                  15

Leu Phe Val Val Ile Met Tyr Gln Tyr Val Ser Pro Ser Cys Thr Ser
                20                  25                  30

Ser Cys Thr Asn Phe Gly Glu Gln Leu Arg Ser Gly Glu Ala Arg Pro
            35                  40                  45

Pro Ala Val Pro Ser Pro Ala Arg Arg Ala Gln Ala Pro Leu Asp Glu
        50                  55                  60

Trp Glu Arg Arg Pro Gln Leu Pro Pro Pro Arg Gly Pro Pro Glu
65                  70                  75                  80

Gly Ser Arg Gly Val Ala Ala Pro Glu Asp Glu Asp Glu Pro Gly
                85                  90                  95

Asp Pro Glu Glu Glu Glu Glu Glu Glu Glu Pro Asp Pro Glu
            100                 105                 110

Ala Pro Glu Asn Gly Ser Leu Pro Arg Phe Val Pro Arg Phe Asn Phe
        115                 120                 125

Thr Leu Lys Asp Leu Thr Arg Phe Val Asp Phe Asn Ile Lys Gly Arg
130                 135                 140

Asp Val Ile Val Phe Leu His Ile Gly His Thr Gly Gly Thr Thr Phe
145                 150                 155                 160

Gly Arg His Leu Val Lys Asn Ile Arg Leu Glu Gln Pro Cys Ser Cys
                165                 170                 175

Lys Ala Gly Gln Lys Lys Cys Thr Cys His Arg Pro Gly Lys Lys Glu
            180                 185                 190

Thr Trp Leu Phe Ser Arg Phe Ser Thr Gly Trp Ser Cys Gly Ser His
        195                 200                 205

Ala Asp Trp Thr Glu Leu Thr Asn Cys Val Pro Ala Ile Met Glu Lys
    210                 215                 220

Lys Asp Cys Pro Arg Asn His Ser His Thr Arg Asn Phe Tyr Tyr Ile
225                 230                 235                 240

Thr Met Leu Arg Asp Pro Val Ser Arg Tyr Leu Ser Gly Trp Lys His
                245                 250                 255

His Gln Arg Gly Gly Ala Asn Lys Thr Ser Leu His Met Cys Asp Gly
            260                 265                 270

Arg Ser Pro Thr Pro Asp Glu Leu Pro Thr Cys Tyr Pro Gly Asp Asp
        275                 280                 285

Trp Ser Gly Val Ser Leu Arg Glu Phe Met Asp Cys Ser Tyr Asn Leu
    290                 295                 300

Gly Asn Asn Arg Gln Val Arg Met Leu Ala Asp Leu Ser Leu Val Gly
305                 310                 315                 320

Cys Tyr Asn Leu Thr Phe Met Asn Glu Ser Glu Arg Asn Thr Ile Leu
                325                 330                 335
```

Leu Gln Ser Ala Lys Asn Asn Leu Lys Asn Met Ala Phe Phe Gly Leu
                340                 345                 350

Thr Glu Phe Gln Arg Lys Thr Gln Phe Leu Phe Glu Arg Thr Phe Asn
            355                 360                 365

Leu Lys Phe Ile Ser Pro Phe Thr Gln Phe Asn Ile Thr Arg Ala Ser
        370                 375                 380

Asn Val Asp Ile Asn Asp Gly Ala Arg Gln His Ile Glu Glu Leu Asn
385                 390                 395                 400

Phe Leu Asp Met Gln Leu Tyr Glu Tyr Ala Lys Asp Leu Phe Gln Gln
                405                 410                 415

Arg Tyr His His Thr Lys Gln Leu Glu His Gln Arg Asp Arg Gln Lys
            420                 425                 430

Arg Arg Glu Glu Arg Leu Gln Arg Glu His Arg Ala His Arg Trp
        435                 440                 445

Pro Lys Glu Asp Arg Ala Met Glu Gly Thr Val Thr Glu Asp Tyr Asn
        450                 455                 460

Ser Gln Val Val Arg Trp
465                 470

<210> SEQ ID NO 123
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfatase 1

<400> SEQUENCE: 123

Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Ala
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Ala Tyr Thr His Met Leu Tyr Asn His Leu Gln Lys His Lys Pro
        115                 120                 125

Tyr Pro Pro Ile Glu Asp Leu Leu Met Arg Asp Gly Arg Leu Asn Leu
    130                 135                 140

Asp Met Val Met Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
            245                 250                 255

Leu Val Gly Arg Thr Phe Asp Trp His
        260                 265

<210> SEQ ID NO 124
<211> LENGTH: 795
<212> TYPE: DNA
<213> ORGANISM: Artificial Sequence
<220> FEATURE:
<223> OTHER INFORMATION: Polynucleotide sequence encoding for engineered
      glucosaminyl 3-O sulfotransferase mutant_sulfatase 1

<400> SEQUENCE: 124
atgggaactg cgtcgaacgg cagtacgcaa cagttaccgc aaaccatcat tattggcgtg    60
ggtcacgggg ggacccgtgc acttctggaa atgttgagtc tgcaccctga cgtggccgct   120
gcagagaacg aagtccactt cttcgattgg gaggagcatt atagtcaagg cttggggtgg   180
tatcttaccc agatgccttt cagctccccc catcagctta ccgttgaaaa gactcatgcc   240
tattttacat cgcccaaagt tcctgaacgt attcatagca tgaaccccac aattcgttta   300
cttttgatcc tgcgtgatcc aagcgagcgc gttttatcgg catacacgca catgttatat   360
aatcatttgc agaagcacaa accttaccca ccaattgagg acttattgat gcgtgatggt   420
cgcttaaatt tagatatggt aatgctgaat cgttcccttt atcacgcaca catgttaaac   480
tggctgcgct tcttcccgtt gggtcatatc catattgtcg atggggatcg cttaattcgc   540
gacccatttc cggagatcca aaaggttgag cgtttcttaa aactgtcgcc tcaaatcaac   600
gcgtcaaact tttacttcaa caagacgaaa ggtttctatt gcctgcgtga tagcggtaag   660
gaccgctgct tgcatgaatc taaagggcgt gctcatccac aagttgatcc taaattactt   720
gataagctgc atgaatactt ccatgaacct aacaaaaagt tcttcaaact tgtcggccgc   780
acatttgatt ggcat                                                    795

<210> SEQ ID NO 125
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfatase 2

<400> SEQUENCE: 125

Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Ala
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu

|  | 100 |  |  |  | 105 |  |  |  | 110 |  |  |
|---|---|---|---|---|---|---|---|---|---|---|---|

Ser Ala Tyr Thr His Leu Leu Tyr Asn His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Arg Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265

<210> SEQ ID NO 126
<211> LENGTH: 795
<212> TYPE: DNA
<213> ORGANISM: Artificial Sequence
<220> FEATURE:
<223> OTHER INFORMATION: Polynucleotide sequence encoding for engineered
      glucosaminyl 3-O sulfotransferase mutant_sulfatase 2

<400> SEQUENCE: 126

```
atgggaactg cgtcgaacgg cagtacgcaa cagttacccc agacaattat tattggcgta      60
gggcacggag gtactcgcgc cttattggag atgctgtcct acatccaga cgtggcagcg     120
gctgaaaacg aggtacattt ctttgactgg gaagaacact actcacaggg actgggatgg     180
tacctgaccc aaatgccctt cagttcaccg catcagttga cagtagagaa gacacatgca     240
tattttacgt cgccaaaagt cccggaacgt attcattcga tgaatcccac gattcgtctg     300
ttgttaatct tgcgtgaccc tagtgagcgt gttctttctg cgtacactca cttgctgtat     360
aaccatttac agaaacacaa gccatatccg ccgattgaag atctgttgat gcgtgacggg     420
cgtcttaacc tggactatcg tggcctgaac cgctctttat accacgcgca catgttgaat     480
tggcttcgct tcttcccctt gggacatatt catattgtgg atggagatcg cttaatccgt     540
gatccattcc cggaaattca gaaggttgag cgtttcctga gttgtctcc acaaattaat     600
gcaagcaact tttactttaa taaaaccaag ggcttctact gtttgcgcga tagcggaaaa     660
gaccgctgcc tgcatgagtc caaaggacgt gcacatcccc aagtcgatcc aaagttgctt     720
gacaaattac acgagtattt ccatgaaccg aataaaaagt ttttaagtt ggtcggccgc     780
acatttgatt ggcat                                                      795
```

<210> SEQ ID NO 127
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfatase 3

<400> SEQUENCE: 127

```
Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Ala
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Ala Tyr Thr His Leu Leu Tyr Asn His Leu Gln Lys His Lys Pro
        115                 120                 125

Tyr Pro Pro Ile Glu Asp Leu Leu Met Arg Asp Gly Arg Leu Asn Leu
130                 135                 140

Asp Tyr Val Gly Leu Asn Arg Ser Leu Tyr His Ala His Met Leu Asn
145                 150                 155                 160

Trp Leu Arg Phe Phe Pro Leu Gly His Ile His Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265
```

<210> SEQ ID NO 128
<211> LENGTH: 795
<212> TYPE: DNA
<213> ORGANISM: Artificial Sequence
<220> FEATURE:
<223> OTHER INFORMATION: Polynucleotide sequence encoding for engineered
    glucosaminyl 3-O sulfotransferase mutant_sulfatase 3

<400> SEQUENCE: 128

```
atgggaactg cgtcgaacgg cagtacgcaa caattgccac agacaattat cattggcgtt      60
ggtcatgggg ggacgcgcgc tctgctggaa atgttgtccc ttcacccaga tgtggccgct     120
gcggagaacg aagttcactt cttcgactgg gaagaacact atagccaagg gttggggtgg     180
tacctgaccc aaatgccgtt cagtagtcct catcaattga ccgttgagaa aactcacgct     240
tactttacct cgcccaaggt acccgagcgc atccacagca tgaaccccac tatccgcctg     300
ctgcttattt tgcgtgaccc ttcagagcgc gttttaagcg cgtatactca tcttctttat     360
aaccaccttc agaagcacaa gccttatcct ccgattgaag atttgttgat gcgcgatggc     420
```

```
cgcttgaact tagactatgt cgggcttaac cgttctcttt accatgccca catgcttaac    480
tggctgcgct tttttccgct tggacacatc cacatcgtcg acggggaccg cttgattcgt    540 gaccccttc ccgagattca aaaggttgaa cgtttcttaa agctttcacc tcaaatcaat    600
gcgtccaact tttattttaa caagactaaa ggcttctact gcttacgcga ctcaggaaaa    660
gatcgctgct tacatgaatc gaagggcgt gcccatccac aagttgatcc taaattattg    720
gataagctgc acgaatactt ccatgagcca aataagaaat tctttaagtt agtcggccgc    780
acatttgatt ggcat                                                    795
```

<210> SEQ ID NO 129
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfatase 4

<400> SEQUENCE: 129

```
Met Gly Thr Ala Ser Asn Gly Ser Thr Gln Gln Leu Pro Gln Thr Ile
1               5                   10                  15

Ile Ile Gly Val Gly His Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Leu
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Trp Tyr Thr His Ala Leu Tyr Ala His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Thr Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265
```

<210> SEQ ID NO 130
<211> LENGTH: 795

<212> TYPE: DNA
<213> ORGANISM: Artificial Sequence
<220> FEATURE:
<223> OTHER INFORMATION: Polynucleotide sequence encoding for engineered
    glucosaminyl 3-O sulfotransferase mutant_sulfatase 4

<400> SEQUENCE: 130

```
atgggaactg cgtcgaacgg cagtacgcaa caattgcctc agactatcat cattggggta    60
ggacacggag gtacacgtgc attgcttgag atgttaagtc ttcatcccga tgttgctgca   120
gctgaaaatg aagtacactt tttcgactgg gaagagcact acagtcaggg actgggttgg   180
tatctgacgc agatgccttt ttcaagcccc catcagttga ccgtagaaaa gactcatctt   240
tacttcacct ccccgaaggt ccccgaacgt attcattcca tgaacccaac catccgttta   300
cttttgatcc ttcgtgatcc cagtgagcgc gtccttagtt ggtacactca tgccctgtac   360
gctcatttac agaaacacaa accatacccg ccgattgagg acctttaat gcgcgatggg    420
cgtcttaatc ttgattatac aggcctgaat cgttctcttt accacgcaca catgttaaat   480
tggctgcgtt tctttccact tggacacatc catatcgtgg atggtgaccg cttaatccgc   540
gatcctttcc cggagattca gaaagttgaa cgcttcctta aactgtcacc gcagatcaat   600
gcctcgaatt tctacttcaa taagactaag ggcttctact gcttgcgcga ctctggcaag   660
gatcgttgct acacgaatc taaggggcgt gctcatccac aggtcgaccc aaagttgctt    720
gacaaattgc acgaatattt tcacgagcca ataaaaagt tctttaagct ggtcggccgc    780
acatttgatt ggcat                                                   795
```

<210> SEQ ID NO 131
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
    mutant_sulfatase 5

<400> SEQUENCE: 131

```
Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
                20                  25                  30

Ser Leu His Pro Asp Val Ala Ala Ala Glu Asn Glu Val His Phe Phe
            35                  40                  45

Asp Trp Glu Glu His Tyr Ser Gln Gly Leu Gly Trp Tyr Leu Thr Gln
        50                  55                  60

Met Pro Phe Ser Ser Pro His Gln Leu Thr Val Glu Lys Thr His Leu
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Leu Tyr Thr His Ala Leu Tyr Asn His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Thr Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175
```

```
Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265

<210> SEQ ID NO 132
<211> LENGTH: 795
<212> TYPE: DNA
<213> ORGANISM: Artificial Sequence
<220> FEATURE:
<223> OTHER INFORMATION: Polynucleotide sequence encoding for engineered
      glucosaminyl 3-O sulfotransferase mutant_sulfatase 5

<400> SEQUENCE: 132
atgggaactg cgtcgaacgg cagtacgcaa caattaccac aaacaatcat catcggggta    60
gggcatggtg gaactcgtgc tttgcttgag atgctttcac tgcatcccga cgtggctgca   120
gcggagaatg aagtgcattt cttcgattgg gaagaacatt atagccaggg ccttgggtgg   180
tatctgaccc agatgccatt cagttctccc catcagctga ccgtcgaaaa gacccatttg   240
tattttactt cgcctaaagt tcccgaacgt atccacagca tgaacccgac gattcgttta   300
ctgctgattc tgcgtgaccc gtcagagcgt gtccttagtt tatatacgca cgctttgtat   360
aaccacttac aaaaacataa accatcccca cccattgaag acttattaat gcgcgacgga   420
cgtctgaact agactacac ggggctgaat cgttcattgt atcatgccca catgcttaac   480
tggttgcgtt ttttccatt gggacacatc catattgttg acggagatcg tctgatccgc   540
gacccttttc ccgagattca aaagtcgaa cgttttttga attatcgcc acaaattaac   600 gcctctaatt tttacttcaa caagactaaa ggttttttatt gtttacgtga tagtggtaag   660
gaccgctgtc ttcatgaatc aaagggacgc gcacatcccc aagtagatcc aaaacttctg   720
gataagttac acgagtattt ccatgagcct aacaagaaat tttttaagct tgtcggccgc   780
acatttgatt ggcat                                                    795

<210> SEQ ID NO 133
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfatase 6

<400> SEQUENCE: 133

Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Ala Glu Asn Glu Val His Phe Phe
        35                  40                  45

Asp Trp Glu Glu His Tyr Ser Gln Gly Leu Gly Trp Tyr Leu Thr Gln
```

```
            50                  55                  60
Met Pro Phe Ser Ser Pro His Gln Leu Thr Val Glu Lys Thr His Thr
 65                  70                  75                  80

Tyr Phe Thr Ser Pro Lys Val Pro Glu Arg Ile His Ser Met Asn Pro
                 85                  90                  95

Thr Ile Arg Leu Leu Ile Leu Arg Asp Pro Ser Glu Arg Val Leu
            100                 105                 110

Ser Leu Tyr Thr His Ala Leu Tyr Met His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Ala Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265

<210> SEQ ID NO 134
<211> LENGTH: 795
<212> TYPE: DNA
<213> ORGANISM: Artificial Sequence
<220> FEATURE:
<223> OTHER INFORMATION: Polynucleotide sequence encoding for engineered
      glucosaminyl 3-O sulfotransferase mutant_sulfatase 6

<400> SEQUENCE: 134
atgggaactg cgtcgaacgg cagtacgcaa caattacctc agaccattat tattggtgtc      60
ggccatggag gaacgcgtgc tctgctggag atgctttcgc ttcaccccga cgtggcggct     120
gccgagaatg aggtacactt ttttgattgg gaagagcatt actcacaagg tttgggctgg     180
taccttactc agatgccctt ttcgtcaccg catcaactga cggtggagaa gacccacact     240
tacttcacca gtccaaaagt ccctgaacgc atccatagca tgaatcctac aattcgtctt     300
cttttgatcc ttcgcgatcc atctgagcgt gtgttatcct tatataccca cgcgctttac     360
atgcaccttc agaagcacaa gccctatccc ccaattgagg acttgctgat gcgcgatggc     420
cgtcttaatt tggattatgc aggactgaat cgttccctgt accacgccca catgctgaac     480
tggttgcgct tctttccact tggccacatc catattgtcg acgggatcg tctgattcgt     540 gatccgttcc cagaaatcca aaggtgtaga ngcttcctga attgagccc acagattaac     600 gcgtcgaatt tttacttaa caaaaccaaa ggattctatt gtcttcgtga cagtggaaaa     660
gatcgctgct tacacgaatc gaaggccgt gctcatcccc aagttgatcc gaagcttctt     720
gataagttgc acgagtactt ccacgaaccg aacaagaagt ttttcaagct ggtcggccgc     780
acatttgatt ggcat                                                      795
```

<210> SEQ ID NO 135
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase mutant_sulfatase 7

<400> SEQUENCE: 135

```
Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Ser
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Val Tyr Thr His Ala Leu Tyr Met His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Met Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265
```

<210> SEQ ID NO 136
<211> LENGTH: 795
<212> TYPE: DNA
<213> ORGANISM: Artificial Sequence
<220> FEATURE:
<223> OTHER INFORMATION: Polynucleotide sequence encoding for engineered glucosaminyl 3-O sulfotransferase mutant_sulfatase 7

<400> SEQUENCE: 136

```
atgggaactg cgtcgaacgg cagtacgcaa cagcttcccc agacgatcat tatcggagtc    60
ggtcatggtg ggacccgcgc attactggag atgttgtcgc ttcaccctga cgtggcggcg    120
gctgaaaatg aggtgcattt ttttgactgg gaagagcatt acagtcaggg tttaggttgg    180
```

-continued

```
tacttaacgc agatgccatt ctcgtctccc catcagttga ctgtcgagaa gactcactcc    240
tattttacaa gcccgaaggt tccagaacgc atccattcta tgaacccaac cattcgttta    300
cttcttattt tgcgtgaccc ctctgagcgt gtccttagtg tttacactca cgcgctgtat    360
atgcaccttc agaaacacaa gccttatccg ccaattgaag atctgttgat gcgcgatggc    420
cgtcttaatt tggactacat gggtttaaat cgtagcttat atcatgcgca catgttgaat    480
tggttgcgct tcttccctct tggtcatatt cacattgtag acggtgatcg tttaattcgc    540
gatccgttcc ccgaaatcca aaaggtagaa cgtttcttga agctttcacc acagatcaac    600
gcgtcgaatt tttacttcaa caagacaaag gcttctact gcttgcgcga ctcaggaaaa     660
gaccgttgtt tacacgagtc taaaggccgt gctcaccctc aagtagaccc taagcttttg    720
gacaaacttc acgagtactt tcatgaacca ataaaaagt tcttcaaatt ggtcggccgc     780
acatttgatt ggcat                                                     795
```

<210> SEQ ID NO 137
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfatase 8

<400> SEQUENCE: 137

```
Met Gly Thr Ala Ser Asn Gly Ser Thr Gln Gln Leu Pro Gln Thr Ile
1               5                   10                  15

Ile Ile Gly Val Gly His Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Thr
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Val Tyr Thr His Ala Leu Tyr Met His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Met Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240
```

Asp Lys Leu His Glu Tyr Phe His Glu Pro Asn Lys Phe Phe Lys
                245                 250                 255

Leu Val Gly Arg Thr Phe Asp Trp His
            260                 265

<210> SEQ ID NO 138
<211> LENGTH: 795
<212> TYPE: DNA
<213> ORGANISM: Artificial Sequence
<220> FEATURE:
<223> OTHER INFORMATION: Polynucleotide sequence encoding for engineered
      glucosaminyl 3-O sulfotransferase mutant_sulfatase 8

<400> SEQUENCE: 138
atgggaactg cgtcgaacgg cagtacgcaa cagttgcccc aaactatcat cattggagtc    60
gggcatggtg gaacacgcgc tctgttggaa atgctgtcct gcacccccga cgttgccgct   120
gcagaaaatg aagtgcactt tttcgattgg gaggaacact actcccaggg tttgggctgg   180
tatcttacac agatgccgtt cagctctcca catcagttga cagtggagaa aacgcacaca   240
tattttacat caccaaaggt cccggagcgt attcattcga tgaatccaac catccgtctt   300
ctgctgatcc ttcgcgatcc cagtgagcgc gtactgtccg tttacaccca tgccttgtat   360
atgcacttac agaaacacaa accctatcct ccaatcgaag accttctgat cgcgatggt    420 cgccttaatc ttgactatat ggggctgaat cgttctctgt accatgcaca catgttgaac   480
tggcttcgct ttttccgtt gggccatatt catattgtgg atggcgaccg tttgattcgt    540
gacccgttcc agagatcca aaaggttgaa cgctttttaa aattatcgcc acaaattaat    600
gcatcgaact tctactttaa taagacgaag ggattttact gtttacgtga ttctggcaaa   660
gatcgttgtc tgcatgaatc taaagggcgt gctcatccgc aggtggaccc aaaactgtta   720
gataagttac acgagtattt tcatgagcct aacaagaaat tctttaagtt ggtcggccgc   780
acatttgatt ggcat                                                    795

<210> SEQ ID NO 139
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfatase 9

<400> SEQUENCE: 139

Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Thr
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Phe Tyr Thr His Ala Leu Tyr Met His Leu Gln Lys His Lys Pro
        115                 120                 125

```
Tyr Pro Pro Ile Glu Asp Leu Leu Met Arg Asp Gly Arg Leu Asn Leu
        130                 135                 140

Asp Tyr Lys Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265
```

<210> SEQ ID NO 140
<211> LENGTH: 795
<212> TYPE: DNA
<213> ORGANISM: Artificial Sequence
<220> FEATURE:
<223> OTHER INFORMATION: Polynucleotide sequence encoding for engineered
      glucosaminyl 3-O sulfotransferase mutant_sulfatase 9

<400> SEQUENCE: 140

```
atgggaactg cgtcgaacgg cagtacgcaa caactgccgc aaactatcat catcggggtg      60
ggtcatggag gtactcgtgc attattagaa atgcttagct tgcatcctga cgtggctgcg     120
gcggaaaacg aggtgcattt tttcgattgg gaggaacatt attctcaggg cttgggatgg     180
taccttactc aaatgccatt tagtagtccg caccagctga cagtagaaaa gacacatacg     240
tacttcacca gtccgaaagt ccccgagcgt attcattcaa tgaacccgac tatccgctta     300
ctgttgattc tgcgcgaccc gtcagaacgt gtattatcat tttatactca cgcgttatat     360
atgcatcttc aaaagcacaa accgtaccca cctatcgagg acctgctgat gcgtgatgga     420
cgcctgaatc tggactataa gggcttaaat cgctctttat atcatgcgca catgctgaat     480
tggcttcgtt tctttccgtt gggacatatt cacatcgtcg acggcgaccg cttgattcgt     540
gacccgttcc ccgaaatcca gaaagttgag cgtttcttga gctgtcacc tcagattaat     600 gccagcaatt tttactttaa taagaccaag gggttctatt gccttcgcga ctccggtaaa     660
gaccgctgct tacacgagtc gaaagggcgt gcccatccac aggtcgaccc taagctgctt     720
gacaagttac acgaatactt ccatgagcca aacaaaaagt tcttcaaact tgtcggccgc     780
acatttgatt ggcat                                                      795
```

<210> SEQ ID NO 141
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfatase 10

<400> SEQUENCE: 141

Met Gly Thr Ala Ser Asn Gly Ser Thr Gln Gln Leu Pro Gln Thr Ile

```
                1               5                   10                  15
            Ile Ile Gly Val Gly His Gly Gly Thr Arg Ala Leu Leu Glu Met Leu
                                20                  25                  30
            Ser Leu His Pro Asp Val Ala Ala Glu Asn Glu Val His Phe Phe
                        35                  40                  45
            Asp Trp Glu Glu His Tyr Ser Gln Gly Leu Gly Trp Tyr Leu Thr Gln
                    50                  55                  60
            Met Pro Phe Ser Ser Pro His Gln Leu Thr Val Glu Lys Thr His Ser
            65                  70                  75                  80
            Tyr Phe Thr Ser Pro Lys Val Pro Glu Arg Ile His Ser Met Asn Pro
                                85                  90                  95
            Thr Ile Arg Leu Leu Leu Ile Leu Arg Asp Pro Ser Glu Arg Val Leu
                            100                 105                 110
            Ser Leu Ala Thr His Leu Leu Tyr Val His Leu Gln Lys His Lys Pro
                        115                 120                 125
            Tyr Pro Pro Ile Glu Asp Leu Leu Met Arg Asp Gly Arg Leu Asn Leu
                    130                 135                 140
            Asp Tyr Thr Gly Leu Asn Arg Ser Leu Tyr His Ala His Met Leu Asn
            145                 150                 155                 160
            Trp Leu Arg Phe Phe Pro Leu Gly His Ile His Ile Val Asp Gly Asp
                                165                 170                 175
            Arg Leu Ile Arg Asp Pro Phe Pro Glu Ile Gln Lys Val Glu Arg Phe
                            180                 185                 190
            Leu Lys Leu Ser Pro Gln Ile Asn Ala Ser Asn Phe Tyr Phe Asn Lys
                        195                 200                 205
            Thr Lys Gly Phe Tyr Cys Leu Arg Asp Ser Gly Lys Asp Arg Cys Leu
                    210                 215                 220
            His Glu Ser Lys Gly Arg Ala His Pro Gln Val Asp Pro Lys Leu Leu
            225                 230                 235                 240
            Asp Lys Leu His Glu Tyr Phe His Glu Pro Asn Lys Lys Phe Phe Lys
                                245                 250                 255
            Leu Val Gly Arg Thr Phe Asp Trp His
                            260                 265

<210> SEQ ID NO 142
<211> LENGTH: 795
<212> TYPE: DNA
<213> ORGANISM: Artificial Sequence
<220> FEATURE:
<223> OTHER INFORMATION: Polynucleotide sequence encoding for engineered
      glucosaminyl 3-O sulfotransferase mutant_sulfatase 10

<400> SEQUENCE: 142
atgggaactg cgtcgaacgg cagtacgcaa caattaccgc aaactattat cattggtgta      60
ggacatggtg ggacgcgcgc gcttcttgaa atgttatcgc tgcaccctga tgtcgctgcc     120
gctgagaatg aagtacactt tttcgattgg gaggaacatt attcccaggg gttagggtgg     180
tatcttacac aaatgccttt tagctccccg caccaactga ccgtggaaaa aacccacagt     240
tattttactt cgccaaaagt acccgaacgt atccactcta tgaatccgac tatccgtttg     300
ttgttaatcc tgcgtgaccc ctcggaacgt gtactttcat tagctacaca tttgttatat     360
gttcatctgc agaagcacaa accgtatccc cctatcgaag atcttcttat gcgtgatggg     420
cgcttgaatc tggactacac tggacttaac cgtagcttgt atcatgccca catgttaaac     480
tggcttcgct ttttttccttt aggccatatt catatcgttg atggcgaccg tcttattcgt     540
```

```
gatccatttc cggaaattca aaaagtggag cgtttcctga aactgagtcc acaaatcaat    600
gcctcaaact tctactttaa taaaaccaag gggttttatt gtcttcgcga cagcggcaaa    660
gatcgctgtc ttcacgagtc aaaaggtcgc gcgcacccgc aagtcgaccc taaattactt    720
gacaagctgc acgagtattt tcacgaaccc aacaagaaat tctttaaatt agtcggccgc    780
acatttgatt ggcat                                                     795
```

<210> SEQ ID NO 143
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase mutant_sulfatase 11

<400> SEQUENCE: 143

```
Met Gly Thr Ala Ser Asn Gly Ser Thr Gln Gln Leu Pro Gln Thr Ile
1               5                   10                  15

Ile Ile Gly Val Gly His Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Ser
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Leu Gly Thr His Met Leu Tyr Val His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Val Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265
```

<210> SEQ ID NO 144
<211> LENGTH: 795
<212> TYPE: DNA
<213> ORGANISM: Artificial Sequence
<220> FEATURE:
<223> OTHER INFORMATION: Polynucleotide sequence encoding for engineered glucosaminyl 3-O sulfotransferase mutant_sulfatase 11

<400> SEQUENCE: 144

```
atgggaactg cgtcgaacgg cagtacgcaa caattaccac agaccattat catcggggtc     60
gggcatgggg gtacacgtgc tttattagaa atgttgtcac ttcacccgga cgtagcagct    120
gcggagaatg aggtccactt tttcgactgg gaggagcatt actctcaagg cttggggtgg    180
tacttgactc aaatgccctt ctcttcgccc catcaattaa cagtcgaaaa gacccactcg    240
tacttcactt cccccaaggt tcccgaacgt attcattcca tgaaccctac cattcgcctt    300
ttgttaatcc tgcgcgatcc gtcggaacgt gtgctttcgt tgggcacaca catgctttac    360
gtccatttac agaagcacaa gccatacccg ccgatcgaag acttgctgat gcgcgacggg    420
cgtctgaatt tggactatgt aggcttgaac cgctcattat atcatgccca catgctgaac    480
tggttgcgtt tctttccatt gggtcacatc catatcgtgg atggtgaccg tttgatccgc    540
gatccattcc ctgagatcca gaaagtcgaa cgcttttta aattgtcccc tcaaattaat    600
gctagtaact tctacttcaa caaaacaaag gggttttatt gtctgcgtga cagcggtaag    660
gatcgttgtt tgcacgaatc gaagggtcgc gcgcaccctc aagtcgatcc taaattgttg    720
gataaactgc acgaatactt ccacgaaccg aacaaaaaat ttttcaaact tgtcggccgc    780
acatttgatt ggcat                                                    795
```

<210> SEQ ID NO 145
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase mutant_sulfatase 12

<400> SEQUENCE: 145

```
Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Ala Glu Asn Glu Val His Phe Phe
        35                  40                  45

Asp Trp Glu Glu His Tyr Ser Gln Gly Leu Gly Trp Tyr Leu Thr Gln
    50

```
Leu Lys Leu Ser Pro Gln Ile Asn Ala Ser Asn Phe Tyr Phe Asn Lys
            195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
            245                 250                 255

Leu Val Gly Arg Thr Phe Asp Trp His
            260                 265

<210> SEQ ID NO 146
<211> LENGTH: 795
<212> TYPE: DNA
<213> ORGANISM: Artificial Sequence
<220> FEATURE:
<223> OTHER INFORMATION: Polynucleotide sequence encoding for engineered
      glucosaminyl 3-O sulfotransferase mutant_sulfatase 12

<400> SEQUENCE: 146
atgggaactg cgtcgaacgg cagtacgcaa caactgcccc aaacgattat tattggcgtt      60
ggtcatgggg ggaccegtgc tttactggaa atgttatcac ttcaccccga tgtggctgct    120
gccgaaaacg aggtgcattt cttttgactgg gaagaacatt acagccaggg attgggatgg    180
tatcttacac aaatgccatt cagcagccct catcagttga cggtggagaa gacgcactct    240
tactttactt ctccgaaggt tccagagcgc attcactcga tgaaccctac gatccgtttg    300
ttacttattt tgcgcgaccc ctctgagcgc gttctgtctc tttatacaca tgcgttatat    360
gtgcatttac aaaagcataa gccctaccca ccaatcgagg atttactgat gcgcgatggt    420
cgcttgaatt tggactatac cggtttaaat cgctcgttgt accatgccca catgttgaac    480
tggcttcgtt ttttcccttt aggtcacatt cacattgtag atggggatcg cttgatccgt    540 gatccttttcc ctgagattca gaaagtagaa cgtttcttaa attatcacc ccaaattaat    600 gcttctaatt tttacttcaa caagactaaa gggttctact gtcttcgcga tagtggtaaa    660
gatcgttgct tgcacgaatc caaaggacgc gcacatccac aggtagatcc aaaattgctt    720
gataagttgc acgaatactt ccacgaaccc aacaaaaaat tctttaagtt agtcggccgc    780
acatttgatt ggcat                                                     795

<210> SEQ ID NO 147
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfotransferase 1

<400> SEQUENCE: 147

Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Ser
65                  70                  75                  80
```

Tyr Phe Thr Ser Pro Lys Val Pro Glu Arg Ile His Ser Met Asn Pro
                85                  90                  95

Thr Ile Arg Leu Leu Ile Leu Arg Asp Pro Ser Glu Arg Val Leu
            100                 105                 110

Ser Ala Tyr Thr His Met Leu Tyr Asn His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Val Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265

<210> SEQ ID NO 148
<211> LENGTH: 795
<212> TYPE: DNA
<213> ORGANISM: Artificial Sequence
<220> FEATURE:
<223> OTHER INFORMATION: Polynucleotide sequence encoding for engineered
      glucosaminyl 3-O sulfotransferase mutant_sulfotransferase 1

<400> SEQUENCE: 148
atgggaactg cgtcgaacgg cagtacgcaa caacttccgc agactatcat cattggcgta      60
ggacatggtg gaactcgtgc tctgttggag atgttatcac ttcaccccga cgtcgcagcg     120
gctgagaatg aagttcactt tttcgattgg gaagagcatt attcgcaggg gttaggttgg     180
tatcttaccc aaatgccttt ttcgagtccc atcagttaa cagtagagaa gacccattct      240
tactttacat caccaaaagt gcctgagcgc atccattcga tgaatccgac tatccgcctt     300
ttactgatct tacgcgatcc atcagaacgc gttctttcgg catataccca catgctttat     360
aaccatttgc agaaacacaa gccatatccc cctattgagg atttattaat gcgcgatgga     420
cgcttgaacc tggattatgt aggattaaat cgctctcttt atcacgccca tatgttaaac     480
tggcttcgct tttttccgct tgggcatatc cacatcgttg atggagaccg tttaattcgt     540
gacccgtttc ctgagatcca aaggtcgaa cgcttcctga attaagtcc tcagattaat       600 gcgagcaatt tctatttcaa caagacgaaa ggattctact gcctgcgcga ctccggtaag     660
gatcgctgcc tgcacgagtc aaaagggcgc gcgcacctc aggtcgaccc aaagctgtta     720
gataaattgc atgagtattt ccacgaacct aataagaagt tcttcaaact tgtcggccgc     780
acatttgatt ggcat                                                     795

<210> SEQ ID NO 149
<211> LENGTH: 265

<210> SEQ ID NO 149
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase mutant_sulfotransferase 2

<400> SEQUENCE: 149

```
Met Gly Thr Ala Ser Asn Gly Ser Thr Gln Gln Leu Pro Gln Thr Ile
1               5                   10                  15
Ile Ile Gly Val Gly His Gly Thr Arg Ala Leu Leu Glu Met Leu
            20                  25                  30
Ser Leu His Pro Asp Val Ala Ala Glu Asn Glu Val His Phe Phe
            35                  40                  45
Asp Trp Glu Glu His Tyr Ser Gln Gly Leu Gly Trp Tyr Leu Thr Gln
50                  55                  60
Met Pro Phe Ser Ser Pro His Gln Leu Thr Val Glu Lys Thr His Ser
65                  70                  75                  80
Tyr Phe Thr Ser Pro Lys Val Pro Glu Arg Ile His Ser Met Asn Pro
                85                  90                  95
Thr Ile Arg Leu Leu Leu Ile Leu Arg Asp Pro Ser Glu Arg Val Leu
            100                 105                 110
Ser Ala Tyr Thr His Met Leu Tyr Asn His Leu Gln Lys His Lys Pro
        115                 120                 125
Tyr Pro Pro Ile Glu Asp Leu Leu Met Arg Asp Gly Arg Leu Asn Leu
130                 135                 140
Asp Tyr Thr Gly Leu Asn Arg Ser Leu Tyr His Ala His Met Leu Asn
145                 150                 155                 160
Trp Leu Arg Phe Phe Pro Leu Gly His Ile His Ile Val Asp Gly Asp
                165                 170                 175
Arg Leu Ile Arg Asp Pro Phe Pro Glu Ile Gln Lys Val Glu Arg Phe
            180                 185                 190
Leu Lys Leu Ser Pro Gln Ile Asn Ala Ser Asn Phe Tyr Phe Asn Lys
        195                 200                 205
Thr Lys Gly Phe Tyr Cys Leu Arg Asp Ser Gly Lys Asp Arg Cys Leu
210                 215                 220
His Glu Ser Lys Gly Arg Ala His Pro Gln Val Asp Pro Lys Leu Leu
225                 230                 235                 240
Asp Lys Leu His Glu Tyr Phe His Glu Pro Asn Lys Lys Phe Phe Lys
                245                 250                 255
Leu Val Gly Arg Thr Phe Asp Trp His
            260                 265
```

<210> SEQ ID NO 150
<211> LENGTH: 795
<212> TYPE: DNA
<213> ORGANISM: Artificial Sequence
<220> FEATURE:
<223> OTHER INFORMATION: Polynucleotide sequence encoding for engineered glucosaminyl 3-O sulfotransferase mutant_sulfotransferase 2

<400> SEQUENCE: 150

```
atgggaactg cgtcgaacgg cagtacgcaa cagttgccgc agacaatcat tattggcgtc    60
ggacatggcg gaacccgtgc tcttttggaa atgctgagtc tgcaccctga cgtggcagcg    120
gcggagaatg aggttcactt ctttgattgg gaggaacatt attcgcaggg gttgggatgg    180
tatctgacgc aaatgccgtt ctccagtcca caccagttga ccgttgaaaa gacgcatagt    240
tattttacga gtcccaaagt acctgagcgt attcatagta tgaacccgac catccgtctg    300
```

```
ttgttgatcc ttcgcgatcc cagcgaacgc gtcttatcag cgtatactca catgctgtac    360
aaccaccttc aaaaacataa gccgtaccct cccatcgagg atcttttaat gcgtgatggt    420
cgtcttaacc ttgattacac aggtttgaac cgcagtttgt atcacgctca catgttgaat    480
tggttgcgct tctttcccct tggtcatatc catattgttg acggggaccg tctgatccgc    540
gacccgttcc cagagattca gaaagtggaa cgtttcctga aattatcccc acagatcaac    600
gcgagtaact tctattttaa caagacgaaa ggtttctatt gcttacgtga tagtgggaag    660
gaccgctgcc tgcacgagag caaaggacgt gctcatcctc aagttgaccc caagttattg    720
gataaactgc acgagtattt tcacgagcct aataaaaagt tctttaagtt agtcggccgc    780
acatttgatt ggcat                                                     795
```

<210> SEQ ID NO 151
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfotransferase 3

<400> SEQUENCE: 151

```
Met Gly Thr Ala Ser Asn Gly Ser Thr Gln Gln Leu Pro Gln Thr Ile
1               5                   10                  15

Ile Ile Gly Val Gly His Gly Thr Arg Ala Leu Leu Glu Met Leu
            20                  25                  30

Ser Leu His Pro Asp Val Ala Ala Glu Asn Glu Val His Phe Phe
            35                  40                  45

Asp Trp Glu Glu His Tyr Ser Gln Gly Leu Gly Trp Tyr Leu Thr Gln
50                  55                  60

Met Pro Phe Ser Ser Pro His Gln Leu Thr Val Glu Lys Thr His Ser
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Leu Gly Thr His Leu Leu Tyr Val His Leu Gln Lys His Lys Pro
            115                 120                 125

Tyr Pro Pro Ile Glu Asp Leu Leu Met Arg Asp Gly Arg Leu Asn Leu
            130                 135                 140

Asp Tyr Thr Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
            195                 200                 205

Thr Lys Gly Phe Tyr Cys Leu Arg Asp Ser Gly Lys Asp Arg Cys Leu
            210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265
```

<210> SEQ ID NO 152
<211> LENGTH: 795
<212> TYPE: DNA
<213> ORGANISM: Artificial Sequence
<220> FEATURE:
<223> OTHER INFORMATION: Polynucleotide sequence encoding for engineered
      glucosaminyl 3-O sulfotransferase mutant_sulfotransferase 3

<400> SEQUENCE: 152

```
atgggaactg cgtcgaacgg cagtacgcaa caacttccac aaactatcat tattggcgtg      60
ggtcacggtg ggactcgcgc tttacttgaa atgttgagct acatccgga tgttgccgca     120
gctgaaaacg aggtccattt ctttgactgg gaggaacact attcccaggg tttggggtgg     180
tatctgacgc agatgccttt ctcgtctcct caccaactta cggttgagaa aactcattca     240
tatttcacgt cccctaaagt accagaacgt atccactcaa tgaacccaac aattcgttta     300
ttgttgattt tgcgcgaccc gtcggaacgt gtgttgtcgt taggtacgca cttgctttac     360
gttcatttgc aaaagcataa accgtatcca ccgattgagg accttttgat gcgtgacgga     420
cgtttgaatt tggactatac gggcctgaat cgctcgctgt atcacgccca catgttgaac     480
tggctgcgct tcttccccct tggtcatatc cacatcgtag atggggaccg tctgatccgt     540
gacccttttcc cggaaatcca gaaagtggag cgtttcctga agttatctcc acaaatcaac     600
gcgagcaatt tttactttaa caagactaaa gggttctact gtttacgtga ttctggcaaa     660
gaccgttgcc ttcatgaaag taaaggccgc gctcaccctc aagtcgaccc caaattatta     720
gataagttgc acgagtactt ccatgaacct aataagaagt tcttcaaact tgtcggccgc     780
acatttgatt ggcat                                                      795
```

<210> SEQ ID NO 153
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_variable
<220> FEATURE:
<221> NAME/KEY: MISC_FEATURE
<222> LOCATION: (80)..(80)
<223> OTHER INFORMATION: Xaa is alanine, leucine, threonine, or serine
<220> FEATURE:
<221> NAME/KEY: MISC_FEATURE
<222> LOCATION: (114)..(114)
<223> OTHER INFORMATION: Xaa is alanine, tryptophan, leucine, valine, or
      phenylalanine
<220> FEATURE:
<221> NAME/KEY: MISC_FEATURE
<222> LOCATION: (115)..(115)
<223> OTHER INFORMATION: Xaa is tyrosine, alanine, or glycine
<220> FEATURE:
<221> NAME/KEY: MISC_FEATURE
<222> LOCATION: (118)..(118)
<223> OTHER INFORMATION: Xaa is methionine, leucine, or alanine
<220> FEATURE:
<221> NAME/KEY: MISC_FEATURE
<222> LOCATION: (121)..(121)
<223> OTHER INFORMATION: Xaa is asparagine, alanine, methionine, or
      valine
<220> FEATURE:
<221> NAME/KEY: MISC_FEATURE
<222> LOCATION: (146)..(146)
<223> OTHER INFORMATION: Xaa is tyrosine or methionine
<220> FEATURE:
<221> NAME/KEY: MISC_FEATURE
<222> LOCATION: (147)..(147)
<223> OTHER INFORMATION: Xaa is lysine, valine, arginine, threonine, alanine, or methionine
<220> FEATURE:
<221> NAME/KEY: MISC_FEATURE
<222> LOCATION: (148)..(148)
<223> OTHER INFORMATION: Xaa is methionine or glycine

<400> SEQUENCE: 153

Met Gly Thr Ala Ser Asn Gly Ser Thr Gln Gln Leu Pro Gln Thr Ile
1               5                   10                  15

Ile Ile Gly Val Gly His Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Xaa
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Xaa Xaa Thr His Xaa Leu Tyr Xaa His Leu Gln Lys His Lys Pro
        115                 120                 125

Tyr Pro Pro Ile Glu Asp Leu Leu Met Arg Asp Gly Arg Leu Asn Leu
    130                 135                 140

Asp Xaa Xaa Xaa Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265

<210> SEQ ID NO 154
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfotransferase 4
<220> FEATURE:
<221> NAME/KEY: MISC_FEATURE
<222> LOCATION: (114)..(114)
<223> OTHER INFORMATION: Xaa is alanine or leucine
<220> FEATURE:
<221> NAME/KEY: MISC_FEATURE
<222> LOCATION: (115)..(115)
<223> OTHER INFORMATION: Xaa is tyrosine or glycine
<220> FEATURE:
<221> NAME/KEY: MISC_FEATURE
<222> LOCATION: (118)..(118)
<223> OTHER INFORMATION: Xaa is methionine or leucine
<220> FEATURE:
<221> NAME/KEY: MISC_FEATURE
<222> LOCATION: (121)..(121)
<223> OTHER INFORMATION: Xaa is asparagine or valine
<220> FEATURE:
<221> NAME/KEY: MISC_FEATURE
<222> LOCATION: (147)..(147)
<223> OTHER INFORMATION: Xaa is valine or threonine

<400> SEQUENCE: 154

```
Met Gly Thr Ala Ser Asn Gly Ser Thr Gln Gln Leu Pro Gln Thr Ile
1               5                   10                  15

Ile Ile Gly Val Gly His Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
50                  55                  60

Met Pro Phe Ser Ser Pro His Gln Leu Thr Val Glu Lys Thr His Ser
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Xaa Xaa Thr His Xaa Leu Tyr Xaa His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Xaa Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265
```

<210> SEQ ID NO 155
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase mutant_sulfotransferase 5

<400> SEQUENCE: 155

```
Met Gly Val Ala Pro Asn Gly Ser Ala Gln Gln Leu Pro Gln Thr Ile
1               5                   10                  15

Ile Ile Gly Val Gly His Gly Gly Thr Arg Ala Leu Leu Glu Met Leu
            20                  25                  30
```

-continued

Ser Leu His Pro Asp Val Ala Ala Glu Asn Glu Val His Phe Phe
            35                  40                  45

Asp Trp Glu Glu His Tyr Ser His Gly Leu Gly Trp Tyr Leu Ser Gln
 50                  55                  60

Met Pro Phe Ser Trp Pro His Gln Leu Thr Val Glu Lys Thr His Ser
 65                  70                  75                  80

Tyr Phe Thr Ser Pro Lys Val Pro Glu Arg Val Tyr Ser Met Asn Pro
                 85                  90                  95

Ser Ile Arg Leu Leu Leu Ile Leu Arg Asp Pro Ser Glu Arg Val Leu
            100                 105                 110

Ser Leu Gly Thr His Leu Phe Tyr Val His Met Gln Lys His Lys Pro
            115                 120                 125

Tyr Pro Ser Ile Glu Glu Phe Leu Val Arg Asp Gly Arg Leu Asn Val
130                 135                 140

Asp Tyr Thr Gly Leu Asn Arg Ser Leu Tyr His Val His Met Gln Asn
145                 150                 155                 160

Trp Leu Arg Phe Phe Pro Leu Arg His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
            195                 200                 205

Thr Lys Gly Phe Tyr Cys Leu Arg Asp Ser Gly Arg Asp Arg Cys Leu
            210                 215                 220

His Glu Ser Lys Gly Arg Ala His Pro Gln Val Asp Pro Lys Leu Leu
225                 230                 235                 240

Asn Lys Leu His Glu Tyr Phe His Glu Pro Asn Lys Lys Phe Phe Glu
                245                 250                 255

Leu Val Gly Arg Thr Phe Asp Trp His
            260                 265

<210> SEQ ID NO 156
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfotransferase 6

<400> SEQUENCE: 156

Met Gly Val Ala Pro Asn Gly Ser Ala Gln Gln Leu Pro Gln Thr Ile
 1               5                  10                  15

Ile Ile Gly Val Gly His Gly Gly Thr Arg Ala Leu Leu Glu Met Leu
             20                  25                  30

Ser Leu His Pro Asp Val Ala Ala Glu Asn Glu Val His Phe Phe
            35                  40                  45

Asp Trp Glu Glu His Tyr Ser His Gly Leu Gly Trp Tyr Leu Ser Gln
 50                  55                  60

Met Pro Phe Ser Trp Pro His Gln Leu Thr Val Glu Lys Thr His Ser
 65                  70                  75                  80

Tyr Phe Thr Ser Pro Lys Val Pro Glu Arg Val Tyr Ser Met Asn Pro
                 85                  90                  95

Ser Ile Arg Leu Leu Leu Ile Leu Arg Asp Pro Ser Glu Arg Val Leu
            100                 105                 110

Ser Ala Tyr Thr His Met Phe Tyr Asn His Met Gln Lys His Lys Pro
            115                 120                 125

```
Tyr Pro Ser Ile Glu Glu Phe Leu Val Arg Asp Gly Arg Leu Asn Val
            130                 135                 140

Asp Tyr Thr Gly Leu Asn Arg Ser Leu Tyr His Val His Met Gln Asn
145                 150                 155                 160

Trp Leu Arg Phe Phe Pro Leu Arg His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
            195                 200                 205

Thr Lys Gly Phe Tyr Cys Leu Arg Asp Ser Gly Arg Asp Arg Cys Leu
            210                 215                 220

His Glu Ser Lys Gly Arg Ala His Pro Gln Val Asp Pro Lys Leu Leu
225                 230                 235                 240

Asn Lys Leu His Glu Tyr Phe His Glu Pro Asn Lys Lys Phe Phe Glu
                245                 250                 255

Leu Val Gly Arg Thr Phe Asp Trp His
            260                 265

<210> SEQ ID NO 157
<211> LENGTH: 265
<212> TYPE: PRT
<213> ORGANISM: Artificial Sequence
<220> FEATURE:
<223> OTHER INFORMATION: Engineered glucosaminyl 3-O sulfotransferase
      mutant_sulfotransferase 7

<400> SEQUENCE: 157

Met Gly Val Ala Pro Asn Gly Ser Ala Gln Gln Leu Pro Gln Thr Ile
1               5                   10                  15

Ile Ile Gly Val Arg Lys Gly Gly Thr Arg Ala Leu Leu Glu Met Leu
            20                  25                  30

Ser Leu His Pro Asp Val Ala Ala Glu Asn Glu Val His Phe Phe
            35                  40                  45

Asp Trp Glu Glu His Tyr Ser His Gly Leu Gly Trp Tyr Leu Ser Gln
50                  55                  60

Met Pro Phe Ser Trp Pro His Gln Leu Thr Val Glu Lys Thr Pro Ala
65                  70                  75                  80

Tyr Phe Thr Ser Pro Lys Val Pro Glu Arg Val Tyr Ser Met Asn Pro
                85                  90                  95

Ser Ile Arg Leu Leu Leu Ile Leu Arg Asp Pro Ser Glu Arg Val Leu
            100                 105                 110

Ser Asp Tyr Thr Gln Val Phe Tyr Asn His Met Gln Lys His Lys Pro
            115                 120                 125

Tyr Pro Ser Ile Glu Glu Phe Leu Val Arg Asp Gly Arg Leu Asn Val
            130                 135                 140

Asp Tyr Lys Ala Leu Asn Arg Ser Leu Tyr His Val His Met Gln Asn
145                 150                 155                 160

Trp Leu Arg Phe Phe Pro Leu Arg His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
            195                 200                 205

Thr Lys Gly Phe Tyr Cys Leu Arg Asp Ser Gly Arg Asp Arg Cys Leu
```

```
            210                 215                 220
His Glu Ser Lys Gly Arg Ala His Pro Gln Val Asp Pro Lys Leu Leu
225                 230                 235                 240

Asn Lys Leu His Glu Tyr Phe His Glu Pro Asn Lys Lys Phe Phe Glu
                245                 250                 255

Leu Val Gly Arg Thr Phe Asp Trp His
            260                 265
```

<210> SEQ ID NO 158
<211> LENGTH: 346
<212> TYPE: PRT
<213> ORGANISM: Artificial Sequence
<220> FEATURE:
<223> OTHER INFORMATION: Engineered glucosaminyl 3-O sulfotransferase mutant_sulfotransferase 8

<400> SEQUENCE: 158

```
Met Leu Phe Lys Gln Gln Val Trp Leu Arg Gln Lys Leu Leu Val Leu
1               5                   10                  15

Gly Ser Leu Ala Val Gly Ser Leu Leu Tyr Leu Val Ala Arg Val Gly
                20                  25                  30

Ser Leu Asp Arg Leu Gln Pro Ile Cys Pro Val Glu Ser Arg Phe Gly
            35                  40                  45

Gly Ala His Asn Gln Ala Glu Leu Pro Leu Arg Ala Leu Gln Phe Lys
        50                  55                  60

Arg Gly Leu Leu His Glu Phe Arg Lys Gly Asn Ser Ser Lys Glu Gln
65                  70                  75                  80

Val His Leu His Asp Leu Val Gln Gln Leu Pro Lys Ala Ile Ile Ile
                85                  90                  95

Gly Val Gly His Gly Gly Thr Arg Ala Leu Leu Glu Met Leu Asn Leu
            100                 105                 110

His Pro Ala Val Val Lys Ala Ser Gln Glu Ile His Phe Phe Asp Asn
        115                 120                 125

Asp Glu Asn Tyr Ala Lys Gly Ile Glu Trp Tyr Arg Lys Lys Met Pro
130                 135                 140

Phe Ser Tyr Pro Gln Gln Ile Thr Ile Glu Lys Ser His Ser Tyr Phe
145                 150                 155                 160

Ile Thr Glu Glu Val Pro Glu Arg Ile Tyr Lys Met Asn Ser Ser Ile
                165                 170                 175

Lys Leu Leu Ile Ile Val Arg Glu Pro Thr Thr Arg Ala Ile Ser Ala
            180                 185                 190

Tyr Thr His Met Leu Glu Gly Lys Glu Arg Lys Asn Lys Thr Tyr Tyr
        195                 200                 205

Lys Phe Glu Lys Leu Ala Ile Asp Pro Asn Thr Cys Glu Val Asn Thr
210                 215                 220

Lys Tyr Val Gly Val Arg Thr Ser Ile Tyr Thr Lys His Leu Glu Arg
225                 230                 235                 240

Trp Leu Lys Tyr Phe Pro Ile Glu Gln Phe His Ile Val Asp Gly Asp
                245                 250                 255

Arg Leu Ile Thr Glu Pro Leu Pro Glu Leu Gln Leu Val Glu Lys Phe
            260                 265                 270

Leu Asn Leu Pro Pro Arg Ile Ser Gln Tyr Asn Leu Tyr Phe Asn Ala
        275                 280                 285

Thr Arg Gly Phe Tyr Cys Leu Arg Phe Asn Ile Ile Phe Asn Lys Cys
290                 295                 300
```

```
Leu Ala Gly Ser Lys Gly Arg Ile His Pro Glu Val Asp Pro Ser Val
305                 310                 315                 320

Ile Thr Lys Leu Arg Lys Phe Phe His Pro Phe Asn Gln Lys Phe Tyr
                325                 330                 335

Gln Ile Thr Gly Arg Thr Leu Asn Trp Pro
                340                 345
```

<210> SEQ ID NO 159
<211> LENGTH: 346
<212> TYPE: PRT
<213> ORGANISM: Artificial Sequence
<220> FEATURE:
<223> OTHER INFORMATION: Engineered glucosaminyl 3-O sulfotransferase mutant_sulfotransferase 9

<400> SEQUENCE: 159

```
Met Leu Phe Lys Gln Gln Val Trp Leu Arg Gln Lys Leu Leu Val Leu
1               5                   10                  15

Gly Ser Leu Ala Val Gly Ser Leu Leu Tyr Leu Val Ala Arg Val Gly
                20                  25                  30

Ser Leu Asp Arg Leu Gln Pro Ile Cys Pro Val Glu Ser Arg Phe Gly
            35                  40                  45

Gly Ala His Asn Gln Ala Glu Leu Pro Leu Arg Ala Leu Gln Phe Lys
        50                  55                  60

Arg Gly Leu Leu His Glu Phe Arg Lys Gly Asn Ser Ser Lys Glu Gln
65                  70                  75                  80

Val His Leu His Asp Leu Val Gln Gln Leu Pro Lys Ala Ile Ile Ile
                85                  90                  95

Gly Val Gly His Gly Gly Thr Arg Ala Leu Leu Glu Met Leu Asn Leu
                100                 105                 110

His Pro Ala Val Val Lys Ala Ser Gln Glu Ile His Phe Phe Asp Asn
                115                 120                 125

Asp Glu Asn Tyr Ala Lys Gly Ile Glu Trp Tyr Arg Lys Lys Met Pro
            130                 135                 140

Phe Ser Tyr Pro Gln Gln Ile Thr Ile Glu Lys Ser His Ser Tyr Phe
145                 150                 155                 160

Ile Thr Glu Glu Val Pro Glu Arg Ile Tyr Lys Met Asn Ser Ser Ile
                165                 170                 175

Lys Leu Leu Ile Ile Val Arg Glu Pro Thr Thr Arg Ala Ile Ser Ala
                180                 185                 190

Tyr Thr His Met Leu Glu Gly Lys Glu Arg Lys Asn Lys Thr Tyr Tyr
            195                 200                 205

Lys Phe Glu Lys Leu Ala Ile Asp Pro Asn Thr Cys Glu Val Asn Thr
        210                 215                 220

Lys Tyr Thr Gly Val Arg Thr Ser Ile Tyr Thr Lys His Leu Glu Arg
225                 230                 235                 240

Trp Leu Lys Tyr Phe Pro Ile Glu Gln Phe His Ile Val Asp Gly Asp
                245                 250                 255

Arg Leu Ile Thr Glu Pro Leu Pro Glu Leu Gln Leu Val Glu Lys Phe
                260                 265                 270

Leu Asn Leu Pro Pro Arg Ile Ser Gln Tyr Asn Leu Tyr Phe Asn Ala
            275                 280                 285

Thr Arg Gly Phe Tyr Cys Leu Arg Phe Asn Ile Ile Phe Asn Lys Cys
        290                 295                 300

Leu Ala Gly Ser Lys Gly Arg Ile His Pro Glu Val Asp Pro Ser Val
305                 310                 315                 320
```

Ile Thr Lys Leu Arg Lys Phe Phe His Pro Phe Asn Gln Lys Phe Tyr
            325                 330                 335

Gln Ile Thr Gly Arg Thr Leu Asn Trp Pro
            340                 345

<210> SEQ ID NO 160
<211> LENGTH: 346
<212> TYPE: PRT
<213> ORGANISM: Artificial Sequence
<220> FEATURE:
<223> OTHER INFORMATION: Engineered glucosaminyl 3-O sulfotransferase
      mutant_sulfotransferase 10

<400> SEQUENCE: 160

Met Leu Phe Lys Gln Gln Val Trp Leu Arg Gln Lys Leu Leu Val Leu
1               5                   10                  15

Gly Ser Leu Ala Val Gly Ser Leu Leu Tyr Leu Val Ala Arg Val Gly
            20                  25                  30

Ser Leu Asp Arg Leu Gln Pro Ile Cys Pro Val Glu Ser Arg Phe Gly
            35                  40                  45

Gly Ala His Asn Gln Ala Glu Leu Pro Leu Arg Ala Leu Gln Phe Lys
            50                  55                  60

Arg Gly Leu Leu His Glu Phe Arg Lys Gly Asn Ser Ser Lys Glu Gln
65                  70                  75                  80

Val His Leu His Asp Leu Val Gln Gln Leu Pro Lys Ala Ile Ile Ile
                    85                  90                  95

Gly Val Gly His Gly Gly Thr Arg Ala Leu Leu Glu Met Leu Asn Leu
            100                 105                 110

His Pro Ala Val Val Lys Ala Ser Gln Glu Ile His Phe Phe Asp Asn
            115                 120                 125

Asp Glu Asn Tyr Ala Lys Gly Ile Glu Trp Tyr Arg Lys Lys Met Pro
            130                 135                 140

Phe Ser Tyr Pro Gln Gln Ile Thr Ile Glu Lys Ser His Ser Tyr Phe
145                 150                 155                 160

Ile Thr Glu Glu Val Pro Glu Arg Ile Tyr Lys Met Asn Ser Ser Ile
                    165                 170                 175

Lys Leu Leu Ile Ile Val Arg Glu Pro Thr Thr Arg Ala Ile Ser Leu
            180                 185                 190

Gly Thr His Leu Leu Glu Val Lys Glu Arg Lys Asn Lys Thr Tyr Tyr
            195                 200                 205

Lys Phe Glu Lys Leu Ala Ile Asp Pro Asn Thr Cys Glu Val Asn Thr
210                 215                 220

Lys Tyr Thr Gly Val Arg Thr Ser Ile Tyr Thr Lys His Leu Glu Arg
225                 230                 235                 240

Trp Leu Lys Tyr Phe Pro Ile Glu Gln Phe His Ile Val Asp Gly Asp
                    245                 250                 255

Arg Leu Ile Thr Glu Pro Leu Pro Glu Leu Gln Leu Val Glu Lys Phe
            260                 265                 270

Leu Asn Leu Pro Pro Arg Ile Ser Gln Tyr Asn Leu Tyr Phe Asn Ala
            275                 280                 285

Thr Arg Gly Phe Tyr Cys Leu Arg Phe Asn Ile Ile Phe Asn Lys Cys
            290                 295                 300

Leu Ala Gly Ser Lys Gly Arg Ile His Pro Glu Val Asp Pro Ser Val
305                 310                 315                 320

Ile Thr Lys Leu Arg Lys Phe Phe His Pro Phe Asn Gln Lys Phe Tyr

```
                            325                 330                 335

Gln Ile Thr Gly Arg Thr Leu Asn Trp Pro
            340                 345

<210> SEQ ID NO 161
<211> LENGTH: 394
<212> TYPE: PRT
<213> ORGANISM: Bacteroides eggerthii
<220> FEATURE:
<221> NAME/KEY: SIGNAL
<222> LOCATION: (1)..(22)
<223> OTHER INFORMATION: Signal Sequence

<400> SEQUENCE: 161

Met Lys Lys Asn Ile Phe Ile Ile Cys Met Ala Met Ala Ala Gly Cys
1               5                   10                  15

Ile Thr Thr Leu Thr Ala Gln Val Lys Asn Ala Glu Thr Leu Val Pro
            20                  25                  30

Leu Thr Lys Arg Val Asn Val Gln Ala Asp Thr Ala Arg Leu Asp Gln
        35                  40                  45

Ile Ile Asp Gly Cys Trp Val Ala Val Gly Thr Asn Lys Lys His Ala
50                  55                  60

Ile Gln Arg Asp Phe Thr Arg Leu Phe Ala Gly Lys Pro Ser Tyr Arg
65                  70                  75                  80

Phe Glu Leu Arg Lys Glu Asp Asn Thr Leu Glu Gly Tyr Gly Lys Gly
                85                  90                  95

Glu Thr Lys Gly Arg Ala Glu Phe Ser Tyr Cys Tyr Ala Thr Ser Ala
            100                 105                 110

Asp Phe Lys Gly Leu Pro Ala Asp Ala Tyr Arg Lys Ala Gln Ile Thr
        115                 120                 125

Lys Thr Val Tyr His His Gly Lys Gly Ile Cys Pro Gln Gly Val Ser
130                 135                 140

Arg Asp Tyr Glu Phe Ser Val Tyr Ile Pro Ser Ala Leu Asp Ser Asn
145                 150                 155                 160

Val Ser Thr Ile Phe Ala Gln Trp His Gly Met Pro Asp Arg Thr Leu
                165                 170                 175

Val Gln Thr Pro Glu Gly Glu Val Lys Lys Leu Thr Val Asp Glu Phe
            180                 185                 190

Leu Glu Leu Asp Lys Thr Thr Ile Phe Lys Lys Asn Thr Gly His Glu
        195                 200                 205

Lys Val Ala Lys Leu Asp Lys Gln Gly Asn Pro Val Lys Asp Lys Lys
210                 215                 220

Gly Asn Pro Val Tyr Lys Ala Gly Lys Lys Asn Gly Trp Leu Val Glu
225                 230                 235                 240

Gln Gly Gly Tyr Pro Pro Leu Ala Phe Gly Phe Ser Gly Gly Trp Phe
                245                 250                 255

Tyr Ile Lys Ala Asn Ser Asp Arg Arg Trp Leu Thr Asp Lys Thr Asp
            260                 265                 270

Arg Cys Asn Ala Ser Pro Glu Lys Thr Pro Val Met Lys Pro Val Thr
        275                 280                 285

Ser Lys Tyr Lys Ser Ser Thr Ile Ala Tyr Lys Met Pro Phe Ala Asp
        290                 295                 300

Phe Pro Lys Asp Cys Trp Val Thr Phe Arg Val His Ile Asp Trp Thr
305                 310                 315                 320

Thr Tyr Gly Lys Glu Ala Glu Asn Ile Val Lys Pro Gly Lys Leu Asp
                325                 330                 335
```

-continued

Val Gln Met Glu Tyr Thr Asp Lys Lys Thr Val Lys Glu His Ile
            340                 345                 350

Val Asn Asn Glu Val Ile Gln Ile Gly Arg Asn Asp Asp Gly Tyr
            355                 360                 365

Tyr Phe Lys Phe Gly Ile Tyr Arg Val Gly Asn Ser Thr Val Pro Val
370                 375                 380

Cys Tyr Asn Leu Ala Gly Tyr Lys Glu Glu
385                 390

<210> SEQ ID NO 162
<211> LENGTH: 773
<212> TYPE: PRT
<213> ORGANISM: Bacteroides eggerthii
<220> FEATURE:
<221> NAME/KEY: SIGNAL
<222> LOCATION: (1)..(22)
<223> OTHER INFORMATION: Signal Sequence

<400> SEQUENCE: 162

Met Lys Lys Ser Ile Leu Phe Ile Thr Ser Leu Phe Leu Cys Ile Phe
1               5                   10                  15

Cys Leu Ser Asn Ala Gln Gln Ser Arg Thr Glu Val Thr Trp Glu
            20                  25                  30

Lys Met Glu Asp Val Thr Val Pro Ile Pro Pro Gln Val His Pro Arg
            35                  40                  45

Leu Tyr Val Arg Ser Ala Asp Leu Pro Asp Leu Lys Lys Arg Met Asn
        50                  55                  60

His Pro His Val Lys Glu Val Leu Ala Thr Leu Asn Lys Leu Gly Lys
65                  70                  75                  80

Asp Arg Thr Pro Glu Glu Ala Lys Val Lys Asp Arg Gly Phe Arg
                85                  90                  95

Tyr Tyr Phe Glu Met Arg Gly Val Thr Ser Arg Val Gln Val Gln Ala
                100                 105                 110

Leu Glu Tyr Leu Val Tyr Gly Asp Lys Lys Gln Ala Arg Arg Ala Ile
            115                 120                 125

Thr Ala Met Leu Asp Thr Leu Gln Asn Val Asn Tyr Gly Thr Gln Gly
        130                 135                 140

Asp Leu Ser Arg Ala Ser Gly Val Met Leu Thr Cys Gly Ala Met Val
145                 150                 155                 160

Tyr Asp Trp Cys Tyr Asp Gln Met Lys Glu Ser Glu Lys Lys Ala Tyr
                165                 170                 175

Val Glu Ser Phe Ile Arg Ile Ala Lys Thr Met Glu Cys Gly Tyr Pro
            180                 185                 190

Pro Arg Asn Asn Glu Pro Ile Ala Gly His Ser Ser Glu Trp Met Ile
        195                 200                 205

Leu Arg Asp Met Leu Ser Ala Gly Ile Ala Ile Tyr Asp Glu Tyr Pro
    210                 215                 220

Asp Met Tyr Asn Tyr Val Ile Lys Met Met Phe Lys Asp Tyr Leu Pro
225                 230                 235                 240

Val Arg Asn Tyr Ile Tyr Ser Gly His Asn Tyr His Gln Gly Thr Ser
                245                 250                 255

Tyr Val Asn Val Arg Phe Ser Asn Asp Leu Phe Ser Leu Trp Ile Leu
            260                 265                 270

Gln Arg Met Gly Ala Gly Ala Ile Tyr Asn Pro Ala Gln Gln Phe Val
        275                 280                 285

```
Leu Tyr Asp Phe Leu Tyr Arg Arg Pro Asp Gly Gln Val Met Pro
290                 295                 300

Ala Gly Asp Thr Asn Pro Ile Arg Lys Asn Thr Pro Ser Tyr Ser Leu
305                 310                 315                 320

Pro Ala Met Leu Ala Ser Ser Phe Tyr Lys Asp Ser Tyr Leu Ala Tyr
            325                 330                 335

Glu Tyr Glu Arg Lys Pro Asn Ile Glu Arg His Cys Leu Ile Phe Asp
            340                 345                 350

Ile Leu Trp Arg Asp Leu Asp Leu Lys Ala Lys Ala Pro Asp Asp Leu
            355                 360                 365

Pro Leu Thr Arg Tyr Ser Gly Ser Pro Phe Gly Trp Met Ile Ala Arg
370                 375                 380

Thr Ala Trp Asp Glu Asn Ser Val Ile Ala Glu Met Lys Ile Asn Glu
385                 390                 395                 400

Gln Phe Val Gly Asn His Gln His Leu Asp Gly Gly Ser Phe Gln Leu
                405                 410                 415

Tyr Tyr Lys Gly Pro Leu Ala Ile Asp Ala Gly Ala Tyr Gln Gly Ser
            420                 425                 430

Ser Gly Gly Tyr Asn Ser Pro His Asn Lys Asn Phe Phe Lys Arg Thr
            435                 440                 445

Ile Ala His Asn Ser Leu Leu Val Tyr Asn Pro Asp Glu Lys Phe Ala
450                 455                 460

Cys Trp Asn Tyr Gly Gly Gly Lys Thr Glu Phe Ala Ala Asn Asp
465                 470                 475                 480

Gly Gly Gln Arg Met Pro Gly Asp Arg Trp Glu Thr Cys Arg Ser Phe
            485                 490                 495

Lys Gln Leu Met Ser Lys Asp Tyr Thr Thr Gly Lys Ala Leu Ala His
            500                 505                 510

Gly Phe Gly Pro Asp Ala Cys Lys Pro Asp Tyr Ser Tyr Leu Lys Gly
            515                 520                 525

Asp Ile Thr Gln Ala Tyr Thr Asp Lys Val Lys Glu Ala Lys Arg Ser
530                 535                 540

Phe Val Phe Leu Asn Leu His Ser Thr Glu Val Pro Gly Ala Leu Ile
545                 550                 555                 560

Val Phe Asp Lys Val Val Ser Ser Asp Pro Gln Phe Lys Lys Phe Trp
                565                 570                 575

Leu Leu His Ser Ile Glu Glu Pro Val Ile Glu Gly Asp Arg Phe Ile
            580                 585                 590

Ile Arg Arg Thr Lys Asn Gly Asp Thr Gly Met Leu Gln Asn Gln Val
            595                 600                 605

Leu Leu Pro Glu Ala Gly Asn Ala Gln Ile Glu Lys Val Gly Gly Lys
610                 615                 620

Gly Lys Glu Phe Trp Val Phe Gly Thr Asn Tyr Pro Asn Asp Ala Leu
625                 630                 635                 640

Pro Asn Arg Pro Asp Asp Ala Asn Glu Arg Gly Ala Trp Arg Val Glu
                645                 650                 655

Val Ser Pro Ala Val Pro Ala Glu Asn Tyr Phe Leu Asn Val Ile
            660                 665                 670

Gln Val Ala Asp Asn Thr Cys Lys Arg Met Asn Asp Val Lys Arg Ile
            675                 680                 685

Asp Ala Gly Lys Val Val Gly Val Gln Ile Ala Asp Arg Ile Val Thr
690                 695                 700

Phe Ser Lys Asn Ser Leu Pro Leu Ser Gly Lys Ile Asp Met Lys Val
```

```
705                 710                 715                 720

Asp Gly Asn Thr Ser Met Lys Phe Val Ile Thr Asp Leu Ile Pro Gly
                725                 730                 735

Thr Trp Gln Ile Lys Lys Asp Gly Lys Val Tyr Ile Pro Ala Met Glu
                740                 745                 750

Val Arg Ser Asp Asp Gly Ile Leu Ser Phe Glu Thr Ala Gly His
                755                 760                 765

Tyr Glu Phe Leu Arg
        770

<210> SEQ ID NO 163
<211> LENGTH: 666
<212> TYPE: PRT
<213> ORGANISM: Bacteroides eggerthii
<220> FEATURE:
<221> NAME/KEY: SIGNAL
<222> LOCATION: (1)..(21)
<223> OTHER INFORMATION: Signal Sequence

<400> SEQUENCE: 163

Met Lys Ile Met Lys Phe Ile Leu Ser Val Phe Leu Leu Thr Ile Ala
1               5                   10                  15

Ile Ile Ala Asp Ala Gln Gln Leu Arg Lys Glu Ala Phe Asp Leu Leu
                20                  25                  30

Asn Leu Asp Tyr Pro Gly Leu Glu Lys Val Lys Thr Ala Cys Ser Arg
            35                  40                  45

Gln Gln Trp Glu Glu Ala Ala Gln Glu Leu Leu Ala Tyr Tyr Arg Asn
        50                  55                  60

Arg Thr Asp Ile Ala His Pro Asp Ile Asp Leu Lys Asn Leu Ala Ile
65                  70                  75                  80

Ser Lys Glu Glu Gln Lys Trp Ala Asp Asp Ala Met Asp His Thr Phe
                85                  90                  95

Phe Val His Lys Gly Tyr Gln Pro Ser Tyr Asn Tyr Gly Lys Asp Ile
            100                 105                 110

Asn Trp Glu Tyr Trp Pro Val Lys Asp Asn Glu Leu Arg Trp Gln Leu
        115                 120                 125

His Arg His Lys Trp Phe Thr Pro Met Gly Lys Ala Tyr Arg Ile Ser
    130                 135                 140

Gly Asp Glu Lys Tyr Ala Lys Glu Trp Ala Phe Gln Tyr Ile Asp Trp
145                 150                 155                 160

Ile Lys Lys Asn Pro Leu Val Lys Met Glu Lys Glu Asn Phe Glu Leu
                165                 170                 175

Val Ser Ala Gly Glu Val Lys Glu Asp Ala Asp Asn Val His Phe Ala
            180                 185                 190

Trp Arg Gln Leu Glu Val Ser Asn Arg Leu Gln Asp Gln Thr Cys Gln
        195                 200                 205

Phe Leu Leu Phe Cys Pro Ala Glu Ala Phe Thr Pro Glu Phe Leu Thr
    210                 215                 220

Glu Phe Leu Val Asn Tyr His Arg His Gly Ala Tyr Leu Phe Lys Asn
225                 230                 235                 240

Tyr Ser Ala Glu Gly Asn His Leu Leu Phe Glu Ala Gln Arg Met Val
                245                 250                 255

Tyr Ala Gly Val Phe Phe Pro Glu Phe Lys Asp Ala Ala Thr Trp Arg
            260                 265                 270

Glu Ser Gly Ile Asn Ile Leu Asn Arg Glu Ile Lys Lys Gln Val Tyr
        275                 280                 285
```

```
Asp Asp Gly Gly Gln Tyr Glu Leu Asp Pro His Tyr His Leu Ala Ala
        290                 295                 300

Ile Asn Ile Phe Cys Lys Ala Leu Arg Met Ala Asp Cys Asn Gly Phe
305                 310                 315                 320

Arg Asn Glu Phe Pro Ala Glu Tyr Leu Asp Thr Val Lys Lys Met Ile
                325                 330                 335

Glu Phe Tyr Thr Asn Ile Cys Phe Pro Asp Tyr Thr Asn Pro Cys Phe
                340                 345                 350

Ser Asp Ala Lys Leu Gly Asp Tyr Lys Ser Glu Leu Ala Asn Tyr Arg
                355                 360                 365

Asp Trp Val Thr Leu Phe Pro Asp Ser Glu Trp Ile Arg Tyr Tyr Ala
370                 375                 380

Thr Glu Gly Arg Glu Gly Ala Pro Leu Pro Tyr Leu Ser His Gly Ser
385                 390                 395                 400

Leu Ala Ser Gly Phe Phe Thr Phe Arg Ser Gly Trp Lys Lys Asp Ala
                405                 410                 415

Ala Val Val Val Lys Ala Gly Pro Lys Gly Glu Trp His Cys Gln
                420                 425                 430

Pro Asp Asn Gly Thr Phe Glu Phe Trp Phe Asn Gly Lys Asn Leu Phe
                435                 440                 445

Pro Asp Ser Gly Ala Tyr Val Tyr Ala Gly Ser Asp Glu Val Met Lys
450                 455                 460

Leu Arg Asn Trp Phe Arg Gln Thr Arg Val His Asn Thr Leu Thr Leu
465                 470                 475                 480

Asp Gly Arg Asn Phe Glu Thr Thr Gln Ser Val Thr Lys Leu Trp Gln
                485                 490                 495

Pro Glu Gly Arg Glu Gln Ile Leu Val Thr Glu Asn Pro Ser Tyr Gln
                500                 505                 510

Gly Leu Lys His Arg Arg Thr Val Phe Phe Val Glu Gln Thr Tyr Tyr
                515                 520                 525

Val Ile Val Asp Glu Ala Val Gly Asp Ala Lys Gly Thr Val Asn Leu
530                 535                 540

Asn Tyr His Phe Cys Glu Gly Thr Val Asn Val Asp Val Lys Lys Asn
545                 550                 555                 560

Met Ala Thr Thr Ala Tyr Ala Gly Pro Ser Asn Val Lys Leu Gln Cys
                565                 570                 575

Phe Pro Glu Lys Lys Ala Ser Leu Lys Lys Glu Glu Gly Trp Arg Ser
                580                 585                 590

Ile Ala Tyr Arg Gln Arg Val Pro Arg Thr Ser Leu Ser Phe Asp Ile
                595                 600                 605

His Lys Asp Asp Ala Glu Ala Val Arg Tyr Ile Thr Val Ile Tyr Pro
610                 615                 620

Val Lys Asp Ala Ala Ser Tyr Pro Val Leu Lys Ala Lys Phe Leu Asn
625                 630                 635                 640

Lys Asp Phe Asp Glu Lys Gly Val Lys Val Glu Val Ser Val Asn Gly
                645                 650                 655

Val Ala Arg Gln Leu Met Ser Gln Leu Lys
                660                 665

<210> SEQ ID NO 164
<211> LENGTH: 309
<212> TYPE: PRT
<213> ORGANISM: Homo sapiens
```

<400> SEQUENCE: 164

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Gln Lys Thr Gly Thr Thr Ala Leu Tyr
        35                  40                  45

Leu Phe Leu Gly Met His Pro Asp Leu Ser Ser Asn Tyr Pro Ser Ser
    50                  55                  60

Glu Thr Phe Glu Glu Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Lys Ser Ala Asn Tyr Phe Asp Ser Glu Val
            100                 105                 110

Ala Pro Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205

Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Lys Ser Lys Gly Arg Lys Tyr Pro Glu Met Asp Leu Asp Ser Arg
            260                 265                 270

Ala Phe Leu Lys Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Asp
    290                 295                 300

Leu Gln Asn Thr Arg
305

<210> SEQ ID NO 165
<211> LENGTH: 309
<212> TYPE: PRT
<213> ORGANISM: Rattus norvegicus

<400> SEQUENCE: 165

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Gln Lys Thr Gly Thr Thr Ala Leu Tyr
        35                  40                  45

```
Leu Phe Leu Gly Met His Pro Asp Leu Ser Ser Asn Tyr Pro Ser Ser
 50                  55                  60

Glu Thr Phe Glu Glu Ile Gln Phe Phe Asn Gly His Asn Tyr His Lys
 65                  70                  75                  80

Gly Ile Asp Trp Tyr Met Glu Phe Phe Pro Ile Pro Ser Asn Thr Thr
                 85                  90                  95

Ser Asp Phe Tyr Phe Glu Lys Ser Ala Asn Tyr Phe Asp Ser Glu Val
             100                 105                 110

Ala Pro Arg Arg Ala Ala Leu Leu Pro Lys Ala Lys Val Leu Thr
         115                 120                 125

Ile Leu Ile Asn Pro Ala Asp Arg Ala Tyr Ser Trp Tyr Gln His Gln
130                 135                 140

Arg Ala His Asp Asp Pro Val Ala Leu Lys Tyr Thr Phe His Glu Val
145                 150                 155                 160

Ile Thr Ala Gly Pro Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Phe His Ala Asn Gln Ile Leu Val Leu Asp Gly Lys Leu Leu
        195                 200                 205

Arg Thr Glu Pro Ala Lys Val Met Asp Thr Val Gln Lys Phe Leu Gly
210                 215                 220

Val Thr Ser Thr Val Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Lys Ser Lys Gly Arg Lys Tyr Pro Glu Met Asp Leu Asp Ser Arg
            260                 265                 270

Ala Phe Leu Lys Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Asp
    290                 295                 300

Leu Gln Asn Thr Arg
305

<210> SEQ ID NO 166
<211> LENGTH: 309
<212> TYPE: PRT
<213> ORGANISM: Mus musculus

<400> SEQUENCE: 166

Met Ser Glu Glu Lys Asp Pro Leu Trp Gln Asp Pro Cys Glu Asp Lys
 1               5                  10                  15

Arg His Lys Asp Ile Trp Ser Lys Glu Lys Thr Cys Asp Arg Phe Pro
                 20                  25                  30

Lys Leu Leu Ile Ile Gly Pro Gln Lys Thr Gly Thr Thr Ala Leu Tyr
             35                  40                  45

Leu Phe Leu Gly Met His Pro Asp Leu Ser Ser Asn Tyr Pro Ser Ser
 50                  55                  60

Glu Thr Phe Glu Glu Ile Gln Phe Phe Asn Gly His Asn Tyr His Lys
 65                  70                  75                  80

Gly Ile Asp Trp Tyr Met Glu Phe Phe Pro Ile Pro Ser Asn Thr Thr
                 85                  90                  95

Ser Asp Phe Tyr Phe Glu Lys Ser Ala Asn Tyr Phe Asp Ser Glu Val
             100                 105                 110
```

```
Ala Pro Arg Arg Ala Ala Ala Leu Leu Pro Lys Ala Lys Ile Leu Ser
            115                 120                 125

Ile Leu Ile Asn Pro Ala Asp Arg Ala Tyr Ser Trp Tyr Gln His Gln
        130                 135                 140

Arg Ala His Asp Asp Pro Val Ala Leu Lys Tyr Thr Phe His Glu Val
145                 150                 155                 160

Ile Thr Ala Gly Pro Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Phe His Ala Asn Gln Ile Leu Val Leu Asp Gly Lys Leu Leu
        195                 200                 205

Arg Thr Glu Pro Ala Lys Val Met Asp Thr Val Gln Lys Phe Leu Gly
210                 215                 220

Val Thr Ser Thr Val Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Lys Ser Lys Gly Arg Lys Tyr Pro Glu Met Asp Leu Asp Ser Arg
            260                 265                 270

Ala Phe Leu Lys Asp Tyr Phe Arg Asp His Asn Ile Glu Leu Ser Lys
        275                 280                 285

Leu Leu Tyr Lys Met Gly Gln Thr Leu Pro Thr Trp Leu Arg Glu Asp
    290                 295                 300

Leu Gln Asn Thr Arg
305

<210> SEQ ID NO 167
<211> LENGTH: 309
<212> TYPE: PRT
<213> ORGANISM: Bos taurus

<400> SEQUENCE: 167

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Gln Lys Thr Gly Thr Thr Ala Leu Tyr
        35                  40                  45

Leu Phe Leu Gly Met His Pro Asp Leu Ser Ser Asn Tyr Pro Ser Ser
    50                  55                  60

Glu Thr Phe Glu Glu Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Lys Ser Ala Asn Tyr Phe Asp Ser Glu Val
            100                 105                 110

Ala Pro Arg Arg Ala Ala Leu Leu Pro Lys Ala Lys Val Leu Thr
            115                 120                 125

Ile Leu Ile Asn Pro Ala Asp Arg Ala Tyr Ser Trp Tyr Gln His Gln
        130                 135                 140

Arg Ala His Asp Asp Pro Val Ala Leu Lys Tyr Thr Phe His Glu Val
145                 150                 155                 160

Ile Thr Ala Gly Pro Asp Ala Ser Leu Lys Leu Arg Thr Leu Gln Asn
```

```
                    165                 170                 175
Arg Cys Leu Val Pro Gly Trp Tyr Ala Thr His Ile Glu Arg Trp Leu
                180                 185                 190

Ser Ala Phe His Thr Asn Gln Ile Leu Val Leu Asp Gly Lys Leu Leu
            195                 200                 205

Arg Thr Glu Pro Ala Lys Val Met Asp Thr Val Gln Lys Phe Leu Gly
        210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Lys Ser Lys Gly Arg Lys Tyr Pro Glu Met Asp Leu Asp Ser Arg
            260                 265                 270

Ala Phe Leu Lys Asp Tyr Tyr Arg Asp His Asn Val Glu Leu Ser Lys
        275                 280                 285

Leu Leu Tyr Lys Met Gly Gln Thr Leu Pro Thr Trp Leu Arg Glu Glu
    290                 295                 300

Leu Gln Asn Thr Arg
305

<210> SEQ ID NO 168
<211> LENGTH: 309
<212> TYPE: PRT
<213> ORGANISM: Sus scrofa

<400> SEQUENCE: 168

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Gln Lys Thr Gly Thr Thr Ala Leu Tyr
        35                  40                  45

Leu Phe Leu Gly Leu His Pro Asp Leu Ser Ser Asn Tyr Pro Ser Ser
    50                  55                  60

Glu Thr Phe Glu Glu Ile Gln Phe Phe Asn Gly His Asn Tyr His Lys
65                  70                  75                  80

Gly Ile Asp Trp Tyr Met Asp Phe Phe Pro Ile Pro Ser Asn Thr Thr
                85                  90                  95

Ser Asp Phe Tyr Phe Glu Lys Ser Ala Asn Tyr Phe Asp Ser Asp Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
            180                 185                 190

Gly Ala Phe His Ala Asn Gln Ile Leu Val Leu Asp Gly Lys Leu Leu
        195                 200                 205

Arg Thr Glu Pro Ala Arg Val Met Asp Thr Val Gln Lys Phe Leu Gly
    210                 215                 220
```

```
Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
            245                 250                 255

Gly Arg Ser Lys Gly Arg Lys Tyr Pro Asp Met Asp Pro Asp Ser Arg
        260                 265                 270

Ala Phe Leu Arg Asp Tyr Tyr Arg Asp His Asn Ile Glu Leu Ser Lys
    275                 280                 285

Leu Leu Tyr Lys Met Gly Gln Thr Leu Pro Thr Trp Leu Arg Glu Glu
    290                 295                 300

Leu Gln Asn Thr Arg
305

<210> SEQ ID NO 169
<211> LENGTH: 309
<212> TYPE: PRT
<213> ORGANISM: Pelodiscus sinensis

<400> SEQUENCE: 169

Met Glu Pro Pro Leu Thr Pro Val Leu Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Gln Lys Thr Gly Thr Thr Ala Leu Tyr
        35                  40                  45

Leu Phe Leu Gly Met His Pro Asp Leu Ser Ser Asn Tyr Pro Ser Ser
    50                  55                  60

Glu Thr Phe Glu Glu Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Leu Tyr Phe Glu Lys Ser Ala Asn Tyr Phe Asp Ser Glu Val
            100                 105                 110

Ala Pro Arg Arg Ala Ala Ala Leu Leu Ser Lys Ala Lys Val Ile Thr
        115                 120                 125

Ile Leu Ile Asn Pro Ala Asp Arg Ala Tyr Ser Trp Tyr Gln His Gln
    130                 135                 140

Arg Ala His Asp Asp Pro Val Ala Leu Lys Tyr Thr Phe His Glu Val
145                 150                 155                 160

Ile Thr Ala Arg Pro Glu Ala Pro Gln Lys Leu Arg Met Leu Gln Asn
                165                 170                 175

Arg Cys Leu Val Pro Gly Trp Tyr Ala Thr His Ile Glu Arg Trp Leu
            180                 185                 190

Ala Ser Val Ala Val Ser Gln Ile Leu Val Leu Asp Gly Lys Leu Leu
        195                 200                 205

Arg Thr Glu Pro Ala Lys Val Met Glu Thr Val Gln Lys Phe Leu Gly
    210                 215                 220

Val Thr Asn Phe Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Lys Ser Lys Gly Arg Lys Tyr Pro Glu Met Asp Ser Asp Ser Arg
            260                 265                 270

Ala Phe Leu Arg Asp Tyr Tyr Arg Asp His Asn Ile Glu Leu Ser Lys
        275                 280                 285
```

```
Leu Leu Tyr Lys Met Gly Gln Thr Leu Pro Thr Trp Leu Arg Glu Glu
    290                 295                 300

Leu Gln Asn Ala Arg
305

<210> SEQ ID NO 170
<211> LENGTH: 309
<212> TYPE: PRT
<213> ORGANISM: Xenopus laevis

<400> SEQUENCE: 170

Met Pro Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
                20                  25                  30

Lys Leu Leu Ile Ile Gly Pro Gln Lys Thr Gly Thr Thr Ala Leu Tyr
            35                  40                  45

Leu Phe Leu Gly Met His Ser Asp Leu Ser Ser Asn Tyr Pro Ser Ser
    50                  55                  60

Glu Thr Phe Glu Glu Ile Gln Phe Tyr Asn Gly Gln Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Lys Ser Ala Asn Tyr Phe Asp Ser Glu Leu
            100                 105                 110

Ala Pro Arg Arg Val Ala Ala Leu Leu Pro Lys Ala Lys Ile Ile Thr
        115                 120                 125

Ile Leu Ile Asn Pro Ala Asp Arg Ala Tyr Ser Trp Tyr Gln His Gln
    130                 135                 140

Arg Ala His Asp Asp Pro Val Ala Ile Lys Tyr Thr Phe Gln Glu Val
145                 150                 155                 160

Ile Lys Ala Gly Pro Glu Ala Pro Gln Arg Leu Arg Ala Leu Gln Asn
                165                 170                 175

Arg Cys Leu Val Pro Gly Trp Tyr Ser Thr His Ile Glu Arg Trp Met
            180                 185                 190

Asn His Phe His Ala Asn Gln Ile Leu Val Leu Asp Gly Lys Leu Leu
        195                 200                 205

Arg Thr Glu Pro Ala Asn Val Met Glu Thr Val Gln Lys Phe Leu Gly
    210                 215                 220

Val Thr Asn Ala Met Asp Tyr His Lys Thr Leu Ala Phe Asp Pro Lys
225                 230                 235                 240

Lys Gly Phe Trp Cys Gln Leu Leu Asp Gly Gly Lys Thr Lys Cys Leu
                245                 250                 255

Gly Lys Ser Lys Gly Arg Lys Tyr Pro Asp Met Asp Ser Asp Ser Arg
            260                 265                 270

Ser Phe Leu Met Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Glu
    290                 295                 300

Leu Gln Asn Thr Arg
305

<210> SEQ ID NO 171
<211> LENGTH: 309
<212> TYPE: PRT
```

<213> ORGANISM: Lepisosteus oculatus

<400> SEQUENCE: 171

Met Pro Glu Glu Lys Asp Pro Val Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Gln Lys Thr Gly Thr Thr Ala Leu Tyr
        35                  40                  45

Leu Phe Leu Gly Met His Pro Asp Leu Thr Ser Asn Tyr Pro Ser Lys
    50                  55                  60

Glu Thr Phe Glu Glu Ile Gln Phe Phe Asn Gly His Asn Tyr His Lys
65                  70                  75                  80

Gly Ile Asp Trp Tyr Met Glu Tyr Phe Pro Leu Pro Ser Asn Thr Ser
                85                  90                  95

Ser Asp Phe Tyr Phe Glu Lys Ser Ala Asn Tyr Phe Asp Ser Glu Met
            100                 105                 110

Ala Pro Lys Arg Ala Ala Ala Leu Leu Pro Lys Ala Lys Ile Ile Thr
        115                 120                 125

Ile Leu Ile Asn Pro Ala Asp Arg Ala Tyr Ser Trp Tyr Gln His Gln
    130                 135                 140

Arg Ala His Asp Asp Pro Val Ala Leu Lys Tyr Thr Phe His Glu Val
145                 150                 155                 160

Ile Thr Ala Gly His Asp Ala Pro Leu Lys Leu Arg Ile Leu Gln Asn
                165                 170                 175

Arg Cys Leu Val Pro Gly Trp Tyr Ser Ile His Leu Glu Arg Trp Leu
            180                 185                 190

Asn Tyr Tyr His Ser Asn Gln Ile Leu Val Leu Asp Gly Gln Met Leu
        195                 200                 205

Arg Thr Glu Pro Ala Leu Val Met Glu Lys Ile Gln Lys Phe Leu Gly
    210                 215                 220

Leu Val Asn Ile Ile Asn Tyr His Lys Ile Leu Ala Phe Asp Pro Lys
225                 230                 235                 240

Lys Gly Phe Trp Cys Gln Leu Leu Glu Gly Lys Thr Lys Cys Leu
                245                 250                 255

Gly Lys Ser Lys Gly Arg Lys Tyr Pro Glu Met Asp Thr Asp Ser Arg
            260                 265                 270

Asp Phe Leu Arg Asn Tyr Tyr Gln Glu His Asn Val Glu Leu Ser Lys
        275                 280                 285

Leu Leu Tyr Lys Met Gly Gln Ser Leu Pro Ser Trp Leu Arg Glu Glu
    290                 295                 300

Leu Val Asn Thr Arg
305

<210> SEQ ID NO 172
<211> LENGTH: 309
<212> TYPE: PRT
<213> ORGANISM: Danio rerio

<400> SEQUENCE: 172

Met Pro Glu Glu Arg Asp Pro Ile Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Gln Lys Thr Gly Thr Thr Ala Leu Tyr

```
            35                  40                  45
Leu Phe Leu Ser Met His Ser Asp Leu Thr Ser Asn Tyr Pro Ser Lys
 50                  55                  60

Glu Thr Phe Glu Glu Ile Gln Phe Phe Asn Gly Arg Asn Tyr His Lys
65                   70                  75                  80

Gly Ile Asp Trp Tyr Met Glu His Phe Pro Leu Pro Ser Asn Thr Ser
                 85                  90                  95

Ser Asp Phe Tyr Phe Glu Lys Ser Ala Asn Tyr Phe Asp Ser Glu Val
            100                 105                 110

Ala Ala Arg Arg Ala Ala Ala Leu Leu Pro Lys Ala Lys Ile Ile Thr
        115                 120                 125

Ile Leu Ile Asn Pro Ala Asp Arg Ala Tyr Ser Trp Tyr Gln His Gln
130                 135                 140

Arg Ala His Asp Asp Pro Val Ala Gln Lys Tyr Thr Phe His Asp Val
145                 150                 155                 160

Ile Thr Ala Gly Arg Asp Ala Pro Ile Lys Leu Arg Val Leu Gln Ser
                165                 170                 175

Arg Cys Leu Val Pro Gly Leu Tyr Ala Thr His Leu Gln Arg Trp Leu
            180                 185                 190

Thr His Tyr His Pro Ser Gln Ile Leu Val Leu Asp Gly Gln Met Leu
        195                 200                 205

Arg Thr Glu Pro Ala Ser Val Met Asp Lys Ile Gln Lys Phe Leu Gly
210                 215                 220

Leu Ile Asn Thr Leu Asn Tyr His Lys Ile Leu Ala Phe Asp Pro Lys
225                 230                 235                 240

Lys Gly Phe Trp Cys Gln Leu Leu Asp Gly Gly Lys Thr Lys Cys Leu
                245                 250                 255

Gly Lys Ser Lys Gly Arg Arg Tyr Pro Asp Met Asp Val Asp Ser Arg
            260                 265                 270

Thr Phe Leu Arg Glu Tyr Tyr His Glu His Asn Ile Glu Leu Ser Lys
        275                 280                 285

Leu Leu Tyr Lys Met Gly Gln Pro Leu Pro Ser Trp Leu Arg Glu Glu
    290                 295                 300

Leu Leu His Ser Arg
305

<210> SEQ ID NO 173
<211> LENGTH: 309
<212> TYPE: PRT
<213> ORGANISM: Homo sapiens

<400> SEQUENCE: 173

Met Pro Glu Gln Lys Asp Pro Leu Trp Gln Asn Pro Cys Asp Asp Lys
1               5                   10                  15

Arg His Lys Asp Ile Trp Ser Arg Glu Lys Thr Cys Asp His Leu Pro
            20                  25                  30

Lys Phe Leu Val Ile Gly Pro Gln Lys Thr Gly Thr Thr Ala Leu Tyr
        35                  40                  45

Leu Phe Leu Leu Met His Pro Ser Ile Ile Ser Asn Leu Pro Ser Pro
 50                  55                  60

Lys Thr Phe Glu Glu Val Gln Phe Phe Asn Gly Asn Asn Tyr His Lys
65                   70                  75                  80

Gly Ile Asp Trp Tyr Met Asp Phe Phe Pro Thr Pro Ser Asn Thr Thr
                 85                  90                  95
```

```
Ser Asp Phe Leu Phe Glu Lys Ser Ala Asn Tyr Phe His Ser Glu Glu
            100                 105                 110

Ala Pro Arg Ala Ala Ser Leu Val Pro Lys Ala Lys Ile Ile Thr
            115                 120                 125

Ile Leu Ile Asp Pro Ser Asp Arg Ala Tyr Ser Trp Tyr Gln His Gln
130                 135                 140

Arg Ser His Glu Asp Pro Ala Ala Leu Arg Phe Asn Phe Tyr Glu Val
145                 150                 155                 160

Ile Ser Thr Gly His Trp Ala Pro Ser Asp Leu Lys Thr Leu Gln Arg
            165                 170                 175

Arg Cys Leu Val Pro Gly Trp Tyr Ala Val His Ile Glu Arg Trp Leu
            180                 185                 190

Thr Tyr Phe Ala Thr Ser Gln Leu Leu Ile Ile Asp Gly Gln Gln Leu
            195                 200                 205

Arg Ser Asp Pro Ala Thr Val Met Asp Glu Val Gln Lys Phe Leu Gly
210                 215                 220

Val Thr Pro Arg Tyr Asn Tyr Ser Glu Ala Leu Thr Phe Asp Pro Gln
225                 230                 235                 240

Lys Gly Phe Trp Cys Gln Leu Leu Glu Gly Gly Lys Thr Lys Cys Leu
            245                 250                 255

Gly Lys Ser Lys Gly Arg Lys Tyr Pro Pro Met Asp Pro Glu Ser Arg
            260                 265                 270

Thr Phe Leu Ser Asn Tyr Tyr Arg Asp His Asn Val Glu Leu Ser Lys
            275                 280                 285

Leu Leu His Arg Leu Gly Gln Pro Leu Pro Ser Trp Leu Arg Gln Glu
            290                 295                 300

Leu Gln Lys Val Arg
305

<210> SEQ ID NO 174
<211> LENGTH: 309
<212> TYPE: PRT
<213> ORGANISM: Homo sapiens

<400> SEQUENCE: 174

Met Pro Asp Gln Lys Asp Pro Leu Trp Gln Asn Pro Cys Asp Asp Lys
1               5                   10                  15

Arg His Arg Asp Ile Trp Ser Lys Glu Lys Thr Cys Asp Arg Leu Pro
            20                  25                  30

Lys Phe Leu Val Ile Gly Pro Gln Lys Thr Gly Thr Thr Ala Leu Tyr
            35                  40                  45

Leu Phe Leu Val Met His Pro Ser Ile Leu Ser Asn Ser Pro Ser Pro
50                  55                  60

Lys Thr Phe Glu Glu Val Gln Phe Phe Asn Arg Asn Asn Tyr His Arg
65                  70                  75                  80

Gly Ile Asp Trp Tyr Met Asp Phe Phe Pro Val Pro Ser Asn Val Thr
            85                  90                  95

Thr Asp Phe Leu Phe Glu Lys Ser Ala Asn Tyr Phe His Ser Glu Glu
            100                 105                 110

Ala Pro Lys Arg Ala Ala Ser Leu Val Pro Lys Ala Lys Ile Ile Thr
            115                 120                 125

Ile Leu Ile Asp Pro Ser Asp Arg Ala Tyr Ser Trp Tyr Gln His Gln
130                 135                 140

Arg Ser His Glu Asp Pro Ala Ala Leu Lys Phe Ser Phe Tyr Glu Val
145                 150                 155                 160
```

```
Ile Ser Ala Gly Pro Arg Ala Pro Ser Glu Leu Arg Ala Leu Gln Lys
                165                 170                 175

Arg Cys Leu Val Pro Gly Trp Tyr Ala Ser His Ile Glu Arg Trp Leu
            180                 185                 190

Val Tyr Phe Pro Pro Phe Gln Leu Leu Ile Ile Asp Gly Gln Gln Leu
        195                 200                 205

Arg Thr Asp Pro Ala Thr Val Met Asp Glu Val Gln Lys Phe Leu Gly
    210                 215                 220

Val Leu Pro His Tyr Asn Tyr Ser Glu Ala Leu Thr Phe Asp Ser His
225                 230                 235                 240

Lys Gly Phe Trp Cys Gln Leu Leu Glu Glu Gly Lys Thr Lys Cys Leu
                245                 250                 255

Gly Lys Ser Lys Gly Arg Lys Tyr Pro Pro Met Asp Ser Asp Ser Arg
            260                 265                 270

Thr Phe Leu Ser Ser Tyr Tyr Arg Asp His Asn Val Glu Leu Ser Lys
        275                 280                 285

Leu Leu His Lys Leu Gly Gln Pro Leu Pro Ser Trp Leu Arg Gln Glu
    290                 295                 300

Leu Gln Lys Val Arg
305

<210> SEQ ID NO 175
<211> LENGTH: 311
<212> TYPE: PRT
<213> ORGANISM: Bos taurus

<400> SEQUENCE: 175

Met Pro Gln Glu Arg Ser Pro Leu Trp Gln Asn Pro Cys Asp Asp Lys
1               5                   10                  15

Arg His Lys Asp Ile Trp Ser Lys Glu Lys Thr Cys Asp Arg Leu Pro
            20                  25                  30

Lys Phe Leu Ile Val Gly Pro Gln Lys Thr Gly Thr Thr Ala Ile His
        35                  40                  45

Phe Phe Leu Ser Leu His Pro Ala Val Thr Ser Ser Phe Pro Ser Pro
    50                  55                  60

Ser Thr Phe Glu Glu Ile Gln Phe Phe Asn Gly Pro Asn Tyr His Lys
65                  70                  75                  80

Gly Ile Asp Trp Tyr Met Asp Phe Phe Pro Val Pro Ser Asn Ala Ser
                85                  90                  95

Thr Asp Phe Leu Phe Glu Lys Ser Ala Thr Tyr Phe Asp Ser Glu Val
            100                 105                 110

Val Pro Arg Arg Gly Ala Ala Leu Leu Pro Arg Ala Lys Ile Ile Thr
        115                 120                 125

Val Leu Thr Asn Pro Ala Asp Arg Ala Tyr Ser Trp Tyr Gln His Gln
    130                 135                 140

Arg Ala His Gly Asp Pro Val Ala Leu Asn Tyr Thr Phe Tyr Gln Val
145                 150                 155                 160

Ile Thr Ala Ser Ser Gln Asp Pro Ala Leu Arg Ser Leu Gln Asn
                165                 170                 175

Arg Cys Leu Val Pro Gly Tyr Tyr Ser Thr His Leu Gln Arg Trp Leu
            180                 185                 190

Thr Tyr Tyr Pro Ser Gly Gln Leu Leu Ile Val Asp Gly Gln Glu Leu
        195                 200                 205

Arg Thr Asn Pro Ala Ala Ser Met Glu Ile Ile Gln Lys Phe Leu Gly
```

```
                210                 215                 220
Ile Thr Pro Phe Leu Asn Tyr Thr Arg Thr Leu Arg Phe Asp Glu Asp
225                 230                 235                 240

Lys Gly Phe Trp Cys Gln Gly Leu Glu Gly Gly Lys Thr Arg Cys Leu
                245                 250                 255

Gly Lys Ser Lys Gly Arg Lys Tyr Pro Asp Met Asp Ala Glu Ser Arg
            260                 265                 270

Leu Phe Leu Thr Asp Phe Phe Arg Asn His Asn Leu Glu Leu Ser Lys
        275                 280                 285

Leu Leu Ser Arg Leu Gly Gln Pro Val Pro Ser Trp Leu Arg Glu Glu
290                 295                 300

Leu Gln His Ser Ser Ser Gly
305                 310

<210> SEQ ID NO 176
<211> LENGTH: 311
<212> TYPE: PRT
<213> ORGANISM: Mus musculus

<400> SEQUENCE: 176

Met Pro Gln Glu Arg Ser Pro Leu Trp Gln Asn Pro Cys Asp Asp Lys
1               5                   10                  15

Arg His Lys Asp Ile Trp Ser Lys Glu Lys Thr Cys Asp Arg Leu Pro
            20                  25                  30

Lys Phe Leu Ile Val Gly Pro Gln Lys Thr Gly Thr Thr Ala Ile His
        35                  40                  45

Phe Phe Leu Ser Leu His Pro Ala Val Thr Ser Ser Phe Pro Ser Pro
    50                  55                  60

Ser Thr Phe Glu Glu Ile Gln Phe Phe Asn Gly Pro Asn Tyr His Lys
65                  70                  75                  80

Gly Ile Asp Trp Tyr Met Asp Phe Phe Pro Val Pro Ser Asn Ala Ser
                85                  90                  95

Thr Asp Phe Leu Phe Glu Lys Ser Ala Thr Tyr Phe Asp Ser Glu Val
            100                 105                 110

Val Pro Arg Arg Gly Ala Ala Leu Leu Pro Arg Ala Lys Ile Ile Thr
        115                 120                 125

Val Leu Ile Asn Pro Ala Asp Arg Ala Tyr Ser Trp Tyr Gln His Gln
    130                 135                 140

Arg Ala His Gly Asp Pro Ile Ala Leu Asn Tyr Thr Phe Tyr Gln Val
145                 150                 155                 160

Ile Ser Ala Ser Ser Gln Ala Pro Leu Leu Leu Arg Ser Leu Gln Asn
                165                 170                 175

Arg Cys Leu Val Pro Gly Tyr Tyr Ser Thr His Leu Gln Arg Trp Leu
            180                 185                 190

Thr Tyr Tyr Pro Ser Gly Gln Leu Leu Ile Met Asp Gly Gln Glu Leu
        195                 200                 205

Arg Val Asn Pro Ala Ala Ser Met Glu Ile Ile Gln Lys Phe Leu Gly
    210                 215                 220

Ile Thr Pro Phe Leu Asn Tyr Thr Arg Thr Leu Arg Phe Asp Glu Asp
225                 230                 235                 240

Lys Gly Phe Trp Cys Gln Gly Leu Glu Gly Gly Lys Thr Arg Cys Leu
                245                 250                 255

Gly Arg Ser Lys Gly Arg Arg Tyr Pro Asp Met Asp Met Glu Ser Arg
            260                 265                 270
```

Leu Phe Leu Thr Asp Phe Phe Arg Asn His Asn Leu Glu Leu Ser Lys
            275                 280                 285

Leu Leu Ser Arg Leu Gly Gln Pro Ala Pro Leu Trp Leu Arg Glu Glu
    290                 295                 300

Leu Gln His Ser Ser Val Gly
305                 310

<210> SEQ ID NO 177
<211> LENGTH: 311
<212> TYPE: PRT
<213> ORGANISM: Homo sapiens

<400> SEQUENCE: 177

Met Pro Gln Glu Arg Ser Pro Leu Trp Gln Asn Pro Cys Asp Asp Lys
1               5                   10                  15

Arg His Lys Asp Ile Trp Ser Lys Glu Lys Thr Cys Asp Arg Leu Pro
            20                  25                  30

Lys Phe Leu Ile Val Gly Pro Gln Lys Thr Gly Thr Thr Ala Ile His
        35                  40                  45

Phe Phe Leu Ser Leu His Pro Ala Val Thr Ser Ser Phe Pro Ser Pro
    50                  55                  60

Ser Thr Phe Glu Glu Ile Gln Phe Phe Asn Ser Pro Asn Tyr His Lys
65                  70                  75                  80

Gly Ile Asp Trp Tyr Met Asp Phe Phe Pro Val Pro Ser Asn Ala Ser
                85                  90                  95

Thr Asp Phe Leu Phe Glu Lys Ser Ala Thr Tyr Phe Asp Ser Glu Val
            100                 105                 110

Val Pro Arg Arg Gly Ala Ala Leu Leu Pro Arg Ala Lys Ile Ile Thr
        115                 120                 125

Val Leu Thr Asn Pro Ala Asp Arg Ala Tyr Ser Trp Tyr Gln His Gln
    130                 135                 140

Arg Ala His Gly Asp Pro Val Ala Leu Asn Tyr Thr Phe Tyr Gln Val
145                 150                 155                 160

Ile Ser Ala Ser Ser Gln Thr Pro Leu Ala Leu Arg Ser Leu Gln Asn
                165                 170                 175

Arg Cys Leu Val Pro Gly Tyr Tyr Ser Thr His Leu Gln Arg Trp Leu
            180                 185                 190

Thr Tyr Tyr Pro Ser Gly Gln Leu Leu Ile Val Asp Gly Gln Glu Leu
        195                 200                 205

Arg Thr Asn Pro Ala Ala Ser Met Glu Ser Ile Gln Lys Phe Leu Gly
    210                 215                 220

Ile Thr Pro Phe Leu Asn Tyr Thr Arg Thr Leu Arg Phe Asp Asp Asp
225                 230                 235                 240

Lys Gly Phe Trp Cys Gln Gly Leu Glu Gly Lys Thr Arg Cys Leu
                245                 250                 255

Gly Arg Ser Lys Gly Arg Arg Tyr Pro Asp Met Asp Thr Glu Ser Arg
            260                 265                 270

Leu Phe Leu Thr Asp Phe Phe Arg Asn His Asn Leu Glu Leu Ser Lys
        275                 280                 285

Leu Leu Ser Arg Leu Gly Gln Pro Val Pro Ser Trp Leu Arg Glu Glu
    290                 295                 300

Leu Gln His Ser Ser Leu Gly
305                 310

<210> SEQ ID NO 178

```
<211> LENGTH: 321
<212> TYPE: PRT
<213> ORGANISM: Drosophila melanogaster

<400> SEQUENCE: 178

Met Pro Glu Glu Val Asp Pro Val Trp Gly Asn Pro Cys Asp Asp Val
1               5                   10                  15

Arg His Lys Lys Ile Trp Ser Lys Thr Lys Asn Cys Asp Ser Leu Pro
            20                  25                  30

Lys Phe Leu Val Ile Gly Pro Gln Lys Thr Gly Thr Thr Ala Leu Tyr
        35                  40                  45

Thr Phe Leu Ser Met His Gly Ser Ile Ala Ser Asn Ile Ala Ser Pro
50                  55                  60

Glu Thr Phe Glu Val Gln Phe Phe Asn Gly Asn Asn Tyr Tyr Arg
65                  70                  75                  80

Gly Leu Asp Trp Tyr Met Asp Phe Phe Pro Ser Glu Ser Leu Pro Asn
                85                  90                  95

Thr Ser Ser Pro Met Pro Thr Gln Leu Gly Ser Pro Arg Phe Met Phe
            100                 105                 110

Glu Lys Ser Ala Thr Tyr Phe Asp Gly Glu Ala Val Pro Lys Arg Ser
        115                 120                 125

His Ala Leu Leu Pro His Ala Lys Ile Val Thr Ile Leu Ile Ser Pro
    130                 135                 140

Ala Lys Arg Ala Tyr Ser Trp Tyr Gln His Gln Arg Ser His Gly Asp
145                 150                 155                 160

Val Ile Ala Asn Asn Tyr Ser Phe Tyr Gln Val Ile Thr Ala Ser Asp
                165                 170                 175

Ser Ala Pro Arg Ala Leu Lys Asp Leu Arg Asn Arg Cys Leu Asn Pro
            180                 185                 190

Gly Lys Tyr Ala Gln His Leu Glu His Trp Leu Ala Tyr Tyr Pro Ala
        195                 200                 205

Gln Gln Leu His Ile Ile Asp Gly Glu Gln Leu Arg Leu Asn Pro Ile
    210                 215                 220

Asp Val Met Asn Glu Leu Gln Arg Phe Leu Lys Ile Gln Pro Leu Leu
225                 230                 235                 240

Asp Tyr Ser Asn His Leu Arg Tyr Asp Val Lys Lys Gly Phe Tyr Cys
                245                 250                 255

Gln Ala Val Ser Glu Lys Arg Asn Lys Cys Leu Gly Lys Ser Lys Gly
            260                 265                 270

Arg Gln Tyr Pro Ala Met Asp Glu Arg Ser Ala Lys Leu Leu Gln Arg
        275                 280                 285

Tyr Tyr Leu Asn His Asn Thr Ala Leu Val Lys Leu Leu Lys Lys Leu
    290                 295                 300

Gly Ser Arg Pro Ile Pro Gln Trp Leu Lys Asp Asp Leu Ser Thr Gly
305                 310                 315                 320

Thr

<210> SEQ ID NO 179
<211> LENGTH: 356
<212> TYPE: PRT
<213> ORGANISM: Gallus gallus

<400> SEQUENCE: 179

Met Gly Leu Leu Arg Ile Met Leu Pro Pro Lys Leu Gln Leu Leu Ala
1               5                   10                  15
```

```
Val Leu Val Phe Gly Val Ala Val Phe Leu Glu Asn Gln Ile Gln
            20                  25                  30

Lys Leu Glu Glu Ser Arg Gly Lys Leu Glu Arg Ala Ile Ala Arg His
        35                  40                  45

Glu Val Arg Glu Ile Glu Gln Arg His Thr Ala Asp Gly Pro Arg Gln
 50                  55                  60

Glu Val Ala Leu Asp Glu Glu Asp Val Val Ile Ile Tyr Asn Arg
 65                  70                  75                  80

Val Pro Lys Thr Ala Ser Thr Ser Phe Thr Asn Ile Ala Tyr Asp Leu
                85                  90                  95

Cys Ala Lys Asn Arg Tyr His Val Leu His Ile Asn Thr Thr Lys Asn
                100                 105                 110

Asn Pro Val Met Ser Leu Gln Asp Gln Val Arg Phe Val Lys Asn Val
            115                 120                 125

Thr Ser Trp Lys Glu Met Lys Pro Gly Phe Tyr His Gly His Val Ser
130                 135                 140

Tyr Leu Asp Phe Ala Lys Phe Gly Val Lys Lys Pro Ile Tyr Ile
145                 150                 155                 160

Asn Val Ile Arg Asp Pro Ile Glu Arg Leu Val Ser Tyr Tyr Phe
                165                 170                 175

Leu Arg Phe Gly Asp Asp Tyr Arg Pro Gly Leu Arg Arg Lys Gln
            180                 185                 190

Gly Asp Lys Lys Thr Phe Asp Glu Cys Val Ala Ala Gly Gly Ser Asp
            195                 200                 205

Cys Ala Pro Glu Lys Leu Trp Leu Gln Ile Pro Phe Phe Cys Gly His
210                 215                 220

Ser Ser Glu Cys Trp Asn Val Gly Ser Arg Trp Ala Leu Glu Gln Ala
225                 230                 235                 240

Lys Tyr Asn Leu Ile Asn Glu Tyr Phe Leu Val Gly Val Thr Glu Glu
                245                 250                 255

Leu Glu Asp Phe Ile Met Leu Leu Glu Ala Ala Leu Pro Arg Phe Phe
            260                 265                 270

Arg Gly Ala Thr Glu Leu Tyr Arg Thr Gly Lys Lys Ser His Leu Arg
275                 280                 285

Lys Thr Thr Glu Lys Lys Leu Pro Thr Lys Glu Thr Ile Ala Lys Leu
290                 295                 300

Gln Gln Ser Glu Ile Trp Lys Met Glu Asn Glu Phe Tyr Glu Phe Ala
305                 310                 315                 320

Leu Glu Gln Phe Gln Phe Val Arg Ala His Ala Val Arg Glu Lys Asp
                325                 330                 335

Gly Glu Leu Tyr Ile Leu Ala Gln Asn Phe Phe Tyr Glu Lys Ile Tyr
                340                 345                 350

Pro Lys Ser Asn
        355

<210> SEQ ID NO 180
<211> LENGTH: 366
<212> TYPE: PRT
<213> ORGANISM: Rhipicephalus appendiculatus

<400> SEQUENCE: 180

Met Ile Gly Arg Ile Leu Gln Trp Lys Val Ile Leu Cys Phe Cys Val
1               5                   10                  15

Ala Ile Ser Phe Val Ser Val Tyr Leu Arg Phe Glu Asn Lys Leu Ala
            20                  25                  30
```

```
Leu Leu Glu Ser Ser Arg Leu Lys Leu Thr Glu Thr Val Gly Arg Leu
         35                  40                  45

Gln Leu Phe Tyr Leu Asn Glu Arg Leu His Asp Phe Pro Pro Val Gln
 50                  55                  60

Glu Ser Arg Thr Asp Ala Pro Leu Asp Asp Phe Gly Leu Pro Glu Lys
 65                  70                  75                  80

Thr Met Asp Asn Leu Val Ile Leu Tyr Asn Arg Val Pro Lys Thr Gly
                 85                  90                  95

Ser Thr Ser Phe Met Gly Val Ala Tyr Asp Leu Cys Ala Thr Asn Lys
                100                 105                 110

Phe His Val Leu His Leu Asn Thr Ser Lys Asn Met His Val Met Ser
                115                 120                 125

Leu Pro Asp Gln Ile Arg Phe Val Tyr Asn Ile Ser Leu Trp His Tyr
130                 135                 140

Met Lys Pro Ala Ile Tyr His Gly His Ile Ala Phe Leu Asn Phe Ala
145                 150                 155                 160

Lys Tyr Gly Val Ile Gln Arg Pro Val Tyr Ile Asn Leu Ile Arg Arg
                165                 170                 175

Pro Leu Asp Arg Leu Val Ser Tyr Phe Tyr Phe Leu Arg His Gly Asp
                180                 185                 190

Asp Phe Arg Pro Tyr Leu Val Arg Arg Gln Gly Asn Lys Met Thr
                195                 200                 205

Phe Asp Glu Cys Val Ala Lys Lys Gly Ala Asp Cys Ala Glu Glu Arg
210                 215                 220

Leu Trp Leu Gln Val Pro Phe Phe Cys Gly His Ala Ala Arg Cys Trp
225                 230                 235                 240

Ile Pro Gly Asn Pro Trp Ala Leu Glu Gln Ala Lys His Asn Leu Val
                245                 250                 255

Asn His Tyr Phe Leu Val Gly Leu Thr Glu Gln Leu Pro Glu Phe Val
                260                 265                 270

Ala Met Leu Glu Ala Ser Phe Pro Arg Ile Phe Lys Gly Ala Thr Asp
                275                 280                 285

Lys Phe Ile Thr Gly Lys Arg Ser His Leu Arg Lys Thr Phe Asn Lys
                290                 295                 300

Val Gln Pro Ser Gln Glu Thr Ile Glu His Phe Lys Arg Ser Pro Ile
305                 310                 315                 320

Trp Gln Met Glu Asn Glu Phe Tyr Glu Phe Ala Ala Glu Gln Phe Glu
                325                 330                 335

Phe Ala Lys Lys Arg Thr Leu Val Ala Thr Gln Asp Gly Gln Leu Thr
                340                 345                 350

Glu Leu Gly Gln Gln Phe Phe Tyr Glu Lys Ile Arg Pro Lys
                355                 360                 365

<210> SEQ ID NO 181
<211> LENGTH: 354
<212> TYPE: PRT
<213> ORGANISM: Takifugu rubripes

<400> SEQUENCE: 181

Met Gly Ile Ser Arg Ile Met Met Ser His Lys Phe Gln Leu Met Ala
 1               5                  10                  15

Val Leu Thr Phe Gly Val Ala Met Leu Phe Ile Glu Asn Gln Ile Gln
                 20                  25                  30

Lys Leu Glu Asp Ser Arg Ala Arg Leu Glu Arg Thr Val Thr Ile His
```

```
                35                  40                  45
Asp Ile Ala Asp Leu Arg His Thr Glu Asp Gly Gly Arg Glu Leu Pro
 50                  55                  60

Leu Leu Ala Asp Lys Asp Asp Arg Val Ile Ile Tyr Asn Arg Val Pro
 65                  70                  75                  80

Lys Thr Gly Ser Thr Ser Phe Thr Asn Ile Ala Tyr Asp Leu Cys Ala
                 85                  90                  95

Lys Asn His Phe His Val Leu His Ile Asn Thr Thr Lys Asn Asn Pro
                100                 105                 110

Val Met Ser Leu Gln Asp Gln Met Arg Phe Val Arg Asn Ile Ser Ser
                115                 120                 125

Trp Arg Glu Met Lys Pro Gly Phe Tyr His Gly His Val Ala Tyr Leu
130                 135                 140

Asp Phe Ser Lys Tyr Gly Ala Lys Val Lys Pro Met Tyr Ile Asn Val
145                 150                 155                 160

Val Arg Asp Pro Ile Glu Arg Leu Val Ser Tyr Tyr Tyr Phe Leu Arg
                165                 170                 175

Phe Gly Asp Asn Tyr Arg Pro Gly Leu Arg Arg Lys Gln Gly Asp
                180                 185                 190

Lys Lys Thr Phe Asp Glu Cys Val Ser Ser Gly Gly Ser Asp Cys Ala
                195                 200                 205

Pro Glu Lys Leu Trp Leu Gln Ile Pro Phe Phe Cys Gly His His Ser
210                 215                 220

Glu Cys Trp Asn Ala Gly Ser Lys Trp Ala Leu Glu Gln Ala Lys Tyr
225                 230                 235                 240

Asn Leu Val Asn Glu Tyr Leu Leu Val Gly Val Thr Glu Glu Leu Glu
                245                 250                 255

Asp Phe Ile Met Ile Leu Glu Ala Val Leu Pro Arg Phe Phe Lys Gly
                260                 265                 270

Ala Thr Glu Leu Phe Lys Thr Gly Lys Lys Ser His Leu Arg Lys Thr
                275                 280                 285

Thr Glu Lys Lys Pro Pro Thr Lys Glu Thr Thr Ala Lys Leu Gln Gln
290                 295                 300

Ser Asn Ile Trp Lys Met Glu Asn Glu Phe Tyr Glu Phe Ala Leu Glu
305                 310                 315                 320

Gln Phe Gln Phe Val Arg Ala His Ala Val Arg Glu Lys Asp Gly Glu
                325                 330                 335

Leu Tyr Val Leu Gly Gln Asn Phe Phe Tyr Glu Lys Ile Tyr Pro Lys
                340                 345                 350

Val Asn

<210> SEQ ID NO 182
<211> LENGTH: 357
<212> TYPE: PRT
<213> ORGANISM: Callorhinchus milii

<400> SEQUENCE: 182

Met Gly Leu Leu Arg Ile Ile Met Pro Pro Lys Leu Gln Leu Leu Ala
 1               5                  10                  15

Val Val Ala Phe Met Ile Thr Met Leu Phe Leu Glu Asn Gln Ile Gln
                 20                  25                  30

Lys Leu Glu Glu Ser Arg Gly Lys Leu Glu Arg Ala Ile Ala Arg His
                 35                  40                  45

Glu Val Arg Glu Ile Glu Gln Arg His Thr Met Asp Ser Pro Arg Gln
```

```
        50                  55                  60
Asp Arg Gly Gly Asp Asp Glu Leu Asp Asp Leu Ile Ile Leu Tyr Asn
 65                  70                  75                  80

Arg Val Pro Lys Thr Ala Ser Thr Ser Phe Thr Asn Ile Ala Tyr Asp
                 85                  90                  95

Leu Cys Gly Arg Asn Lys Tyr His Val Leu His Ile Asn Thr Thr Lys
                100                 105                 110

Asn Asn Pro Val Met Ser Leu Gln Asp Gln Ala Arg Phe Val Lys Asn
            115                 120                 125

Val Thr Thr Trp Lys Glu Met Lys Pro Gly Phe Tyr His Gly His Val
        130                 135                 140

Ala Tyr Leu Asp Phe Thr Lys Tyr Gly Val Lys Lys Pro Ile Tyr
145                 150                 155                 160

Leu Asn Val Ile Arg Asp Pro Ile Glu Arg Leu Val Ser Tyr Tyr Tyr
                165                 170                 175

Phe Leu Arg Phe Gly Asp Asp Tyr Arg Pro Gly Leu Lys Arg Arg Lys
            180                 185                 190

Gln Gly Asp Lys Lys Thr Phe Asp Glu Cys Val Ala Ala Gly Gly Ser
        195                 200                 205

Asp Cys Ala Pro Glu Lys Leu Trp Leu Gln Ile Pro Phe Phe Cys Gly
210                 215                 220

His Ser Ser Glu Cys Trp Asn Ile Gly Ser Lys Trp Ala Leu Glu Gln
225                 230                 235                 240

Ala Arg Tyr Asn Leu Val Asn Glu Tyr Leu Leu Val Gly Val Thr Glu
                245                 250                 255

Glu Leu Glu Asp Phe Ile Met Leu Leu Glu Ala Ala Leu Pro Arg Phe
            260                 265                 270

Phe Arg Gly Ala Thr Glu Leu Tyr Arg Thr Gly Lys Lys Ser His Leu
        275                 280                 285

Arg Lys Thr Thr Glu Lys Lys Leu Pro Thr Lys Glu Thr Ile Ala Arg
290                 295                 300

Leu Gln Leu Ser Glu Ile Trp Lys Met Glu Asn Glu Phe Tyr Glu Phe
305                 310                 315                 320

Ala Leu Glu Gln Phe Gln Phe Ile Arg Ala His Ala Val Arg Glu Lys
                325                 330                 335

Asp Gly Glu Leu Tyr Leu Leu Ser Gln Ser Phe Phe Tyr Glu Lys Ile
            340                 345                 350

Tyr Pro Lys Thr Asn
        355

<210> SEQ ID NO 183
<211> LENGTH: 356
<212> TYPE: PRT
<213> ORGANISM: Xenopus laevis

<400> SEQUENCE: 183

Met Gly Leu Leu Arg Ile Met Met Pro Pro Lys Leu Gln Leu Leu Ala
 1               5                  10                  15

Val Leu Thr Phe Gly Val Leu Met Leu Phe Leu Glu Asn Gln Ile Gln
                20                  25                  30

Asn Leu Glu Glu Ser Arg Glu Lys Leu Glu Arg Ala Ile Ala Arg His
            35                  40                  45

Glu Val Arg Glu Ile Glu Gln Arg His Ser Met Asp Gly Ser Arg Gln
        50                  55                  60
```

```
Glu Ile Ala Leu Asp Asp Asp Glu Asp Ile Leu Ile Tyr Asn Arg
 65                  70                  75                  80

Val Pro Lys Thr Ala Ser Thr Ser Phe Thr Asn Ile Ala Tyr Asp Leu
                 85                  90                  95

Cys Ala Lys Asn Lys Tyr His Val Leu His Ile Asn Thr Thr Lys Asn
                100                 105                 110

Asn Pro Val Met Ser Leu Gln Asp Gln Val Arg Phe Val Lys Asn Val
                115                 120                 125

Ser Ser Trp Arg Glu Met Lys Pro Gly Phe Tyr His Gly His Val Ser
130                 135                 140

Phe Leu Asp Phe Thr Lys Phe Gly Val Lys Lys Lys Pro Ile Tyr Ile
145                 150                 155                 160

Asn Val Ile Arg Asp Pro Ile Glu Arg Leu Val Ser Tyr Tyr Tyr Phe
                165                 170                 175

Leu Arg Phe Gly Asp Asp Tyr Arg Pro Gly Leu Arg Arg Arg Lys Gln
                180                 185                 190

Gly Asp Lys Lys Thr Phe Asp Glu Cys Val Ala Ala Gly Gly Ser Asp
                195                 200                 205

Cys Ala Pro Glu Lys Leu Trp Leu Gln Ile Pro Phe Phe Cys Gly His
                210                 215                 220

Ser Ser Glu Cys Trp Asn Val Gly Ser Arg Trp Ala Leu Asp Gln Ala
225                 230                 235                 240

Lys Tyr Asn Leu Val Asn Glu Tyr Phe Leu Val Gly Val Thr Glu Glu
                245                 250                 255

Leu Glu Asp Phe Ile Met Leu Leu Glu Ala Ala Leu Pro Arg Phe Phe
                260                 265                 270

Arg Gly Ala Thr Glu Leu Tyr Arg Ser Gly Lys Lys Ser His Leu Arg
                275                 280                 285

Lys Thr Thr Glu Lys Lys Ala Pro Ser Lys Glu Thr Thr Ala Lys Leu
                290                 295                 300

Gln Gln Ser Asp Ile Trp Lys Met Glu Asn Glu Phe Tyr Glu Phe Ala
305                 310                 315                 320

Leu Glu Gln Phe Gln Phe Val Arg Ala His Ala Val Arg Glu Lys Asp
                325                 330                 335

Gly Glu Leu Tyr Val Leu Ala Pro Asn Phe Phe Tyr Glu Lys Ile Tyr
                340                 345                 350

Pro Lys Ser Asn
            355

<210> SEQ ID NO 184
<211> LENGTH: 356
<212> TYPE: PRT
<213> ORGANISM: mus musculus

<400> SEQUENCE: 184

Met Gly Leu Leu Arg Ile Met Met Pro Pro Lys Leu Gln Leu Leu Ala
  1               5                  10                  15

Val Val Ala Phe Ala Val Ala Met Leu Phe Leu Glu Asn Gln Ile Gln
                 20                  25                  30

Lys Leu Glu Glu Ser Arg Ala Lys Leu Glu Arg Ala Ile Ala Arg His
                 35                  40                  45

Glu Val Arg Glu Ile Glu Gln Arg His Thr Met Asp Gly Pro Arg Gln
                 50                  55                  60

Asp Ala Thr Leu Asp Glu Glu Glu Asp Ile Ile Ile Ile Tyr Asn Arg
 65                  70                  75                  80
```

```
Val Pro Lys Thr Ala Ser Thr Ser Phe Thr Asn Ile Ala Tyr Asp Leu
            85                  90                  95

Cys Ala Lys Asn Arg Tyr His Val Leu His Ile Asn Thr Thr Lys Asn
            100                 105                 110

Asn Pro Val Met Ser Leu Gln Asp Gln Val Arg Phe Val Lys Asn Ile
            115                 120                 125

Thr Thr Trp Asn Glu Met Lys Pro Gly Phe Tyr His Gly His Ile Ser
130                 135                 140

Tyr Leu Asp Phe Ala Lys Phe Gly Val Lys Lys Pro Ile Tyr Ile
145                 150                 155                 160

Asn Val Ile Arg Asp Pro Ile Glu Arg Leu Val Ser Tyr Tyr Phe
            165                 170                 175

Leu Arg Phe Gly Asp Asp Tyr Arg Pro Gly Leu Arg Arg Lys Gln
            180                 185                 190

Gly Asp Lys Lys Thr Phe Asp Glu Cys Val Ala Glu Gly Gly Ser Asp
            195                 200                 205

Cys Ala Pro Glu Lys Leu Trp Leu Gln Ile Pro Phe Phe Cys Gly His
            210                 215                 220

Ser Ser Glu Cys Trp Asn Val Gly Ser Arg Trp Ala Met Asp Gln Ala
225                 230                 235                 240

Lys Ser Asn Leu Ile Asn Glu Tyr Phe Leu Val Gly Val Thr Glu Glu
            245                 250                 255

Leu Glu Asp Phe Ile Met Leu Leu Glu Ala Ala Leu Pro Arg Phe Phe
            260                 265                 270

Arg Gly Ala Thr Asp Leu Tyr Arg Thr Gly Lys Lys Ser His Leu Arg
            275                 280                 285

Lys Thr Thr Glu Lys Lys Leu Pro Thr Lys Gln Thr Ile Ala Lys Leu
            290                 295                 300

Gln Gln Ser Asp Ile Trp Lys Met Glu Asn Glu Phe Tyr Glu Phe Ala
305                 310                 315                 320

Leu Glu Gln Phe Gln Phe Ile Arg Ala His Ala Val Arg Glu Lys Asp
            325                 330                 335

Gly Asp Leu Tyr Ile Leu Ala Gln Asn Phe Phe Tyr Glu Lys Ile Tyr
            340                 345                 350

Pro Lys Ser Asn
            355

<210> SEQ ID NO 185
<211> LENGTH: 356
<212> TYPE: PRT
<213> ORGANISM: Sus scrofa

<400> SEQUENCE: 185

Met Gly Leu Leu Arg Ile Met Met Pro Pro Lys Leu Gln Leu Leu Ala
1               5                   10                  15

Val Val Ala Phe Ala Val Ala Met Leu Phe Leu Glu Asn Gln Ile Gln
            20                  25                  30

Lys Leu Glu Glu Ser Arg Ser Lys Leu Glu Arg Ala Ile Ala Arg His
            35                  40                  45

Glu Val Arg Glu Ile Glu Gln Arg His Thr Met Asp Gly Pro Arg Gln
            50                  55                  60

Glu Ala Ala Leu Asp Glu Glu Asp Leu Val Ile Ile Tyr Asn Arg
65                  70                  75                  80

Val Pro Lys Thr Ala Ser Thr Ser Phe Thr Asn Ile Ala Tyr Asp Leu
```

```
                85                  90                  95
Cys Ala Lys Asn Lys Tyr His Val Leu His Ile Asn Thr Thr Lys Asn
            100                 105                 110
Asn Pro Val Met Ser Leu Gln Asp Gln Val Arg Phe Val Lys Asn Ile
            115                 120                 125
Thr Ser Trp Lys Glu Met Lys Pro Gly Phe Tyr His Gly His Val Ser
            130                 135                 140
Tyr Leu Asp Phe Ala Lys Phe Gly Val Lys Lys Pro Ile Tyr Ile
145                 150                 155                 160
Asn Val Val Arg Asp Pro Ile Glu Arg Leu Val Ser Tyr Tyr Phe
                165                 170                 175
Leu Arg Phe Gly Asp Asp Tyr Arg Pro Gly Leu Arg Arg Lys Gln
                180                 185                 190
Gly Asp Lys Lys Thr Phe Asp Glu Cys Val Ala Glu Gly Gly Ser Asp
            195                 200                 205
Cys Ala Pro Glu Lys Leu Trp Leu Gln Ile Pro Phe Phe Cys Gly His
            210                 215                 220
Ser Ser Glu Cys Trp Asn Val Gly Ser Arg Trp Ala Met Asp Gln Ala
225                 230                 235                 240
Lys Tyr Asn Leu Ile Asn Glu Tyr Phe Leu Val Gly Val Thr Glu Glu
                245                 250                 255
Leu Glu Asp Phe Val Met Leu Leu Glu Ala Ala Leu Pro Arg Phe Phe
                260                 265                 270
Arg Gly Ala Thr Glu Leu Tyr Arg Thr Gly Lys Lys Ser His Leu Arg
                275                 280                 285
Lys Thr Thr Glu Lys Lys Leu Pro Thr Lys Gln Thr Ile Ala Lys Leu
            290                 295                 300
Gln Gln Ser His Ile Trp Lys Met Glu Asn Glu Phe Tyr Glu Phe Ala
305                 310                 315                 320
Leu Glu Gln Phe Gln Phe Ile Arg Ala His Ala Val Arg Glu Lys Asp
                325                 330                 335
Gly Asp Leu Phe Ile Leu Ala Gln Asn Phe Phe Tyr Glu Lys Ile Tyr
                340                 345                 350
Pro Lys Ser Asn
            355

<210> SEQ ID NO 186
<211> LENGTH: 356
<212> TYPE: PRT
<213> ORGANISM: Homo sapiens

<400> SEQUENCE: 186

Met Gly Leu Leu Arg Ile Met Met Pro Pro Lys Leu Gln Leu Leu Ala
1               5                   10                  15
Val Val Ala Phe Ala Val Ala Met Leu Phe Leu Glu Asn Gln Ile Gln
            20                  25                  30
Lys Leu Glu Glu Ser Arg Ser Lys Leu Glu Arg Ala Ile Ala Arg His
            35                  40                  45
Glu Val Arg Glu Ile Glu Gln Arg His Thr Met Asp Gly Pro Arg Gln
            50                  55                  60
Asp Ala Thr Leu Asp Glu Glu Asp Met Val Ile Ile Tyr Asn Arg
65                  70                  75                  80
Val Pro Lys Thr Ala Ser Thr Ser Phe Thr Asn Ile Ala Tyr Asp Leu
                85                  90                  95
```

```
Cys Ala Lys Asn Lys Tyr His Val Leu His Ile Asn Thr Thr Lys Asn
                100                 105                 110

Asn Pro Val Met Ser Leu Gln Asp Gln Val Arg Phe Val Lys Asn Ile
            115                 120                 125

Thr Ser Trp Lys Glu Met Lys Pro Gly Phe Tyr His Gly His Val Ser
        130                 135                 140

Tyr Leu Asp Phe Ala Lys Phe Gly Val Lys Lys Pro Ile Tyr Ile
145                 150                 155                 160

Asn Val Ile Arg Asp Pro Ile Glu Arg Leu Val Ser Tyr Tyr Phe
                165                 170                 175

Leu Arg Phe Gly Asp Asp Tyr Arg Pro Gly Leu Arg Arg Lys Gln
            180                 185                 190

Gly Asp Lys Lys Thr Phe Asp Glu Cys Val Ala Glu Gly Gly Ser Asp
        195                 200                 205

Cys Ala Pro Glu Lys Leu Trp Leu Gln Ile Pro Phe Phe Cys Gly His
        210                 215                 220

Ser Ser Glu Cys Trp Asn Val Gly Ser Arg Trp Ala Met Asp Gln Ala
225                 230                 235                 240

Lys Tyr Asn Leu Ile Asn Glu Tyr Phe Leu Val Gly Val Thr Glu Glu
                245                 250                 255

Leu Glu Asp Phe Ile Met Leu Leu Glu Ala Ala Leu Pro Arg Phe Phe
            260                 265                 270

Arg Gly Ala Thr Glu Leu Tyr Arg Thr Gly Lys Lys Ser His Leu Arg
        275                 280                 285

Lys Thr Thr Glu Lys Lys Leu Pro Thr Lys Gln Thr Ile Ala Lys Leu
        290                 295                 300

Gln Gln Ser Asp Ile Trp Lys Met Glu Asn Glu Phe Tyr Glu Phe Ala
305                 310                 315                 320

Leu Glu Gln Phe Gln Phe Ile Arg Ala His Ala Val Arg Glu Lys Asp
                325                 330                 335

Gly Asp Leu Tyr Ile Leu Ala Gln Asn Phe Phe Tyr Glu Lys Ile Tyr
            340                 345                 350

Pro Lys Ser Asn
        355

<210> SEQ ID NO 187
<211> LENGTH: 356
<212> TYPE: PRT
<213> ORGANISM: Physeter catodon

<400> SEQUENCE: 187

Met Gly Leu Leu Arg Ile Met Met Pro Pro Lys Leu Gln Leu Leu Ala
1               5                   10                  15

Val Val Ala Phe Ala Val Ala Met Leu Phe Leu Glu Asn Gln Ile Gln
                20                  25                  30

Lys Leu Glu Glu Ser Arg Ser Lys Leu Glu Arg Ala Ile Ala Arg His
            35                  40                  45

Glu Val Arg Glu Ile Glu Gln Arg His Thr Met Asp Gly Pro Arg Gln
        50                  55                  60

Asp Ala Ala Leu Asp Glu Glu Asp Met Val Ile Ile Tyr Asn Arg
65                  70                  75                  80

Val Pro Lys Thr Ala Ser Thr Ser Phe Thr Asn Ile Ala Tyr Asp Leu
                85                  90                  95

Cys Ala Lys Asn Lys Tyr His Val Leu His Ile Asn Thr Thr Lys Asn
                100                 105                 110
```

Asn Pro Val Met Ser Leu Gln Asp Gln Val Arg Phe Val Lys Asn Ile
            115                 120                 125

Thr Ser Trp Lys Glu Met Lys Pro Gly Phe Tyr His Gly His Ile Ser
            130                 135                 140

Tyr Leu Asp Phe Ala Lys Phe Gly Val Lys Lys Pro Ile Tyr Ile
145                 150                 155                 160

Asn Val Ile Arg Asp Pro Ile Glu Arg Leu Val Ser Tyr Tyr Phe
                165                 170                 175

Leu Arg Phe Gly Asp Asp Tyr Arg Pro Gly Leu Arg Arg Lys Gln
                180                 185                 190

Gly Asp Lys Lys Thr Phe Asp Glu Cys Val Ala Glu Gly Gly Ser Asp
                195                 200                 205

Cys Ala Pro Glu Lys Leu Trp Leu Gln Ile Pro Phe Phe Cys Gly His
                210                 215                 220

Ser Ser Glu Cys Trp Asn Val Gly Ser Arg Trp Ala Met Asp Gln Ala
225                 230                 235                 240

Lys Tyr Asn Leu Val Asn Glu Tyr Phe Leu Val Gly Val Thr Glu Glu
                245                 250                 255

Leu Glu Asp Phe Ile Met Leu Leu Glu Ala Ala Leu Pro Arg Phe Phe
                260                 265                 270

Arg Gly Ala Thr Glu Leu Tyr Arg Thr Gly Lys Lys Ser His Leu Arg
                275                 280                 285

Lys Thr Thr Glu Lys Lys Leu Pro Thr Lys Gln Thr Ile Ala Lys Leu
                290                 295                 300

Gln Gln Ser Asp Ile Trp Lys Met Glu Asn Glu Phe Tyr Glu Phe Ala
305                 310                 315                 320

Leu Glu Gln Phe Gln Phe Ile Arg Ala His Ala Val Arg Glu Lys Asp
                325                 330                 335

Gly Asp Leu Tyr Ile Leu Ala Gln Asn Phe Phe Tyr Glu Lys Ile Tyr
                340                 345                 350

Pro Lys Ser Asn
            355

<210> SEQ ID NO 188
<211> LENGTH: 356
<212> TYPE: PRT
<213> ORGANISM: Crotalus horridus

<400> SEQUENCE: 188

Met Gly Leu Le

```
            115                 120                 125
Thr Ser Trp Lys Glu Met Lys Pro Gly Phe Tyr His Gly His Ile Ser
        130                 135                 140

Phe Leu Asp Phe Ala Lys Phe Gly Val Lys Lys Pro Ile Tyr Ile
145                 150                 155                 160

Asn Val Ile Arg Asp Pro Ile Glu Arg Leu Val Ser Tyr Tyr Phe
                165                 170                 175

Leu Arg Phe Gly Asp Asp Tyr Arg Pro Gly Leu Arg Arg Lys Gln
            180                 185                 190

Gly Asp Lys Lys Thr Phe Asp Glu Cys Val Ala Ala Gly Gly Ser Asp
                195                 200                 205

Cys Ala Pro Glu Lys Leu Trp Leu Gln Ile Pro Phe Phe Cys Gly His
            210                 215                 220

Ser Ser Glu Cys Trp Asn Val Gly Ser Arg Trp Ala Leu Glu Gln Ala
225                 230                 235                 240

Lys Tyr Asn Leu Ile Asn Glu Tyr Phe Leu Val Gly Val Thr Glu Glu
                245                 250                 255

Leu Glu Asp Phe Ile Met Leu Leu Glu Ala Ala Leu Pro Arg Phe Phe
                260                 265                 270

Arg Gly Ala Thr Glu Leu Tyr Arg Thr Gly Lys Lys Ser His Leu Arg
            275                 280                 285

Lys Thr Thr Glu Lys Lys Leu Pro Ser Lys Glu Thr Ile Ala Lys Leu
        290                 295                 300

Gln Gln Ser Glu Ile Trp Lys Met Glu Asn Glu Phe Tyr Glu Phe Ser
305                 310                 315                 320

Leu Glu Gln Phe Gln Phe Val Arg Ala His Ala Val Arg Glu Lys Asp
                325                 330                 335

Gly Glu Leu Tyr Ile Leu Ala Gln Asn Phe Phe Tyr Glu Lys Ile Tyr
            340                 345                 350

Pro Lys Ser Asn
        355

<210> SEQ ID NO 189
<211> LENGTH: 354
<212> TYPE: PRT
<213> ORGANISM: Danio rerio

<400> SEQUENCE: 189

Met Gly Leu Leu Arg Leu Met Met Pro Pro Lys Phe Gln Leu Leu Ala
1               5                   10                  15

Leu Leu Ala Phe Ala Ile Ala Met Ile Phe Leu Glu Asn Gln Ile Gln
                20                  25                  30

Lys Leu Glu Glu Ser Arg Gly Lys Leu Glu Gln Ala Ile Ala Arg His
            35                  40                  45

Glu Val Arg Glu Ile Glu Arg Arg His Ser Gln Val Gly Val Lys Glu
        50                  55                  60

Val Gln Leu Glu Glu Asp Asp Thr Val Val Ile Tyr Asn Arg Val Pro
65                  70                  75                  80

Lys Thr Ala Ser Thr Ser Phe Thr Asn Ile Ala Tyr Asp Leu Cys Asn
                85                  90                  95

Lys Asn His Tyr His Val Leu His Ile Asn Thr Ser Lys Asn Asn Pro
                100                 105                 110

Val Met Ser Leu Gln Asp Gln Val Arg Phe Val Lys Asn Val Thr Leu
            115                 120                 125
```

Trp Lys Glu Met Lys Pro Ala Phe Tyr His Gly His Val Ser Phe Leu
            130                 135                 140

Asp Phe Thr Lys Phe Gly Val Lys Lys Pro Ile Tyr Ile Asn Val
145                 150                 155                 160

Ile Arg Asp Pro Ile Glu Arg Leu Val Ser Tyr Tyr Phe Leu Arg
                    165                 170                 175

Phe Gly Asp Asp Tyr Arg Pro Gly Leu Arg Arg Lys Gln Gly Asp
                180                 185                 190

Lys Lys Thr Phe Asp Glu Cys Val Ser Ala Gly Ser Asp Cys Ala
            195                 200                 205

Pro Glu Lys Leu Trp Leu Gln Ile Pro Phe Cys Gly His Tyr Ser
    210                 215                 220

Glu Cys Trp Asn Ile Gly Ser Arg Trp Ala Leu Glu Gln Ala Lys Tyr
225                 230                 235                 240

Asn Leu Val Asn Glu Tyr Met Leu Val Gly Val Thr Glu Glu Leu Glu
                245                 250                 255

Asp Phe Val Met Met Leu Glu Ala Ala Leu Pro Arg Phe Phe Lys Gly
                260                 265                 270

Ala Thr Glu Leu Tyr Lys Thr Gly Lys Arg Ser His Leu Arg Lys Thr
    275                 280                 285

Ser Glu Lys Lys Pro Pro Thr Lys Glu Ser Ile Ala Arg Leu Gln Gln
290                 295                 300

Ser Asn Ile Trp Lys Met Glu Asn Glu Phe Tyr Glu Phe Ala Leu Glu
305                 310                 315                 320

Gln Phe Gln Tyr Val Arg Ala His Ala Val Arg Glu Lys Asp Gly Glu
                325                 330                 335

Leu Tyr Leu Leu Thr Gln Asn Phe Phe Tyr Glu Lys Ile Tyr Pro Lys
                340                 345                 350

Ser Asn

<210> SEQ ID NO 190
<211> LENGTH: 368
<212> TYPE: PRT
<213> ORGANISM: Fundulus heteroclitus

<400> SEQUENCE: 190

Met Gly Leu Leu Arg Val Met Met Pro Pro Lys Leu Gln Leu Leu Ala
1               5                   10                  15

Leu Leu Ala Phe Ala Ala Leu Leu Ala Phe Ala Val Ala Met Phe Phe
                20                  25                  30

Leu Glu Asn Gln Ile Gln Lys Leu Glu Glu Ser Arg Gly Lys Leu Glu
            35                  40                  45

Arg Ala Ile Ala Arg His Glu Val Arg Glu Ile Glu Gln Arg His Thr
    50                  55                  60

Gln Asp Gly Gln Arg Glu Arg Glu Thr Ala Glu Thr Ala Ala Thr Leu
65                  70                  75                  80

Ser Asp Ser Asp Asp Leu Val Ile Ile Tyr Asn Arg Val Pro Lys
                85                  90                  95

Thr Ala Ser Thr Ser Phe Thr Asn Ile Ala Tyr Asp Leu Cys Gly Lys
                100                 105                 110

Asn Arg Tyr His Val Leu His Ile Asn Thr Thr Lys Asn Asn Pro Val
            115                 120                 125

Met Ser Ile Gln Asp Gln Val Arg Phe Val Lys Asn Val Thr Glu Trp
    130                 135                 140

```
Arg Glu Met Lys Pro Ala Phe Tyr His Gly His Val Ser Phe Leu Asp
145                 150                 155                 160

Phe Thr Lys Phe Gly Val Lys Arg Lys Pro Val Tyr Ile Asn Leu Ile
                165                 170                 175

Arg Asp Pro Ile Glu Arg Leu Val Ser Tyr Tyr Phe Leu Arg Phe
            180                 185                 190

Gly Asp Asp Tyr Arg Pro Gly Leu Arg Arg Arg Lys Gln Gly Asp Lys
        195                 200                 205

Lys Thr Phe Asp Glu Cys Val Ser Ala Gly Gly Ser Asp Cys Ala Pro
    210                 215                 220

Glu Arg Leu Trp Leu Gln Ile Pro Phe Phe Cys Gly His Tyr Ser Glu
225                 230                 235                 240

Cys Trp Asn Val Gly Ser Gln Trp Ala Leu Glu Gln Ala Lys Tyr Asn
                245                 250                 255

Leu Val Asn Glu Tyr Met Leu Val Gly Val Thr Glu Leu Glu Asp
            260                 265                 270

Phe Val Met Met Leu Glu Ala Ala Leu Pro Arg Phe Phe Arg Gly Ala
        275                 280                 285

Thr Glu Leu Tyr Lys Thr Gly Lys Lys Ser His Leu Arg Arg Thr Ser
    290                 295                 300

Glu Lys Lys Pro Pro Thr Lys Glu Ser Val Ala Arg Leu Gln Gln Ser
305                 310                 315                 320

Asp Ile Trp Lys Met Glu Asn Glu Phe Tyr Glu Phe Ala Leu Glu Gln
                325                 330                 335

Phe Gln Phe Val Arg Ala His Ala Val Arg Gly Lys Asp Gly Glu Leu
            340                 345                 350

Tyr Met Leu Ala Gln Asn Phe Phe Tyr Glu Lys Ile Tyr Pro Lys Asn
        355                 360                 365

<210> SEQ ID NO 191
<211> LENGTH: 311
<212> TYPE: PRT
<213> ORGANISM: Mus musculus

<400> SEQUENCE: 191

Lys Tyr Tyr Phe Pro Val Arg Glu Leu Glu Arg Ser Leu Arg Phe Asp
1               5                   10                  15

Met Lys Gly Asp Asp Val Ile Val Phe Leu His Ile Gln Lys Thr Gly
                20                  25                  30

Gly Thr Thr Phe Gly Arg His Leu Val Gln Asn Val Arg Leu Glu Val
            35                  40                  45

Pro Cys Asp Cys Arg Pro Gly Gln Lys Lys Cys Thr Cys Tyr Arg Pro
        50                  55                  60

Asn Arg Arg Glu Thr Trp Leu Phe Ser Arg Phe Ser Thr Gly Trp Ser
65                  70                  75                  80

Cys Gly Leu His Ala Asp Trp Thr Glu Leu Thr Asn Cys Val Pro Gly
                85                  90                  95

Val Leu Asp Arg Arg Asp Pro Ala Gly Leu Arg Ser Pro Arg Lys Phe
            100                 105                 110

Tyr Tyr Ile Thr Leu Leu Arg Asp Pro Val Ser Arg Tyr Leu Ser Glu
        115                 120                 125

Trp Arg His Val Gln Arg Gly Ala Thr Trp Lys Thr Ser Leu His Met
    130                 135                 140

Cys Asp Gly Arg Thr Pro Thr Pro Glu Glu Leu Pro Pro Cys Tyr Glu
145                 150                 155                 160
```

```
Gly Thr Asp Trp Ser Gly Cys Thr Leu Gln Glu Phe Met Asp Cys Pro
            165                 170                 175

Tyr Asn Leu Ala Asn Asn Arg Gln Val Arg Met Leu Ala Asp Leu Ser
            180                 185                 190

Leu Val Gly Cys Tyr Asn Leu Ser Phe Ile Pro Glu Ser Lys Arg Ala
            195                 200                 205

Gln Leu Leu Leu Glu Ser Ala Lys Lys Asn Leu Arg Gly Met Ala Phe
    210                 215                 220

Phe Gly Leu Thr Glu Phe Gln Arg Lys Thr Gln Tyr Leu Phe Glu Arg
225                 230                 235                 240

Thr Phe Asn Leu Lys Phe Ile Arg Pro Phe Met Gln Tyr Asn Ser Thr
                245                 250                 255

Arg Ala Gly Gly Val Glu Val Asp Glu Asp Thr Ile Arg His Ile Glu
            260                 265                 270

Glu Leu Asn Asp Leu Asp Met Gln Leu Tyr Asp Tyr Ala Lys Asp Leu
            275                 280                 285

Phe Gln Gln Arg Tyr Gln Tyr Lys Arg Gln Leu Glu Arg Arg Glu Gln
    290                 295                 300

Arg Leu Arg Asn Arg Glu Glu
305                 310

<210> SEQ ID NO 192
<211> LENGTH: 311
<212> TYPE: PRT
<213> ORGANISM: Homo sapiens

<400> SEQUENCE: 192

Lys Tyr Tyr Phe Pro Val Arg Glu Leu Glu Arg Ser Leu Arg Phe Asp
1               5                   10                  15

Met Lys Gly Asp Asp Val Ile Val Phe Leu His Ile Gln Lys Thr Gly
            20                  25                  30

Gly Thr Thr Phe Gly Arg His Leu Val Gln Asn Val Arg Leu Glu Val
            35                  40                  45

Pro Cys Asp Cys Arg Pro Gly Gln Lys Lys Cys Thr Cys Tyr Arg Pro
    50                  55                  60

Asn Arg Arg Glu Thr Trp Leu Phe Ser Arg Phe Ser Thr Gly Trp Ser
65                  70                  75                  80

Cys Gly Leu His Ala Asp Trp Thr Glu Leu Thr Asn Cys Val Pro Gly
                85                  90                  95

Val Leu Asp Arg Arg Asp Ser Ala Ala Leu Arg Thr Pro Arg Lys Phe
            100                 105                 110

Tyr Tyr Ile Thr Leu Leu Arg Asp Pro Val Ser Arg Tyr Leu Ser Glu
            115                 120                 125

Trp Arg His Val Gln Arg Gly Ala Thr Trp Lys Thr Ser Leu His Met
    130                 135                 140

Cys Asp Gly Arg Thr Pro Thr Pro Glu Glu Leu Pro Pro Cys Tyr Glu
145                 150                 155                 160

Gly Thr Asp Trp Ser Gly Cys Thr Leu Gln Glu Phe Met Asp Cys Pro
                165                 170                 175

Tyr Asn Leu Ala Asn Asn Arg Gln Val Arg Met Leu Ala Asp Leu Ser
            180                 185                 190

Leu Val Gly Cys Tyr Asn Leu Ser Phe Ile Pro Glu Gly Lys Arg Ala
            195                 200                 205

Gln Leu Leu Leu Glu Ser Ala Lys Lys Asn Leu Arg Gly Met Ala Phe
```

```
                        210                 215                 220

Phe Gly Leu Thr Glu Phe Gln Arg Lys Thr Gln Tyr Leu Phe Glu Arg
225                 230                 235                 240

Thr Phe Asn Leu Lys Phe Ile Arg Pro Phe Met Gln Tyr Asn Ser Thr
                245                 250                 255

Arg Ala Gly Gly Val Glu Val Asp Glu Asp Thr Ile Arg Arg Ile Glu
            260                 265                 270

Glu Leu Asn Asp Leu Asp Met Gln Leu Tyr Asp Tyr Ala Lys Asp Leu
        275                 280                 285

Phe Gln Gln Arg Tyr Gln Tyr Lys Arg Gln Leu Glu Arg Arg Glu Gln
290                 295                 300

Arg Leu Arg Ser Arg Glu Glu
305                 310

<210> SEQ ID NO 193
<211> LENGTH: 311
<212> TYPE: PRT
<213> ORGANISM: Sus scrofa

<400> SEQUENCE: 193

Lys Tyr Tyr Phe Pro Val Arg Glu Leu Glu Arg Ser Leu His Phe Asp
1               5                   10                  15

Met Lys Gly Asp Asp Val Ile Val Phe Leu His Ile Gln Lys Thr Gly
            20                  25                  30

Gly Thr Thr Phe Gly Arg His Leu Val Gln Asn Val Arg Leu Glu Val
        35                  40                  45

Pro Cys Asp Cys Arg Pro Gly Gln Lys Lys Cys Thr Cys Tyr Arg Pro
    50                  55                  60

Asn Arg Arg Glu Thr Trp Leu Phe Ser Arg Phe Ser Thr Gly Trp Ser
65                  70                  75                  80

Cys Gly Leu His Ala Asp Trp Thr Glu Leu Thr Asn Cys Val Pro Gly
                85                  90                  95

Val Leu Asp Arg Arg Asp Pro Ala Ala Leu Arg Thr Pro Arg Lys Phe
            100                 105                 110

Tyr Tyr Ile Thr Leu Leu Arg Asp Pro Val Ser Arg Tyr Leu Ser Glu
        115                 120                 125

Trp Arg His Val Gln Arg Gly Ala Thr Trp Lys Thr Ser Leu His Met
    130                 135                 140

Cys Asp Gly Arg Thr Pro Thr Pro Glu Glu Leu Pro Pro Cys Tyr Glu
145                 150                 155                 160

Gly Thr Asp Trp Ser Gly Cys Thr Leu Gln Glu Phe Met Asp Cys Pro
                165                 170                 175

Tyr Asn Leu Ala Asn Asn Arg Gln Val Arg Met Leu Ala Asp Leu Ser
            180                 185                 190

Leu Val Gly Cys Tyr Asn Leu Ser Phe Ile Pro Glu Gly Lys Arg Ser
        195                 200                 205

Gln Leu Leu Leu Glu Ser Ala Lys Lys Asn Leu Arg Gly Met Ala Phe
    210                 215                 220

Phe Gly Leu Thr Glu Phe Gln Arg Lys Thr Gln Tyr Leu Phe Glu Arg
225                 230                 235                 240

Thr Phe Asn Leu Lys Phe Ile Arg Pro Phe Met Gln Tyr Asn Ser Thr
                245                 250                 255

Arg Ala Gly Gly Val Glu Val Gly Glu Asp Thr Ile Arg Ile Glu
            260                 265                 270
```

```
Glu Leu Asn Asp Leu Asp Met Gln Leu Tyr Asp Tyr Ala Arg Asp Leu
            275                 280                 285

Phe Gln Gln Arg Tyr Gln Tyr Lys Arg Gln Leu Glu Arg Arg Gln Gln
    290                 295                 300

Arg Leu Arg Ser Arg Glu Glu
305                 310

<210> SEQ ID NO 194
<211> LENGTH: 311
<212> TYPE: PRT
<213> ORGANISM: Macaca mulatta

<400> SEQUENCE: 194

Lys Tyr Tyr Phe Pro Val Arg Glu Leu Glu Arg Ser Leu Arg Phe Asp
1               5                   10                  15

Met Lys Gly Asp Asp Val Ile Val Phe Leu His Ile Gln Lys Thr Gly
            20                  25                  30

Gly Thr Thr Phe Gly Arg His Leu Val Gln Asn Val Arg Leu Glu Val
        35                  40                  45

Pro Cys Asp Cys Arg Pro Gly Gln Lys Lys Cys Thr Cys Tyr Arg Pro
    50                  55                  60

Asn Arg Arg Glu Thr Trp Leu Phe Ser Arg Phe Ser Thr Gly Trp Ser
65                  70                  75                  80

Cys Gly Leu His Ala Asp Trp Thr Glu Leu Thr Asn Cys Val Pro Gly
                85                  90                  95

Val Leu Asp Arg Arg Asp Ser Ala Ala Leu Arg Thr Pro Arg Lys Phe
            100                 105                 110

Tyr Tyr Ile Thr Leu Leu Arg Asp Pro Val Ser Arg Tyr Leu Ser Glu
        115                 120                 125

Trp Arg His Val Gln Arg Gly Ala Thr Trp Lys Thr Ser Leu His Met
130                 135                 140

Cys Asp Gly Arg Thr Pro Thr Pro Glu Glu Leu Pro Pro Cys Tyr Glu
145                 150                 155                 160

Gly Thr Asp Trp Ser Gly Cys Thr Leu Gln Glu Phe Met Asp Cys Pro
                165                 170                 175

Tyr Asn Leu Ala Asn Asn Arg Gln Val Arg Met Leu Ala Asp Leu Ser
            180                 185                 190

Leu Val Gly Cys Tyr Asn Leu Ser Phe Ile Pro Glu Gly Lys Arg Ala
        195                 200                 205

Gln Leu Leu Leu Glu Ser Ala Lys Lys Asn Leu Arg Gly Met Ala Phe
    210                 215                 220

Phe Gly Leu Thr Glu Phe Gln Arg Lys Thr Gln Tyr Leu Phe Glu Arg
225                 230                 235                 240

Thr Phe Asn Leu Lys Phe Ile Arg Pro Phe Met Gln Tyr Asn Ser Thr
                245                 250                 255

Arg Ala Gly Gly Val Glu Val Asp Glu Asp Thr Ile Arg Arg Ile Glu
            260                 265                 270

Glu Leu Asn Asp Leu Asp Met Gln Leu Tyr Asp Tyr Ala Lys Asp Leu
        275                 280                 285

Phe Gln Gln Arg Tyr Gln Tyr Lys Arg Gln Leu Glu Arg Glu Gln Gln
    290                 295                 300

Arg Leu Arg Ser Arg Glu Glu
305                 310

<210> SEQ ID NO 195
```

```
<211> LENGTH: 311
<212> TYPE: PRT
<213> ORGANISM: Gallus gallus

<400> SEQUENCE: 195

Lys Tyr Tyr Phe Pro Val Arg Glu Leu Glu Arg Glu Leu Ala Phe Asp
1               5                   10                  15

Met Lys Gly Glu Asp Val Ile Val Phe Leu His Ile Gln Lys Thr Gly
            20                  25                  30

Gly Thr Thr Phe Gly Arg His Leu Val Gln Asn Val Arg Leu Glu Val
        35                  40                  45

Pro Cys Asp Cys Arg Pro Gly Gln Lys Cys Thr Cys Tyr Arg Pro
    50                  55                  60

Asn Arg Arg Glu Thr Trp Leu Phe Ser Arg Phe Ser Thr Gly Trp Ser
65              70                  75                  80

Cys Gly Leu His Ala Asp Trp Thr Glu Leu Thr Asn Cys Val Pro Gly
            85                  90                  95

Val Leu Gly Arg Arg Glu Ser Ala Pro Asn Arg Thr Pro Arg Lys Phe
        100                 105                 110

Tyr Tyr Ile Thr Leu Leu Arg Asp Pro Val Ser Arg Tyr Leu Ser Glu
    115                 120                 125

Trp Arg His Val Gln Arg Gly Ala Thr Trp Lys Thr Ser Leu His Met
130                 135                 140

Cys Asp Gly Arg Thr Pro Thr Pro Glu Glu Leu Pro Ser Cys Tyr Glu
145                 150                 155                 160

Gly Thr Asp Trp Ser Gly Cys Thr Leu Gln Glu Phe Met Asp Cys Pro
                165                 170                 175

Tyr Asn Leu Ala Asn Asn Arg Gln Val Arg Met Leu Ala Asp Leu Ser
            180                 185                 190

Leu Val Gly Cys Tyr Asn Met Ser Phe Ile Pro Glu Asn Lys Arg Ala
        195                 200                 205

Gln Ile Leu Leu Glu Ser Ala Lys Lys Asn Leu Lys Asp Met Ala Phe
    210                 215                 220

Phe Gly Leu Thr Glu Phe Gln Arg Lys Thr Gln Tyr Leu Phe Glu Arg
225                 230                 235                 240

Thr Phe Asn Leu Lys Phe Ile Arg Pro Phe Met Gln Tyr Asn Ser Thr
                245                 250                 255

Arg Ala Gly Gly Val Glu Val Asp Asn Asp Thr Ile Arg Arg Ile Glu
            260                 265                 270

Glu Leu Asn Asp Leu Asp Met Gln Leu Tyr Asp Tyr Ala Lys Asp Leu
        275                 280                 285

Phe Gln Gln Arg Tyr Gln Tyr Lys Arg Gln Leu Glu Arg Met Glu Gln
    290                 295                 300

Arg Ile Lys Asn Arg Glu Glu
305                 310

<210> SEQ ID NO 196
<211> LENGTH: 309
<212> TYPE: PRT
<213> ORGANISM: Danio rerio

<400> SEQUENCE: 196

Lys Phe Tyr Phe Pro Ile Arg Asp Leu Glu Arg Thr Val Asp Phe Glu
1               5                   10                  15

Ile Lys Gly Asp Asp Val Ile Val Phe Leu His Ile Gln Lys Thr Gly
            20                  25                  30
```

```
Gly Thr Thr Phe Gly Arg His Leu Val Gln Asn Val Arg Leu Glu Val
            35                  40                  45

Pro Cys Asp Cys Arg Pro Gly Gln Lys Lys Cys Thr Cys Tyr Arg Pro
 50                  55                  60

Asn Arg Lys Glu Thr Trp Leu Phe Ser Arg Phe Ser Thr Gly Trp Ser
 65                  70                  75                  80

Cys Gly Leu His Ala Asp Trp Thr Glu Leu Thr Asn Cys Val Pro Gly
                85                  90                  95

Val Leu Asn Lys Lys Glu Ser Arg Met Lys Asn Gln Arg Lys Phe Tyr
                100                 105                 110

Tyr Ile Thr Leu Leu Arg Asp Pro Val Ser Arg Tyr Leu Ser Glu Trp
            115                 120                 125

Arg His Val Gln Arg Gly Ala Thr Trp Lys Thr Ser Leu His Met Cys
130                 135                 140

Asp Gly Arg Thr Pro Thr Pro Glu Glu Leu Pro Pro Cys Tyr Glu Gly
145                 150                 155                 160

Thr Asp Trp Ser Gly Cys Thr Leu Gln Gln Phe Met Asp Cys Pro Tyr
                165                 170                 175

Asn Leu Ala Asn Asn Arg Gln Val Arg Met Leu Ala Asp Leu Ser Leu
                180                 185                 190

Val Gly Cys Tyr Asn Met Ser Phe Ile Pro Glu Lys Lys Arg Ala Gln
            195                 200                 205

Val Leu Leu Glu Ser Ala Lys Lys Asn Leu Arg Asp Met Ala Phe Phe
            210                 215                 220

Gly Leu Thr Glu Phe Gln Arg Lys Thr Gln Tyr Leu Phe Glu Arg Thr
225                 230                 235                 240

Phe Arg Leu Lys Phe Ile Arg Pro Phe Met Gln Tyr Asn Ser Thr Arg
                245                 250                 255

Ala Ala Gly Val Asp Leu Asp Asn Asp Thr Ile Gln Arg Ile Glu Glu
                260                 265                 270

Leu Asn Asp Leu Asp Met Gln Leu Tyr Asp Tyr Ala Arg Asp Leu Phe
            275                 280                 285

Gln Gln Arg Tyr Met Tyr Lys Arg Gln Leu Glu Arg Arg Glu Gln Arg
            290                 295                 300

Leu Lys Asn Gln Pro
305

<210> SEQ ID NO 197
<211> LENGTH: 310
<212> TYPE: PRT
<213> ORGANISM: Homo Sapiens

<400> SEQUENCE: 197

Arg Tyr Asn Phe Thr Arg Gly Asp Leu Leu Arg Lys Val Asp Phe Asp
 1               5                  10                  15

Ile Lys Gly Asp Asp Leu Ile Val Phe Leu His Ile Gln Lys Thr Gly
            20                  25                  30

Gly Thr Thr Phe Gly Arg His Leu Val Arg Asn Ile Gln Leu Glu Gln
            35                  40                  45

Pro Cys Glu Cys Arg Val Gly Gln Lys Lys Cys Thr Cys His Arg Pro
 50                  55                  60

Gly Lys Arg Glu Thr Trp Leu Phe Ser Arg Phe Ser Thr Gly Trp Ser
 65                  70                  75                  80

Cys Gly Leu His Ala Asp Trp Thr Glu Leu Thr Ser Cys Val Pro Ser
```

85                  90                  95
Val Val Asp Gly Lys Arg Asp Ala Arg Leu Arg Pro Ser Arg Asn Phe
            100                 105                 110

His Tyr Ile Thr Ile Leu Arg Asp Pro Val Ser Arg Tyr Leu Ser Glu
            115                 120                 125

Trp Arg His Val Gln Arg Gly Ala Thr Trp Lys Ala Ser Leu His Val
            130                 135                 140

Cys Asp Gly Arg Pro Pro Thr Ser Glu Glu Leu Pro Ser Cys Tyr Thr
145                 150                 155                 160

Gly Asp Asp Trp Ser Gly Cys Pro Leu Lys Glu Phe Met Asp Cys Pro
                165                 170                 175

Tyr Asn Leu Ala Asn Asn Arg Gln Val Arg Met Leu Ser Asp Leu Thr
                180                 185                 190

Leu Val Gly Cys Tyr Asn Leu Ser Val Met Pro Glu Lys Gln Arg Asn
                195                 200                 205

Lys Val Leu Leu Glu Ser Ala Lys Ser Asn Leu Lys His Met Ala Phe
            210                 215                 220

Phe Gly Leu Thr Glu Phe Gln Arg Lys Thr Gln Tyr Leu Phe Glu Lys
225                 230                 235                 240

Thr Phe Asn Met Asn Phe Ile Ser Pro Phe Thr Gln Tyr Asn Thr Thr
                245                 250                 255

Arg Ala Ser Ser Val Glu Ile Asn Glu Glu Ile Gln Lys Arg Ile Glu
                260                 265                 270

Gly Leu Asn Phe Leu Asp Met Glu Leu Tyr Ser Tyr Ala Lys Asp Leu
                275                 280                 285

Phe Leu Gln Arg Tyr Gln Phe Met Arg Gln Lys Glu His Gln Glu Ala
            290                 295                 300

Arg Arg Lys Arg Gln Glu
305                 310

<210> SEQ ID NO 198
<211> LENGTH: 313
<212> TYPE: PRT
<213> ORGANISM: Danio rerio

<400> SEQUENCE: 198

Arg Phe Asn Phe Thr Thr Lys Asp Leu Ser Arg Ala Val Asp Phe His
1               5                   10                  15

Ile Lys Gly Asp Asp Val Ile Val Phe Leu His Ile Gln Lys Thr Gly
            20                  25                  30

Gly Thr Thr Phe Gly Arg His Leu Val Arg Asn Ile Gln Leu Glu Arg
        35                  40                  45

Pro Cys Glu Cys His Ala Gly Gln Lys Lys Cys Thr Cys Tyr Arg Pro
    50                  55                  60

Gly Lys Arg Asp Thr Trp Leu Phe Ser Arg Phe Ser Thr Gly Trp Ser
65                  70                  75                  80

Cys Gly Leu His Ala Asp Trp Thr Glu Leu Thr Asn Cys Val Pro Ser
                85                  90                  95

Phe Met Ser Asn Arg Glu Ser Gln Glu Arg Met Thr Pro Ser Arg
            100                 105                 110

Asn Tyr Tyr Tyr Ile Thr Ile Leu Arg Asp Pro Val Trp Arg Tyr Leu
            115                 120                 125

Ser Glu Trp Arg His Val Gln Arg Gly Ala Thr Trp Lys Ala Ser Lys
            130                 135                 140

-continued

```
His Met Cys Asp Gly Arg Leu Pro Thr Leu Thr Glu Leu Pro Ser Cys
145                 150                 155                 160

Tyr Pro Gly Asp Asp Trp Ser Gly Cys Ser Leu Glu Glu Phe Met Val
                165                 170                 175

Cys Pro Tyr Asn Leu Ala Asn Asn Arg Gln Thr Arg Met Leu Ala Asp
            180                 185                 190

Leu Ser Leu Val Gly Cys Tyr Asn Leu Thr Val Met Ser Glu Asn Gln
        195                 200                 205

Arg Trp Ala Met Leu Leu Glu Ser Ala Lys Arg Asn Leu Arg Asn Met
210                 215                 220

Ala Phe Phe Gly Leu Thr Glu Tyr Gln Arg Lys Thr Gln Tyr Leu Phe
225                 230                 235                 240

Glu His Thr Phe Arg Leu Ser Phe Ile Ala Pro Phe Thr Gln Leu Asn
                245                 250                 255

Gly Thr Arg Ala Ala Ser Val Glu Val Gly Pro Glu Thr Gln Arg Arg
            260                 265                 270

Ile Arg Glu Leu Asn Gln Trp Asp Val Glu Leu Tyr Tyr Ala Arg
        275                 280                 285

Asp Leu Phe Leu Gln Arg Phe Gln Phe Ala Arg Gln Gln Glu Arg Arg
290                 295                 300

Glu Ala Arg Gln Arg Arg Ile Gln Glu
305                 310
```

<210> SEQ ID NO 199
<211> LENGTH: 310
<212> TYPE: PRT
<213> ORGANISM: Mus musculus

<400> SEQUENCE: 199

```
Arg Tyr Asn Phe Ser Arg Gly Asp Leu Leu Arg Lys Val Asp Phe Asp
1               5                   10                  15

Ile Lys Gly Asp Asp Leu Ile Val Phe Leu His Ile Gln Lys Thr Gly
                20                  25                  30

Gly Thr Thr Phe Gly Arg His Leu Val Arg Asn Ile Gln Leu Glu Gln
            35                  40                  45

Pro Cys Glu Cys Arg Val Gly Gln Lys Lys Cys Thr Cys His Arg Pro
        50                  55                  60

Gly Lys Arg Glu Thr Trp Leu Phe Ser Arg Phe Ser Thr Gly Trp Ser
65                  70                  75                  80

Cys Gly Leu His Ala Asp Trp Thr Glu Leu Thr Ser Cys Val Pro Ala
                85                  90                  95

Val Val Asp Gly Lys Arg Asp Ala Arg Leu Arg Pro Ser Arg Asn Phe
            100                 105                 110

His Tyr Ile Thr Ile Leu Arg Asp Pro Val Ser Arg Tyr Leu Ser Glu
        115                 120                 125

Trp Arg His Val Gln Arg Gly Ala Thr Trp Lys Ala Ser Leu His Val
130                 135                 140

Cys Asp Gly Arg Pro Pro Thr Ser Glu Glu Leu Pro Ser Cys Tyr Thr
145                 150                 155                 160

Gly Asp Asp Trp Ser Gly Cys Pro Leu Lys Glu Phe Met Asp Cys Pro
                165                 170                 175

Tyr Asn Leu Ala Asn Asn Arg Gln Val Arg Met Leu Ser Asp Leu Thr
            180                 185                 190

Leu Val Gly Cys Tyr Asn Leu Ser Val Met Pro Glu Lys Gln Arg Asn
        195                 200                 205
```

-continued

Lys Val Leu Leu Glu Ser Ala Lys Ser Asn Leu Lys His Met Ala Phe
210                 215                 220

Phe Gly Leu Thr Glu Phe Gln Arg Lys Thr Gln Tyr Leu Phe Glu Lys
225                 230                 235                 240

Thr Phe Asn Met Asn Phe Ile Ser Pro Phe Thr Gln Tyr Asn Thr Thr
                245                 250                 255

Arg Ala Ser Ser Val Glu Ile Asn Glu Glu Ile Gln Lys Arg Ile Glu
            260                 265                 270

Gly Leu Asn Phe Leu Asp Met Glu Leu Tyr Ser Tyr Ala Lys Asp Leu
        275                 280                 285

Phe Leu Gln Arg Tyr Gln Phe Met Arg Gln Lys Glu His Gln Asp Ala
290                 295                 300

Arg Arg Lys Arg Gln Glu
305                 310

<210> SEQ ID NO 200
<211> LENGTH: 310
<212> TYPE: PRT
<213> ORGANISM: Gallus gallus

<400> SEQUENCE: 200

Arg Phe Asn Phe Ser Ala Gly Asp Leu Leu Arg Arg Val Asp Phe Asn
1               5                   10                  15

Ile Lys Gly Asp Asp Leu Ile Val Phe Leu His Ile Gln Lys Thr Gly
            20                  25                  30

Gly Thr Thr Phe Gly Arg His Leu Val Arg Asn Ile Gln Leu Glu Gln
        35                  40                  45

Pro Cys Glu Cys Arg Ala Gly Gln Lys Lys Cys Thr Cys His Arg Pro
    50                  55                  60

Gly Lys Arg Glu Thr Trp Leu Phe Ser Arg Phe Ser Thr Gly Trp Ser
65                  70                  75                  80

Cys Gly Leu His Ala Asp Trp Thr Glu Leu Thr Asn Cys Val Pro Ser
                85                  90                  95

Val Val Asp Ser Lys Lys Glu Val Arg Leu Arg Pro Ser Arg Asn Phe
            100                 105                 110

Tyr Tyr Ile Thr Ile Leu Arg Asp Pro Val Ser Arg Tyr Leu Ser Glu
        115                 120                 125

Trp Arg His Val Gln Arg Gly Ala Thr Trp Lys Ala Ser Leu His Val
130                 135                 140

Cys Asp Gly Arg Ser Pro Thr Thr Glu Glu Leu Pro Ser Cys Tyr Thr
145                 150                 155                 160

Gly Asp Asp Trp Ser Gly Cys Ser Leu Gln Glu Phe Met Asp Cys Pro
                165                 170                 175

Tyr Asn Leu Ala Asn Asn Arg Gln Val Arg Met Leu Ser Asp Leu Ser
            180                 185                 190

Leu Val Gly Cys Tyr Asn Leu Ser Val Met Pro Glu Glu Gln Arg Asn
        195                 200                 205

Lys Val Leu Leu Asp Ser Ala Lys Glu Asn Leu Lys Arg Met Ala Phe
210                 215                 220

Phe Gly Leu Thr Glu Phe Gln Arg Lys Thr Gln Tyr Leu Phe Glu Lys
225                 230                 235                 240

Thr Phe Asn Met Asn Phe Ile Ser Pro Phe Thr Gln Tyr Asn Ser Thr
                245                 250                 255

Arg Ala Ser Ser Val Glu Ile Asp Glu Gln Thr Gln Gln Arg Ile Glu

```
                    260                 265                 270
Ala Leu Asn Phe Leu Asp Met Glu Leu Tyr Asp Tyr Ala Lys Asp Leu
                275                 280                 285

Phe Leu Gln Arg Tyr Gln Tyr Met Arg Gln Lys Glu His Gln Glu Ala
            290                 295                 300

Arg Arg Lys Arg Gln Glu
305                 310

<210> SEQ ID NO 201
<211> LENGTH: 312
<212> TYPE: PRT
<213> ORGANISM: Mus musculus

<400> SEQUENCE: 201

Arg Phe Asn Phe Thr Leu Lys Asp Leu Thr Arg Phe Val Asp Phe Asn
1               5                   10                  15

Ile Lys Gly Arg Asp Val Ile Val Phe Leu His Ile Gln Lys Thr Gly
            20                  25                  30

Gly Thr Thr Phe Gly Arg His Leu Val Lys Asn Ile Arg Leu Glu Gln
        35                  40                  45

Pro Cys Ser Cys Lys Ala Gly Gln Lys Lys Cys Thr Cys His Arg Pro
    50                  55                  60

Gly Lys Lys Glu Thr Trp Leu Phe Ser Arg Phe Ser Thr Gly Trp Ser
65                  70                  75                  80

Cys Gly Leu His Ala Asp Trp Thr Glu Leu Thr Asn Cys Val Pro Ala
                85                  90                  95

Ile Met Glu Lys Lys Asp Cys Pro Arg Asn His Ser His Thr Arg Asn
            100                 105                 110

Phe Tyr Tyr Ile Thr Met Leu Arg Asp Pro Val Ser Arg Tyr Leu Ser
        115                 120                 125

Glu Trp Lys His Val Gln Arg Gly Ala Thr Trp Lys Thr Ser Leu His
    130                 135                 140

Met Cys Asp Gly Arg Ser Pro Thr Pro Asp Glu Leu Pro Thr Cys Tyr
145                 150                 155                 160

Pro Gly Asp Asp Trp Ser Gly Val Ser Leu Arg Glu Phe Met Asp Cys
                165                 170                 175

Ser Tyr Asn Leu Ala Asn Asn Arg Gln Val Arg Met Leu Ala Asp Leu
            180                 185                 190

Ser Leu Val Gly Cys Tyr Asn Leu Thr Phe Met Asn Glu Ser Glu Arg
        195                 200                 205

Asn Thr Ile Leu Leu Gln Ser Ala Lys Asn Asn Leu Lys Asn Met Ala
    210                 215                 220

Phe Phe Gly Leu Thr Glu Phe Gln Arg Lys Thr Gln Phe Leu Phe Glu
225                 230                 235                 240

Arg Thr Phe Asn Leu Lys Phe Ile Ser Pro Phe Thr Gln Phe Asn Ile
                245                 250                 255

Thr Arg Ala Ser Asn Val Asp Ile Asn Asp Gly Ala Arg Gln His Ile
            260                 265                 270

Glu Glu Leu Asn Phe Leu Asp Met Gln Leu Tyr Glu Tyr Ala Lys Asp
        275                 280                 285

Leu Phe Gln Gln Arg Tyr His His Thr Lys Gln Leu Glu His Gln Arg
    290                 295                 300

Asp Arg Gln Lys Arg Arg Glu Glu
305                 310
```

```
<210> SEQ ID NO 202
<211> LENGTH: 312
<212> TYPE: PRT
<213> ORGANISM: Homo sapiens

<400> SEQUENCE: 202

Arg Phe Asn Phe Ser Leu Lys Asp Leu Thr Arg Phe Val Asp Phe Asn
1               5                   10                  15

Ile Lys Gly Arg Asp Val Ile Val Phe Leu His Ile Gln Lys Thr Gly
            20                  25                  30

Gly Thr Thr Phe Gly Arg His Leu Val Lys Asn Ile Arg Leu Glu Gln
        35                  40                  45

Pro Cys Ser Cys Lys Ala Gly Gln Lys Lys Cys Thr Cys His Arg Pro
    50                  55                  60

Gly Lys Lys Glu Thr Trp Leu Phe Ser Arg Phe Ser Thr Gly Trp Ser
65                  70                  75                  80

Cys Gly Leu His Ala Asp Trp Thr Glu Leu Thr Asn Cys Val Pro Ala
                85                  90                  95

Ile Met Glu Lys Lys Asp Cys Pro Arg Asn His Ser His Thr Arg Asn
            100                 105                 110

Phe Tyr Tyr Ile Thr Met Leu Arg Asp Pro Val Ser Arg Tyr Leu Ser
        115                 120                 125

Glu Trp Lys His Val Gln Arg Gly Ala Thr Trp Lys Thr Ser Leu His
    130                 135                 140

Met Cys Asp Gly Arg Ser Pro Thr Pro Asp Glu Leu Pro Thr Cys Tyr
145                 150                 155                 160

Pro Gly Asp Asp Trp Ser Gly Val Ser Leu Arg Glu Phe Met Asp Cys
                165                 170                 175

Thr Tyr Asn Leu Ala Asn Asn Arg Gln Val Arg Met Leu Ala Asp Leu
            180                 185                 190

Ser Leu Val Gly Cys Tyr Asn Leu Thr Phe Met Asn Glu Ser Glu Arg
        195                 200                 205

Asn Thr Ile Leu Leu Gln Ser Ala Lys Asn Asn Leu Lys Asn Met Ala
    210                 215                 220

Phe Phe Gly Leu Thr Glu Phe Gln Arg Lys Thr Gln Phe Leu Phe Glu
225                 230                 235                 240

Arg Thr Phe Asn Leu Lys Phe Ile Ser Pro Phe Thr Gln Phe Asn Ile
                245                 250                 255

Thr Arg Ala Ser Asn Val Glu Ile Asn Glu Gly Ala Arg Gln Arg Ile
            260                 265                 270

Glu Asp Leu Asn Phe Leu Asp Met Gln Leu Tyr Glu Tyr Ala Lys Asp
        275                 280                 285

Leu Phe Gln Gln Arg Tyr His His Thr Lys Gln Leu Glu His Gln Arg
    290                 295                 300

Asp Arg Gln Lys Arg Arg Glu Glu
305                 310

<210> SEQ ID NO 203
<211> LENGTH: 312
<212> TYPE: PRT
<213> ORGANISM: Bos taurus

<400> SEQUENCE: 203

Arg Phe Asn Phe Thr Pro Lys Asp Leu Thr Arg Phe Val Asp Phe Asn
1               5                   10                  15
```

-continued

Ile Lys Gly Arg Asp Val Ile Val Phe Leu His Ile Gln Lys Thr Gly
              20                  25                  30

Gly Thr Thr Phe Gly Arg His Leu Val Lys Asn Ile Arg Leu Glu Gln
          35                  40                  45

Pro Cys Ser Cys Lys Ala Gly Gln Lys Cys Thr Cys His Arg Pro
    50                  55                  60

Gly Lys Lys Glu Thr Trp Leu Phe Ser Arg Phe Ser Thr Gly Trp Ser
65                  70                  75                  80

Cys Gly Leu His Ala Asp Trp Thr Glu Leu Thr Asn Cys Val Pro Ala
              85                  90                  95

Ile Met Glu Lys Lys Asp Cys Pro Arg Asn His Ser Thr Arg Asn
          100                 105                 110

Phe Tyr Tyr Ile Thr Met Leu Arg Asp Pro Val Ser Arg Tyr Leu Ser
              115                 120                 125

Glu Trp Lys His Val Gln Arg Gly Ala Thr Trp Lys Thr Ser Leu His
130                 135                 140

Met Cys Asp Gly Arg Ser Pro Thr Pro Asp Glu Leu Pro Thr Cys Tyr
145                 150                 155                 160

Pro Gly Asp Asp Trp Ser Gly Val Ser Leu Arg Glu Phe Met Asp Cys
              165                 170                 175

Thr Tyr Asn Leu Ala Asn Asn Arg Gln Val Arg Met Leu Ala Asp Leu
          180                 185                 190

Ser Leu Val Gly Cys Tyr Asn Leu Thr Phe Met Asn Glu Ser Glu Arg
      195                 200                 205

Asn Ala Ile Leu Leu Gln Ser Ala Lys Ser Asn Leu Lys Asn Met Ala
    210                 215                 220

Phe Phe Gly Leu Thr Glu Phe Gln Arg Lys Thr Gln Phe Leu Phe Glu
225                 230                 235                 240

Arg Thr Phe Asn Leu Lys Phe Ile Ser Pro Phe Thr Gln Phe Asn Ile
              245                 250                 255

Thr Arg Ala Ser Asn Val Glu Ile Asn Glu Gly Ala Arg Arg Ile
          260                 265                 270

Glu Glu Leu Asn Phe Leu Asp Val Gln Leu Tyr Glu Tyr Ala Lys Asp
      275                 280                 285

Leu Phe Gln Gln Arg Tyr His Arg Thr Lys Gln Leu Glu Arg Gln Arg
    290                 295                 300

Asp Arg Gln Arg Arg Gly Glu
305                 310

<210> SEQ ID NO 204
<211> LENGTH: 309
<212> TYPE: PRT
<213> ORGANISM: Danio rerio

<400> SEQUENCE: 204

Lys Phe Asn Phe Thr Glu Arg Asp Leu Thr Arg Asp Val Asp Phe Asn
1               5                   10                  15

Ile Lys Gly Asp Asp Val Ile Val Phe Leu His Ile Gln Lys Thr Gly
              20                  25                  30

Gly Thr Thr Phe Gly Arg His Leu Val Arg Asn Ile Arg Leu Glu Gln
          35                  40                  45

Pro Cys Asp Cys Lys Ala Gly Gln Lys Lys Cys Thr Cys His Arg Pro
    50                  55                  60

Gly Lys Gln Glu Ser Trp Leu Phe Ser Arg Phe Ser Thr Gly Trp Ser
65                  70                  75                  80

Cys Gly Leu His Ala Asp Trp Thr Glu Leu Thr Asn Cys Val Pro Val
                85                  90                  95

Ile Met Asp Lys Arg Gln Pro Lys Arg Lys Arg Asn Phe Tyr Tyr
            100                 105                 110

Ile Thr Met Leu Arg Asp Pro Val Ser Arg Tyr Leu Ser Glu Trp Lys
            115                 120                 125

His Val Gln Arg Gly Ala Thr Trp Lys Thr Ser Leu His Met Cys Asp
        130                 135                 140

Gly Arg Ser Pro Thr Gln Asp Glu Leu Pro Thr Cys Tyr Asn Gly Asp
145                 150                 155                 160

Asp Trp Ser Gly Val Thr Leu His Asp Phe Met Asp Cys Pro Ser Asn
                165                 170                 175

Leu Ala Asn Asn Arg Gln Val Arg Met Leu Ala Asp Leu Ser Leu Val
            180                 185                 190

Gly Cys Tyr Asn Leu Ser Thr Met Asn Glu Ser Glu Arg Asn Pro Ile
        195                 200                 205

Leu Leu Ala Ser Ala Lys Ser Asn Leu Lys Asn Met Ala Phe Tyr Gly
210                 215                 220

Leu Thr Glu Phe Gln Arg Lys Thr Gln Tyr Leu Phe Glu Arg Thr Phe
225                 230                 235                 240

His Leu Arg Phe Ile Ser Ala Phe Thr Gln Ile Asn Ser Thr Arg Ala
                245                 250                 255

Ala Asn Val Glu Leu Arg Asp Asp Met Arg Ser Arg Ile Glu Gln Leu
            260                 265                 270

Asn Met Leu Asp Met Gln Leu Tyr Glu Phe Ala Lys Asp Leu Phe Leu
        275                 280                 285

Gln Arg Tyr Gln Phe Val Arg Gln Arg Glu Arg Gln Glu Glu Arg Leu
290                 295                 300

Lys Arg Arg Glu Glu
305

<210> SEQ ID NO 205
<211> LENGTH: 313
<212> TYPE: PRT
<213> ORGANISM: Cynoglossus semilaevis

<400> SEQUENCE: 205

Arg Leu Asn Phe Ser Glu Arg Asp Met Asp Arg Arg Val Gln Phe Asn
1               5                   10                  15

Ile Arg Gly Asp Asp Val Met Val Phe Leu His Ile Gln Lys Thr Gly
            20                  25                  30

Gly Thr Thr Phe Gly Arg His Leu Val Lys Asn Ile His Leu Glu Arg
        35                  40                  45

Pro Cys Asn Cys Thr Ala Gly Gln Arg Lys Cys Thr Cys His Arg Pro
    50                  55                  60

Gly Lys Ala Glu Ser Trp Leu Phe Ser Arg Phe Ser Thr Gly Trp Ser
65                  70                  75                  80

Cys Gly Leu His Ala Asp Trp Thr Glu Leu Ser Ser Cys Val Pro Val
                85                  90                  95

Val Met Ser Gln Arg Asp Arg Lys Lys Val Gln Lys Lys Lys Arg
            100                 105                 110

Ser Phe Tyr Tyr Ile Thr Met Leu Arg Asp Pro Val Ser Arg Tyr Leu
        115                 120                 125

Ser Glu Trp Lys His Val Gln Arg Gly Ala Thr Trp Lys Thr Ala Leu

```
            130                 135                 140
His Met Cys Asp Gly Arg Pro Pro Thr Gln Asp Glu Leu Pro Ala Cys
145                 150                 155                 160

Tyr Asn Gly Glu Asp Trp Thr Gly Val Pro Leu Ala Asp Phe Met Asn
                165                 170                 175

Cys Pro Ser Asn Leu Ala Asn Asn Arg Gln Val Arg Met Leu Ala Asp
                180                 185                 190

Leu Ser Leu Val Gly Cys Tyr Asn Met Ser Ser Met Ser Glu Leu Glu
            195                 200                 205

Arg Gly Arg Val Leu Leu Ala Ser Ala Lys Ala Asn Leu Arg Asn Met
210                 215                 220

Ala Phe Tyr Gly Leu Thr Glu Phe Gln Arg Lys Thr Gln Tyr Leu Phe
225                 230                 235                 240

Glu Arg Thr Phe Gly Leu Arg Phe Ile Lys Ala Phe Thr Gln Ile Asn
                245                 250                 255

Ser Thr Arg Ala Ala Ser Val Gly Ile Ser Glu Lys Val Arg Trp Arg
                260                 265                 270

Ile Glu Gly Leu Asn Ala Leu Asp Met Glu Leu Tyr Glu Tyr Ala Lys
            275                 280                 285

Asn Leu Phe Leu Leu Arg Tyr Gln Tyr Ser Arg Gln Arg Gln His Gln
290                 295                 300

Glu Glu Arg Leu Arg Arg Arg Gln Glu
305                 310

<210> SEQ ID NO 206
<211> LENGTH: 307
<212> TYPE: PRT
<213> ORGANISM: Homo sapiens

<400> SEQUENCE: 206

Met Ala Ala Leu Leu Leu Gly Ala Val Leu Leu Val Ala Gln Pro Gln
1               5                   10                  15

Leu Val Pro Ser Arg Pro Ala Glu Leu Gly Gln Gln Glu Leu Leu Arg
                20                  25                  30

Lys Ala Gly Thr Leu Gln Asp Asp Val Arg Asp Gly Val Ala Pro Asn
            35                  40                  45

Gly Ser Ala Gln Gln Leu Pro Gln Thr Ile Ile Gly Val Arg Lys
50                  55                  60

Gly Gly Thr Arg Ala Leu Leu Glu Met Leu Ser Leu His Pro Asp Val
65                  70                  75                  80

Ala Ala Ala Glu Asn Glu Val His Phe Phe Asp Trp Glu Glu His Tyr
                85                  90                  95

Ser His Gly Leu Gly Trp Tyr Leu Ser Gln Met Pro Phe Ser Trp Pro
            100                 105                 110

His Gln Leu Thr Val Glu Lys Thr Pro Ala Tyr Phe Thr Ser Pro Lys
        115                 120                 125

Val Pro Glu Arg Val Tyr Ser Met Asn Pro Ser Ile Arg Leu Leu Leu
    130                 135                 140

Ile Leu Arg Asp Pro Ser Glu Arg Val Leu Ser Asp Tyr Thr Gln Val
145                 150                 155                 160

Phe Tyr Asn His Met Gln Lys His Lys Pro Tyr Pro Ser Ile Glu Glu
                165                 170                 175

Phe Leu Val Arg Asp Gly Arg Leu Asn Val Asp Tyr Lys Ala Leu Asn
            180                 185                 190
```

Arg Ser Leu Tyr His Val His Met Gln Asn Trp Leu Arg Phe Phe Pro
            195                 200                 205

Leu Arg His Ile His Ile Val Asp Gly Asp Arg Leu Ile Arg Asp Pro
    210                 215                 220

Phe Pro Glu Ile Gln Lys Val Glu Arg Phe Leu Lys Leu Ser Pro Gln
225                 230                 235                 240

Ile Asn Ala Ser Asn Phe Tyr Phe Asn Lys Thr Lys Gly Phe Tyr Cys
                245                 250                 255

Leu Arg Asp Ser Gly Arg Asp Arg Cys Leu His Glu Ser Lys Gly Arg
            260                 265                 270

Ala His Pro Gln Val Asp Pro Lys Leu Leu Asn Lys Leu His Glu Tyr
        275                 280                 285

Phe His Glu Pro Asn Lys Lys Phe Phe Glu Leu Val Gly Arg Thr Phe
    290                 295                 300

Asp Trp His
305

<210> SEQ ID NO 207
<211> LENGTH: 307
<212> TYPE: PRT
<213> ORGANISM: Macaca mulatta

<400> SEQUENCE: 207

Met Ala Ala Leu Leu Gly Ala Val Leu Val Ala Gln Pro Gln
1               5                   10                  15

Leu Val Pro Ser Arg Pro Ala Glu Leu Gly Gln Gln Glu Leu Leu Arg
            20                  25                  30

Lys Ala Gly Thr Leu Gln Asp Val Arg Tyr Gly Ala Ala Asn
        35                  40                  45

Gly Ser Ala Gln Gln Leu Pro Gln Thr Ile Ile Gly Val Arg Lys
    50                  55                  60

Gly Gly Thr Arg Ala Leu Leu Glu Met Leu Ser Leu His Pro Asp Val
65                  70                  75                  80

Ala Ala Ala Glu Asn Glu Val His Phe Phe Asp Trp Glu Glu His Tyr
                85                  90                  95

Gly His Gly Leu Gly Trp Tyr Leu Ser Gln Met Pro Phe Ser Trp Pro
            100                 105                 110

His Gln Leu Thr Val Glu Lys Thr Pro Ala Tyr Phe Thr Ser Pro Lys
        115                 120                 125

Val Pro Glu Arg Val His Ser Met Asn Pro Ser Ile Arg Leu Leu Leu
    130                 135                 140

Ile Leu Arg Asp Pro Ser Glu Arg Val Leu Ser Asp Tyr Thr Gln Val
145                 150                 155                 160

Phe Tyr Asn His Met Gln Lys Arg Lys Pro Tyr Pro Ser Ile Glu Glu
                165                 170                 175

Phe Leu Val Arg Asp Gly Arg Leu Asn Val Asp Tyr Lys Ala Leu Asn
            180                 185                 190

Arg Ser Leu Tyr His Val His Met Gln Asn Trp Leu Arg Phe Phe Pro
        195                 200                 205

Leu Arg His Ile His Ile Val Asp Gly Asp Arg Leu Ile Arg Asp Pro
    210                 215                 220

Phe Pro Glu Ile Gln Lys Val Glu Arg Phe Leu Lys Leu Ser Pro Gln
225                 230                 235                 240

Ile Asn Ala Ser Asn Phe Tyr Phe Asn Lys Thr Lys Gly Phe Tyr Cys
                245                 250                 255

```
Leu Arg Asp Ser Gly Arg Asp Arg Cys Leu His Glu Ser Lys Gly Arg
            260                 265                 270

Ala His Pro Gln Val Asp Pro Lys Leu Leu Asn Lys Leu His Glu Tyr
            275                 280                 285

Phe His Glu Pro Asn Lys Lys Phe Phe Glu Leu Val Gly Arg Thr Phe
            290                 295                 300

Asp Trp His
305

<210> SEQ ID NO 208
<211> LENGTH: 261
<212> TYPE: PRT
<213> ORGANISM: Ailuropoda melanoleuca

<400> SEQUENCE: 208

Pro Asn Gly Ser Ala Gln Gln Leu Pro Gln Thr Ile Ile Ile Gly Val
1               5                   10                  15

Arg Lys Gly Gly Thr Arg Ala Leu Leu Glu Met Leu Ser Leu His Pro
            20                  25                  30

Asp Val Ala Ala Ala Glu Asn Glu Val His Phe Phe Asp Trp Glu Glu
        35                  40                  45

His Tyr Ser Gln Gly Leu Gly Trp Tyr Leu Gly Gln Met Pro Phe Ser
    50                  55                  60

Ser Pro His Gln Leu Thr Val Glu Lys Thr Pro Ala Tyr Phe Thr Ser
65                  70                  75                  80

Ser Lys Val Pro Glu Arg Val His Ser Met Asn Pro Gly Ile Arg Leu
                85                  90                  95

Leu Leu Ile Leu Arg Asp Pro Ser Glu Arg Val Leu Ser Asp Tyr Thr
            100                 105                 110

Gln Val Phe Tyr Asn His Val Gln Lys Arg Pro Tyr Pro Ser Ile
        115                 120                 125

Glu Glu Phe Leu Val Arg Asp Gly Arg Leu Asn Val Gly Tyr Lys Ala
    130                 135                 140

Leu Asn Arg Ser Leu Tyr His Val His Leu Gln Asn Trp Leu Arg Phe
145                 150                 155                 160

Phe Pro Leu Arg Arg Ile His Ile Val Asp Gly Asp Arg Leu Ile Arg
                165                 170                 175

Asp Pro Phe Pro Glu Ile Gln Lys Val Glu Arg Phe Leu Lys Leu Ser
            180                 185                 190

Pro Gln Ile Asn Ala Ser Asn Phe Tyr Phe Asn Lys Thr Lys Gly Phe
        195                 200                 205

Tyr Cys Leu Arg Asp Gly Gly Arg Asp Arg Cys Leu His Glu Ser Lys
    210                 215                 220

Gly Arg Ala His Pro Gln Val Asp Pro Arg Leu Leu Asn Lys Leu His
225                 230                 235                 240

Glu Tyr Phe His Glu Pro Asn Lys Lys Phe Phe Glu Leu Val Gly Arg
                245                 250                 255

Thr Phe Asp Trp His
            260

<210> SEQ ID NO 209
<211> LENGTH: 311
<212> TYPE: PRT
<213> ORGANISM: Equus caballus

<400> SEQUENCE: 209
```

Met Ala Ala Leu Leu Leu Gly Ala Val Leu Val Ala Gln Leu Gln
1               5                   10                  15

Leu Met Pro Cys Arg Pro Ala Ala Gly Ala Glu Pro Gly Gln Gln
            20                  25                  30

Glu Leu Val Gly Lys Ala Ala Thr Leu Gln Asn Glu Val Arg Ala Gly
            35                  40                  45

Ala Ala Pro Asn Gly Ser Ala Gln Gln Leu Pro Gln Thr Ile Ile Ile
50                      55                  60

Gly Val Arg Lys Gly Gly Thr Arg Ala Leu Leu Glu Met Leu Ser Leu
65                  70                  75                  80

His Pro Asp Val Ala Ala Glu Asn Glu Val His Phe Phe Asp Trp
                85                  90                  95

Glu Glu His Phe Ser Gln Gly Leu Gly Trp Tyr Leu Ser Gln Met Pro
                100                 105                 110

Phe Ser Ala Pro His Gln Leu Thr Val Glu Lys Thr Pro Ala Tyr Phe
            115                 120                 125

Thr Ser Pro Lys Val Pro Glu Arg Val His Ser Met Asn Pro Ser Ile
            130                 135                 140

Arg Leu Leu Leu Ile Leu Arg Asp Pro Ser Glu Arg Val Leu Ser Asp
145                 150                 155                 160

Tyr Thr Gln Val Phe Tyr Asn His Val Gln Lys His Lys Pro Tyr Pro
                165                 170                 175

Ser Ile Glu Glu Phe Leu Val Arg Asp Gly Arg Leu Asn Val Asp Tyr
                180                 185                 190

Lys Ala Leu Asn Arg Ser Leu Tyr His Val His Met Gln Asn Trp Leu
            195                 200                 205

Arg Phe Phe Pro Leu Arg His Ile His Ile Val Asp Gly Asp Arg Leu
210                 215                 220

Ile Arg Asp Pro Phe Pro Glu Ile Gln Lys Val Glu Arg Phe Leu Lys
225                 230                 235                 240

Leu Ala Pro Gln Ile Asn Ala Ser Asn Phe Tyr Phe Asn Lys Thr Lys
            245                 250                 255

Gly Phe Tyr Cys Leu Arg Asp Ser Gly Arg Asp Arg Cys Leu His Glu
            260                 265                 270

Ser Lys Gly Arg Ala His Pro Gln Val Asp Pro Lys Leu Leu Asn Lys
275                 280                 285

Leu His Glu Tyr Phe His Glu Pro Asn Lys Lys Phe Phe Glu Leu Val
            290                 295                 300

Gly Arg Thr Phe Asp Trp His
305                 310

<210> SEQ ID NO 210
<211> LENGTH: 311
<212> TYPE: PRT
<213> ORGANISM: Sus scrofa

<400> SEQUENCE: 210

Met Ala Ala Leu Leu Leu Gly Ala Val Met Leu Val Leu Gln Leu Gln
1               5                   10                  15

Leu Val Pro Cys Arg Pro Ala Met Pro Gly Ala Gly Pro Ser Gln Gln
            20                  25                  30

Glu Leu Val Arg Lys Ala Ala Thr Leu Gln Asp Glu Val Arg Asp Ser
            35                  40                  45

Ala Ala Pro Asn Gly Ser Val Gln Gln Leu Pro Gln Thr Ile Ile Ile

```
                    50                  55                  60

Gly Val Arg Lys Gly Gly Thr Arg Ala Leu Leu Glu Met Leu Ser Leu
 65                  70                  75                  80

His Pro Asp Val Ala Ala Ala Glu Asn Glu Val His Phe Phe Asp Trp
                     85                  90                  95

Glu Glu His Tyr Ser Gln Gly Leu Asp Trp Tyr Leu Ser Gln Met Pro
                100                 105                 110

Phe Ser Tyr Pro His Gln Leu Thr Val Glu Lys Thr Pro Ala Tyr Phe
            115                 120                 125

Thr Ser Pro Lys Val Pro Glu Arg Val His Arg Met Asn Pro Ser Ile
        130                 135                 140

Arg Leu Leu Leu Ile Leu Arg Asp Pro Ser Glu Arg Val Leu Ser Asp
145                 150                 155                 160

Tyr Thr Gln Val Phe Tyr Asn His Val Gln Lys His Lys Pro Tyr Pro
                165                 170                 175

Ser Ile Glu Glu Phe Leu Val Arg Asp Gly Arg Leu Asn Val Asp Tyr
            180                 185                 190

Lys Ala Leu Asn Arg Ser Leu Tyr His Val His Met Gln Asn Trp Leu
        195                 200                 205

Arg Phe Phe Pro Leu Arg Arg Ile His Ile Val Asp Gly Asp Arg Leu
210                 215                 220

Ile Arg Asp Pro Phe Pro Glu Ile Gln Lys Val Glu Arg Phe Leu Met
225                 230                 235                 240

Leu Ser Pro Gln Ile Asn Ala Ser Asn Phe Tyr Phe Asn Lys Thr Lys
                245                 250                 255

Gly Phe Tyr Cys Leu Arg Asp Gly Gly Arg Asp Arg Cys Leu His Glu
            260                 265                 270

Ser Lys Gly Arg Ala His Pro Gln Ile Asp Pro Lys Leu Leu Asn Lys
        275                 280                 285

Leu His Glu Tyr Phe His Glu Pro Asn Lys Lys Phe Phe Glu Leu Val
290                 295                 300

Gly Arg Thr Phe Asp Trp His
305                 310

<210> SEQ ID NO 211
<211> LENGTH: 312
<212> TYPE: PRT
<213> ORGANISM: Bos taurus

<400> SEQUENCE: 211

Met Ala Pro Leu Leu Leu Gly Ala Val Met Leu Val Ala Gln Leu Gln
  1               5                  10                  15

Leu Val Pro Ser Arg Pro Ala Val Pro Gly Asp Glu Pro Gly Leu
                 20                  25                  30

Pro Glu Leu Val Arg Lys Ala Ala Leu Gln Glu Glu Ile Ser Asp
             35                  40                  45

Gly Ala Ala Pro Asn Gly Ser Ala Gln Gln Leu Pro Gln Thr Ile Ile
         50                  55                  60

Ile Gly Val Arg Lys Gly Gly Thr Arg Ala Leu Leu Glu Met Leu Ser
 65                  70                  75                  80

Leu His Pro Asp Val Ala Ala Ala Glu Asn Glu Val His Phe Phe Asp
                     85                  90                  95

Trp Glu Glu His Tyr Ser Gln Gly Leu Gly Trp Tyr Leu Ser Gln Met
                100                 105                 110
```

```
Pro Phe Ser Ala Pro His Gln Leu Thr Val Glu Lys Thr Pro Ala Tyr
            115                 120                 125

Phe Thr Ser Pro Lys Val Pro Glu Arg Val His Gly Met Asn Pro Ala
130                 135                 140

Ile Arg Leu Leu Leu Ile Leu Arg Asp Pro Ser Glu Arg Val Leu Ser
145                 150                 155                 160

Asp Tyr Thr Gln Val Phe Tyr Asn His Val Gln Lys Arg Lys Pro Tyr
                165                 170                 175

Pro Ser Ile Glu Glu Phe Leu Val Arg Asp Gly Arg Leu Asn Val Asp
            180                 185                 190

Tyr Lys Ala Leu Asn Arg Ser Leu Tyr His Leu His Met Gln Asn Trp
        195                 200                 205

Leu Arg Phe Phe Pro Leu Arg Arg Ile His Ile Val Asp Gly Asp Arg
    210                 215                 220

Leu Ile Arg Asp Pro Phe Pro Glu Ile Gln Lys Val Glu Arg Phe Leu
225                 230                 235                 240

Arg Leu Ser Pro Gln Ile Asn Ala Ser Asn Phe Tyr Phe Asn Lys Thr
                245                 250                 255

Lys Gly Phe Tyr Cys Leu Arg Asp Ser Gly Arg Asp Arg Cys Leu His
            260                 265                 270

Glu Ser Lys Gly Arg Ala His Pro Gln Val Asp Pro Arg Leu Leu Asn
        275                 280                 285

Lys Leu His Glu Tyr Phe His Glu Pro Asn Lys Lys Phe Phe Glu Leu
    290                 295                 300

Val Gly Arg Thr Phe Asp Trp His
305                 310

<210> SEQ ID NO 212
<211> LENGTH: 311
<212> TYPE: PRT
<213> ORGANISM: Rattus norvegicus

<400> SEQUENCE: 212

Met Thr Leu Leu Leu Gly Ala Val Leu Val Ala Gln Pro Gln
1               5                   10                  15

Leu Val Pro Ser His Pro Ala Ala Pro Gly Pro Gly Leu Lys Gln Gln
                20                  25                  30

Gly Leu Leu Arg Lys Val Ile Ile Leu Pro Glu Asp Thr Gly Glu Gly
            35                  40                  45

Ala Ala Thr Asn Gly Ser Thr Gln Gln Leu Pro Gln Thr Ile Ile Ile
        50                  55                  60

Gly Val Arg Lys Gly Gly Thr Arg Ala Leu Leu Glu Met Leu Ser Leu
65                  70                  75                  80

His Pro Asp Val Ala Ala Ala Glu Asn Glu Val His Phe Phe Asp Trp
                85                  90                  95

Glu Glu His Tyr Ser Gln Gly Leu Gly Trp Tyr Leu Thr Gln Met Pro
            100                 105                 110

Phe Ser Ser Pro His Gln Leu Thr Val Glu Lys Thr Pro Ala Tyr Phe
        115                 120                 125

Thr Ser Pro Lys Val Pro Glu Arg Ile His Ser Met Asn Pro Thr Ile
    130                 135                 140

Arg Leu Leu Leu Ile Leu Arg Asp Pro Ser Glu Arg Val Leu Ser Asp
145                 150                 155                 160

Tyr Thr Gln Val Leu Tyr Asn His Leu Gln Lys His Lys Pro Tyr Pro
                165                 170                 175
```

```
Pro Ile Glu Asp Leu Leu Met Arg Asp Gly Arg Leu Asn Val Asp Tyr
            180                 185                 190

Lys Ala Leu Asn Arg Ser Leu Tyr His Ala His Met Leu Asn Trp Leu
        195                 200                 205

Arg Phe Phe Pro Leu Gly His Ile His Ile Val Asp Gly Asp Arg Phe
    210                 215                 220

Ile Arg Asp Pro Phe Pro Glu Ile Gln Lys Val Glu Arg Phe Leu Lys
225                 230                 235                 240

Leu Ser Pro Gln Ile Asn Ala Ser Asn Phe Tyr Phe Asn Lys Thr Lys
                245                 250                 255

Gly Phe Tyr Cys Leu Arg Asp Ser Gly Lys Asp Arg Cys Leu His Glu
            260                 265                 270

Ser Lys Gly Arg Ala His Pro Gln Val Asp Pro Lys Leu Leu Asp Lys
        275                 280                 285

Leu His Glu Tyr Phe Arg Glu Pro Asn Lys Lys Phe Phe Lys Leu Val
    290                 295                 300

Gly Arg Thr Phe Asp Trp His
305                 310

<210> SEQ ID NO 213
<211> LENGTH: 311
<212> TYPE: PRT
<213> ORGANISM: Mus musculus

<400> SEQUENCE: 213

Met Thr Leu Leu Leu Gly Ala Val Leu Val Ala Gln Pro Gln
1               5                   10                  15

Leu Val His Ser His Pro Ala Ala Pro Gly Pro Gly Leu Lys Gln Gln
                20                  25                  30

Glu Leu Leu Arg Lys Val Ile Ile Leu Pro Glu Asp Thr Gly Glu Gly
            35                  40                  45

Thr Ala Ser Asn Gly Ser Thr Gln Gln Leu Pro Gln Thr Ile Ile Ile
    50                  55                  60

Gly Val Arg Lys Gly Gly Thr Arg Ala Leu Leu Glu Met Leu Ser Leu
65                  70                  75                  80

His Pro Asp Val Ala Ala Ala Glu Asn Glu Val His Phe Phe Asp Trp
                85                  90                  95

Glu Glu His Tyr Ser Gln Gly Leu Gly Trp Tyr Leu Thr Gln Met Pro
            100                 105                 110

Phe Ser Ser Pro His Gln Leu Thr Val Glu Lys Thr Pro Ala Tyr Phe
    115                 120                 125

Thr Ser Pro Lys Val Pro Glu Arg Ile His Ser Met Asn Pro Thr Ile
130                 135                 140

Arg Leu Leu Leu Ile Leu Arg Asp Pro Ser Glu Arg Val Leu Ser Asp
145                 150                 155                 160

Tyr Thr Gln Val Leu Tyr Asn His Leu Gln Lys His Lys Pro Tyr Pro
                165                 170                 175

Pro Ile Glu Asp Leu Leu Met Arg Asp Gly Arg Leu Asn Leu Asp Tyr
            180                 185                 190

Lys Ala Leu Asn Arg Ser Leu Tyr His Ala His Met Leu Asn Trp Leu
        195                 200                 205

Arg Phe Phe Pro Leu Gly His Ile His Ile Val Asp Gly Asp Arg Leu
    210                 215                 220

Ile Arg Asp Pro Phe Pro Glu Ile Gln Lys Val Glu Arg Phe Leu Lys
```

```
225                 230                 235                 240
Leu Ser Pro Gln Ile Asn Ala Ser Asn Phe Tyr Phe Asn Lys Thr Lys
                245                 250                 255

Gly Phe Tyr Cys Leu Arg Asp Ser Gly Lys Asp Arg Cys Leu His Glu
                260                 265                 270

Ser Lys Gly Arg Ala His Pro Gln Val Asp Pro Lys Leu Leu Asp Lys
                275                 280                 285

Leu His Glu Tyr Phe His Glu Pro Asn Lys Lys Phe Phe Lys Leu Val
                290                 295                 300

Gly Arg Thr Phe Asp Trp His
305                 310

<210> SEQ ID NO 214
<211> LENGTH: 320
<212> TYPE: PRT
<213> ORGANISM: Gallus gallus

<400> SEQUENCE: 214

Met Ala Ala Phe Leu Gly Ala Val Leu Ile Val Gln Pro Gln
1               5                   10                  15

Ile Val Pro Ser Arg Pro Ala Ile Asn Ser Lys Ala Glu Thr Ser Ala
                20                  25                  30

Gln Ser Ala Gln Arg Glu Leu Leu Lys Lys Thr Ser Gln Lys Asn Asp
                35                  40                  45

Phe Lys Glu Asn Ile His Ser Asn Gly Ser Cys Arg Gln Leu Pro Gln
    50                  55                  60

Thr Ile Ile Ile Gly Val Arg Lys Gly Gly Thr Arg Ala Leu Leu Glu
65                  70                  75                  80

Met Leu Ser Leu His Pro Asp Ile Ala Ala Ala Glu Ser Glu Val His
                85                  90                  95

Phe Phe Asp Trp Glu Asp His Tyr Arg Asn Gly Leu Gln Trp Tyr Ile
                100                 105                 110

Asn Gln Met Pro Phe Ser Tyr Pro His Gln Ile Thr Val Glu Lys Thr
                115                 120                 125

Pro Ala Tyr Phe Thr Ser Pro Glu Val Pro Arg Val Tyr Asn Met
                130                 135                 140

Asn Gln Ser Met Arg Leu Leu Leu Ile Leu Arg Asp Pro Ser Glu Arg
145                 150                 155                 160

Val Leu Ser Asp Tyr Thr Gln Val Phe Tyr Asn His Met Gln Lys His
                165                 170                 175

Lys Pro Tyr Pro Ser Ile Glu Gln Phe Leu Ile Lys Asp Gly Glu Leu
                180                 185                 190

Asn Val Asp Tyr Lys Ala Ile Asn Arg Ser Leu Tyr Tyr Ile His Met
                195                 200                 205

Gln Asn Trp Leu Lys Tyr Phe Pro Leu Asp His Ile His Ile Val Asp
                210                 215                 220

Gly Asp Lys Leu Ile Lys Asp Pro Phe Pro Glu Ile Glu Lys Val Glu
225                 230                 235                 240

Arg Phe Leu Lys Leu Ser Pro Gln Ile Asn Ala Ser Asn Phe Tyr Phe
                245                 250                 255

Asn Lys Thr Lys Gly Phe Tyr Cys Leu Arg Asp Ser Gly Arg Glu Arg
                260                 265                 270

Cys Leu His Glu Ser Lys Gly Arg Ala His Pro Gln Val Asp Thr Arg
                275                 280                 285
```

Leu Leu Glu Lys Leu His Glu Tyr Phe Tyr Glu Pro Asn Lys Lys Phe
    290                 295                 300

Phe Glu Leu Val Gly Arg Thr Phe Asp Trp His Ser Ser Val Ala Ser
305                 310                 315                 320

<210> SEQ ID NO 215
<211> LENGTH: 308
<212> TYPE: PRT
<213> ORGANISM: Anolis carolinensis

<400> SEQUENCE: 215

Met Ala Val Phe Leu Leu Gly Ala Ala Leu Leu Ile Val Gln Pro Gln
1               5                   10                  15

Val Val Pro Ser Arg Pro Thr Ala Ser Ser Lys Val Asp Ser Thr Thr
            20                  25                  30

Pro Lys Glu Ser Phe Arg Lys Arg Asp Phe Lys Asp Trp Ile His Pro
        35                  40                  45

Asn Glu Thr Leu Arg Gln Leu Pro Gln Thr Ile Ile Ile Gly Val Arg
    50                  55                  60

Lys Gly Gly Thr Arg Ala Leu Leu Glu Met Leu Ser Leu His Pro Asp
65                  70                  75                  80

Ile Ala Ala Ala Glu Ser Glu Val His Phe Phe Asp Trp Glu Glu His
                85                  90                  95

Tyr Gly Lys Gly Leu Gln Trp Tyr Ile Asn Gln Met Pro Leu Ser Asp
            100                 105                 110

Ile His Gln Ile Thr Val Glu Lys Thr Pro Ala Tyr Phe Thr Ser Ser
        115                 120                 125

Lys Val Pro Glu Arg Val Tyr Lys Met Asn Lys Phe Thr Arg Leu Leu
    130                 135                 140

Leu Ile Leu Arg Asp Pro Thr Glu Arg Val Leu Ser Asp Tyr Thr Gln
145                 150                 155                 160

Val Phe Phe Asn His Val Gln Lys His Lys Pro Tyr Pro Ser Ile Glu
                165                 170                 175

Glu Phe Leu Val Lys Asp Gly Glu Leu Asn Val Asn Tyr Lys Ala Ile
            180                 185                 190

Asn Arg Ser Leu Tyr Tyr Val His Met Gln Asn Trp Leu Lys Tyr Phe
        195                 200                 205

Pro Leu Asp His Ile His Val Asp Gly Asp Lys Leu Ile Lys Asp
    210                 215                 220

Pro Phe Ser Glu Ile Ile Lys Val Glu Glu Phe Leu Lys Leu Pro Pro
225                 230                 235                 240

Gln Ile Asn Ala Ser Asn Phe Tyr Phe Asn Lys Thr Lys Gly Phe Tyr
                245                 250                 255

Cys Leu Arg Asp Ser Gly Arg Asp Arg Cys Leu His Glu Ser Lys Gly
            260                 265                 270

Arg Ala His Pro Lys Val Asp Pro Ile Leu Leu Glu Lys Leu His Lys
        275                 280                 285

Tyr Phe Cys Glu Pro Asn Gln Lys Phe Phe Glu Leu Val Gly Arg Thr
    290                 295                 300

Phe Asp Trp His
305

<210> SEQ ID NO 216
<211> LENGTH: 307
<212> TYPE: PRT
<213> ORGANISM: Oreochromis niloticus

<400> SEQUENCE: 216

| | | | | | | | | | | | | | | |
|---|---|---|---|---|---|---|---|---|---|---|---|---|---|---|
|Met|Ala|Ala|Leu|Leu|Gly|Leu|Leu|Leu|Phe|Ala|Met|Gln|Ser|Pro|
|1| | |  |5|   |   |   |   |10 |   |   |   |   |15 |

Pro Ile Pro Ser Arg Pro Val Ala Asp Gly Asp Glu Gly Pro Pro Leu
                20                  25                  30

Pro Pro Thr Ser Ser Pro Ala Asp Asn Gly Thr Thr Ser His Pro Asn
            35                  40                  45

Gly Thr Leu Gln Gln Leu Pro His Ile Leu Ile Ile Gly Val Arg Lys
        50                  55                  60

Gly Gly Thr Arg Ala Leu Ile Glu Met Leu Ser Leu His Ser Ser Val
65                  70                  75                  80

Ala Ala Ala Gln Asn Glu Val His Phe Phe Asp Trp Glu Ser His Phe
                85                  90                  95

Gln Arg Gly Leu Pro Trp Tyr Leu Ser Gln Met Pro Tyr Ala Phe Pro
                100                 105                 110

Asp Gln Leu Thr Val Glu Lys Thr Pro Ala Tyr Phe Thr Ser Ser Lys
            115                 120                 125

Val Pro Lys Arg Ile His Gln Met Asn Thr Asp Ile Lys Leu Leu Leu
130                 135                 140

Ile Leu Arg Asp Pro Thr Glu Arg Val Leu Ser Asp Tyr Thr Gln Val
145                 150                 155                 160

Phe Tyr Asn Arg Leu Gln Lys His Lys Arg Tyr Gln Pro Ile Glu Ser
                165                 170                 175

Val Leu Val Lys Asp Gly Glu Ile Asn Leu Gly Tyr Lys Ala Leu Asn
            180                 185                 190

Arg Ser Leu Tyr Tyr Val His Met Gln Asn Trp Leu Gln Tyr Phe Pro
        195                 200                 205

Leu Glu Ser Ile His Ile Val Asp Gly Asp Glu Leu Ile Arg Asp Pro
210                 215                 220

Phe Pro Glu Met Lys Lys Val Glu Arg Phe Leu Lys Leu Glu Pro Gln
225                 230                 235                 240

Ile Asn Ala Ser Asn Phe Tyr Phe Asn Lys Thr Lys Gly Phe Tyr Cys
                245                 250                 255

Leu Arg Asp His Gly Arg Glu Arg Cys Leu His Asp Ser Lys Gly Arg
            260                 265                 270

Ala His Pro His Val Ala Pro Ala Ile Leu Gln Lys Leu Tyr Gln Phe
        275                 280                 285

Phe His Glu Pro Asn Lys Lys Phe Phe Glu Leu Val Gly Arg Thr Phe
    290                 295                 300

Thr Trp Lys
305

<210> SEQ ID NO 217
<211> LENGTH: 315
<212> TYPE: PRT
<213> ORGANISM: Callorhinchus milii

<400> SEQUENCE: 217

Met Ala Thr Phe Phe Leu Gly Leu Leu Leu Phe Leu Val His Pro Val
1               5                   10                  15

Val Val Pro Ser Arg Pro Arg Phe Asp Leu Lys Tyr Arg Ile Pro Pro
            20                  25                  30

His Ala Met Arg Tyr Thr Leu Pro Asn Asn Tyr Ser Ser Gln Lys Ile
        35                  40                  45

Tyr Gln Pro Leu Val Phe Pro Asn Gly Thr Ser Gln Arg Leu Pro Gln
            50                  55                  60

Thr Ile Ile Ile Gly Val Arg Lys Gly Gly Thr Arg Ala Leu Leu Glu
 65                  70                  75                  80

Met Leu Asn Leu His Pro Asp Val Thr Ala Ala Glu Ser Glu Ile His
                85                  90                  95

Phe Phe Asp Trp Glu Glu Asn Tyr Ala Lys Gly Leu Gln Trp Tyr Gly
            100                 105                 110

Lys Gln Met Pro Leu Ser Tyr Pro Arg Gln Leu Thr Val Glu Lys Thr
            115                 120                 125

Pro Ala Tyr Phe Thr Ser Ser Glu Val Pro Glu Arg Ile Tyr Asn Met
            130                 135                 140

Asn Lys Thr Thr Arg Leu Leu Leu Ile Leu Arg Asp Pro Thr Glu Arg
145                 150                 155                 160

Val Ile Ser Asp Tyr Thr Gln Val Phe Phe Asn Arg Met Gln Lys His
                165                 170                 175

Lys Pro Phe Gln Ser Val Glu Glu Met Leu Ile Arg Asn Gly Arg Val
            180                 185                 190

Asn Leu Asp Tyr Lys Ala Val Asn Arg Ser Leu Tyr Tyr Ile His Met
            195                 200                 205

Gln Asn Trp Leu Lys Tyr Phe Pro Leu Ser Gln Ile His Ile Val Asp
            210                 215                 220

Gly Asp Gln Leu Ile Lys Glu Pro Phe Pro Glu Met Glu Lys Val Glu
225                 230                 235                 240

Arg Phe Leu Met Leu Ser Pro Arg Ile Asn Ala Ser Asn Phe Tyr Phe
                245                 250                 255

Asn Lys Thr Lys Gly Phe Tyr Cys Leu Arg Asp Gly Val Arg Glu Arg
            260                 265                 270

Cys Leu His Glu Ser Lys Gly Arg Thr His Pro Gln Val Asp Ser Thr
            275                 280                 285

Val Leu Asn Lys Leu His Glu Phe Phe Ser Glu Pro Asn Arg Lys Phe
            290                 295                 300

Phe Glu Thr Val Gly Arg Thr Phe Asp Trp His
305                 310                 315

<210> SEQ ID NO 218
<211> LENGTH: 312
<212> TYPE: PRT
<213> ORGANISM: Pygocentrus nattereri

<400> SEQUENCE: 218

Met Ala Ala Thr Leu Phe Ala Phe Leu Leu Phe Leu Ser Trp Ser Pro
 1               5                  10                  15

Pro Val Pro Ser Arg Pro Thr Val Tyr Pro Gly Pro Ser Pro Ser
            20                  25                  30

Arg Met Leu Gln Asn Gly Thr Arg His Leu Pro Asp Ile Ile Ile
            35                  40                  45

Gly Val Arg Lys Gly Gly Thr Arg Ala Leu Ile Glu Met Leu Ser Leu
 50                  55                  60

His Ser Ser Ile Thr Ser Ala Glu Asn Glu Val His Phe Phe Asp Trp
 65                  70                  75                  80

Glu Ser His Tyr Gln Gln Gly Leu Thr Trp Tyr Ala Ser Gln Met Pro
                85                  90                  95

Ser Ala Gln Pro Gly Gln Leu Thr Val Glu Lys Thr Pro Ala Tyr Phe

```
            100                 105                 110
Thr Cys Ala Lys Val Pro Glu Arg Val Phe His Met Asn Pro Asn Val
            115                 120                 125

Arg Leu Leu Leu Ile Val Arg Asp Pro Val Asp Arg Val Leu Ser Asp
            130                 135                 140

Tyr Thr Gln Val Phe Tyr Asn His Leu Gln Lys Arg Lys Gln Pro Gln
145                 150                 155                 160

Pro Ile Glu Asp Leu Leu Leu Lys Asp Gly Gln Leu Asn Leu Ala
            165                 170                 175

Tyr Lys Ala Leu Asn Arg Ser Leu Tyr Tyr Thr His Met Gln Gln Trp
            180                 185                 190

Leu Thr Ile Phe Pro Arg Thr Ser Phe His Val Val Asp Gly Asp Ala
            195                 200                 205

Leu Ile Arg Glu Pro Leu Asp Glu Met Arg Lys Val Glu Asn Phe Leu
            210                 215                 220

Gly Leu Glu Pro Gln Ile Asn Ala Glu Asn Phe Tyr Phe Asn Arg Thr
225                 230                 235                 240

Lys Gly Phe Tyr Cys Leu Arg Asp Arg Glu Gly His Glu Arg Cys Leu
            245                 250                 255

His Ser Ser Lys Gly Arg Thr His Pro Gln Val Ser Pro Glu Ile Leu
            260                 265                 270

Gln Lys Leu Arg Asp Tyr Phe His Lys Pro Asn Arg Lys Phe Phe Glu
            275                 280                 285

Leu Val Gly Arg Thr Phe Asp Trp Asn Gln Ala Ser Glu Asp Arg Gln
            290                 295                 300

Glu Thr Gln Thr Leu Lys Gly Glu
305                 310

<210> SEQ ID NO 219
<211> LENGTH: 308
<212> TYPE: PRT
<213> ORGANISM: Crotalus horridus

<400> SEQUENCE: 219

Met Ala Phe Leu Leu Val Ser Ala Tyr Leu Leu Thr Pro Ala Gln
1               5                   10                  15

Ala Ala Pro Val Glu Asn Gly Ala Leu Val Glu Met Leu Met Pro Gln
            20                  25                  30

Val Leu Leu Ser Asn Lys Ser Glu His Tyr Leu Ala Gln Val Arg Pro
            35                  40                  45

Pro Gly Thr Ser Arg Gln Ile Pro Gln Thr Ile Ile Gly Val Arg
            50                  55                  60

Lys Gly Gly Thr Arg Ala Leu Leu Glu Met Leu Asp Val His Pro Asn
65                  70                  75                  80

Ile Val Val Ala Ala Ile Glu Val His Phe Phe Asp Trp Asp Glu Asn
            85                  90                  95

Tyr Val Lys Gly Ile Asp Trp Tyr Arg Ser Leu Met Pro Phe Ser Tyr
            100                 105                 110

Glu Asn Gln Ile Thr Ile Glu Lys Thr Pro Gly Tyr Phe Thr Ser Pro
            115                 120                 125

Gln Ala Pro Glu Arg Ile His Asp Met Asn Ser Ser Ile Lys Leu Leu
            130                 135                 140

Leu Ile Leu Arg Asp Pro Thr Glu Arg Val Ile Ser Asp Tyr Thr Gln
145                 150                 155                 160
```

```
Val Tyr Tyr Asn Arg Leu Glu Asn His Lys Ser Val Gln Pro Phe Glu
                165                 170                 175

Asp Ile Val Ile Lys Asn Gly Ala Leu Asn Thr Lys Tyr Lys Ala Ile
            180                 185                 190

Gln Arg Ser Leu Tyr Asp Ile His Met Gly Arg Trp Leu Lys Tyr Phe
        195                 200                 205

His Leu Asp Gln Ile His Ile Val Asp Gly Asn Thr Leu Ile Arg Asp
    210                 215                 220

Pro Leu Pro Glu Leu Gln Lys Val Glu Arg Phe Leu Asn Leu Pro Ser
225                 230                 235                 240

Lys Ile Leu Ser Ser Asn Phe Tyr Phe Asn Gln Thr Lys Gly Phe Tyr
                245                 250                 255

Cys Ile Arg Ser Asp Gly Arg Glu Arg Cys Leu His Glu Ser Lys Gly
            260                 265                 270

Arg Pro His Pro Val Val Asn Ser Thr Val Leu Glu Gln Leu Tyr Ser
        275                 280                 285

Tyr Phe Arg Glu His Asn Glu Lys Phe Tyr Arg Met Ile Asn His Ser
    290                 295                 300

Phe Asp Trp His
305

<210> SEQ ID NO 220
<211> LENGTH: 346
<212> TYPE: PRT
<213> ORGANISM: Homo sapiens

<400> SEQUENCE: 220

Met Leu Phe Lys Gln Gln Ala Trp Leu Arg Gln Lys Leu Leu Val Leu
1               5                   10                  15

Gly Ser Leu Ala Val Gly Ser Leu Leu Tyr Leu Val Ala Arg Val Gly
                20                  25                  30

Ser Leu Asp Arg Leu Gln Pro Ile Cys Pro Ile Glu Gly Arg Leu Gly
            35                  40                  45

Gly Ala Arg Thr Gln Ala Glu Phe Pro Leu Arg Ala Leu Gln Phe Lys
        50                  55                  60

Arg Gly Leu Leu His Glu Phe Arg Lys Gly Asn Ala Ser Lys Glu Gln
65                  70                  75                  80

Val Arg Leu His Asp Leu Val Gln Gln Leu Pro Lys Ala Ile Ile Ile
                85                  90                  95

Gly Val Arg Lys Gly Gly Thr Arg Ala Leu Leu Glu Met Leu Asn Leu
                100                 105                 110

His Pro Ala Val Val Lys Ala Ser Gln Glu Ile His Phe Phe Asp Asn
            115                 120                 125

Asp Glu Asn Tyr Gly Lys Gly Ile Glu Trp Tyr Arg Lys Lys Met Pro
        130                 135                 140

Phe Ser Tyr Pro Gln Gln Ile Thr Ile Glu Lys Ser Pro Ala Tyr Phe
145                 150                 155                 160

Ile Thr Glu Glu Val Pro Glu Arg Ile Tyr Lys Met Asn Ser Ser Ile
                165                 170                 175

Lys Leu Leu Ile Ile Val Arg Glu Pro Thr Thr Arg Ala Ile Ser Asp
            180                 185                 190

Tyr Thr Gln Val Leu Glu Gly Lys Glu Arg Lys Asn Lys Thr Tyr Tyr
        195                 200                 205

Lys Phe Glu Lys Leu Ala Ile Asp Pro Asn Thr Cys Glu Val Asn Thr
    210                 215                 220
```

```
Lys Tyr Lys Ala Val Arg Thr Ser Ile Tyr Thr Lys His Leu Glu Arg
225                 230                 235                 240

Trp Leu Lys Tyr Phe Pro Ile Glu Gln Phe His Val Val Asp Gly Asp
                245                 250                 255

Arg Leu Ile Thr Glu Pro Leu Pro Glu Leu Gln Leu Val Glu Lys Phe
                260                 265                 270

Leu Asn Leu Pro Pro Arg Ile Ser Gln Tyr Asn Leu Tyr Phe Asn Ala
            275                 280                 285

Thr Arg Gly Phe Tyr Cys Leu Arg Phe Asn Ile Ile Phe Asn Lys Cys
        290                 295                 300

Leu Ala Gly Ser Lys Gly Arg Ile His Pro Glu Val Asp Pro Ser Val
305                 310                 315                 320

Ile Thr Lys Leu Arg Lys Phe Phe His Pro Phe Asn Gln Lys Phe Tyr
                325                 330                 335

Gln Ile Thr Gly Arg Thr Leu Asn Trp Pro
            340                 345

<210> SEQ ID NO 221
<211> LENGTH: 7
<212> TYPE: PRT
<213> ORGANISM: Artificial Sequence
<220> FEATURE:
<223> OTHER INFORMATION: NST conserved amino acid sequence motif 1

<400> SEQUENCE: 221

Gln Lys Thr Gly Thr Thr Ala
1               5

<210> SEQ ID NO 222
<211> LENGTH: 4
<212> TYPE: PRT
<213> ORGANISM: Artificial Sequence
<220> FEATURE:
<223> OTHER INFORMATION: NST conserved amino acid sequence motif 2

<400> SEQUENCE: 222

Thr Phe Glu Glu
1

<210> SEQ ID NO 223
<211> LENGTH: 5
<212> TYPE: PRT
<213> ORGANISM: Artificial Sequence
<220> FEATURE:
<223> OTHER INFORMATION: NST conserved amino acid sequence motif 3

<400> SEQUENCE: 223

Phe Glu Lys Ser Ala
1               5

<210> SEQ ID NO 224
<211> LENGTH: 5
<212> TYPE: PRT
<213> ORGANISM: Artificial Sequence
<220> FEATURE:
<223> OTHER INFORMATION: NST conserved amino acid sequence motif 4

<400> SEQUENCE: 224

Ser Trp Tyr Gln His
1               5

<210> SEQ ID NO 225
```

```
<211> LENGTH: 8
<212> TYPE: PRT
<213> ORGANISM: Artificial Sequence
<220> FEATURE:
<223> OTHER INFORMATION: NST conserved amino acid sequence motif 5
<220> FEATURE:
<221> NAME/KEY: MISC_FEATURE
<222> LOCATION: (4)..(4)
<223> OTHER INFORMATION: Xaa is either lysine or arginine

<400> SEQUENCE: 225

Cys Leu Gly Xaa Ser Lys Gly Arg
1               5

<210> SEQ ID NO 226
<211> LENGTH: 7
<212> TYPE: PRT
<213> ORGANISM: Artificial Sequence
<220> FEATURE:
<223> OTHER INFORMATION: NST engineered amino acid sequence motif 1
<220> FEATURE:
<221> NAME/KEY: MISC_FEATURE
<222> LOCATION: (2)..(2)
<223> OTHER INFORMATION: Xaa is either glycine or lysine
<220> FEATURE:
<221> NAME/KEY: MISC_FEATURE
<222> LOCATION: (5)..(5)
<223> OTHER INFORMATION: Xaa is either glycine or valine

<400> SEQUENCE: 226

His Xaa Thr Gly Xaa His Ala
1               5

<210> SEQ ID NO 227
<211> LENGTH: 7
<212> TYPE: PRT
<213> ORGANISM: Artificial Sequence
<220> FEATURE:
<223> OTHER INFORMATION: NST engineered amino acid sequence motif 2

<400> SEQUENCE: 227

His Gly Thr Gly Gly His Ala
1               5

<210> SEQ ID NO 228
<211> LENGTH: 7
<212> TYPE: PRT
<213> ORGANISM: Artificial Sequence
<220> FEATURE:
<223> OTHER INFORMATION: NST engineered amino acid sequence motif 3

<400> SEQUENCE: 228

His Lys Thr Gly Val His Ala
1               5

<210> SEQ ID NO 229
<211> LENGTH: 8
<212> TYPE: PRT
<213> ORGANISM: Artificial Sequence
<220> FEATURE:
<223> OTHER INFORMATION: NST engineered amino acid sequence motif 4
<220> FEATURE:
<221> NAME/KEY: MISC_FEATURE
<222> LOCATION: (4)..(4)
<223> OTHER INFORMATION: Xaa is either lysine or arginine

<400> SEQUENCE: 229

Cys Leu Gly Xaa Ser Leu Gly Arg
1               5
```

```
<210> SEQ ID NO 230
<211> LENGTH: 8
<212> TYPE: PRT
<213> ORGANISM: Artificial Sequence
<220> FEATURE:
<223> OTHER INFORMATION: NST engineered amino acid sequence motif 5
<220> FEATURE:
<221> NAME/KEY: MISC_FEATURE
<222> LOCATION: (4)..(4)
<223> OTHER INFORMATION: Xaa is either lysine or arginine

<400> SEQUENCE: 230

Cys Leu Gly Xaa Ser Val Gly Arg
1               5

<210> SEQ ID NO 231
<211> LENGTH: 4
<212> TYPE: PRT
<213> ORGANISM: Artificial Sequence
<220> FEATURE:
<223> OTHER INFORMATION: NST engineered amino acid sequence motif 6

<400> SEQUENCE: 231

Thr Phe Glu His
1

<210> SEQ ID NO 232
<211> LENGTH: 5
<212> TYPE: PRT
<213> ORGANISM: Artificial Sequence
<220> FEATURE:
<223> OTHER INFORMATION: NST engineered amino acid sequence motif 7

<400> SEQUENCE: 232

Phe Glu His Ser Ala
1               5

<210> SEQ ID NO 233
<211> LENGTH: 8
<212> TYPE: PRT
<213> ORGANISM: Artificial Sequence
<220> FEATURE:
<223> OTHER INFORMATION: NST engineered amino acid sequence motif 8
<220> FEATURE:
<221> NAME/KEY: MISC_FEATURE
<222> LOCATION: (4)..(4)
<223> OTHER INFORMATION: Xaa is either lysine or arginine

<400> SEQUENCE: 233

Cys Leu Gly Xaa His Lys Gly Arg
1               5

<210> SEQ ID NO 234
<211> LENGTH: 7
<212> TYPE: PRT
<213> ORGANISM: Artificial Sequence
<220> FEATURE:
<223> OTHER INFORMATION: NST engineered amino acid sequence motif 9
<220> FEATURE:
<221> NAME/KEY: MISC_FEATURE
<222> LOCATION: (1)..(1)
<223> OTHER INFORMATION: Xaa is either serine or alanine
<220> FEATURE:
<221> NAME/KEY: MISC_FEATURE
<222> LOCATION: (6)..(6)
<223> OTHER INFORMATION: Xaa is either tryptophan or phenylalanine
<220> FEATURE:
<221> NAME/KEY: MISC_FEATURE
<222> LOCATION: (7)..(7)
<223> OTHER INFORMATION: Xaa is either alanine or leucine
```

<400> SEQUENCE: 234

Xaa Lys Thr Gly Ala Xaa Xaa
1               5

<210> SEQ ID NO 235
<211> LENGTH: 7
<212> TYPE: PRT
<213> ORGANISM: Artificial Sequence
<220> FEATURE:
<223> OTHER INFORMATION: NST engineered amino acid sequence motif 10
<220> FEATURE:
<221> NAME/KEY: MISC_FEATURE
<222> LOCATION: (6)..(6)
<223> OTHER INFORMATION: Xaa is either tryptophan or phenylalanine
<220> FEATURE:
<221> NAME/KEY: MISC_FEATURE
<222> LOCATION: (7)..(7)
<223> OTHER INFORMATION: Xaa is either alanine or leucine

<400> SEQUENCE: 235

Ser Lys Thr Gly Ala Xaa Xaa
1               5

<210> SEQ ID NO 236
<211> LENGTH: 7
<212> TYPE: PRT
<213> ORGANISM: Artificial Sequence
<220> FEATURE:
<223> OTHER INFORMATION: NST engineered amino acid sequence motif 11
<220> FEATURE:
<221> NAME/KEY: MISC_FEATURE
<222> LOCATION: (6)..(6)
<223> OTHER INFORMATION: Xaa is either tryptophan or phenylalanine
<220> FEATURE:
<221> NAME/KEY: MISC_FEATURE
<222> LOCATION: (7)..(7)
<223> OTHER INFORMATION: Xaa is either alanine or leucine

<400> SEQUENCE: 236

Ala Lys Thr Gly Ala Xaa Xaa
1               5

<210> SEQ ID NO 237
<211> LENGTH: 4
<212> TYPE: PRT
<213> ORGANISM: Artificial Sequence
<220> FEATURE:
<223> OTHER INFORMATION: NST engineered amino acid sequence motif 12

<400> SEQUENCE: 237

Thr His Gly Ser
1

<210> SEQ ID NO 238
<211> LENGTH: 4
<212> TYPE: PRT
<213> ORGANISM: Artificial Sequence
<220> FEATURE:
<223> OTHER INFORMATION: NST engineered amino acid sequence motif 13

<400> SEQUENCE: 238

Thr Gly His Ser
1

<210> SEQ ID NO 239
<211> LENGTH: 8
<212> TYPE: PRT
<213> ORGANISM: Artificial Sequence

```
<220> FEATURE:
<223> OTHER INFORMATION: NST engineered amino acid sequence motif 14
<220> FEATURE:
<221> NAME/KEY: MISC_FEATURE
<222> LOCATION: (4)..(4)
<223> OTHER INFORMATION: Xaa is either lysine or arginine

<400> SEQUENCE: 239

Cys His Gly Xaa Ser Leu Gly Arg
1               5

<210> SEQ ID NO 240
<211> LENGTH: 8
<212> TYPE: PRT
<213> ORGANISM: Artificial Sequence
<220> FEATURE:
<223> OTHER INFORMATION: NST engineered amino acid sequence motif 15
<220> FEATURE:
<221> NAME/KEY: MISC_FEATURE
<222> LOCATION: (4)..(4)
<223> OTHER INFORMATION: Xaa is either lysine or arginine

<400> SEQUENCE: 240

Cys Leu Gly Xaa His Leu Gly Arg
1               5

<210> SEQ ID NO 241
<211> LENGTH: 8
<212> TYPE: PRT
<213> ORGANISM: Artificial Sequence
<220> FEATURE:
<223> OTHER INFORMATION: NST engineered amino acid sequence motif 16
<220> FEATURE:
<221> NAME/KEY: MISC_FEATURE
<222> LOCATION: (4)..(4)
<223> OTHER INFORMATION: Xaa is either lysine or arginine

<400> SEQUENCE: 241

Cys His Gly Xaa Ser Trp Gly Arg
1               5

<210> SEQ ID NO 242
<211> LENGTH: 8
<212> TYPE: PRT
<213> ORGANISM: Artificial Sequence
<220> FEATURE:
<223> OTHER INFORMATION: NST engineered amino acid sequence motif 17
<220> FEATURE:
<221> NAME/KEY: MISC_FEATURE
<222> LOCATION: (4)..(4)
<223> OTHER INFORMATION: Xaa is either lysine or arginine

<400> SEQUENCE: 242

Cys Leu Gly Xaa His Trp Gly Arg
1               5

<210> SEQ ID NO 243
<211> LENGTH: 8
<212> TYPE: PRT
<213> ORGANISM: Artificial Sequence
<220> FEATURE:
<223> OTHER INFORMATION: NST engineered amino acid sequence motif 18
<220> FEATURE:
<221> NAME/KEY: MISC_FEATURE
<222> LOCATION: (2)..(2)
<223> OTHER INFORMATION: Xaa is either glycine or leucine
<220> FEATURE:
<221> NAME/KEY: MISC_FEATURE
<222> LOCATION: (4)..(4)
<223> OTHER INFORMATION: Xaa is either lysine or arginine
<220> FEATURE:
```

```
<221> NAME/KEY: MISC_FEATURE
<222> LOCATION: (5)..(5)
<223> OTHER INFORMATION: Xaa is either serine or histidine
<220> FEATURE:
<221> NAME/KEY: MISC_FEATURE
<222> LOCATION: (6)..(6)
<223> OTHER INFORMATION: Xaa is either leucine or valine
<220> FEATURE:
<221> NAME/KEY: MISC_FEATURE
<222> LOCATION: (8)..(8)
<223> OTHER INFORMATION: Xaa is either serine or arginine

<400> SEQUENCE: 243

Cys Xaa Gly Xaa Xaa Xaa Gly Xaa
1               5

<210> SEQ ID NO 244
<211> LENGTH: 8
<212> TYPE: PRT
<213> ORGANISM: Artificial Sequence
<220> FEATURE:
<223> OTHER INFORMATION: 2OST conserved amino acid sequence motif 1
<220> FEATURE:
<221> NAME/KEY: MISC_FEATURE
<222> LOCATION: (6)..(6)
<223> OTHER INFORMATION: Xaa is either alanine or glycine

<400> SEQUENCE: 244

Arg Val Pro Lys Thr Xaa Ser Thr
1               5

<210> SEQ ID NO 245
<211> LENGTH: 8
<212> TYPE: PRT
<213> ORGANISM: Artificial Sequence
<220> FEATURE:
<223> OTHER INFORMATION: 2OST conserved amino acid sequence motif 2
<220> FEATURE:
<221> NAME/KEY: MISC_FEATURE
<222> LOCATION: (4)..(4)
<223> OTHER INFORMATION: Xaa is either phenylalanine or histidine
<220> FEATURE:
<221> NAME/KEY: MISC_FEATURE
<222> LOCATION: (7)..(7)
<223> OTHER INFORMATION: Xaa is either aspartic acid or asparagine
<220> FEATURE:
<221> NAME/KEY: MISC_FEATURE
<222> LOCATION: (8)..(8)
<223> OTHER INFORMATION: Xaa is either phenylalanine or tyrosine

<400> SEQUENCE: 245

Phe Leu Arg Xaa Gly Asp Xaa Xaa
1               5

<210> SEQ ID NO 246
<211> LENGTH: 5
<212> TYPE: PRT
<213> ORGANISM: Artificial Sequence
<220> FEATURE:
<223> OTHER INFORMATION: 2OST conserved amino acid sequence motif 3
<220> FEATURE:
<221> NAME/KEY: MISC_FEATURE
<222> LOCATION: (3)..(3)
<223> OTHER INFORMATION: Xaa is either lysine or arginine

<400> SEQUENCE: 246

Arg Arg Xaa Gln Gly
1               5

<210> SEQ ID NO 247
<211> LENGTH: 6
```

```
<212> TYPE: PRT
<213> ORGANISM: Artificial Sequence
<220> FEATURE:
<223> OTHER INFORMATION: 2OST conserved amino acid sequence motif 4
<220> FEATURE:
<221> NAME/KEY: MISC_FEATURE
<222> LOCATION: (5)..(5)
<223> OTHER INFORMATION: Xaa is either lysine or arginine

<400> SEQUENCE: 247

Ser His Leu Arg Xaa Thr
1               5

<210> SEQ ID NO 248
<211> LENGTH: 8
<212> TYPE: PRT
<213> ORGANISM: Artificial Sequence
<220> FEATURE:
<223> OTHER INFORMATION: 2OST engineered amino acid sequence motif 1

<400> SEQUENCE: 248

Arg Val Pro His Thr Ala Ser Thr
1               5

<210> SEQ ID NO 249
<211> LENGTH: 8
<212> TYPE: PRT
<213> ORGANISM: Artificial Sequence
<220> FEATURE:
<223> OTHER INFORMATION: 2OST engineered amino acid sequence motif 2

<400> SEQUENCE: 249

Arg Val His Arg Thr Ala Ser His
1               5

<210> SEQ ID NO 250
<211> LENGTH: 6
<212> TYPE: PRT
<213> ORGANISM: Artificial Sequence
<220> FEATURE:
<223> OTHER INFORMATION: 2OST engineered amino acid sequence motif 3

<400> SEQUENCE: 250

Ser His Leu His Lys Thr
1               5

<210> SEQ ID NO 251
<211> LENGTH: 8
<212> TYPE: PRT
<213> ORGANISM: Artificial Sequence
<220> FEATURE:
<223> OTHER INFORMATION: 2OST engineered amino acid sequence motif 4

<400> SEQUENCE: 251

His Leu Arg Phe Gly Asp Asp Tyr
1               5

<210> SEQ ID NO 252
<211> LENGTH: 8
<212> TYPE: PRT
<213> ORGANISM: Artificial Sequence
<220> FEATURE:
<223> OTHER INFORMATION: 2OST engineered amino acid sequence motif 5

<400> SEQUENCE: 252

Phe Leu Arg Phe Gly Ser Asp Lys
1               5
```

<210> SEQ ID NO 253
<211> LENGTH: 5
<212> TYPE: PRT
<213> ORGANISM: Artificial Sequence
<220> FEATURE:
<223> OTHER INFORMATION: 2OST engineered amino acid sequence motif 6

<400> SEQUENCE: 253

Met Arg Lys Gln Gly
1               5

<210> SEQ ID NO 254
<211> LENGTH: 6
<212> TYPE: PRT
<213> ORGANISM: Artificial Sequence
<220> FEATURE:
<223> OTHER INFORMATION: 6OST conserved amino acid sequence motif 1

<400> SEQUENCE: 254

Gln Lys Thr Gly Gly Thr
1               5

<210> SEQ ID NO 255
<211> LENGTH: 6
<212> TYPE: PRT
<213> ORGANISM: Artificial Sequence
<220> FEATURE:
<223> OTHER INFORMATION: 6OST conserved amino acid sequence motif 2

<400> SEQUENCE: 255

Cys Gly Leu His Ala Asp
1               5

<210> SEQ ID NO 256
<211> LENGTH: 13
<212> TYPE: PRT
<213> ORGANISM: Artificial Sequence
<220> FEATURE:
<223> OTHER INFORMATION: 6OST conserved amino acid sequence motif 3
<220> FEATURE:
<221> NAME/KEY: MISC_FEATURE
<222> LOCATION: (4)..(4)
<223> OTHER INFORMATION: Xaa is either lysine or arginine

<400> SEQUENCE: 256

Ser Glu Trp Xaa His Val Gln Arg Gly Ala Thr Trp Lys
1               5                   10

<210> SEQ ID NO 257
<211> LENGTH: 6
<212> TYPE: PRT
<213> ORGANISM: Artificial Sequence
<220> FEATURE:
<223> OTHER INFORMATION: 6OST engineered amino acid sequence motif 1

<400> SEQUENCE: 257

Gly His Thr Gly Gly Thr
1               5

<210> SEQ ID NO 258
<211> LENGTH: 6
<212> TYPE: PRT
<213> ORGANISM: Artificial Sequence
<220> FEATURE:
<223> OTHER INFORMATION: 6OST engineered amino acid sequence motif 2
<220> FEATURE:
<221> NAME/KEY: MISC_FEATURE
<222> LOCATION: (4)..(4)

```
<223> OTHER INFORMATION: Xaa is asparagine, arginine, or histidine

<400> SEQUENCE: 258

Cys Gly Thr Xaa Ala Asp
1               5

<210> SEQ ID NO 259
<211> LENGTH: 6
<212> TYPE: PRT
<213> ORGANISM: Artificial Sequence
<220> FEATURE:
<223> OTHER INFORMATION: 6OST engineered amino acid sequence motif 3
<220> FEATURE:
<221> NAME/KEY: MISC_FEATURE
<222> LOCATION: (4)..(4)
<223> OTHER INFORMATION: Xaa is asparagine, arginine, or histidine

<400> SEQUENCE: 259

Cys Gly Ser Xaa Ala Asp
1               5

<210> SEQ ID NO 260
<211> LENGTH: 13
<212> TYPE: PRT
<213> ORGANISM: Artificial Sequence
<220> FEATURE:
<223> OTHER INFORMATION: 6OST engineered amino acid sequence motif 4
<220> FEATURE:
<221> NAME/KEY: MISC_FEATURE
<222> LOCATION: (1)..(1)
<223> OTHER INFORMATION: Xaa is either serine or glycine
<220> FEATURE:
<221> NAME/KEY: MISC_FEATURE
<222> LOCATION: (2)..(2)
<223> OTHER INFORMATION: Xaa is either glycine or histidine
<220> FEATURE:
<221> NAME/KEY: MISC_FEATURE
<222> LOCATION: (6)..(6)
<223> OTHER INFORMATION: Xaa is either threonine or histidine
<220> FEATURE:
<221> NAME/KEY: MISC_FEATURE
<222> LOCATION: (11)..(11)
<223> OTHER INFORMATION: Xaa is either threonine or alanine

<400> SEQUENCE: 260

Xaa Xaa Trp Arg His Xaa Gln Arg Gly Gly Xaa Asn Lys
1               5                   10

<210> SEQ ID NO 261
<211> LENGTH: 13
<212> TYPE: PRT
<213> ORGANISM: Artificial Sequence
<220> FEATURE:
<223> OTHER INFORMATION: 6OST engineered amino acid sequence motif 5
<220> FEATURE:
<221> NAME/KEY: MISC_FEATURE
<222> LOCATION: (2)..(2)
<223> OTHER INFORMATION: Xaa is either glycine or histidine
<220> FEATURE:
<221> NAME/KEY: MISC_FEATURE
<222> LOCATION: (6)..(6)
<223> OTHER INFORMATION: Xaa is either threonine or histidine

<400> SEQUENCE: 261

Gly Xaa Trp Arg His Xaa Gln Arg Gly Gly Thr Asn Lys
1               5                   10

<210> SEQ ID NO 262
<211> LENGTH: 13
<212> TYPE: PRT
<213> ORGANISM: Artificial Sequence
```

```
<220> FEATURE:
<223> OTHER INFORMATION: 6OST engineered amino acid sequence motif 6
<220> FEATURE:
<221> NAME/KEY: MISC_FEATURE
<222> LOCATION: (2)..(2)
<223> OTHER INFORMATION: Xaa is either glycine or histidine
<220> FEATURE:
<221> NAME/KEY: MISC_FEATURE
<222> LOCATION: (6)..(6)
<223> OTHER INFORMATION: Xaa is either threonine or histidine

<400> SEQUENCE: 262

Ser Xaa Trp Arg His Xaa Gln Arg Gly Gly Ala Asn Lys
1               5                   10

<210> SEQ ID NO 263
<211> LENGTH: 13
<212> TYPE: PRT
<213> ORGANISM: Artificial Sequence
<220> FEATURE:
<223> OTHER INFORMATION: 6OST engineered amino acid sequence motif 7
<220> FEATURE:
<221> NAME/KEY: MISC_FEATURE
<222> LOCATION: (1)..(1)
<223> OTHER INFORMATION: Xaa is either serine or glycine
<220> FEATURE:
<221> NAME/KEY: MISC_FEATURE
<222> LOCATION: (11)..(11)
<223> OTHER INFORMATION: Xaa is either threonine or alanine

<400> SEQUENCE: 263

Xaa Gly Trp Arg His His Gln Arg Gly Gly Xaa Asn Lys
1               5                   10

<210> SEQ ID NO 264
<211> LENGTH: 13
<212> TYPE: PRT
<213> ORGANISM: Artificial Sequence
<220> FEATURE:
<223> OTHER INFORMATION: 6OST engineered amino acid sequence motif 8
<220> FEATURE:
<221> NAME/KEY: MISC_FEATURE
<222> LOCATION: (1)..(1)
<223> OTHER INFORMATION: Xaa is either serine or glycine
<220> FEATURE:
<221> NAME/KEY: MISC_FEATURE
<222> LOCATION: (11)..(11)
<223> OTHER INFORMATION: Xaa is either threonine or alanine

<400> SEQUENCE: 264

Xaa His Trp Arg His Thr Gln Arg Gly Gly Xaa Asn Lys
1               5                   10

<210> SEQ ID NO 265
<211> LENGTH: 6
<212> TYPE: PRT
<213> ORGANISM: Artificial Sequence
<220> FEATURE:
<223> OTHER INFORMATION: 3OST conserved amino acid sequence motif 1

<400> SEQUENCE: 265

Gly Val Arg Lys Gly Gly
1               5

<210> SEQ ID NO 266
<211> LENGTH: 4
<212> TYPE: PRT
<213> ORGANISM: Artificial Sequence
<220> FEATURE:
<223> OTHER INFORMATION: 3OST conserved amino acid sequence motif 2
<220> FEATURE:
```

```
<221> NAME/KEY: MISC_FEATURE
<222> LOCATION: (2)..(2)
<223> OTHER INFORMATION: Xaa is either alanine or glycine

<400> SEQUENCE: 266

Pro Xaa Tyr Phe
1

<210> SEQ ID NO 267
<211> LENGTH: 6
<212> TYPE: PRT
<213> ORGANISM: Artificial Sequence
<220> FEATURE:
<223> OTHER INFORMATION: 3OST conserved amino acid sequence motif 3

<400> SEQUENCE: 267

Ser Asp Tyr Thr Gln Val
1               5

<210> SEQ ID NO 268
<211> LENGTH: 6
<212> TYPE: PRT
<213> ORGANISM: Artificial Sequence
<220> FEATURE:
<223> OTHER INFORMATION: 3OST engineered amino acid sequence motif 1

<400> SEQUENCE: 268

Gly Val Gly His Gly Gly
1               5

<210> SEQ ID NO 269
<211> LENGTH: 4
<212> TYPE: PRT
<213> ORGANISM: Artificial Sequence
<220> FEATURE:
<223> OTHER INFORMATION: 3OST engineered amino acid sequence motif 2

<400> SEQUENCE: 269

His Ser Tyr Phe
1

<210> SEQ ID NO 270
<211> LENGTH: 6
<212> TYPE: PRT
<213> ORGANISM: Artificial Sequence
<220> FEATURE:
<223> OTHER INFORMATION: 3OST engineered amino acid sequence motif 3

<400> SEQUENCE: 270

Ser Ala Tyr Thr His Met
1               5

<210> SEQ ID NO 271
<211> LENGTH: 12
<212> TYPE: PRT
<213> ORGANISM: Artificial Sequence
<220> FEATURE:
<223> OTHER INFORMATION: Conserved sulfatase signature sequence I
<220> FEATURE:
<221> NAME/KEY: MISC_FEATURE
<222> LOCATION: (1)..(1)
<223> OTHER INFORMATION: Xaa is either cysteine or serine
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(4)
```

```
<223> OTHER INFORMATION: Xaa can be either serine or any other amino
      acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be either leucine or any other amino
      acid
<220> FEATURE:
<221> NAME/KEY: MISC_FEATURE
<222> LOCATION: (10)..(10)
<223> OTHER INFORMATION: Xaa can be either threonine or any other amino
      acid
<220> FEATURE:
<221> NAME/KEY: MISC_FEATURE
<222> LOCATION: (11)..(11)
<223> OTHER INFORMATION: Xaa can be either glycine or any other amino
      acid
<220> FEATURE:
<221> NAME/KEY: MISC_FEATURE
<222> LOCATION: (12)..(12)
<223> OTHER INFORMATION: Xaa can be either arginine or any other amino
      acid

<400> SEQUENCE: 271

Xaa Xaa Pro Xaa Arg Xaa Xaa Xaa Xaa Xaa Xaa Xaa
1               5                   10

<210> SEQ ID NO 272
<211> LENGTH: 12
<212> TYPE: PRT
<213> ORGANISM: Artificial Sequence
<220> FEATURE:
<223> OTHER INFORMATION: Conserved sulfatase signature seqeuence II
<220> FEATURE:
<221> NAME/KEY: MISC_FEATURE
<222> LOCATION: (2)..(2)
<223> OTHER INFORMATION: Xaa can be either tyrosine or valine
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be either serine or threonine
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid
```

```
<220> FEATURE:
<221> NAME/KEY: MISC_FEATURE
<222> LOCATION: (11)..(11)
<223> OTHER INFORMATION: Xaa can be any amino acid

<400> SEQUENCE: 272

Gly Xaa Xaa Xaa Xaa Xaa Xaa Gly Lys Xaa Xaa His
1               5                   10

<210> SEQ ID NO 273
<211> LENGTH: 5
<212> TYPE: PRT
<213> ORGANISM: Artificial Sequence
<220> FEATURE:
<223> OTHER INFORMATION: 2OST conserved amino acid sequence motif 5
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa is either serine or threonine

<400> SEQUENCE: 273

Asn Thr Xaa Lys Asn
1               5

<210> SEQ ID NO 274
<211> LENGTH: 4
<212> TYPE: PRT
<213> ORGANISM: Artificial Sequence
<220> FEATURE:
<223> OTHER INFORMATION: 2OST conserved amino acid sequence motif 6

<400> SEQUENCE: 274

Tyr His Gly His
1

<210> SEQ ID NO 275
<211> LENGTH: 6
<212> TYPE: PRT
<213> ORGANISM: Artificial Sequence
<220> FEATURE:
<223> OTHER INFORMATION: 6OST conserved amino acid sequence motif 4

<400> SEQUENCE: 275

Leu Arg Asp Val Pro Ser
1               5

<210> SEQ ID NO 276
<211> LENGTH: 5
<212> TYPE: PRT
<213> ORGANISM: Artificial Sequence
<220> FEATURE:
<223> OTHER INFORMATION: 6OST conserved amino acid sequence motif 5
<220> FEATURE:
<221> NAME/KEY: MISC_FEATURE
<222> LOCATION: (4)..(4)
<223> OTHER INFORMATION: Xaa can be either phenylalanine or tyrosine

<400> SEQUENCE: 276

Leu Thr Glu Xaa Gln
1               5

<210> SEQ ID NO 277
<211> LENGTH: 10
<212> TYPE: PRT
<213> ORGANISM: Artificial Sequence
```

```
<220> FEATURE:
<223> OTHER INFORMATION: NST conserved amino acid sequence motif 6

<400> SEQUENCE: 277

Gln Lys Thr Gly Thr Thr Ala Leu Tyr Leu
1               5                   10

<210> SEQ ID NO 278
<211> LENGTH: 10
<212> TYPE: PRT
<213> ORGANISM: Artificial Sequence
<220> FEATURE:
<223> OTHER INFORMATION: NST engineered amino  acid sequence motif 19
<220> FEATURE:
<221> NAME/KEY: MISC_FEATURE
<222> LOCATION: (1)..(1)
<223> OTHER INFORMATION: Xaa is either glutamine, serine, or alanine
<220> FEATURE:
<221> NAME/KEY: MISC_FEATURE
<222> LOCATION: (6)..(6)
<223> OTHER INFORMATION: Xaa is either tryptophan or phenylalanine
<220> FEATURE:
<221> NAME/KEY: MISC_FEATURE
<222> LOCATION: (7)..(7)
<223> OTHER INFORMATION: Xaa is either alanine or leucine
<220> FEATURE:
<221> NAME/KEY: MISC_FEATURE
<222> LOCATION: (9)..(9)
<223> OTHER INFORMATION: Xaa is either tyrosine, threonine, or histidine

<400> SEQUENCE: 278

Xaa Lys Thr Gly Ala Xaa Xaa Leu Xaa His
1               5                   10

<210> SEQ ID NO 279
<211> LENGTH: 4
<212> TYPE: PRT
<213> ORGANISM: Artificial Sequence
<220> FEATURE:
<223> OTHER INFORMATION: NST engineered amino acid sequence 20
<220> FEATURE:
<221> NAME/KEY: MISC_FEATURE
<222> LOCATION: (2)..(2)
<223> OTHER INFORMATION: Xaa is either histidine or glycine
<220> FEATURE:
<221> NAME/KEY: MISC_FEATURE
<222> LOCATION: (3)..(3)
<223> OTHER INFORMATION: Xaa is either glycine, histidine, or serine

<400> SEQUENCE: 279

Thr Xaa Xaa Ser
1

<210> SEQ ID NO 280
<211> LENGTH: 10
<212> TYPE: PRT
<213> ORGANISM: Artificial Sequence
<220> FEATURE:
<223> OTHER INFORMATION: NST engineered amino acid sequence motif 21
<220> FEATURE:
<221> NAME/KEY: MISC_FEATURE
<222> LOCATION: (6)..(6)
<223> OTHER INFORMATION: Xaa is either tryptophan or phenylalanine
<220> FEATURE:
<221> NAME/KEY: MISC_FEATURE
<222> LOCATION: (7)..(7)
<223> OTHER INFORMATION: Xaa is either alanine or leucine

<400> SEQUENCE: 280

Asn Lys Thr Gly Ala Xaa Xaa Leu Tyr His
1               5                   10
```

```
<210> SEQ ID NO 281
<211> LENGTH: 8
<212> TYPE: PRT
<213> ORGANISM: Artificial Sequence
<220> FEATURE:
<223> OTHER INFORMATION: NST engineered amino acid sequence motif 22
<220> FEATURE:
<221> NAME/KEY: MISC_FEATURE
<222> LOCATION: (4)..(4)
<223> OTHER INFORMATION: Xaa is either lysine or arginine

<400> SEQUENCE: 281

Cys Leu Gly Xaa Ser His Gly Arg
1               5

<210> SEQ ID NO 282
<211> LENGTH: 10
<212> TYPE: PRT
<213> ORGANISM: Artificial Sequence
<220> FEATURE:
<223> OTHER INFORMATION: NST engineered amino acid sequence motif 23
<220> FEATURE:
<221> NAME/KEY: MISC_FEATURE
<222> LOCATION: (6)..(6)
<223> OTHER INFORMATION: Xaa is either tryptophan or phenylalanine
<220> FEATURE:
<221> NAME/KEY: MISC_FEATURE
<222> LOCATION: (7)..(7)
<223> OTHER INFORMATION: Xaa is either alanine or leucine

<400> SEQUENCE: 282

Ser Lys Thr Gly Ala Xaa Xaa Leu Thr His
1               5                   10

<210> SEQ ID NO 283
<211> LENGTH: 8
<212> TYPE: PRT
<213> ORGANISM: Artificial Sequence
<220> FEATURE:
<223> OTHER INFORMATION: NST engineered amino acid sequence motif 24
<220> FEATURE:
<221> NAME/KEY: MISC_FEATURE
<222> LOCATION: (4)..(4)
<223> OTHER INFORMATION: Xaa is either lysine or arginine

<400> SEQUENCE: 283

Cys His Gly Xaa Arg Trp Gly Arg
1               5

<210> SEQ ID NO 284
<211> LENGTH: 10
<212> TYPE: PRT
<213> ORGANISM: Artificial Sequence
<220> FEATURE:
<223> OTHER INFORMATION: NST engineered amino acid sequence motif 25
<220> FEATURE:
<221> NAME/KEY: MISC_FEATURE
<222> LOCATION: (6)..(6)
<223> OTHER INFORMATION: Xaa is either tryptophan or phenylalanine
<220> FEATURE:
<221> NAME/KEY: MISC_FEATURE
<222> LOCATION: (7)..(7)
<223> OTHER INFORMATION: Xaa is either alanine or leucine

<400> SEQUENCE: 284

Ala Lys Thr Gly Ala Xaa Xaa Leu His His
1               5                   10

<210> SEQ ID NO 285
<211> LENGTH: 4
```

```
<212> TYPE: PRT
<213> ORGANISM: Artificial Sequence
<220> FEATURE:
<223> OTHER INFORMATION: NST conserved amino acid sequence motif 26

<400> SEQUENCE: 285

Thr His Ser Ser
1

<210> SEQ ID NO 286
<211> LENGTH: 8
<212> TYPE: PRT
<213> ORGANISM: Artificial Sequence
<220> FEATURE:
<223> OTHER INFORMATION: NST engineered amino acid sequence motif 27
<220> FEATURE:
<221> NAME/KEY: MISC_FEATURE
<222> LOCATION: (4)..(4)
<223> OTHER INFORMATION: Xaa is either lysine or arginine

<400> SEQUENCE: 286

Cys Ala His Xaa Gly Leu Gly Arg
1               5

<210> SEQ ID NO 287
<211> LENGTH: 8
<212> TYPE: PRT
<213> ORGANISM: Artificial Sequence
<220> FEATURE:
<223> OTHER INFORMATION: NST engineered amino acid sequence motif 28
<220> FEATURE:
<221> NAME/KEY: MISC_FEATURE
<222> LOCATION: (4)..(4)
<223> OTHER INFORMATION: Xaa is either lysine or arginine

<400> SEQUENCE: 287

Cys Gly Gly Xaa His Leu Gly Arg
1               5

<210> SEQ ID NO 288
<211> LENGTH: 5
<212> TYPE: PRT
<213> ORGANISM: Artificial Sequence
<220> FEATURE:
<223> OTHER INFORMATION: NST engineered amino acid sequence motif 29

<400> SEQUENCE: 288

Phe Glu His Ser Gly
1               5

<210> SEQ ID NO 289
<211> LENGTH: 4
<212> TYPE: PRT
<213> ORGANISM: Artificial Sequence
<220> FEATURE:
<223> OTHER INFORMATION: NST engineered amino acid sequence motif 30

<400> SEQUENCE: 289

Thr Gly Asn His
1

<210> SEQ ID NO 290
<211> LENGTH: 7
<212> TYPE: PRT
<213> ORGANISM: Artificial Sequence
<220> FEATURE:
<223> OTHER INFORMATION: 6OST conserved amino acid sequence motif 6

<400> SEQUENCE: 290
```

```
Asn Leu Ala Asn Asn Arg Gln
1               5

<210> SEQ ID NO 291
<211> LENGTH: 6
<212> TYPE: PRT
<213> ORGANISM: Artificial Sequence
<220> FEATURE:
<223> OTHER INFORMATION: 6OST engineered amino acid sequence motif 9
<220> FEATURE:
<221> NAME/KEY: MISC_FEATURE
<222> LOCATION: (3)..(3)
<223> OTHER INFORMATION: Xaa is either threonine or serine
<220> FEATURE:
<221> NAME/KEY: MISC_FEATURE
<222> LOCATION: (4)..(4)
<223> OTHER INFORMATION: Xaa is either asparagine, arginine, or
      histidine

<400> SEQUENCE: 291

Cys Gly Xaa Xaa Ala Asp
1               5

<210> SEQ ID NO 292
<211> LENGTH: 7
<212> TYPE: PRT
<213> ORGANISM: Artificial Sequence
<220> FEATURE:
<223> OTHER INFORMATION: 6OST engineered amino acid sequence motif 10
<220> FEATURE:
<221> NAME/KEY: MISC_FEATURE
<222> LOCATION: (3)..(3)
<223> OTHER INFORMATION: Xaa is either alanine or glycine

<400> SEQUENCE: 292

Asn Leu Xaa Asn Asn Arg Gln
1               5

<210> SEQ ID NO 293
<211> LENGTH: 7
<212> TYPE: PRT
<213> ORGANISM: Artificial Sequence
<220> FEATURE:
<223> OTHER INFORMATION: 6OST engineered amino acid sequence motif 11

<400> SEQUENCE: 293

Asn Leu Gly Asn Asn Arg Gln
1               5

<210> SEQ ID NO 294
<211> LENGTH: 7
<212> TYPE: PRT
<213> ORGANISM: Artificial Sequence
<220> FEATURE:
<223> OTHER INFORMATION: 6OST engineered amino acid sequence motif 12

<400> SEQUENCE: 294

Asn Leu Ala Asn Asn Arg Gln
1               5

<210> SEQ ID NO 295
<211> LENGTH: 411
<212> TYPE: PRT
<213> ORGANISM: Mus musculus

<400> SEQUENCE: 295

Met Arg Arg Arg Arg Ala Gly Gly Arg Thr Met Val Glu Arg Ala Ser
1               5                   10                  15
```

```
Lys Phe Val Leu Val Ala Gly Ser Ala Cys Phe Met Leu Ile Leu
             20                  25                  30

Tyr Gln Tyr Ala Gly Pro Gly Leu Ser Leu Gly Ala Pro Gly Gly Arg
         35                  40                  45

Val Pro Pro Asp Asp Leu Asp Leu Phe Pro Thr Pro Asp Pro His Tyr
 50                  55                  60

Glu Lys Lys Tyr Tyr Phe Pro Val Arg Glu Leu Glu Arg Ser Leu Arg
 65                  70                  75                  80

Phe Asp Met Lys Gly Asp Val Ile Val Phe Leu His Ile Gln Lys
                 85                  90                  95

Thr Gly Gly Thr Thr Phe Gly Arg His Leu Val Gln Asn Val Arg Leu
             100                 105                 110

Glu Val Pro Cys Asp Cys Arg Pro Gly Gln Lys Lys Cys Thr Cys Tyr
             115                 120                 125

Arg Pro Asn Arg Arg Glu Thr Trp Leu Phe Ser Arg Phe Ser Thr Gly
130                 135                 140

Trp Ser Cys Gly Leu His Ala Asp Trp Thr Glu Leu Thr Asn Cys Val
145                 150                 155                 160

Pro Gly Val Leu Asp Arg Arg Asp Pro Ala Gly Leu Arg Ser Pro Arg
                 165                 170                 175

Lys Phe Tyr Tyr Ile Thr Leu Leu Arg Asp Pro Val Ser Arg Tyr Leu
                 180                 185                 190

Ser Glu Trp Arg His Val Gln Arg Gly Ala Thr Trp Lys Thr Ser Leu
             195                 200                 205

His Met Cys Asp Gly Arg Thr Pro Thr Pro Glu Glu Leu Pro Pro Cys
    210                 215                 220

Tyr Glu Gly Thr Asp Trp Ser Gly Cys Thr Leu Gln Glu Phe Met Asp
225                 230                 235                 240

Cys Pro Tyr Asn Leu Ala Asn Asn Arg Gln Val Arg Met Leu Ala Asp
                 245                 250                 255

Leu Ser Leu Val Gly Cys Tyr Asn Leu Ser Phe Ile Pro Glu Ser Lys
             260                 265                 270

Arg Ala Gln Leu Leu Leu Glu Ser Ala Lys Lys Asn Leu Arg Gly Met
    275                 280                 285

Ala Phe Phe Gly Leu Thr Glu Phe Gln Arg Lys Thr Gln Tyr Leu Phe
290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Asp Glu Asp Thr Ile Arg His
                 325                 330                 335

Ile Glu Glu Leu Asn Asp Leu Asp Met Gln Leu Tyr Asp Tyr Ala Lys
                 340                 345                 350

Asp Leu Phe Gln Gln Arg Tyr Gln Tyr Lys Arg Gln Leu Glu Arg Arg
             355                 360                 365

Glu Gln Arg Leu Arg Asn Arg Glu Glu Arg Leu Leu His Arg Ser Lys
    370                 375                 380

Glu Ala Leu Pro Arg Glu Asp Pro Glu Glu Pro Gly Arg Val Pro Thr
385                 390                 395                 400

Glu Asp Tyr Met Ser His Ile Ile Glu Lys Trp
                 405                 410

<210> SEQ ID NO 296
<211> LENGTH: 411
```

<212> TYPE: PRT
<213> ORGANISM: Homo sapiens

<400> SEQUENCE: 296

Met Arg Arg Arg Ala Gly Arg Thr Met Val Glu Arg Ala Ser
1               5                   10                  15

Lys Phe Val Leu Val Val Ala Gly Ser Val Cys Phe Met Leu Ile Leu
                20                  25                  30

Tyr Gln Tyr Ala Gly Pro Gly Leu Ser Leu Gly Ala Pro Gly Gly Arg
            35                  40                  45

Ala Pro Pro Asp Asp Leu Asp Leu Phe Pro Thr Pro Asp Pro His Tyr
        50                  55                  60

Glu Lys Lys Tyr Tyr Phe Pro Val Arg Glu Leu Glu Arg Ser Leu Arg
65                  70                  75                  80

Phe Asp Met Lys Gly Asp Asp Val Ile Val Phe Leu His Ile Gln Lys
                85                  90                  95

Thr Gly Gly Thr Thr Phe Gly Arg His Leu Val Gln Asn Val Arg Leu
            100                 105                 110

Glu Val Pro Cys Asp Cys Arg Pro Gly Gln Lys Lys Cys Thr Cys Tyr
        115                 120                 125

Arg Pro Asn Arg Arg Glu Thr Trp Leu Phe Ser Arg Phe Ser Thr Gly
        130                 135                 140

Trp Ser Cys Gly Leu His Ala Asp Trp Thr Glu Leu Thr Asn Cys Val
145                 150                 155                 160

Pro Gly Val Leu Asp Arg Arg Asp Ser Ala Ala Leu Arg Thr Pro Arg
                165                 170                 175

Lys Phe Tyr Tyr Ile Thr Leu Leu Arg Asp Pro Val Ser Arg Tyr Leu
            180                 185                 190

Ser Glu Trp Arg His Val Gln Arg Gly Ala Thr Trp Lys Thr Ser Leu
        195                 200                 205

His Met Cys Asp Gly Arg Thr Pro Thr Pro Glu Glu Leu Pro Pro Cys
    210                 215                 220

Tyr Glu Gly Thr Asp Trp Ser Gly Cys Thr Leu Gln Glu Phe Met Asp
225                 230                 235                 240

Cys Pro Tyr Asn Leu Ala Asn Asn Arg Gln Val Arg Met Leu Ala Asp
                245                 250                 255

Leu Ser Leu Val Gly Cys Tyr Asn Leu Ser Phe Ile Pro Glu Gly Lys
            260                 265                 270

Arg Ala Gln Leu Leu Leu Glu Ser Ala Lys Lys Asn Leu Arg Gly Met
        275                 280                 285

Ala Phe Phe Gly Leu Thr Glu Phe Gln Arg Lys Thr Gln Tyr Leu Phe
    290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Asp Glu Asp Thr Ile Arg Arg
                325                 330                 335

Ile Glu Glu Leu Asn Asp Leu Asp Met Gln Leu Tyr Asp Tyr Ala Lys
            340                 345                 350

Asp Leu Phe Gln Gln Arg Tyr Gln Tyr Lys Arg Gln Leu Glu Arg Arg
        355                 360                 365

Glu Gln Arg Leu Arg Ser Arg Glu Arg Leu Leu His Arg Ala Lys
    370                 375                 380

Glu Ala Leu Pro Arg Glu Asp Ala Asp Glu Pro Gly Arg Val Pro Thr
385                 390                 395                 400

Glu Asp Tyr Met Ser His Ile Ile Glu Lys Trp
            405                 410

<210> SEQ ID NO 297
<211> LENGTH: 411
<212> TYPE: PRT
<213> ORGANISM: Sus scrofa

<400> SEQUENCE: 297

Met Arg Arg Arg Arg Ala Gly Ser Arg Thr Met Val Glu Arg Ala Ser
1               5                   10                  15

Lys Phe Val Leu Val Ala Gly Ser Ala Cys Phe Met Leu Ile Leu
            20                  25                  30

Tyr Gln Tyr Ala Gly Pro Gly Leu Ser Leu Gly Ala Pro Gly Gly Arg
            35                  40                  45

Ala Pro Pro Asp Asp Leu Asp Leu Phe Pro Thr Pro Asp Pro His Tyr
        50                  55                  60

Glu Lys Lys Tyr Tyr Phe Pro Val Arg Glu Leu Glu Arg Ser Leu His
65                  70                  75                  80

Phe Asp Met Lys Gly Asp Asp Val Ile Val Phe Leu His Ile Gln Lys
                85                  90                  95

Thr Gly Gly Thr Thr Phe Gly Arg His Leu Val Gln Asn Val Arg Leu
            100                 105                 110

Glu Val Pro Cys Asp Cys Arg Pro Gly Gln Lys Lys Cys Thr Cys Tyr
            115                 120                 125

Arg Pro Asn Arg Arg Glu Thr Trp Leu Phe Ser Arg Phe Ser Thr Gly
    130                 135                 140

Trp Ser Cys Gly Leu His Ala Asp Trp Thr Glu Leu Thr Asn Cys Val
145                 150                 155                 160

Pro Gly Val Leu Asp Arg Arg Asp Pro Ala Ala Leu Arg Thr Pro Arg
                165                 170                 175

Lys Phe Tyr Tyr Ile Thr Leu Leu Arg Asp Pro Val Ser Arg Tyr Leu
            180                 185                 190

Ser Glu Trp Arg His Val Gln Arg Gly Ala Thr Trp Lys Thr Ser Leu
        195                 200                 205

His Met Cys Asp Gly Arg Thr Pro Thr Pro Glu Glu Leu Pro Pro Cys
    210                 215                 220

Tyr Glu Gly Thr Asp Trp Ser Gly Cys Thr Leu Gln Glu Phe Met Asp
225                 230                 235                 240

Cys Pro Tyr Asn Leu Ala Asn Asn Arg Gln Val Arg Met Leu Ala Asp
                245                 250                 255

Leu Ser Leu Val Gly Cys Tyr Asn Leu Ser Phe Ile Pro Glu Gly Lys
            260                 265                 270

Arg Ser Gln Leu Leu Leu Glu Ser Ala Lys Lys Asn Leu Arg Gly Met
        275                 280                 285

Ala Phe Phe Gly Leu Thr Glu Phe Gln Arg Lys Thr Gln Tyr Leu Phe
    290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Gly Asp Thr Ile Arg Arg
                325                 330                 335

Ile Glu Glu Leu Asn Asp Leu Asp Met Gln Leu Tyr Asp Tyr Ala Arg
            340                 345                 350

Asp Leu Phe Gln Gln Arg Tyr Gln Tyr Lys Arg Gln Leu Glu Arg Arg

```
                355                 360                 365
Gln Gln Arg Leu Arg Ser Arg Glu Glu Arg Leu Leu His Arg Ala Lys
    370                 375                 380

Glu Ala Pro Pro Arg Gly Asp Thr Glu Glu Pro Gly Arg Val Pro Thr
385                 390                 395                 400

Glu Asp Tyr Met Ser His Ile Ile Glu Lys Trp
                405                 410

<210> SEQ ID NO 298
<211> LENGTH: 6
<212> TYPE: PRT
<213> ORGANISM: Artificial Sequence
<220> FEATURE:
<223> OTHER INFORMATION: 3OST conserved amino acid sequence motif 4
<220> FEATURE:
<221> NAME/KEY: MISC_FEATURE
<222> LOCATION: (2)..(2)
<223> OTHER INFORMATION: Xaa is either valine or isoleucine

<400> SEQUENCE: 298

Glu Xaa His Phe Phe Asp
1               5

<210> SEQ ID NO 299
<211> LENGTH: 6
<212> TYPE: PRT
<213> ORGANISM: Artificial Sequence
<220> FEATURE:
<223> OTHER INFORMATION: 3OST engineered amino acid sequence motif 4
<220> FEATURE:
<221> NAME/KEY: MISC_FEATURE
<222> LOCATION: (2)..(2)
<223> OTHER INFORMATION: Xaa is either alanine or leucine
<220> FEATURE:
<221> NAME/KEY: MISC_FEATURE
<222> LOCATION: (3)..(3)
<223> OTHER INFORMATION: Xaa is either tyrosine or glycine
<220> FEATURE:
<221> NAME/KEY: MISC_FEATURE
<222> LOCATION: (6)..(6)
<223> OTHER INFORMATION: Xaa is either methionine or leucine

<400> SEQUENCE: 299

Ser Xaa Xaa Thr His Xaa
1               5

<210> SEQ ID NO 300
<211> LENGTH: 6
<212> TYPE: PRT
<213> ORGANISM: Artificial Sequence
<220> FEATURE:
<223> OTHER INFORMATION: 3OST engineered amino acid sequence motif 5

<400> SEQUENCE: 300

Ser Leu Gly Thr His Leu
1               5
```

ENGINEERED ARYL SULFATE-DEPENDENT ENZYMES

CROSS-REFERENCE TO RELATED APPLICATIONS

The instant application is a continuation-in-part of International Application No. PCT/US2020/013677, filed Jan. 15, 2020, which claims of the benefit of U.S. Provisional Applications 62/792,440, filed on Jan. 15, 2019; 62/797,466, filed on Jan. 28, 2019; 62/808,074, filed on Feb. 20, 2019; and 62/853,261, filed May 28, 2019, the disclosures of which are hereby incorporated by reference in their entireties.

FIELD OF THE INVENTION

The present invention relates to non-natural sulfotransferase enzymes that are engineered to react with an aryl sulfate compound, instead of 3'-phosphoadenosine 5'-phosphosulfate, as a sulfo group donor.

REFERENCE TO SEQUENCE LISTING

The present application is being filed along with a sequence listing in electronic format. The sequence listing is provided as a file entitled "OPT-001XRT-Sequence-Listing.txt" created on Feb. 23, 2022, and which is 585,369 bytes in size. The information in electronic format of the sequence listing is incorporated by reference in its entirety.

BACKGROUND OF THE INVENTION

Sulfotransferases are a vital class of enzymes that catalyze the transfer of a sulfo group from a sulfo group donor to a sulfo group acceptor. Sulfotransferases are nearly ubiquitous in nature, and they exist in nearly all types of organisms, including bacteria, yeast, and animals, including humans. Similarly, sulfotransferase enzymes play an integral role in the sulfation of a wide array of sulfo group acceptors, including many types of steroids, polysaccharides, proteins, xenobiotics, and other molecules.

There are several polysaccharides that can be utilized as sulfo group acceptors, including, for example, dermatan, keratan, heparosan, and chondroitin. In particular, heparosan comprises repeating disaccharide units of 1→4 glycosidically-linked, glucuronic acid and N-acetylated glucosamine ($[\beta(1,4)GlcA-\alpha(1,4)GlcNAc]_n$) residues, any of which can be further modified by one or more enzyme-catalyzed deacetylation, sulfation, or epimerization reactions. Sulfation of heparosan-based polysaccharides can be catalyzed by up to four sulfotransferase enzymes to form heparan sulfate (HS), and when performed in a particular order along with deacetylation of one or more glucosamine residues and epimerization of one or more glucuronic acid residues, can be utilized to form heparin.

However, as wide-ranging and voluminous as the set of sulfo group acceptors can be, there are only a couple of molecules that can be utilized by sulfotransferase enzymes as sulfo group donors. The nearly ubiquitous sulfo group donor, including for each of the four HS sulfotransferases, is 3'-phosphoadenosine 5'-phosphosulfate (PAPS). These in vivo systems have evolved to exclusively utilize PAPS because it has a short half-life and can readily be synthesized and metabolized, as needed, by the organism. However, that same short half-life renders PAPS to be unsuitable for most in vitro syntheses, particularly in large scale syntheses, that utilize sulfotransferases because it can readily decompose into adenosine 3',5'-diphosphate, which actively inhibits the sulfotransferases' biological activity.

Aryl sulfate compounds, such asp-nitrophenyl sulfate (PNS) and 4-methylumbelliferyl sulfate (MUS) have been identified as cheap, widely-available compounds that can be useful as sulfo donors with a very limited number of sulfotransferases to synthesize certain small molecule products (see Malojcic, G., et al. (2008) *Proc. Nat. Acad. Sci.* 105 (49):19217-19222 and Kaysser, L., et al., (2010) *J. Biol. Chem.* 285 (17):12684-12694, the disclosures of which are incorporated by reference in their entireties). Yet, only a small number of bacterial sulfotransferases have been shown to react with aryl sulfate compounds as sulfo group donors, and none of these react with polysaccharides, let alone heparosan-based polysaccharides, as sulfo group acceptors. As a result, when sulfotransferases are used in the in vitro synthesis of sulfated polysaccharides, PAPS must be included in the reaction mixture to effectively catalyze sulfo group transfer, and aryl sulfate compounds can only be used indirectly, to repopulate the system with PAPS (see U.S. Pat. No. 6,255,088, the disclosure of which is incorporated by reference in its entirety).

Consequently, there is a need to develop sulfotransferase enzymes that react with aryl sulfate compounds as sulfo group donors, as well as polysaccharides as sulfo group acceptors. In particular, the development of sulfotransferase enzymes that are capable of both reacting with aryl sulfate compounds as sulfo group donors and with heparosan-based polysaccharides as sulfo group acceptors would present a large step forward toward the development of large-scale syntheses of heparin in vitro.

SUMMARY OF THE INVENTION

The present invention provides several engineered, biologically-active enzymes that are capable of recognizing, binding to, and reacting with aryl sulfate compounds as substrates. According to the present invention, the engineered enzyme can have sulfatase activity. According to the present invention, the engineered enzyme can have sulfotransferase activity.

According to the present invention, an engineered enzyme having sulfatase and/or sulfotransferase activity can react with an aryl sulfate compound, preferably selected from the group consisting of p-nitrophenyl sulfate (PNS), 4-methylumbelliferyl sulfate, 7-hydroxycoumarin sulfate, phenyl sulfate, 4-acetylphenyl sulfate, indoxyl sulfate, 1-naphthyl sulfate, 2-naphthyl sulfate (2NapS), and 4-nitrocatechol sulfate (NCS). According to the present invention, an engineered sulfotransferase can recognize, bind, and react with PNS as the sulfo group donor. According to the present invention, an engineered sulfotransferase can recognize, bind, and react with NCS as the sulfo group donor. According to the present invention, an engineered sulfotransferase can recognize, bind, and react with either PNS or NCS as the sulfo group donor.

In an aspect of the invention, an engineered enzyme of the present invention can have sulfatase biological activity. According to the present invention, sulfatase activity comprises the nucleophilic attack of a sulfur atom within an aryl sulfate compound, causing hydrolysis of a sulfate group and releasing the aromatic moiety from the active site. According to the present invention, the nucleophilic attack of the sulfur atom can be initiated by an amino acid residue within the active site of the engineered enzyme, particularly a histidine residue. According to the present invention, the reaction with the aryl sulfate compound can result in a sulfohistidine intermediate, in which a sulfate group is covalently bound to the amino acid nucleophile, particularly a histidine residue.

According to the present invention, an engineered enzyme of the present invention having sulfatase activity differs from other known sulfatases, which typically comprise greater than 500 amino acid residues, at least one cysteine or serine residue that is post-translationally modified to become α-formylglycine, and one or more characteristic signature sequences, C/S-X-P-S/X-R-X-X-X-L/X-T/X-G/X-R/X or G-Y/V-X-S/T-X-X-X-G-K-X-X-H, which correspond to SEQ ID NO: 271 and SEQ ID NO: 272 in the sequence listing, respectively, and direct the post-translational modification of the cysteine or serine into α-formylglycine. Thus, according to the present invention, engineered enzymes having sulfatase activity can comprise less than 500 amino acid residues. According to the present invention, engineered enzymes having sulfatase activity can have zero α-formylglycine residues. According to the present invention, engineered enzymes having sulfatase activity can have no amino acid sequence motifs comprising the amino acid sequences of either SEQ ID NO: 271 or SEQ ID NO: 272.

According to the present invention, engineered enzymes of the present invention that have sulfatase activity can comprise any amino acid sequence, so long as nucleophilic attack of the aryl sulfate compound is initiated by an active site amino acid residue, preferably a histidine residue. According to the present invention, an engineered enzyme having sulfatase activity can have an amino acid sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, and SEQ ID NO: 151. According to the present invention, an engineered enzyme having sulfatase activity can have an amino acid sequence selected from the group consisting of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 66, SEQ ID NO: 68, SEQ ID NO: 69, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 153, SEQ ID NO: 154, SEQ ID NO: 155, SEQ ID NO: 156, SEQ ID NO: 157, SEQ ID NO: 158, SEQ ID NO: 159, and SEQ ID NO: 160. According to the present invention, an engineered enzyme having sulfatase activity can have comprise any amino acid sequence that is a biological equivalent of any of the amino acid sequences above.

In another aspect of the present invention, an engineered enzyme of the present invention can have sulfotransferase biological activity. According to the present invention, sulfotransferase activity comprises the enzymatic transfer of a sulfo group from an aryl sulfate compound to a sulfo group acceptor. According to the present invention, the sulfo group acceptor can be a polysaccharide. According to the present invention, the sulfo group acceptor polysaccharide can be a heparosan-based polysaccharide. According to the present invention, the heparosan-based polysaccharide can be N-deacetylated heparosan. According to the present invention, the heparosan-based polysaccharide can be N-sulfated heparosan. According to the present invention, the heparosan-based polysaccharide can be N-sulfated, 2-O sulfated heparan sulfate (N,2O-HS). According to the present invention, the heparosan-based polysaccharide can be N-sulfated, 2-O sulfated, 6-O sulfated heparan sulfate (N,2O,6O-HS). According to the present invention, the heparosan-based polysaccharide can be N-sulfated, 2-O sulfated, 3-O sulfated, 6-O sulfated heparan sulfate (N,2O,3O,6O-HS). According the present invention, and as described below, the N,2O,3O,6O-HS product can have one or more molecular weight properties and/or anticoagulant activity that are similar or equivalent to heparin. According to the present invention, the heparosan-based polysaccharide can be sulfated at any of the N-, 2-O, 3-O, and/or 6-O positions, within any of the disaccharide units comprising the heparosan-based polysaccharide. According to the present invention, the heparosan-based polysaccharide can comprise one or more iduronic acid residues substituted in place of a glucuronic acid residue. According to the present invention, one or more of the iduronic acid residues can be 2-O sulfated.

According to the present invention, the sulfotransfer reaction catalyzed by an engineered sulfotransferase enzyme can proceed via a reaction mechanism in which a sulfohistidine intermediate is first formed upon the reaction between the enzyme and an aryl sulfate compound, followed by the binding of a heparosan-based polysaccharide within the active site, and subsequent transfer of the sulfo group from the sulfohistidine intermediate to the polysaccharide. Alternatively, according to the present invention, the sulfotransfer reaction catalyzed by an engineered sulfotransferase enzyme can proceed via a reaction mechanism in which both an aryl sulfate compound and a heparosan-based polysaccharide are bound within the active site, and the enzyme catalyzes the direct transfer of the sulfo group from the aryl sulfate compound to the polysaccharide.

According to the present invention, an engineered sulfotransferase enzyme can have a biological activity based on the position within the heparosan-based polysaccharide that receives the sulfo group, including glucosaminyl N-sulfotransferase activity, hexuronyl 2-O sulfotransferase activity, glucosaminyl 6-O sulfotransferase activity, or glucosaminyl 3-O sulfotransferase activity. Each biological activity is described in further detail, below.

In an aspect of the invention, an engineered sulfotransferase enzyme can have glucosaminyl N-sulfotransferase activity, comprising the transfer of a sulfo group from an aryl sulfate compound to the N-position of an unsubstituted glucosamine residue within a heparosan-based polysaccharide. According to the present invention, an engineered glucosaminyl N-sulfotransferase (NST) enzyme can comprise any amino acid sequence, so long as the sulfo group donor is an aryl sulfate compound and the sulfo group acceptor is a heparosan-based polysaccharide.

According to the present invention, engineered NST enzymes can be mutants of the N-sulfotransferase domain of natural N-deacetylase/N-sulfotransferase (NDST) enzymes, which are members of enzyme class (EC) 2.8.2.8. In contrast to the engineered NST enzymes of the present invention, natural enzymes within EC 2.8.2.8 do not react with aryl sulfate compounds, and only react with 3'-phosphoadenosine 5'-phosphosulfate (PAPS) as a sulfo group donor. However, the engineered NST enzymes can retain the same biological activity as the natural enzymes within EC 2.8.2.8 with heparosan-based polysaccharides as sulfo group acceptors. According to the present invention, heparosan-based polysaccharides that can be utilized as sulfo acceptors with any of the engineered NST enzymes can comprise one or more disaccharide units having the structure of Formula II, below:

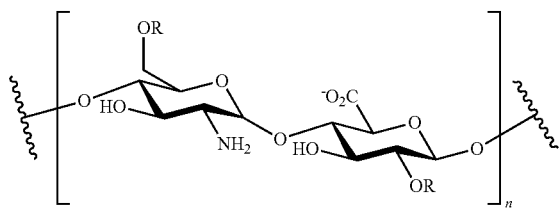

wherein n is an integer and R is selected from the group consisting of a hydrogen atom or a sulfo group. According to the present invention, both R groups within the disaccharide unit can be a hydrogen atom. According to the present invention, all of the R groups within the same polysaccharide molecule can be hydrogen atoms. When the sulfo acceptor polysaccharide comprises the structure of Formula II, upon transfer of the sulfo group from an aryl sulfate compound, the sulfated polysaccharide product comprises the structure of Formula III, below:

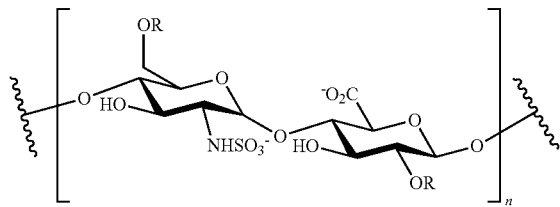

wherein n is an integer and R is selected from the group consisting of a hydrogen atom or a sulfo group.

According to the present invention, although the glucosamine residue that receives the sulfo group is N-unsubstituted, as illustrated in Formula II and Formula III above, other glucosamine residues within the same polysaccharide molecule can be N-acetylated, N-sulfated, or N-unsubstituted, 3-O sulfated, and/or 6-O sulfated. Similarly, hexuronic acid residues in other positions within the polysaccharide that are not adjacent to the glucosamine residue receiving the sulfo group can be glucuronic acid or iduronic acid residues, any of which can be optionally 2-O sulfated. According to the present invention, and in some preferred embodiments, the heparosan-based polysaccharide can be N-deacetylated heparosan, in which all of the glucosamine residues are N-unsubstituted, or are present as a mixture of N-acetylglucosamine and N-unsubstituted glucosamine.

According to the present invention, an engineered NST enzyme can consist of a single N-sulfotransferase domain that is capable of binding and reacting with an aryl sulfate compound as a sulfo group donor. However, most natural NDST enzymes within EC 2.8.2.8 have dual N-deacetylase/N-sulfotransferase activity, with one domain structurally configured for N-deacetylase activity and another domain structurally configured for N-sulfotransferase activity. Therefore, according to the present invention, the engineered NST enzyme can also comprise an N-deacetylase domain having either an identical or mutated amino acid sequence to the N-deacetylase domain of any of the NDST enzymes in EC 2.8.2.8.

To facilitate its exclusive reactivity with PAPS as the sulfo group donor, natural NDST enzymes typically comprise highly-conserved or identical amino acid sequences that define the active site and govern the enzyme's recognition, binding, and reactivity with PAPS. According to the present invention, the amino acid sequence of an engineered NST enzyme can comprise one or more mutations relative to the N-sulfotransferase domain of a natural NDST enzyme, in order to facilitate binding of an aryl sulfate compound instead of PAPS. According to the present invention, an engineered NST enzyme can comprise an amino acid sequence having at least one amino acid mutation relative to the N-sulfotransferase domain of a natural NDST enzyme, including at least two, three, four, five, six, seven, eight, nine, ten, eleven, twelve, thirteen, fourteen, fifteen, twenty, thirty, forty, fifty, up to at least one hundred amino acid mutations. According to the present invention, an engineered NST enzyme can comprise at least one amino acid mutation relative to the amino acid sequence of any of the NDST enzymes, in regions that are known to define the enzyme's active site, including at least two, three, four, five, six, seven, eight, nine, ten, eleven, twelve, thirteen, fourteen, or fifteen amino acid mutations, up to at least twenty amino acid mutations.

According to the present invention, the amino acid sequence of an engineered NST enzyme can be expressed as a "percent identity" or "% identity" relative to the amino acid sequence of one or more of the natural NDST enzymes within EC 2.8.2.8, particularly relative to their N-sulfotransferase domains, and including biological functional fragments thereof. According to the present invention, an engineered NST enzyme can have at least 50% sequence identity, and up to at least 97% sequence identity, with the N-sulfotransferase domain of any of the enzymes within EC 2.8.2.8. In a non-limiting example, the amino acid sequence of the non-natural NST enzyme can have at least 80% sequence identity with the amino acid sequence of the N-sulfotransferase domain of a natural NDST enzyme, the natural NDST enzyme selected from the group consisting of: the human NDST1 enzyme (SEQ ID NO: 164, UniProtKB Accession No. P52848); the human NDST2 enzyme (SEQ ID NO: 177, UniProtKB Accession No. P52849); the human NDST3 enzyme (SEQ ID NO: 174, UniProtKB Accession No. O95803); and the human NDST4 enzyme (SEQ ID NO: 173, UniProtKB Accession No. Q9H3R1). According to the present invention, such engineered NST enzymes can also have an N-deacetylase domain that is either identical to, or contains one or more amino acid mutations relative to, any of the enzymes within EC 2.8.2.8.

According to the present invention, an engineered NST enzyme can comprise one or more mutated amino acid sequence motifs relative to conserved amino acid sequence motifs found in one or more natural NDST enzymes within EC 2.8.2.8. Each mutated amino acid sequence motif, when present, can have at least one amino acid mutation relative to the corresponding conserved amino acid sequence motif within the natural NDSTs. According to the present invention, an engineered NST enzyme can comprise one, two, three, four, or five mutated amino acid sequence motifs relative to the following conserved NST amino acid sequence motifs: (Q-K-T-G-T-T-A), (T-F-E-E), (F-E-K-S-A), (S-W-Y-Q-H), and (C-L-G-K/R-S-K-G-R), which correspond to SEQ ID NO: 221, SEQ ID NO: 222, SEQ ID NO: 223, SEQ ID NO: 224, and SEQ ID NO: 225 in the sequence listing, respectively. In some embodiments, within the amino acid sequence of the engineered NST enzyme, the conserved Q-K-T-G-T-T-A amino acid sequence motif (SEQ ID NO: 221) is mutated to an amino acid sequence motif selected from the group consisting of: H-$X_1$-T-G-$X_2$-H-A (SEQ ID NO: 226), wherein $X_1$ and $X_2$ are either both glycine (as indicated in SEQ ID NO: 227), or wherein $X_1$ is lysine and $X_2$ is valine (as indicated in SEQ ID NO: 228); and $X_3$-K-T-G-A-W/F-A/L (SEQ ID NO: 234), wherein $X_3$ can optionally be mutated to a serine (as indicated in SEQ ID NO: 235) or alanine (as indicated in SEQ ID NO: 236). In some embodiments, when the mutated amino acid sequence motif H-$X_1$-T-G-$X_2$-H-A (SEQ ID NO: 226) is selected, the C-terminal lysine residue within the conserved C-L-G-K/R-S-K-G-R amino acid sequence motif (SEQ ID NO: 225) is mutated to either a leucine or valine residue (see, as non-limiting examples, SEQ ID NO: 229, SEQ ID NO: 230, and SEQ ID NO: 243), and the amino acid sequence of the non-natural NST enzyme contains at least one additional mutation to a histidine residue, at a position selected from the group consisting of: the C-terminal glutamic acid residue in the conserved T-F-E-E amino acid sequence (as illustrated in SEQ ID NO: 231); the lysine residue in the conserved F-E-K-S-A amino acid sequence (as illustrated in SEQ ID NO: 232); and the serine residue in the conserved C-L-G-K/R-S-K-G-R amino acid sequence (as illustrated in SEQ ID NO: 233). In some embodiments, when the mutated amino acid sequence motif $X_3$-K-T-G-A-W/F-A/L (SEQ ID NO: 234) is selected, the final three residues in the conserved T-F-E-E amino acid sequence motif are mutated such that the C-terminal glutamic acid residue in SEQ ID NO: 222 is mutated to a serine residue, and the mutated amino acid sequence motif is selected from the group consisting of: T-H-G-S(SEQ ID NO: 237); T-G-H-S(SEQ ID NO: 238); the conserved C-L-G-K/R-S-K-G-R amino acid sequence motif (SEQ ID NO: 225) is mutated to include a histidine residue, at a position selected from the group consisting of the leucine residue, the serine residue, or the C-terminal lysine residue (as illustrated in SEQ ID NO: 239, SEQ ID NO: 240, or SEQ ID NO: 243, respectively), and if the histidine is substituted within the conserved C-L-G-K/R-S-K-G-R amino acid sequence motif at the leucine or serine residue, the C-terminal lysine residue is mutated to either a leucine (as illustrated in SEQ ID NO: 239 or SEQ ID NO: 240) or a tryptophan residue (as illustrated in SEQ ID NO: 241 or SEQ ID NO: 242). Additional non-limiting examples of mutated amino acid sequence motifs are described in further detail, below.

According to the present invention, an engineered NST enzyme can comprise an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25, each of which contains several amino acid mutations made relative to highly conserved amino acid sequences that define the N-sulfotransferase domain of natural enzymes within EC 2.8.2.8. According to the present invention, engineered NST enzymes utilized in accordance with any of the methods described herein can also comprise any amino acid sequence that is a biological equivalent, and/or a functional fragment, of an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

According to the present invention, any of the engineered NST enzymes described above can possess one or more residue differences or mutations as compared to the amino acid sequences disclosed by an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25. Non-limiting examples of such residue differences include amino acid insertions, deletions, substitutions, or any combination of such changes. According to the present invention, differences from the disclosed amino acid sequences in an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25 can comprise non-conservative substitutions, conservative substitutions, as well as combinations of conservative and non-conservative amino acid substitutions. According to the present invention, an amino acid mutation can be made at any position within SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25, so long as the mutated enzyme retains its NST activity with an aryl sulfate compound as a sulfo group donor and a heparosan-based polysaccharide comprising the structure of Formula II as the sulfo group acceptor.

According to the present invention, an engineered NST enzyme can comprise the amino acid sequence of SEQ ID NO: 18. Within SEQ ID NO: 18, residues having the designation, "Xaa," illustrate known instances in which there is a lack of identity at a particular position within the amino acid sequences of SEQ ID NO: 5, SEQ ID NO: 7, and SEQ ID NO: 15. Thus, an "Xaa" designation indicates the amino acid at that position can be selected from a group of two or more amino acids, as defined by SEQ ID NO: 18.

According to the present invention, an engineered NST enzyme can comprise the amino acid sequence of SEQ ID NO: 19. Within SEQ ID NO: 19, residues having the designation, "Xaa," illustrate known instances in which there is a lack of identity at a particular position within the amino acid sequences of SEQ ID NO: 9, SEQ ID NO: 11, and SEQ ID NO: 13. Thus, an "Xaa" designation indicates the amino acid at that position can be selected from a group of two or more amino acids, as defined by SEQ ID NO: 19.

Additionally, and according to the present invention, amino acid mutations can be made at one or more positions within SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25 so long as the mutated enzyme retains its glucosaminyl N-sulfotransferase activity with an aryl sulfate compound as a sulfo group donor. According to the present invention, an aryl sulfate-dependent enzyme comprising the amino acid sequence of SEQ ID NO: 18 or SEQ ID NO: 19 can optionally comprise one or more amino acid mutations at positions not designated as "Xaa," while still retaining its glucosaminyl N-sulfotransferase activity with an aryl sulfate compound as a sulfo group donor.

In an aspect of the invention, an engineered sulfotransferase enzyme can have hexuronyl 2-O sulfotransferase activity, comprising the transfer of a sulfo group from an aryl sulfate compound to the 2-O position of a hexuronic acid residue within a heparosan-based polysaccharide. According to the present invention, an engineered 2OST can comprise any amino acid sequence, so long as the sulfo group donor is an aryl sulfate compound and the sulfo group acceptor is a heparosan-based polysaccharide.

According to the present invention, engineered 2OST enzymes can be mutants of natural sulfotransferases that have 2OST activity, which are members of enzyme class (EC) 2.8.2.-. In contrast to the engineered 2OST enzymes of the present invention, natural 2OST enzymes within EC 2.8.2.- do not react with aryl sulfate compounds, and only react with PAPS as a sulfo group donor. However, the engineered 2OST enzymes can retain the same biological activity as the natural 2OST enzymes within EC 2.8.2.- with heparosan-based polysaccharides as sulfo group acceptors. According to the present invention, heparosan-based polysaccharides that can be utilized as sulfo acceptors with any of the engineered 2OST enzymes can comprise one or more structural motifs having the structure of Formula IV, below:

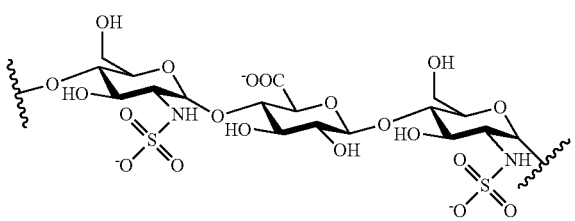

As indicated in Formula IV, the hexuronic acid residue is glucuronic acid. According to the present invention, and in another non-limiting example, when the hexuronic acid residue is iduronic acid, the heparosan-based polysaccharide comprises the structure of Formula V, below:

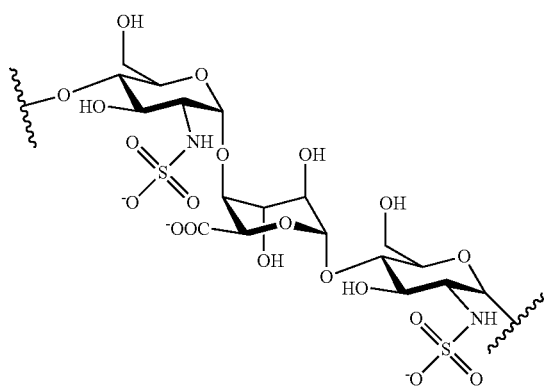

According to the present invention, when the heparosan-based polysaccharide comprises the structure of Formula IV, the 2-O sulfated polysaccharide product comprises the structure of Formula VI, below:

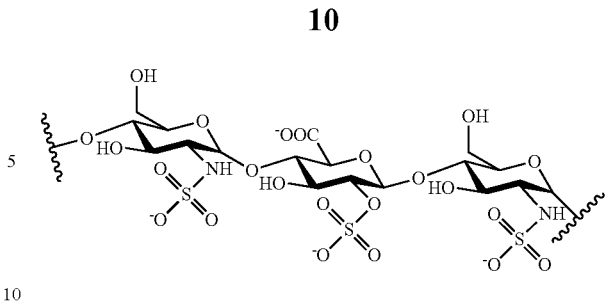

According to the present invention, when the heparosan-based polysaccharide comprises the structure of Formula V, the 2-O sulfated polysaccharide product comprises the structure of Formula VII, below:

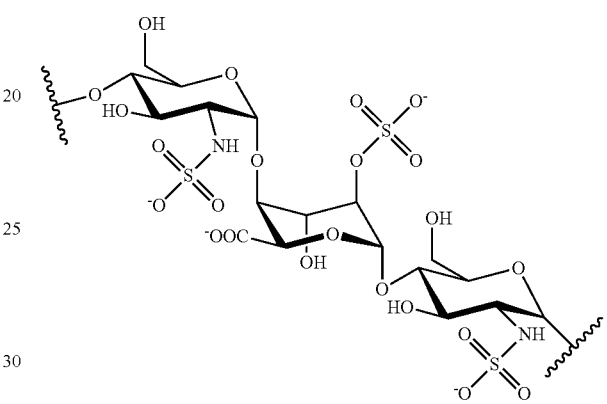

According to the present invention, the heparosan-based polysaccharide comprising the structure of Formula IV or Formula V can be N-sulfated heparosan. According to the present invention, a sulfo group acceptor for an engineered 2OST enzyme can comprise multiple motifs comprising the structure of Formula IV and/or Formula V, any or all of which can be sulfated by the enzyme. According to the present invention, and as illustrated in Formula IV and Formula V above, both of the glucosamine residues adjacent to the hexuronic acid residue that receives the sulfo group are N-sulfated. According to the present invention, a sulfo group acceptor for an engineered 2OST enzyme can be the sulfated polysaccharide product of an engineered NST enzyme, described above. According to the present invention, a sulfated polysaccharide product formed by an engineered 2OST enzyme, and comprising the structure(s) of Formula VI and/or Formula VII, is an N,2O-HS product.

According to the present invention, glucosamine residues within the polysaccharide that are not adjacent to the hexuronic acid residue receiving the sulfo group can optionally be N-, 3-O, and/or 6-O sulfated, N-acetylated, or N-unsubstituted. Similarly, hexuronic acid residues in other positions within the polysaccharide that are not adjacent to the glucosamine residue receiving the sulfo group can be glucuronic acid or iduronic acid residues, any of which can be optionally 2-O sulfated.

According to the present invention, polysaccharides comprising the structures of Formula IV and/or Formula V can be reacted with a glucuronyl $C_5$-epimerase enzyme to reversibly invert the stereochemistry of the $C_5$-carbon to form iduronic acid from glucuronic acid, and vice versa. However, once a hexuronic acid residue has been 2-O sulfated, it can no longer react with the glucuronyl $C_5$-epimerase. In some preferred embodiments, a glucuronyl C$_5$-epimerase enzyme can be used to invert the stereochemistry of hexuronic acid residues within N-sulfated heparosan polysaccharides comprising the structure of Formula III and form a structural motif comprising the structure of Formula V, prior to reacting with a 2OST enzyme. According to the present invention, the glucuronyl $C_5$-epimerase enzyme can comprise the amino acid sequence of SEQ ID NO: 67, preferably residues 34-617 of SEQ ID NO: 67. According to the present invention, the glucuronyl $C_5$-epimerase enzyme can be used to catalyze the conversion of one or more glucuronic acid residues within N-sulfated heparosan to iduronic acid residues, prior to reacting with an engineered 2OST enzyme.

To facilitate its exclusive reactivity with PAPS as the sulfo group donor, natural 2OST enzymes within EC 2.8.2.- typically comprise highly-conserved or identical amino acid sequences that define the active site and govern the enzyme's recognition, binding, and reactivity with PAPS. According to the present invention, the amino acid sequence of an engineered 2OST enzyme can comprise one or more mutations relative to one or more natural 2OST enzymes within EC 2.8.2.-, in order to facilitate binding of an aryl sulfate compound instead of PAPS. According to the present invention, an engineered 2OST enzyme can comprise an amino acid sequence having at least one amino acid mutation relative to any of the natural 2OST enzymes within EC 2.8.2.-, including at least two, three, four, five, six, seven, eight, nine, ten, eleven, twelve, thirteen, fourteen, fifteen, twenty, thirty, forty, fifty, up to at least one hundred amino acid mutations. According to the present invention, an engineered 2OST enzyme can comprise at least one amino acid mutation relative to the amino acid sequence of any of the natural 2OST enzymes within EC 2.8.2.-, in regions that are known to define the enzyme's active site, including at least two, three, four, five, six, seven, eight, nine, ten, eleven, twelve, thirteen, fourteen, or fifteen amino acid mutations, up to at least twenty amino acid mutations.

According to the present invention, the amino acid sequence of an engineered 2OST enzyme can be expressed as a "percent identity" or "% identity" relative to the amino acid sequence of one or more of the natural 2OST enzymes within EC 2.8.2.-, including biological functional fragments thereof. According to the present invention, an engineered 2OST enzyme can have at least 50% sequence identity, and up to at least 97% sequence identity, with any of the 2OST enzymes within EC 2.8.2.-. In a non-limiting example, the amino acid sequence of the engineered 2OST enzyme can have at least 80% sequence identity with the amino acid sequence of the chicken 2OST1 enzyme (SEQ ID NO: 179, UniProtKB Accession No. Q76KB1).

According to the present invention, an engineered 2OST enzyme can comprise one or more mutated amino acid sequence motifs relative to conserved amino acid sequence motifs found in one or more natural 2OST enzymes within EC 2.8.2.-. Each mutated amino acid sequence motif, when present, can have at least one amino acid mutation relative to the corresponding conserved amino acid sequence motif within the natural 2OST enzymes within EC 2.8.2.-. According to the present invention, an engineered 2OST enzyme can comprise one, two, three, four, five, or six mutated amino acid sequence motifs relative to the following conserved 2OST amino acid sequence motifs: (R-V-P-K-T-A/G-S-T), (N-T-S/T-K-N), (Y-H-G-H), (F-L-R-F/H-G-D-D/N-F/Y), (R-R-K/R-Q-G), and (S-H-L-R-K/R-T), which correspond to SEQ ID NO: 244, SEQ ID NO: 273, SEQ ID NO: 274, SEQ ID NO: 245, SEQ ID NO: 246, and SEQ ID NO: 247 in the sequence listing, respectively. In some embodiments, within the amino acid sequence of the engineered 2OST enzyme, the conserved R-V-P-K-T-A/G-S-T amino acid sequence motif (SEQ ID NO: 244) is mutated to the amino acid sequence motif R-V-$X_1$-$X_2$-T-A-S-$X_3$, wherein the amino acid sequence motif R-V-$X_1$-$X_2$-T-A-S-$X_3$ is selected from the group consisting of R-V-P-H-T-A-S-T and R-V-H-R-T-A-S-H (corresponding to SEQ ID NO: 248 and SEQ ID NO: 249 in the sequence listing, respectively), and the conserved S-H-L-R-K/R-T amino acid sequence motif (SEQ ID NO: 247) is mutated to S-H-L-H-K-T (SEQ ID NO: 250). In a further embodiment, when the amino acid sequence R-V-P-H-T-A-S-T (SEQ ID NO: 248) is selected, the conserved F-L-R-F/H-G-D-D/N-F/Y sequence motif (SEQ ID NO: 245) can be mutated to H-L-R-F-G-D-D-Y (SEQ ID NO: 251). Additional non-limiting examples of mutated amino acid sequence motifs are described in further detail, below.

According to the present invention, an engineered 2OST enzyme can comprise an amino acid sequence selected from the group consisting of SEQ ID NO: 63, SEQ ID NO: 65, SEQ ID NO: 68, and SEQ ID NO: 69, each of which contains several amino acid mutations made relative to highly conserved amino acid sequences that define the natural 2OST enzymes within EC 2.8.2.-. According to the present invention, engineered 2OST enzymes utilized in accordance with any of the methods described herein can also comprise any amino acid sequence that is a biological equivalent, and/or a functional fragment, of an amino acid sequence selected from the group consisting of SEQ ID NO: 63, SEQ ID NO: 65, SEQ ID NO: 68, and SEQ ID NO: 69.

According to the present invention, any of the engineered 2OST enzymes described above can possess one or more residue differences or mutations as compared to the amino acid sequences disclosed by an amino acid sequence selected from the group consisting of SEQ ID NO: 63, SEQ ID NO: 65, SEQ ID NO: 68, and SEQ ID NO: 69. Non-limiting examples of such residue differences include amino acid insertions, deletions, substitutions, or any combination of such changes. According to the present invention, differences from the disclosed amino acid sequences in an amino acid sequence selected from the group consisting of SEQ ID NO: 63, SEQ ID NO: 65, SEQ ID NO: 68, and SEQ ID NO: 69 can comprise non-conservative substitutions, conservative substitutions, as well as combinations of conservative and non-conservative amino acid substitutions. According to the present invention, an amino acid mutation can be made at any position within SEQ ID NO: 63, SEQ ID NO: 65, SEQ ID NO: 68, or SEQ ID NO: 69, so long as the mutated enzyme retains its hexuronyl 2-O sulfotransferase activity with an aryl sulfate compound as a sulfo group donor and a heparosan-based polysaccharide comprising the structure of Formula IV and/or Formula V as the sulfo group acceptor.

In an aspect of the invention, an engineered sulfotransferase enzyme can have glucosaminyl 6-O sulfotransferase activity, comprising the transfer of a sulfo group from an aryl sulfate compound to the 6-O position of a glucosamine residue within a heparosan-based polysaccharide. According to the present invention, an engineered 6OST enzyme can comprise any amino acid sequence, so long as the sulfo group donor is an aryl sulfate compound and the sulfo group acceptor is a heparosan-based polysaccharide.

According to the present invention, engineered 6OST enzymes can be mutants of natural sulfotransferases that have glucosaminyl 6-O sulfotransferase activity, which are members of EC 2.8.2.-. In contrast to the engineered 6OST enzymes of the present invention, natural 6OST enzymes within EC 2.8.2.- do not react with aryl sulfate compounds, and only react with PAPS as a sulfo group donor. However, the engineered 6OST enzymes can retain the same biological activity as the natural 6OST enzymes within EC 2.8.2.- with heparosan-based polysaccharides as sulfo group acceptors.

According to the present invention, the glucosamine residue receiving the sulfo group at the 6-O position can be N-sulfated, N-unsubstituted, and/or 3-O sulfated, prior to reacting with the enzyme. According to the present invention, any other glucosamine residue within the sulfo acceptor polysaccharide can be optionally be N-, 3-O, and/or 6-O sulfated, N-acetylated, or N-unsubstituted. According to the present invention, any of the hexuronic acid residues within the heparosan-based polysaccharide, including hexuronic acid residues adjacent to the glucosamine residue receiving the sulfo group, can optionally be iduronic acid or glucuronic acid, and can optionally be 2-O sulfated, prior to reacting with the 6OST enzyme.

One non-limiting example of a heparosan-based polysaccharide that can be utilized as a sulfo acceptor with any of the engineered 6OST enzymes is a heparosan-based polysaccharide comprising one or more structural motifs having the structure of Formula VIII, below:

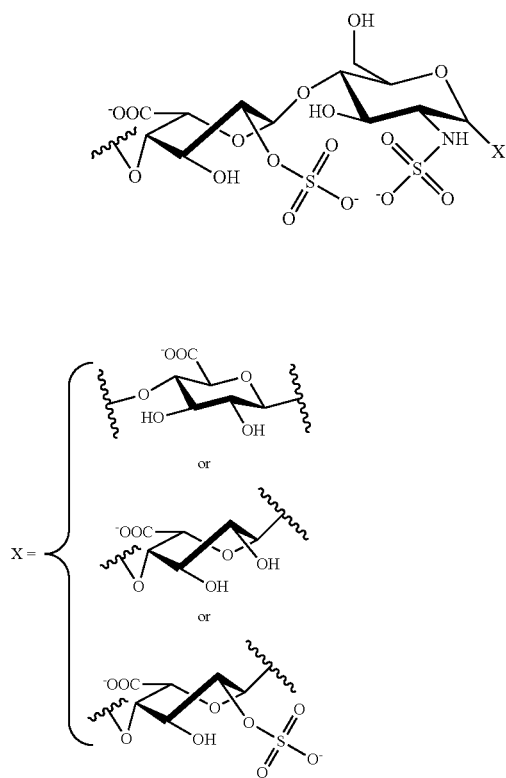

wherein X comprises any of the hexuronic acid residues depicted in Formula VIII above. When the sulfo acceptor polysaccharide comprises the structure of Formula VIII, upon transfer of the sulfo group from an aryl sulfate compound, the sulfated polysaccharide product comprises the structure of Formula IX, below:

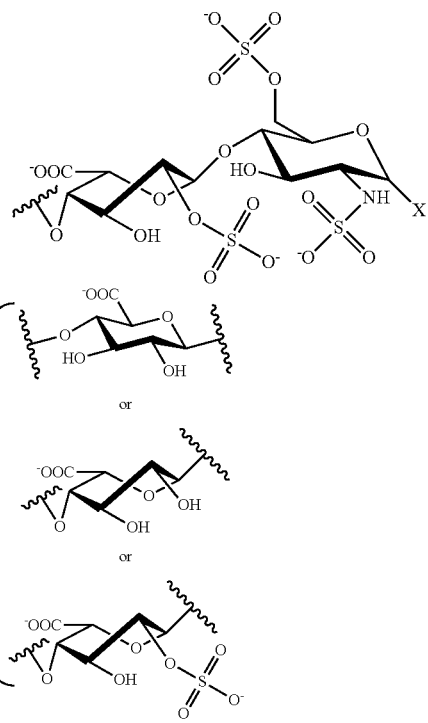

wherein X comprises any of the hexuronic acid residues depicted in Formula IX, above.

According to the present invention, the sulfo group acceptor for the engineered 6OST enzyme can comprise multiple structural motifs comprising the structure of Formula VIII, any or all of which can be sulfated by an engineered 6OST enzyme. According to the present invention, the sulfo group acceptor can be N-deacetylated heparosan. According to the present invention, the sulfo group acceptor can be N-sulfated heparosan. According to the present invention, the sulfo group acceptor for the engineered 6OST can be N,2O-HS. According to the present invention, the sulfo group acceptor for the engineered 6OST enzyme can be a sulfated polysaccharide product formed by an engineered NST enzyme, described above. According to the present invention, the sulfo group acceptor for the engineered 6OST enzyme can be a sulfated polysaccharide product formed by an engineered 2OST enzyme, as described above. According to the present invention, the sulfated polysaccharide product of an engineered 6OST enzyme is an N,2O,6O-HS product.

To facilitate its exclusive reactivity with PAPS as the sulfo group donor, natural 6OST enzymes within EC 2.8.2.- typically comprise highly-conserved or identical amino acid sequences that define the active site and govern the enzyme's recognition, binding, and reactivity with PAPS. According to the present invention, the amino acid sequence of an engineered 6OST enzyme can comprise one or more mutations relative to natural 6OST enzymes within EC 2.8.2.-, in order to facilitate binding of an aryl sulfate compound instead of PAPS. According to the present invention, an engineered 6OST enzyme can comprise an amino acid sequence having at least one amino acid mutation relative to any of the natural 6OST enzymes within EC 2.8.2.-, including at least two, three, four, five, six, seven, eight, nine, ten, eleven, twelve, thirteen, fourteen, fifteen, twenty, thirty, forty, fifty, up to at least one hundred amino acid mutations. According to the present invention, an engineered 6OST enzyme can comprise at least one amino acid mutation relative to the amino acid sequence of any of the natural 6OST enzymes within EC 2.8.2.-, in regions that are known to define the enzyme's active site, including at least two, three, four, five, six, seven, eight, nine, ten, eleven, twelve, thirteen, fourteen, or fifteen amino acid mutations, up to at least twenty amino acid mutations.

According to the present invention, the amino acid sequence of an engineered 6OST enzyme can be expressed as a "percent identity" or "% identity" relative to the amino acid sequence of one or more of the natural 6OST enzymes within EC 2.8.2.-, particularly relative to one or more of the natural 6OST enzymes within EC 2.8.2.-, and including biological functional fragments thereof. According to the present invention, an engineered 6OST enzyme can have at least 50% sequence identity, and up to at least 97% sequence identity, with any of the natural 6OST enzymes within EC 2.8.2.-. In a non-limiting example, the amino acid sequence of the non-natural 6OST enzyme can have at least 80% sequence identity with the amino acid sequence of a natural 6OST enzyme, the natural 6OST enzyme selected from the group consisting of the mouse 6OST1 enzyme (SEQ ID NO: 191, UniProtKB Accession No. Q9QYK5), the mouse 6OST2 enzyme (SEQ ID NO: 199, UniProtKB Accession No. Q80UW0), and the mouse 6OST3 enzyme (SEQ ID NO: 201, UniProtKB Accession No. Q9QYK4).

According to the present invention, an engineered 6OST enzyme can comprise one or more mutated amino acid sequence motifs relative to conserved amino acid sequence motifs found in one or more natural 6OST enzymes within EC 2.8.2.-. Each mutated amino acid sequence motif, when present, can have at least one amino acid mutation relative to the corresponding conserved amino acid sequence motif within the natural 6OST enzymes within EC 2.8.2.-. According to the present invention, an engineered 6OST enzyme can comprise one, two, three, four, or five mutated amino acid sequence motifs relative to the following conserved 6OST amino acid sequence motifs: (Q-K-T-G-G-T), (C-G-L-H-A-D), (L-R-D-V-P-S), (S-E-W-R/K-H-V-Q-R-G-A-T-W-K), or (L-T-E-F/Y-Q), which correspond to SEQ ID NO: 254, SEQ ID NO: 255, SEQ ID NO: 275, SEQ ID NO: 256, and SEQ ID NO: 276 in the sequence listing, respectively. In some embodiments, the conserved Q-K-T-G-G-T amino acid sequence motif (SEQ ID NO: 254) is mutated to G-H-T-G-G-T (SEQ ID NO: 257); the leucine residue within the conserved C-G-L-H-A-D amino acid sequence motif (SEQ ID NO: 255) is mutated to a alcohol residue selected from the group consisting of a threonine and a serine (as indicated in SEQ ID NO: 258 or SEQ ID NO: 259, respectively), and the conserved S-E-W-R/K-H-V-Q-R-G-A-T-W-K amino acid sequence motif (SEQ ID NO: 256) is mutated to the amino acid sequence motif $X_1$-$X_2$-W-R-H-$X_3$-Q-R-G-G-$X_4$-N-K (SEQ ID NO: 260), wherein: $X_1$ can be selected from the group consisting of serine or glycine; $X_2$ can be selected from the group consisting of glycine and histidine; $X_3$ can be selected from the group consisting of threonine and histidine; and $X_4$ can be selected from the group consisting of threonine and alanine. In some further embodiments, the identity of $X_1$ and $X_4$ are dependent on each other such that when $X_1$ is glycine, $X_4$ is threonine (as illustrated in SEQ ID NO: 261), and when $X_1$ is serine, $X_4$ is alanine (as illustrated in SEQ ID NO: 262). In other further embodiments, the identity of $X_2$ and $X_3$ are dependent on each other such that when $X_2$ is glycine, $X_3$ is histidine (as illustrated in SEQ ID NO: 263), and when $X_2$ is histidine, $X_3$ is threonine (as illustrated in SEQ ID NO: 264). Additional non-limiting examples of mutated amino acid sequence motifs are described in further detail, below.

According to the present invention, an engineered 6OST enzyme can comprise an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122, each of which contains several amino acid mutations made relative to highly conserved amino acid sequences of natural 6OST enzymes within EC 2.8.2.-. According to the present invention, engineered 6OST enzymes utilized in accordance with any of the methods described herein can also comprise any amino acid sequence that is a biological equivalent, and/or a functional fragment, of an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122.

According to the present invention, any of the engineered 6OST enzymes described above can possess one or more residue differences or mutations as compared to the amino acid sequences disclosed by an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122. Non-limiting examples of such residue differences include amino acid insertions, deletions, substitutions, or any combination of such changes. According to the present invention, differences from the disclosed amino acid sequences in an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122 can comprise non-conservative substitutions, conservative substitutions, as well as combinations of conservative and non-conservative amino acid substitutions. According to the present invention, an amino acid mutation can be made at any position within SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122, so long as the mutated enzyme retains its 6OST activity with an aryl sulfate compound as a sulfo group donor and any of the heparosan-based polysaccharides described above as a sulfo group acceptor.

According to the present invention, an engineered 6OST enzyme can comprise the amino acid sequence of SEQ ID NO: 112. Within SEQ ID NO: 112, residues having the designation, "Xaa," illustrate known instances in which there is a lack of identity at a particular position within the amino acid sequences of SEQ ID NO: 104, SEQ ID NO: 106, and SEQ ID NO: 108. Thus, an "Xaa" designation indicates the amino acid at that position can be selected from a group of two or more amino acids, as defined by SEQ ID NO: 112.

According to the present invention, an engineered 6OST enzyme can comprise the amino acid sequence of SEQ ID NO: 113. According to the present invention, within SEQ ID NO: 113, residues having the designation, "Xaa," illustrate known instances in which there is a lack of identity at a particular position within the amino acid sequences of SEQ ID NO: 104, SEQ ID NO: 106, and SEQ ID NO: 108. According to the present invention, SEQ ID NO: 113 also comprises N-terminal residues 1-66, and C-terminal residues 378-411, of several full-length 6OST enzymes within EC 2.8.2.-, including, as non-limiting examples, the mouse, human, and pig 6OST enzymes. Thus, an "Xaa" designation indicates the amino acid at that position can be selected from a group of two or more amino acids, as defined by SEQ ID NO: 113.

Additionally, and according to the present invention, amino acid mutations can be made at one or more positions within SEQ ID NO: 104, SEQ ID NO: 106, SEQ ID NO: 108, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122 so long as the mutated enzyme retains its glucosaminyl 6-O sulfotransferase activity with an aryl sulfate compound as a sulfo group donor. According to the present invention, an aryl sulfate-dependent enzyme comprising the amino acid sequence of SEQ ID NO: 132 or SEQ ID NO: 133 can optionally comprise one or more amino acid mutations at positions not designated as "Xaa," while still retaining its glucosaminyl 6-O sulfotransferase activity with an aryl sulfate compound as a sulfo group donor.

In an aspect of the invention, an engineered sulfotransferase enzyme can have glucosaminyl 3-O sulfotransferase activity, comprising the transfer of a sulfo group from an aryl sulfate compound to the 3-O position of a glucosamine residue within a heparosan-based polysaccharide. According to the present invention, an engineered 3OST can comprise any amino acid sequence, so long as the sulfo group donor is an aryl sulfate compound and the sulfo group acceptor is a heparosan-based polysaccharide.

According to the present invention, engineered 3OST enzymes can be mutants of natural sulfotransferases that have 3OST activity, which are members of EC 2.8.2.23. In contrast to the engineered 3OST enzymes of the present invention, natural 3OST enzymes within EC 2.8.2.23 do not react with aryl sulfate compounds, and only react with PAPS as a sulfo group donor. However, the engineered 3OST enzymes can retain the same biological activity as the natural 3OST enzymes within EC 2.8.2.23 with heparosan-based polysaccharides as sulfo group acceptors.

According to the present invention, glucosamine residues within the heparosan-based polysaccharide that can receive a sulfo group at the 3-O position are N-sulfated, and can optionally comprise a 6-O sulfo group as well. According to the present invention, any other glucosamine residue within the sulfo acceptor polysaccharide can be optionally be N-, 3-O, and/or 6-O sulfated, N-acetylated, or N-unsubstituted. According to the present invention, one or more of the glucosamine residues within the heparosan-based polysaccharide, including the glucosamine residue being 3-O sulfated, can be both N-sulfated and 6-O sulfated. According to the present invention, the glucosamine residue being 3-O sulfated can be adjacent to an unsulfated glucuronic acid residue at the non-reducing end and an iduronic acid residue at the reducing end. According to the present invention, the iduronic acid residue at the reducing end of the glucosamine residue being 3-O sulfated can optionally be 2-O sulfated. According to the present invention, any of the other hexuronic acid residues within the heparosan-based polysaccharide acting as the sulfo group acceptor for the 3OST can optionally be iduronic acid or glucuronic acid, and can optionally be 2-O sulfated. One non-limiting example of a heparosan-based polysaccharide that can be utilized as a sulfo acceptor with any of the engineered 3OST enzymes is a heparosan-based polysaccharide comprising one or more structural motifs having the structure of Formula X, below:

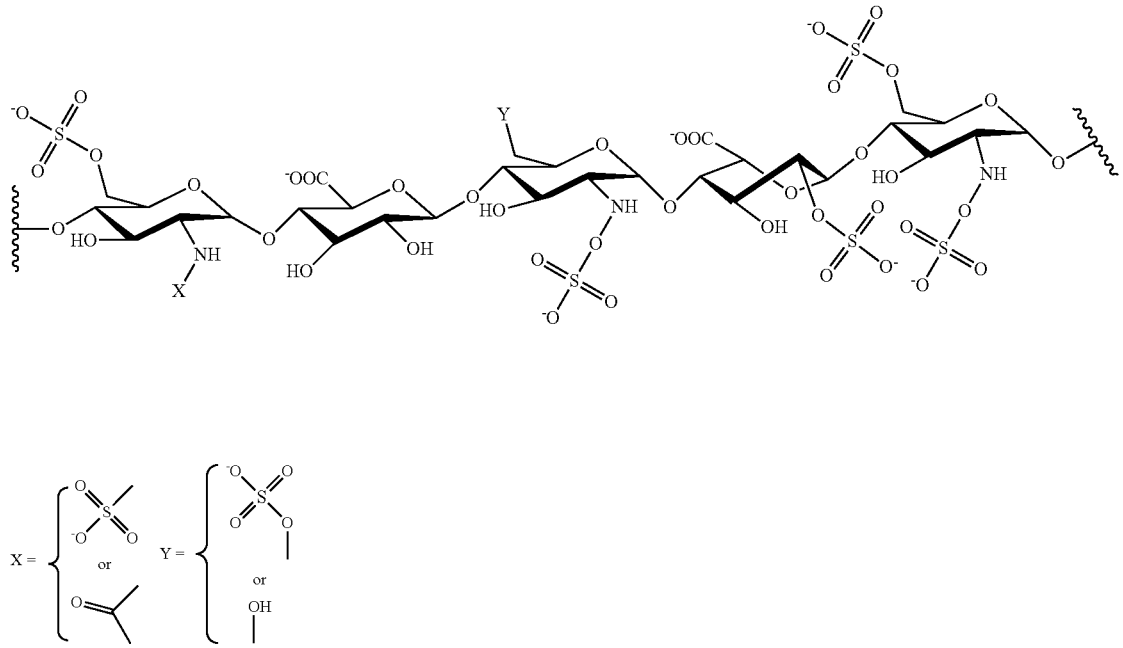

wherein X is either a sulfo group or an acetate group and Y is either a sulfo group or a hydroxyl group. According to the present invention, in some preferred embodiments, X can be a sulfo group and Y can be a sulfo group. When the heparosan-based polysaccharide comprises the structure of Formula X, the 3-O sulfated polysaccharide product comprises the structure of Formula I, below:

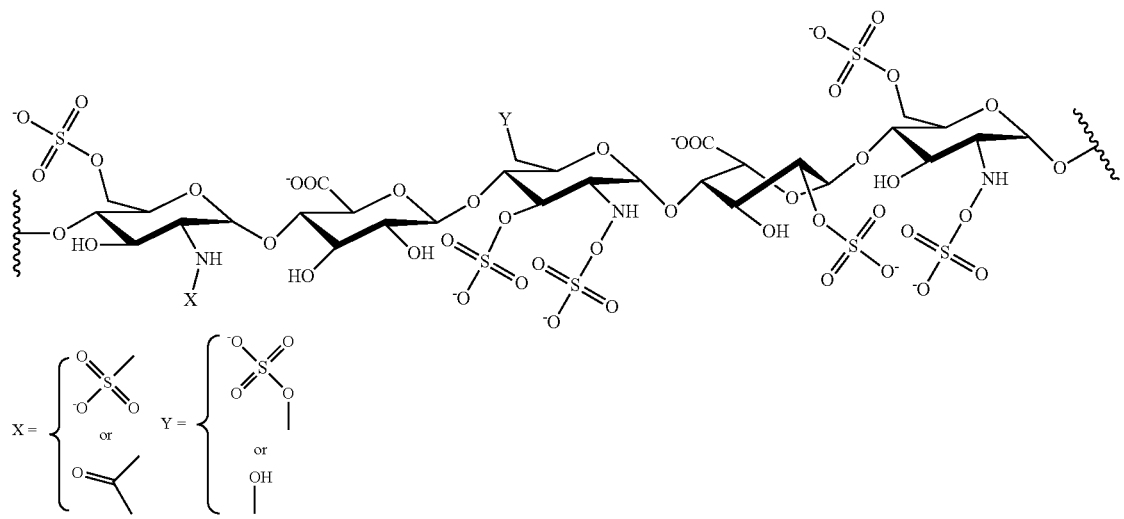

wherein X is either a sulfo group or an acetate group and Y is either a sulfo group or a hydroxyl group. According to the present invention, in some preferred embodiments, X can be a sulfo group and Y can be a sulfo group. According to the present invention, an N,2O,3O,6O-HS products comprising the structure of Formula I and which are formed upon reacting with an engineered 3OST enzyme can have anticoagulant activity and have similar or equivalent physical properties to heparin. The anticoagulant activity of heparin and other N,2O,3O,6O-HS polysaccharides is described in further detail, below.

According to the present invention, the sulfo group acceptor for the engineered 3OST enzyme can comprise multiple structural motifs comprising the structure of Formula X, any or all of which can be sulfated by an engineered 3OST enzyme. According to the present invention, the sulfo group acceptor for the engineered 3OST can be N,2O,6O-HS. According to the present invention, the sulfo group acceptor for the engineered 3OST enzyme can be a sulfated polysaccharide product formed by an engineered 6OST enzyme, described above.

To facilitate its exclusive reactivity with PAPS as the sulfo group donor, natural 3OST enzymes within EC 2.8.2.23 typically comprise highly-conserved or identical amino acid sequences that define the active site and govern the enzyme's recognition, binding, and reactivity with PAPS. According to the present invention, the amino acid sequence of an engineered 3OST enzyme can comprise one or more mutations relative to natural 3OST enzymes within EC 2.8.2.23, in order to facilitate binding of an aryl sulfate compound instead of PAPS. According to the present invention, an engineered 3OST enzyme can comprise an amino acid sequence having at least one amino acid mutation relative to any of the natural 3OST enzymes within EC 2.8.2.23, including at least two, three, four, five, six, seven, eight, nine, ten, eleven, twelve, thirteen, fourteen, fifteen, twenty, thirty, forty, fifty, up to at least one hundred amino acid mutations. According to the present invention, an engineered 3OST enzyme can comprise at least one amino acid mutation relative to the amino acid sequence of any of the natural 3OST enzymes within EC 2.8.2.23, in regions that are known to define the enzyme's active site, including at least two, three, four, five, six, seven, eight, nine, ten, eleven, twelve, thirteen, fourteen, or fifteen amino acid mutations, up to at least twenty amino acid mutations.

According to the present invention, the amino acid sequence of an engineered 3OST enzyme can be expressed as a "percent identity" or "% identity" relative to the amino acid sequence of one or more of the natural 3OST enzymes within EC 2.8.2.23, particularly relative to one or more of the natural 3OST enzymes within EC 2.8.2.23, and including biological functional fragments thereof. According to the present invention, an engineered 3OST enzyme can have at least 50% sequence identity, and up to at least 97% sequence identity, with any of the natural 3OST enzymes within EC 2.8.2.23. In a non-limiting example, the amino acid sequence of the engineered 3OST enzyme can have at least 80% sequence identity with the amino acid sequence of a natural 3OST enzyme, the natural 3OST enzyme selected from the group consisting of the human 3OST1 enzyme (SEQ ID NO: 206, UniProtKB Accession No. O14792) and the human 3OST5 enzyme (SEQ ID NO: 220, UniProtKB Accession No. Q8IZT8).

According to the present invention, an engineered 3OST enzyme can comprise one or more mutated amino acid sequence motifs relative to conserved amino acid sequence motifs found in one or more natural 3OST enzymes within EC 2.8.2.23. Each mutated amino acid sequence motif, when present, can have at least one amino acid mutation relative to the corresponding conserved amino acid sequence motif within the natural 3OST enzymes within EC 2.8.2.23. According to the present invention, an engineered 3OST enzyme can comprise one, two, three, or four mutated amino acid sequence motifs relative to the following conserved 3OST amino acid sequence motifs: (G-V-R-K-G-G), (P-A/G-Y-F), (S-D-Y-T-Q-V), or (Y-K-A). The conserved amino acid sequence motifs G-V-R-K-G-G, P-A/G-Y-F, and S-D-Y-T-Q-V correspond to SEQ ID NO: 265, SEQ ID NO: 266, and SEQ ID NO: 267 in the sequence listing, respectively. In some embodiments, within the amino acid sequence of the engineered 3OST enzyme, the conserved G-V-R-K-G-G amino acid sequence motif (SEQ ID NO: 265) is mutated to G-V-G-H-G-G (SEQ ID NO: 268), the conserved P-A/G-Y-F amino acid sequence motif (SEQ ID NO: 266) is mutated to H-S-Y-F (SEQ ID NO: 269), and the conserved Y-K-A amino acid sequence motif is mutated to Y-V/T-G.

Additional non-limiting examples of mutated amino acid sequence motifs are described in further detail, below.

According to the present invention, an engineered 3OST enzyme can comprise an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160, each of which contains several amino acid mutations made relative to highly conserved amino acid sequences of natural 3OST enzymes within EC 2.8.2.23. According to the present invention, engineered 3OST enzymes utilized in accordance with any of the methods described herein can also comprise any amino acid sequence that is a biological equivalent, and/or a functional fragment, of an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160.

According to the present invention, any of the engineered 3OST enzymes described above can possess one or more residue differences or mutations as compared to the amino acid sequences disclosed by an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160. Non-limiting examples of such residue differences include amino acid insertions, deletions, substitutions, or any combination of such changes. According to the present invention, differences from the disclosed amino acid sequences in an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160 can comprise non-conservative substitutions, conservative substitutions, as well as combinations of conservative and non-conservative amino acid substitutions. According to the present invention, an amino acid mutation can be made at any position within SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160, so long as the mutated enzyme retains its glucosaminyl 3-O sulfotransferase activity with an aryl sulfate compound as a sulfo group donor and any of the heparosan-based polysaccharides described above as a sulfo group acceptor.

According to the present invention, an engineered 3OST enzyme can comprise the amino acid sequence of SEQ ID NO: 154. Within SEQ ID NO: 154, residues having the designation, "Xaa," illustrate known instances in which there is a lack of identity at a particular position within the amino acid sequences of SEQ ID NO: 147, SEQ ID NO: 149, and SEQ ID NO: 151. Thus, an "Xaa" designation indicates the amino acid at that position can be selected from a group of two or more amino acids, as defined by SEQ ID NO: 154.

Additionally, and according to the present invention, amino acid mutations can be made at one or more positions within SEQ ID NO: 147, SEQ ID NO: 149, SEQ ID NO: 151, SEQ ID NO: 155, SEQ ID NO: 156, SEQ ID NO: 157, SEQ ID NO: 158, SEQ ID NO: 159, and SEQ ID NO: 160 so long as the mutated enzyme retains its glucosaminyl 3-O sulfotransferase activity with an aryl sulfate compound as a sulfo group donor. According to the present invention, an aryl sulfate-dependent enzyme comprising the amino acid sequence of SEQ ID NO: 154 can optionally comprise one or more amino acid mutations at positions not designated as "Xaa," while still retaining its glucosaminyl 3-O sulfotransferase activity with an aryl sulfate compound as a sulfo group donor.

In another aspect, the invention provides methods for enzymatically transferring a sulfo group from an aryl sulfate compound to a polysaccharide to form a sulfated polysaccharide product. According to the present invention, the polysaccharide can be a heparosan-based polysaccharide. According to the present invention, a method for enzymatically transferring a sulfo group from an aryl sulfate compound to a heparosan-based polysaccharide can comprise the following steps: (a) providing an aryl sulfate compound; (b) providing any of the engineered sulfotransferase enzymes described above, wherein the engineered sulfotransferase enzyme has biological activity with an aryl sulfate compound as a sulfo group donor; (c) providing a heparosan-based polysaccharide; (d) combining the aryl sulfate compound, the sulfotransferase enzyme, and the heparosan-based polysaccharide into a reaction mixture; and (e) transferring the sulfo group from the aryl sulfate compound to the heparosan-based polysaccharide, using the sulfotransferase enzyme, thereby forming the sulfated polysaccharide product. According to the present invention, the aryl sulfate compound can be selected from the consisting of PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS. According to the present invention, the aryl sulfate compound can be PNS. According to the present invention, the aryl sulfate compound can be NCS.

According to the present invention, the engineered sulfotransferase can be any of the engineered NST enzymes described above, preferably an engineered NST enzyme comprising an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25. According to the present invention, and useful in combination with any one or more of the above aspects and embodiments, the heparosan-based polysaccharide can be N-deacetylated heparosan. According to the present invention, and useful in combination with any one or more of the above aspects and embodiments, the heparosan-based polysaccharide can comprise one or more disaccharide units comprising the structure of Formula II. According to the present invention, and useful in combination with any one or more of the above aspects and embodiments, the sulfated polysaccharide product comprises the structure of Formula III.

According to the present invention, the engineered sulfotransferase can be any of the engineered 2OST enzymes described above, preferably an engineered 2OST enzyme comprising an amino acid sequence selected from the group consisting of SEQ ID NO: 65, SEQ ID NO: 66, SEQ ID NO: 67, and SEQ ID NO: 69. According to the present invention, and useful in combination with any one or more of the above aspects and embodiments, the heparosan-based polysaccharide can be N-sulfated heparosan. According to the present invention, and useful in combination with any one or more of the above aspects and embodiments, the heparosan-based polysaccharide can comprise one or more structural motifs comprising the structure of Formula IV and/or Formula V, and preferably at least one structural motif comprising the structure of Formula V. According to the present invention, and useful in combination with any one or more of the above aspects and embodiments, the method can further comprise the step of providing a glucuronyl $C_5$-epimerase, preferably a glucuronyl $C_5$-epimerase comprising the amino acid sequence of SEQ ID NO: 67, and more preferably residues 34-617 of SEQ ID NO: 67. According to the present invention, and useful in combination with any one or more of the above aspects and embodiments, the sulfated polysaccharide product comprises the structure of Formula VI and/or Formula VII.

According to the present invention, the engineered sulfotransferase can be any of the engineered 6OST enzymes described above, preferably an engineered 6OST enzyme comprising an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122. According to the present invention, and useful in combination with any one or more of the above aspects and embodiments, the heparosan-based polysaccharide can be any of the heparosan-based polysaccharides described above that are suitable sulfo acceptors for an engineered 6OST enzyme. According to the present invention, and useful in combination with any one or more of the above aspects and embodiments, the heparosan-based polysaccharide can be N,2O-HS. According to the present invention, and useful in combination with any one or more of the above aspects and embodiments, the heparosan-based polysaccharide can comprise one or more structural motifs comprising the structure of Formula VIII. According to the present invention, and useful in combination with any one or more of the above aspects and embodiments, the sulfated polysaccharide product comprises the structure of Formula IX.

According to the present invention, the engineered sulfotransferase can be any of the engineered 3OST enzymes described above, preferably an engineered 3OST enzyme comprising an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160. According to the present invention, and useful in combination with any one or more of the above aspects and embodiments, the heparosan-based polysaccharide can be N,2O,6O-HS. According to the present invention, and useful in combination with any one or more of the above aspects and embodiments, the heparosan-based polysaccharide can comprise one or more structural motifs comprising the structure of Formula X. According to the present invention, and useful in combination with any one or more of the above aspects and embodiments, the sulfated polysaccharide product comprises the structure of Formula I. According to the present invention, and useful in combination with any one or more of the above aspects and embodiments, the sulfated polysaccharide product comprising the structure of Formula I can have anticoagulant activity. According to the present invention, and useful in combination with any one or more of the above aspects and embodiments, the sulfated polysaccharide product comprising the structure of Formula I can have one or more similar or equivalent molecular weight properties and/or anticoagulant activity relative to heparin.

According to the present invention, and useful in combination with any one or more of the above aspects and embodiments, within any reaction mixture or composition comprising a heparosan-based polysaccharide used as a starting material or a sulfated polysaccharide product, the polysaccharides can be present as a polydisperse mixture of polysaccharides having variable chain lengths, molecular weights, N-acetylation, and/or N-, 2-O, 6-O, or 3-O sulfation. Alternatively, according to the present invention, any of the polysaccharides described above can be present as a homogeneous composition comprised of polysaccharides having identical chain lengths, molecular weights, N-acetylation, and/or N-, 2-O, 6-0, or 3-O sulfation.

According to the present invention, and useful in combination with one or more of the above aspects and embodiments, an engineered enzyme of the present invention having sulfatase and/or sulfotransferase activity with an aryl sulfate compounds as a substrate can be expressed from a nucleic acid comprising any nucleotide sequence that encodes for a polypeptide having the amino acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160. According to the present invention, such nucleotide sequences can be selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, and SEQ ID NO: 152, which encode for the amino acid sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151, respectively. Persons skilled in the art can determine appropriate nucleotide sequences that encode for polypeptides having the amino acid sequence of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 66, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160, based on the nucleotide sequences listed above and the identity of the desired engineered enzyme.

According to the present invention, and useful in combination with one or more of the above aspects and embodiments, a nucleic acid comprising a nucleotide sequence encoding for any of the engineered enzymes described above can be inserted into an expression vector that is engineered to be inserted into biological host cells configured to retain the expression vector and overexpress the desired enzyme. According to the present invention, the nucleic acid inserted into an expression vector can comprise any nucleotide sequence encoding for any of the engineered enzymes described above, particularly those comprising the amino acid sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. According to the present invention, the nucleic acid inserted into an expression vector can comprise any nucleotide sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, and SEQ ID NO: 152.

According to the present invention, and useful in combination with one or more of the above aspects and embodiments, the expression vector can optionally further comprise one or more nucleic acid sequences or genes encoding for proteins or host recognition sites that supplement the production of engineered enzymes of the present invention. Non-limiting examples include promoter sequences, antibiotic resistance genes, and genes encoding for fusion proteins that assist in the folding and stability of the engineered sulfotransferase enzyme. According to the present invention, any of the expression vectors described above can further comprise the malE gene from *Escherichia coli*, which encodes for maltose binding protein (MBP). According to the present invention, any of the expression vectors described above can further comprise a gene encoding for a small ubiquitin-related modifier (SUMO) protein, preferably the SUMO1 gene, which encodes for the SUMO1 protein. As a result, and according to the present invention, once protein expression is initiated, a fusion protein can be formed that comprises either MBP or SUMO, as well as an engineered enzyme having an amino acid sequence selected from the group consisting of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO:

120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160.

Expression vectors are typically transformed into host cells from which the enzyme can be overexpressed and extracted. According to the present invention, and useful in combination with one or more of the above aspects and embodiments, host cells can be transformed with expression vectors containing a nucleic acid sequence set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, or any sequence that encodes for an enzyme having the amino acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. According to the present invention, any of the above expression vectors transformed into the host cell can further comprise the malE or SUMO1 gene. According to the present invention, the transformed host cells can be bacterial, yeast, insect, or mammalian cells. According to the present invention, the host cells can be bacterial cells. According to the present invention, the bacterial cells can be from a non-pathogenic strain of *Escherichia coli* (*E. coli*).

In another aspect of the invention, kits for forming a sulfated polysaccharide product, particularly N,2O,3O,6O-HS products having anticoagulant activity similar or equivalent to heparin, according to any of the methods described above, are provided. According to the present invention, the kit can comprise at least one engineered aryl sulfate-dependent sulfotransferase and at least one aryl sulfate compound, preferably PNS or NCS. According to the present invention, and useful in combination with any one or more of the above aspects and embodiments, the kit can comprise an engineered NST, an engineered 2OST, an engineered 6OST, and/or an engineered 3OST, each of which is dependent on reacting with an aryl sulfate compound as a sulfo group donor to catalyze a transfer of the sulfo group to a polysaccharide, preferably a heparosan-based polysaccharide. According to the present invention, and useful in combination with any one or more of the above aspects and embodiments, the kit can further comprise any of the heparosan-based polysaccharides described above as sulfo group donor. According to the present invention, and useful in combination with any one or more of the above aspects and embodiments, the kit can further comprise a glucuronyl $C_5$-epimerase, preferably an epimerase comprising the amino acid sequence of SEQ ID NO: 67, and more preferably an epimerase comprising amino acid residues 34-617 of SEQ ID NO: 67.

According to the present invention, and useful in combination with any one or more of the above aspects and embodiments, any of the sulfated polysaccharide products, including anticoagulant N,2O,3O,6O-HS products, prepared according to any of the methods described above can be prepared as pharmaceutically-acceptable salts, particularly alkali or alkali earth salts including, but not limited to, sodium, lithium, or calcium salts.

These and other embodiments of the present invention will be apparent to one of ordinary skill in the art from the following detailed description.

BRIEF DESCRIPTION OF THE FIGURES

FIG. 6A, FIG. 6B, and FIG. 6C show a multiple sequence alignment for the N-sulfotransferase domains of fifteen wild type EC 2.8.2.8 enzymes, illustrating conserved amino acid sequence motifs that are present regardless of overall sequence identity.

Figure 17D:
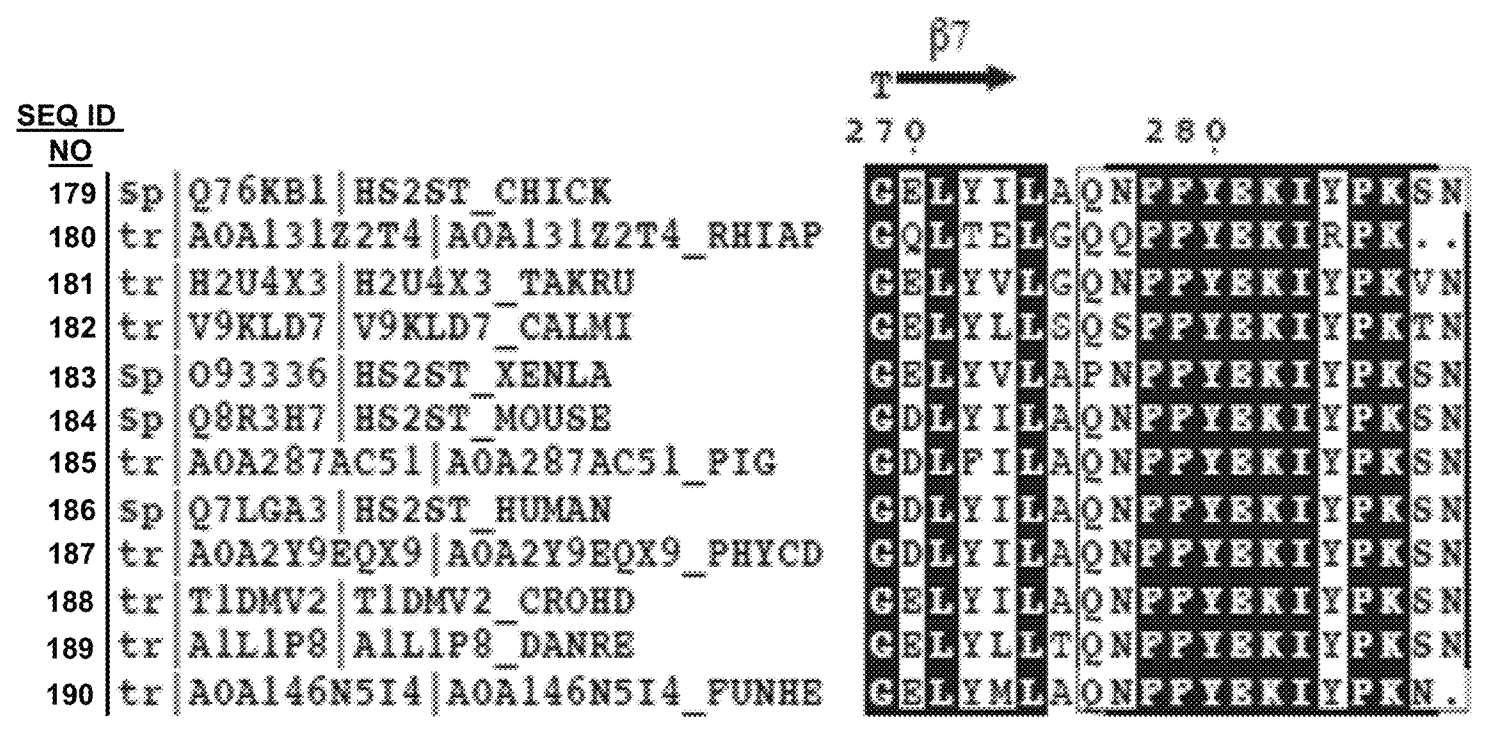

FIG. 17A, FIG. 17B, FIG. 17C, and FIG. 17D show a multiple sequence alignment for twelve wild-type 2OST enzymes within EC 2.8.2.-, illustrating conserved amino acid sequence motifs that are present regardless of overall sequence identity.

FIG. 18A, FIG. 18B, and FIG. 18C show a proposed reaction mechanism, transition state, and products formed as a result of a sulfotransfer reaction between conserved residues within natural 2OST enzymes, PAPS, and a heparosan-based polysaccharide.

Figure 21E:
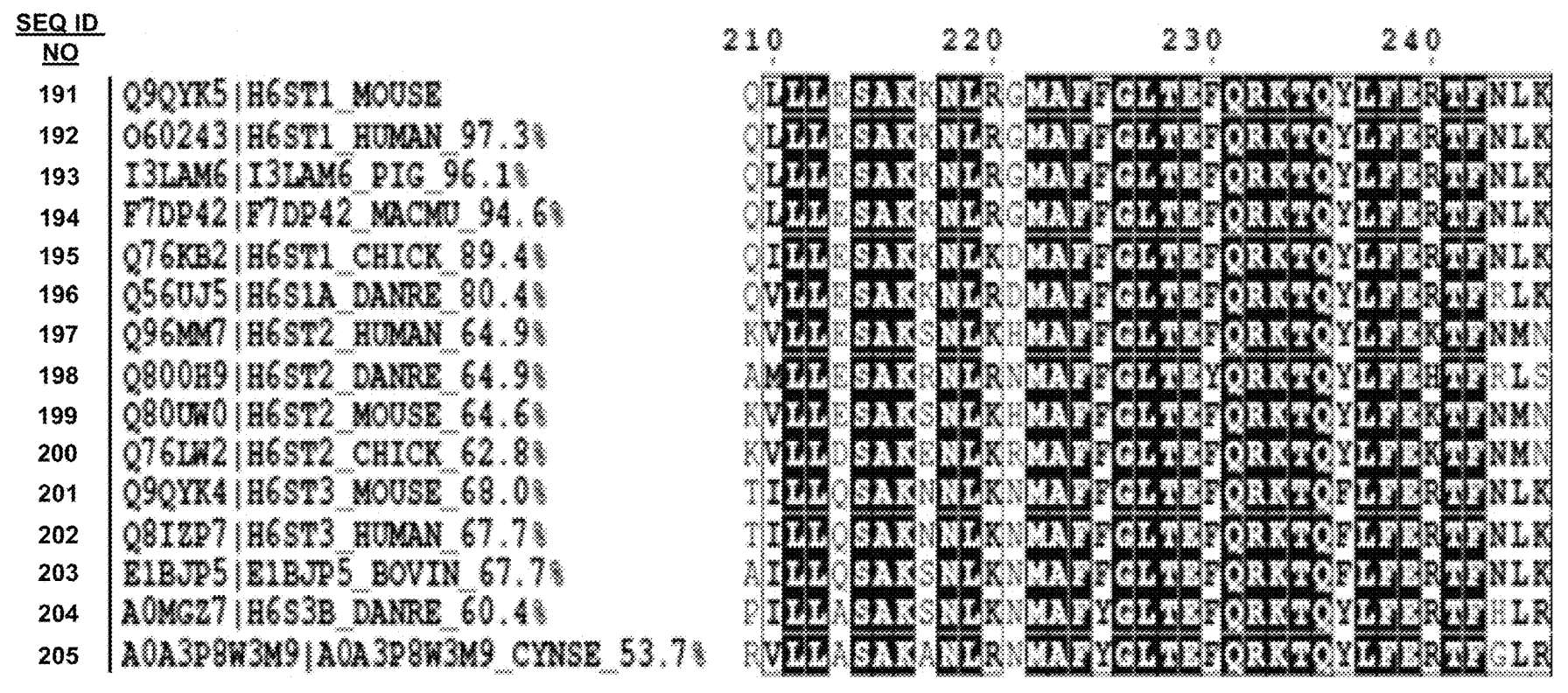
Figure 21F:
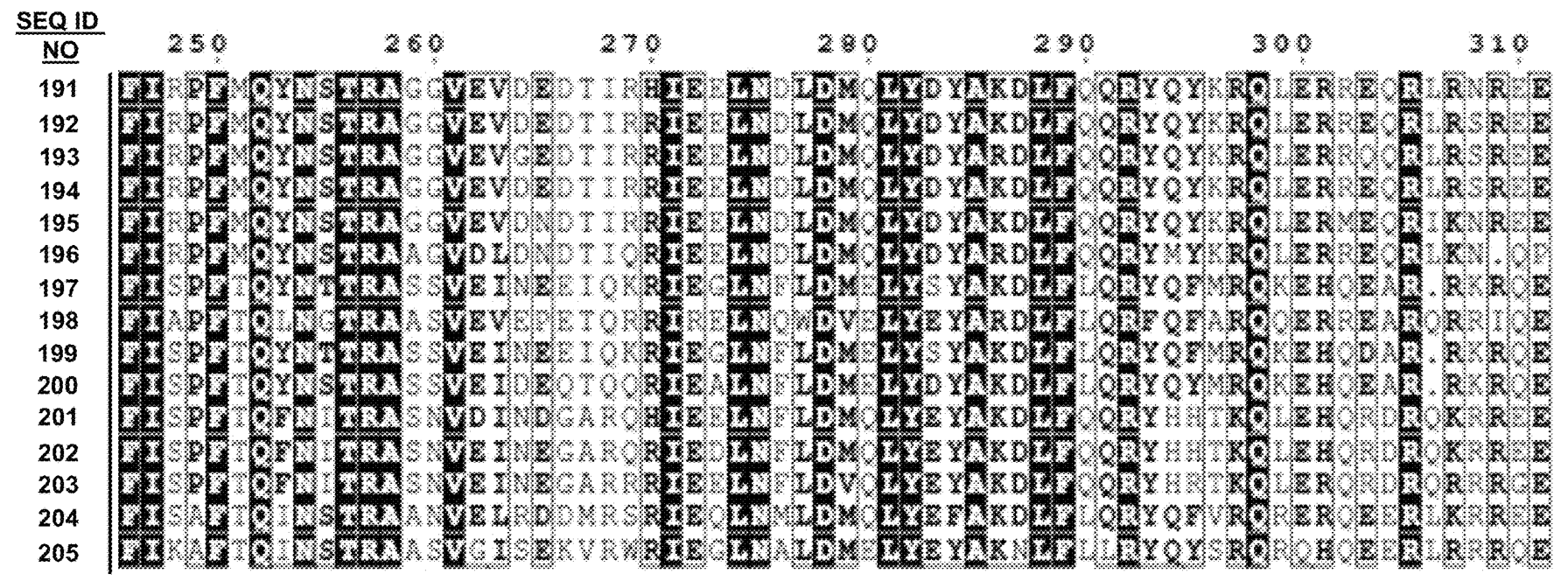

FIGS. 21A-21F show a multiple sequence alignment for fifteen wild-type 6OST enzymes within EC 2.8.2.-, illustrating con

DEFINITIONS

Figure 1:
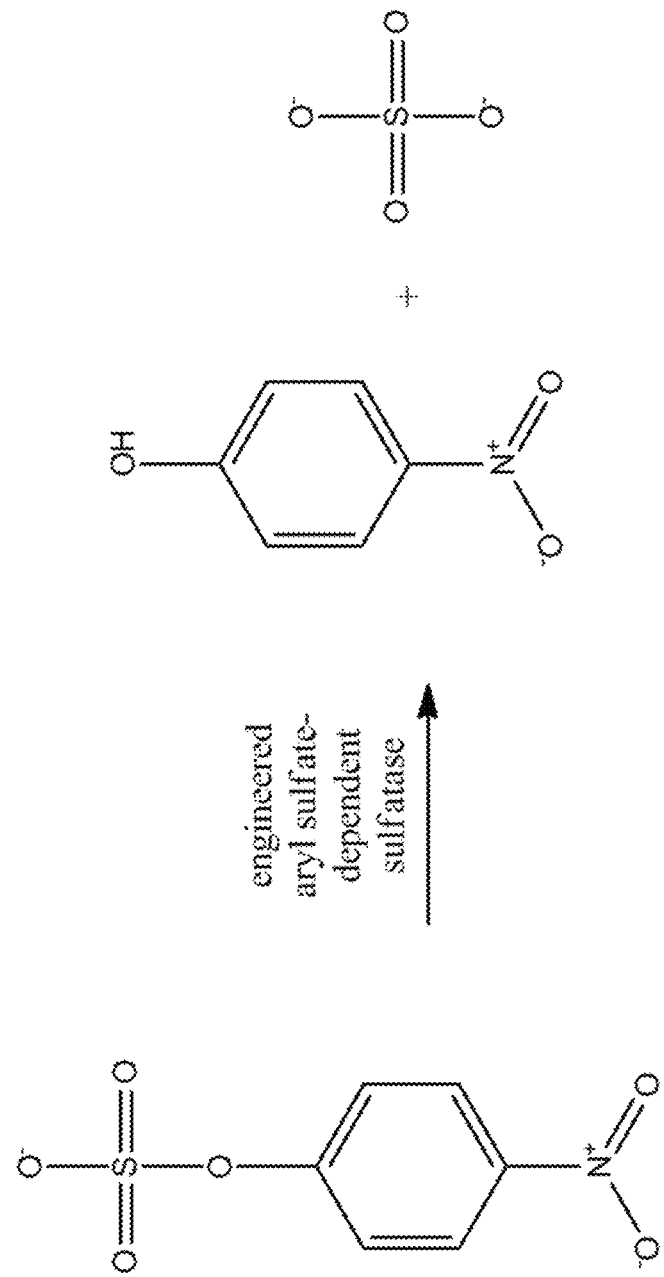
FIG. 1 shows the sulfatase activity catalyzed by one of the engineered enzymes of the present invention, when PNS is the substrate.

The term, "active site," refers to sites in catalytic proteins, in which catalysis occurs, and can include one or more substrate binding sites. Active sites are of significant utility in the identification of compounds that specifically interact with, and modulate the activity of, a particular polypeptide. The association of natural ligands or substrates with the active sites of their corresponding receptors or enzymes is the basis of many biological mechanisms of action. Similarly, many compounds exert their biological effects through association with the active sites of receptors and enzymes. Such associations may occur with all or any parts of the active site. An understanding of such associations helps lead to the design of engineered active sites within sulfotransferases that are capable of binding to and reacting with aryl sulfate compounds instead of PAPS.

The term, "amino acid," refers to a molecule having the structure wherein a central carbon atom (the alpha-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino and carboxylic groups in the dehydration reaction that links one amino acid to another. As a result, when incorporated into a protein, an amino acid is referred to as an "amino acid residue." In the case of naturally occurring proteins, an amino acid residue's R group differentiates the 20 amino acids from which proteins are synthesized, although one or more amino acid residues in a protein may be derivatized or modified following incorporation into protein in biological systems (e.g., by glycosylation and/or by the formation of cysteine through the oxidation of the thiol side chains of two non-adjacent cysteine amino acid residues, resulting in a disulfide covalent bond that frequently plays an important role in stabilizing the folded conformation of a protein, etc.). Additionally, when an alpha-carbon atom has four different groups (as is the case with the 20 amino acids used by biological systems to synthesize proteins, except for glycine, which has two hydrogen atoms bonded to the carbon atom), two different enantiomeric forms of each amino acid exist, designated D and L. In mammals, only L-amino acids are incorporated into naturally occurring polypeptides. Engineered enzymes utilized of the present invention can incorporate one or more D- and L-amino acids, or can be comprised solely of D- or L-amino acid residues.

Non-naturally occurring amino acids can also be incorporated into any of the engineered enzymes of the present invention, particularly engineered sulfotransferase enzymes having aryl sulfate-dependent activity. Non-limiting examples of such amino acids include: alpha-amino isobutyric acid, 4-amino butyric acid, L-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butyl glycine, t-butyl alanine, phenylglycine, cyclohexyl alanine, beta-alanine, fluoro-amino acids, designer amino acids (e.g., beta-methyl amino acids, alpha-methyl amino acids, alpha-methyl amino acids) and amino acid analogs in general.

The term, "and/or," when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

The terms, "aryl sulfate" or "aryl sulfate compound," refer to any compound, functional group, or substituent derived from an aromatic ring in which one or more of the hydrogen atoms directly bonded to the aromatic ring is replaced by a sulfate functional group. Typically, the sulfate functional group is covalently bound to the aromatic moiety of an aryl sulfate compound through a sulfate ester linkage. Non-limiting examples of aryl sulfate compounds that can be used as substrates with any of the engineered enzymes of the present invention include, but are not limited to, PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS.

The term, "aryl sulfate-dependent sulfotransferase," refers to the collective group of engineered sulfotransferases that possess biological or catalytic activity with aryl sulfate compounds as sulfo donors. Non-limiting examples of aryl sulfate compounds upon which the biological activity of the sulfotransferase can be dependent include PNS and NCS. As described herein, engineered sulfotransferases having biological activity with aryl sulfate compounds as sulfo group donors can possess biological activity with polysaccharides, particularly heparosan-based polysaccharides, as sulfo group acceptors. "Aryl sulfate-dependent sulfotransferase" also includes both nucleic acids and polypeptides encoding for any aryl sulfate-dependent sulfotransferase, including mutants derived from the sequences disclosed herein.

The term, "average molecular weight," with respect to any of the polysaccharide starting materials, intermediates, and/or products used or generated according to any of the methods of the present invention, and unless otherwise indicated, can refer to any accepted measure of determining the molar mass distribution or molar mass average of a mixture of polymers having varying degrees of polymerization, functionalization, and molar mass, including but not limited to "number-average molecular weight," "mass-average molecular weight," "weight-average molecular weight," "Z (centrifugation) average molar mass," or "viscosity average molar mass."

The term, "weight-average molecular weight," refers to a method of reporting the average molecular weight of polysaccharides in a mixture, calculated using the mole fraction distribution of the polysaccharides within the sample, using the equation $M_w = \sum_i N_i M_i^2 / \sum_i N_i M_i$, wherein $N_i$ is the number of polysaccharides of molecular mass $M_i$.

The term, "number-average molecular weight," refers to a method of reporting the average molecular weight of polysaccharides in a mixture, calculated by dividing the total weight of all of the polysaccharides in the sample divided by the number of polysaccharides in a sample, using the equation, $M_n = \sum M_i N_i / \sum N_i$, wherein $N_i$ is the number of polysaccharides of molecular mass $M_i$. Accordingly, the weight-average molecular weight, $M_w$, is necessarily skewed toward higher values corresponding to polysaccharides within the sample that are larger than other polysaccharides within the same mixture, and will always be larger than the number-average molecular weight, $M_n$, except when the sample is monodisperse, and $M_w$ equals $M_n$. If a particular sample of polysaccharides within the sample has a large dispersion of actual weights, then $M_w$ will be much larger than $M_n$. Conversely, as the weight dispersion of polysaccharides in a sample narrows, $M_w$ approaches $M_n$.

The terms, "relative molecular weight" or "relative molar mass" ($M_r$), refers to another method of reporting the average molecular weight of polysaccharides in a mixture as a unitless quantity, most broadly determined by dividing the average mass of the molecule by an atomic mass constant, such as 1 atomic mass unit (amu) or 1 Dalton (Da). With respect to polysaccharides, $M_r$ does not take into account the different chain-lengths, functionalization, and/or weight distribution of the polysaccharides in the sample, and instead simply represents the true average mass of the polysaccharides in the sample in a manner similar to small molecules.

The terms, "biological activity" or "catalytic activity," refer to the ability of an enzyme to catalyze a particular chemical reaction by specific recognition of a particular substrate or substrates to generate a particular product or products. In some embodiments, the engineered enzymes of the present invention possess a biological or catalytic activity that is dependent on binding and reacting with aryl sulfate compounds, particularly PNS or NCS, as substrates. Additionally, some engineered enzymes are capable of having promiscuous catalytic activity with one or more alternate aryl sulfate compounds in addition to PNS, including but not limited to MUS, 7-hydroxycoumarin sulfate, phenyl sulfate, 4-acetylphenyl sulfate, indoxyl sulfate, 1-naphthyl sulfate, and 2NapS.

The term, "coding sequence," refers to that portion of a nucleic acid, for example, a gene, that encodes an amino acid sequence of a protein.

The term, "codon-optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, it is well known that codon usage by particular organisms is non-random and biased toward particular codon triplets. In some embodiments of the invention, the polynucleotide encoding for an engineered enzyme may be codon optimized for optimal production from the host organism selected for expression.

The terms, "corresponding to," "reference to," or "relative to," when used in the context of the numbering of a given amino acid or polynucleotide sequence, refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence.

The term, "deletion," refers to modification of a polypeptide by removal of one or more amino acids from the reference polypeptide. Deletions can comprise removal of 1 or more amino acids, the net result of which is retaining the catalytic activity of the reference polypeptide. Deletions can be directed to the internal portions and/or terminal portions of a polypeptide. Additionally, deletions can comprise continuous segments or they can be discontinuous.

The term, "disaccharide unit," refers to the smallest repeating backbone unit within many polysaccharides, including linear polysaccharides, in which the smallest repeating unit consists of two sugar residues. With respect to a heparosan-based polysaccharide, the disaccharide unit consists of a hexuronic acid residue and a glucosamine residue, either of which can be functionalized and in which the hexuronic acid residue can either be glucuronic acid or iduronic acid. Each disaccharide unit within the heparosan-based polysaccharide can be described by its backbone structure and by the number and position of sulfo groups that are present. Further, the relative abundance of disaccharide units having the same structure within the same polysaccharide, and/or within the same sample of polysaccharides, can be characterized to determine the amount of sulfation at a particular position as a result of reacting with any of the sulfotransferases described herein.

The terms, "fragment" or "segment," refer to a polypeptide that has an amino- or carboxy-terminal deletion, but where the remaining amino acid sequence is identical to the corresponding positions in a reference sequence. Fragments can be at least 50 amino acids or longer, and comprise up to 70%, 80%, 90%, 95%, 98%, and 99% of the amino acid sequence of an enzyme.

The terms, "functional site" or "functional domain," generally refer to any site in a protein that confers a function on the protein. Representative examples include active sites (i.e., those sites in catalytic proteins where catalysis occurs) and ligand binding sites. Ligand binding sites include, but are not limited to, metal binding sites, co-factor binding sites, antigen binding sites, substrate channels and tunnels, and substrate binding domains. In an enzyme, a ligand binding site that is a substrate binding domain may also be an active site. Functional sites may also be composites of multiple functional sites, wherein the absence of one or more sites comprising the composite results in a loss of function. As a non-limiting example, the active site of a particular sulfotransferase enzyme may include multiple binding sites or clefts, including one site for the sulfo donor and one site for the sulfo acceptor.

The terms, "gene," "gene sequence," and "gene segment," refer to a functional unit of nucleic acid unit encoding for a functional protein, polypeptide, or peptide. As would be understood by those skilled in the art, this functional term includes both genomic sequences and cDNA sequences. The terms, "gene," "gene sequence," and "gene segment," additionally refer to any DNA sequence that is substantially identical to a polynucleotide sequence disclosed herein encoding for engineered enzyme gene product, protein, or polysaccharide, and can comprise any combination of associated control sequence. The terms also refer to RNA, or antisense sequences, complementary to such DNA sequences. As used herein, the term "DNA segment" includes isolated DNA molecules that have been isolated free of recombinant vectors, including but not limited to plasmids, cosmids, phages, and viruses.

The term, "glycosaminoglycan," refers to long, linear polysaccharides consisting of repeating disaccharide units. Examples of glycosaminoglycans (GAGs) include chondroitin, dermatan, heparosan, hyaluronic acid, and keratan. GAGs are generally heterogeneous with respect to mass, length, disaccharide unit structure and functionalization, degree of sulfation.

The term, "heparosan," refers to a particular GAG having repeating [β(1,4)GlcA-α(1,4)GlcNAc]$_n$ disaccharide units, in which GlcA is glucuronic acid and GlcNAc is N-acetyl glucosamine.

The term, "heparosan-based polysaccharide," refers to polysaccharides having the same backbone structure as heparosan, in which the disaccharide unit contains 1→4 glycosidically-linked hexuronic acid and glucosamine residues. The hexuronic acid residue can either be glucuronic acid, as in heparosan, or iduronic acid, and can optionally have a sulfo group at the 2-O position. The glucosamine residue can either be N-acetylated, as in heparosan, N-sulfated, or N-unsubstituted, and can optionally be sulfated at the N-, 3-O, or 6-O position. As used herein, the term "N-unsubstituted," with respect to a glucosamine residue, is equivalent to an "N-deacetylated" glucosamine residue, and refers to an amine functional group that is capable of receiving a sulfo group either chemically, or enzymatically using a NST. According to the present invention, heparosan-based polysaccharides can be utilized as starting materials, formed as intermediates, acting as sulfo group acceptors and/or synthesized as products according to any of the methods described herein.

The term, "insertion," refers to modifications to the polypeptide by addition of one or more amino acids to the reference polypeptide. Insertions can be in the internal portions of the polypeptide, or to the C- or N-termini of the polypeptide. Insertions can include fusion proteins as is known in the art and described below. The insertions can comprise a continuous segment of amino acids or multiple insertions separated by one or more of the amino acids in the reference polypeptide.

The term, "isolated nucleic acid" as used herein with respect to nucleic acids derived from naturally-occurring sequences, means a ribonucleic or deoxyribonucleic acid which comprises a naturally-occurring nucleotide sequence and which can be manipulated by standard recombinant DNA techniques, but which is not covalently joined to the nucleotide sequences that are immediately contiguous on its 5' and 3' ends in the naturally-occurring genome of the organism from which it is derived. As used herein with respect to synthetic nucleic acids, the term "isolated nucleic acid" means a ribonucleic or deoxyribonucleic acid which comprises a nucleotide sequence which does not occur in nature and which can be manipulated by standard recombinant DNA techniques. An isolated nucleic acid can be manipulated by standard recombinant DNA techniques when it may be used in, for example, amplification by polymerase chain reaction (PCR), in vitro translation, ligation to other nucleic acids (e.g., cloning or expression vectors), restriction from other nucleic acids (e.g., cloning or expression vectors), transformation of cells, hybridization screening assays, or the like.

The terms, "naturally occurring" or "wild-type," refer to forms of an enzyme found in nature. For example, a naturally occurring or wild-type polypeptide or polynucleotide sequence is a sequence present in an organism that can be isolated from a source in nature and which has not been intentionally modified by human manipulation. A wild-type polypeptide or polynucleotide sequence can also refer to recombinant proteins or nucleic acids that can be synthesized, amplified, and/or expressed in vitro, and which have the same sequence and biological activity as an enzyme produced in vivo. In contrast to naturally occurring or wild-type sulfotransferase enzymes, the engineered sulfotransferase enzymes utilized in accordance with methods of the present invention have unique amino acid and nucleic acid sequences, have biological activity with aryl sulfate compounds as sulfo group donors instead of PAPS, and cannot be found in nature.

The term, "oligosaccharide," refers to saccharide polymers containing a small number, typically three to nine, sugar residues within each molecule.

The term, "percent identity," refers to a quantitative measurement of the similarity between two or more nucleic acid or amino acid sequences. As a non-limiting example, the percent identity can be assessed between two or more engineered enzymes of the present invention, two or more naturally occurring enzymes, or between one or more engineered enzymes and one or more naturally occurring enzymes. Percent identity can be assessed relative to two or more full-length sequences, two or more truncated sequences, or a combination of full-length sequences and truncated sequences.

The term, "polysaccharide," refers to polymeric carbohydrate structures formed of repeating units, typically monosaccharide or disaccharide units, joined together by glycosidic bonds, and which can range in structure from a linear chain to a highly-branched three-dimensional structure. Although the term "polysaccharide," as used in the art, can refer to saccharide polymers having more than ten sugar residues per molecule, "polysaccharide" is used within this application to describe saccharide polymers having more than one sugar residue, including saccharide polymers that have three to nine sugar residues that may be defined in the art as an "oligosaccharide." According to the present invention, the term "polysaccharide," is also used to generally describe GAGs and GAG-based compounds, including chondroitin, dermatan, heparosan, hyaluronic acid, and keratan compounds.

The terms, "protein," "gene product," "polypeptide," and "peptide" can be used interchangeably to describe a biomolecule consisting of one or more chains of amino acid residues. In addition, proteins comprising multiple polypeptide subunits (e.g., dimers, trimers or tetramers), as well as other non-proteinaceous catalytic molecules will also be understood to be included within the meaning of "protein" as used herein. Similarly, "protein fragments," i.e., stretches of amino acid residues that comprise fewer than all of the amino acid residues of a protein, are also within the scope of the invention and may be referred to herein as "proteins." Additionally, "protein domains" are also included within the term "protein." A "protein domain" represents a portion of a protein comprised of its own semi-independent folded region having its own characteristic spherical geometry with hydrophobic core and polar exterior.

The term, "recombinant," when used with reference to, for example, a cell, nucleic acid, or polypeptide, refers to a material that has been modified in a manner that would not otherwise exist in nature. Non-limiting examples include, among others, recombinant cells expressing genes that are not found within the native (non-recombinant) form of the cell or express native genes that are otherwise expressed at a different level.

The term, "reference sequence," refers to a disclosed or defined sequence used as a basis for sequence comparison. A reference sequence may be a subset of a larger sequence, for example, a segment of a full-length gene or polypeptide sequence. Generally, a reference sequence refers to at least a portion of a full-length sequence, typically at least 20 amino acids, or the full-length sequence of the nucleic acid or polypeptide.

The term, "saccharide," refers to a carbohydrate, also known as a sugar, which is a broad term for a chemical compound comprised of carbon, hydrogen, and oxygen, wherein the number of hydrogen atoms is essentially twice that of the number of oxygen atoms. Often, the number of repeating units may vary in a saccharide. Thus, disaccharides, oligosaccharides, and polysaccharides are all examples of chains composed of saccharide units that are recognized by the engineered sulfotransferase enzymes of the present invention as sulfo group acceptors.

The term, "substantially equivalent," with respect to polysaccharides utilized as starting materials, formed as intermediates, acting as sulfo group acceptors, and/or synthesized as products according to any of the methods described herein, refers to one or more properties of a polysaccharide sample that are identical to those found in a polysaccharide sample characterized in the prior art. Such properties may include, but are not limited to, chemical structure, sulfation frequency and location, disaccharide unit composition, molecular weight profile, and/or anticoagulant activity. Even if the two polysaccharide samples have additional properties that may be different, such differences do not significantly affect their substantial equivalence. In a non-limiting example, anticoagulant N,2O,3O,6O-HS products synthesized using engineered 3OSTs according to methods of the present invention can be substantially equivalent to the United States Pharmacopeia (USP) reference standard (CAS No: 9041-08-1) with respect to chemical structure, molecular weight profile, and/or anticoagulant activity, but can be produced at a different purity than the USP reference standard, which is isolated from natural sources and can contain non-trace amounts of other GAGs in the same sample.

The term, "substantially pure," with respect to protein preparations, refers to a preparation which contains at least 60% (by dry weight) the protein of interest, exclusive of the weight of other intentionally included compounds. Particularly the preparation is at least 75%, more particularly at least 90%, and most particularly at least 99%, by dry weight the protein of interest, exclusive of the weight of other intentionally included compounds. Purity can be measured by any appropriate method, e.g., column chromatography, gel electrophoresis, or high-performance liquid chromatography (HPLC) analysis. If a preparation intentionally includes two or more different proteins of the invention, a "substantially pure" preparation means a preparation in which the total dry weight of the proteins of the invention is at least 60% of the total dry weight, exclusive of the weight of other intentionally included compounds. Particularly, for such preparations containing two or more proteins of the invention, the total weight of the proteins of the invention can be at least 75%, more particularly at least 90%, and most particularly at least 99%, of the total dry weight of the preparation, exclusive of the weight of other intentionally included compounds.

The terms, "sulfo" or "sulfuryl" refer to a functional group, substituent, or moiety having the chemical formula $SO_3H^-$ that can be removed from an aryl sulfate compound and/or be transferred from a donor compound to an acceptor compound. In some embodiments, the engineered sulfotransferases of the present invention catalyze the transfer of sulfo groups from aryl sulfate compounds to a polysaccharide, particularly heparosan and/or heparosan-based polysaccharides.

The term, "sulfotransferase," refers to any enzyme in an in vivo or in vitro process that is used to catalyze the transfer of a sulfo group from a sulfo donor compound to a sulfo acceptor compound. "Sulfotransferase" can be used interchangeably to describe enzymes that catalyze sulfotransfer reactions in vivo or to describe engineered enzymes of the present invention that catalyze sulfotransfer reactions in vitro.

The term, "transformation," refers to any method of introducing exogenous a nucleic acid into a cell including, but not limited to, transformation, transfection, electroporation, microinjection, direct injection of naked nucleic acid, particle-mediated delivery, viral-mediated transduction or any other means of delivering a nucleic acid into a host cell which results in transient or stable expression of said nucleic acid or integration of said nucleic acid into the genome of said host cell or descendant thereof.

DETAILED DESCRIPTION OF THE INVENTION

The present disclosure describes engineered enzymes that are configured to recognize, bind, and react with aryl sulfate compounds as substrates. The enzymes of the present invention are especially useful because many sulfate-containing compounds that are common substrates for bacterial and eukaryotic enzymes in vivo, including sulfatases and sulfotransferases, are often impractical to use as substrates for those same reactions in vitro. Aryl sulfate compounds are ubiquitous, cheap, stable, and comparatively easy to work with in a laboratory setting, but they are can react with very few enzymes in vivo. In particular, eukaryotic sulfotransferases cannot bind or react with aryl sulfate compounds as sulfo group donors, and instead can only react with 3'-phosphoadenosine 5'-phosphosulfate (PAPS) as a sulfo group donor. As a result, the sulfotransferases' nearly universal reliance on PAPS has been an insurmountable roadblock to the large-scale chemoenzymatic or enzymatic in vitro synthesis of sulfated products, particularly sulfated polysaccharide products.

The engineered enzymes of the present invention, disclosed below, are mutants of natural sulfotransferase enzymes that exclusively recognize, bind, and react with PAPS, but instead are engineered to bind and react with aryl sulfate compounds as substrates. In an embodiment of the invention, many of the engineered enzymes possess sulfatase activity, in which the enzyme catalyzes hydrolysis of a sulfo group from an aryl sulfate compound. Without being limited by a particular theory, it is believed that the reaction mechanism for the sulfatase is unique relative to known natural sulfatases, which possess conserved signal sequences and post-translationally modified amino acids. The sulfatase activity of both natural enzymes and the engineered enzymes of the present invention is described in further detail below.

In another embodiment of the invention, several of the engineered enzymes possess sulfotransferase activity, in which the enzyme catalyzes the transfer of a sulfo group from an aryl sulfate compound to a sulfo group acceptor. In another embodiment, the sulfo group acceptor is a polysaccharide, particularly a heparosan-based polysaccharide. Without being limited by a particular theory, it is believed that sulfotransferase enzymes that recognize polysaccharides as sulfo group acceptors, but also bind and react with aryl sulfate compounds as sulfo donors, have neither been observed in nature nor described previously. Those skilled in the art will appreciate that the engineered aryl sulfate-dependent sulfotransferase enzymes of the present invention have several advantages over in vitro and in vivo reaction mechanisms that are unable to bind and react with aryl sulfate compounds in order to catalyze sulfo transfer.

It should be understood that while reference is made to exemplary embodiments and specific language is used to describe them, no limitation of the scope of the invention is intended. Further modifications of the methods described herein, as well as additional applications of the principles of those inventions as described, which would occur to one skilled in the relevant art and having possession of this disclosure, are to be considered within the scope of this invention. Furthermore, unless defined otherwise, all technical and scientific terms used herein have the same meaning as commonly understood by one of ordinary skill in the art to which embodiments of this particular invention pertain. The terminology used is for the purpose of describing those embodiments only, and is not intended to be limiting unless specified as such. Headings are provided for convenience only and are not to be construed to limit the invention in any way. Additionally, throughout the specification and claims, a given chemical formula or name shall encompass all optical isomers and stereoisomers, as well as racemic mixtures where such isomers and mixtures exist.

Aryl Sulfate-Dependent Sulfatases

In an embodiment of the invention, several of the engineered enzymes disclosed herein have sulfatase activity, and are capable of hydrolyzing the sulfate ester within an aryl sulfate compound (see Recksiek, et al., (1998) *J. Biol. Chem.* 273 (11):6096-6103, the disclosure of which is incorporated by reference in its entirety). Upon binding with an aryl sulfate compound in an aqueous solution, engineered enzymes having sulfatase activity can catalyze the hydrolysis of the aryl sulfate compound to produce an aromatic compound and a sulfate ion. Non-limiting examples of aryl sulfate compounds include p-nitrophenyl sulfate (PNS), 4-methylumbelliferyl sulfate, 7-hydroxycoumarin sulfate, phenyl sulfate, 4-acetylphenyl sulfate, indoxyl sulfate, 1-naphthyl sulfate, 2-naphthyl sulfate (2NapS), and 4-nitrocatechol sulfate (NCS). As a non-limiting example and as illustrated in FIG. 1, when the aryl sulfate compound is PNS, the products are p-nitrophenol and a sulfate ion. In reactions conducted at a pH greater than the pKa of p-nitrophenol, the aromatic product is the p-nitrophenolate ion.

Figure 2:
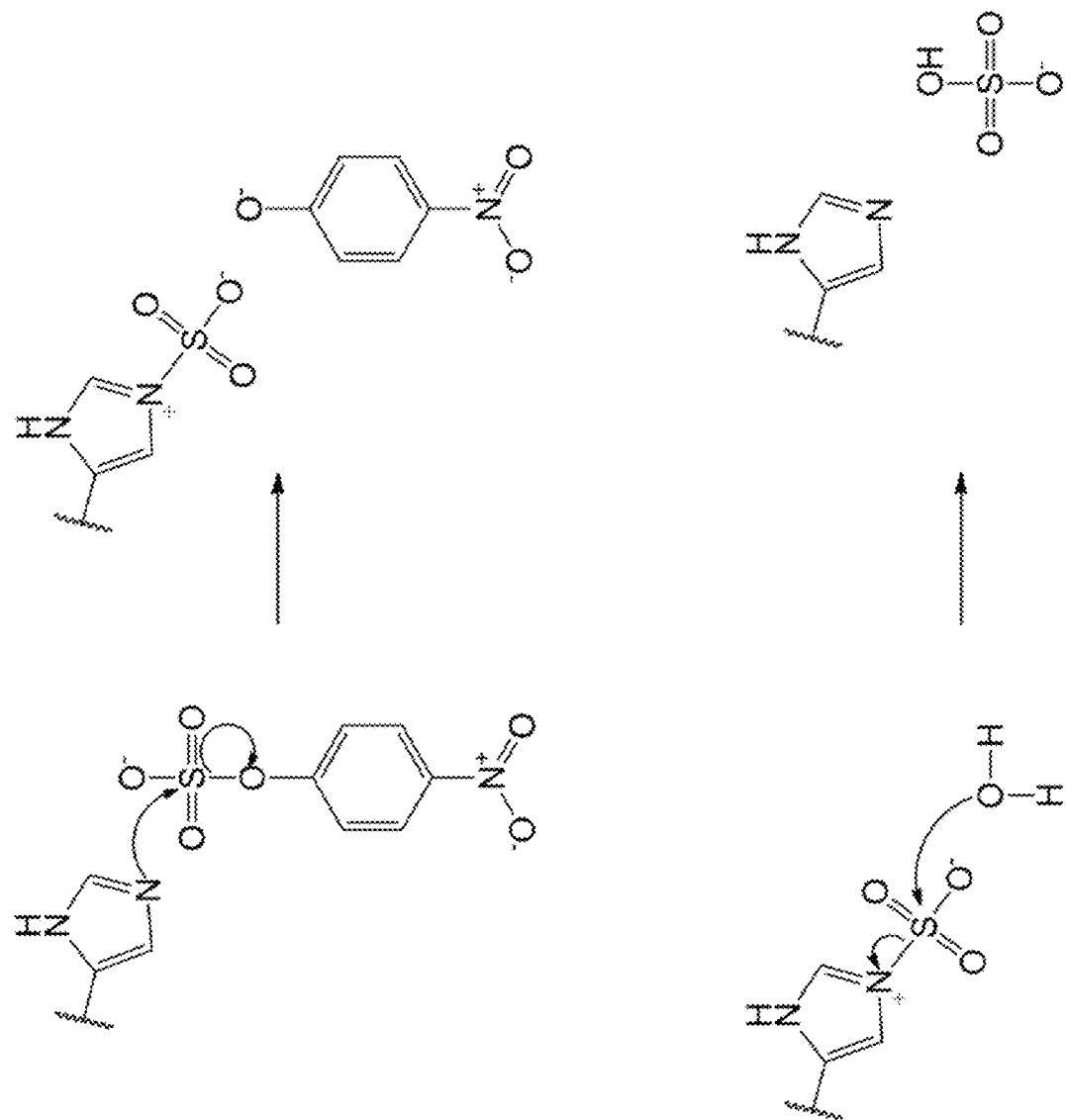
FIG. 2 shows a theoretical reaction mechanism for the hydrolysis of the sulfate ester linkage and formation of a sulfohistidine intermediate.

Without being limited by any particular theory, the hydrolysis of the sulfate ester catalyzed by an engineered enzyme of the present invention can occur upon binding of an aryl sulfate compound within the active site of the enzyme. As illustrated in FIG. 2, the lone pair of the basic nitrogen atom within the imidazole ring of an active site histidine residue initiates a nucleophilic attack of the sulfur atom within PNS, causing hydrolysis of the adjacent C—O bond and formation of a sulfohistidine intermediate. In a second step, the sulfohistidine intermediate itself can be nucleophilically attacked by a water molecule within the active site to cause a release of the sulfo group from the histidine side chain and restore the enzyme to its pre-reaction state.

Proceeding through a reaction mechanism that utilizes a histidine residue within the active site to hydrolyze the sulfate ester creates a unique niche for the engineered enzymes of the present invention relative to other known sulfatases. In nature, sulfatases comprise a class of enzymes (EC 3.1.5.6) that are highly conserved sequentially, structurally, and mechanistically across both prokaryotic and eukaryotic species, having functions such as cell development and detoxification, sulfur scavenging, degradation of compounds, and osmoprotection. Such similarities among natural sulfatases include a highly conserved N-terminal sequence region containing consensus sequence motifs, as well as unique, post-translationally modified active-site aldehyde residue, α-formylglycine, which is necessary for natural sulfatase activity (see Hanson, S. R., et al., (2004) *Agnew. Chem. Int. Ed.* 43:5736-5763, the disclosure of which is incorporated by reference in its entirety). Additionally, natural sulfatases are typically large proteins that often comprise more than 500 amino acid residues, including up to about 800 amino acid residues for some eukaryotic sulfatases.

Without being limited by a particular theory, it is believed that all known natural hydrolytic sulfatases contain two highly homologous amino acid motifs that have been previously identified as sulfatase signature sequences I and II, both of which are found in the N-terminal sequence region (see Hanson, S. R., et al., above). Signature sequence I comprises the amino acids C/S-X-P-S/X-R-X-X-X-L/X-T/X-G/X-R/X, whereas signature sequence II comprises the amino acids G-Y/V-X-S/T-X-X-X-G-K-X-X-H. Both signature sequences correspond to SEQ ID NO: 271 and SEQ ID NO: 272 in the sequence listing, respectively, and play a vital role in the natural sulfatase enzyme activity. Signature sequence I is necessary for directing the post-translational modification of the active site to contain an α-formylglycine residue (described in further detail below) and signature sequence II contains important binding contacts that are important for optimizing sulfate ester catalysis within the α-formylglycine-containing active site.

In particular, the presence of α-formylglycine within the active site is the most salient feature within natural sulfatases, having been found in every characterized prokaryotic and eukaryotic sulfatase to date (see Uhlhorn-Dierls, G., et al., (1998) *Agnew. Chem.* 37:2453, and Uhlhorn-Dierls, G., et al., (1998) *Agnew. Chem.* 110:2591, the disclosures of which are incorporated by reference in their entireties). α-formylglycine residues can be formed from cysteine (most common) or serine residues within the active site, the modification of which has been determined to be directed by signature sequence I.

Figure 3A:
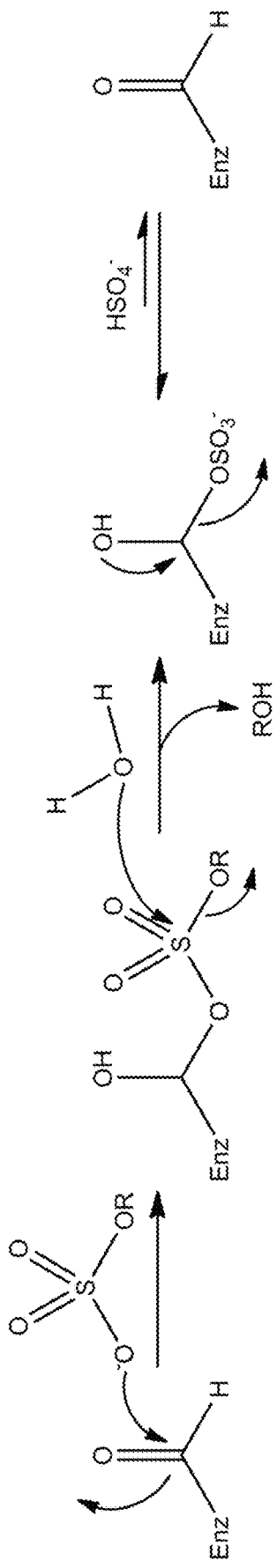
FIG. 3A and FIG. 3B show two proposed reaction mechanisms for natural sulfatase enzymes, catalyzed using an α-formylglycine residue.

Based on the crystal structures of several natural sulfatases, two reaction mechanisms that prominently utilize the α-formylglycine residue for catalysis have been proposed. A first mechanism, illustrated in FIG. 3A, has been proposed in which the α-formylglycine residue, in its aldehyde form, is nucleophilically attacked by one of the sulfate group oxygen atoms within the substrate to form a sulfate diester. The alcohol conjugate is then released through the action of a nucleophile, such as an activated water molecule to form a sulfate hemiacetal. Subsequent attack by the alcohol of the nucleophilic center within the sulfate hemiacetal causes the release of the sulfate molecule from the active site, regenerating the enzyme for future catalysis. A second mechanism, illustrated in FIG. 3B, the α-formylglycine in its hydrated form can nucleophilically attack the sulfate atom via an $S_N2$ reaction to form the sulfate hemiacetal, and ultimately release the sulfate group from the active site, similar to the mechanism in FIG. 3A. Subsequent addition of water rehydrates the α-formylglycine aldehyde to reform the hydrated α-formylglycine residue.

However, and in another embodiment, the engineered enzymes of the present invention can be synthesized without signature sequence I, signature sequence II, and/or any α-formylglycine residues being present. In another embodiment, an enzyme that does not contain signature sequence I, signature sequence II, and/or any α-formylglycine residues, and which has been shown to have sulfatase activity (see the Examples, below) can be selected from the group consisting of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151. In another embodiment, an engineered enzyme having sulfatase activity can comprise an amino acid sequence that is substantially identical, or is a biological equivalent, to the amino acid sequence of any of the above polypeptides having sulfatase activity, as defined in the "Nucleic Acid and Polypeptide Preparation" section, below.

Accordingly, in another embodiment, the invention provides a method for enzymatically hydrolyzing an aryl sulfate compound, comprising the steps of: providing an aryl sulfate compound; providing an engineered enzyme having an active site configured to bind with an aryl sulfate compound and a polysaccharide, preferably a heparosan-based polysaccharide; combining the aryl sulfate compound and the engineered enzyme into a reaction mixture; and catalyzing the hydrolysis of the aryl sulfate compound using the engineered enzyme. In another embodiment, the aryl sulfate compound is selected from the group consisting of PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS. In another embodiment, the aryl sulfate compound is PNS. In another embodiment, the aryl sulfate compound is NCS. In another embodiment, the aryl sulfate compound is 2NapS. In another embodiment, hydrolysis of the aryl sulfate compound proceeds by a mechanism comprising the nucleophilic attack of the sulfur atom within the aryl sulfate compound, causing hydrolysis of the adjacent C—O bond and formation of a sulfohistidine intermediate. In another embodiment, the nucleophilic attack is initiated by a histidine residue.

Aryl Sulfate-Dependent Sulfotransferases

In another embodiment, and as described above, several of the engineered enzymes of the present invention have sulfotransferase activity with aryl sulfate compounds as sulfo group donors. In another embodiment, the sulfo group donor is a polysaccharide, preferably a heparosan-based polysaccharide. In each sulfotransfer reaction, the aryl sulfate compound participates as a sulfo group donor, while the polysaccharide participates as a sulfo group acceptor. Sulfotransferase enzymes that recognize polysaccharides as sulfo group acceptors, but also bind and react with aryl sulfate compounds as sulfo group donors, have neither been observed in nature nor described previously.

One particular polysaccharide, heparosan, is a starting material in the synthesis of a multitude of sulfated polysaccharides in vivo, particularly within eukaryotic organisms. Typically, heparosan is synthesized as a glycosaminoglycan (GAG) by the organism within the Golgi apparatus, and comprises repeating co-polymers of $[\beta(1,4)\text{GlcA-}\alpha(1,4)\text{GlcNAc}]_n$ disaccharide units, in which GlcA is glucuronic acid and GlcNAc is N-acetyl glucosamine. Heparosan GAGs can then be modified, particularly by one or more heparan sulfate (HS)-sulfotransferase enzymes, to form functionalized heparosan-based polysaccharide products, particularly HS and heparin. Such modifications to heparosan includes N-deacetylation and N-sulfation of glucosamine, $C_5$-epimerization of glucuronic acid to form iduronic acid, 2-O-sulfation of iduronic and/or glucuronic acid, as well as 6-O-sulfation and 3-O-sulfation of glucosamine residues. The natural sulfotransferases that catalyze N-acetylation and N-sulfation, 2-O-sulfation, 6-O-sulfation, and 3-O-sulfation of heparosan and heparosan-based polysaccharides in vivo exclusively recognize and bind with PAPS as the sulfo group donor. Without being limited by a particular theory, it is believed that none of the four natural HS sulfotransferase enzymes—NDST, 2OST, 6OST, and 3OST—are active with any aryl sulfate compounds as a sulfo group donor.

Figure 4A:
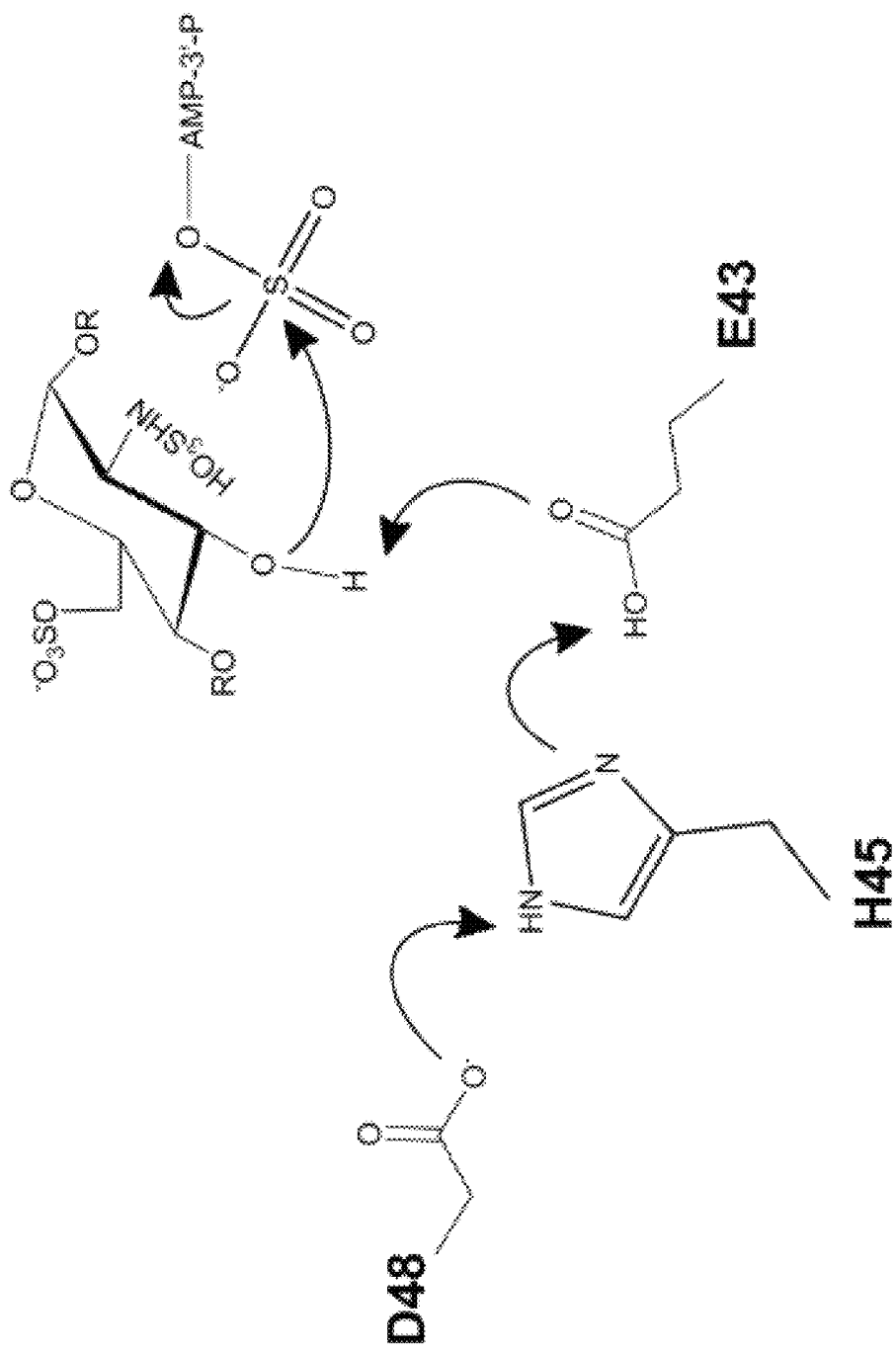
FIG. 4A, FIG. 4B, and FIG. 4C show a proposed reaction mechanism, transition state, and products formed as a result of a sulfotransfer reaction between the natural human 3OST enzyme, PAPS, and a heparosan-based polysaccharide.
Figure 4B:
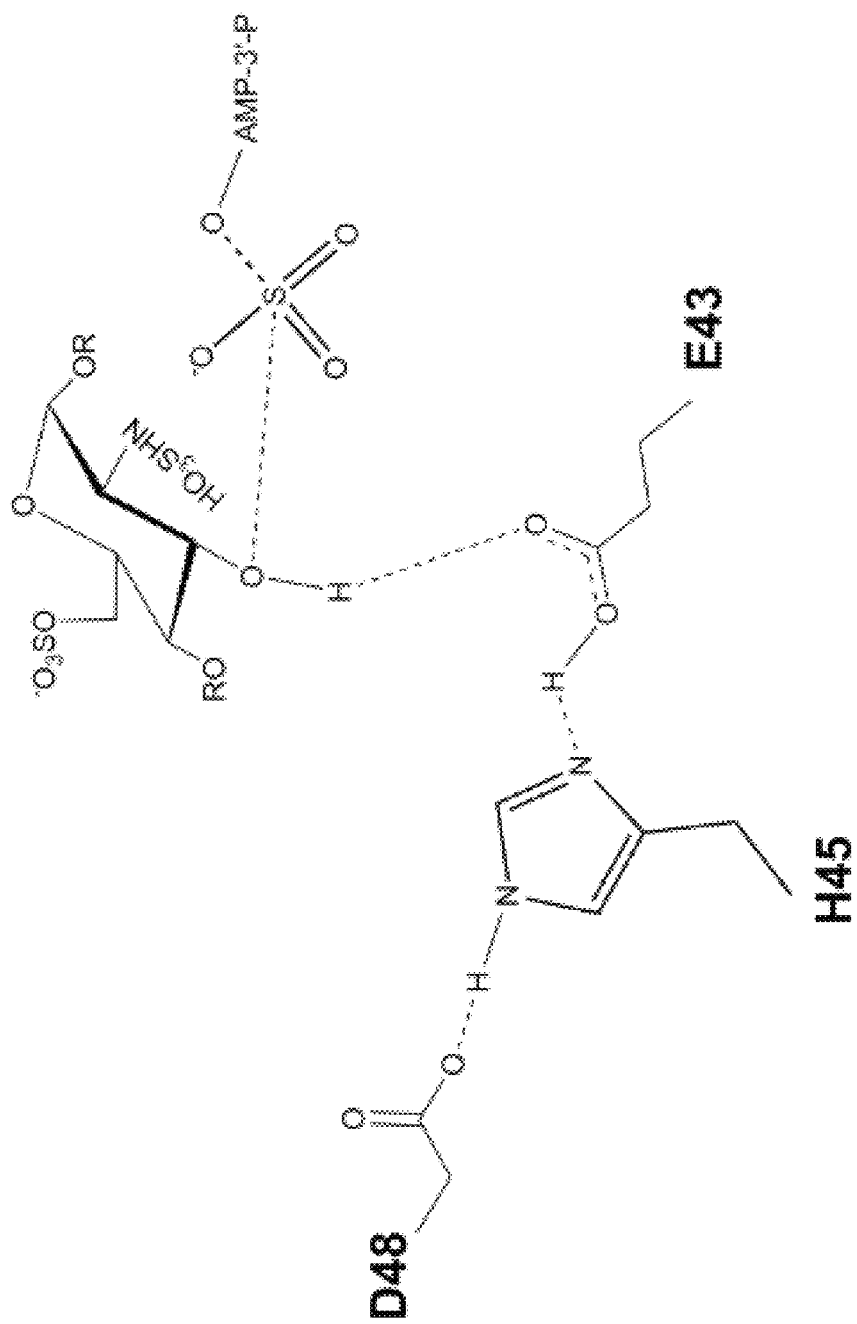
Figure 4C:
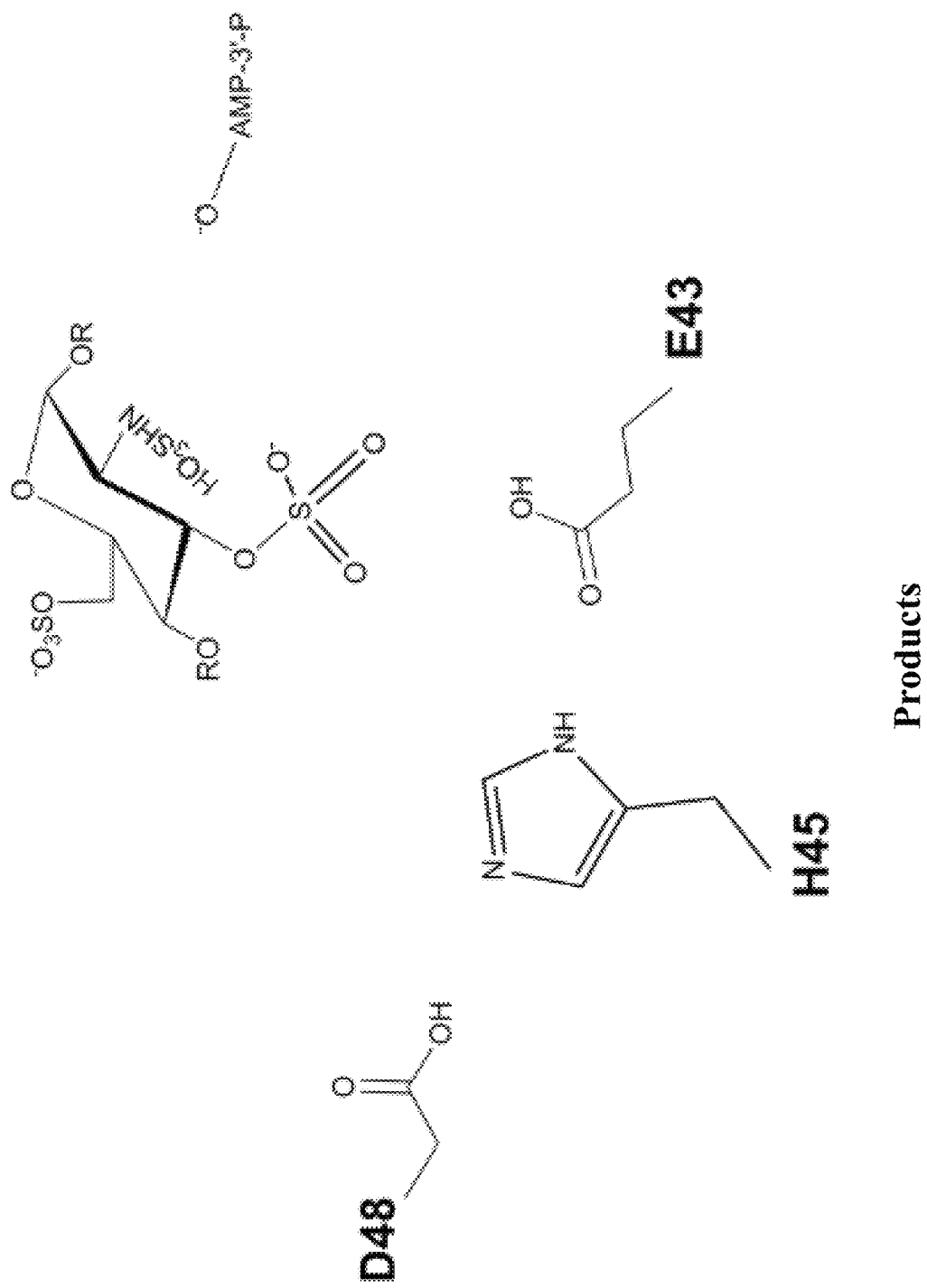

Each of the four natural HS sulfotransferase enzymes generally catalyze the direct transfer of a sulfo group from PAPS to a heparosan-based polysaccharide in a single step. An example of a typical sulfotransfer reaction mechanism catalyzed by an HS sulfotransferase enzyme is illustrated in FIG. 4A, FIG. 4B, and FIG. 4C, which collectively show a proposed mechanism, transition state, and products formed in a reaction between the human 3OST enzyme, PAPS, and a heparosan-based polysaccharide. In particular, the glutamic acid residue at position 43 abstracts the proton from the 3-O position of an N-, 6-O sulfated sulfoglucosamine residue within the heparosan-based polysaccharide, enabling the nucleophilic attack and removal of the sulfo group from PAPS, whereas His-45 and Asp-48 coordinate to stabilize the transition state of the enzyme before the sulfated polysaccharide product is released from the active site.

However, although PAPS is the exclusive sulfo donor in eukaryotes, it has a short half-life and can readily decompose into adenosine 3',5'-diphosphate, which acts as a competitive inhibitor during sulfotransfer reactions. Animals can efficiently utilize PAPS because they can metabolize adenosine 3',5'-diphosphate to prevent competitive inhibition and also replenish PAPS for each sulfotransfer reaction, as needed. On the other hand, aryl sulfate compounds, which can be utilized as sulfo donors in a limited number of bacterial systems (see Malojcic, G., et al., above), cannot react with any of the known native sulfotransferase enzymes in eukaryotes, including those that are involved in synthesizing HS and other heparosan-based polysaccharides in vivo. Without being limited by a particular theory, it is believed that the binding pockets for PAPS within the active sites of eukaryotic sulfotransferases either do not have a high enough affinity for aryl sulfate compounds to facilitate binding, and/or that the aryl sulfate compounds are sterically hindered from entering the active site at all.

Heparin, HS, and other heparosan-based polysaccharides play critical roles in a variety of important biological processes in vivo, including assisting viral infection, regulating blood coagulation and embryonic development, suppressing tumor growth, and controlling the eating behavior of test subjects by interacting with specific regulatory proteins. Depending on their role, heparosan polysaccharides can contain one or more unique patterns or motifs recognized by specific protein(s) involved in the particular biological process. In particular, heparin and other heparan sulfate polysaccharides, as well as routes to synthesizing such polysaccharides in vitro, are topics of extreme interest within the pharmaceutical industry.

The present disclosure includes engineered sulfotransferase enzymes, described in further detail below, which have activity with aryl sulfate compounds as sulfo group donors and heparosan-based polysaccharides as sulfo group acceptors. Each of the engineered sulfotransferase enzymes is designed to be a mutant of a corresponding natural HS sulfotransferase: glucosaminyl N-deacetylase/N-sulfotransferase (NDST) (via its N-sulfotransferase (NST) domain), hexuronyl 2-O sulfotransferase (2OST), glucosaminyl 6-O sulfotransferase (6OST), and glucosaminyl 3-O sulfotransferase (3OST). In each instance, the engineered sulfotransferase enzyme has activity with one or more aryl sulfate compounds (instead of PAPS) as a sulfo group donor, but retains the affinity of the native HS-sulfotransferase enzyme for a particular heparosan-based polysaccharide as a sulfo group acceptor. As a non-limiting example, an engineered 2OST enzyme has sulfotransferase activity with an aryl sulfate compound as a sulfo group donor and N-sulfated heparosan as a sulfo group acceptor. In contrast, natural 2OST enzymes have sulfotransferase activity with PAPS as the sole sulfo group donor and N-sulfated heparosan as a sulfo group acceptor. Each of the engineered sulfotransferase enzymes, including their sequences, structures, and biological activities, are described in further detail below. Methods of synthesizing sulfated heparosan-based polysaccharides in vitro using an engineered sulfotransferase enzyme and an aryl sulfate compound are also described below. In some embodiments of the invention, HS polysaccharides having anticoagulant activity, including those having anticoagulant activity similar or equivalent to heparin, can be synthesized in vitro.

Engineered NSTs

In nature, HS NDST enzymes have dual N-deacetylase and N-sulfotransferase activity, in which the same enzyme first catalyzes the removal of an N-acetyl group from a glucosamine residue within heparosan, and then catalyzes the transfer of a sulfo group from PAPS to the same glucosamine residue that was N-deacetylated in the first step. The dual N-deacetylase and N-sulfotransferase activity of the enzymes is achieved via two separate structural domains—an N-deacetylase domain and an N-sulfotransferase domain. However, the activity of one of the domains is not a pre-requisite for the activity of the other domain, and recombinant single-domain enzymes comprising either N-deacetylase or N-sulfotransferase activity can be expressed and purified. Similarly, and in an embodiment of the invention, engineered enzymes with NST activity can be expressed and purified as a single N-sulfotransferase domain, without additionally comprising an N-deacetylase domain.

Naturally-occurring NDST enzymes that utilize PAPS as the sulfo group donor are members of the EC 2.8.2.8 enzyme class. Generally, the N-deacetylase domain of an NDST enzyme can deacetylate one or more of the N-acetyl glucosamine residues within heparosan to form N-deacetylated heparosan, which can then be recognized as a sulfo group acceptor by the enzyme's N-sulfotransferase domain. However, the N-sulfotransferase domains of NDST enzymes have been shown to have sulfotransferase activity with N-deacetylated heparosan having one or more disaccharide units comprising the structure of Formula II, below:

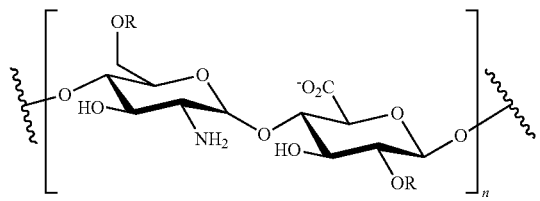

wherein n is an integer and R is selected from the group consisting of a hydrogen atom or a sulfo group. Further, although the portion of the N-deacetylated heparosan that reacts with the enzyme comprises the structure of Formula II, other glucosamine residues within the polysaccharide can be N-sulfated, N-acetylated, 3-O sulfated, and/or 6-O sulfated, and hexuronyl residues can be glucuronic acid or iduronic acid, either of which can be 2-O sulfated. Typically, N-deacetylated heparosan and other heparosan-based polysaccharides comprising the structure of Formula II comprise at least four disaccharide units, or at least eight sugar residues total. Sulfotransfer reactions in which N-deacetylated heparosan is utilized as the sulfo group acceptor for NDST enzymes are discussed in Sheng, J., et al., (2011) *J. Biol. Chem.* 286 (22):19768-76, as well as Gesteira, T. F., et al., (2013) *PLoS One* 8 (8):e70880, the disclosures of which are incorporated by reference in their entireties.

Upon successfully binding PAPS and N-deacetylated heparosan, the N-sulfotransferase domain of natural NDST enzymes can catalyze transfer of the sulfo group to an unsubstituted glucosamine residue, forming an N-sulfated heparosan product comprising the structure of Formula III, below:

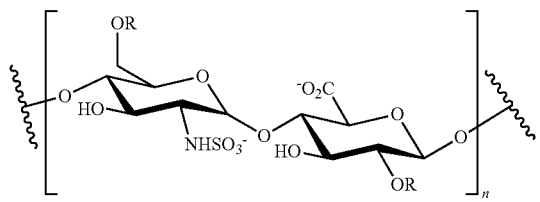

wherein n is an integer and R is selected from the group consisting of a hydrogen atom or a sulfo group.

Figure 5:
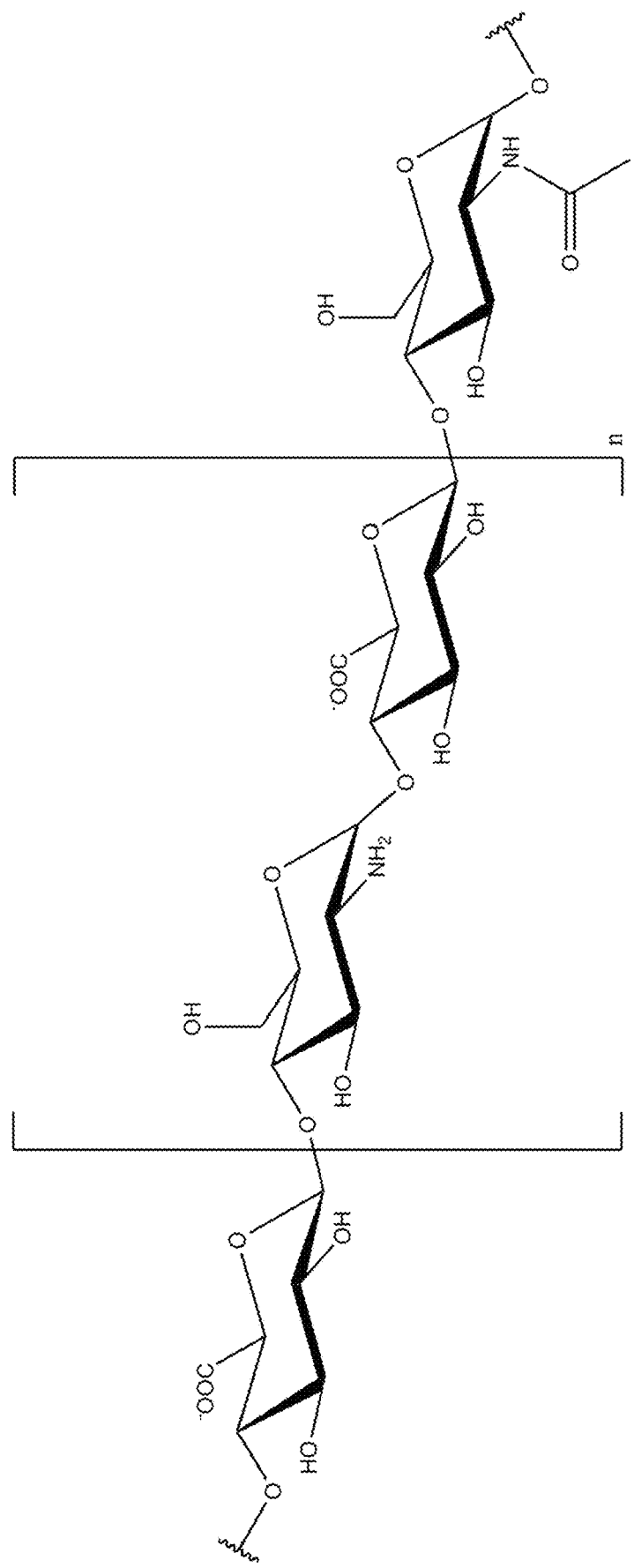
FIG. 5 shows a non-limiting example of a heparosan-based polysaccharide that can be used as a sulfo group acceptor with engineered NST enzymes of the present invention.

In another embodiment, each of the repeating disaccharide units within the N-deacetylated heparosan comprises the structure of Formula II. In another embodiment, both of the R groups at the 6-O position of the glucosaminyl residues and the 2-O position of the glucuronic acid residues are hydrogen atoms, in one or more, including all, of the disaccharide units within the polysaccharide. In another embodiment, in some locations within the polysaccharide, at least a portion of the glucosamine residues are still N-acetylated, as shown in FIG. 5, although glucosaminyl residues within the polymer that are N-acetylated cannot directly participate as sulfo group acceptors with the engineered sulfotransferases of the present invention. However, the presence of N-acetylated residues within the polysaccharide does not affect the binding affinity that the engineered sulfotransferases have for non-acetylated glucosamine residues within the same polysaccharide. In another embodiment, regardless of the structure of the heparosan-based polysaccharide, a disaccharide unit comprising the structure of Formula II can be recognized as a sulfo acceptor by an engineered NST enzyme and an aryl sulfate compound to generated an N-sulfated product comprising the structure of Formula III.

In another embodiment, when there are multiple disaccharide units within the N-deacetylated heparosan that comprise the structure of Formula II, the glucosamine residue within any of those disaccharide units can be N-sulfated. Similarly, and in another embodiment, within a polysaccharide comprising multiple disaccharide units having the structure of Formula II, a plurality of glucosamine residues can be N-sulfated, including and up to all of the available glucosamine residues within the polysaccharide.

The N-sulfotransferase domains of natural NDST enzymes typically comprise approximately 300 to 350 amino acid residues that can vary greatly in their sequence, yet ultimately have the exact same function, namely, to catalyze the N-sulfation of unsubstituted glucosamine residues within N-deacetylated heparosan. Without being limited by a particular theory, it is believed that each of the natural NDST enzymes can catalyze the same chemical reaction because there are multiple amino acid sequence motifs and secondary structures that are either identical or highly conserved across all species.

Figure 6A:
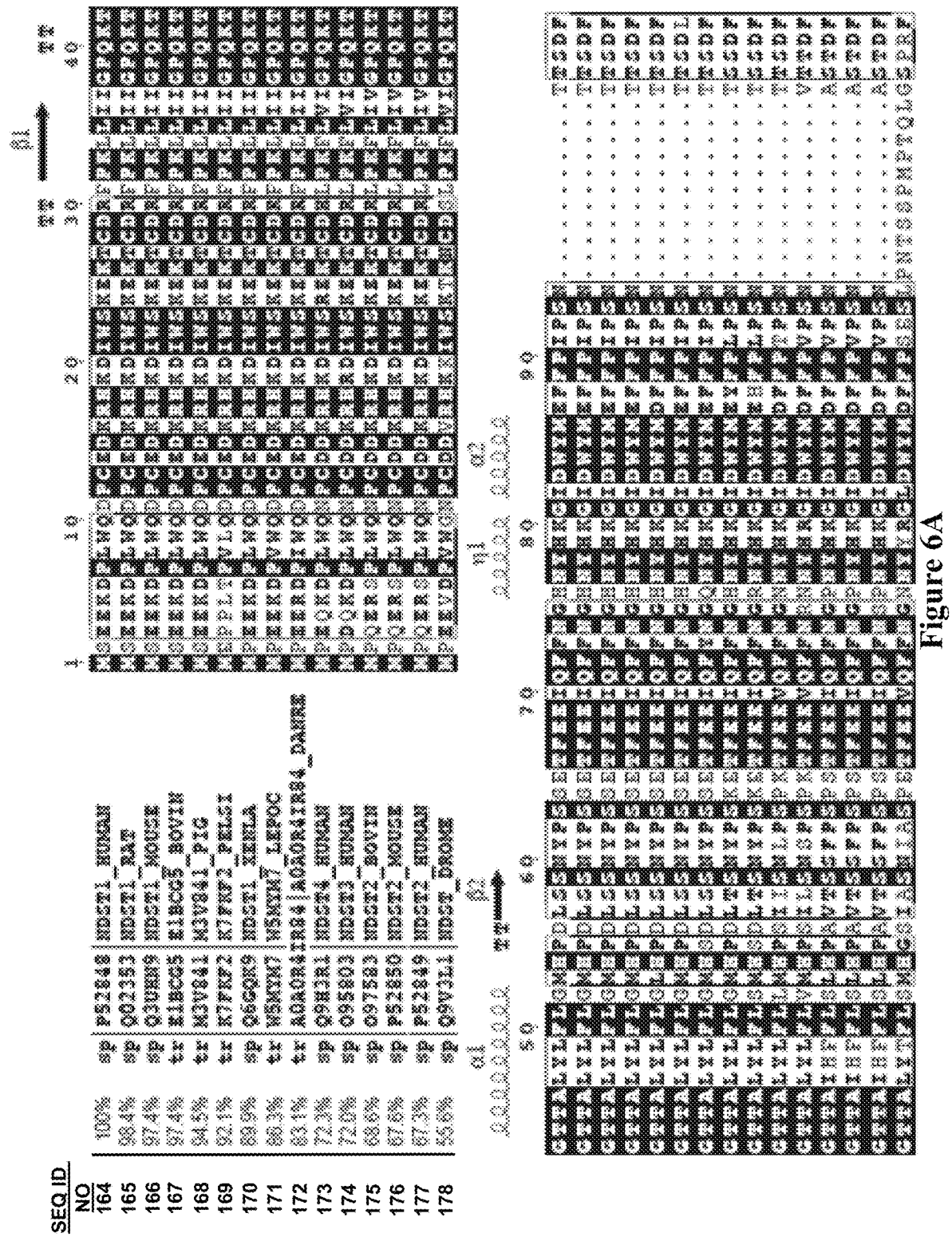
Figure 6B:
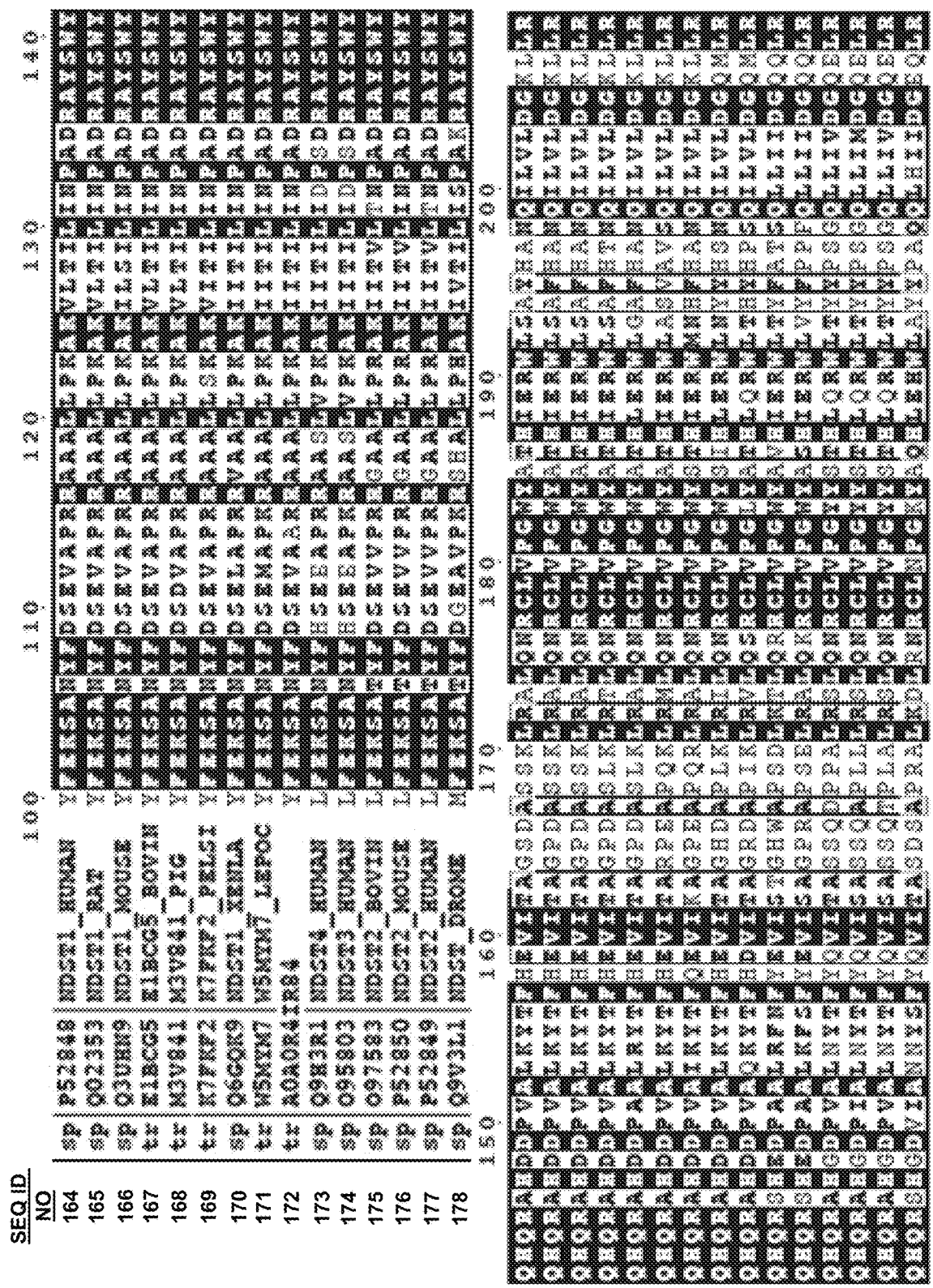
Figure 6C:
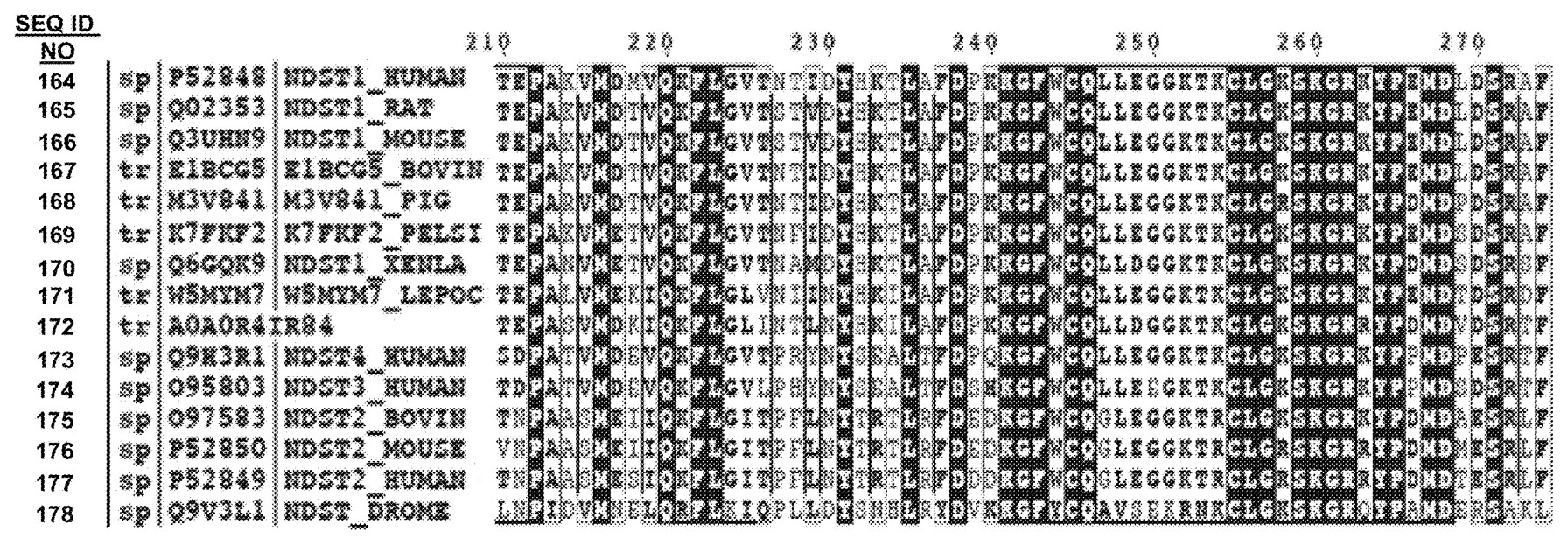

Further, it is believed that several of the conserved amino acid sequence motifs within the natural N-sulfotransferase domains are directly involved in binding of either PAPS and/or the polysaccharide, or participate in the chemical reaction itself. The identity of conserved amino acid sequence motifs can be demonstrated by comparing the amino acid sequence of the N-sulfotransferase domain (SEQ ID NO: 164) of the human NDST enzyme, which has a known crystal structure (PDB code: 1NST) in which amino acid residues within the active site have been identified, alongside the amino acid sequences of the N-sulfotransferase domains of other natural NDST enzymes. A multiple sequence alignment of the amino acid sequences of the N-sulfotransferase domains of fifteen NDST enzymes, including several eukaryotic organisms and several isoforms of the human NDST enzyme, is shown in FIG. 6A, FIG. 6B, and FIG. 6C, along with percent identity relative to the N-sulfotransferase domain of human NDST1 (UniProtKB Accession No. P52848). As illustrated in FIG. 6A, FIG. 6B, and FIG. 6C, each amino acid sequence, corresponding to SEQ ID NOs: 164-178, ranges from having 98.4% sequence identity with the P52848 reference sequence (SEQ ID NO: 165, entry splQ02353NDST1_RAT) for the rat N-sulfotransferase domain down to 55.6% sequence identity (SEQ ID NO: 178, entry spJQ9V3L1NDST_DROME) for the fruit fly N-sulfotransferase domain. Those skilled in the art would appreciate that the multiple sequence alignment was limited to fifteen sequences for clarity, and that there are hundreds of amino acid sequences encoding for the N-sulfotransferase domains of other wild-type NDST enzymes that have been identified and that have highly conserved active site and/or binding regions as well.

Within FIG. 6A, FIG. 6B, and FIG. 6C, amino acids that are depicted in white with a black background at a particular position, are 100% identical across all sequences. Amino acids that are highly conserved at a particular position, meaning that the amino acids are either identical or chemically or structurally similar, are enclosed with a black outline. Within highly conserved regions, consensus amino acids that are present in a majority of the sequences are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the N-sulfotransferase domain of the human NDST1 enzyme as a reference. The R symbol adjacent to an arrow refers to a β-sheet, whereas a coil adjacent to an α symbol or β symbol refers to a helix secondary structure.

Within the fifteen aligned sequences in FIG. 6A, FIG. 6B, and FIG. 6C, there are several conserved amino acid motifs that include one or more amino acids that comprise the active site, based on the crystal structure of the N-sulfotransferase domain of human NDST1. These conserved amino acid sequence motifs, based on the numbering of the amino acid residues within FIG. 6A, FIG. 6B, and FIG. 6C include residues 40-46 (Q-K-T-G-T-T-A); residues 66-69 (T-F-E-E); residues 101-105 (F-E-K-S-A); residues 139-143 (S-W-Y-Q-H); and residues 255-262 (C-L-G-K/R-S-K-G-R) which correspond to SEQ ID NO: 221, SEQ ID NO: 222, SEQ ID NO: 223, SEQ ID NO: 224, and SEQ ID NO: 225 in the sequence listing, respectively. In further embodiments, some NDST enzymes that comprise the conserved amino acid sequence motif Q-K-T-G-T-T-A (SEQ ID NO: 221) further comprise the expanded conserved amino acids L-Y-L, from residues 47-49, to form an expanded amino acid sequence motif Q-K-T-G-T-T-A-L-Y-L (SEQ ID NO: 277).

Figure 7A:
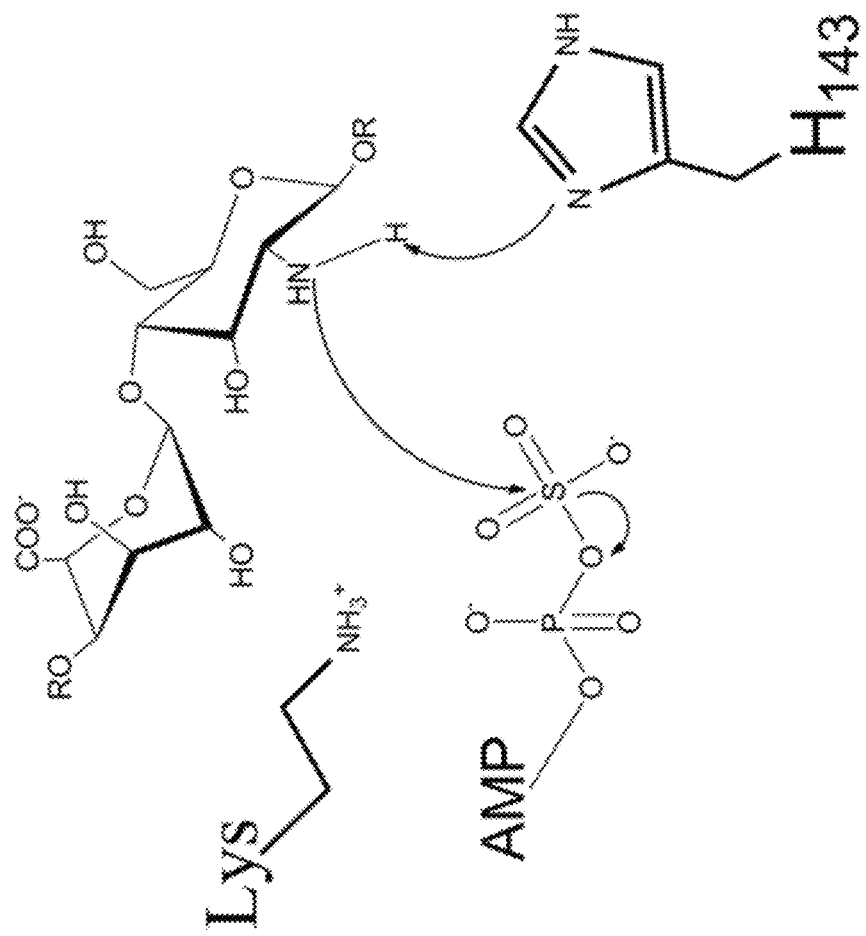
FIG. 7A, FIG. 7B, and FIG. 7C show a proposed reaction mechanism, transition state, and products formed as a result of a sulfotransfer reaction between a natural NDST enzyme, PAPS, and N-deacetylated heparosan.
Figure 7B:
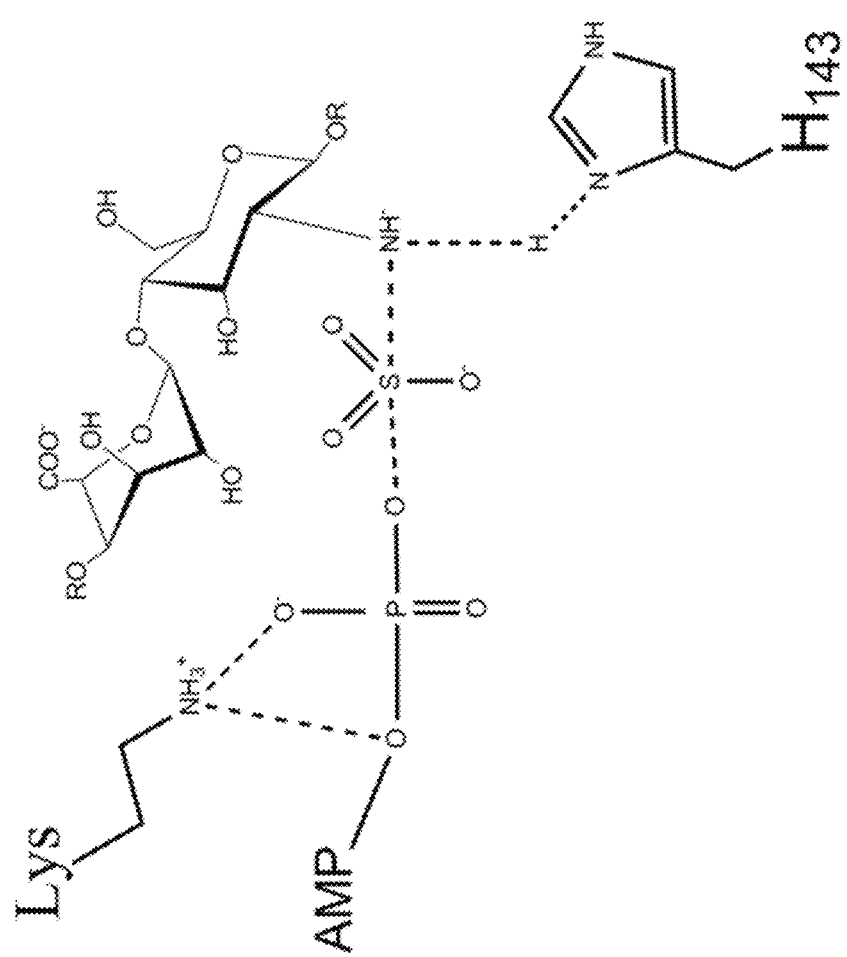
Figure 7C:
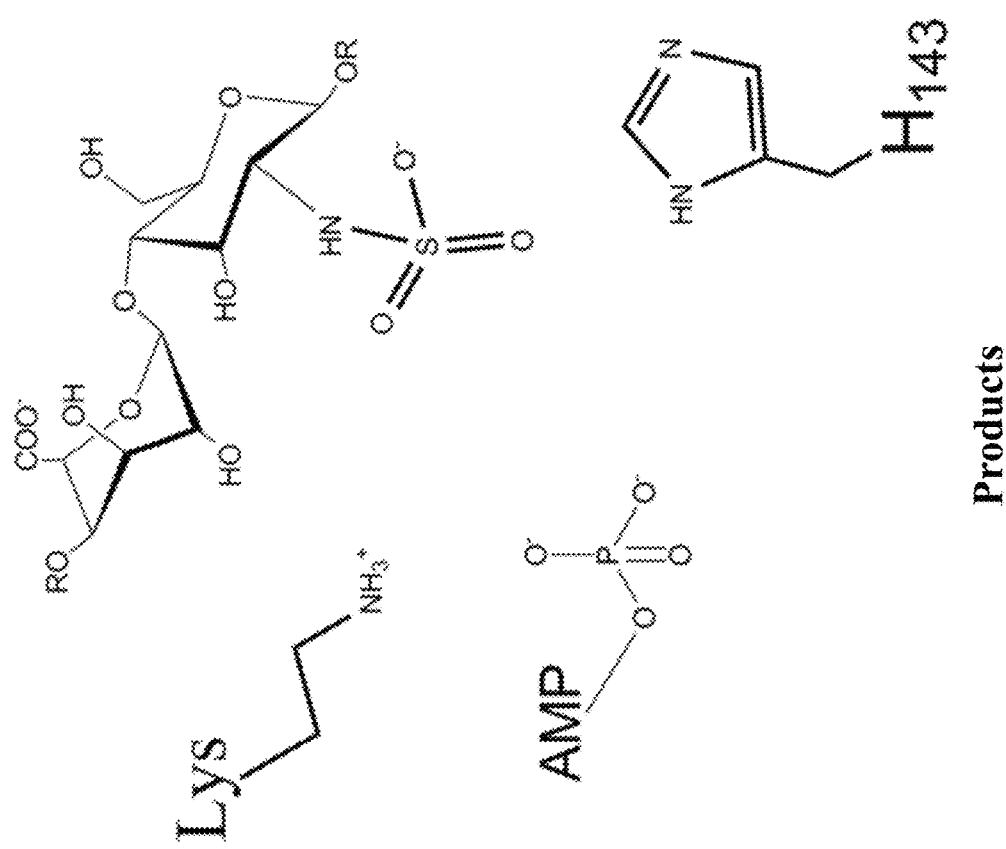

Without being limited by a particular theory, it is believed that these residues either facilitate or participate in the chemical reaction, or enable binding of PAPS or the polysaccharide within the active site. In particular and as illustrated in FIG. 7A, FIG. 7B, and FIG. 7C, the histidine residue at position 143 of the N-sulfotransferase domain (SEQ ID NO: 164) of the human NDST1 enzyme is in position to abstract one of the two protons within the amine functional group of an unsubstituted glucosaminyl residue, enabling the nitrogen atom to initiate the nucleophilic attack of PAPS and remove the sulfate functional group. Additionally, lysine residues at position 41 and 260 are also universally conserved, and are thought to coordinate with the sulfate moiety, driving binding of PAPS within the active site as well as stabilizing the transition state during the course of the reaction (see Gesteira, T. F., et al., above, as well as Sueyoshi, T., et al., (1998) *FEBS Letters* 433:211-214, the disclosure of which is incorporated by reference in its entirety).

However, as described above, natural NDST enzymes are unable to catalyze the transfer of the sulfate group from an aryl sulfate compound to the polysaccharide, because it is believed that the binding pocket for PAPS within the natural active site either does not have a high enough affinity for aryl sulfate compounds to facilitate binding and/or that the aryl sulfate compounds are sterically hindered from entering the active site altogether. Consequently, and in another embodiment, the N-sulfotransferase domain of a natural NDST enzyme can be mutated in several locations to enable binding of the aryl sulfate compound within the active site and/or to optimally position the aryl sulfate compound so transfer of the sulfate group to the polysaccharide can occur.

Accordingly, and in another embodiment, engineered NST enzymes of the present invention can comprise a single N-sulfotransferase domain that is mutated relative to the N-sulfotransferase domain of any of the natural NDST enzymes within EC 2.8.2.8, including enzymes having the amino acid sequences illustrated in FIG. 6A, FIG. 6B, and FIG. 6C. In other embodiments, engineered NST enzymes of the present invention can further comprise an N-deacetylase domain that has an identical or mutated amino acid sequence of the N-deacetylase domain of any of the natural NDST enzymes within EC 2.8.2.8.

In another embodiment, mutations engineered into the amino acid sequences of the engineered NST enzymes facilitate a biological activity in which aryl sulfate compounds can both bind and react with the enzyme as sulfo group donors. In another embodiment, although the engineered NST enzymes can bind and react with an aryl sulfate compound as a sulfo group donor, they retain the natural NDSTs' biological activity with heparosan-based polysaccharides comprising disaccharide units having the structure of Formula II, including but not limited to N-deacetylated heparosan, as a sulfo group acceptor. Without being limited by a particular theory, it is believed that because of the mutations inserted into the amino acid sequences of the engineered NST enzymes, their sulfotransferase activity may comprise the direct transfer of a sulfo group from an aryl sulfate compound to the sulfo acceptor polysaccharide, using a similar mechanism as described in FIGS. 7A-7C above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by an N-unsubstituted glucosamine within N-deacetylated heparosan to form the N-sulfated product. By either mechanism, the engineered NST enzymes are able to achieve sulfo transfer from an aryl sulfate compound to a heparosan-based polysaccharide, as described in the examples, below.

In another embodiment, an engineered NST enzyme can comprise one or more mutated amino acid sequence motifs relative to the conserved amino acid sequence motifs, corresponding to SEQ ID NOs 221-225, which are found in the N-sulfotransferase domains of natural NDSTs, as described above and indicated in the multiple sequence alignment in FIG. 6A, FIG. 6B, and FIG. 6C. In another embodiment, each mutated amino acid sequence motif that is present in the amino acid sequence of the engineered NST enzyme comprises at least one amino acid mutation relative to the corresponding conserved amino acid sequence motif within the N-sulfotransferase domains of natural NDST enzymes within EC 2.8.2.8. In another embodiment, an engineered NST enzyme comprises one mutated amino acid sequence motif. In another embodiment, an engineered NST enzyme comprises two mutated amino acid sequence motifs. In another embodiment, an engineered NST enzyme comprises three mutated amino acid sequence motifs. In another embodiment, an engineered NST enzyme comprises four mutated amino acid sequence motifs. In another embodiment, an engineered NST enzyme comprises five mutated amino acid sequence motifs. In another embodiment, an engineered NST enzyme that includes at least one mutated amino acid sequence motif can have an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

Figure 8:
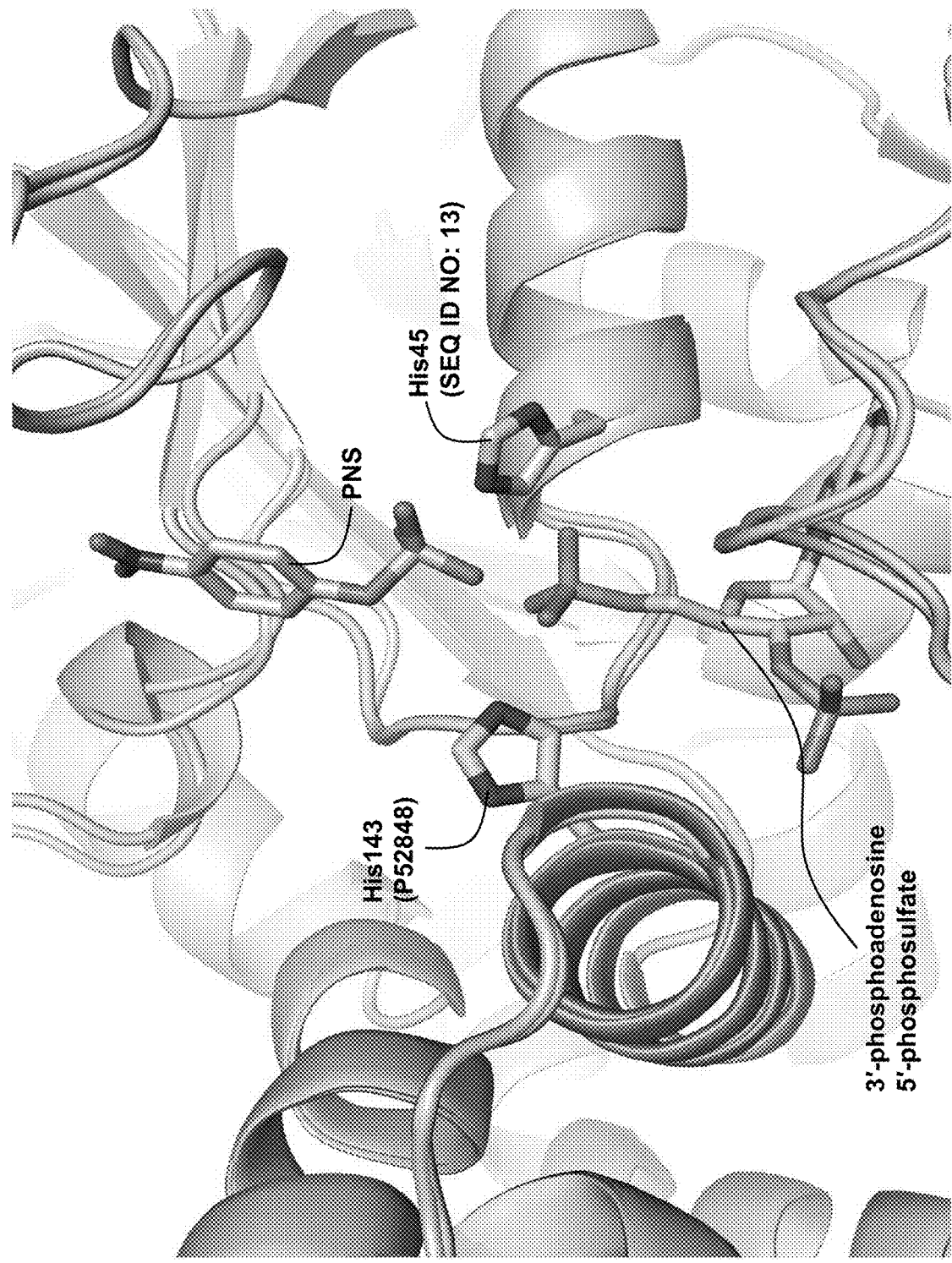
FIG. 8 shows a three-dimensional model of PNS bound within the active site of an engineered NST enzyme, superimposed over the crystal structure of the N-sulfotransferase domain of a natural enzyme from the EC. 2.8.2.8 enzyme class.

In another embodiment, upon viewing the crystal structure of the N-sulfotransferase domain of the human NDST1 (PDB code: 1NST) within a 3D molecular visualization system (including, as a non-limiting example, the open-source software, PyMOL), the structure of related sequences, such as those of engineered NST enzymes that contain one or more amino acid sequence motifs that are mutated relative to the human NDST1 N-sulfotransferase domain (SEQ ID NO: 164), can be modeled for comparison as illustrated in FIGS. 8-11. In one non-limiting example, FIG. 8 shows a magnified view of the active site of the human NDST1 N-sulfotransferase domain that is overlaid with an engineered NST enzyme comprising the amino acid sequence of SEQ ID NO: 13, in which the structure of the engineered enzyme is calculated upon making mutations relative to the human N-sulfotransferase domain amino acid sequence. Adenosine 3',5'-diphosphate, which is the product of a sulfotransfer reaction in which PAPS is the sulfo donor, and which was co-crystallized with the NDST1 N-sulfotransferase domain, is also illustrated within the active site. PNS is also modeled into the engineered enzyme active site, using the consensus solutions of molecular dynamics (MD) simulations that designed to calculate the optimized position and orientation of a ligand within an enzyme active site adjacent to the polysaccharide binding site (not shown), if such solutions are possible.

As illustrated in FIG. 8, although there are several mutations within SEQ ID NO: 13 made relative to sequence of the human NDST1 N-sulfotransferase domain (SEQ ID NO: 164, UniProtKB Accession No. P52848) indicated in FIG. 6A, FIG. 6B, and FIG. 6C, the respective protein backbones are in a nearly identical location to one another, enabling a one-to-one comparison of the active sites. Within the structure of the engineered enzyme comprising the sequence of SEQ ID NO: 13, the consensus solutions from MD simulations indicate that the sulfate moiety within PNS is favored to bind adjacent to a histidine residue, His-45, that has been mutated relative to the natural threonine residue at that position, which is universally conserved within EC 2.8.2.8. On the other hand, within the human NDST1 N-sulfotransferase domain, the adenosine 3',5'-diphosphate is located near to the conserved His-143, described above. Although the sulfo group that would be comprised within the PAPS substrate is not shown, those skilled in the art would appreciate that if PAPS were present, the sulfate group would be oriented in a position immediately adjacent to His-143 and partially overlapping with the sulfate group within PNS. Without being limited by a particular theory, it is believed that the nearly overlapping location of the sulfate groups accounts for the engineered enzyme's ability to facilitate sulfo group transfer by using His-143 as a base to remove the proton from the glucosaminyl residue within the polysaccharide.

Figure 9:
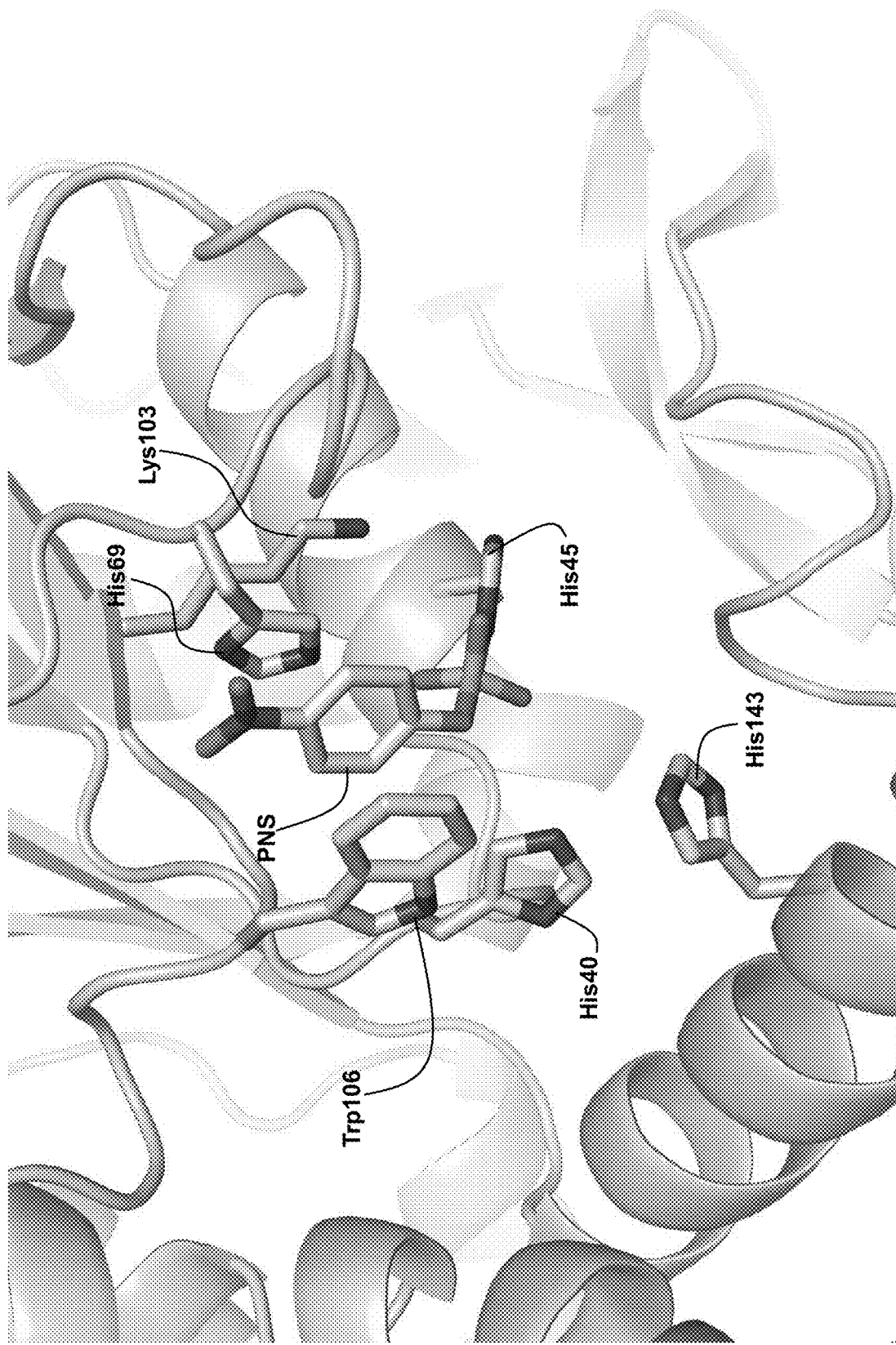
FIG. 9 shows a three-dimensional model of the engineered enzyme modeled in FIG. 8, illustrating amino acid mutations present within the active site.

However, even though the sulfate groups appear to bind in a nearly identical location within the active site, aryl sulfate compounds cannot be utilized with natural NDST enzymes to facilitate sulfo group transfer to a polysaccharide. As described above, the amino acid residues within the active site of the natural sulfotransferases are evolved to have strong binding affinity for PAPS, and without being limited by a particular theory, it is believed that the enzymes likely do not have enough affinity for aryl sulfate compounds to drive binding and sulfotransferase activity. Consequently, it is believed that other mutations can assist to drive binding of aryl sulfate compounds within the active site. FIG. 9 illustrates other mutations that surround PNS within the engineered enzyme comprising the amino acid sequence of SEQ ID NO: 13, including Trp-106, His-69, and His-40. PNS carbon atoms are positioned between Trp-106 and His-69, and appear to provide π-π stacking binding contacts with both amino acid side chains. Additionally, the ε2 nitrogen atoms within His-69 and His-40 appear to coordinate with the sulfuryl group of PNS directly. Lysine residues retained from the natural enzyme sequence, Lys-41 (not shown, for clarity) and Lys-103 appear to be in position to coordinate with the sulfate group during transfer in order to stabilize the transition state. Of note, the natural amino acid residue, Lys-260, which also coordinates with the sulfate group in PAPS, is mutated to a valine residue within the engineered enzyme sequence. Without being limited by a particular theory, it is believed that His-45, which is necessary for the reaction with PNS, would exhibit charge repulsion with a lysine residue at position 260, and that the mutation to a valine residue retains some steric bulk within the binding site while eliminating the charge repulsion. Lys-103 is nonetheless positioned to coordinate with the sulfuryl group, particularly when the sulfuryl group is associated or bound to His-45, as shown in FIG. 9.

Figure 10:
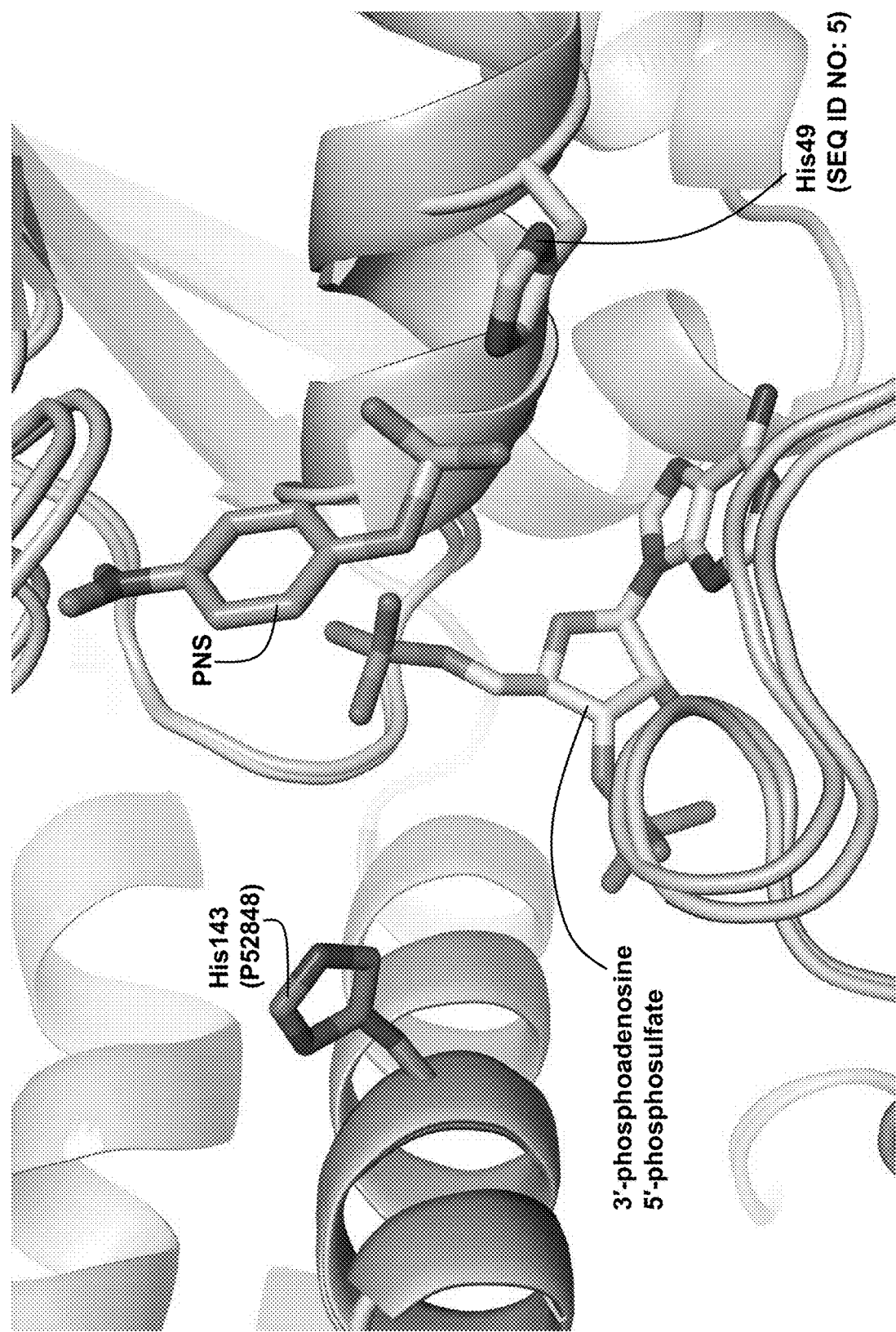
FIG. 10 shows another three-dimensional model of PNS bound within the active site of an engineered NST enzyme, superimposed over the crystal structure of the N-sulfotransferase domain of a natural enzyme from the EC. 2.8.2.8 enzyme class.
Figure 11:
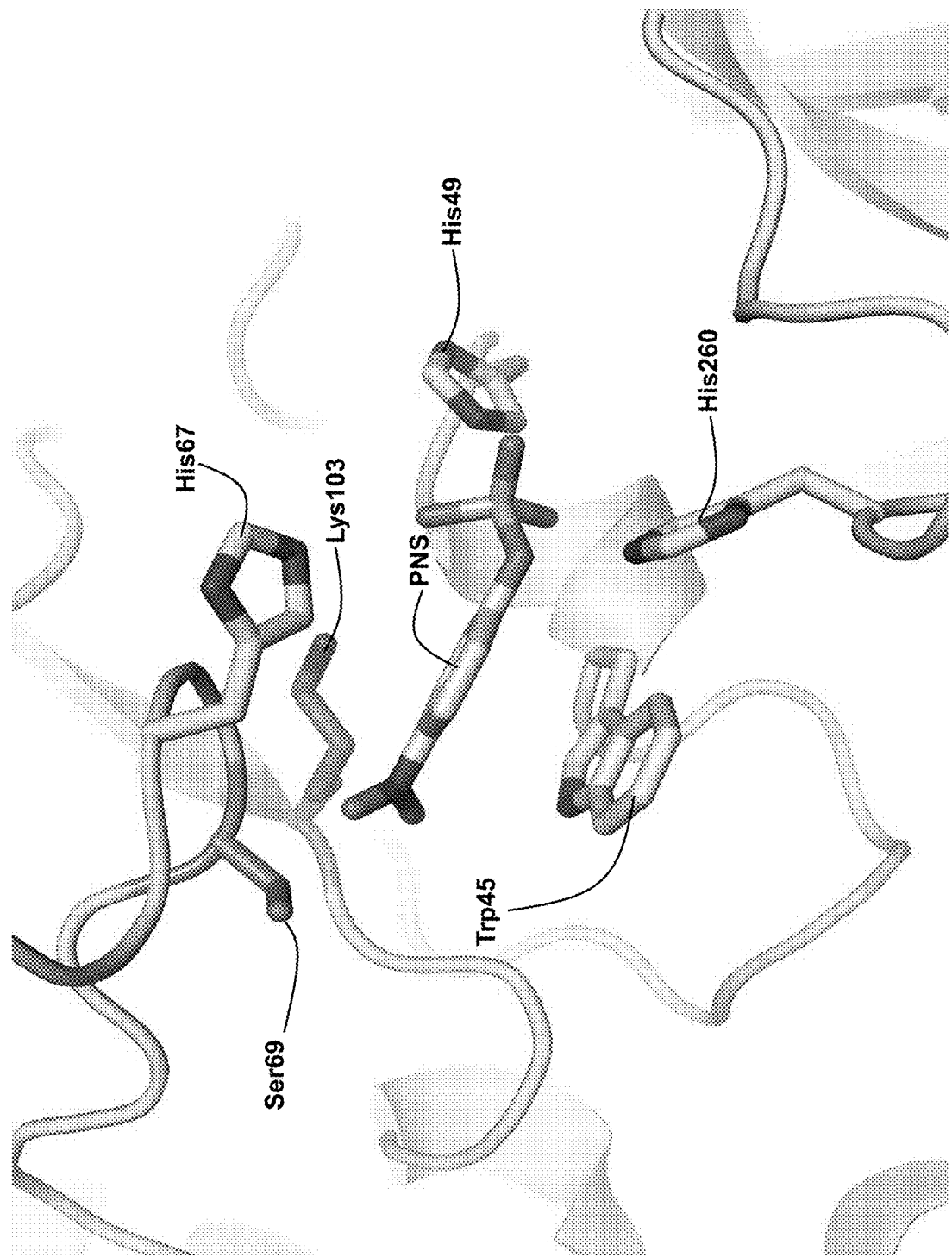
FIG. 11 shows a three-dimensional model of the engineered enzyme modeled in FIG. 10, illustrating amino acid mutations present within the active site.

In another non-limiting example, FIG. 10 shows a magnified view of the active site of the N-sulfotransferase domain of human NDST1 (SEQ ID NO: 164, UniProtKB Accession No. P52848) overlaid with a different engineered NST enzyme, comprising the amino acid sequence of SEQ ID NO: 5. PNS is modeled into the engineered enzyme active site, as described above. As with the engineered enzyme comprising the amino acid sequence SEQ ID NO: 13, the protein backbone of the engineered enzyme comprising the amino acid sequence of SEQ ID NO: 5 also has a nearly identical structure to the N-sulfotransferase domain of the human enzyme. However, the consensus solutions from MD simulations indicate that the sulfate moiety within PNS is favored to bind adjacent to a different histidine mutation (His-49), which is mutated from a leucine residue that is conserved within the active site of the natural NDST enzymes. Consequently, mutations within SEQ ID NO: 13 that formed binding contacts with PNS are not necessarily present in SEQ ID NO: 5. As illustrated in FIG. 11 and similar to SEQ ID NO: 13, there are two mutations present within SEQ ID NO: 5 that appear to form π-π stacking binding contacts surrounding the aromatic moiety of PNS, Trp-45 and His-67. Other mutations that comprise side chains that appear to coordinate with PNS include Ser-69 (coordinating with the nitro functional group of PNS) and His-260 (coordinating with the sulfate moiety). Similar to SEQ ID NO: 13, because the natural lysine residue at position 260 is mutated, the natural Lys-103 residue is utilized within SEQ ID NO: 5 to coordinate with the sulfate moiety within PNS.

Those skilled in the art would appreciate that engineered NST enzymes of any other amino acid sequence, including, but not limited to, those described by SEQ ID NO: 7, SEQ ID NO: 9, SEQ ID NO: 11, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25, would likely exhibit a similar structure to the N-sulfotransferase domain of human NDST1 and engineered NST enzymes having the amino acid sequence of SEQ ID NO: 5 and SEQ ID NO: 13. Without being limited by a particular theory, it is also believed that NCS would bind in a similar position as PNS within the active site of any of the engineered NST enzymes, since the structures of the two aryl sulfate compounds are very similar, except that the sulfate group is located ortho on the aromatic ring relative to the nitro group, rather than para to the nitro group.

Further, the engineered NST enzymes of the present invention can include mutated amino acid sequence motifs that comprise one or more of the above-described mutations as well as other mutations that facilitate binding of substrates, the sulfotransfer reaction, or the stability of the enzyme during protein expression. In another embodiment, an engineered NST enzyme can include the mutated amino acid sequence motif, $X_1$-K-T-G-A-W/F-A/L-L-$X_2$-H (SEQ ID NO: 278), mutated from the conserved amino acid sequence Q-K-T-G-T-T-A-L-Y-L (SEQ ID NO: 277) within natural NDST enzymes, wherein $X_1$ is selected from the group consisting of glutamine, serine, and alanine; and $X_2$ is selected from the group consisting of tyrosine, threonine, and histidine. Engineered NST enzymes that include the mutated amino acid sequence motif $X_1$-K-T-G-A-W/F-A/L-L-$X_2$-H (SEQ ID NO: 278) include, but are not limited to SEQ ID NO: 5 (described above), as well as SEQ ID NO: 7, SEQ ID NO: 15; SEQ ID NO: 18, SEQ ID NO: 20, SEQ ID NO: 21, and SEQ ID NO: 25. In further embodiments, engineered NST enzymes can further include the mutated amino acid sequence motif, T-$X_3$-$X_4$-S(SEQ ID NO: 279), mutated from the conserved amino acid sequence T-F-E-E (SEQ ID NO: 222), wherein $X_3$ is a mutation selected from the group consisting of histidine and glycine; $X_4$ is a mutation selected from the group consisting of glycine, histidine, and serine; and wherein at least one of $X_3$ and $X_4$ is a histidine residue. In some even further embodiments, $X_1$ is glutamine and $X_2$ is tyrosine (SEQ ID NO: 280), $X_3$ is histidine and $X_4$ is glycine (SEQ ID NO: 237), and the engineered NST enzyme further comprises the mutated amino acid sequence motif, C-L-G-K/R-S-H-G-R (SEQ ID NO: 281). In other even further embodiments, $X_1$ is serine and $X_2$ is threonine (SEQ ID NO: 282), $X_3$ is glycine and $X_4$ is histidine (SEQ ID NO: 238), and the engineered NST enzyme further comprises the mutated amino acid sequence motif, C-H-G-K/R-R-W-G-R (SEQ ID NO: 283). In sill other even further embodiments, $X_1$ is alanine and $X_2$ is histidine (SEQ ID NO: 284), $X_3$ is histidine and $X_4$ is serine (SEQ ID NO: 285), and the engineered NST enzyme further comprises the mutated amino acid sequence motif, C-A-H-K/R-G-L-G-R (SEQ ID NO: 286).

In another embodiment, engineered NST enzymes can include the mutated amino acid sequence motif, H-$X_5$-T-G-$X_6$-H-A (SEQ ID NO: 226), mutated from the conserved amino acid sequence Q-K-T-G-T-T-A (SEQ ID NO: 221), wherein $X_5$ is selected from the group consisting of lysine and glycine; and $X_6$ is a mutation selected from the group consisting of glycine and valine. Engineered NST enzymes that include the mutated amino acid sequence motif H-$X_5$-T-G-$X_6$-H-A (SEQ ID NO: 226) include, but are not limited to SEQ ID NO: 13 (described above), as well as SEQ ID NO: 9, SEQ ID NO: 11; SEQ ID NO: 19, SEQ ID NO: 22, SEQ ID NO: 23, and SEQ ID NO: 24. In further embodiments, $X_5$ is glycine and $X_6$ is glycine (SEQ ID NO: 227). In some even further embodiments, the engineered NST enzyme further comprises the mutated amino acid sequence motif, C-G-G-K/R-H-L-G-R (SEQ ID NO: 287). In other even further embodiments, the engineered NST enzyme further comprises the mutated amino acid sequence motif, F-E-H-S-G (SEQ ID NO: 288).

In another embodiment, within any of the engineered NST enzymes that include the mutated amino acid sequence motif, H-$X_5$-T-G-$X_6$-H-A (SEQ ID NO: 226), $X_5$ is selected to be lysine and $X_6$ is selected to be valine (SEQ ID NO: 228), and the engineered NST enzyme further comprises the mutated amino acid sequence motif, T-G-N-H (SEQ ID NO: 289).

Figure 12A:
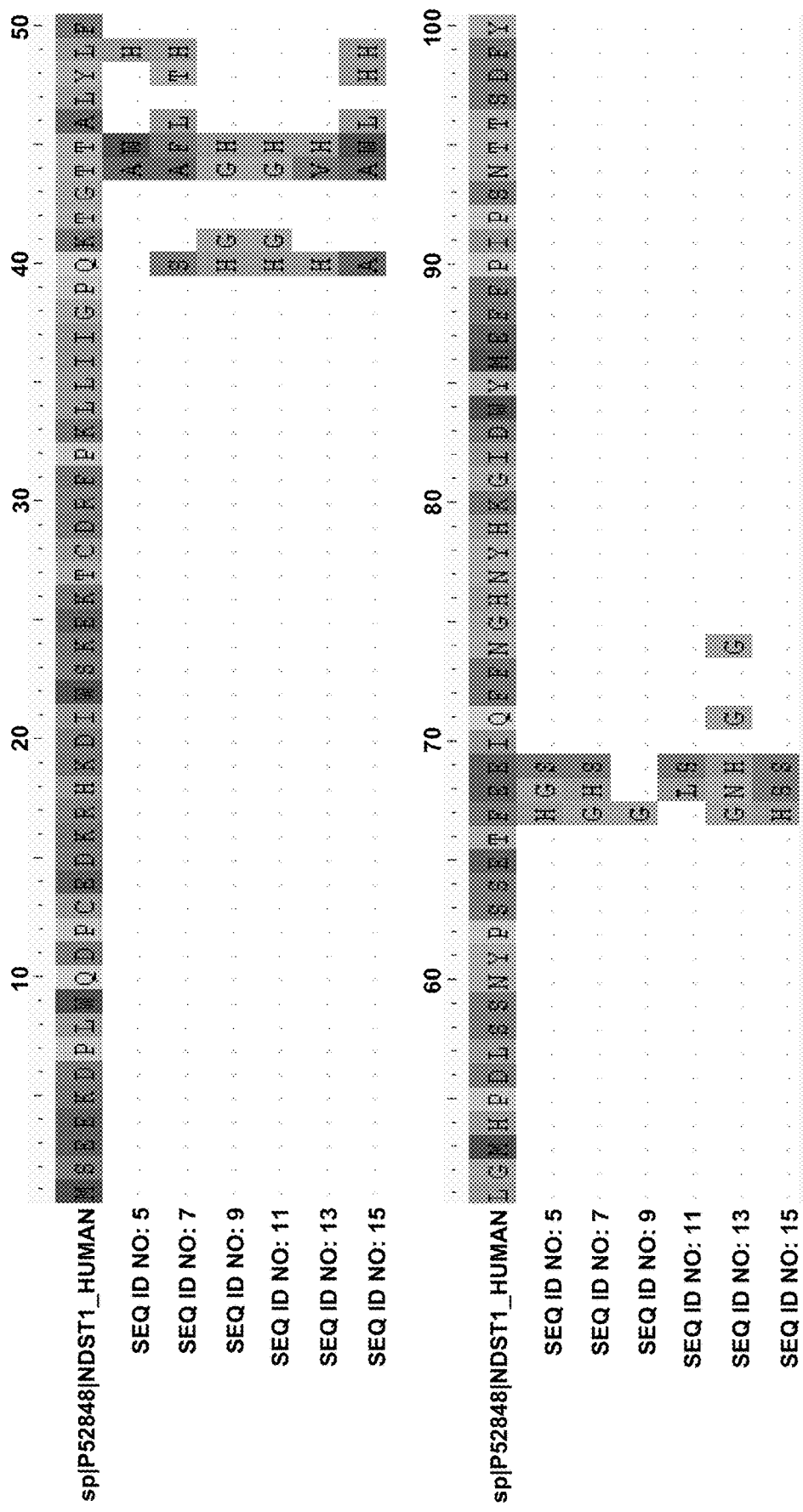
FIGS. 12A-12C shows a sequence alignment of polypeptides comprising the amino acid sequences of SEQ ID NO: 5, SEQ ID NO: 7, SEQ ID NO: 9, SEQ ID NO: 11, SEQ ID NO: 13, and SEQ ID NO: 15, respectively, depicting the position and identity of amino acid residues differences between each of the illustrated sequences.
Figure 12B:
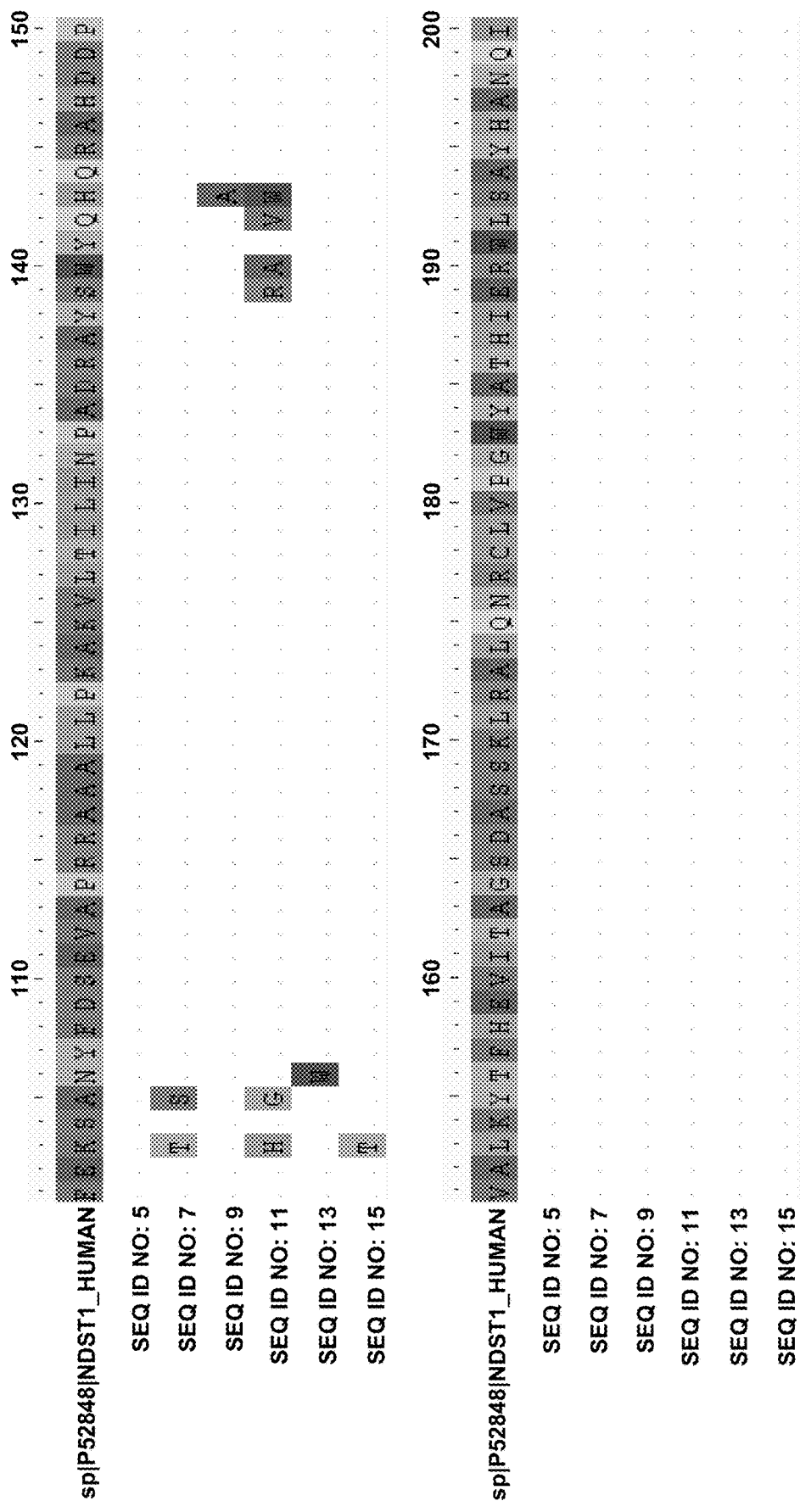
Figure 12C:
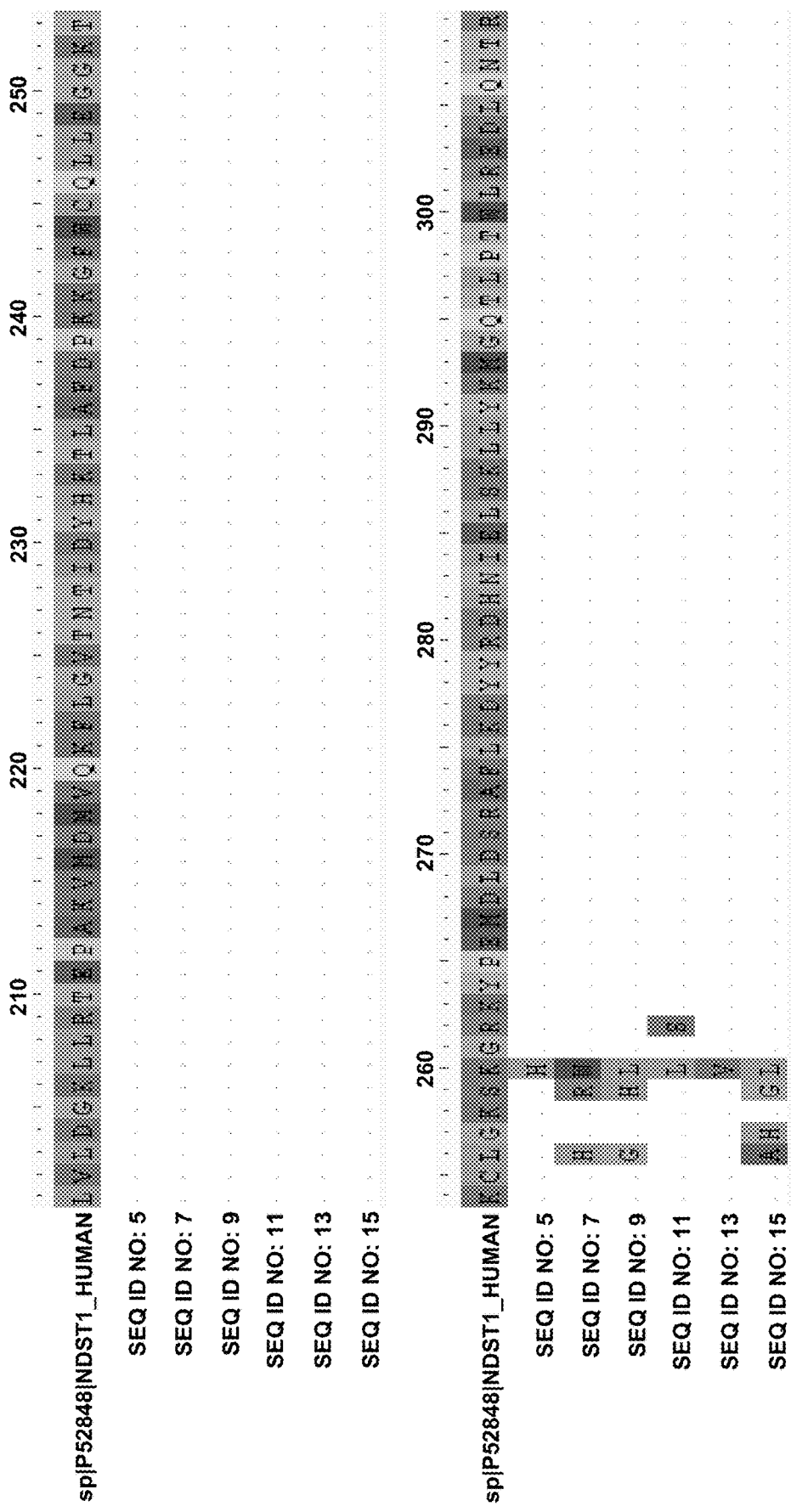

Furthermore, the amino acid sequences (SEQ ID NO: 5, SEQ ID NO: 7 SEQ ID NO: 9, SEQ ID NO: 11, SEQ ID NO: 13, SEQ ID NO: 15) of six engineered NST enzymes, which have been experimentally determined to be active with aryl sulfate compounds as sulfo group donors (see Example 3 below) can be compared with the amino acid sequence of the N-sulfotransferase domain of the human NDST1 enzyme (SEQ ID NO: 164,_entry sp|P52848|NDST1_HUMAN) in a multiple sequence alignment to determine if there are relationships between mutations among each of the enzymes. Within the multiple sequence alignment, a period within the amino acid sequence of an engineered enzyme indicates identity at a particular position with the N-sulfotransferase domain of human NDST1. As shown in FIGS. 12A-12C, the sequence alignment demonstrates that while over 90% of the amino acid residues within the six sulfotransferase sequences are identical, there are several positions in which multiple amino acids can be chosen. Without being limited by a particular theory, these enzymes appear to have a similar relationship with each other as the N-sulfotransferase domains of the NDST enzymes that comprise EC 2.8.2.8. As a result, and in another embodiment, engineered NST enzymes comprising an amino acid sequence in which multiple amino acids can be chosen at defined positions are disclosed as SEQ ID NO: 18 and SEQ ID NO: 19. Positions at which the identity of an amino acid can be chosen from a selection of possible residues are denoted in terms "Xaa," "Xn," or "position n," where n refers to the residue position.

In another embodiment, within an engineered NST enzyme comprising the amino acid sequence of SEQ ID NO: 18 or SEQ ID NO: 19, the amino acid residue at position 41 is lysine, the amino acid residue at position 44 is alanine, the amino acid residue at position 45 is an aromatic amino acid residue, preferably tyrosine or phenylalanine, and the amino acid residue at position 49 is histidine. In another embodiment, when the engineered NST enzyme comprises the above residues from positions 41-49, the amino acid residue at position 67 is glycine or histidine, the amino acid residue at position 68 is selected from the group consisting of glycine, histidine, and serine, and the amino acid residue at position 69 is serine.

In another embodiment, within an engineered NST enzyme comprising the amino acid sequence of SEQ ID NO: 18 or SEQ ID NO: 19, the amino acid residue at position 40 is histidine and the amino acid residue at position 45 is histidine. In further embodiments, the amino acid residue at position 41 is glycine and the amino acid residue at position 44 is glycine. In other further embodiments, the amino acid residue at position 41 is lysine and the amino acid residue at position 44 is valine. In even further embodiments, the amino acid residue at position 67 is glycine and the amino acid residue at position 69 is histidine. In still further embodiments, the amino acid residue at position 106 is tryptophan. In even still further embodiments, the amino acid residue at position 260 is valine.

In another embodiment, within an engineered NST enzyme comprising the amino acid sequence of SEQ ID NO: 18 or SEQ ID NO: 19, the amino acid sequence can optionally include one or more mutations at residue positions not specified by an "Xn" or "Xaa," so long as any such mutations do not eliminate the NST and/or aryl sulfate-dependent activity of the enzyme. In another embodiment, such mutations not eliminating aryl sulfate-dependent activity at positions not specified by an "Xn" or "Xaa" can include substitutions, deletions, and/or additions.

Accordingly, in another embodiment, an engineered NST enzyme utilized in accordance with any of the methods of the present invention can comprise an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25. In another embodiment, engineered NST enzymes comprising the amino acid sequence of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, or SEQ ID NO: 25 can react with any aryl sulfate compound. In further embodiments, the aryl sulfate compound is selected from the group consisting of PNS, MUS, 7-hydroxycoumarin sulfate, phenyl sulfate, 4-acetylphenyl sulfate, indoxyl sulfate, 1-naphthyl sulfate, 2NapS, and NCS. In some even further embodiments, the aryl sulfate compound is PNS. In other even further embodiments, the aryl sulfate compound is NCS.

Engineered 2OSTs

In nature, 2OSTs recognize, bind, and react with N-sulfated heparosan polysaccharides as sulfo group acceptors. Within the N-sulfated heparosan, a majority of the glucosaminyl residues are generally N-sulfated, and the sulfo group is transferred to the 2-O position of a hexuronic acid residue, generally glucuronic acid or iduronic acid. As with the natural NDST enzymes described above, natural 2OSTs transfer the sulfo group to the polysaccharide upon reacting with PAPS as a sulfo group donor. However, natural 2OSTs are members of the EC 2.8.2.- enzyme class. N-sulfated heparosan that react with natural 2OST enzymes as sulfo group acceptors typically comprise at least one of two distinct structural motifs. In a first non-limiting example, natural 2OST enzymes can recognize, bind, and react with N-sulfated heparosan having the structure of Formula IV, below:

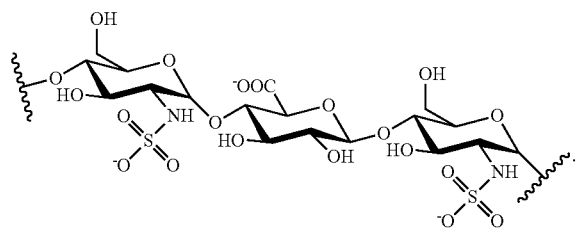

In another non-limiting example, natural 2OST enzymes can recognize, bind, and react with N-sulfated heparosan having the structure of Formula V, below:

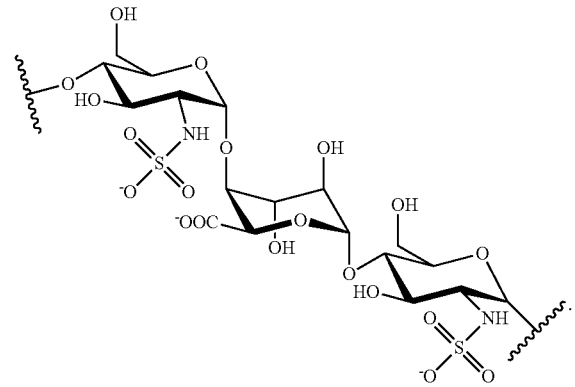

In both instances, the hexuronic acid residue (glucuronic acid in Formula IV, iduronic acid in Formula V) is flanked on either side by N-sulfated glucosamine residues that are otherwise unsubstituted at the 3-O and 6-O positions. Natural 2OST enzymes, and their biological activity with polysaccharides comprising the structures of Formula IV or Formula V, have been described by Rong, J., et al., (2001) *Biochemistry* 40 (18):5548-5555, the disclosure of which is incorporated by reference in its entirety.

As described above, although the portion of the N-sulfated heparosan comprising the structure of Formula IV or Formula V contains N-sulfated glucosamine residues, other glucosamine residues within the polysaccharide can be N-sulfated, N-acetylated, 3-O sulfated, and/or 6-O sulfated, and hexuronyl residues can be glucuronic acid or iduronic acid, either of which can be 2-O sulfated. Similarly, heparosan-based polysaccharides can comprise one or more structural motifs comprising the structure of Formula IV and/or the structure of Formula V within the same polysaccharide, any of which can be 2-O sulfated by the same enzyme. Typically, N-sulfated heparosan capable of reacting with 2OST comprises at least eight monosaccharide residues. In another embodiment, the engineered 2OSTs of the present invention have identical preference as natural 2OSTs for N-sulfated heparosan as a sulfo group acceptor, particularly N-sulfated heparosan comprising the structure(s) of Formula IV and/or Formula V.

The stereochemistry of the hexuronic acid residue in N-sulfated heparosan comprising the structure of Formula IV or Formula V can be controlled by the presence of a glucuronyl $C_5$-epimerase, which reversibly inverts the stereochemistry of the $C_5$-carbon of hexuronic acid residues. However, once the hexuronyl residue within a polysaccharide comprising the structure of Formula IV or Formula V is 2-O sulfated, the hexuronic acid residue can no longer be epimerized. Generally, N-sulfated heparosan that can react with a 2OST in vivo are almost exclusively synthesized as disaccharide units of N-sulfoglucosamine and glucuronic acid. One or more of these glucuronic acid residues are often epimerized to an iduronic acid residue prior to reacting with the 2OST enzyme to form 2-O sulfated iduronic acid residues. However, and without being limited by a particular theory, it is believed that natural 2OST enzymes generally have preference for binding and reacting with N-sulfated heparosan comprising the structure of Formula V, and that most N,2O-HS polysaccharides produced in vivo generally comprise 2-O sulfated iduronic acid.

Upon successfully binding PAPS and N-sulfated heparosan comprising the structure of Formula IV, natural 2OST enzymes can catalyze transfer of the sulfo group to the 2-O position of a glucuronic acid residue, forming an N,2O-HS product comprising the structure of Formula VI, below:

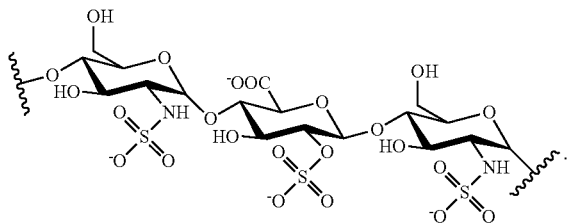

Upon successfully binding PAPS and N-sulfated heparosan comprising the structure of Formula V, natural 2OST can catalyze transfer of the sulfo group to the 2-O position of an iduronic acid residue, forming an N,2O-HS product comprising the structure of Formula VII, below:

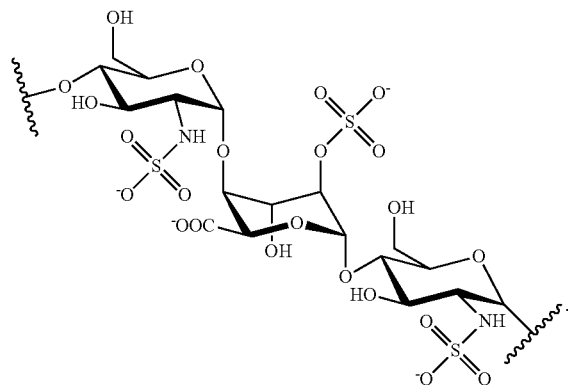

Figure 13:
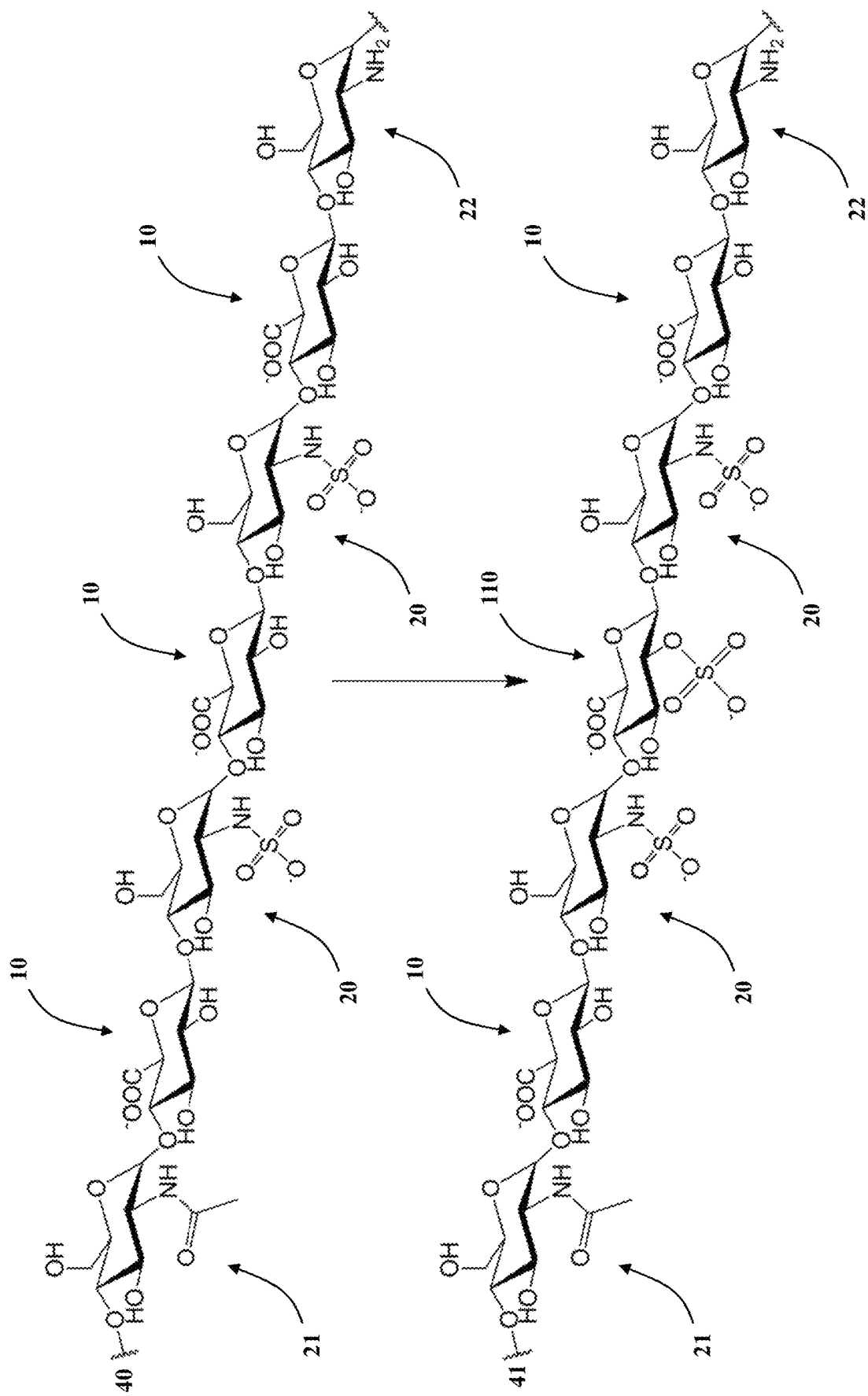
FIG. 13 shows a non-limiting example of a heparosan-based polysaccharide that can be used as a sulfo group acceptor with engineered 2OST enzymes of the present invention.

In another embodiment, in order to be 2-O sulfated, a glucuronic acid or iduronic acid residue must be adjacent to two N-sulfated glucosamine residues, as shown in Formula IV and Formula V. A non-limiting example of one such polysaccharide is illustrated in FIG. 13. In FIG. 13, hexuronyl residues 10 within polysaccharide 40 are flanked by glucosaminyl residues 20, 21, and 22, that are either N-sulfated, N-acetylated, or unsubstituted, respectively. In another embodiment, upon reacting the polysaccharide 40 with an engineered 2OST, only the hexuronyl residue 10 flanked by two N-sulfated glucosamine residues 20 can be 2-O sulfated, ultimately forming a 2-O sulfated hexuronyl residue 110 within the product polysaccharide 41.

Figure 14:
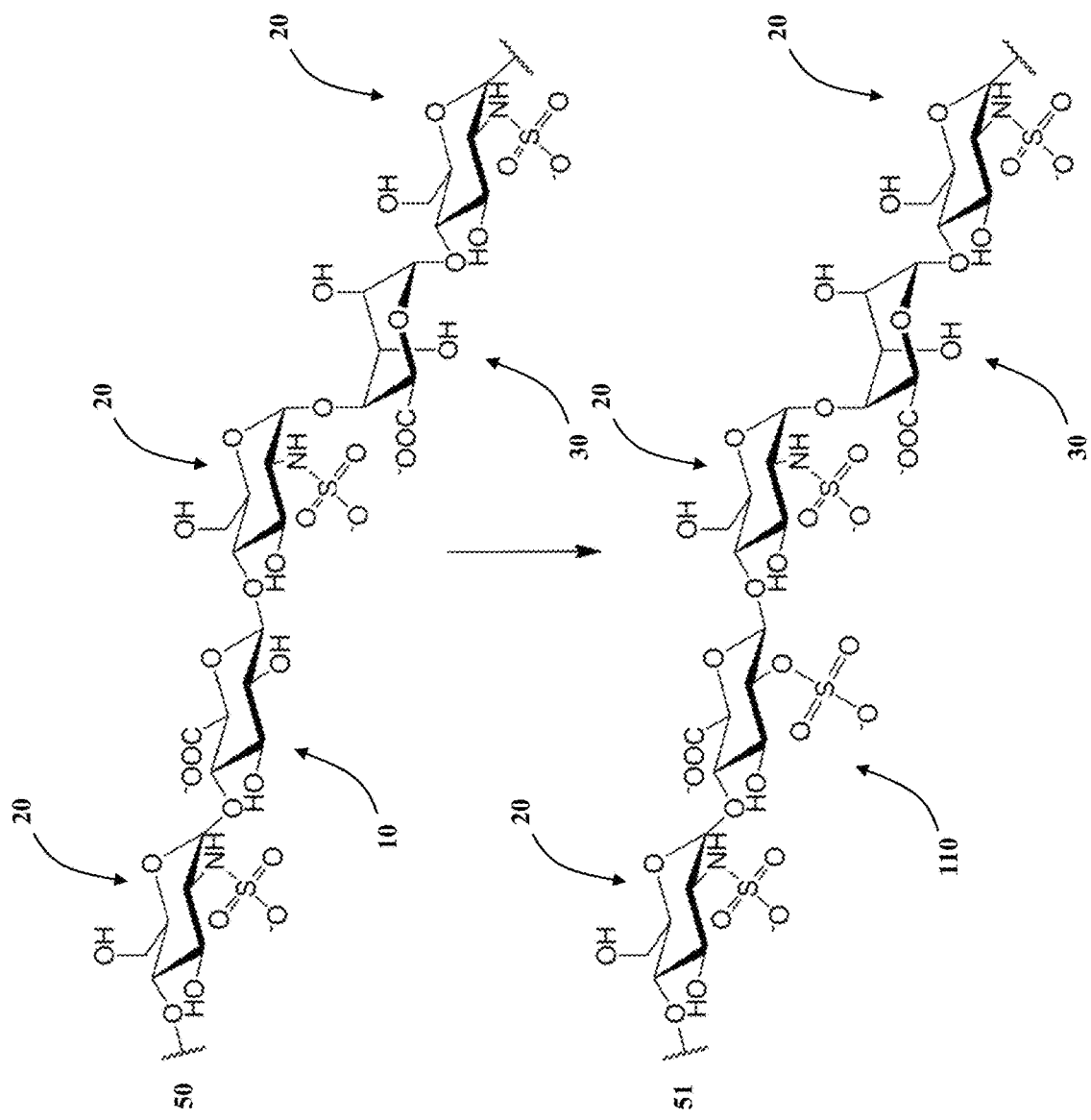
FIG. 14 shows another non-limiting example of a heparosan-based polysaccharide that can be used as a sulfo group acceptor with engineered 2OST enzymes of the present invention, where a sulfate group is transferred to the 2-O position of a glucuronic acid residue within the heparosan-based polysaccharide.
Figure 15:
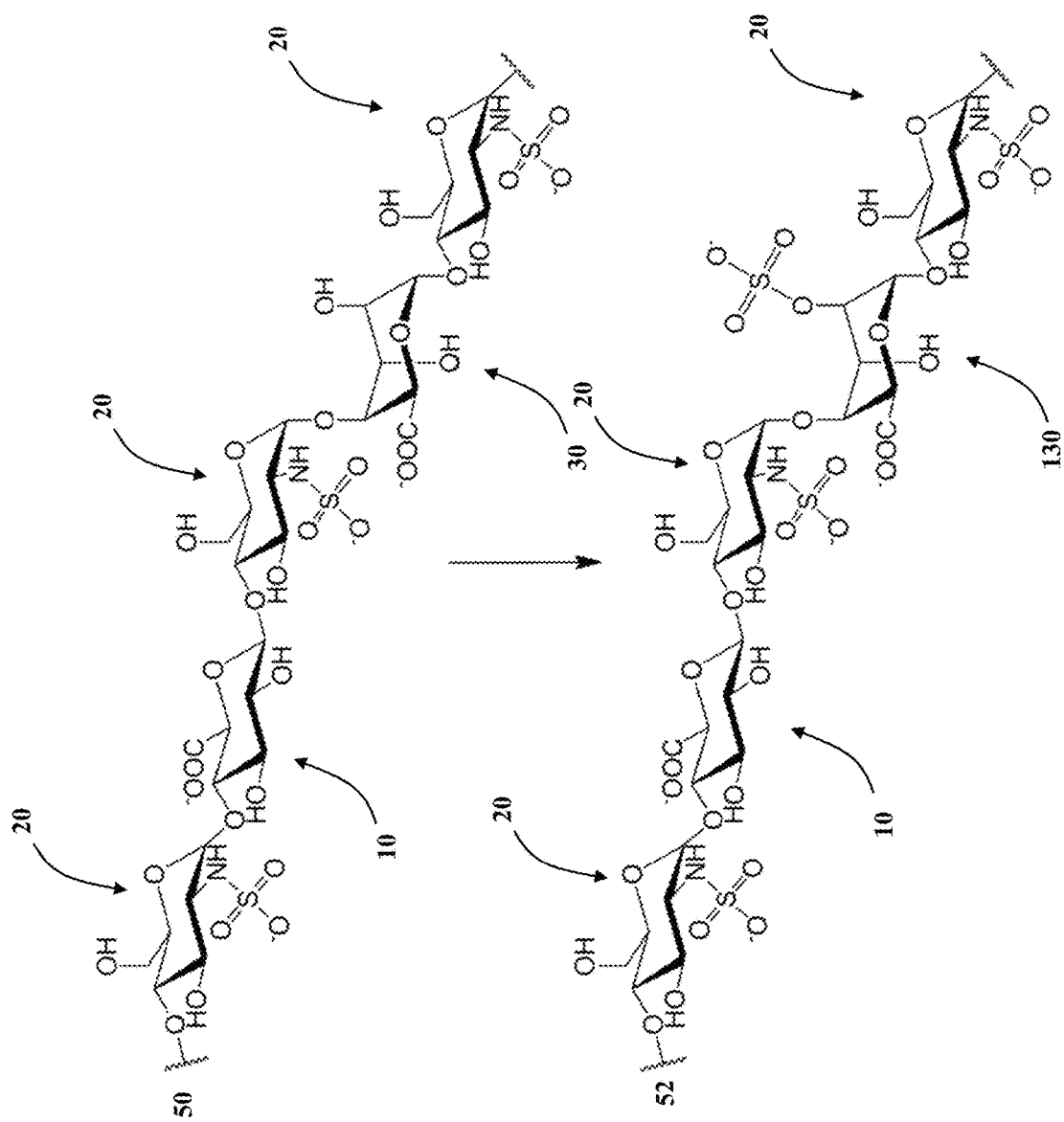
FIG. 15 shows another non-limiting example of a heparosan-based polysaccharide that can be used as a sulfo group acceptor with engineered 2OST enzymes of the present invention, where a sulfate group is transferred to the 2-O position of an iduronic acid residue within the polysaccharide.
Figure 16:
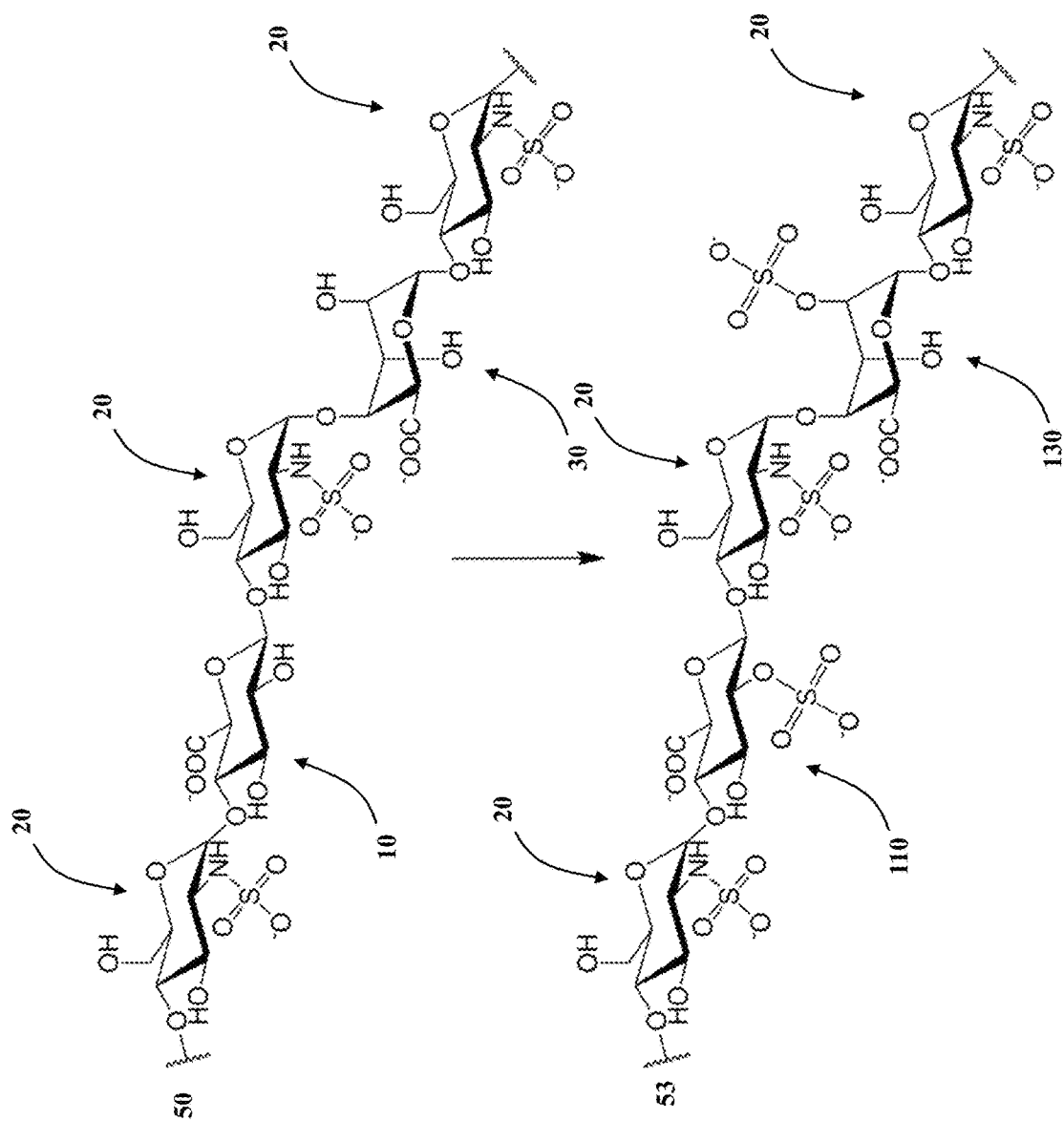
FIG. 16 shows another non-limiting example of a heparosan-based polysaccharide that can be used as a sulfo group acceptor with engineered 2OST enzymes of the present invention, where a sulfate group is transferred to both the 2-O position of a glucuronic acid residue and the 2-O position of an iduronic acid residue within the polysaccharide.
Figure 17C:
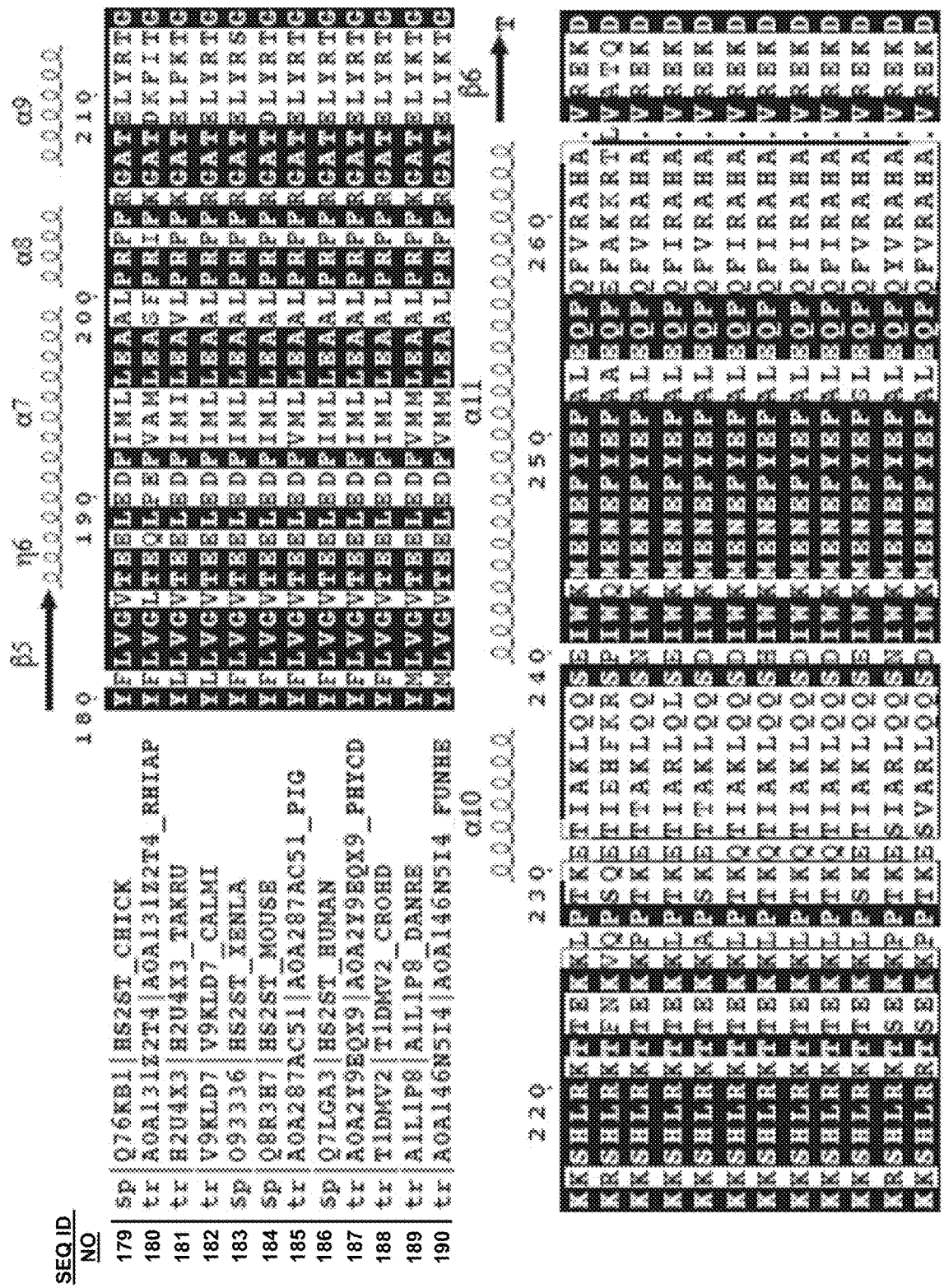

In another non-limiting example, portions of N-sulfated heparosan comprising the structures of Formula IV and Formula V are illustrated by polysaccharide 50 in each of FIG. 14, FIG. 15, and FIG. 16. In FIG. 14, FIG. 15, and FIG. 16, a hexuronyl residue 10 and an epimerized hexuronyl residue 30 are alternated between three N-sulfoglucosaminyl residues 20 within polysaccharide 50. Although hexuronyl residues 10 and 30 are represented in a chair conformation, those skilled in the art can appreciate that such monosaccharide residues within a longer oligo- or polysaccharide chain can adopt several different conformations, including chair, half-chair, boat, skew, and skew boat conformations, and that those additional conformations are omitted for clarity.

In another embodiment, upon reacting polysaccharide 50 with an engineered aryl sulfate-dependent 2OST enzyme, the enzyme can catalyze sulfo group transfer to hexuronyl residue 10 to form a sulfated hexuronyl residue 110 within product polysaccharide 51 (FIG. 14), to epimerized hexuronyl residue 30 to form a sulfated epimerized hexuronyl residue 130 within product polysaccharide 52 (FIG. 15), or to both hexuronyl residue 10 and epimerized hexuronyl residue 30 to form a sulfated hexuronyl residue 110 and a sulfated epimerized hexuronyl residue 130, respectively, within product polysaccharide 53 (FIG. 16).

Natural 2OSTs generally comprise approximately 325-375 amino acid residues that in some cases vary greatly in their sequence, yet ultimately have the exact same function, namely, to catalyze the transfer of a sulfo group from PAPS to the 2-O position of hexuronyl residues within N-sulfated heparosan. Without being limited by a particular theory, it is believed that each of the natural 2OSTs can catalyze the same chemical reaction because there are multiple amino acid sequence motifs and secondary structures, particularly in region(s) that define their active sites, that are either identical or highly conserved across all species.

Further, it is believed that several of the conserved amino acid sequence motifs are directly involved in binding of either PAPS and/or the polysaccharide, or participate in the chemical reaction itself. The identity between the natural 2OST enzymes can be demonstrated by comparing the amino acid sequence of the chicken 2OST (SEQ ID NO: 179), which has known crystal structures (PDB codes: 3F5F and 4NDZ) in which amino acid residues within the active site have been identified, alongside the amino acid sequences of other natural 2OSTs within EC 2.8.2.-. A multiple sequence alignment of twelve enzymes, including the chicken, human, and other eukaryotic 2OST enzymes (SEQ ID NOs 179-190), is shown in FIG. 17A, FIG. 17B, FIG. 17C, and FIG. 17D, along with percent identity relative to the chicken 2OST reference sequence (SEQ ID NO: 179, UniProtKB Accession No. Q76KB1). As illustrated in FIG. 17A, FIG. 17B, FIG. 17C, and FIG. 17D, sequences range from having 94.9% sequence identity with the Q76KB1 reference sequence (SEQ ID NO: 188, entry trT1DMV2T1DMV2_CROHD) for the timber rattlesnake 2OST, down to 56.3% sequence identity (SEQ ID NO: 180, entry tr|A0A131Z2T4|A0A131Z2T4_RHIAP) for the brown ear tick 2OST. The human enzyme (SEQ ID NO: 186, entry sp|Q7LGA3|HS2ST_HUMAN) has 94.1% sequence identity with the Q76KB1 reference sequence. Those skilled in the art would appreciate that the multiple sequence alignment was limited to twelve sequences for clarity, and that there are hundreds of amino acid sequences encoding for natural 2OST enzymes that have been identified and that have highly conserved active site and/or binding regions as well.

Within FIG. 17A, FIG. 17B, FIG. 17C, and FIG. 17D, amino acids that are depicted in white with a black background at a particular position, are 100% identical across all sequences. Amino acids that are highly conserved, meaning that the amino acids are either identical, or chemically or structurally similar, at a particular position are enclosed with a black outline. Within highly conserved regions, consensus amino acids that are present in a majority of the sequences are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the natural chicken HS 2OST enzyme as a reference. The β symbol adjacent to an arrow refers to a β-sheet, whereas a coil adjacent to an α symbol or η symbol refers to a helix secondary structure.

Figure 18A:
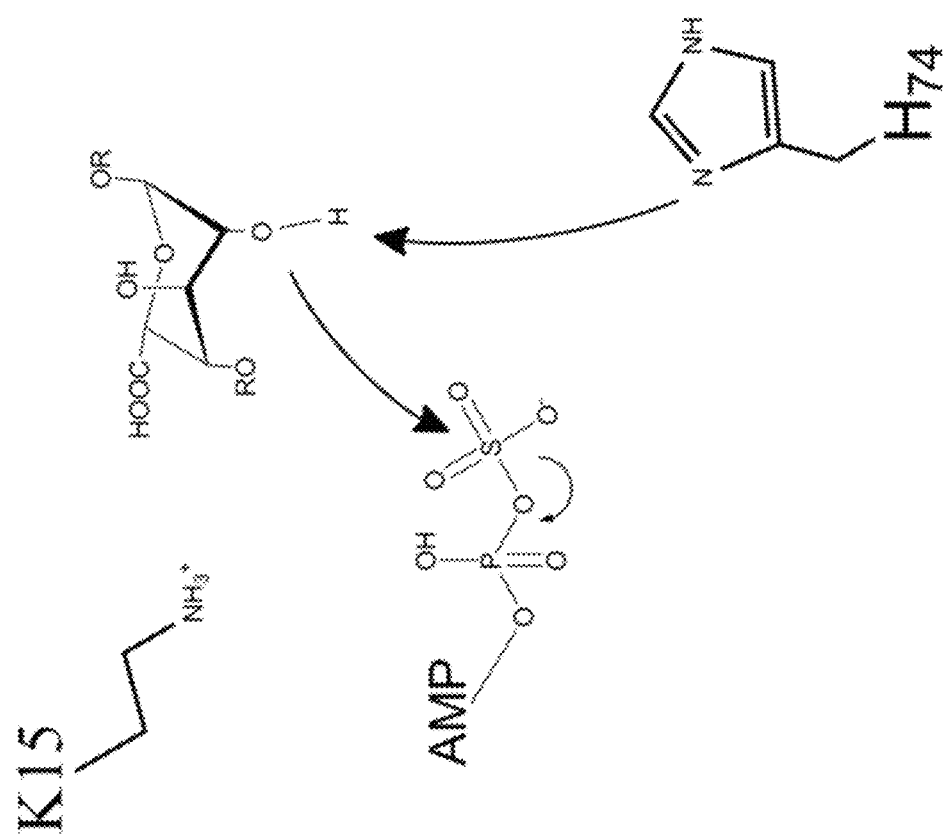
Figure 18C:
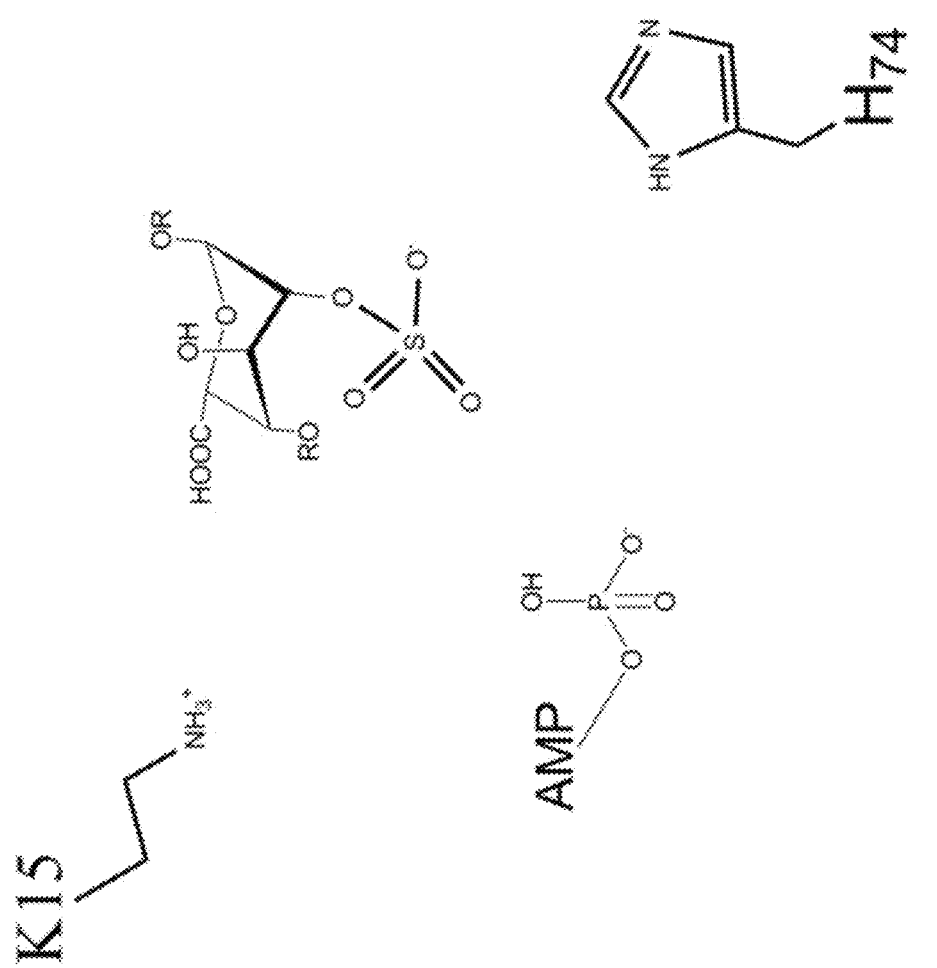

Within the twelve aligned sequences in FIG. 17A, FIG. 17B, FIG. 17C, and FIG. 17D, there are several conserved amino acid motifs that include one or more amino acids that comprise the active site, based on the crystal structures of the chicken 2OST enzyme described above. Based on the numbering of the amino acid residues within FIG. 17A, FIG. 17B, FIG. 17C, and FIG. 17D, these motifs include residues 12-19 (R-V-P-K-T-A/G-S-T), residues 40-44 (N-T-S/T-K-N), residues 71-74 (Y-H-G-H), residues 108-115 (F-L-R-F/H-G-D-D/N-F/Y), residues 121-125 (R-R-K/R-Q-G), and residues 217-222 (S-H-L-R-K/R-T), which correspond to SEQ ID NO: 244, SEQ ID NO: 273, SEQ ID NO: 274, SEQ ID NO: 245, SEQ ID NO: 246, and SEQ ID NO: 247 in the sequence listing, respectively. Without being limited by a particular theory, it is believed that these residues either facilitate or participate in the chemical reaction, or enable binding of PAPS or the polysaccharide within the active site. In particular and as illustrated in FIG. 18A, FIG. 18B, and FIG. 18C, the histidine residue at position 74 abstracts the proton from the 2-O position of the iduronic acid residue within the polysaccharide, enabling nucleophilic attack and removal of the sulfo group from PAPS, whereas the lysine residue at position 15 coordinates with the phosphate moiety of PAPS to stabilize the transition state of the enzyme before the N,2O-HS product is released from the active site.

However, as described above, the natural 2OST enzymes within EC 2.8.2.- are unable to catalyze the transfer of the sulfate group from an aryl sulfate compound to the polysaccharide. As with the natural NDST enzymes, it is believed that the binding pocket for PAPS within the active site of the natural sulfotransferase either does not have a high enough affinity for aryl sulfate compounds to facilitate binding and/or that the aryl sulfate compounds are sterically hindered from entering the active site altogether. Consequently, and in another embodiment, any natural 2OST enzyme can be selected and mutated in several locations within its amino acid sequence to enable binding of the aryl sulfate compound within the active site and/or to optimally position the aryl sulfate compound so transfer of the sulfate group to the polysaccharide can occur.

Accordingly, and in another embodiment, the engineered 2OST enzymes of the present invention can be mutants of natural 2OST enzymes within EC 2.8.2.-, including enzymes having the amino acid sequences illustrated in FIG. 17A, FIG. 17B, FIG. 17C, and FIG. 17D (SEQ ID NOs 179-190). In another embodiment, mutations engineered into the amino acid sequences of the engineered 2OSTs facilitate a biological activity in which aryl sulfate compounds can both bind and react with the enzyme as sulfo group donors. In another embodiment, although the engineered 2OSTs can bind and react with an aryl sulfate compound as a sulfo group donor, they can retain the natural 2OST enzymes' biological activity with N-sulfated heparosan as a sulfo group acceptor. Without being limited by a particular theory, it is believed that because of the mutations inserted into the amino acid sequences of the engineered 2OST enzymes, their sulfotransferase activity may comprise the direct transfer of a sulfuryl group from an aryl sulfate compound to the heparosan-based polysaccharide, using a similar mechanism as described in Figured 18A-18C above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by the oxygen atom at the 2-O position of a hexuronic acid residue, to form the N,2O-HS product. By either mechanism, engineered 2OST enzymes are able to achieve sulfo transfer from an aryl sulfate compound to a heparosan-based polysaccharide, as described in the examples, below.

In another embodiment, an engineered 2OST enzyme can comprise one or more mutated amino acid sequence motifs relative to the conserved amino acid sequence motifs that are found in the natural 2OST enzymes within EC 2.8.2.-, as described above and indicated in the multiple sequence alignment in FIG. 17A, FIG. 17B, FIG. 17C, and FIG. 17D. In another embodiment, each mutated amino acid sequence motif that is present in the amino acid sequence of the engineered enzyme comprises at least one amino acid mutation relative to the corresponding conserved amino acid sequence motif within the natural 2OST enzymes. In another embodiment, an engineered 2OST enzyme can comprise one mutated amino acid sequence motif. In another embodiment, an engineered 2OST enzyme can comprise two mutated amino acid sequence motifs. In another embodiment, an engineered 2OST enzyme can comprise three mutated amino acid sequence motifs. In another embodiment, an engineered 2OST enzyme can comprise four mutated amino acid sequence motifs. In another embodiment, an engineered 2OST enzyme can comprise five mutated amino acid sequence motifs. In another embodiment, an engineered 2OST enzyme can comprise six mutated amino acid sequence motifs. In another embodiment, an engineered 2OST enzyme that includes at least one mutated amino acid sequence motif relative to any of the natural enzymes within EC 2.8.2.- can have an amino acid sequence selected from the group consisting of SEQ ID NO: 63, SEQ ID NO: 65, SEQ ID NO: 68, and SEQ ID NO: 69.

Figure 19:
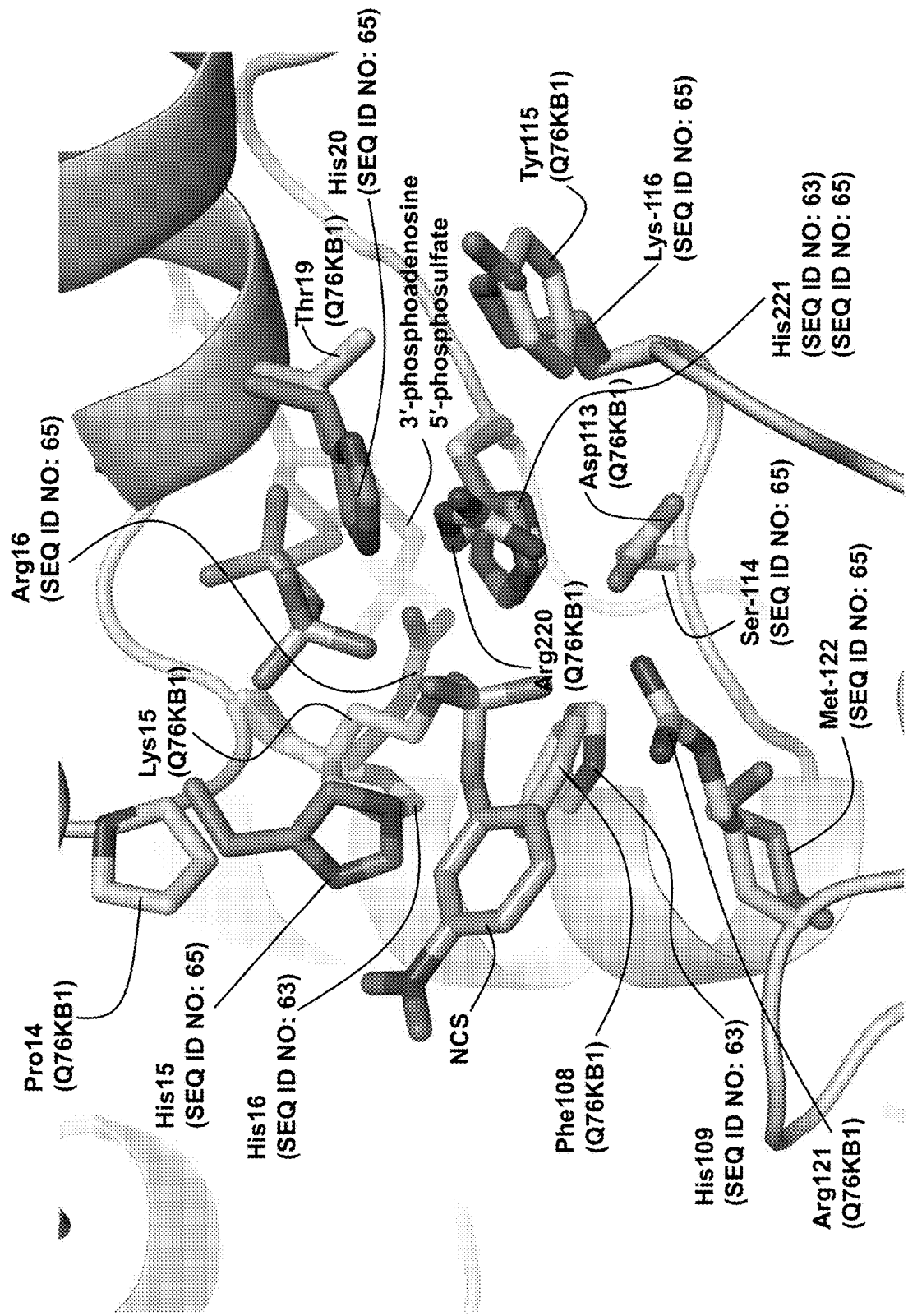
FIG. 19 shows a three-dimensional model of a mutated amino acid sequence motif enabling binding of NCS within the active site of an engineered 2OST enzyme, superimposed over the crystal structure of a natural 2-O sulfotransferase enzyme.

In another embodiment, upon viewing a crystal structure of the chicken 2OST (PDB code: 3F5F) within a 3D molecular visualization system (including, as a non-limiting example, the open-source software, PyMOL), the structure of related sequences, such as those of engineered 2OST enzymes that contain one or more mutated amino acid sequence motifs relative to the chicken 2OST amino acid sequence (SEQ ID NO: 179), can be modeled for comparison as illustrated in FIG. 19. FIG. 19 shows a magnified view of the active site of the chicken 2OST enzyme overlaid with the modeled active sites of two engineered 2OST enzymes, comprising the amino acid sequences of SEQ ID NO: 63 and SEQ ID NO: 65, in which the structure of the engineered enzyme is calculated upon making mutations relative to the chicken 2OST amino acid sequence. Adenosine 3',5'-diphosphate, which is the product of a sulfotransfer reaction in which PAPS is the sulfo donor, and which was co-crystallized with the chicken 2OST, is also illustrated within the active site. The sulfate group that would be present in the natural substrate, PAPS, is modeled onto the 5'-phosphate functional group to illustrate its approximate position within the active site prior to initiating the reaction. NCS is also modeled into the active site of the engineered enzymes, using the consensus solutions of molecular dynamics (MD) simulations that designed to calculate the optimized position and orientation of a ligand within an enzyme active site adjacent to the polysaccharide binding site (not shown), if such solutions are possible. Hydrogen atoms are not shown.

As illustrated in FIG. 19, although there are several mutations made to SEQ ID NO: 63 and SEQ ID NO: 65, relative to the chicken 2OST, the respective protein backbones appear to be in a nearly identical location to one another, enabling a one-to-one comparison of the active sites. When comparing the models of the two active sites, PAPS is located in the background and adjacent to a lysine residue (position 15 of SEQ ID NO: 179), whereas the convergent solutions from the above MD simulations indicate that binding of NCS appears to be favored on the opposite side of the active site. However, binding of NCS would be sterically hindered in the natural 2OST enzyme in part by the lysine residue as well as the phenylalanine residue located on the nearby α-helix (position 108 of SEQ ID NO: 179). Without being limited by a particular theory, it is believed that binding of NCS in the active site of the engineered enzyme comprising the amino acid sequence of SEQ ID NO: 63 is facilitated by the mutation of the lys-15 residue to a histidine residue, which creates additional space within the active site and provides a π-π stacking partner for the aromatic ring within NCS. Also without being limited by a particular theory, it is believed that binding of NCS in the active site of the engineered enzyme comprising the amino acid sequence of SEQ ID NO: 65 is facilitated by the mutation of the lys-15 to an arginine residue in concert with the adjacent mutation of the proline residue (position 14 of SEQ ID NO: 179) to a histidine residue. The increased number of conformational degrees of freedom of the arginine side chain appears to facilitate entry of the NCS while still being in a position to provide a polar contact to stabilize the transition state during the transfer reaction, while the adjacent histidine appears to provide additional binding contacts for NCS.

Another mutation of note includes the mutation from an arginine residue (position 220 of SEQ ID NO: 179) to a histidine residue, a mutation that is found at position 221 in both SEQ ID NO: 63 and SEQ ID NO: 65. Without being limited by a particular theory, it is believed that the mutated histidine residue appears to be in a favorable position to facilitate removal of the sulfate group from NCS. Other illustrated mutations from the chicken 2OST enzyme amino acid sequence (SEQ ID NO: 179), particularly mutations present in SEQ ID NO: 65 (His-20, Ser-114, Lys-116, Met-122) may similarly drive binding of NCS within the active site, either by providing a direct binding contact with the sulfate moiety within NCS (His-20), coordinating with other mutated residues (Ser-114 coordinating with His-221), or by increasing the hydrophobic environment near NCS (Met-122).

Those skilled in the art would appreciate that engineered 2OST enzymes of any other amino acid sequence, including, but not limited to, those disclosed by SEQ ID NO: 68 and SEQ ID NO: 69, would likely exhibit a similar structure to the chicken 2OST, as well as engineered 2OSTs having the amino acid sequence of SEQ ID NO: 63 and SEQ ID NO: 65. Without being limited by a particular theory, it is believed that PNS would bind in a similar position as NCS within the active site of any of the engineered 2OST enzymes, since the structures of the two aryl sulfate compounds are very similar, except that the sulfate group is located ortho on the aromatic ring relative to the nitro group in NCS, rather than para to the nitro group in PNS.

Accordingly, in another embodiment, an engineered 2OST enzyme of the present invention can comprise an amino acid sequence selected from the group consisting of SEQ ID NO: 63, SEQ ID NO: 65, SEQ ID NO: 68, and SEQ ID NO: 69. In another embodiment, engineered 2OST enzymes comprising the amino acid sequence of SEQ ID NO: 63, SEQ ID NO: 65, SEQ ID NO: 68, or SEQ ID NO: 69 can react with any aryl sulfate compound. In further embodiments, the aryl sulfate compound is selected from the group consisting of PNS, US, 7-hydroxycoumarin sulfate, phenyl sulfate, 4-acetylphenyl sulfate, indoxyl sulfate, 1-naphthyl sulfate, 2-naphthyl sulfate, and NCS. In some even further embodiments, the aryl sulfate compound is PNS. In other even further embodiments, the aryl sulfate compound is NCS.

In another embodiment, within reaction mixtures that comprise any natural or engineered 2OST enzyme, particularly an engineered 2OST enzyme comprising the amino acid sequence of SEQ ID NO: 63, SEQ ID NO: 65, SEQ ID NO: 68, or SEQ ID NO: 69, the reaction mixture can further comprise a glucuronyl $C_5$-epimerase to catalyze formation of an N,2O-HS product. In some embodiments, the N,2O-HS product can comprise the structure of Formula VI. In other embodiments, the N,2O-HS product can comprise the structure of Formula VII. In another embodiment, the glucuronyl $C_5$-epimerase can comprise the amino acid sequence of SEQ ID NO: 67. In another embodiment, the glucuronyl C$_5$-epimerase can comprise residues 34-617 of SEQ ID NO: 67.

Engineered 6OSTs

In nature, 6OSTs generally recognize, bind, and react with N-, 2-O sulfated heparosan-based polysaccharides (N,2O-HS) as sulfo group acceptors. Additionally, either adjacent hexuronic acid residue can be either glucuronic acid or iduronic acid, and can optionally be 2-O sulfated. Typically, the hexuronic acid at the non-reducing end of the glucosamine residue receiving the 6-O sulfo group is 2-O sulfated iduronic acid, and in many instances, the glucosamine residue itself is also N-sulfated. Similar to the natural NDST and 2OST enzymes, natural 6OST enzymes transfer the sulfo group to the polysaccharide upon reacting with PAPS as a sulfo group donor. As with wild-type 2OSTs, natural 6OST enzymes are also members of the EC 2.8.2.- enzyme class. In a non-limiting example, natural 6OST enzymes can recognize, bind, and react with N,2O-HS polysaccharides comprising the structure of Formula VIII, below:

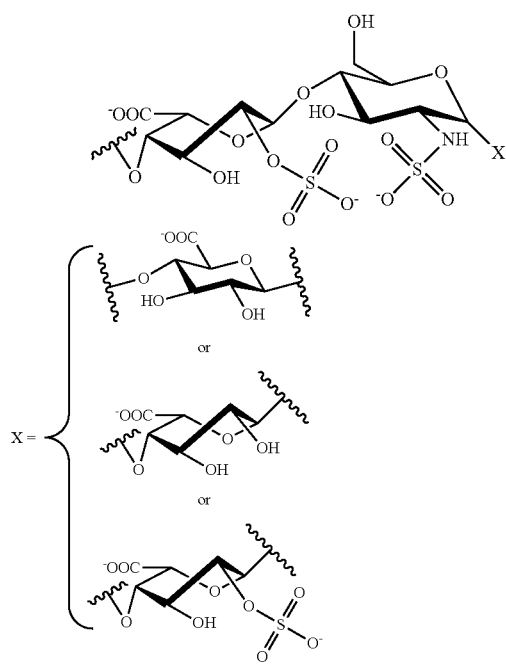

wherein the glucosamine residue receiving the 6-O sulfo group is N-sulfated and is adjacent to a 2-O sulfated iduronic acid residue at its non-reducing end, and X comprises any of the hexuronyl residues depicted in Formula VIII, above. Natural 6OST enzymes having biological activity with N,2O-HS, including but not limited to those comprising the structure of Formula VIII, have been described by Xu, Y., et al., (2017) ACS Chem. Biol. 12 (1):73-82 and Holmborn, K., et al., (2004) J. Biol. Chem. 279, (41):42355-42358, the disclosures of which are incorporated by reference in their entireties.

As described above, although the portion of the heparosan-based polysaccharide that reacts with the 6OST enzyme can comprise the structure of Formula VIII, other glucosamine residues within the polysaccharide can be N-sulfated, N-acetylated, 3-O sulfated, and/or 6-O sulfated, and hexuronyl residues can be glucuronic acid or iduronic acid, either of which can be 2-O sulfated. Similar to the other engineered sulfotransferase enzymes above, engineered 6OST enzymes can transfer a sulfo group to multiple glucosamine residues within the same polysaccharide molecule, and multiple glucosamine residues within the same polysaccharide molecule can be 6-O sulfated by the same polypeptide. Typically, heparosan-based polysaccharides that can react with the engineered 6OST enzymes, including N,2O-HS polysaccharides comprising the structure of Formula VIII, can comprise at least three monosaccharide residues. In another embodiment, engineered 6OSTs of the present invention can have the same preference as natural 6OST enzymes for N,2O-HS, particularly with N,2O-HS comprising the structure of Formula VIII, as a sulfo group acceptor.

Upon successfully binding PAPS and an N,2O-HS comprising the structure of Formula VIII, natural 6OST enzymes can catalyze transfer of the sulfo group to the 6-O position of the glucosamine residue, forming an N,2O,6O-HS product comprising the structure of Formula IX, below:

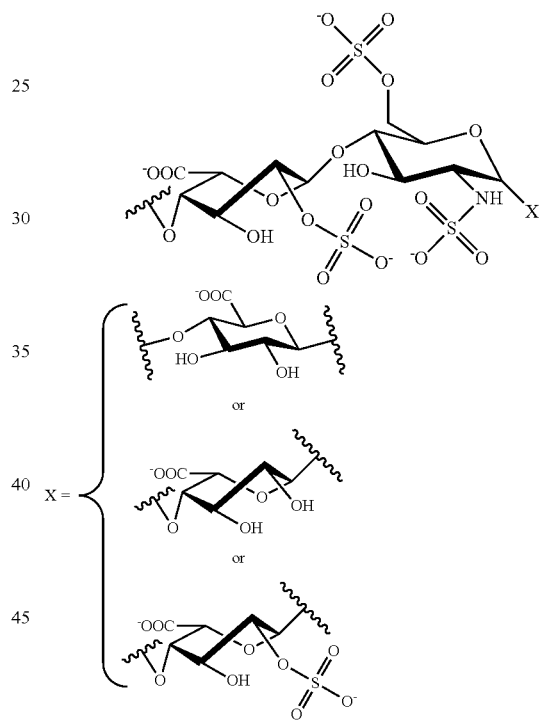

wherein X comprises any of the hexuronyl residues depicted in Formula IX, above.

Figure 20:
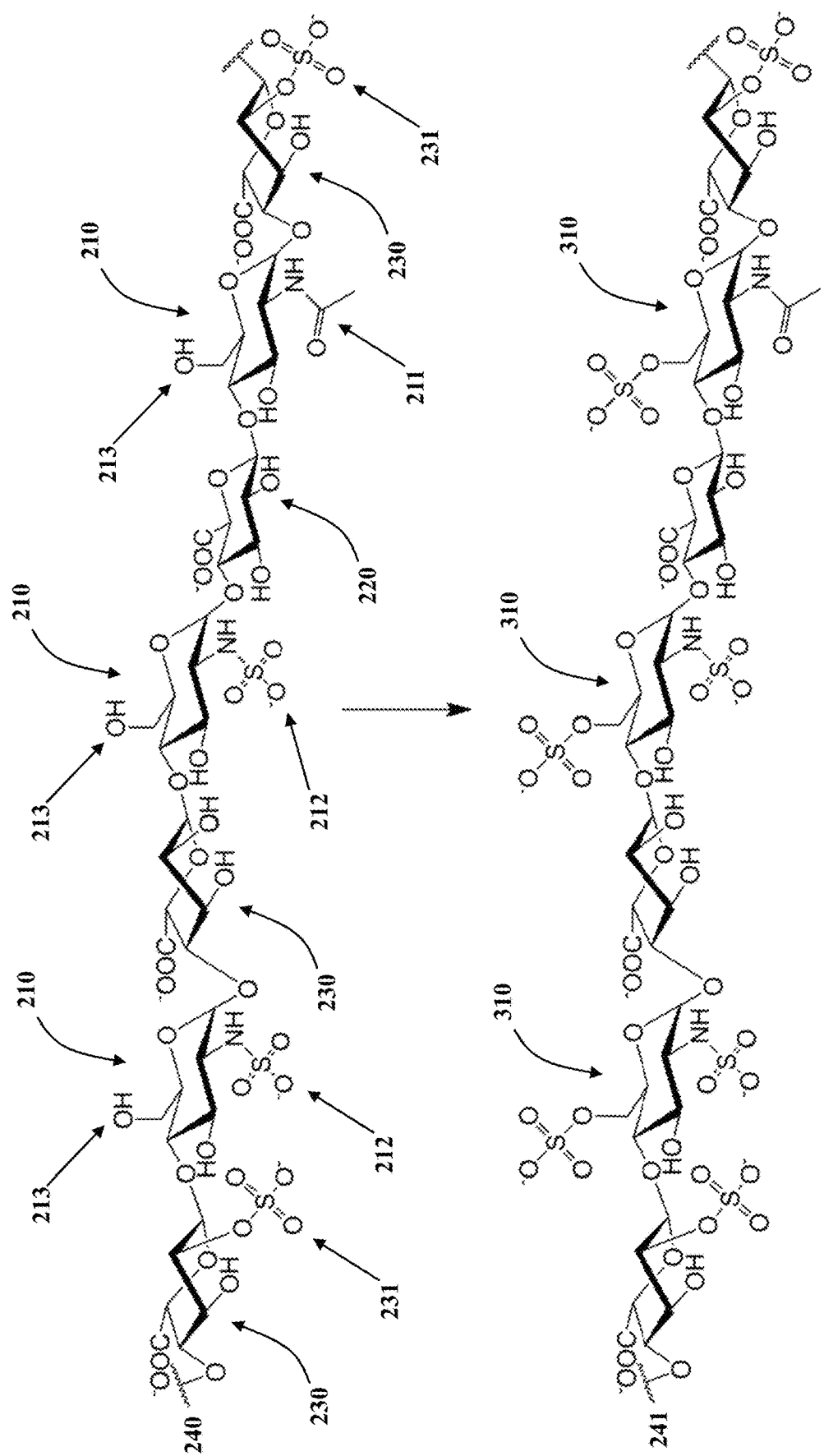
FIG. 20 shows a non-limiting example of a heparosan-based polysaccharide that can be used as a sulfo group acceptor with engineered 6OST enzymes of the present invention, in which the 6-O position of multiple glucosamine residues can receive a sulfo group.
Figure 21A:
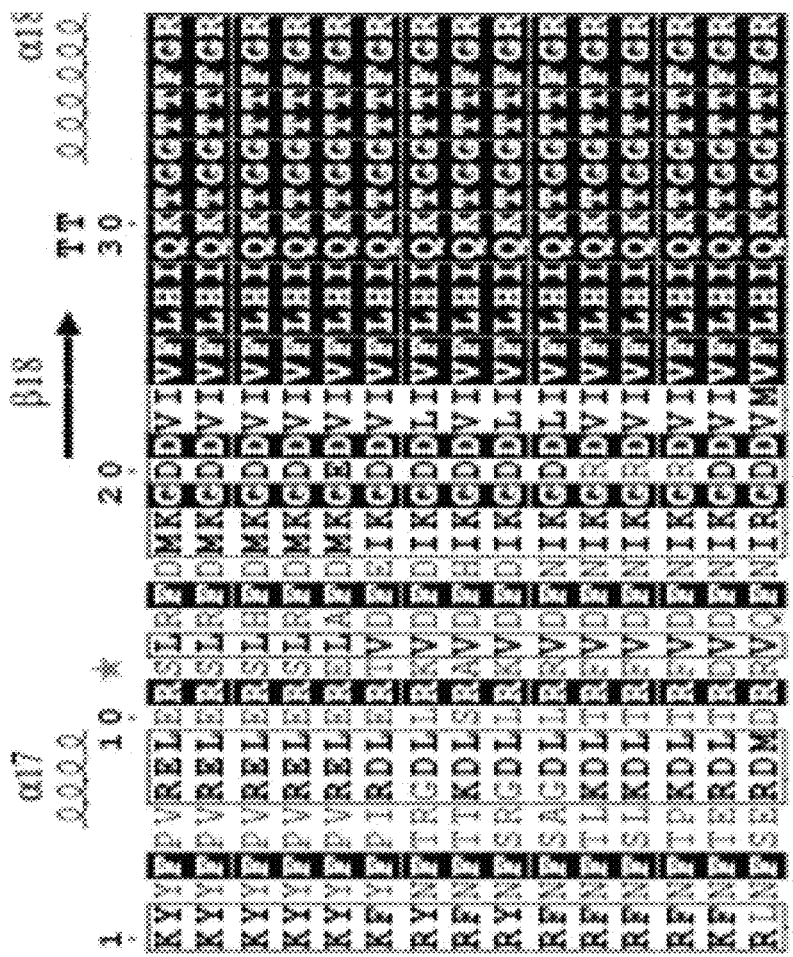
Figure 21B:
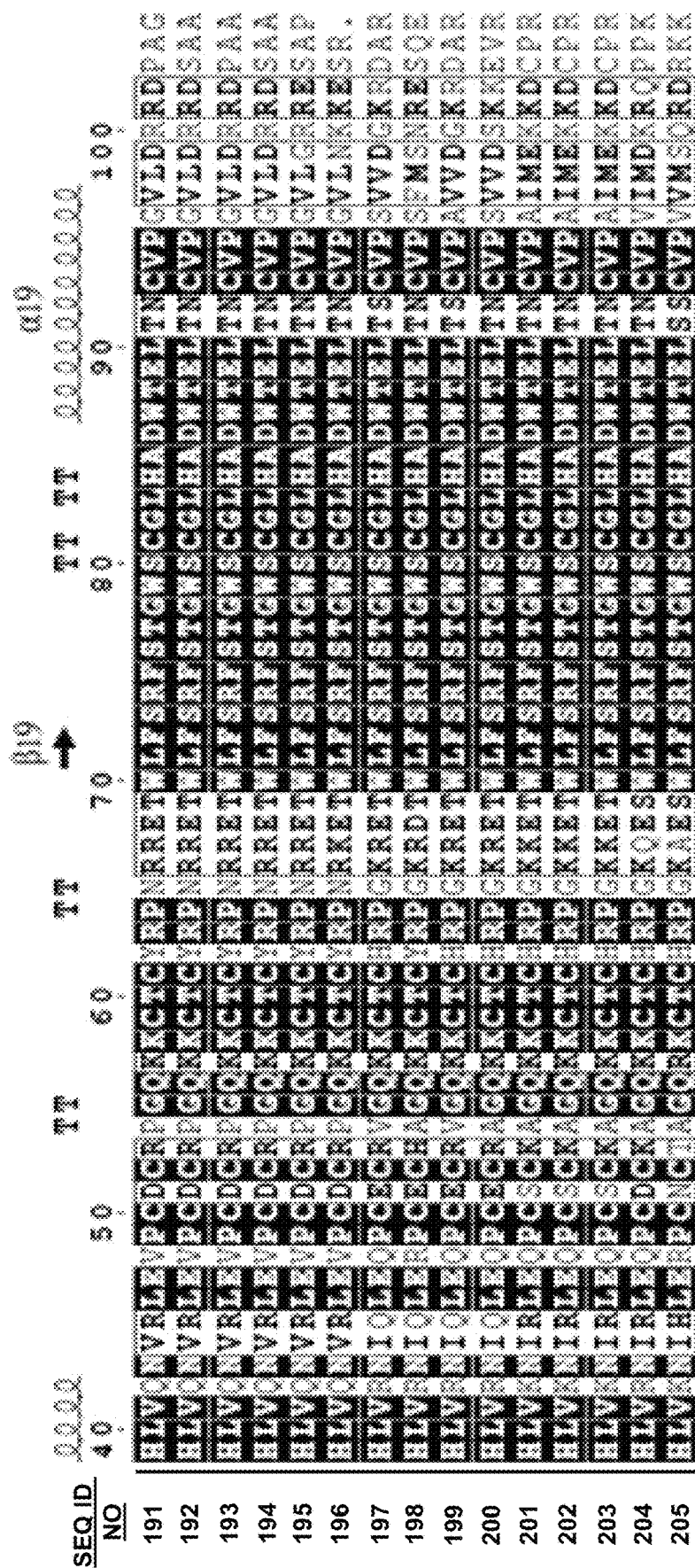
Figure 21C:
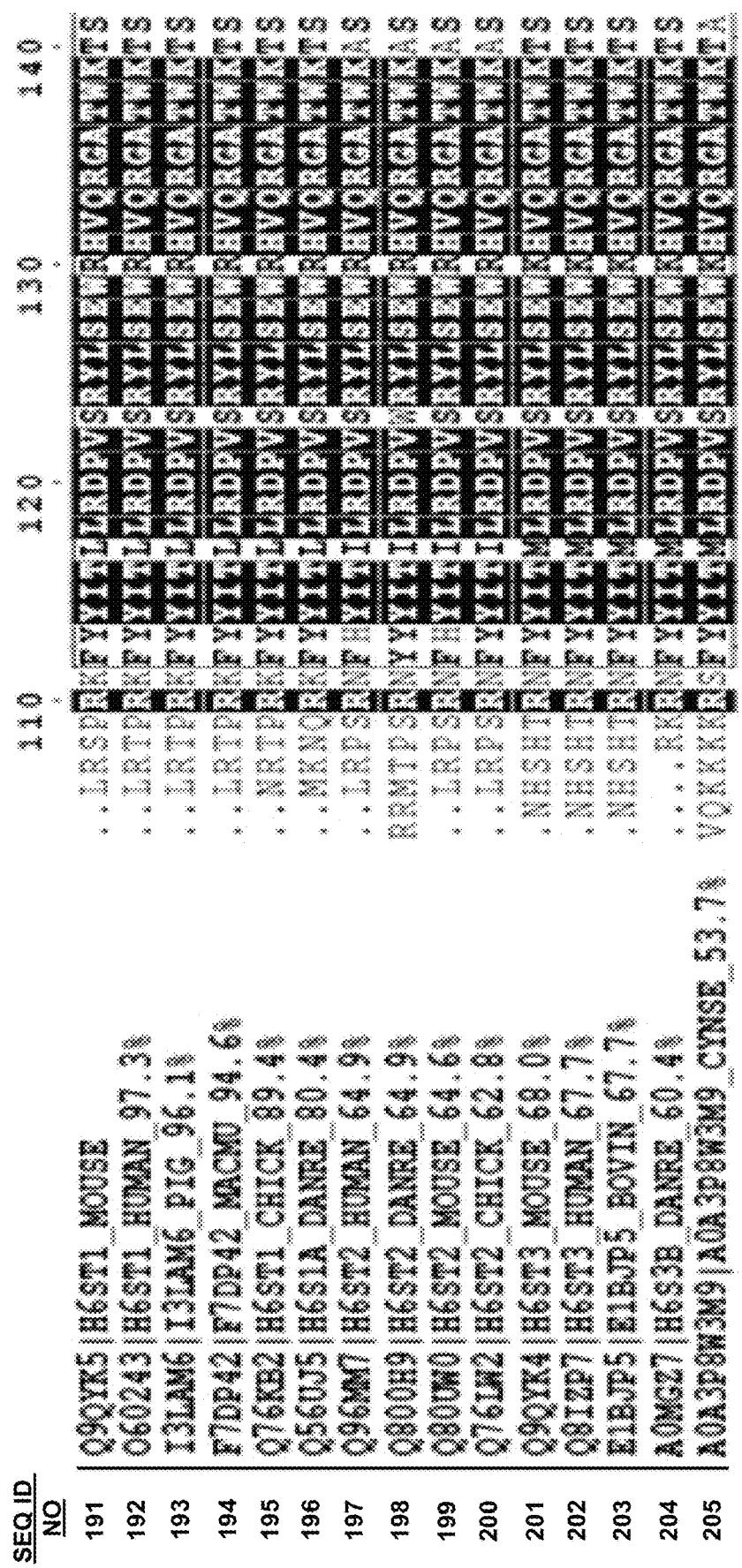
Figure 21D:
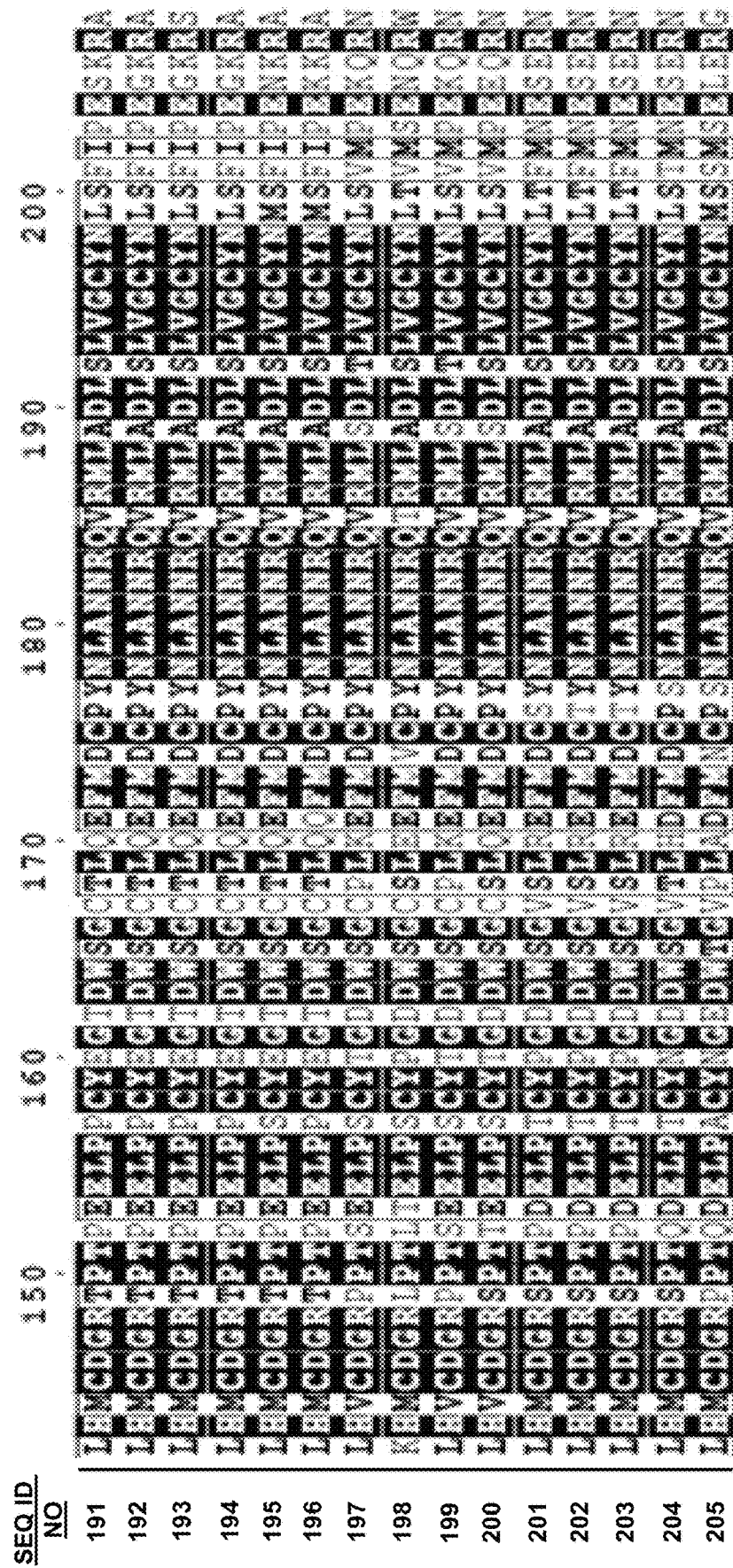

In another embodiment, engineered 6OSTs of the present invention can bind and react with any of the heparosan-based polysaccharides described herein, including heparosan-based polysaccharides that are recognized as sulfo group acceptors by the engineered NSTs, engineered 2OSTs, and engineered 3OSTs (described in further detail below). In another embodiment, engineered 6OSTs of the present invention can bind and react with N,2O-HS comprising the structure of Formula VIII, in order to form N,2O,6O-HS products comprising the structure of Formula IX. A non-limiting example of one such heparosan-based polysaccharide that can react with an engineered 6OST enzyme as a sulfo group acceptor is illustrated in FIG. 20. FIG. 20 shows a polysaccharide 240 that includes three N-substituted glucosamine residues 210 that can be N-substituted with either an acetyl group 211 or a sulfate group 212. Within the polysaccharide 240, N-substituted glucosamine residues 210 that are capable of acting as a sulfo acceptor are flanked by two hexuronyl residues. Hexuronyl residues can include any residue represented by the functional group "X" in Formula VIII, particularly glucuronyl residue 220 and iduronyl residue 230. Either the glucuronyl residue 220 or iduronyl residue 230 can further be substituted by a sulfate group 231 at the 2-O position. Upon reacting the polysaccharide 240 with an engineered 6OST enzyme and a sulfo group donor, the 6-O position 213 of any of the glucosamine residues 210 can be sulfated, ultimately forming 6-O sulfated glucosamine residues 310 within the product polysaccharide 241.

Natural 6OST enzymes generally comprise approximately 300-700 amino acid residues that can in some cases vary greatly in their sequence, yet ultimately have the exact same function, namely, to catalyze the transfer of a sulfo group from PAPS to the 6-O position of glucosamine residues within N,2O-HS, particularly those comprising the structure of Formula VIII. Without being limited by a particular theory, it is believed that each of the natural 6OSTs can catalyze the same chemical reaction because there are multiple amino acid sequence motifs and secondary structures that are either identical or highly conserved across all species.

Further, it is believed that several of the conserved amino acid sequence motifs are directly involved in binding of either PAPS and/or the polysaccharide, or participate in the chemical reaction itself. The identity between the natural 6OST enzymes can be demonstrated by comparing the amino acid sequence of the zebrafish 6OST isoform 3-B enzyme (SEQ ID NO: 204), which has known crystal structures (PDB codes 5T03, 5T05 and 5TOA) in which amino acid residues within the active site have been identified, alongside the amino acid sequences of other natural 6OSTs. A multiple sequence alignment of fifteen enzymes (SEQ ID NOs 191-205) is shown in FIGS. 21A-21F, along with the percent identity of each sequence relative to the mouse 6OST (isoform 1) reference sequence (SEQ ID NO: 191, UniProtKB Accession No. Q9QYK5). As illustrated in FIGS. 21A-21F, sequences range from having 97.3% identity with the Q9QYK5 reference sequence (SEQ ID NO: 192, entry O60243|H6ST1_HUMAN) down to 53.7% identity (SEQ ID NO: 205, entry A0A3P8W3M9|A0A3P8W3M9_CYSNE). For comparison, the zebrafish 6OST3-B enzyme (SEQ ID NO: 204, entry A0MGZ7|H6S3B_DANRE) has 60.4% sequence identity with SEQ ID NO: 191. Those skilled in the art would appreciate that the multiple sequence alignment was limited to fifteen sequences for clarity, and that there are hundreds of amino acid sequences encoding for natural 6OST enzymes that have been identified and that have highly conserved active site and/or binding regions as well.

Within FIGS. 21A-21F, amino acids that are depicted in white with a black background at a particular position, are 100% identical across all sequences. Amino acids that are highly conserved, meaning that the amino acids are either identical or chemically or structurally similar, at a particular position are enclosed with a black outline. Within highly conserved regions, consensus amino acids that are present in a majority of the sequences, are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the natural zebrafish 6OST enzyme (SEQ ID NO: 204) as a reference. The β symbol adjacent to an arrow refers to a β-sheet, whereas a coil adjacent to an α symbol refers to a helix secondary structure. Each of the fifteen aligned sequences illustrated in FIGS. 21A-21F (SEQ ID NOs 191-205) have been truncated relative to their natural full-length sequences to coincide with the engineered enzymes of the present invention, particularly those having the amino acid sequences SEQ ID NO: 104, SEQ ID NO: 106, and SEQ ID NO: 108. In particular, the residues illustrated in FIGS. 21A-21F are aligned with residues 67-377 of SEQ ID NO: 191.

Figure 22A:
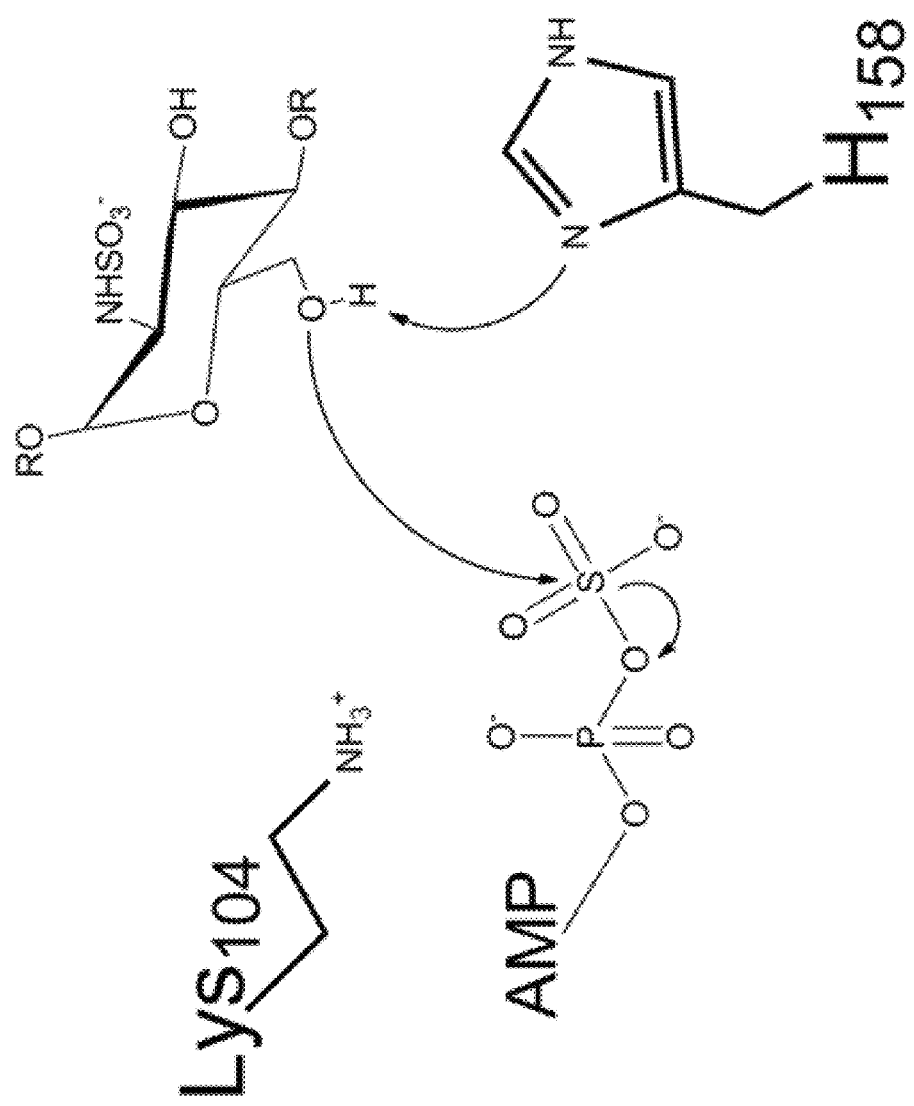
Figure 22B:
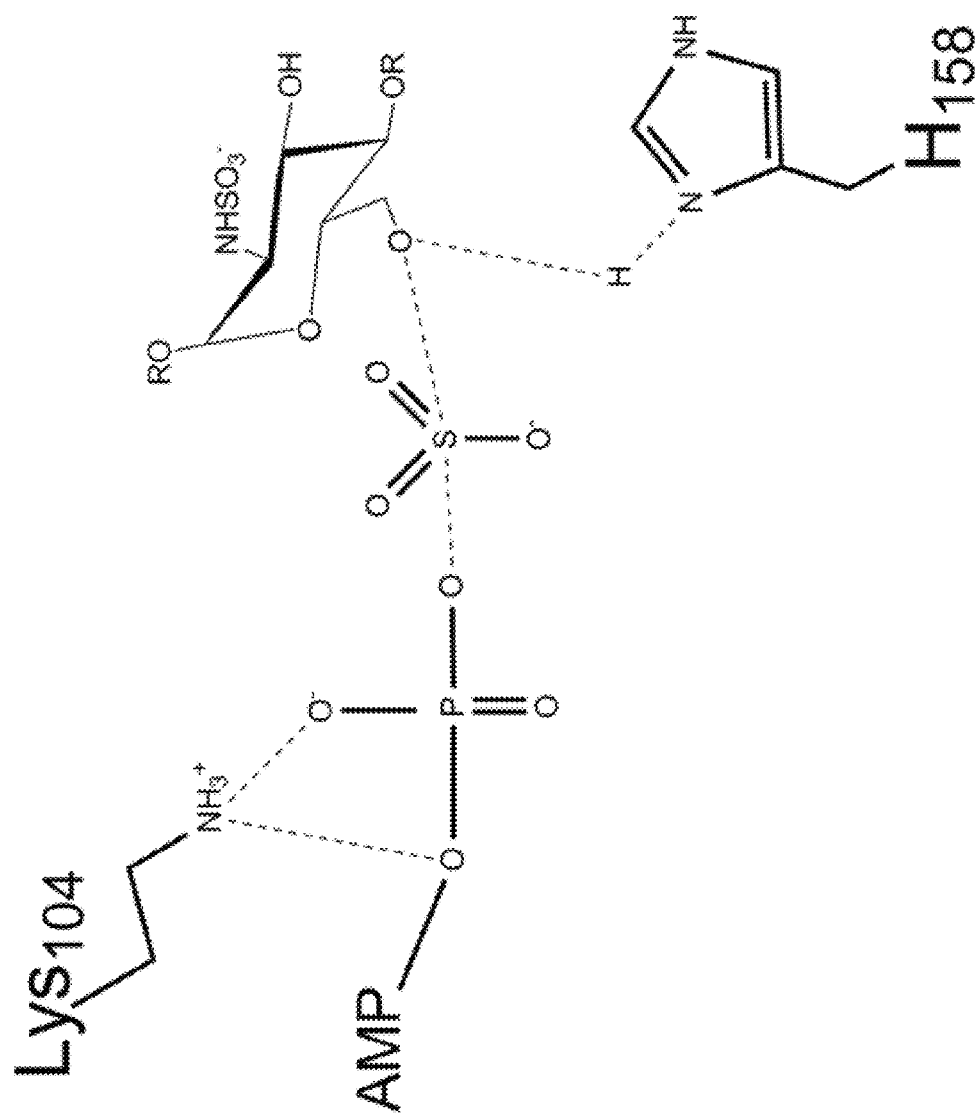
Figure 22C:
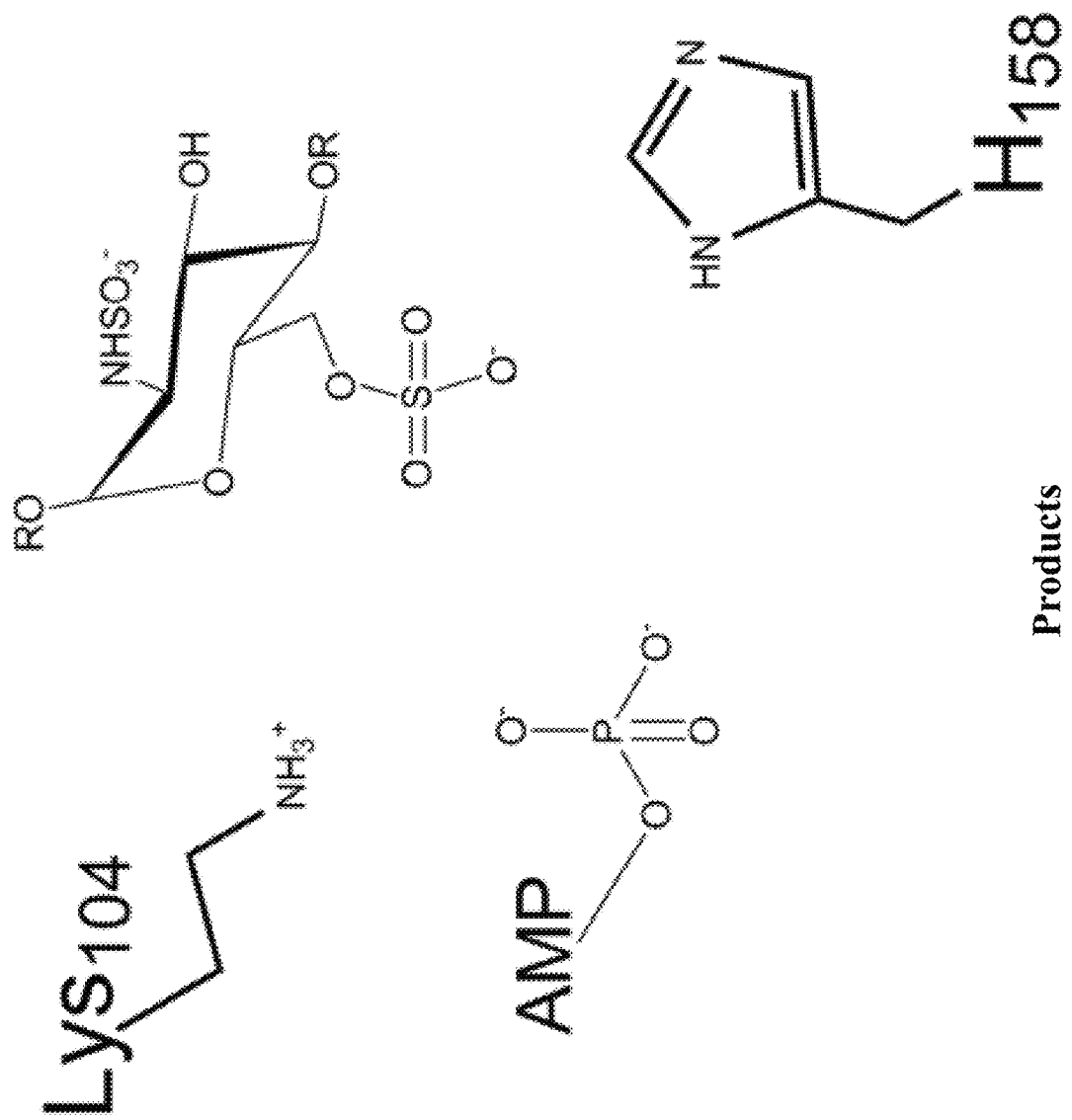

Within the fifteen aligned sequences in FIGS. 21A-21F, there are several conserved amino acid sequence motifs that include one or more amino acids that comprise the active site, based on the crystal structure of the zebrafish 6OST3-B enzyme (SEQ ID NO: 204, entry A0MGZ7|H6S3B_DANRE) described above. Based on the numbering of the amino acid residues within FIGS. 21A-21F, these conserved amino acid sequence motifs include amino acid residues 29 through 34 (Q-K-T-G-G-T); 81 through 86 (C-G-L-H-A-D); 127 through 139 (S-E-W-R/K-H-V-Q-R-G-A-T-W-K); 178 through 184 (N-L-A-N-N-R-Q); and 227 through 231 (L-T-E-F/Y-Q), which correspond to SEQ ID NO: 254, SEQ ID NO: 255, SEQ ID NO: 256, SEQ ID NO: 290, and SEQ ID NO: 276 in the sequence listing, respectively. In particular, and as illustrated in FIG. 22A, FIG. 22B, and FIG. 22C, the histidine residue within the C-G-L-H-A-D conserved amino acid sequence motif (SEQ ID NO: 255) appears to be in position to abstract the hydrogen atom from the 6'-hydroxyl group of an N-sulfoglucosamine residue, enabling the negatively-charged oxygen atom to then initiate the nucleophilic attack of PAPS and remove the sulfate group. Additionally, the universally conserved lysine residue within the Q-K-T-G-G-T conserved amino acid sequence motif (SEQ ID NO: 254) appears to coordinate with the 5'-phosphate in PAPS, while the universally conserved histidine and tryptophan residues at positions 131 and 138 coordinate with the N-sulfoglucosamine residue (see Xu, Y., et al., above).

However, as described above, natural 6OST enzymes are unable to catalyze the transfer of the sulfate group from an aryl sulfate compound to a polysaccharide. Without being limited by a particular theory, and as with the natural NDST and 2OST enzymes described above, it is believed that the binding pocket for PAPS within the active site of the natural 6OST either does not have a high enough affinity for aryl sulfate compounds to facilitate binding and/or that the aryl sulfate compounds are sterically hindered from entering the active site. Consequently, and in another embodiment, a natural 6OST enzyme can be mutated in several locations to enable binding of the aryl sulfate compound within the active site and/or to optimally position the aryl sulfate compound so transfer of the sulfate group to the polysaccharide can occur.

Accordingly, and in another embodiment, engineered 6OST enzymes of the present invention can be mutants of natural 6OST enzymes within EC 2.8.2.-, including enzymes having the amino acid sequences illustrated in FIGS. 21A-21F (SEQ ID NOs 191-205). In another embodiment, mutations engineered into the amino acid sequences of the engineered 6OST enzymes facilitate a biological activity in which aryl sulfate compounds can both bind and react with the enzyme as sulfo group donors. In another embodiment, although the engineered 6OST enzymes can bind and react with an aryl sulfate compound as a sulfo group donor, they can retain the natural 6OST enzymes' biological activity with N,2O-HS polysaccharides, including but not limited to those comprising the structure of Formula VIII, as sulfo group acceptors. Without being limited by a particular theory, it is believed that because of the mutations selected for the amino acid sequences of the engineered 6OST enzymes, their sulfotransferase activity may comprise the direct transfer of a sulfuryl group from an aryl sulfate compound to the heparosan-based polysaccharide, using a similar mechanism as described in FIGS. 22A-22C, above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by the oxygen atom at the 6-O position of a glucosamine residue, to form a 6-O sulfated HS product. In another embodiment, the 6-O sulfated HS product of either sulfotransfer mechanism is an N,2O,6O-HS product. Engineered 6OST enzymes of the present invention are able to achieve sulfo group transfer from an aryl sulfate compound to N,2O-HS, as described in the examples below.

In another embodiment, an engineered 6OST enzyme can comprise one or more mutated amino acid sequence motifs relative to the conserved amino acid sequence motifs (SEQ ID NO: 254, SEQ ID NO: 255, SEQ ID NO: 256, SEQ ID NO: 290, and SEQ ID NO: 276) found in natural 6OST enzymes, as described above and indicated in the multiple sequence alignment of SEQ ID NOs 191-205 in FIGS. 21A-21F. In another embodiment, each mutated amino acid sequence motif that is present in the amino acid sequence of the engineered 6OST enzyme comprises at least one amino acid mutation relative to the corresponding conserved amino acid sequence motif within the natural 6OST enzymes. In another embodiment, an engineered 6OST enzyme can comprise one mutated amino acid sequence motif. In another embodiment, an engineered 6OST enzyme can comprise two mutated amino acid sequence motifs. In another embodiment, an engineered 6OST enzyme can comprise three mutated amino acid sequence motifs. In another embodiment, an engineered 6OST enzyme can comprise four mutated amino acid sequence motifs. In another embodiment, an engineered 6OST enzyme can comprise five mutated amino acid sequence motifs. In another embodiment, an engineered 6OST enzyme that includes at least one mutated amino acid sequence motif relative to any of the natural 6OST enzymes within EC 2.8.2.- can have an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122.

Figure 23:
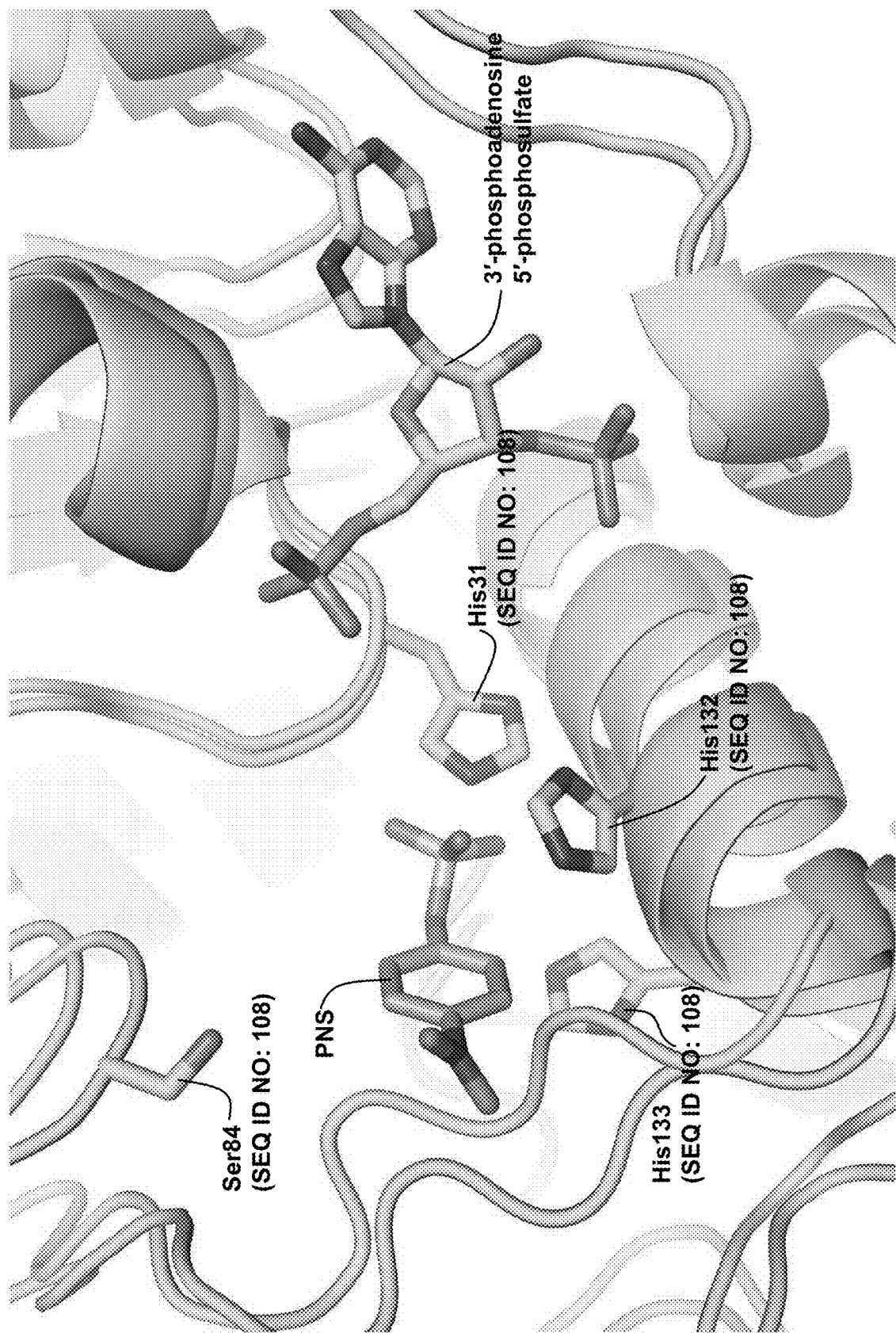

In another embodiment, upon viewing any of the crystal structures of the zebrafish 6OST3-B (SEQ ID NO: 204, UniProtKB Accession No. A0MGZ7) within a 3D molecular visualization system (including, as a non-limiting example, the open-source software, PyMOL), the structure of related sequences, such as those of engineered 6OST enzymes that contain one or more mutated amino acid sequence motifs relative to any of the zebrafish 6OST structures, can be modeled for comparison as illustrated in FIG. 23. FIG. 23 shows a magnified view of the active site of the zebrafish 6OST3-B enzyme (PDB code: 5T03) overlaid with one of the engineered enzymes of the present invention, comprising the amino acid sequence of SEQ ID NO: 108, in which the structure of the engineered 6OST enzyme is calculated upon making mutations relative to the zebrafish 6OST amino acid sequence. Adenosine 3',5'-diphosphate, which is the product of a sulfotransfer reaction in which PAPS is the sulfo donor, and which was co-crystallized with the zebrafish 6OST3-B, is also illustrated within the active site. PNS is also modeled into the active site of the engineered enzymes, using the consensus solutions of molecular dynamics (MD) simulations that designed to calculate the optimized position and orientation of a ligand within an enzyme active site adjacent to the polysaccharide binding site (not shown), if such solutions are possible. Hydrogen atoms are not shown for clarity.

As illustrated in FIG. 23, although there are several mutations made SEQ ID NO: 108, relative to the zebrafish 6OST enzyme, the respective protein backbones appear to be in a nearly identical location to one another, enabling a one-to-one comparison of the active sites. However, when comparing the two active sites, the adenosine 3',5'-diphosphate product appears to be located on the opposite side of the central α-helix as the PNS molecule, as determined by the convergent solutions from the above MD simulations. Without being limited by a particular theory, it is believed that the convergent MD simulation solutions place PNS on the opposite side of the α-helix because there is not enough of an affinity toward PNS in the same or similar position as PAPS within the zebrafish enzyme. As described by Xu, Y., et al., above, the conserved histidine abstracts the proton from the 6' hydroxyl group of N-sulfoglucosamine, which is then subsequently able to react with PAPS to initiate sulfo group transfer. Yet, despite the apparent differences in the binding pocket for PAPS and PNS, engineered 6OST enzymes comprising the amino acid sequences of SEQ ID NO: 104, SEQ ID NO: 106, and SEQ ID NO: 108 all achieved sulfo group transfer from an aryl sulfate compound to the 6-O position of one or more glucosamine residues within a heparosan-based polysaccharide, as described in the examples below.

As a result, and without being limited by a particular theory, one or more of the mutations present within the active site of engineered 6OST enzymes may assist binding of the sulfate moiety of the aryl sulfate compound in a position in which it can be transferred to the sulfo acceptor HS polysaccharide. As illustrated in FIG. 23, the engineered enzyme has the amino acid sequence SEQ ID NO: 108, and the aryl sulfate compound is PNS. However, a heparosan-based polysaccharide is not illustrated. In a non-limiting example, the histidine residue engineered into position 31 of SEQ ID NO: 108 may be in position to facilitate removal of the sulfate group from PNS using a ping-pong mechanism, similar to the mechanism described in Malojcic, et al, above. Additionally, the histidine residue engineered into position 133 of SEQ ID NO: 108 may further coordinate with the sulfate moiety along with the conserved histidine at position 132 of SEQ ID NO: 108 (corresponding to position 131 in each of SEQ ID NOs 190-205). Mutation to G-A-N at positions 137-139 of SEQ ID NO: 22 (corresponding to the conserved A-T-W motif at positions 136-138 of SEQ ID NOs 190-205) removes steric bulk that may prevent binding of PNS in a position where the sulfate can be abstracted by the engineered histidine at position 31 of SEQ ID NO: 108. The mutations to G-A-N within the loop containing A-T-W also appears to cause the loop to move away from PNS, which may further assist PNS to reach its binding pocket.

Finally, a serine residue engineered into position 84 of SEQ ID NO: 108 may create an additional hydrogen-binding contact to assist the engineered enzyme in retaining the zebrafish enzyme's natural activity with the sulfo acceptor polysaccharide.

Those skilled in the art would appreciate that engineered 6OST enzymes of any other amino acid sequence, including, but not limited to, those disclosed by SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122, would likely exhibit similar structural motifs, particularly within the active site. Without being limited by a particular theory, it is believed that NCS would bind in a similar position as PNS within any of the engineered enzymes, since the structures of the two aryl sulfate compounds are very similar, except that the sulfate group is located ortho on the aromatic ring relative to the nitro group, rather than para to the nitro group.

In another embodiment, engineered 6OST enzymes that can be utilized in accordance with methods of the present invention can comprise one or more mutated amino acid sequence motifs, which can be determined in-part by comparing conserved amino acid sequence motifs indicated in the multiple sequence alignment of SEQ ID NOs 191-205 in FIGS. 21A-21F with the known structure(s) of natural enzymes and/or modeled engineered enzymes, including but not limited to, as a non-limiting example, enzymes illustrated in FIG. 23. In another embodiment, mutated amino acid sequence motifs that can be comprised within an engineered 6OST enzyme can be selected from the group consisting of (a) G-H-T-G-G-T (SEQ ID NO: 257); (b) C-G-$X_1$-$X_2$-A-D (SEQ ID NO: 291), wherein $X_1$ is selected from the group consisting of threonine and serine, and $X_2$ is selected from the group consisting of asparagine, arginine, and histidine; (c) $X_3$-$X_4$-W-R-H-$X_5$-Q-R-G-G-$X_6$-N-K (SEQ ID NO: 260), wherein $X_3$ is selected from the group consisting of serine and glycine, $X_4$ is selected from the group consisting of glycine and histidine, $X_5$ is selected from the group consisting of histidine and threonine, and $X_6$ is selected from the group consisting of alanine and threonine; and (d) N-L-$X_7$-N-N-R-Q (SEQ ID NO: 292), wherein $X_7$ is selected from the group consisting of alanine and glycine; including any combination thereof. Each of the mutated amino acid sequence motifs corresponds with a conserved amino acid motif indicated in FIGS. 21A-21F above: SEQ ID NO: 257 corresponds to the conserved amino acid sequence motif, Q-K-T-G-G-T (SEQ ID NO: 254); mutated amino acid sequence motif SEQ ID NO: 291 corresponds to the conserved amino acid sequence motif, C-G-L-H-A-D (SEQ ID NO: 255); mutated amino acid sequence motif SEQ ID NO: 260 corresponds to the conserved amino acid sequence motif, S-E-W-(R/K)-H-V-Q-R-G-A-T-W-K (SEQ ID NO: 256); and mutated amino acid sequence motif SEQ ID NO: 292 corresponds to the conserved amino acid sequence motif, N-L-A-N-N-R-Q (SEQ ID NO: 290). In another embodiment, engineered 6OST enzymes comprising at least one mutated amino acid sequence motif described above can be selected from the group consisting of: SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122.

In another embodiment and in one non-limiting example, engineered 6OST enzymes can comprise the mutated amino acid sequence motifs SEQ ID NO: 291 and SEQ ID NO: 260 within the same amino acid sequence. Engineered enzymes comprising the mutated amino acid sequence motifs SEQ ID NO: 291 and SEQ ID NO: 260 include, but are not limited to, enzymes comprising the amino acid sequences of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122. In another embodiment, each of the engineered 6OST enzymes comprising the mutated amino acid sequence motifs SEQ ID NO: 291 and SEQ ID NO: 260 have a similar active site as SEQ ID NO: 108, as illustrated in FIG. 23. Without being limited to another theory, it is believed that several of the mutations comprised within mutated amino acid sequence motifs SEQ ID NO: 291 and SEQ ID NO: 260 have one or more functions during sulfotransferase activity, including not limited to: increasing the affinity of aryl sulfate compounds to the active site by reducing the size of the binding pocket, increasing the hydrophobicity of the pocket, removing or creating polar or hydrogen bonding contacts, and/or creating π-π interactions with the aromatic moieties of the aryl sulfate compounds; stabilizing the transition state of the enzyme during the chemical reaction; and/or participating in the chemical reaction itself.

In another embodiment, within engineered 6OST enzymes that comprise the mutated amino acid sequence motifs SEQ ID NO: 291 and SEQ ID NO: 260, $X_4$ is glycine and $X_5$ is histidine (as illustrated in SEQ ID NO: 263). In other embodiments, $X_4$ is histidine and $X_5$ is threonine (as illustrated in SEQ ID NO: 264).

In another embodiment, within engineered 6OST enzymes comprising the mutated amino acid sequence motifs SEQ ID NO: 291 and SEQ ID NO: 260, $X_3$ is serine and $X_6$ is alanine (as illustrated in SEQ ID NO: 262), and $X_7$ is glycine (as illustrated in SEQ ID NO: 293). In other embodiments, $X_3$ is glycine and $X_6$ is threonine (as illustrated in SEQ ID NO: 261), and $X_7$ is alanine (as illustrated in SEQ ID NO: 294).

Figure 24A:
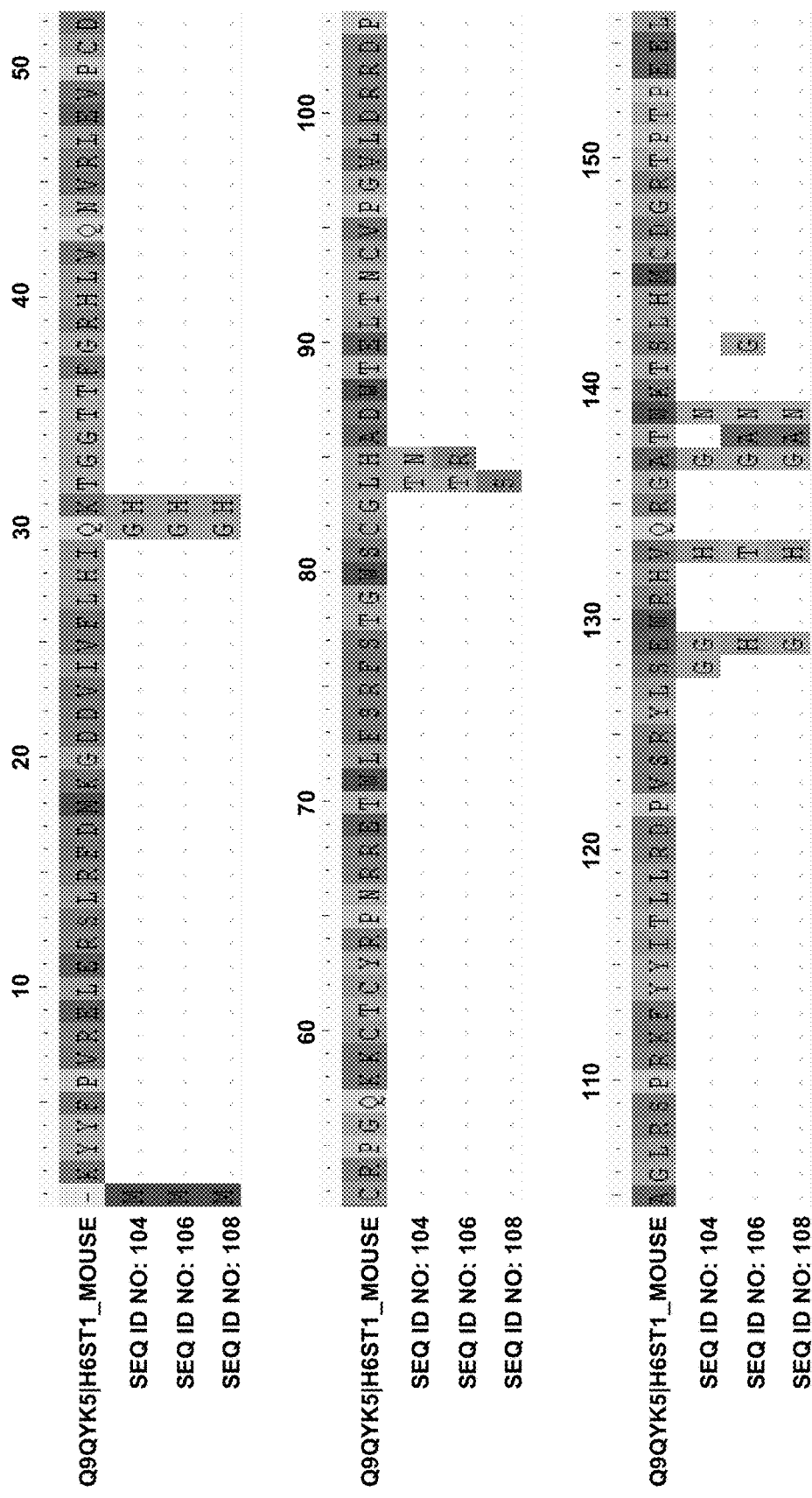
Figure 24B:
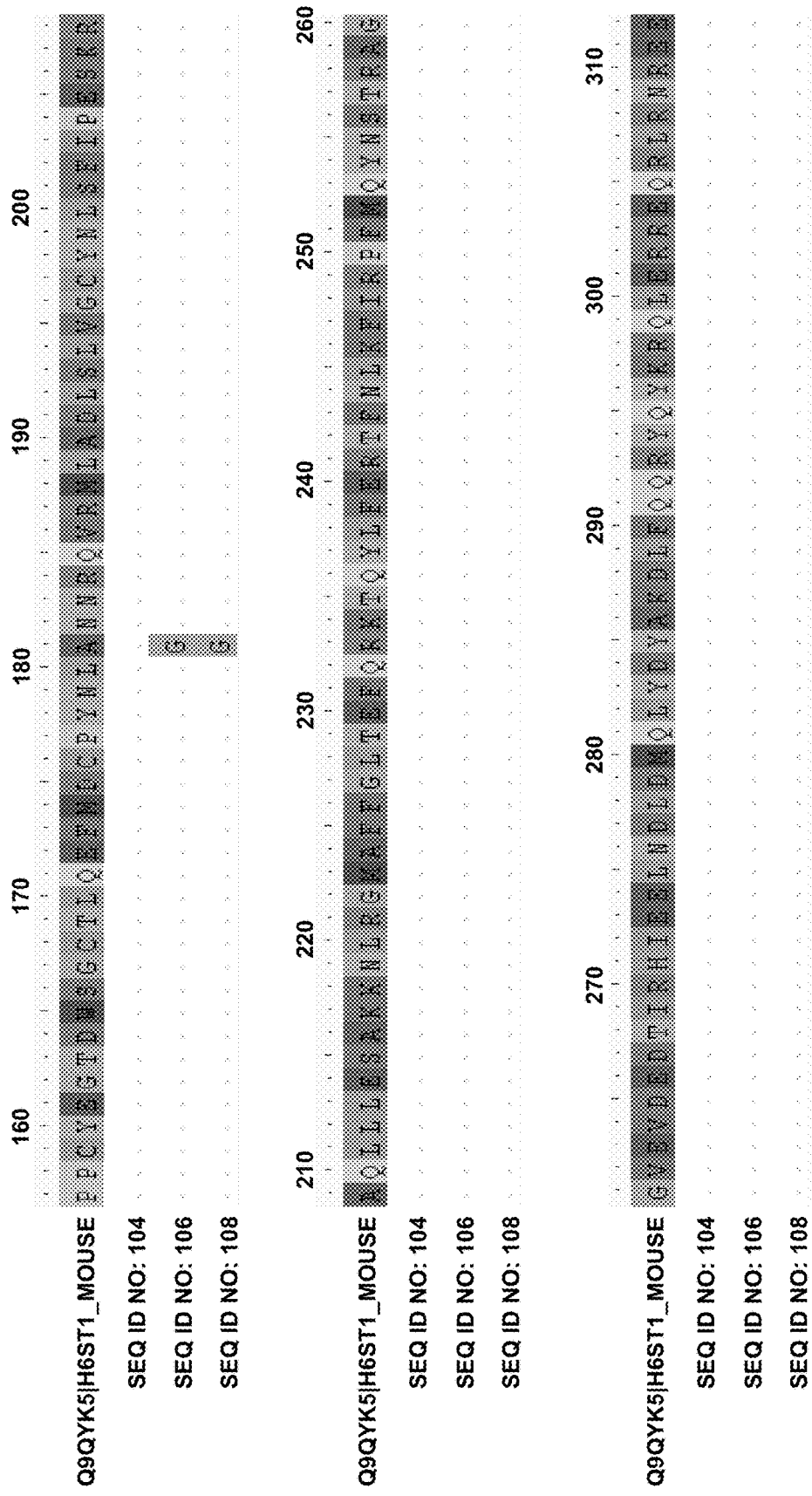

Furthermore, the amino acid sequences (SEQ ID NO: 104, SEQ ID NO: 106, and SEQ ID NO: 108) of three engineered 6OST enzymes, which have been experimentally determined to be active sulfotransferases with aryl sulfate compounds as sulfo group donors (see Example 5 below) can be compared with the amino acid sequence of the mouse 6OST1 enzyme (SEQ ID NO: 191, entry Q9QYK5|H6ST1_MOUSE) in a multiple sequence alignment to determine if there are relationships between mutations among each of the enzymes. A period within the amino acid sequence of an engineered enzyme indicates identity at a particular position with the mouse 6OST enzyme. As shown in FIGS. 24A-24B, the sequence alignment demonstrates that while over 90% of the amino acid residues within the three sulfotransferase sequences are identical, there are several positions in which multiple amino acids can be chosen. Without being limited by a particular theory, these enzymes have a similar relationship with each other as the natural 6OST enzymes within EC 2.8.2.-. As a result, and in another embodiment, engineered 6OST enzymes comprising an amino acid sequence in which multiple amino acids can be chosen at defined positions are disclosed as SEQ ID NO: 112 and SEQ ID NO: 113. Positions at which the identity of an amino acid can be chosen from a selection of possible residues are denoted in terms "Xaa," "Xn," or "position n," where n refers to the residue position.

In another embodiment, within SEQ ID NO: 112, residues having the designation, "Xaa," illustrate known instances in which there is a lack of identity at a particular position within the amino acid sequences of SEQ ID NO: 104, SEQ ID NO: 106, and SEQ ID NO: 108. In another embodiment, the amino acid sequence, SEQ ID NO: 113, also illustrates known instances in which there is a lack of identity at a particular position within the amino acid sequences of SEQ ID NO: 104, SEQ ID NO: 106, and SEQ ID NO: 108, but SEQ ID NO: 113 further comprises N-terminal residues 1-66, and C-terminal residues 378-411, of several natural full-length 6OST enzymes within EC 2.8.2.-, including, as non-limiting examples, the mouse, human, and pig 6OST1 enzymes (SEQ ID NOs 295-297). In contrast, amino acid residues in SEQ ID NO: 104, SEQ ID NO: 106, SEQ ID NO: 108, and SEQ ID NO: 112 correspond with residues 67-377 of several full-length 6OST enzymes within EC 2.8.2.-, including, as non-limiting examples, the mouse, human, and pig 6OST enzymes (SEQ ID NOs 191-193). To facilitate protein expression, an N-terminal methionine residue was added to each of the SEQ ID NO: 104, SEQ ID NO: 106, SEQ ID NO: 108, and SEQ ID NO: 112 amino acid sequences, relative to residues 67-377 of the mouse, human, and pig 6OST1 enzymes (SEQ ID NOs 191-193).

In another embodiment, any selection can be made for an Xaa residue, defined by the amino acid sequence SEQ ID NO: 112 or SEQ ID NO: 113, so long as the resulting enzyme maintains its 6OST activity upon reacting with an aryl sulfate compound as a sulfo group donor.

In another embodiment, within an engineered 6OST enzyme comprising the amino acid sequence of SEQ ID NO: 112, the amino acid residue at position 129 is glycine and the amino acid residue at position 133 is histidine. In another embodiment, within an engineered 6OST enzyme comprising the amino acid sequence of SEQ ID NO: 112, the amino acid residue at position 129 is histidine and the amino acid residue at position 133 is threonine. In another embodiment, within an engineered 6OST enzyme comprising the amino acid sequence of SEQ ID NO: 113, the amino acid residue at position 194 is glycine and the amino acid residue at position 198 is histidine. In another embodiment, within an engineered 6OST enzyme comprising the amino acid sequence of SEQ ID NO: 113, the amino acid residue at position 194 is histidine and the amino acid residue at position 198 is threonine.

In another embodiment, within an engineered 6OST enzyme comprising the amino acid sequence of SEQ ID NO: 112, the amino acid residue at position 128 is serine, the amino acid residue at position 138 is alanine, and the amino acid residue at position 181 is glycine. In another embodiment, within an engineered 6OST enzyme comprising the amino acid sequence of SEQ ID NO: 112, the amino acid residue at position 128 is glycine, the amino acid residue at position 138 is threonine, and the amino acid residue at position 181 is alanine. In another embodiment, within an engineered 6OST enzyme comprising the amino acid sequence of SEQ ID NO: 113, the amino acid residue at position 193 is serine, the amino acid residue at position 203 is alanine, and the amino acid residue at position 246 is glycine. In another embodiment, within an engineered 6OST enzyme comprising the amino acid sequence of SEQ ID NO: 113, the amino acid residue at position 193 is glycine, the amino acid residue at position 203 is threonine, and the amino acid residue at position 246 is alanine.

In another embodiment, within an engineered 6OST enzyme comprising the amino acid sequence of SEQ ID NO: 112 or SEQ ID NO: 113, the amino acid sequence can optionally include one or more mutations at residue positions not specified by an "Xn" or "Xaa," so long as any such mutations do not eliminate the 6OST and/or aryl sulfate-dependent activity of the enzyme. In another embodiment, such mutations not eliminating aryl sulfate-dependent activity at positions not specified by an "Xn" or "Xaa" can include substitutions, deletions, and/or additions.

Accordingly, in another embodiment, an engineered 6OST enzyme utilized in accordance with any of the methods of the present invention can comprise an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122. In another embodiment, engineered 6OST enzymes comprising the amino acid sequence of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122 can react with any aryl sulfate compound. In further embodiments, the aryl sulfate compound is selected from the group consisting of PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS. In some even further embodiments, the aryl sulfate compound is PNS. In other even further embodiments, the aryl sulfate compound is NCS.

Engineered 3OSTs

In nature, HS 3OSTs generally recognize, bind, and react with N,2O-HS and N,2O,6O-HS heparosan-based polysaccharides as sulfo group acceptors. Generally, the glucosamine residue that receives the sulfo group at the 3-O position is N-sulfated, and is optionally also 6-O sulfated. Additionally, either adjacent hexuronic acid residue can be glucuronic acid or iduronic acid, either of which can optionally be 2-O sulfated. Often, the glucosamine residue being 3-O sulfated is adjacent to a glucuronic acid on its non-reducing end and a 2-O sulfated iduronic acid on its reducing end. Similar to each of the natural sulfotransferases described above, naturally-occurring 3OSTs transfer a sulfo group to the heparosan-based polysaccharide upon reacting with PAPS as a sulfo group donor. Natural 3OST enzymes that utilize PAPS as the sulfo group donor are members of the EC 2.8.2.23 enzyme class. In a non-limiting example, natural 3OST enzymes can recognize, bind, and react with N,2O,6O-HS polysaccharides comprising the structure of Formula X, below:

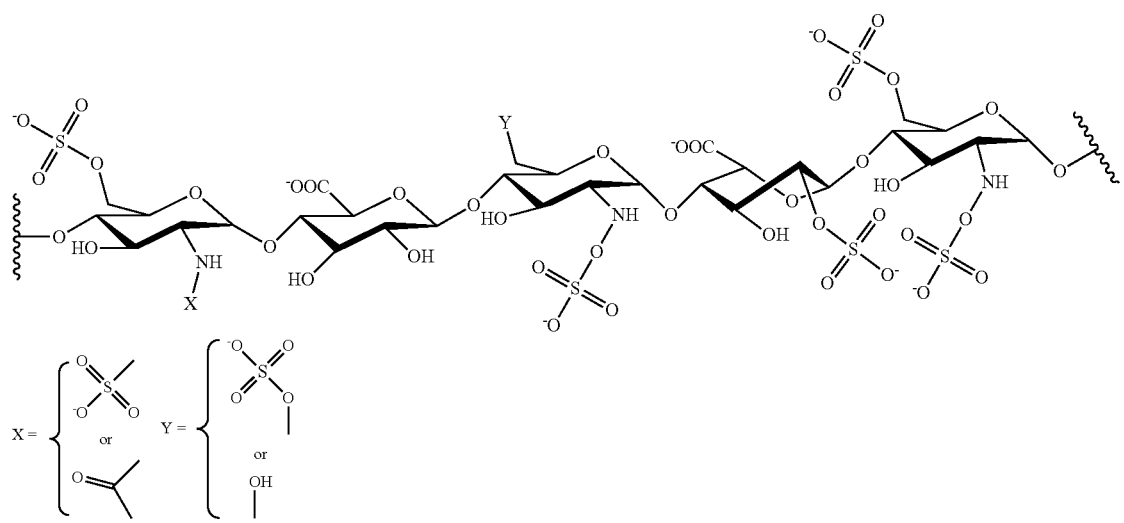

wherein the central glucosamine residue is N-sulfated and is adjacent to glucuronic acid at its non-reducing end and a 2-O sulfated iduronic acid residue at its reducing end, X can optionally be a sulfate group or an acetyl group, and Y can optionally be a sulfate group or a hydroxyl group.

As described above, although the portion of the heparosan-based polysaccharide that reacts with the 3OST enzyme can comprise the structure of Formula X, other glucosamine residues within the polysaccharide can be N-sulfated, N-acetylated, 3-O sulfated, and/or 6-O sulfated, and hexuronyl residues can be glucuronic acid or iduronic acid, either of which can be 2-O sulfated. Similar to the other engineered sulfotransferase enzymes above, engineered 3OST enzymes can transfer a sulfo group to multiple glucosamine residues within the same polysaccharide molecule, and multiple glucosamine residues within a polysaccharide molecule can be 3-O sulfated by the same polypeptide. Typically, N,2O,6O-HS polysaccharides that can react with natural 3OSTs as sulfo group acceptors typically comprise at least five monosaccharide residues, as shown in Formula X. In another embodiment, N,2O,6O-HS polysaccharides comprising the structure of Formula X and can react with natural 3OSTs as sulfo group acceptors can comprise at least thirty-two monosaccharide residues. In another embodiment, engineered 3OSTs of the present invention can have the same preference as natural 3OST enzymes for N,2O, 6O-HS, particularly with N,2O,6O-HS comprising the structure of Formula X, as sulfo group acceptors.

Upon successfully binding PAPS and an N,2O,6O-HS polysaccharide comprising the structure of Formula X, natural 3OST enzymes can catalyze transfer of the sulfo group to the 3-O position of the central glucosamine residue, forming an N,2O,3O,6O-HS product comprising the structure of Formula I, below:

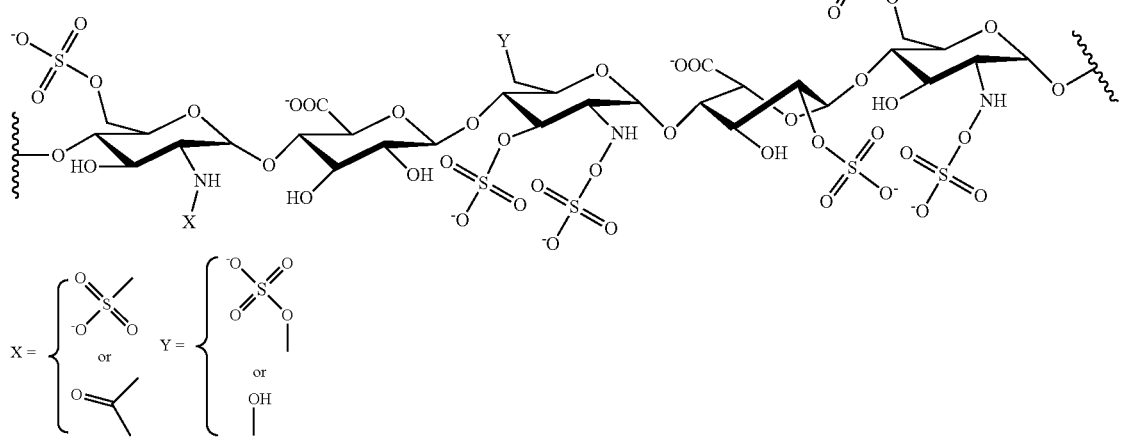

wherein X is either a sulfo group or an acetate group and Y is either a sulfo group or a hydroxyl group. Natural 3OST enzymes, which have biological activity with N,2O,6O-HS polysaccharides comprising the structure of Formula X as sulfo group acceptors and form N,2O,3O,6O-HS products comprising the structure of Formula I, have been described by Xu, D., et al., (2008) *Nat. Chem. Biol.* 4(3): 200-202 and Edavettal, S. C., et al., (2004) *J. Biol. Chem.* 24(11):

25789-25797, the disclosures of which are incorporated by reference in their entireties. Further, N,2O,3O,6O-HS products comprising the structure of Formula I can be found within unfractionated heparin (UFH), as well as low molecular weight heparins (LMWH) that are derived from UFH. Methods for forming anticoagulant N,2O,3O,6O-HS, including UFH, using engineered 3OSTs are described in further detail, below.

Figure 25:
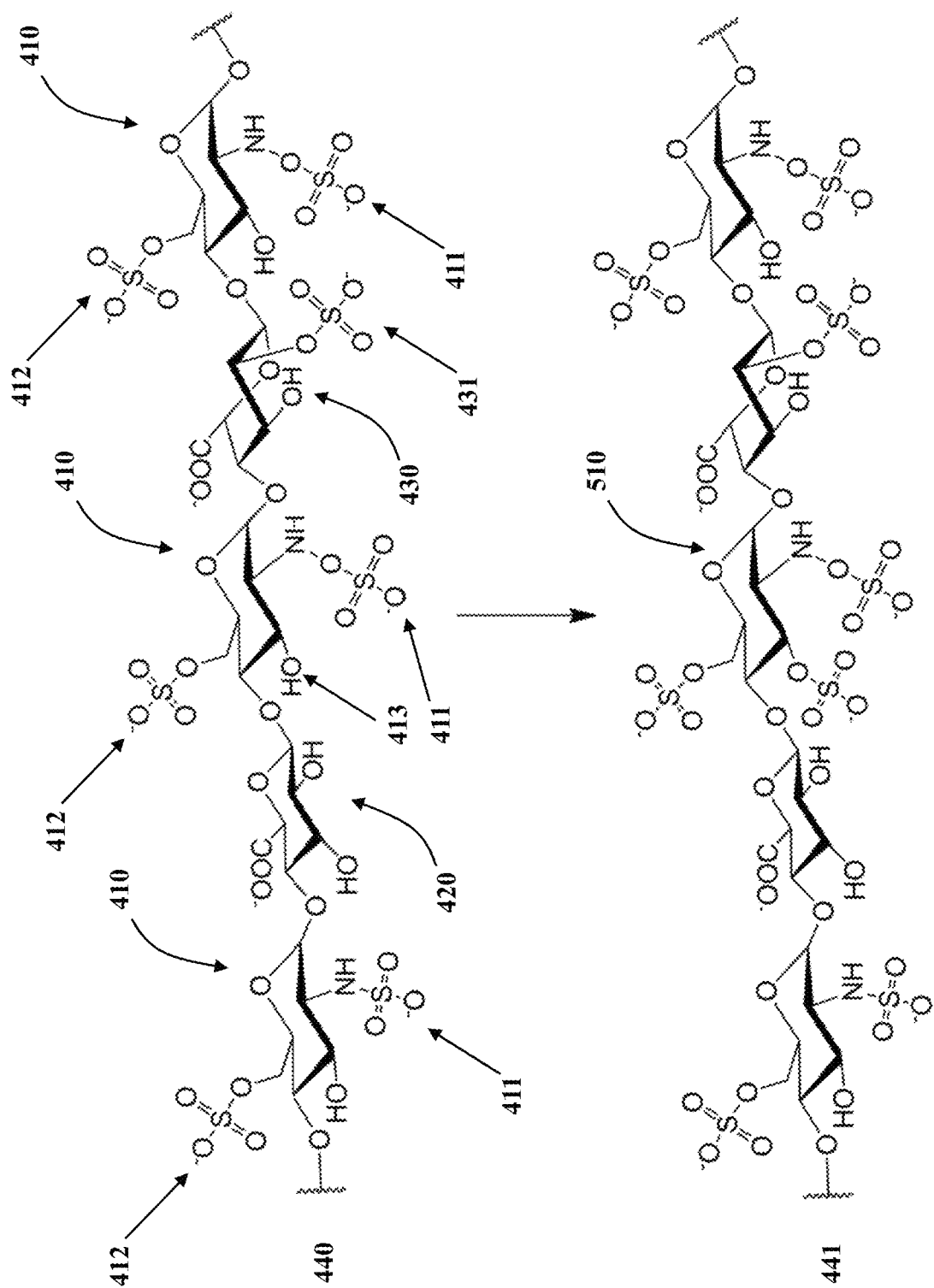
Figure 26C:
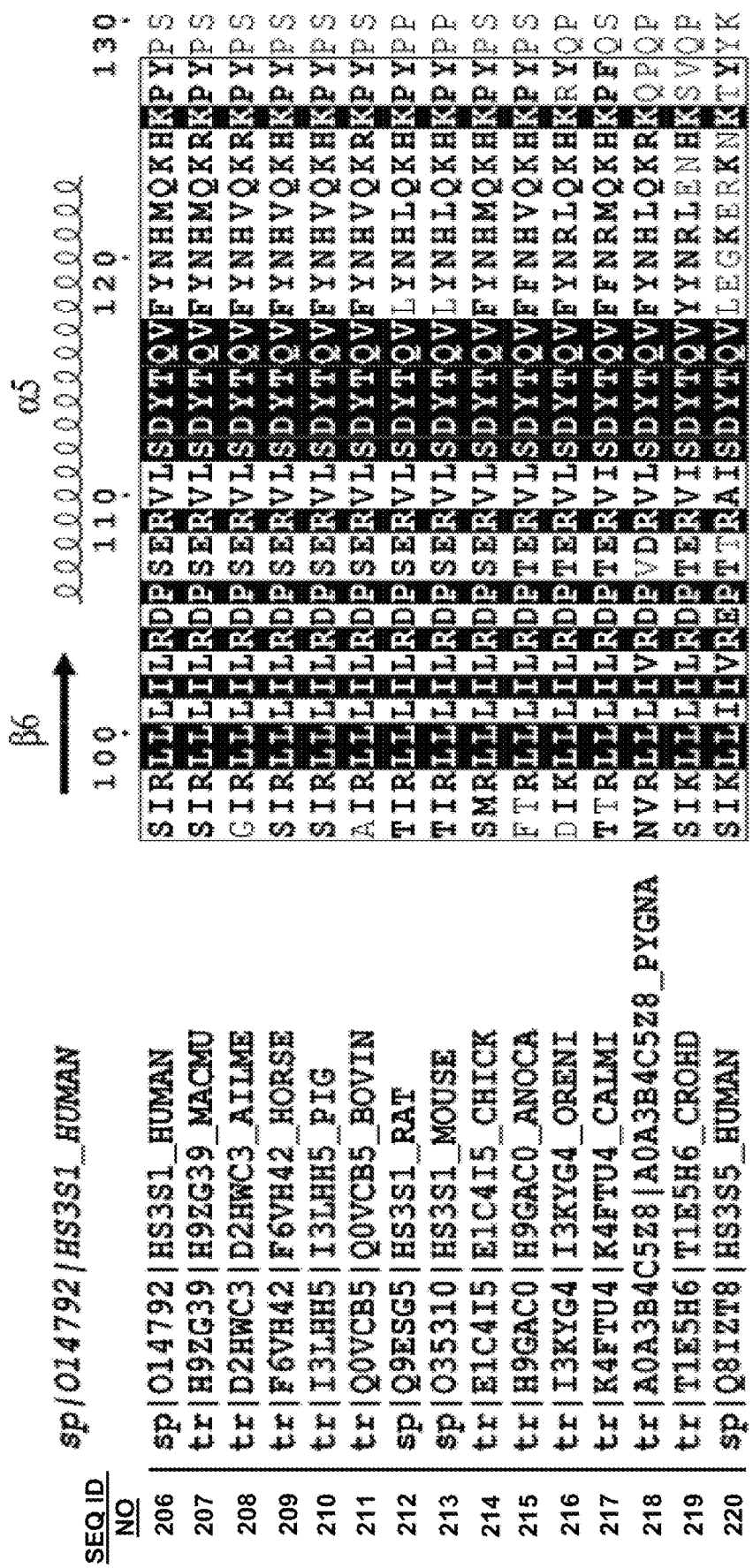
Figure 26E:
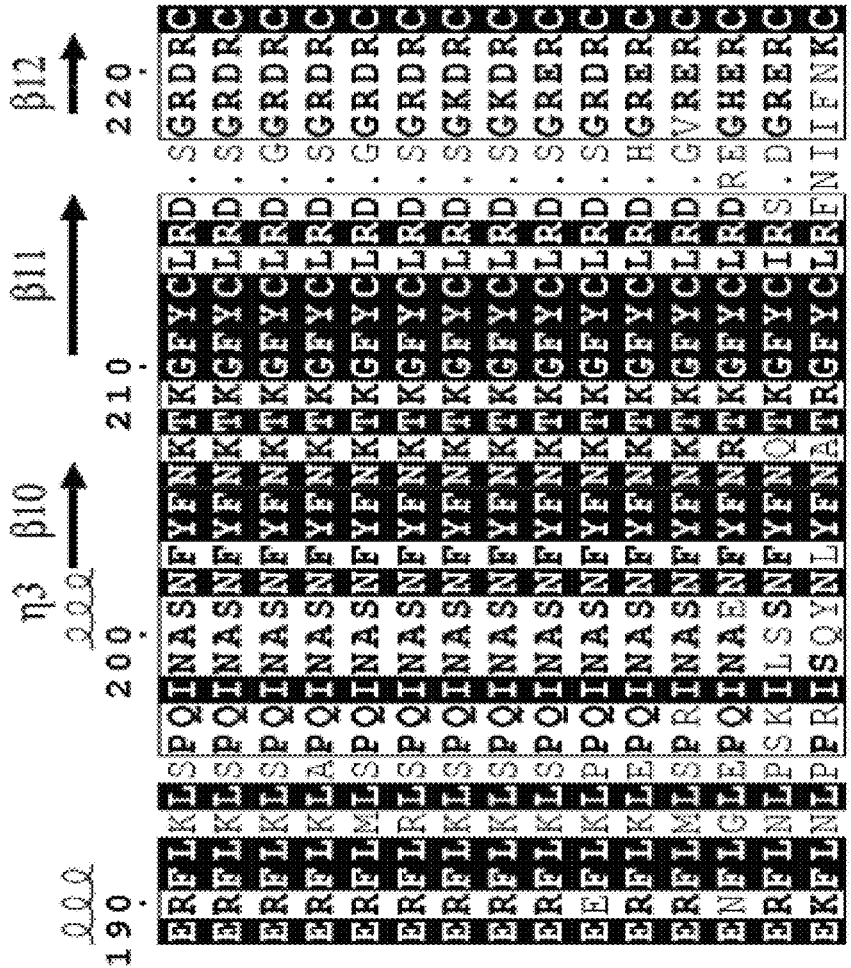

A non-limiting example of N,2O,6O-HS that can react as a sulfo group acceptor with engineered 3OST enzymes of the present invention is illustrated in FIG. 25. FIG. 25 shows a polysaccharide 440 that includes three glucosamine residues 410 comprising an N-sulfo group 411 at each N-position and an O-sulfo group 412 at each 6-O position. Within the polysaccharide 440, glucosamine residues 410 that are capable of acting as a sulfo acceptor must be flanked by two hexuronic acid residues. Hexuronic acid residues can include any residue represented by the functional group "X" in Formula X, and are shown in FIG. 25 as glucuronic acid residue 420 and iduronic acid residue 430. Either hexuronic acid residue can further be substituted by a sulfo group 431 at the 2-O position. Upon reacting the polysaccharide 440 with an 3OST enzyme and a sulfo group donor, the 3-O position 413 of any of the glucosaminyl residues 410 can be sulfated. As shown in FIG. 25, the central glucosamine residue 410 receives a sulfo group, ultimately forming a 3-O sulfated glucosaminyl residue 510 within the sulfated product polysaccharide 441. Also as shown, sulfated product polysaccharide 441 comprises the structure of Formula I.

Natural 3OST enzymes within EC 2.8.2.23 generally comprise approximately 300-325 amino acid residues that can in some cases vary greatly in their sequence, yet ultimately have the exact same function, namely, to catalyze the transfer of a sulfuryl group from PAPS to the 3-O position of N-sulfoglucosamine residues within N,2O-HS or N,2O,6O-HS polysaccharides, particularly those comprising the structure of Formula X. Without being limited by a particular theory, it is believed that each of the natural 3OSTs within the EC 2.8.2.23 enzyme class can catalyze the same chemical reaction because there are multiple amino acid sequence motifs and secondary structures that are either identical or highly conserved across all species.

Further, it is believed that several of the conserved amino acid sequence motifs are directly involved in binding of either PAPS and/or the polysaccharide, or participate in the chemical reaction itself. The identity between the natural 3OST enzymes can be demonstrated by comparing the amino acid sequences of the mouse or human 3OST1 enzyme (SEQ ID NO: 213 and SEQ ID NO: 206, respectively), which have known crystal structures (PDB codes 3UAN and 1ZRH, respectively) in which amino acid residues within the active site have been identified, alongside the amino acid sequences of other natural 3OSTs within EC 2.8.2.23. Further, a direct comparison of the mouse and human 3OST structures indicate that both enzymes have nearly identical active sites and overall folds, even though the two enzymes have only an 83% sequence identity with one another.

A multiple sequence alignment of the amino acid sequences of fifteen enzymes within EC 2.8.2.23 (SEQ ID NOs 206-220), including the mouse (SEQ ID NO: 213) and human 3OST1 (SEQ ID NO: 206) enzymes, is shown in FIGS. 26A-26F, along with the percent identity of each sequence relative to the human 3OST1 reference sequence (SEQ ID NO: 206, UniProtKB Accession No. 014792). As illustrated in FIGS. 26A-26F, sequences range from having 98% identity with SEQ ID NO: 206 (SEQ ID NO: 207, entry tr|H9ZG39|H9ZG39_MACMU) for the rhesus monkey 3OST1, down to 53% identity (SEQ ID NO: 220, entry sp|Q8IZT8|HS3S5_HUMAN) for human 3OST5. Those skilled in the art would appreciate that the multiple sequence alignment was limited to fifteen sequences for clarity, and that there are hundreds of amino acid sequences encoding for natural 3OST enzymes that have been identified and that have highly conserved active site and/or binding regions as well.

Within FIGS. 26A-26F, amino acids that are depicted in white with a black background at a particular position, are 100% identical across all sequences. Amino acids that are highly conserved, meaning that the amino acids are either identical or chemically or structurally similar, at a particular position are enclosed with a black outline. Within highly conserved regions, consensus amino acids that are present in a majority of the sequences, are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the natural human sulfotransferase enzyme as a reference. The R symbol adjacent to an arrow refers to a β-sheet, whereas a coil adjacent to an α symbol or η symbol refers to a helix secondary structure.

Within the fifteen aligned sequences in FIGS. 26A-26F (SEQ ID NOs 206-220), there are several conserved amino acid sequence motifs that include one or more amino acids that comprise the active site, based on the crystal structures of the mouse (SEQ ID NO: 213, entry sp|O353101|HS3S1_MOUSE) and human 3OST1 (SEQ ID NO: 206, entry sp|O14792|HS3S1_HUMAN) enzymes described above. Based on the numbering of the amino acid residues within FIGS. 26A-26F, these motifs include residues 16-27 (including G-V-R-K-G-G from residues 18-23), residues 43-48 (E-V/I-H-F-F-D), residues 78-81 (P-A/G-Y-F), residues 112-117 (including S-D-Y-T-Q-V), and residues 145-147 (Y-K-A). The conserved amino acid sequence motifs G-V-R-K-G-G, E-V/I-H-F-F-D, P-A/G-Y-F, and S-D-Y-T-Q-V correspond to SEQ ID NO: 265, SEQ ID NO: 298, SEQ ID NO: 266, and SEQ ID NO: 267 in the sequence listing, respectively. It is believed that these residues either facilitate or participate in the chemical reaction, or enable binding of PAPS or the polysaccharide within the active site. In particular, within residues 43-48, as described above and as illustrated in FIG. 4A, FIG. 4B, and FIG. 4C, the glutamic acid residue at position 43 abstracts the proton from the 3-O position of the N-sulfoglucosamine residue within the polysaccharide, enabling the nucleophilic attack and removal of the sulfo group from PAPS, whereas His-45 and Asp-48 coordinate to stabilize the transition state of the enzyme before the sulfurylated polysaccharide product is released from the active site.

However, as described above, the natural 3OST enzymes are unable to catalyze the transfer of the sulfate group from an aryl sulfate compound to a polysaccharide. Without being limited by a particular theory, and as with the natural NDST, 2OST, and 6OST enzymes described above, it is believed that the binding pocket for PAPS within the active site of the natural sulfotransferase either does not have a high enough affinity for aryl sulfate compounds to facilitate binding and/or that the aryl sulfate compounds are sterically hindered from entering the active site. Consequently, and in another embodiment, a natural 3OST enzyme can be mutated in several locations within its amino acid sequence to enable binding of the aryl sulfate compound within the active site and/or to optimally position the aryl sulfate compound so transfer of the sulfate group to the polysaccharide can occur.

Accordingly, and in another embodiment, engineered 3OST enzymes of the present invention can be mutants of natural 3OST enzymes within EC 2.8.2.23, including enzymes having the amino acid sequences of SEQ ID NOs 206-220. In another embodiment, mutations engineered into the amino acid sequences of the engineered 3OST enzymes facilitate a biological activity in which aryl sulfate compounds can both bind and react with the enzyme as sulfo group donors. In another embodiment, although the engineered 3OST enzymes can bind and react with an aryl sulfate compound as a sulfo group donor, they can retain the natural 3OST enzymes' biological activity with N,2O,6O-HS, including but not limited to those comprising the structure of Formula X, as sulfo group acceptors. Without being limited by a particular theory, it is believed that because of the mutations inserted into the amino acid sequences of the engineered 3OST enzymes, their sulfotransferase activity may comprise the direct transfer of a sulfuryl group from an aryl sulfate compound to the heparosan-based polysaccharide, using a similar mechanism as described in FIGS. 4A-4C, above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by the oxygen atom at the 3-O position of a glucosamine residue, to form a 3-O sulfated HS product. In another embodiment, the 3-O sulfated product of either sulfotransfer mechanism is an N,2O, 3O,6O-HS product.

In another embodiment, an engineered 3OST enzyme can comprise one or more mutated amino acid sequence motifs relative to the conserved amino acid sequence motifs (SEQ ID NO: 265, SEQ ID NO: 298, SEQ ID NO: 266, and SEQ ID NO: 267) found in natural 3OST enzymes, as described above and indicated in the multiple sequence alignment in FIGS. 26A-26F and SEQ ID NOs 206-220. In another embodiment, each mutated amino acid sequence motif that is present in the amino acid sequence of the engineered enzyme comprises at least one amino acid mutation relative to the corresponding conserved amino acid sequence motif within the natural 3OST enzymes. In another embodiment, an engineered 3OST enzyme can comprise one mutated amino acid sequence motif. In another embodiment, an engineered 3OST enzyme can comprise two mutated amino acid sequence motifs. In another embodiment, an engineered 3OST enzyme can comprise three mutated amino acid sequence motifs. In another embodiment, an engineered 3OST enzyme can comprise four mutated amino acid sequence motifs. In another embodiment, an engineered 3OST enzyme can comprise five mutated amino acid sequence motifs. In another embodiment, an engineered 3OST enzyme that includes at least one mutated amino acid sequence motif relative to any of the wild-type 3OST enzymes within EC 2.8.2.23 can have an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160.

Figure 27:
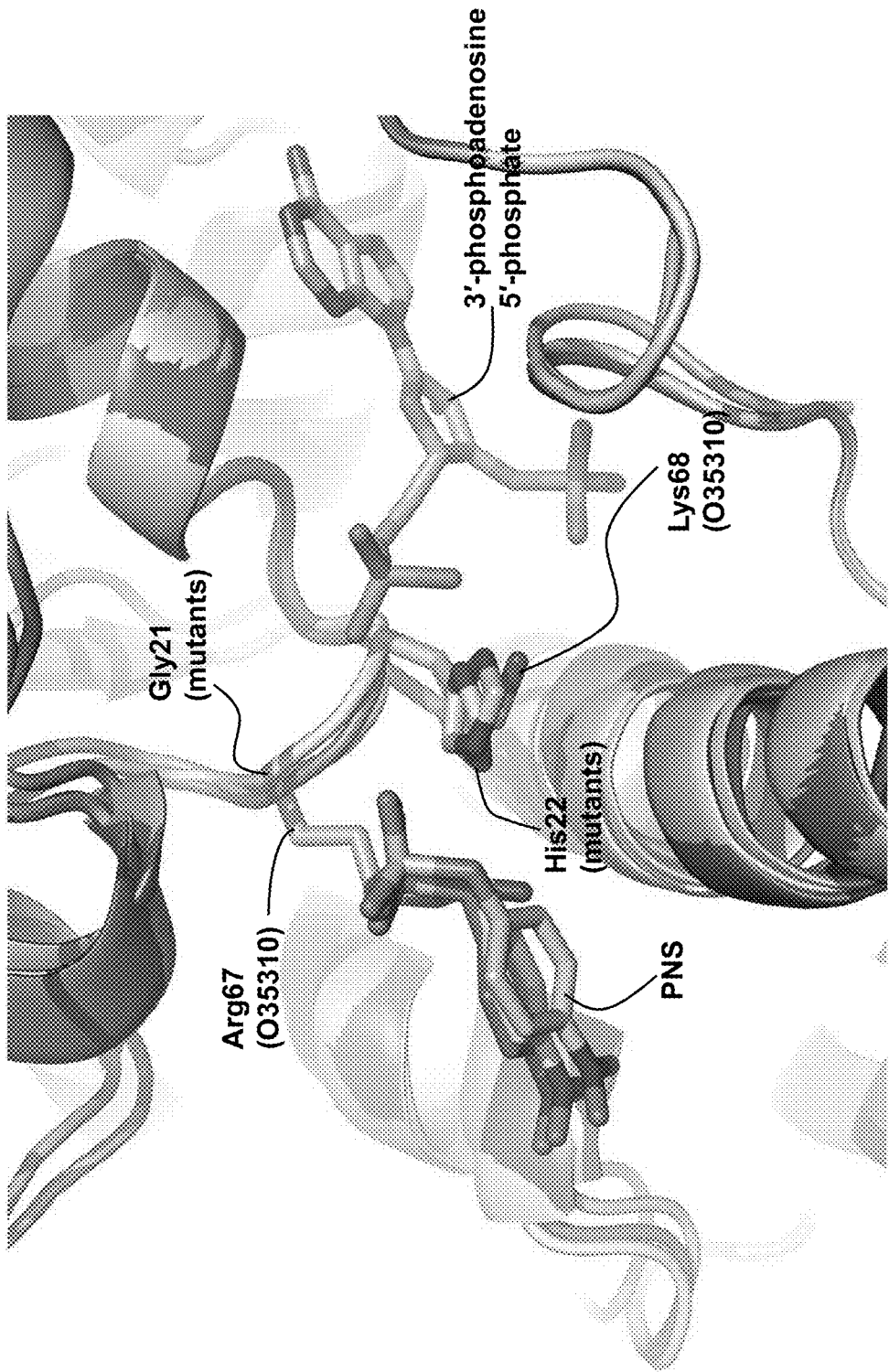

In another embodiment, upon viewing the crystal structure of the mouse 3OST within a 3D molecular visualization system (including, as a non-limiting example, the open-source software, PyMOL), the structure of related sequences, such as those of engineered 3OST enzymes that contain one or more mutated amino acid sequence motifs relative to the mouse 3OST1 (SEQ ID NO: 213, UniProtKB Accession No. 035310) structure, can be modeled for comparison as illustrated in FIG. 27. FIG. 27 shows a magnified view of the active site of the mouse 3OST1 enzyme (PDB code: 3UAN) with three engineered 3OST enzymes, comprising the amino acid sequences of SEQ ID NO: 147, SEQ ID NO: 149, and SEQ ID NO: 151. Adenosine 3',5'-diphosphate, which is the product of a sulfotransfer reaction in which PAPS is the sulfo donor, and which was co-crystallized with the mouse 3OST1, is also illustrated within the active site. PNS is also modeled into the active site of the engineered enzymes, using the consensus solutions of molecular dynamics (MD) simulations that designed to calculate the optimized position and orientation of a ligand within an enzyme active site adjacent to the polysaccharide binding site (not shown), if such solutions are possible. Hydrogen atoms are not shown for clarity.

As illustrated in FIG. 27, although there are several mutations made to SEQ ID NO: 147, SEQ ID NO: 149, and SEQ ID NO: 151 relative to the amino acid sequence of the natural mouse 3OST1 enzyme (SEQ ID NO: 213), the respective protein backbones are in a nearly identical location to one another, enabling a one-to-one comparison of the active sites. However, when comparing the two active sites, the adenosine 3',5'-diphosphate product from the natural sulfotransfer reaction is adjacent to the lysine residue (shown in FIG. 27 as Lys68), whereas the convergent solutions from the above MD simulations indicate that PNS binding within the engineered enzymes is favored on the opposite side of the active site. Without being limited by a particular theory, it is believed that the convergent MD simulation solutions place PNS on the opposite side of the active site because there is not enough of an affinity toward PNS in the same or similar position as PAPS. Yet, despite the apparent differences in the binding pocket for PAPS and PNS, engineered 3OST enzymes comprising the amino acid sequences of SEQ ID NO: 147, SEQ ID NO: 149, and SEQ ID NO: 151 all achieved sulfo transfer from an aryl sulfate compound to the 3-O position of one or more positions within a heparosan-based polysaccharide, as described in the examples below.

Further, the arginine residue corresponding to position 20 of the mouse 3OST1 (SEQ ID NO: 213) and which is conserved in all of the other 3OST enzymes in SEQ ID NOs 206-220, would appear to block PNS from binding in the position indicated in FIG. 27. Accordingly, and in another embodiment, engineered 3OST enzymes that bind PNS can comprise a mutation of the active site arginine residue to a glycine residue, which removes all steric hindrance for PNS to bind within the binding pocket. As indicated in the amino acid sequences for SEQ ID NO: 147, SEQ ID NO: 149, SEQ ID NO: 151, SEQ ID NO: 154, SEQ ID NO: 155, SEQ ID NO: 156, and SEQ ID NO: 157, the arginine to glycine mutation is at position 21. As indicated in the amino acid sequences for SEQ ID NO: 158, SEQ ID NO: 159, and SEQ ID NO: 160, the arginine to glycine mutation is at position 99.

Similarly, the next amino acid residue in each of the engineered enzymes, corresponding to position 22 in the amino acid sequences SEQ ID NO: 147, SEQ ID NO: 149, SEQ ID NO: 151, SEQ ID NO: 154, SEQ ID NO: 155, SEQ ID NO: 156, and SEQ ID NO: 157, is mutated to a histidine residue. Without being limited by a particular theory, it is believed that the mutation to a histidine residue from the conserved lysine residue (corresponding to position 21 in each of the amino acid sequences in FIG. 26A) facilitates removal of the sulfate group from PNS, using a similar mechanism as described by Malojcic, et al., above. As indicated in the amino acid sequences for SEQ ID NO: 158, SEQ ID NO: 159, and SEQ ID NO: 160, the lysine to histidine residue is at position 100.

Those skilled in the art would appreciate that engineered 3OST enzymes of any other amino acid sequence, including, but not limited to, those disclosed by SEQ ID NO: 154, SEQ ID NO: 155, SEQ ID NO: 156, SEQ ID NO: 157, SEQ ID NO: 158, SEQ ID NO: 159, and SEQ ID NO: 160, would likely exhibit a similar structure would exhibit similar structural motifs as engineered enzymes having the amino acid sequences of SEQ ID NO: 147, SEQ ID NO: 149, and SEQ ID NO: 151, particularly within the active site. Without being limited by a particular theory, it is also believed that NCS would bind in a similar position as PNS within the active site of any of the engineered enzymes, since the structures of the two aryl sulfate compounds are very similar, except that the sulfate group is located ortho on the aromatic ring relative to the nitro group, rather than para to the nitro group.

In another embodiment, engineered 3OST enzymes of the present invention can comprise one or more mutated amino acid sequence motifs, which can be determined in-part by comparing conserved amino acid sequence motifs (SEQ ID NO: 265, SEQ ID NO: 298, SEQ ID NO: 266, and SEQ ID NO: 267) indicated in the multiple sequence alignment of SEQ ID NOs 206-220 in FIGS. 26A-26F with the known structure(s) of native 3OST enzymes and/or modeled engineered enzymes, including but not limited to the engineered 3OST enzymes illustrated in FIG. 27. In another embodiment, mutated amino acid sequence motifs that can be comprised within an engineered 3OST enzyme can be selected from the group consisting of (a) G-V-G-H-G-G (SEQ ID NO: 268); (b) H-S-Y-F (SEQ ID NO: 269); (c) S-$X_1$-$X_2$-T-H-$X_3$ (SEQ ID NO: 299), wherein $X_1$ is selected from the group consisting of alanine and leucine; $X_2$ is selected from the group consisting of tyrosine and glycine, and $X_3$ is selected from the group consisting of methionine and leucine; and (d) Y-$X_4$-G, wherein $X_4$ is selected from the group consisting of valine and threonine; including any combination thereof. Each of the mutated amino acid sequence motifs corresponds with a conserved amino acid motif indicated in FIGS. 26A-26F above: SEQ ID NO: 268 corresponds to the conserved amino acid sequence motif G-V-R-K-G-G (SEQ ID NO: 265); SEQ ID NO: 269 corresponds to the conserved amino acid sequence motif P-A/G-Y-F (SEQ ID NO: 266); SEQ ID NO: 299 corresponds to the conserved amino acid sequence motif S-D-Y-T-Q-V (SEQ ID NO: 257); and the mutated amino acid sequence motif Y-$X_4$-G corresponds to the conserved amino acid sequence motif Y-K-A. In another embodiment, an engineered 3OST enzyme comprising each of the mutated amino acid sequence motifs above can be selected from the group consisting of: SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160.

In another embodiment, each of the mutated amino acid sequence motifs can comprise at least one mutation that is made relative to the conserved amino acids found in the natural 3OST enzymes within EC 2.8.2.23. In another embodiment, SEQ ID NO: 268 contains an R-K to G-H mutation, relative to the conserved amino acid sequence motif, G-V-R-K-G-G (SEQ ID NO: 265). In another embodiment, SEQ ID NO: 269 contains a P-A/G to an H-S mutation relative to the conserved amino acid sequence motif, P-A/G-Y-F (SEQ ID NO: 266). In another embodiment, in addition to potential mutations made at the $X_1$, $X_2$, and $X_3$ positions, SEQ ID NO: 299 comprises a Q to H mutation, relative to the conserved amino acid sequence motif, S-D-Y-T-Q-V (SEQ ID NO: 267). In another embodiment, in addition to a mutation at the $X_4$ position, mutated amino acid sequence motif Y-$X_4$-G comprises an A to G mutation, relative to the conserved amino acid sequence motif, Y-K-A.

In another embodiment, $X_1$ is alanine, $X_2$ is tyrosine and $X_3$ is methionine (SEQ ID NO: 270), and $X_4$ is valine or threonine. In other embodiments, $X_1$ is leucine, $X_2$ is glycine, and $X_3$ is leucine (SEQ ID NO: 300), and $X_4$ is threonine. Without being limited to another theory, it is believed that one or more of the mutations comprised within mutated amino acid sequence motifs SEQ ID NO: 269, SEQ ID NO: 299, and Y-$X_4$-G play a role in stabilizing the transition state of the enzyme during the chemical reaction, or in increasing the affinity of aryl sulfate compounds to the active site, including by reducing the size of the binding pocket, increasing the hydrophobicity of the pocket, and/or creating π-π interactions with the aromatic moieties of the aryl sulfate compounds.

Figure 28A:
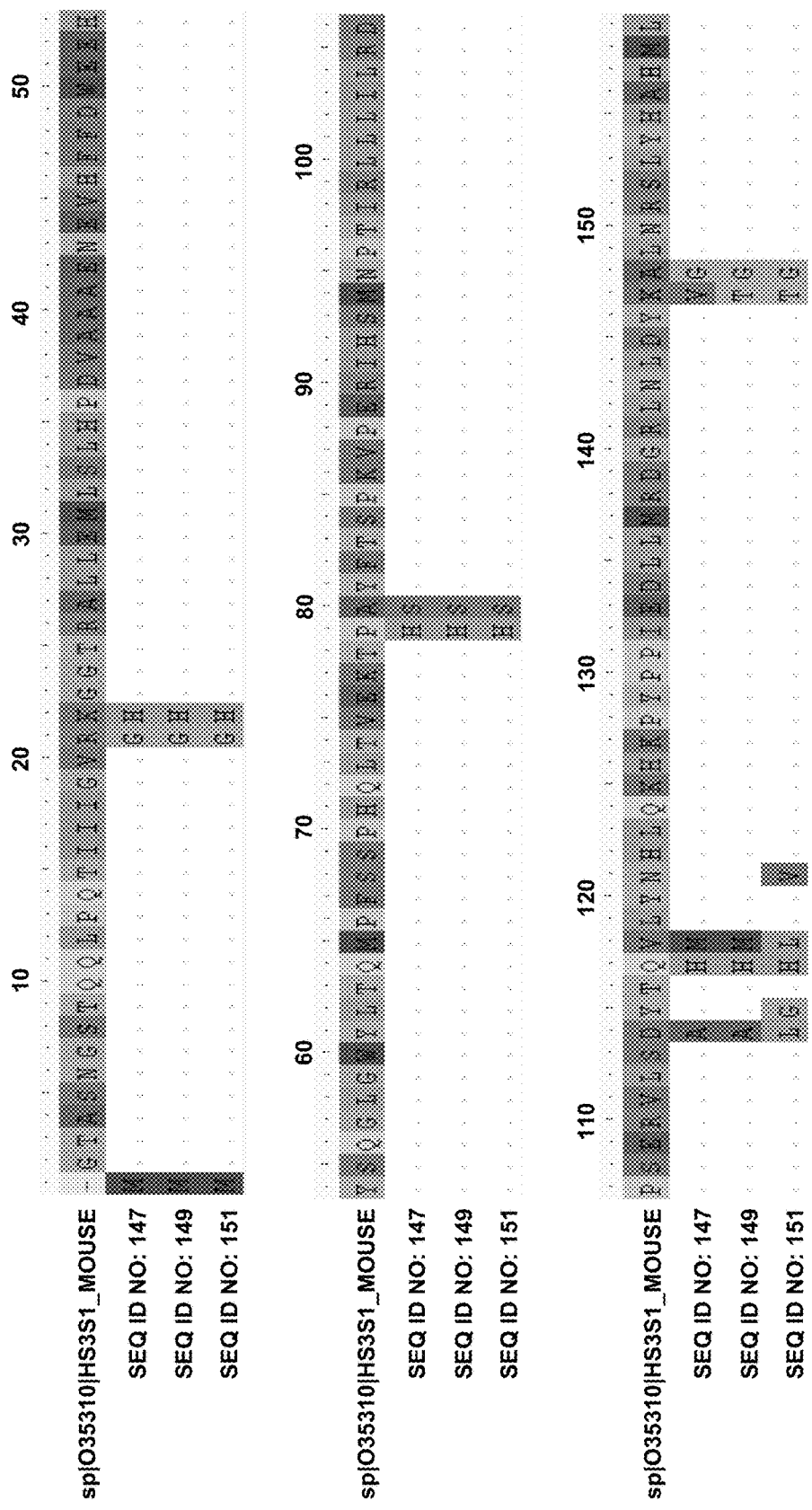
Figure 28B:
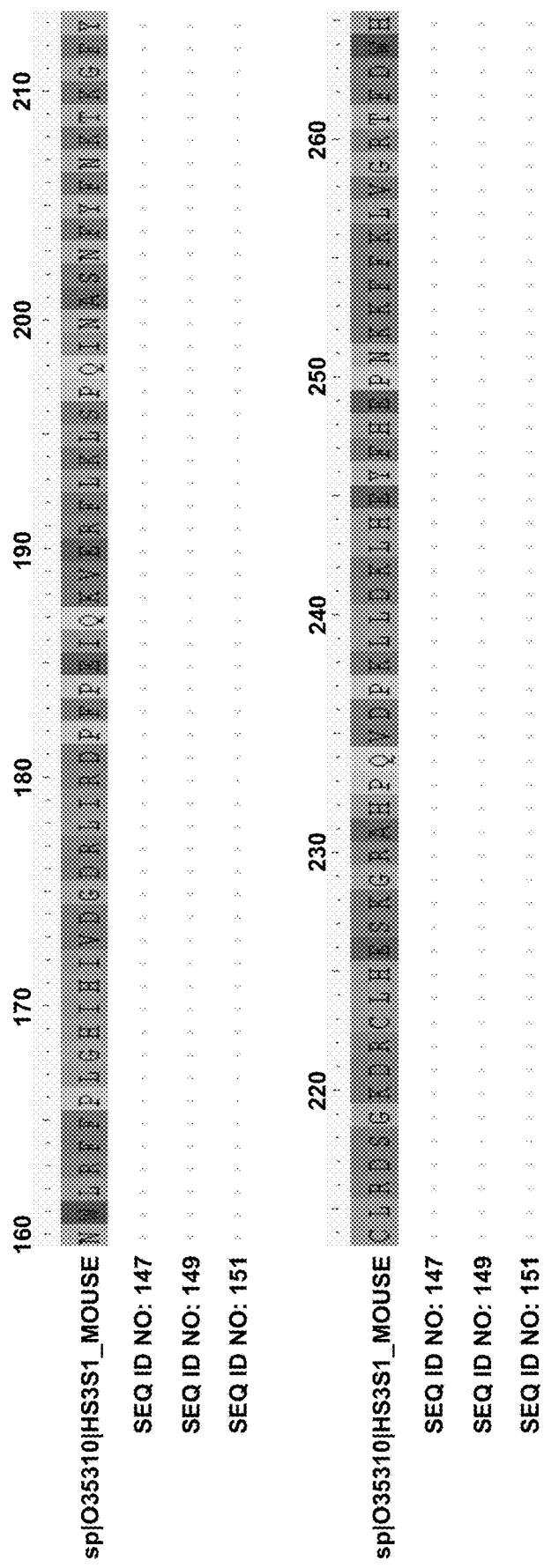

Furthermore, the amino acid sequences (SEQ ID NO: 147, SEQ ID NO: 149, and SEQ ID NO: 151) of three engineered 3OST enzymes, which have been experimentally determined to be active with aryl sulfate compounds as sulfo group donors (see Example 6 below) can be compared with the amino acid sequence of the human 3OST1 enzyme (SEQ ID NO: 206, entry sp|O14792|HS3S1_HUMAN) in a multiple sequence alignment to determine if there are relationships between mutations among each of the enzymes. A period within the amino acid sequence of an engineered enzyme indicates identity at a particular position with the human 3OST enzyme. As shown in FIG. 28, the sequence alignment demonstrates that while over 90% of the amino acid residues within the three sulfotransferase sequences are identical, there are several positions in which multiple amino acids can be chosen. As a result, and in another embodiment, an engineered 3OST enzyme comprising an amino acid sequence in which multiple amino acids can be chosen at defined positions is disclosed as SEQ ID NO: 154. Positions at which the identity of an amino acid can be chosen from a selection of possible residues are denoted in terms "Xaa," "Xn," or "position n," where n refers to the residue position.

In another embodiment, within an engineered 3OST enzyme comprising the amino acid sequence of SEQ ID NO: 154, the amino acid residue at position 114 is alanine and the amino acid residue at position 118 is methionine. In further embodiments, the amino acid residue at position 147 is selected from the group consisting of valine and threonine.

In another embodiment, within an engineered 3OST enzyme comprising the amino acid sequence of SEQ ID NO: 154, the amino acid residue at position 114 is leucine, the amino acid residue at position 118 is leucine, and the amino acid residue at position 121 is valine. In further embodiments, the amino acid residue at position 115 is glycine. In even further embodiments, the amino acid residue at position 147 is threonine.

In another embodiment, within an engineered 3OST enzyme comprising the amino acid sequence of SEQ ID NO:

154, the amino acid sequence can optionally include one or more mutations at residue positions not specified by an "Xn" or "Xaa," so long as any such mutations do not eliminate the 3OST and/or aryl sulfate-dependent activity of the enzyme. In another embodiment, such mutations not eliminating aryl sulfate-dependent activity at positions not specified by an "Xn" or "Xaa" can include substitutions, deletions, and/or additions.

Accordingly, in another embodiment, an engineered 3OST enzyme utilized in accordance with any of the methods of the present invention can comprise an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160. In another embodiment, engineered 3OST enzymes comprising the amino acid sequence of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160 can react with any aryl sulfate compound. In further embodiments, the aryl sulfate compound is selected from the group consisting of PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS. In some even further embodiments, the aryl sulfate compound is PNS. In other even further embodiments, the aryl sulfate compound is NCS.

In Vitro Synthesis of Sulfated Polysaccharides

In an embodiment of the invention, any of the engineered sulfotransferase enzymes described above can be utilized to synthesize HS polysaccharide products. Generally, sulfation can be accomplished by treating a heparosan-based polysaccharide and an aryl sulfate compound with an engineered sulfotransferase enzyme to form the sulfated product. As described above and without being limited by a particular theory, it is believed that sulfotransferase enzymes that recognize heparosan-based polysaccharides as sulfo group acceptors, but also bind and react with aryl sulfate compounds as sulfo donors, have neither been observed in nature nor described previously.

HS polysaccharide compositions that are utilized for industrial, commercial, or pharmaceutical uses can be obtained in large quantities by isolating them from animal sources, particularly pigs and cattle, within which the polysaccharides are produced in vivo. (see Xu, Y., et al., (2011) *Science* 334 (6055): 498-501). A worldwide contamination crisis in 2007 and 2008 of heparin obtained from pigs shone a spotlight on the fragility of solely relying on obtaining them from animal sources. Consequently, there has been a push to develop synthetic routes to synthesizing heparin, LMWH, and other anticoagulant HS polysaccharides in vitro in large enough quantities to compliment or replace animal-sourced products. That push has only been strengthened even further by the African swine flu epidemic that decimated the worldwide pig population, especially in China, in 2019.

In order to synthesize HS polysaccharides in vitro, there have historically been two reaction schemes: total chemical synthesis and chemoenzymatic synthesis. While both types of reaction schemes have led to purified products that in some instances are homogeneous, synthetic routes as a whole have been inadequate to produce specific HS polysaccharide compositions, particularly heparin, on an industrial scale. For example, the production of such polysaccharides using total chemical synthesis has historically required as many as 60 steps and resulted in very low yields (see Balagurunathan, K., et al., (eds.) (2015) *Glycosaminoglycans: Chemistry and Biology*, Methods in Molecular Biology, vol. 1229, DOI 10.1007/978-1-4939-1714-3_2, © Springer Science+Business Media New York).

Chemoenzymatic synthesis routes, on the other hand, generally utilize far fewer steps and increase the scale of the generated anticoagulant products into multi-milligram amounts (See U.S. Pat. Nos. 8,771,995 and 9,951,149, the disclosures of which are incorporated by reference in its entirety). The improvements in the quantity of obtainable product can be attributed to the ability to combine recombinant versions of natural HS sulfotransferases with PAPS in a reaction vessel in order to catalyze the transfer of sulfo groups to heparosan-based polysaccharides. Yet, chemoenzymatic methods to this point are still not suitable to synthesize gram- or larger-scale amounts of anticoagulant HS polysaccharides because of the wild-type sulfotransferases' reliance on PAPS for their activity, as described in U.S. Pat. Nos. 5,541,095, 5,817,487, 5,834,282, 6,861,254, 8,771,995, 9,951,149, and U.S. Pat. Pubs. 2009/0035787, 2013/0296540, and 2016/0122446, the disclosures of which are incorporated by reference in their entireties. PAPS is a highly expensive and unstable molecule that has been an obstacle to the large-scale production of enzymatically sulfated products, including heparin, because the half-life of PAPS at pH 8.0 is only about 20 hours.

Furthermore, product inhibition by adenosine 3',5'-diphosphate has also been a limiting factor to large-scale synthesis of sulfated products. The highly negative impact of the product inhibition by adenosine 3',5'-diphosphate can be somewhat reduced by employing a PAPS regeneration system (see U.S. Pat. No. 6,255,088, above, and Burkhart, et al. (2000) *J. Org. Chem.* 65: 5565-5574) that converts adenosine 3',5'-diphosphate into PAPS. Despite the PAPS regeneration system, however, the absolute necessity to supply PAPS to initiate the chemical reaction with PAPS-dependent sulfotransferases nonetheless creates an insurmountably high-cost barrier to synthesize sulfated products, including heparin, on an industrial, production-grade scale.

In contrast to the known syntheses of heparin that require PAPS as sulfo donors in order to drive enzyme activity, the methods of the present invention obviate the need to use PAPS altogether, because each of the sulfotransferases of the present invention have been engineered to recognize, bind, and react with aryl sulfate compounds, which do not react with natural HS sulfotransferases, as sulfo donors. Without being limited by a particular theory, it is believed that the engineered sulfotransferases of the present invention are the only known sulfotransferases that are capable of reacting with aryl sulfate compounds as sulfo group donors, while also reacting with polysaccharides, particularly heparosan-based polysaccharides, as sulfo group acceptors.

Thus, in another embodiment, the invention provides methods and kits for synthesizing HS polysaccharides. Generally, a method for sulfating a heparosan-based polysaccharide using the engineered sulfotransferases of the present invention comprises the following steps: (a) providing an aryl sulfate compound; (b) providing any of the engineered sulfotransferase enzymes described above, wherein the engineered sulfotransferase enzyme has biological activity with an aryl sulfate compound as a sulfo group donor; (c) providing a heparosan-based polysaccharide; (d) combining the aryl sulfate compound, the sulfotransferase enzyme, and the heparosan-based polysaccharide into a reaction mixture; and (e) transferring the sulfo group from the aryl sulfate compound to the heparosan-based polysaccharide, using the sulfotransferase enzyme, thereby forming the sulfated polysaccharide product. In another embodiment, the aryl sulfate compound can be selected from the consisting of PNS, 4-methylumbelliferyl sulfate, 7-hydroxycoumarin sulfate, phenyl sulfate, 4-acetylphenyl sulfate, indoxyl sulfate, 1-naphthyl sulfate, 2NapS, and NCS. According to the present invention, the aryl sulfate compound is PNS. According to the present invention, the aryl sulfate compound is NCS.

In another embodiment, when the engineered sulfotransferase enzyme is a NST enzyme, the heparosan-based polysaccharide can be an N-deacetylated heparosan polysaccharide comprising one or more disaccharide units comprising the structure of Formula II, and the engineered sulfotransferase can have an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25. In another embodiment, the N-sulfated HS polysaccharide comprises one or more disaccharide units having the structure of Formula III.

In another embodiment, N-deacetylated heparosan and/or other heparosan-based polysaccharides comprising disaccharide units having the structure of Formula II can be obtained commercially. In another embodiment, heparosan can be isolated from natural sources and chemically modified to N-deacetylate glucosamine residues and also control the molecular weight of the polysaccharides within the composition. In particular, heparosan can be found within bacteria as capsules that regulate cell entry by metabolites and other exogenous materials. Such bacteria, include, but are not limited to, *Pasteurella multocida* and *Escherichia coli* (*E. coli*). In some embodiments, heparosan can be extracted and purified from *E. coli*, particularly the K5 strain of *E. coli*, as a polydisperse mixture of polysaccharide molecules having varying molecular weights. Procedures for isolating heparosan from the K5 strain of *E. coli* are discussed and provided in Wang, Z., et al., (2010) *Biotechnol. Bioeng.* 107 (6):964-973, the disclosure of which is incorporated by reference in its entirety; see also DeAngelis, P. L. (2015) *Expert Opinion on Drug Delivery* 12 (3):349-352; Ly, M., et al., (2010) *Anal. Bioanal. Chem.* 399:737-745; and Zhang, C., et al., (2012)*Metabolic Engineering* 14:521-527, the disclosures of which are also incorporated in their entireties.

In another embodiment, a portion or all of the heparosan composition can be N-deacetylated by treating it with a base, particularly lithium hydroxide or sodium hydroxide (see Wang, Z., et al., (2011) *Appl. Microbiol. Biotechnol.* 91 (1):91-99, the disclosure of which is incorporated by reference in its entirety; see also PCT publication PCT/US2012/026081, the disclosure of which is incorporated by reference in its entirety). In another embodiment, the base is sodium hydroxide. Depending on the degree of N-deacetylation desired, the concentration of the heparosan, and the concentration of the base, one skilled in the art can determine how long to incubate heparosan with the base according to the procedures described in Wang, et al., (2011), above.

In another embodiment, N-deacetylated heparosan can be obtained with molecular weight and N-acetyl glucosamine contents useful for synthesizing UFH that meets one or more of the benchmarks set forth by the United States Pharmacopeia (USP), described in further detail below. In another embodiment, heparosan can be incubated with a base, preferably sodium hydroxide, until a desired amount of N-acetylated glucosamine residues remains within the N-deacetylated product. In another embodiment, N-acetyl glucosamine residues can comprise less than 60%, including less than 30%, 20%, 18%, 16%, 14%, 12%, or 10%, down to less than 5%, and preferably in a range from 12% and up to 18%, of the glucosamine residues within the N-deacetylated heparosan. In another embodiment, the N-acetyl glucosamine can comprise about 15% of the glucosamine residues within the N-deacetylated heparosan.

Additionally, and without being limited by a particular theory, it is believed that in addition to N-deacetylating glucosamine residues, the reaction between heparosan and a base can simultaneously depolymerize the heparosan polysaccharides and reduce their molecular weight, which can in turn reduce the weight-average molecular weight ($M_w$) of the N-deacetylated heparosan. Typically, heparosan polysaccharides isolated from bacteria, including but not limited to *E. coli*, have a molecular weight ranging from about 3,000 Da to about 150,000 Da, and compositions of isolated heparosan can have a $M_w$ in the range of about 25,000 Da up to about 50,000 Da (see Ly, M., et al. and Wang, et al., (2011), above). In another embodiment, a heparosan composition either obtained from commercial sources or isolated from bacteria, including but not limited to *E. coli*, can be treated with a base, preferably sodium hydroxide, for a time sufficient to reduce the $M_w$ of the N-deacetylated heparosan to a target or desired level. In another embodiment, the N-deacetylated heparosan can have an $M_w$ of at least 1,000 Da, including at least 2,000 Da, 4,000 Da, 6,000 Da, 7,000 Da, 8,000 Da, 8,500 Da, 9,000 Da, 9,500 Da, 10,000 Da, 10,500 Da, 11,000 Da, 11,500 Da, 12,000 Da, 12,500 Da, 13,000 Da, 13,500 Da, 14,000 Da, 15,000 Da, 16,000 Da, or 18,000 Da, up to at least 20,000 Da. In another embodiment, the N-deacetylated heparosan can have an $M_w$ of less than 20,000 Da, including less than 18,000 Da, 16,000 Da, 15,000 Da, 14,000 Da, 13,500 Da, 13,000 Da, 12,500 Da, 12,000 Da, 11,500 Da, 11,000 Da, 10,500 Da, 10,000 Da, 9,500 Da, 9,000 Da, 8,500 Da, 8,000 Da, 7,000 Da, 6,000 Da, or 4,000 Da, down to less than 2,000 Da. In another embodiment, the N-deacetylated heparosan can have an $M_w$ in any range listed above between and inclusive of 1,000 Da and 20,000 Da, and preferably in any range listed above between and inclusive of 9,000 Da and 12,500 Da.

The preparation of N-deacetylated heparosan having such molecular weight properties and N-acetyl glucosamine content is described in detail in Wang, et al., (2011), above. In another embodiment, the time sufficient to react a heparosan with a base, preferably sodium hydroxide, to form an N-deacetylated heparosan product having an $M_w$ in a range between 9,000 Da and 12,500 Da, as well as an N-acetyl glucosamine content in a range from 12% and up to 18%, can be at least 1 hour, including at least 2, 4, 6, 8, 10, 12, or 18 hours, and up to at least 24 hours, depending on the molecular weight properties and concentration of the heparosan starting material, and the identity and concentration of the base used to carry out the reaction.

In another embodiment, when the engineered sulfotransferase enzyme is a 2OST enzyme, the heparosan-based polysaccharide can be an N-sulfated HS polysaccharide comprising one or more structural motifs comprising the structure of Formula IV and/or Formula V, and the engineered sulfotransferase can have an amino acid sequence selected from the group consisting of SEQ ID NO: 65, SEQ ID NO: 66, SEQ ID NO: 67, and SEQ ID NO: 69. In another embodiment, the method can further comprise the step of providing a glucuronyl $C_5$-epimerase, preferably a glucuronyl $C_5$-epimerase comprising the amino acid sequence of SEQ ID NO: 67, and more preferably residues 34-617 of SEQ ID NO: 67, and combining the glucuronyl $C_5$-epimerase with the reaction mixture. In another embodiment, the N-sulfated HS can be commercially obtained. In another embodiment, the N-sulfated HS can be the sulfated product of an engineered NST or natural NDST enzyme. In another embodiment, the sulfated polysaccharide product of the engineered 2OST enzyme is an N,2O-HS polysaccharide comprising the structure of Formula VI and/or Formula VII.

In another embodiment, the N-sulfated HS can be obtained by chemically N-sulfating N-deacetylated heparosan. In another embodiment, the N-deacetylated heparosan can be chemically sulfated by adding a composition comprising sulfur trioxide and/or one or more sulfur-trioxide containing compounds or adducts. Chemical N-sulfation of glucosamine residues within polysaccharides using sulfur trioxide is commonly known in the art (see Lloyd, A. G., et al., (1971) *Biochem. Pharmacol.* 20 (3):637-648; Nadkarni, V. D., et al., (1996) *Carbohydrate Research* 290:87-96; Kuberan, B., et al., (2003) *J. Biol. Chem.* 278 (52):52613-52621; Zhang, Z., et al., (2008) *J. Am. Chem. Soc.* 130 (39):12998-13007; and Wang, et al., (2011), above; see also U.S. Pat. No. 6,991,183 and U.S. Pat. Pub. 2008/020789, the disclosures of which are incorporated by reference in their entireties). Sulfur trioxide complexes are generally mild enough bases to enable the selected N-sulfation of polysaccharides without causing depolymerization, unlike sodium hydroxide (see Gilbert, E. E., (1962) *Chem. Rev.* 62 (6): 549-589). Non-limiting examples of sulfur trioxide-containing complexes include sulfur dioxide-pyridine, sulfur dioxide-dioxane, sulfur dioxide-trimethylamine, sulfur dioxide-triethylamine, sulfur dioxide-dimethylaniline, sulfur dioxide-thioxane, sulfur dioxide-Bis(2-chloroethyl) ether, sulfur dioxide-2-methylpyridine, sulfur dioxide-quinoline, or sulfur dioxide-dimethylformamide.

In another embodiment, when the engineered sulfotransferase enzyme is a 6OST enzyme, the heparosan-based polysaccharide is an N,2O-HS polysaccharide comprising one or more structural motifs comprising the structure of Formula VIII. In another embodiment, the engineered 6OST enzyme can have an amino acid sequence selected from the group consisting of SEQ ID NO: 104, SEQ ID NO: 106, SEQ ID NO: 108, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122. In another embodiment, the heparosan-based polysaccharide for reacting with the engineered 6OST enzyme can be commercially obtained. In another embodiment, the heparosan-based polysaccharide for the engineered 6OST enzyme can be the sulfated N,2O-HS polysaccharide product of an engineered or natural 2OST enzyme. In another embodiment, the sulfated polysaccharide product of the engineered 6OST enzyme is an N,2O,6O-HS polysaccharide comprising the structure of Formula IX.

In another embodiment, when the engineered sulfotransferase enzyme is a 3OST enzyme, the heparosan-based polysaccharide can be an N,2O,6O-HS polysaccharide comprising one or more structural motifs comprising the structure of Formula X. In another embodiment, the engineered 3OST can have an amino acid sequence selected from the group consisting of SEQ ID NO: 147, SEQ ID NO: 149, SEQ ID NO: 151, SEQ ID NO: 154, SEQ ID NO: 155, SEQ ID NO: 156, SEQ ID NO: 157, SEQ ID NO: 158, SEQ ID NO: 159, and SEQ ID NO: 160. In another embodiment, the heparosan-based polysaccharide for reacting with the engineered 3OST enzyme can be commercially obtained. In another embodiment, the heparosan-based polysaccharide for the engineered 3OST enzyme can be the sulfated N,2O,6O-HS polysaccharide product of an engineered or natural 6OST enzyme. In another embodiment, the sulfated polysaccharide product is an N,2O,3O,6O-HS polysaccharide comprising the structure of Formula I. In another embodiment, the N,2O,3O,6O-HS is obtained as a polydisperse composition having one or more molecular weight properties and/or anticoagulant activities as UFH.

As described above, UFH, LMWH, and other heparin compositions that have anticoagulant activity are comprised of N,2O,3O,6O-HS polysaccharides that include the structure of Formula I. (see Desai, U. R., et al., (1998) *J. Biol. Chem.* 273 (13):7478-7487). The medical use of UFH, LMWH, and other heparins has been well documented for decades. The anticoagulant activity of heparins can include, but are not limited to, inactivation of Factor IIa (thrombin) and/or Factor Xa, two proteins that are vital in the blood-clotting cascade. In particular, when a N,2O,3O,6O-HS polysaccharide binds to antithrombin (AT), it causes a conformational change in the enzyme that enables the formation of a ternary complex between the polysaccharide, AT, and either thrombin or Factor Xa (see Li, W., et al., (2004) *Nat. Struct. Mol. Biol.* 11 (9):857-862, the disclosure of which is incorporated by reference in its entirety). In order to bind with AT and induce its conformational change, an N,2O,3O,6O-HS polysaccharide comprises a specific five-residue AT-recognition sequence, which is equivalent to the structure of Formula I.

While anticoagulation can be induced by binding antithrombin with an oligosaccharide consisting only of the AT-recognition sequence, there is typically enhanced anticoagulant activity when the composition comprises N,2O, 3O,6O-HS polysaccharides having more than five sugar residues (see Grey, E., et al., (2008) *Thromb. Haemost.* 99:807-818, the disclosure of which is incorporated by reference in its entirety). As reported by Grey, et al, a secondary binding interaction can be formed between the polysaccharide and thrombin when the N,2O,3O,6O-HS polysaccharide comprises at least thirteen sugar residues on either side of the AT-recognition sequence to act as a "bridge" that allows the polysaccharide to bind to thrombin while also bound to AT. As a result, N,2O,3O,6O-HS polysaccharides typically require a minimum of eighteen sugar residues in order to potentially form the ternary complex between the N,2O,3O,6O-HS polysaccharide, AT, and thrombin. However, and without being limited by a particular theory, it is believed that because the distribution of the AT-recognition sequence within a particular polysaccharide molecule is random, some N,2O,3O,6O-HS polysaccharides between eighteen and thirty-one sugar residues can theoretically comprise an AT-recognition sequence toward the center of the molecule that does not have thirteen adjacent sugar residues on either side. Consequently, the N,2O,3O, 6O-HS polysaccharide must be at least thirty-two sugar residues long to guarantee that the thirteen residue "bridge" adjacent to the AT-recognition sequence can be formed, no matter where the AT-recognition sequence is within the molecule. As a result, in some embodiments, the N,2O,3O, 6O-HS polysaccharide product of the engineered 3OST enzyme can be at least five sugar residues, preferably at least eighteen sugar residues, and more preferably at least thirty-two sugar residues.

In another embodiment, anticoagulant N,2O,3O,6O-HS products of the engineered 3OST enzyme can satisfy benchmark requirements determined by the USP for pharmaceutical UFH compositions with regard to product purity, particularly purity from other sulfated polysaccharides, including but not limited to chondroitin sulfate. In particular, over-sulfated chondroitin sulfate (OSCS) was determined to be the source of contamination within pharmaceutical UFH compositions that caused hundreds of deaths worldwide in 2007 and 2008. In another embodiment, and without being limited by a particular theory, anticoagulant N,2O,3O,6O-HS products prepared using an engineered 3OST enzyme can be formed from to be substantially free from chondroitin sulfate, particularly OSCS, because the heparosan-based polysaccharides using as starting material can be provided and/or prepared in vitro without the same polysaccharide contaminants that are inherently present in anticoagulant N,2O,3O,6O-HS polysaccharides isolated from animal sources.

The USP has defined a reference standard (Chemical Abstracts Service (CAS) No: 9041-08-1) for UFH by which all pharmaceutical compositions are measured. The molecular weight properties of USP-compliant UFH must satisfy all of the following benchmarks: (1) the proportion of polysaccharides within the composition having a molecular weight over 24,000 Da is not more than 20%; (2) the $M_w$ of the composition itself is between 15,000 Da and 19,000 Da; and (3) the ratio of the number of polysaccharides within the composition having a molecular weight between 8,000 Da and 16,000 Da relative to the number of polysaccharides within the composition having a molecular weight between 16,000 Da and 24,000 Da is not less than 1.0:1 (see Mulloy, B., et al., (2014) *Anal. Bioanal. Chem.* 406:4815-4823, the disclosure of which is incorporated by reference in its entirety). Further, the anticoagulant activity of USP-compliant UFH must satisfy all of the following benchmarks: an anti-IIa activity of not less than 180 International Units per milligram (IU mg$^{-1}$); an anti-Xa activity of not less than 180 IU mg$^{-1}$; and a ratio of anti-Xa to anti-IIa activity in a range of 0.9:1 up to 1.1:1. In another embodiment, anticoagulant N,2O,3O,6O-HS products prepared by an engineered 3OST enzyme can satisfy any or more of the above anticoagulant activity and molecular weight requirements determined by the United States Pharmacopeia (USP) for pharmaceutical UFH compositions.

With respect to the molecular weight properties of the N,2O,3O,6O-HS product of engineered 3OST in particular, these can be controlled in part based on the control of the molecular weight properties of the heparosan-based polysaccharide utilized as the sulfo group acceptor. The most controllable opportunity to control the molecular weight of a heparosan-based polysaccharide is by N-deacetylating and depolymerizing heparosan, as described above. Thus, in another embodiment, a series of sulfotransferase reactions can be performed in order to control the molecular weight of the anticoagulant N,2O,3O,6O-HS product. In another embodiment, a series of sulfotransferase reactions can be performed according to the following steps: (a) forming an N-sulfated heparosan product from N-deacetylated heparosan using a NST; (b) forming an N,2O-HS polysaccharide product using a 2OST and the N-sulfated heparosan product of step (a); (c) forming an N,2O,6O-HS polysaccharide product using a 6OST and the N,2O-HS polysaccharide product of step (b); and (d) forming an anticoagulant N,2O,3O,6O-HS polysaccharide product using a 3OST and the N,2O,6O-HS polysaccharide product of step (c). In another embodiment, all of the sulfotransferases are engineered sulfotransferases, and the sulfo donor in each reaction is an aryl sulfate compound, preferably PNS or NCS. In another embodiment, the N-deacetylated heparosan has an $M_w$ in a range between 9,000 Da and 12,500 Da, as well as an N-acetyl glucosamine content in a range from 12% and up to 18%, as described in Wang, et al., (2011), above. Alternatively, and in another embodiment, the N-sulfated heparosan product utilized as the sulfo group acceptor for the 2OST can be chemically sulfated from N-deacetylated heparosan, as described above.

Thus, in another embodiment, an N,2O,3O,6O-HS product prepared by an engineered 3OST enzyme can have an $M_w$ of at least 1,000 Da, including at least 2,000 Da, 3,000 Da, 4,000 Da, 5,000 Da, 6,000 Da, 7,000 Da, 8,000 Da, 9,000 Da, 10,000 Da, 11,000 Da, 12,000 Da, 13,000 Da, 14,000 Da, 15,000 Da, 16,000 Da, 17,000 Da, 18,000 Da, 19,000 Da, 20,000 Da, 21,000 Da, 22,000 Da, 23,000 Da, or 24,000 Da, up to at least 50,000 Da. In another embodiment, an N,2O,3O,6O-HS product prepared by an engineered 3OST enzyme can have an $M_w$ of less than 50,000 Da, including less than 24,000 Da, 23,000 Da, 22,000 Da, 21,000 Da, 20,000 Da, 19,000 Da, 18,000 Da, 17,000 Da, 16,000 Da, 15,000 Da, 14,000 Da, 13,000 Da, 12,000 Da, 11,000 Da, 10,000 Da, 9,000 Da, 8,000 Da, 7,000 Da, 6,000 Da, 5,000 Da, 4,000 Da, or 3,000 Da, down to less than 2,000 Da. In another embodiment, an N,2O,3O,6O-HS product prepared by an engineered 3OST enzyme can have an $M_w$ in any range listed above between and inclusive of 1,000 Da and 50,000 Da, and preferably in any range listed above between and inclusive of 15,000 Da and about 19,000 Da.

Similarly, in another embodiment, an N,2O,3O,6O-HS product prepared by an engineered 3OST enzyme can have a size distribution such that less than 50%, including less than 45%, 40%, 35%, 30%, 25%, 20%, 15%, 10%, 5%, 3%, or 2%, down to less than 1% of the N,2O,3O,6O-HS polysaccharides within the N,2O,3O,6O-HS product have a molecular weight greater than 24,000 Da. In another embodiment, less than or equal to 20% of the N,2O,3O,6O-HS polysaccharides within the N,2O,3O,6O-HS product have a molecular weight greater than 24,000 Da. In another embodiment, when less than or equal to 20% of the N,2O,3O,6O-HS polysaccharides within the N,2O,3O,6O-HS product have a molecular weight greater than 24,000 Da, the N,2O,3O,6O-HS product can have an $M_w$ in any range listed above between and inclusive of 1,000 Da and 24,000 Da, and preferably in any range listed above between and inclusive of 15,000 Da and about 19,000 Da.

In another embodiment, an N,2O,3O,6O-HS product prepared by an engineered 3OST enzyme can have a size distribution such that the ratio of the number of polysaccharides within the composition having a molecular weight between 8,000 Da and 16,000 Da relative to the number of polysaccharides within the composition having a molecular weight between 16,000 Da and 24,000 Da is not less than 0.5:1, including not less than 0.75:1, 0.9:1, 1.0:1, 1.1:1, 1.3:1, or 1.5:1, up to not less than 2.0:1, and preferably not less than 1.0:1. In another embodiment, N,2O,3O,6O-HS products in which the ratio of the number of polysaccharides within the composition having a molecular weight between 8,000 Da and 16,000 Da relative to the number of polysaccharides within the composition having a molecular weight between 16,000 Da and 24,000 Da is not less than 1.0:1 can also have an $M_w$ in any range listed above between and inclusive of 1,000 Da and 24,000 Da, and preferably in any range listed above between and inclusive of 15,000 Da and about 19,000 Da, in which less than or equal to 20% of the N,2O,3O,6O-HS polysaccharides within the N,2O,3O,6O-HS product have a molecular weight greater than 24,000 Da.

In another embodiment, an anticoagulant N,2O,3O,6O-HS product prepared by an engineered 3OST enzyme can have an anti-Xa activity of at least about 1 IU mg$^{-1}$, including at least about 50 IU mg$^{-1}$, at least 75 IU mg$^{-1}$, 100 IU mg$^{-1}$, 150 IU mg$^{-1}$, 200 IU mg$^{-1}$, or 500 IU mg$^{-1}$, up to at least about 1,000 IU mg$^{-1}$. In another embodiment, an anticoagulant N,2O,3O,6O-HS product prepared by an engineered 3OST enzyme can have an anti-IIa activity of at least about 1 IU mg$^{-1}$, including at least about 50 IU mg$^{-1}$, at least 75 IU mg$^{-1}$, 100 IU mg$^{-1}$, 150 IU mg$^{-1}$, 200 IU mg$^{-1}$, or 500 IU mg$^{-1}$, up to at least about 1,000 IU mg$^{-1}$. In another embodiment, an anticoagulant N,2O,3O,6O-HS product prepared by an engineered 3OST enzyme can have a ratio of anti-Xa activity to anti-of at least 0.5:1, including at least 0.75:1, 0.9:1, 1:1, 1.1:1, 1.3:1, 1.5:1, 2.0:1, 3.0:1, 4.0:1, 5.0:1, 6.0:1, 7.0:1, 8.0:1, 9.0:1, 10.0:1, 20:1, 40:1, 60:1, or 80:1, up to at least 100:1. However, anticoagulant N,2O,3O,6O-HS polysaccharides that are thirty-two sugar residues or longer and are able to form the tertiary complex with AT and thrombin typically have a ratio of anti-Xa activity to anti-IIa activity that is usually close to 1:1, approximately between 0.9:1 to 1.1:1 (see Keire, D. A., et al., (2011) *Anal. Bioanal. Chem.* 399:581-591, the disclosure of which is incorporated by reference in its entirety).

Preparation of Engineered Aryl Sulfate-Dependent Enzymes

In general, the engineered enzymes encoded by the disclosed nucleic acid and amino acid sequences can be expressed and purified using any microbiological technique known in the art, including as described below. The aryl sulfate-dependent activity of each purified enzyme can be determined spectrophotometrically or fluorescently and/or using mass spectrometry (MS) or nuclear magnetic resonance (NMR) spectroscopy to characterize the starting materials and/or sulfated polysaccharide products. Such methods are described below in the Examples section.

The engineered gene products, proteins and polypeptides of the present invention can also include analogs that contain insertions, deletions, or mutations relative to the disclosed DNA or peptide sequences, and that also encode for enzymes that catalyze reactions in which aryl sulfate compounds are substrates. In another embodiment, each analog similarly catalyzes sulfotransfer reactions in which aryl sulfate compounds are utilized as sulfo donors. Analogs can be derived from nucleotide or amino acid sequences as disclosed herein, or they can be designed synthetically in silico or de novo using computer modeling techniques. Those skilled in the art will appreciate that other analogs, as yet undisclosed or undiscovered, can be used to design and/or construct different sulfate-dependent enzymes of the present invention. There is no need for a gene product, protein, or polypeptide to comprise all or substantially all of a nucleic acid or amino acid sequence of an engineered enzyme as disclosed herein. Such sequences are herein referred to as "segments." Further, the gene products, proteins, and polypeptides discussed and disclosed herein can also include fusion or recombinant engineered enzymes comprising full-length sequences or biologically functional segments of sequences disclosed in the present invention. Methods of preparing such proteins are known in the art.

In addition to the nucleic acid and amino acid sequences disclosed herein, any of the methods of the present invention can be practiced by engineered enzymes comprising amino acid sequences that are substantially identical to a disclosed amino acid sequence (SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160), or expressed from nucleic acids comprising a nucleotide sequence that is substantially identical to a disclosed nucleotide sequence (SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152). Those skilled in the art can determine appropriate nucleotide sequences that encode for polypeptides having the amino acid sequence of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 66, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160 based on the nucleotide sequences SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152.

"Substantially identical" sequences, as used in the art, refer to sequences which differ from a particular reference sequence by one or more deletions, substitutions, or additions, the net effect of which is to retain at least some of the biological activity of the engineered polypeptide encoded by the reference sequence. Namely, the biological activity of the engineered sulfotransferase enzymes comprises the transfer of a sulfo group from an aryl sulfate compound to a polysaccharide acting as a sulfo group acceptor. In another embodiment, the polysaccharide is a heparosan-based and/or HS polysaccharide. Accordingly, as used to describe the engineered enzymes of the present invention, "substantial identity" can refer either to identity with a particular gene product, polypeptide or amino acid sequence of an engineered enzyme, or a gene or nucleic acid sequence encoding for an engineered enzyme. Such sequences can include mutations of the disclosed sequences or a sequence in which the biological activity is altered, enhanced, or diminished to some degree but retains at least some of the original biological activity of a disclosed reference amino acid sequence or polypeptide encoded by a disclosed reference nucleic acid sequence.

Alternatively, DNA analog sequences are substantially identical to the specific DNA sequences disclosed herein if: (a) the DNA analog sequence is derived from coding regions of the any of the disclosed nucleic acid sequences; or (b) the DNA analog sequence is capable of hybridization of DNA sequences of (a) under stringent conditions and which encode for a biologically-active gene product; or (c) the DNA sequences are degenerate as a result of alternative genetic code to the DNA analog sequences defined in (a) and/or (b). Substantially identical analog proteins will be greater than about 60% identical to the corresponding sequence of the native protein. Sequences having lesser degrees of identity but comparable biological activity, namely, transferring a sulfo group from an aryl sulfate compound to polysaccharides, particularly heparosan-based or HS polysaccharides, are also considered to be substantially identical. In determining the substantial identity of nucleic acid sequences, all subject nucleic acid sequences capable of encoding substantially identical amino acid sequences are considered to be substantially identical to a reference nucleic acid sequence, regardless of differences in codon sequences or amino acid substitutions to create biologically functional equivalents.

At a biological level, identity is just that, i.e. the same amino acid at the same relative position in a given family member of a gene family. Homology and similarity are generally viewed as broader terms. For example, biochemically similar amino acids, for example leucine and isoleucine or glutamic acid/aspartic acid, can be alternatively present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine.

In some embodiments, the genes and gene products include within their respective sequences a sequence "essentially as that" of a gene encoding for an engineered enzyme or its corresponding protein. A sequence essentially as that of a gene encoding for an engineered enzyme refers to sequences that are substantially identical or substantially similar to a portion of a disclosed nucleic acid sequence and contains a minority of bases or amino acids (whether DNA or protein) that are not identical to those of a disclosed protein or a gene, or which are not a biologically functional equivalent. Biological functional equivalence is well understood in the art and is further discussed in detail below. Nucleotide sequences are "essentially the same" where they have between about 75% and about 85%, or particularly, between about 86% and about 90%, or more particularly greater than 90%, or even more particularly between about 91% and about 95%, or still more particularly, between about 96% and about 99%, of nucleic acid residues which are identical to the nucleotide sequence of a disclosed gene. Similarly, peptide sequences which have about 80%, or 90%, or particularly from 90-95%, or more particularly greater than 96%, or even more particularly 95-98%, or still more particularly 99% or greater amino acids which are identical or functionally equivalent or biologically functionally equivalent to the amino acids of a disclosed polypeptide sequence will be sequences which are "essentially the same."

Additionally, alternate nucleic acid sequences that include functionally equivalent codons are also encompassed by this invention. Functionally equivalent codons refer to codons that encode the same amino acid, such as the ACG and AGU codons for serine. Thus, substitution of functionally equivalent codons of Table 1, below, into the sequence examples of any of the nucleotide sequences disclosed above ultimately encode for biologically functional equivalent enzymes that are dependent on binding and reacting with aryl sulfate compounds in order to catalyze sulfo transfer. Thus, the present invention includes amino acid and nucleic acid sequences comprising such substitutions but which are not set forth herein in their entirety for convenience.

Those skilled in the art would recognize that amino acid and nucleic acid sequences can include additional residues, such as additional N- or C-terminal amino acids or 5' or 3' nucleic acid sequences, and yet still be essentially as set forth in one of the sequences disclosed herein, so long as the sequence retains its biological activity with respect to binding and reacting with aryl sulfate compounds as sulfo donors. The addition of terminal sequences particularly applies to nucleic acid sequences which can, for example, include various non-coding sequences flanking either of the 5' or 3' portions of the coding region or can include various internal sequences, or introns, which are known to occur within genes.

TABLE 1

Functionally Equivalent Codons

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glutamic Acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |

TABLE 1-continued

Functionally Equivalent Codons

| Amino Acids | | | Codons |
|---|---|---|---|
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

As discussed above, modifications and changes can be made in the sequence of any of the disclosed engineered enzymes, including conservative and non-conserved mutations, deletions, and additions while still constituting a molecule having like or otherwise desirable characteristics. For example, certain amino acids can be substituted for other amino acids in a protein structure without appreciable loss of interactive capacity with particular structures or compounds, particularly aryl sulfate compounds and/or sulfo acceptor polysaccharides. This can occur because the ability of a protein to recognize, bind, and react with other structures or compounds within its environment defines that protein's biological functional activity, not the sequence itself. Consequently, certain amino acid sequence substitutions can be made in that protein's sequence to obtain a protein with the equal, enhanced, or diminished properties. One non-limiting example of such amino acid substitutions that can occur without an appreciable loss of interactive activity include substitutions in external domains or surfaces of the protein that do not affect the folding and solubility of the protein. Similarly, amino acids can potentially be added to either terminus of the protein so long as the ability of the protein to fold or to recognize and bind its substrates is not deleteriously affected. One skilled in the art can appreciate that several other methods and/or strategies can be utilized to alter an enzyme's sequence without affecting its activity.

Consequently, mutations, deletions, additions, or other alterations to a parent enzyme's structure or sequence in which the modified enzyme retains the parent enzyme's biological activity can be defined to be biologically functionally equivalent to the parent enzyme. Thus, biologically functional equivalent enzymes, with respect to the engineered aryl sulfate-dependent enzymes, can include any substitution or modification of an amino acid sequence disclosed in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160, in which the resultant modified enzyme is dependent on interacting with aryl sulfate compounds, particularly PNS or NCS, to catalyze sulfo transfer to polysaccharides, particularly heparosan-based and/or HS polysaccharides. In particular, such substitutions or modifications can result from conservative mutations in the amino acid sequence in any portion of the protein, as described below, although non-conservative mutations in non-catalytically active regions of the enzyme are also contemplated. Consequently, the engineered enzymes can be expressed from any nucleic acid having a nucleotide sequence that encodes for a biologically functional equivalent enzyme, although such nucleotide sequences are not set forth herein in their entirety for convenience.

Alternatively, recombinant DNA technology can be used to create biologically functionally equivalent proteins or peptides in which changes in the protein structure can be engineered, based on considerations of the properties of the amino acids being exchanged. Rationally-designed changes can be introduced through the application of site-directed mutagenesis techniques, for example, to test whether certain mutations affect positively or negatively affect the enzyme's aryl sulfate-dependent catalytic activity and/or binding of sulfo donors or acceptors within the enzyme's active site.

Amino acid substitutions, such as those which might be employed in modifying any of the engineered enzymes described herein, are generally based on the relative similarity of the amino acid side-chain substituents, for example, their hydrophobicity, hydrophilicity, charge, size, and the like. Those skilled in the art are familiar with the similarities between certain amino acids, such as the size, shape and type of the amino acid side-chain substituents. Non-limiting examples include relationships such as that arginine, lysine and histidine are all positively charged residues; that alanine, glycine and serine are all of similar size; and that phenylalanine, tryptophan and tyrosine all have a generally similar shape. Consequently, the amino acids that comprise the following groups-arginine, lysine and histidine; alanine, glycine and serine; and phenylalanine, tryptophan and tyrosine—are defined herein as biologically functional equivalents to the other amino acids in the same group. Other biologically functionally equivalent changes will be appreciated by those of skill in the art.

One such method to evaluate biologically functional equivalents is to evaluate and consider the hydropathic index of each of the amino acids. Each of the twenty common amino acids has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6);

histidine (−3.2); glutamic acid (−3.5); glutamine (−3.5); aspartic acid (−3.5); asparagine (−3.5); lysine (−3.9); and arginine (−4.5).

The relationship between an amino acid residue's hydropathic index and the biological function of a protein is generally understood in the art. (Kyte, J., et al., (1982) *J. Mol. Biol.* 157 (1):105-132.) It is known that certain amino acids can be substituted for other amino acids having a similar hydropathic index or score and still retain a similar biological activity. In making changes based upon the hydropathic index, the substitution of amino acids whose hydropathic indices are within ±2 of the original value is the preferred measure to determine whether the substitution is biologically functionally equivalent, though those substitutions which are within ±1 of the original value are particularly preferred, and those within ±0.5 of the original value are even more particularly preferred.

Similarly, it is also understood in the art that the substitution of like amino acids can be made effectively on the basis of hydrophilicity. U.S. Pat. No. 4,554,101, the disclosure of which is incorporated by reference in its entirety, states that the greatest local average hydrophilicity of a protein, as governed by the hydrophilicity of its adjacent amino acids, correlates with its immunogenic, antigenic, and other biological properties of the protein. It is understood that an amino acid can be substituted for another having a similar hydrophilicity value and still obtain a biologically equivalent protein. As reported in U.S. Pat. No. 4,554,101, the following hydrophilicity values have been assigned to amino acid residues: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

As when making mutations based on the hydropathic index of an amino acid, similar changes can be made with regard to hydrophilicity. Thus, the substitution of amino acids whose hydrophilicity values are within 2 of the original value is the preferred measure to determine whether the substitution is biologically functionally equivalent, though those substitutions which are within +1 of the original value are particularly preferred, and those within +0.5 of the original value are even more particularly preferred.

In another embodiment, isolated nucleic acids, or functional fragments thereof, that encode for the engineered enzymes of the present invention are provided. In some embodiments, the engineered enzymes comprise an amino acid sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, and SEQ ID NO: 160. In other embodiments, the present invention provides isolated nucleic acids encoding functional fragments of the engineered enzymes of the present invention, or mutants thereof in which conservative substitutions have been made for particular residues in the amino acid sequences of any of the engineered enzymes listed above.

Additionally, isolated nucleic acids used to express any of the engineered enzymes of the present invention may be joined to other nucleic acid sequences for use in various applications. Thus, for example, the isolated nucleic acids may be ligated into cloning or expression vectors, as are commonly known in the art and as described in the examples below. Additionally, nucleic acids may be joined in-frame to sequences encoding another polypeptide so as to form a fusion protein, as is commonly known in the art. Fusion proteins can comprise a coding region for the engineered enzyme that is aligned within the same expression unit with other proteins or peptides having desired functions, such as for solubility, purification, or immunodetection. Thus, in another embodiment, cloning, expression and fusion vectors comprising any of the above-described nucleic acids, that encode for an engineered enzyme of the present invention are also provided.

Furthermore, nucleic acid segments of the present invention, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. Those skilled in the art would recognize that a nucleic acid fragment of almost any length can be employed, with the total length typically being limited by the ease of preparation and use in the intended recombinant DNA protocol.

In particular, recombinant vectors in which the coding portion of the gene or DNA segment is positioned under the control of a promoter are especially useful. In some embodiments, the coding DNA segment can be associated with promoters isolated from bacterial, viral, eukaryotic, or mammalian cells. Promoters specific to the cell type chosen for expression are often the most effective. The use of promoter and cell type combinations for protein expression is generally known to those of skill in the art of molecular biology (See, e.g., Sambrook et al. (2012) Molecular Cloning: A Laboratory Manual, Fourth Edition, Cold Spring Harbor Laboratory Press, Cold Spring Harbor, N.Y., incorporated by reference in its entirety). The promoters employed can be constitutive or inducible and can be used under the appropriate conditions to direct high-level expression of the introduced DNA segment, such as is advantageous in the large-scale production of recombinant proteins or peptides. Appropriate promoter systems that are often effective for high-level expression include, but are not limited to, the vaccinia virus promoter, the baculovirus promoter, and the Ptac promoter.

Thus, in some embodiments, an expression vector can be utilized that comprises a nucleotide sequence encoding for a biologically-active, engineered enzyme suitable the present invention. In one example, an expression vector can comprise any nucleotide sequence that encodes for an aryl sulfate-dependent gene product. In further embodiments, an expression vector comprises a nucleic acid comprising the nucleotide sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152. In other further embodiments, the expression vector comprises a nucleic acid comprising any nucleotide sequence that encodes for a polypeptide comprising the amino acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. In even further embodiments, any nucleic acid sequence encoding for an engineered enzyme of the present invention can be codon-optimized based on the expression host used to produce the enzyme. The preparation of recombinant vectors and codon optimization are well known to those of skill in the art and described in many references, such as, for example, Sambrook et al. (2012) Molecular Cloning: A Laboratory Manual, Fourth Edition, Cold Spring Harbor Laboratory Press, Cold Spring Harbor, N.Y.

Those skilled in the art would recognize that the DNA coding sequences to be expressed, in this case those encoding the engineered gene products, are positioned in a vector adjacent to and under the control of a promoter. As is known in the art, a promoter is a region of a DNA molecule typically within about 100 nucleotide pairs upstream of (i.e., 5' to) the point at which transcription begins (i.e., a transcription start site). That region typically contains several types of DNA sequence elements that are located in similar relative positions in different genes. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter.

One can also desire to incorporate into the transcriptional unit of the vector an appropriate polyadenylation site (e.g., 5'-AATAAA-3'), if one was not contained within the original inserted DNA. Typically, poly-A addition sites are placed about 30 to 2000 nucleotides "downstream" of the coding sequence at a position prior to transcription termination.

Another type of discrete transcription regulatory sequence element is an enhancer. An enhancer imposes specificity of time, location and expression level on a particular coding region or gene. A major function of an enhancer is to increase the level of transcription of a coding sequence in a cell that contains one or more transcription factors that bind to that enhancer. An enhancer can function when located at variable distances from transcription start sites so long as a promoter is present.

Optionally, an expression vector of the invention comprises a polynucleotide operatively linked to an enhancer-promoter. As used herein, the phrase "enhancer-promoter" means a composite unit that contains both enhancer and promoter elements. For example, an expression vector can comprise a polynucleotide operatively linked to an enhancer-promoter that is a eukaryotic promoter and the expression vector further comprises a polyadenylation signal that is positioned 3' of the carboxy-terminal amino acid and within a transcriptional unit of the encoded polypeptide. As used herein, the phrase "operatively linked" means that an enhancer-promoter is connected to a coding sequence in such a way that the transcription of that coding sequence is controlled and regulated by that enhancer-promoter. Techniques for operatively linking an enhancer-promoter to a coding sequence are well known in the art; the precise orientation and location relative to a coding sequence of interest is dependent, inter alia, upon the specific nature of the enhancer-promoter.

An enhancer-promoter used in a vector construct of the present invention can be any enhancer-promoter that drives expression in a cell to be transfected. By employing an enhancer-promoter with well-known properties, the level and pattern of gene product expression can be optimized.

Engineered enzymes of the present invention can be expressed within cells or cell lines, either prokaryotic or eukaryotic, into which have been introduced the nucleic acids of the present invention so as to cause clonal propagation of those nucleic acids and/or expression of the proteins or peptides encoded thereby. Such cells or cell lines are useful for propagating and producing nucleic acids, including those disclosed in sequences SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152. Such cells or cell lines are also useful for producing the engineered enzymes themselves, including those described by sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. As used herein, the term "transformed cell" is intended to embrace any cell, or the descendant of any cell, into which has been introduced any of the nucleic acids of the invention, whether by transformation, transfection, transduction, infection, or other means. Methods of producing appropriate vectors, transforming cells with those vectors, and identifying transformants are well known in the art. (See, e.g., Sambrook et al. (2012) Molecular Cloning: A Laboratory Manual, Fourth Edition, Cold Spring Harbor Laboratory Press, Cold Spring Harbor, N.Y.)

Prokaryotic cells useful for producing transformed cells include members of the bacterial genera *Escherichia* (e.g., *E. coli*), *Pseudomonas* (e.g., *P. aeruginosa*), and *Bacillus* (e.g., *B. subtilus, B. stearothermophilus*), as well as many others well known and frequently used in the art. Prokaryotic cells are particularly useful for the production of large quantities of the proteins or peptides (e.g., engineered enzymes comprising the amino acid sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160, fragments of those sequences thereof, or fusion proteins including those sequences). Bacterial cells (e.g., *E. coli*) may be used with a variety of expression vector systems including, for example, plasmids with the T7 RNA polymerase/promoter system, bacteriophage λ regulatory sequences, or M13 Phage regulatory elements. Bacterial hosts may also be transformed with fusion protein vectors that create, for example, Protein A, lacZ, trpE, maltose-binding protein (MBP), small ubiquitin-related modifier (SUMO), poly-His tag, or glutathione-S-transferase (GST) fusion proteins. All of these, as well as many other prokaryotic expression systems, are well known in the art and widely available commercially (e.g., pGEX-27 (Amrad, USA) for GST fusions).

In some embodiments of the invention, expression vectors comprising nucleic acid sequences as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152 can also comprise genes or nucleic acid sequences encoding for fusion proteins with any engineered enzyme. In further embodiments, expression vectors can additionally include the malE gene, which encodes for the maltose binding protein. Upon inducing protein expression from such expression vectors, the expressed gene product comprises a fusion protein that includes maltose binding protein and an engineered enzyme comprising the amino acid sequence set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. In other further embodiments, an expression vector that includes any of the above nucleic acids that encode for any of the above engineered enzymes can additionally include a gene encoding for a SUMO modifier, such as, in a non-limiting example, SUMO-1.

In other embodiments, expression vectors according to the present invention can additionally include a nucleic acid sequence encoding for a poly-His tag. Upon inducing protein expression from such expression vectors, the expressed gene product comprises a fusion protein that includes the poly-His tag and an engineered enzyme comprising the amino acid sequence set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. In a further embodiment, expression vectors can include both a nucleic acid sequence encoding for a poly-His tag and the malE gene or a SUMO gene, from which a fusion protein can be expressed that includes a poly-His tag, MBP, or SUMO, along with any engineered enzyme.

Eukaryotic cells and cell lines useful for producing transformed cells include mammalian cells (e.g., endothelial cells, mast cells, COS cells, CHO cells, fibroblasts, hybridomas, oocytes, embryonic stem cells), insect cells lines (e.g., Drosophila Schneider cells), yeast, and fungi. Non-limiting examples of such cells include, but are not limited to, COS-7 cells, CHO, cells, murine primary cardiac microvascular endothelial cells (CME), murine mast cell line C57.1, human primary endothelial cells of umbilical vein (HU-VEC), F9 embryonal carcinoma cells, rat fat pad endothelial cells (RFPEC), and L cells (e.g., murine LTA tk- cells).

Vectors may be introduced into the recipient or "host" cells by various methods well known in the art including, but not limited to, calcium phosphate transfection, strontium phosphate transfection, DEAE dextran transfection, electroporation, lipofection, microinjection, ballistic insertion on micro-beads, protoplast fusion or, for viral or phage vectors, by infection with the recombinant virus or phage.

In some embodiments, the present invention provides substantially pure preparations of engineered enzymes dependent on reacting with aryl sulfate compounds for biological activity. In further embodiments, purified engineered enzymes can comprise the amino acid sequence disclosed as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160.

In another embodiment, the present invention provides engineered enzyme variants in which conservative or non-conservative substitutions have been made for certain residues within the amino acid sequence disclosed as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160. Conservative or non-conservative substitutions can be made at any point in the amino acid sequence, including residues that surround the active site or are involved in catalysis, provided that the enzyme retains measurable catalytic activity; namely, the transfer of a sulfo group from an aryl sulfate compound to a polysaccharide, particularly a heparosan-based and/or HS polysaccharide. In other embodiments, the aryl sulfate compound is PNS. In still other embodiments, the aryl sulfate compound is NCS.

In another embodiment, the engineered sulfotransferase enzymes have at least 50%, including at least 60%, 70%, 80%, 85%, 90% or 95% up to at least 99% amino acid sequence identity to an amino acid sequence disclosed as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160, while retaining its catalytic activity of transfer of a sulfo group from an aryl sulfate compound to a polysaccharide, particularly a heparosan-based and/or HS polysaccharide. Such sequences may be routinely produced by those of ordinary skill in the art, and sulfotransferase activity may be tested by routine methods such as those disclosed herein.

Further, and in another embodiment, the amino acid sequence(s) of any of the engineered sulfotransferases utilized in accordance with any of the methods described herein can be characterized as a percent identity relative to a natural sulfotransferase that catalyzes the same reaction using PAPS as the sulfo donor, so long as the sulfotransferase has aryl sulfate-dependent activity. For example, and in another embodiment, an engineered aryl sulfate-dependent NST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of the N-sulfotransferase domain of any of the natural NDST enzymes within EC 2.8.2.8, including biological functional fragments thereof. In a further embodiment, the engineered NST can comprise at least 50%, including at least 55%, 60%, 65%, 70%, 75%, 80%, 85%, 90%, or 95%, up to at least 97% sequence identity with the amino acid sequence of the N-sulfotransferase domain of the human NDST1 enzyme (entry sp|P52848|NDST_1_HUMAN, in FIG. 6A, FIG. 6B, and FIG. 6C, above).

In another embodiment, an engineered aryl sulfate-dependent 2OST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of any of the natural 2OST enzymes within EC 2.8.2.-, including biological functional fragments thereof. In a further embodiment, the engineered 2OST can comprise at least 50%, including at least 55%, 60%, 65%, 70%, 75%, 80%, 85%, 90%, or 95%, up to at least 97% sequence identity with the amino acid sequence of the natural chicken 2OST enzyme (entry sp|Q76KB|HS2ST_CHICK, in FIG. 17A, FIG. 17B, FIG. 17C, and FIG. 17D, above).

In another embodiment, an engineered aryl sulfate-dependent 6OST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of any of the natural 6OST enzymes within EC 2.8.2.-, including biological functional fragments thereof. In a further embodiment, the engineered 6OST can comprise at least 50%, including at least 55%, 60%, 65%, 70%, 75%, 80%, 85%, 90%, or 95%, up to at least 97% sequence identity with the amino acid sequence of the mouse 6OST1 enzyme (UniProtKB Accession No. Q9QYK5). In a further embodiment, the engineered 6OST can comprise at least 50%, including at least 55%, 60%, 65%, 70%, 75%, 80%, 85%, 90%, or 95%, up to at least 97% sequence identity with residues 67-377 of the amino acid sequence of the mouse 6OST1 enzyme (entry Q9QYK5|H6ST1_MOUSE, in FIGS. 21A-21F, above).

In another embodiment, an engineered aryl sulfate-dependent 3OST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of any of the natural enzymes within EC 2.8.2.23, including biological functional fragments thereof. In a further embodiment, the engineered 3OST can comprise at least 50%, including at least 55%, 60%, 65%, 70%, 75%, 80%, 85%, 90%, or 95%, up to at least 97% sequence identity with residues 48-311 of the amino acid sequence of the natural human 3OST1 enzyme (entry O14792|HS3S1_HUMAN, in FIGS. 26A-26F, above).

Substantially pure engineered enzymes may be joined to other polypeptide sequences for use in various applications. Thus, for example, engineered enzymes may be joined to one or more additional polypeptides so as to form a fusion protein, as is commonly known in the art. The additional polypeptides may be joined to the N-terminus, C-terminus or both termini of the engineered enzyme. Such fusion proteins may be particularly useful if the additional polypeptide sequences are easily identified (e.g., by providing an antigenic determinant), are easily purified (e.g., by providing a ligand for affinity purification), or enhance the solubility of the engineered enzyme in solution.

In another embodiment, substantially pure proteins may comprise only a portion or fragment of the amino acid sequence of an engineered enzyme. In some instances, it may be preferable to employ a minimal fragment retaining aryl sulfate-dependent activity, particularly if the minimal fragment enhances the solubility or reactivity of the enzyme. Thus, in some embodiments, methods of the present invention can be practiced using substantially pure engineered sulfotransferases of any length, including full-length forms described by the amino acid sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 66, SEQ ID NO: 68, SEQ ID NO: 69, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 154, SEQ ID NO: 155, SEQ ID NO: 156, SEQ ID NO: 157, SEQ ID NO: 158, SEQ ID NO: 159, or SEQ ID NO: 160, including minimal functional fragments thereof. Additionally, these proteins may also comprise conservative or non-conservative substitution variants as described above.

The engineered enzymes may be substantially purified by any of a variety of methods selected on the basis of the properties revealed by their protein sequences. Typically, the engineered enzymes, fusion proteins, or fragments thereof, can be purified from cells transformed or transfected with expression vectors, as described above. Insect, yeast, eukaryotic, or prokaryotic expression systems can be used, and are well known in the art. In the event that the protein or fragment localizes within microsomes derived from the Golgi apparatus, endoplasmic reticulum, or other membrane-containing structures of such cells, the protein may be purified from the appropriate cell fraction. Alternatively, if the protein does not localize within these structures, or aggregates in inclusion bodies within the recombinant cells (e.g., prokaryotic cells), the protein may be purified from whole lysed cells or from solubilized inclusion bodies by standard means.

Purification can be achieved using standard protein purification procedures including, but not limited to, affinity chromatography, gel-filtration chromatography, ion-exchange chromatography, high-performance liquid chromatography (RP-HPLC, ion-exchange HPLC, size-exclusion HPLC), high-performance chromatofocusing chromatography, hydrophobic interaction chromatography, immunoprecipitation, or immunoaffinity purification. Gel electrophoresis (e.g., PAGE, SDS-PAGE) can also be used to isolate a protein or peptide based on its molecular weight, charge properties and hydrophobicity.

An engineered enzyme, or a fragment thereof, may also be conveniently purified by creating a fusion protein including the desired sequence fused to another peptide such as an antigenic determinant, a poly-histidine tag (e.g., QIAexpress vectors, QIAGEN Corp., Chatsworth, Calif.), or a larger protein (e.g., GST using the pGEX-27 vector (Amrad, USA), green fluorescent protein using the Green Lantern vector (GlBCO/BRL. Gaithersburg, Md.), maltose binding protein using the pMAL vector (New England Biolabs, Ipswich, Mass.), or a SUMO protein. The fusion protein may be expressed and recovered from prokaryotic or eukaryotic cells and purified by any standard method based upon the fusion vector sequence. For example, the fusion protein may be purified by immunoaffinity or immunoprecipitation with an antibody to the non-aryl sulfate-dependent enzyme portion of the fusion or, in the case of a poly-His tag, by affinity binding to a nickel column. The desired engineered enzyme protein or fragment can then be further purified from the fusion protein by enzymatic cleavage of the fusion protein. Methods for preparing and using such fusion constructs for the purification of proteins are well known in the art and numerous kits are now commercially available for this purpose.

Furthermore, in some embodiments, isolated nucleic acids encoding for any engineered enzyme may be used to transform host cells. The resulting proteins may then be substantially purified by well-known methods including, but not limited to, those described in the examples below. Alternatively, isolated nucleic acids may be utilized in cell-free in vitro translation systems. Such systems are also well known in the art.

While particular embodiments of the invention have been described, the invention can be further modified within the spirit and scope of this disclosure. Those skilled in the art will recognize, or be able to ascertain using no more than routine experimentation, numerous equivalents to the specific procedures, embodiments, claims, and examples described herein. As such, such equivalents are considered to be within the scope of the invention, and this application is therefore intended to cover any variations, uses or adaptations of the invention using its general principles. Further, the invention is intended to cover such departures from the present disclosure as come within known or customary practice in the art to which this invention pertains and which fall within the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The contents of all references, patents, and patent applications mentioned in this specification are hereby incorporated by reference, and shall not be construed as an admission that such reference is available as prior art to the present invention. All of the incorporated publications and patent applications in this specification are indicative of the level of ordinary skill in the art to which this invention pertains, and are incorporated to the same extent as if each individual publication or patent application was specifically indicated and individually indicated by reference.

The invention is further illustrated by the following working and prophetic examples, neither of which should be construed as limiting the invention. Additionally, to the extent that section headings are used, they should not be construed as necessarily limiting. Any use of the past tense to describe an example otherwise indicated as constructive or prophetic is not intended to reflect that the constructive or prophetic example has actually been carried out.

EXAMPLES

The following working and prophetic examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. Thus, while the present invention has been described above with particularity, the following examples provide further detail in connection with what are presently deemed to be the most practical and preferred embodiments of the invention.

Example 1: Cloning, Expression, and Purification of the Engineered Aryl Sulfate-Dependent Enzymes A study was conducted in accordance with embodiments of the present disclosure to determine whether genes according to the present invention could be transformed into host cells capable of overexpressing engineered aryl sulfate-dependent enzymes, particularly enzymes having sulfotransferase activity. After expression, each aryl sulfate-dependent enzyme was isolated and purified from the host cell.

Generally, DNA coding for genes of any sequence can be synthesized de novo by methods commonly known in the art, including but not limited to oligonucleotide synthesis and annealing. Alternatively, DNA can be synthesized commercially and purchased from any one of several laboratories that regularly synthesize genes of a given sequence, including but not limited to ThermoFisher Scientific, GenScript, DNA 2.0, or OriGene. Persons skilled in the art would appreciate that there are several companies that provide the same services, and that the list provided above is merely a small sample of them. Genes of interest can be synthesized independently and subsequently inserted into a bacterial or other expression vector using conventional molecular biology techniques, or the genes can be synthesized concurrently with the DNA comprising the expression vector itself. Similar to genes of interest, suitable expression vectors can also be synthesized or obtained commercially. Often, bacterial expression vectors include genes that confer selective antibiotic resistance to the host cell, as well as genes that permit the cell to overproduce the protein of interest in response to the addition of isopropyl β-D-1-thiogalactopyranoside (IPTG). Bacterial production of proteins of interest using IPTG to induce protein expression is widely known in the art.

As described above, expression vectors can also include genes that enable production of fusion proteins that include the desired protein that is co-expressed with an additional, known protein to aid in protein folding and solubility. Non-limiting examples of fusion proteins that are commonly produced and are well-known in the art include fusions with MBP, SUMO, or green fluorescent protein. In particular, MBP fusion proteins facilitate easier purification because MBP possesses high affinity for amylose-based resins used in some affinity chromatography columns, while SUMO fusion proteins can include a poly-histidine tag that enables affinity purification on columns with $Ni^{2+}$-based resins as a stationary phase. Often, fusion proteins between the protein of interest and MBP and/or SUMO can optionally include an amino acid linking sequence that connects the two proteins. Non-limiting examples of commercial expression vectors that can be purchased to produce MBP fusion proteins include the pMAL-c5E™ and pMAL-c5X™ vectors, which can be obtained from New England Biolabs. Similarly, and in another non-limiting example, commercial expression vectors can also be purchased to produce SUMO fusion proteins, such as the pE-SUMOpro AMP vector, available from LifeSensors, Inc. Once the fusion proteins are produced and purified, proteases can be utilized to cleave the fused protein and any associated linker sequences from the enzyme, if cleavage is necessary for activity.

Additionally, expression vectors can also include DNA coding for a poly-histidine tag that can be synthesized at either the N- or C-terminus of the protein of interest. As with MBP fusions, proteins that include a poly-histidine tag simplify the enzyme purification because the tag has a high affinity for $Ni^{2+}$ resins that are utilized in many purification columns. Additionally, poly-histidine tags can optionally be cleaved after purification if it is necessary for optimal activity of the enzyme. A non-limiting example of an expression vector encoding for a C-terminal poly-histidine tag is the pET21b vector, available from Novagen. Another non-limiting example of an expression vector encoding for a poly-histidine tag is the pE-SUMO vector, which encodes for a poly-histidine tag at the N-terminus of the SUMO protein.

In the present example, double-stranded DNA fragments comprising the nucleotide sequences of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO:

107, SEQ ID NO: 109, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152, encoding for engineered aryl sulfate-dependent enzymes comprising the amino acid sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151, respectively, were synthesized using Integrated DNA Technologies' (IDT) gBlocks® Gene Fragments synthesis service. Polymerase chain reactions (PCR) were initiated to generate copies of each double-stranded DNA fragment, using forward and reverse primers comprising appropriate restriction enzyme recognition sequences to facilitate insertion into an expression vector. Genes comprising the nucleotide sequences SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152, encoding for engineered enzymes comprising the amino acid sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151, respectively, contained NdeI and BamHI restriction enzyme recognition sequences, and were ligated into the pMAL-c5x expression vector using quick ligation kits provided by NEB. Expression vectors were then transformed into competent DH5-α E. coli cells. Single clones were incubated in LB medium with 100 μL/mL ampicillin. Nucleotide sequences of each gene and expression vector within the transformed host cells were confirmed by commercial DNA sequencing (GeneWiz).

Protein expression of engineered enzymes comprising the amino acid sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151 was achieved by transforming confirmed DNA constructs into competent SHuffle® T7 Express lysY E. coli cells, although protein expression has also been achieved by transforming confirmed DNA constructs into competent BL21 (DE3) E. coli cells. From either construct, resultant colonies were used to inoculate 250 mL cultures in LB medium, which were allowed to shake and incubate at 32° C. until an optical density at 600 nM (OD 600) of approximately 0.4 to 0.6 was observed. Expression was induced by the addition of 100 μM IPTG to each culture at 18° C.

Upon incubation at 18° C. overnight, expressed cells were harvested by centrifuging at 3,620 g and resuspending the pellet in 10 mL of resuspension buffer (25 mM Tris-HCl, pH 7.5; 0.15 M NaCl; 0.2 mg/mL lysozyme; 10 μg/ml DNase I; 5 mM $MgCl_2$; and 0.1% (w/v) Triton-X 100). Resuspended cells were lysed upon sonication on ice for three pulses of 10 seconds each, and subsequently passed through a 0.45-μm syringe filter. The resulting supernatant was loaded into a 5-mL spin column (G-biosciences) comprising Dextrin Sepharose® resin (GE Biosciences) suspended in a binding buffer comprising 25 mM Tris-HCl, pH 7.5 and 0.15 M NaCl. Enzymes of interest were eluted from the column upon adding an elution buffer comprising 25 mM Tris-HCl, pH 7.5; 0.15 M NaCl; and 40 mM maltose.

On the other hand, genes comprising the nucleotide sequences SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, or SEQ ID NO: 109, encoding for engineered enzymes comprising the amino acid sequences SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, or SEQ ID NO: 108, respectively, contained BsaI and XbaI restriction enzyme recognition sequences, and were ligated into the pE-SUMO vector (LifeSensors, Inc.). Expression vectors were then transformed into competent BL21-DE3 E. coli cells. Single clones were incubated in Terrific Broth with 100 μL/mL ampicillin. Nucleotide sequences of each gene and expression vector within the transformed host cells were confirmed by commercial DNA sequencing (GeneWiz).

Protein expression of engineered enzymes comprising the amino sequences SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, or SEQ ID NO: 108 was achieved by inoculating 500 mL cultures in Terrific Broth with ampicillin and allowing the cultures to incubate with shaking at 35° C. until an OD 600 of approximately 0.6-0.8 was reached. Protein expression was induced by the addition of 0.2 mM IPTG at 18° C. Cultures were then allowed to incubate at 18° C. overnight, and were subsequently lysed and filtered using an identical procedure as described above. The engineered enzymes were subsequently purified in a 5-mL spin column (G-biosciences) comprising HisPur Ni-NTA resin (Thermofisher) suspended in a binding buffer comprising 25 mM Tris-HCl, pH 7.5, 0.15 M NaCl, 5 mM $MgCl_2$, and 30 mM imidazole. Enzymes of interest were eluted from the column upon adding an elution buffer comprising 25 mM Tris-HCl, pH 7.5, 0.15 M NaCl, 5 mM $MgCl_2$, and 300 mM imidazole.

Example 2: Confirmation of Aryl Sulfate-Dependent Sulfatase Activity

Generally, the sulfatase activity of the aryl sulfate-dependent enzymes can be readily determined because the desulfurylated aromatic products of many aryl sulfate compounds, including but not limited to, PNS, MUS, 7-hydroxycoumarin sulfate, phenyl sulfate, 4-acetylphenyl sulfate, indoxyl sulfate, 1 naphthyl sulfate, 2NapS, and NCS each have the ability to absorb light or fluoresce in the near ultraviolet or visible spectrum. The absorbance or fluorescence by the desulfurylated aromatic product can be detected using a spectrophotometer or a fluorimeter, respectively. Those skilled in the art would readily be able to determine which instrument to use to monitor the progress of a reaction based on the spectral properties of the particular aryl sulfate compound and its desulfurylated aromatic product(s).

In one non-limiting example, reactions in which PNS is utilized as a substrate produce p-nitrophenol as a product upon hydrolysis of the sulfate ester linkage. Reaction mixtures having a pH greater than the pKa of p-nitrophenol (about 7.15) turn yellow because the negatively-charged p-nitrophenolate ion is prevalent over the neutrally-charged p-nitrophenol. Typically, the maximum absorbance of visible light by a solution containing the p-nitrophenolate ion can be observed at a wavelength of about 405 nm. Consequently, an absorbance value under reaction conditions that is greater than a negative control containing only PNS in identical buffer conditions indicates that the enzyme is active. Similarly, as more p-nitrophenolate ion is produced as a result of catalysis by a particular aryl sulfate-dependent enzyme, the absorbance of the reaction mixture as a function of time can be measured at about 405 nm to determine reaction rate and other kinetic information. As another non-limiting example, the production of the desulfurylated product of NCS, 4-nitrocatechol, upon hydrolysis of the sulfate ester linkage can be measured in reactions having a pH greater than the pKa of 4-nitrocatechol (about 7.17), by observing the absorbance of visible light at a wavelength of about 515 nm.

As another limiting example, the desulfurylated products of 2NapS can fluoresce in solution in response to being excited by radiation at a lower wavelength. Depending on the pH of the solution, the desulfurylated product is either 2-naphthol or the 2-naphtholate ion (pKa=9.5). To ensure the presence of a single 2-naphthyl species in solution, compositions with completed reactions are typically quenched with either an acid or a base in order to drive equilibrium to either the complete formation of 2-naphthol, which has an emission maximum of around 355 nM, or the 2-naphtholate ion, which has an emission maximum of about 410 nm. In either instance, the desulfurylated product can be excited at a wavelength of around 320 nm.

Thus, a study was conducted in accordance with embodiments of the present disclosure to determine the sulfatase activity of purified enzymes comprising the amino acid sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151. Non-steady state sulfatase activity with PNS, NCS, and 2NapS was monitored in 100-µL reactions containing 50 µM enzyme and 5 mM of substrate in elution buffer. In reactions containing PNS, the absorbance of the reaction mixture as a result of the production of p-nitrophenolate was measured at 401 nm. In reactions containing NCS, the absorbance of the reaction mixture as a result of the production of 4-nitrocatechol was measured at 515 nm. Reaction mixtures containing 2NapS were quenched by adding 0.1M NaOH to convert all of the 2-naphthol produced as a result of the reaction to the 2-naphtholate ion. All of the sets of activity experiments were conducted using a Spectramax M2 Microplate Reader (Molecular Dynamics). Additionally, a negative control reaction condition was set up for each experiment, which contained the aryl sulfate compound in the elution buffer (see above), but with no enzyme present. Activity experiments for the engineered enzymes were conducted in several data sets. All raw data were normalized and evaluated as a percentage of the increase in signal over a control in which all other components but enzyme was added, with results reported below in Tables 2-10. In particular, the results of enzymes that are mutants of natural NDST enzymes are reported in Table 2, Table 3, and Table 4, the results of enzymes that are mutants of natural 2OSTs are reported in Table 5 and Table 6, the results of enzymes that are mutants of natural 6OSTs are reported in Table 7 and Table 8, and the results of enzymes that are mutants of natural 3OSTs are reported in Table 9 and Table 10.

TABLE 2

| | PNS ($Abs_{401}$) | (−) control | % increase |
|---|---|---|---|
| SEQ ID NO: 1 | 0.078 | 0.055 | 42% |
| SEQ ID NO: 3 | 0.1095 | 0.055 | 99% |
| SEQ ID NO: 5 | 0.0965 | 0.055 | 75% |
| SEQ ID NO: 7 | 0.0925 | 0.055 | 68% |
| SEQ ID NO: 9 | 0.107 | 0.079 | 35% |
| SEQ ID NO: 11 | 0.128 | 0.079 | 62% |
| SEQ ID NO: 15 | 0.083 | 0.059 | 42% |

TABLE 3

| | NCS (Abs$_{515}$) | (−) control | % increase |
|---|---|---|---|
| SEQ ID NO: 3 | 0.0545 | 0.041 | 33% |
| SEQ ID NO: 5 | 0.0545 | 0.041 | 33% |
| SEQ ID NO: 7 | 0.057 | 0.041 | 39% |
| SEQ ID NO: 9 | 0.168 | 0.083 | 102% |
| SEQ ID NO: 11 | 0.213 | 0.083 | 157% |
| SEQ ID NO: 13 | 0.201 | 0.083 | 143% |

TABLE 4

| | 2NapS ($\lambda_{em,\,410}$) | (−) control | % increase |
|---|---|---|---|
| SEQ ID NO: 3 | 2.974 × 10$^6$ | 1.804 × 10$^6$ | 65% |
| SEQ ID NO: 5 | 3.188 × 10$^6$ | 1.804 × 10$^6$ | 76% |
| SEQ ID NO: 9 | 2.972 × 10$^6$ | 1.804 × 10$^6$ | 65% |
| SEQ ID NO: 11 | 2.965 × 10$^6$ | 1.804 × 10$^6$ | 64% |

TABLE 5

| | NCS (Abs$_{515}$) | (−) control | % increase |
|---|---|---|---|
| SEQ ID NO: 27 | 0.064 | 0.046 | 39% |
| SEQ ID NO: 29 | 0.063 | 0.046 | 37% |
| SEQ ID NO: 33 | 0.072 | 0.046 | 56% |
| SEQ ID NO: 45 | 0.085 | 0.046 | 85% |
| SEQ ID NO: 53 | 0.082 | 0.046 | 78% |
| SEQ ID NO: 63 | 0.069 | 0.046 | 50% |
| SEQ ID NO: 65 | 0.065 | 0.046 | 41% |

TABLE 6

| | PNS (Abs$_{401}$) | (−) control | % increase |
|---|---|---|---|
| SEQ ID NO: 27 | 0.103 | 0.073 | 41% |
| SEQ ID NO: 33 | 0.077 | 0.046 | 67% |
| SEQ ID NO: 35 | 0.076 | 0.046 | 65% |
| SEQ ID NO: 37 | 0.089 | 0.046 | 93% |
| SEQ ID NO: 39 | 0.076 | 0.046 | 65% |
| SEQ ID NO: 41 | 0.084 | 0.046 | 82% |
| SEQ ID NO: 45 | 0.124 | 0.080 | 55% |
| SEQ ID NO: 47 | 0.194 | 0.095 | 105% |
| SEQ ID NO: 51 | 0.210 | 0.095 | 121% |
| SEQ ID NO: 53 | 0.120 | 0.080 | 50% |
| SEQ ID NO: 55 | 0.067 | 0.046 | 45% |
| SEQ ID NO: 57 | 0.072 | 0.046 | 57% |
| SEQ ID NO: 59 | 0.073 | 0.046 | 59% |
| SEQ ID NO: 61 | 0.068 | 0.046 | 48% |
| SEQ ID NO: 63 | 0.105 | 0.073 | 44% |
| SEQ ID NO: 65 | 0.105 | 0.080 | 31% |

TABLE 7

| | PNS (Abs$_{401}$) | (−) control | % increase |
|---|---|---|---|
| SEQ ID NO: 70 | 0.1340 | 0.114 | 18% |
| SEQ ID NO: 72 | 0.0740 | 0.065 | 14% |
| SEQ ID NO: 74 | 0.1150 | 0.103 | 12% |
| SEQ ID NO: 76 | 0.0990 | 0.075 | 32% |
| SEQ ID NO: 78 | 0.1020 | 0.075 | 36% |
| SEQ ID NO: 80 | 0.1010 | 0.075 | 35% |
| SEQ ID NO: 82 | 0.1160 | 0.103 | 13% |
| SEQ ID NO: 86 | 0.0950 | 0.075 | 27% |
| SEQ ID NO: 88 | 0.1070 | 0.075 | 43% |
| SEQ ID NO: 90 | 0.1290 | 0.106 | 22% |
| SEQ ID NO: 92 | 0.0910 | 0.08 | 14% |
| SEQ ID NO: 94 | 0.0980 | 0.08 | 23% |
| SEQ ID NO: 106 | 0.0810 | 0.068 | 19% |
| SEQ ID NO: 108 | 0.0840 | 0.068 | 23% |

TABLE 8

| | NCS (Abs$_{515}$) | (−) control | % increase |
|---|---|---|---|
| SEQ ID NO: 70 | 0.097 | 0.077 | 27% |
| SEQ ID NO: 74 | 0.079 | 0.072 | 9% |
| SEQ ID NO: 76 | 0.06 | 0.044 | 36% |
| SEQ ID NO: 78 | 0.056 | 0.044 | 27% |
| SEQ ID NO: 80 | 0.057 | 0.044 | 30% |
| SEQ ID NO: 82 | 0.08 | 0.072 | 10% |
| SEQ ID NO: 84 | 0.064 | 0.056 | 14% |
| SEQ ID NO: 86 | 0.06 | 0.049 | 22% |
| SEQ ID NO: 88 | 0.067 | 0.049 | 37% |
| SEQ ID NO: 90 | 0.087 | 0.072 | 20% |
| SEQ ID NO: 92 | 0.058 | 0.05 | 16% |
| SEQ ID NO: 94 | 0.061 | 0.05 | 22% |
| SEQ ID NO: 96 | 0.093 | 0.077 | 22% |
| SEQ ID NO: 98 | 0.092 | 0.077 | 20% |
| SEQ ID NO: 100 | 0.049 | 0.044 | 11% |
| SEQ ID NO: 102 | 0.053 | 0.047 | 12% |
| SEQ ID NO: 104 | 0.054 | 0.044 | 23% |
| SEQ ID NO: 106 | 0.064 | 0.056 | 15% |

TABLE 9

| | PNS (Abs$_{401}$) | (−) control | % increase |
|---|---|---|---|
| SEQ ID NO: 123 | 0.0730 +/− .00283 | 0.0545 | 34% |
| SEQ ID NO: 127 | 0.0745 +/− .00354 | 0.0544 | 37% |
| SEQ ID NO: 129 | 0.0730 +/− .00141 | 0.0545 | 34% |
| SEQ ID NO: 133 | 0.0730 +/− 0.0 | 0.0544 | 34% |
| SEQ ID NO: 135 | 0.1000 +/− .00566 | 0.0658 | 52% |
| SEQ ID NO: 137 | 0.1060 +/− .00141 | 0.0658 | 61% |
| SEQ ID NO: 141 | 0.0860 +/− .00283 | 0.0589 | 46% |
| SEQ ID NO: 143 | 0.1030 +/− 0.0 | 0.0792 | 30% |
| SEQ ID NO: 147 | 0.0865 +/− .00071 | 0.0588 | 47% |
| SEQ ID NO: 149 | 0.0890 +/− 0.0 | 0.0589 | 51% |
| SEQ ID NO: 151 | 0.0900 +/− 0.0 | 0.0588 | 53% |

TABLE 10

| | NCS (Abs$_{515}$) | (−) control | % increase |
|---|---|---|---|
| SEQ ID NO: 123 | 0.0505 +/− .00354 | 0.0391 | 29% |
| SEQ ID NO: 125 | 0.0505 +/− .00495 | 0.0391 | 29% |
| SEQ ID NO: 131 | 0.0560 +/− .00141 | 0.0409 | 37% |
| SEQ ID NO: 135 | 0.0735 +/− .01768 | 0.0420 | 75% |
| SEQ ID NO: 137 | 0.0560 +/− .00283 | 0.0421 | 61% |
| SEQ ID NO: 139 | 0.1550 +/− .00265 | 0.0829 | 87% |
| SEQ ID NO: 141 | 0.0560 +/− .00141 | 0.0409 | 37% |
| SEQ ID NO: 143 | 0.1520 +/− .00954 | 0.0831 | 83% |
| SEQ ID NO: 145 | 0.1850 +/− .001 | 0.0830 | 123% |
| SEQ ID NO: 149 | 0.0565 +/− .00212 | 0.0409 | 38% |
| SEQ ID NO: 151 | 0.0585 +/− .00212 | 0.0409 | 43% |

As can be observed in the Tables above, some of the enzymes are active with PNS, some are active with NCS, and many are active with both PNS and NCS. Generally, reaction mixtures containing enzymes active with either aryl sulfate compound demonstrated an absorbance that was approximately 1.1 to 2.5 times greater than the negative control.

Example 3: Mass Spectrometric Characterization of the N-Sulfated Polysaccharide Products of Engineered Aryl Sulfate-Dependent NST Enzymes A study was conducted in accordance with embodiments of the present disclosure to confirm glucosaminyl N-sulfotransferase activity of enzymes comprising the amino acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15 by detecting the presence of N-sulfated polysaccharide products formed as a result of their sulfotransfer reaction, using mass spectrometry (MS). Each engineered enzyme was purified according to the procedure of Example 1. Sulfotransferase activity was monitored in 100 μL reactions containing 50 μM of enzyme. To each purified protein solution, 20 mg of an aryl sulfate compound (either PNS or NCS) was dissolved in 2 mL of reaction buffer (50 mM MES pH 7.0, 2 mM $CaCl_2$)), added to the protein solution, and incubated at 37° C. for 10 min. 2.5 mL of 2 mg/mL solution of N-deacetylated heparosan was added to protein/donor solution and incubated overnight at 37° C. The N-deacetylated heparosan was synthesized according to the protocol described in Balagurunathan, K. et al (eds.) (2015), *Glycosaminoglycans: Chemistry and Biology*, Methods in Molecular Biology, vol. 1229, DOI 10.1007/978-1-4939-1714-3_2, ©Springer Science+Business Media, New York, pp. 11-19 (section 3.1). To purify the N-sulfated product, the incubated reaction mixture was centrifuged the following day at 5,000×g for 10 min. The filter was washed once with 2 mL water, and centrifuged again. The filtrate was added to a 1 K MWCO Dialysis membrane, dialyzed for 2 days in Milli-Q water, with water changes at 1 h, 2 h, 8 h, 16 h, 32 h, and then lyophilized.

The lyophilized N-sulfated products from each reaction were subsequently digested with a mixture of three carbon-oxygen lyases comprising the amino acid sequences of SEQ ID NO: 161, SEQ ID NO: 162, and SEQ ID NO: 163, which catalyze the β-eliminative cleavage of heparosan-based polysaccharides. Such lyases are available from New England Biolabs, among other chemical and biological commercial entities. 1 μL of each lyase was incubated with 50 μg of the lyophilized sulfated polysaccharide product and the provided digestion buffer, and incubated over 24 hours according to the packaged instructions provided by New England Biolabs with each lyase. After digestion, the lyase enzymes were inactivated by heating to 100° C. for 5 minutes. Samples were centrifuged at 14,000 rpm for 30 minutes before introduction to a strong anion exchange, high performance liquid chromatography (SAX) analysis. SAX analysis was performed on a Dionex Ultimate 3000 LC system interface. Separation was carried out on a 4.6×250 mm Waters Spherisorb analytical column with 5.0 μm particle size at 45° C. Mobile phase solution A was 2.5 mM sodium phosphate, pH 3.5, while mobile phase solution B was 2.5 mM sodium phosphate, pH 3.5, and 1.2 M Sodium perchlorate. After each sample was loaded onto the column, mobile phase solutions were applied to the column at a ratio of 98% mobile phase solution A and 2% mobile phase solution B for five minutes at a flow rate of 1.4 mL/min. After five minutes, a linear gradient of increasing mobile phase solution B was applied until the ratio of mobile phase solution A to mobile phase solution B was 50:50.

Using the SAX analysis, it was determined that six of the eight tested enzymes were active as sulfotransferases. However, each of the sulfotransferases were not necessarily active with both PNS and NCS. Enzymes having the amino acid sequences of SEQ ID NO: 5, SEQ ID NO: 7, and SEQ ID NO: 13 had activity with NCS only, and the enzyme having the amino acid sequence of SEQ ID NO: 15 had activity with PNS only. Enzymes having the amino acid sequences of SEQ ID NO: 9 and SEQ ID NO: 11 had activity with both aryl sulfate compounds.

Figure 29:
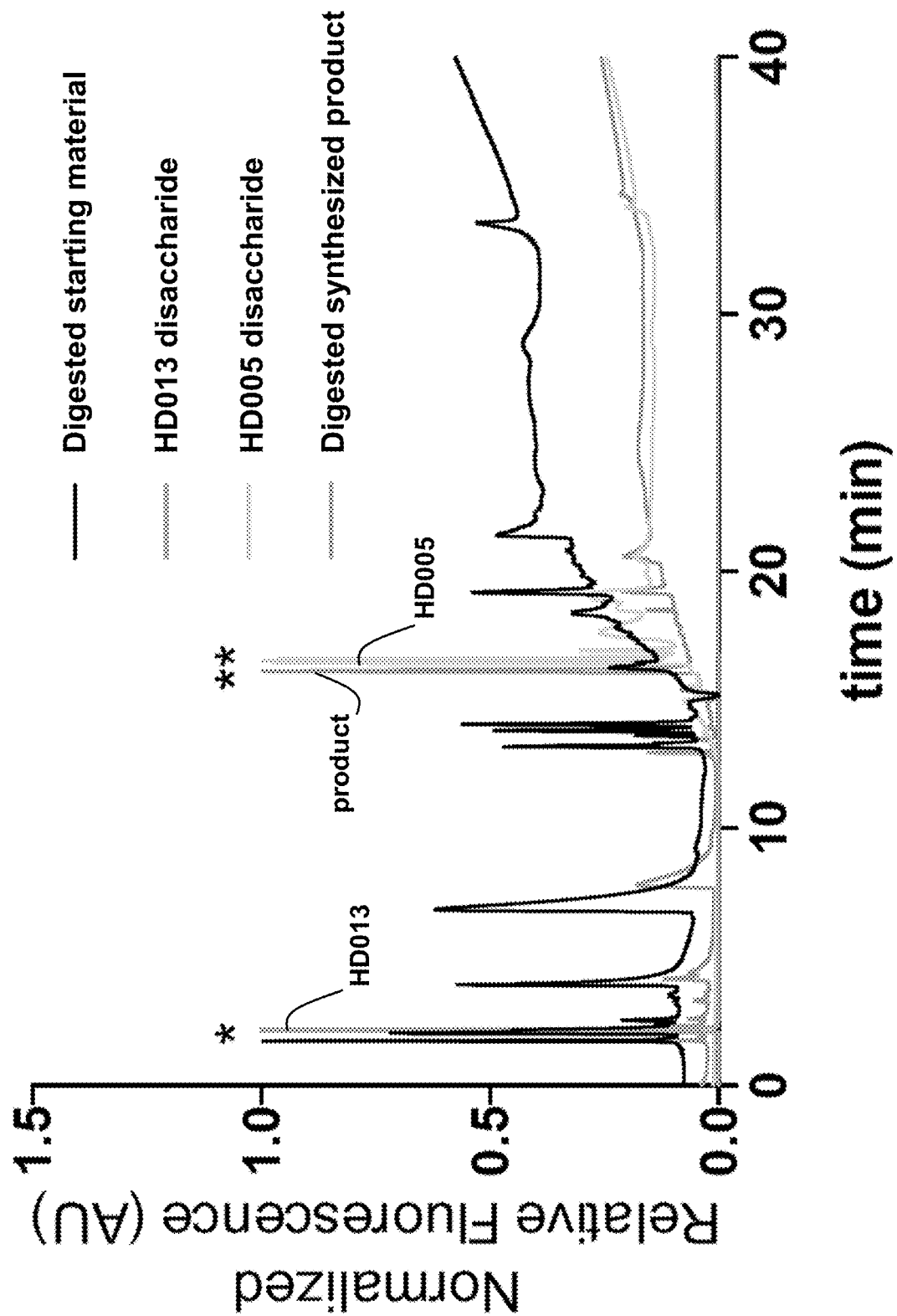

Representative chromatograms from SAX analysis illustrating the presence of N-sulfated products produced as a result of the reaction are shown in FIG. 29. Both the N-deacetylated heparosan starting material and the N-sulfated product produced by SEQ ID NO: 13 were digested with the lyases having the amino acid sequence of SEQ ID NO: 161, SEQ ID NO: 162, and SEQ ID NO: 163 according the digestion procedure described above. Two disaccharide standards (HD005 and HD013) that are commercially available from Iduron, Ltd were also analyzed using SAX. The HD013 disaccharide comprises an unsubstituted glucosamine residue and a reduced hexuronic acid. The HD005 disaccharide is the same as HD013 except that the glucosamine residue is N-sulfated. All of the overlaid chromatograms are normalized so the most prominent peak in each chromatogram is assigned a normalized relative fluorescence value of 1.0.

As shown in FIG. 29, the most prominent peak for HD013 disaccharide (illustrated with a * symbol) elutes almost immediately, whereas the most prominent peak for the HD005 disaccharide (illustrated with a ** symbol) elutes after approximately 17 minutes. This is expected under SAX conditions because positively-charged species (like HD013) typically do not bind to the column, whereas negatively-charged species (like HD005) do bind to the column. The N-deacetylated heparosan, which is similarly non-sulfated, most prominently elutes at a nearly identical time as HD013. Similarly, the lyophilized sample produced during the reaction shows a peak at a nearly identical time as HD005, indicating that the sample contains an N-sulfated product. Other peaks within each of the chromatograms, particularly within the synthesized starting materials and products, indicate a lack of sample purity based on the use of spin-filtration columns as the sole basis of purifying the polysaccharides in each instance. Those skilled in the art would appreciate that there are several other separations techniques that can be utilized if a more purified product is desired. Additionally, the drifting upward of the baseline of the fluorescent signal in the chromatograms is a known phenomenon when increasing amounts of salt are introduced onto the column via the mobile phase.

Example 4: Mass Spectrometric Characterization of the 2-O Sulfated Polysaccharide Products of Engineered Aryl Sulfate-Dependent 2OST Enzymes A study was conducted in accordance with embodiments of the present disclosure to confirm hexuronyl 2-O sulfotransferase activity of enzymes comprising the amino acid sequence of SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65 by detecting the presence of 2-O sulfated polysaccharide products formed as a result of their sulfotransfer reaction, using a similar procedure as in Example 3, except that the sulfo acceptor polysaccharide was commercial heparan sulfate in which the 2-O sulfate groups had been selectively removed by chemical means (product DSH001/2, available from Galen Laboratory Supplies) and analysis of each of the digested samples containing sulfated products was conducted using mass spectrometry, coupled with SAX-based high performance liquid chromatography (LCMS).

Disaccharides obtained by digesting the 2-O sulfated products using the carbon-oxygen lyases having the amino acid sequence of SEQ ID NO: 161, SEQ ID NO: 162, and SEQ ID NO: 163 and according to the procedure described above in Example 3 were quantified on a Shimadzu LCMS-8050 Triple Quadrupole Liquid Chromatograph Mass Spectrometer. 100 ng of each of the digested samples, diluted in 10 mM ammonium bicarbonate (pH 10). The disaccharides were separated on a Thermo Hypercarb HPLC column (100×2.1 mm, 5 μm). The mobile phase consisted of 10 mM ammonium bicarbonate (pH 10), and the disaccharides were eluted with an acetonitrile gradient of 0% to 20% for 2.5 min, held at 20% for the next 2.5 min, with 2 min of equilibration at 0% before the next injection; the flow rate was 0.2 mL/min, and the total run time was 7.1 min.

Figure 3B:
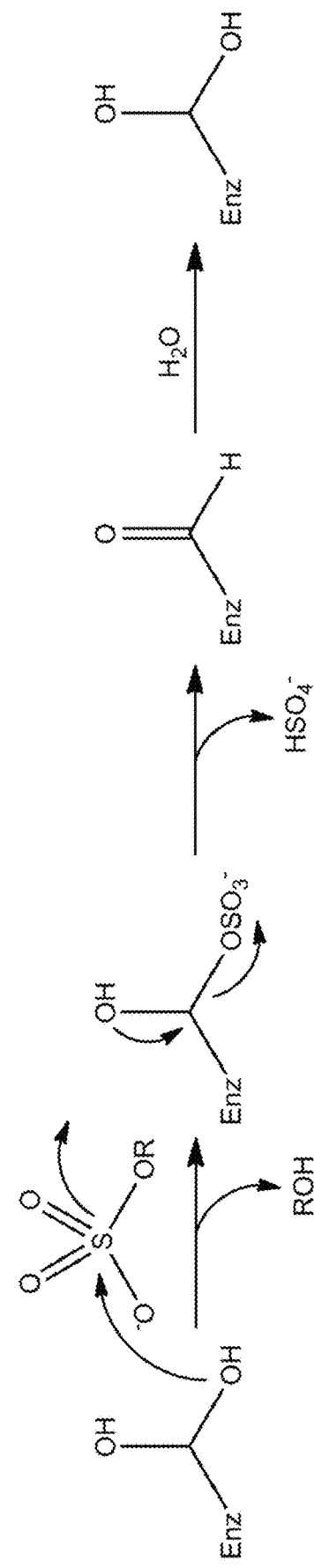
Figure 30A:
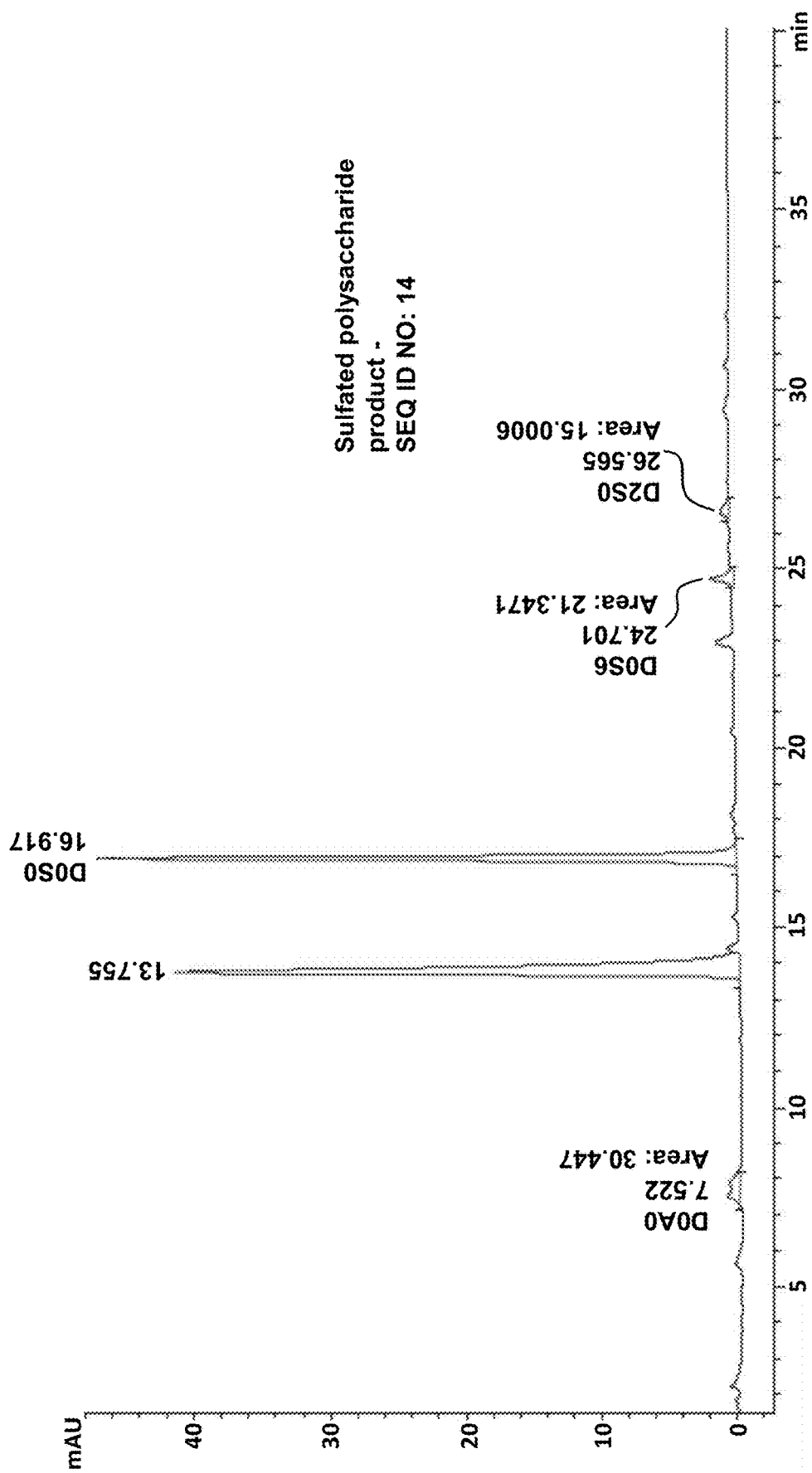
Figure 30B:
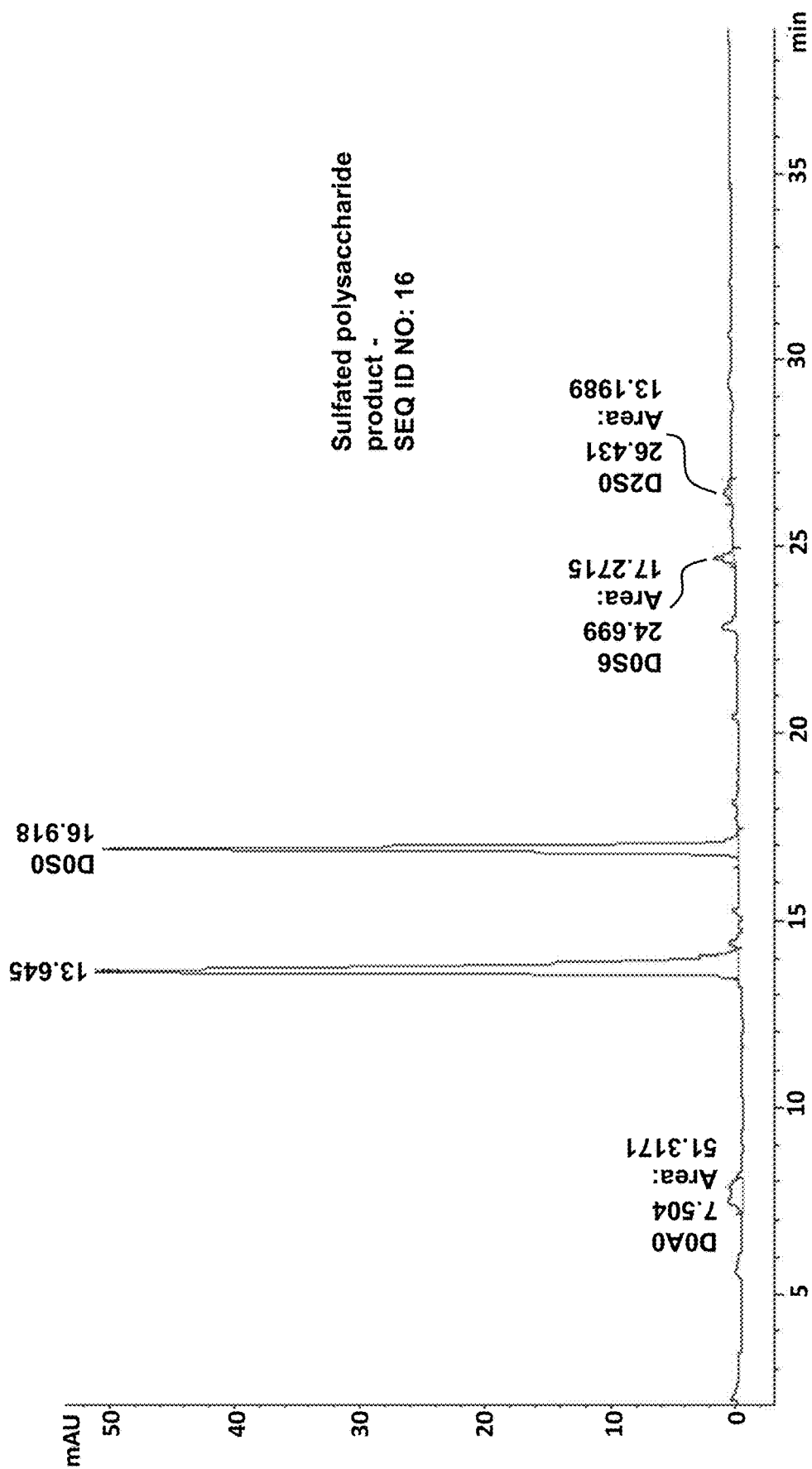

The extracted ion chromatograms from the LCMS are shown in FIG. 30A and FIG. 3B, corresponding to 2-O sulfated products obtained from reactions with engineered enzymes having the amino acid sequences of SEQ ID NO: 63 or SEQ ID NO: 65, respectively. Peaks were compared with chromatograms of a series of eight disaccharide standards, as well as a chromatogram from 100 ng of a commercial UFH polysaccharide (CAS code: 9041-08-1, available from Millipore Sigma), which was also digested using the lyase mixture. The eight reference disaccharide standards (D0A0, D0S0, D0A6, D2A0, D0S6, D2S0, D2A6, D2S6) represent disaccharides that are variably sulfated at the N-, 2-O and 6-O positions. In particular, the disaccharide D2S0 represents a disaccharide having a hexuronyl residue sulfated at the 2-O position and an N-sulfated glucosamine residue. The retention time and peak areas from the spectra from all of the disaccharide standards (not shown), the digested commercial sulfated polysaccharide (not shown), and the sulfated polysaccharide products of the engineered enzymes having the amino acid sequence of SEQ ID NO: 63 or SEQ ID NO: 65 are collected in Table 11, below. Since the ionization of each individual disaccharide is different, the present percent in EIC chromatograms may not represent their actual abundance. However, the ionization efficiency is identical for each disaccharide from sample to sample. Therefore, it is believed that comparing the peak area percent of the same saccharides from sample to sample can still be achieved.

TABLE 11

| Peak No. | Disaccharides | Peak Area % | | |
|---|---|---|---|---|
| | | Commercial standard | SEQ ID NO: 63 | SEQ ID NO: 65 |
| 1 | D0A0 | 3.9 | 5.9 | 9.1 |
| 2 | D0S0 | 3.9 | 87.1 | 85.5 |
| 3 | D0A6 | 3.4 | ND | ND |
| 4 | D2A0 | 1.8 | ND | ND |
| 5 | D0S6 | 11.8 | 4.1 | 3.1 |
| 6 | D2S0 | 6.6 | 2.9 | 2.3 |
| 7 | D2A6 | 1.6 | ND | ND |
| 8 | D2S6 | 67.0 | ND | ND |

Sulfotransferase activity of the engineered enzymes was confirmed by the re-sulfation at the 2-O position of hexuronic acid residues within the sulfo acceptor polysaccharide that had previously been desulfated prior to the reaction. This is illustrated by the presence of D2S0 disaccharides within the products isolated from reactions of both engineered enzymes and NCS. Without being limited by a particular theory, it is also believed that the activity of the engineered enzyme is dependent on reacting with a portion of the polysaccharide in which the hexuronic acid residue is adjacent to a glucosamine residue that is N-sulfated, but not 6-O sulfated. This is illustrated by the lack of D2S6 (2-O sulfated hexuronic acid residue and an N,6-sulfated glucosamine residue) and D2A6 (2-O sulfated hexuronic acid residue and a 6-O sulfated N-acetyl glucosamine residue) disaccharides detected within the isolated sulfated polysaccharide product. This is a similar sulfo acceptor reactivity to natural 2OST enzymes EC 2.8.2.-, which react with N-sulfated heparosan comprising either the structure of Formula IV or Formula V.

Example 5: Mass Spectrometric Characterization of the 6-O Sulfated Polysaccharide Products of Engineered Aryl Sulfate-Dependent 6OST Enzymes A study was conducted in accordance with embodiments of the present disclosure to confirm glucosaminyl 6-O sulfotransferase activity of enzymes comprising the amino acid sequence of SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO 102, SEQ ID NO: 104, SEQ ID NO: 106, or SEQ ID NO: 108 by detecting the presence of 6-O sulfated polysaccharide products as a result of their sulfotransfer reaction, using a similar LCMS procedure as in Example 4, except that the sulfo acceptor polysaccharide was prepared by chemically 6-O desulfating commercially available UFH (CAS code: 9041-08-1, available from Millipore Sigma), according to the procedure provided by Kariya, Y., et al., (2000) *J. Biol. Chem.* 275 (34):25949-25958).

Figure 31A:
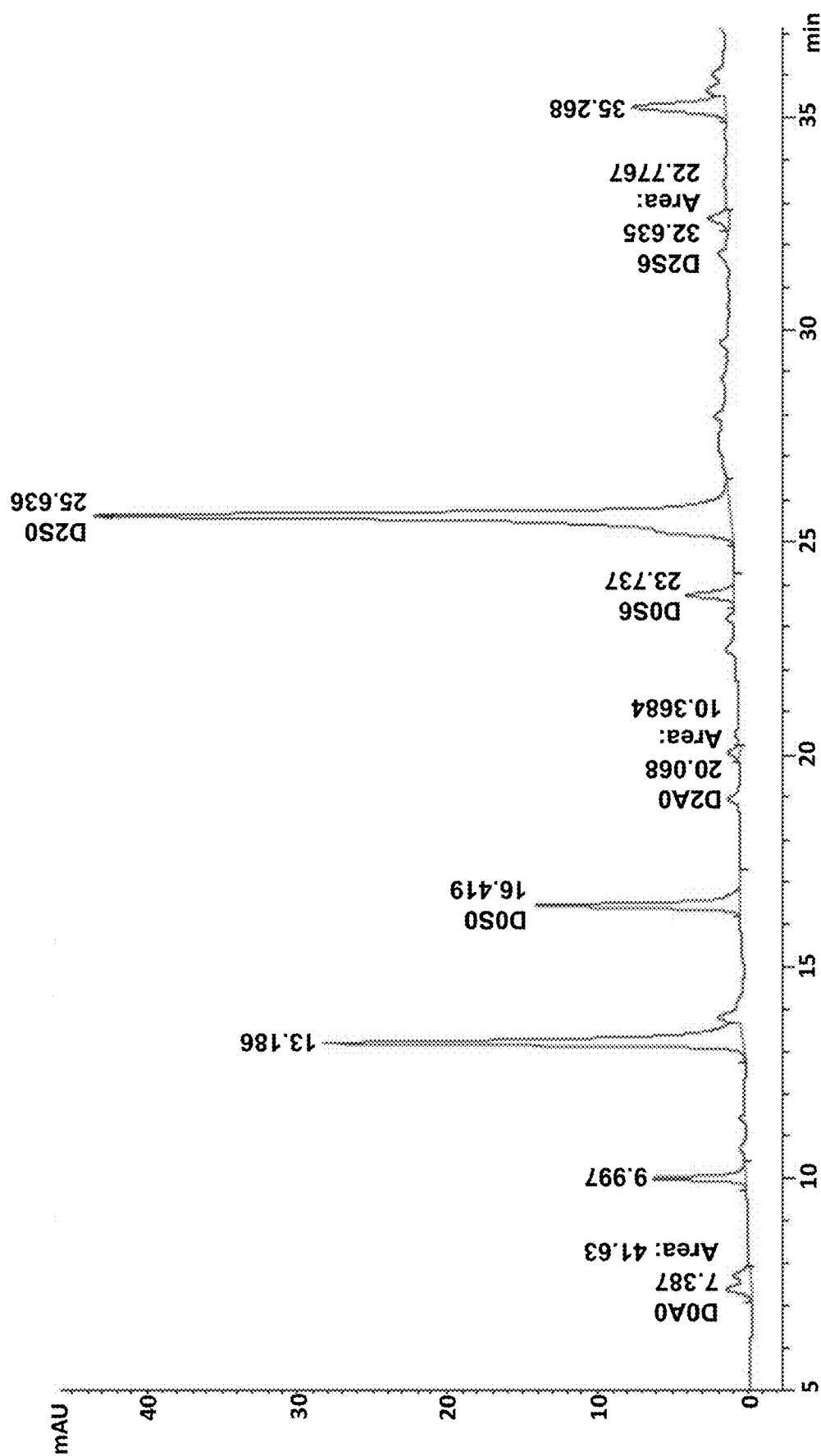
Figure 31B:
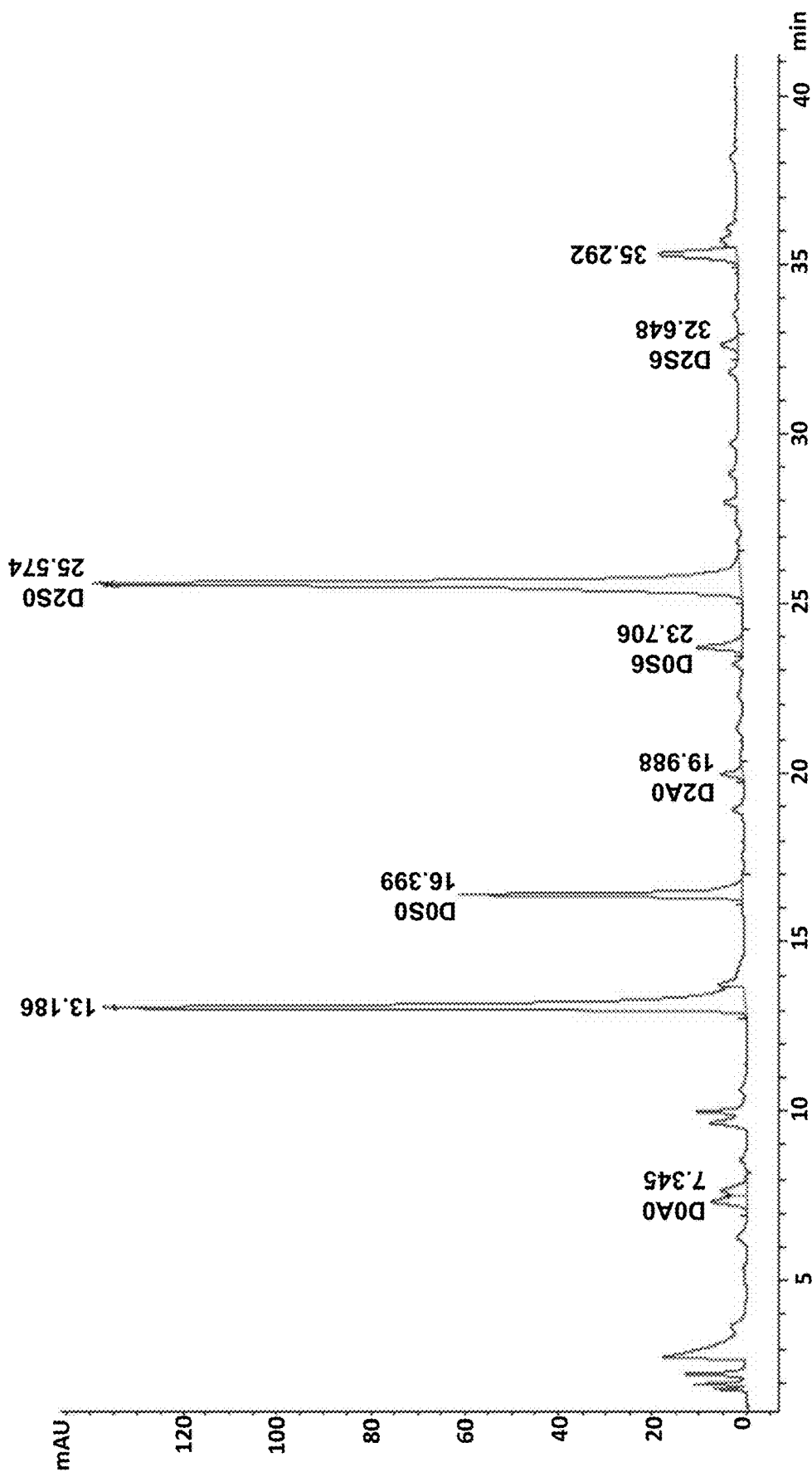
Figure 31C:
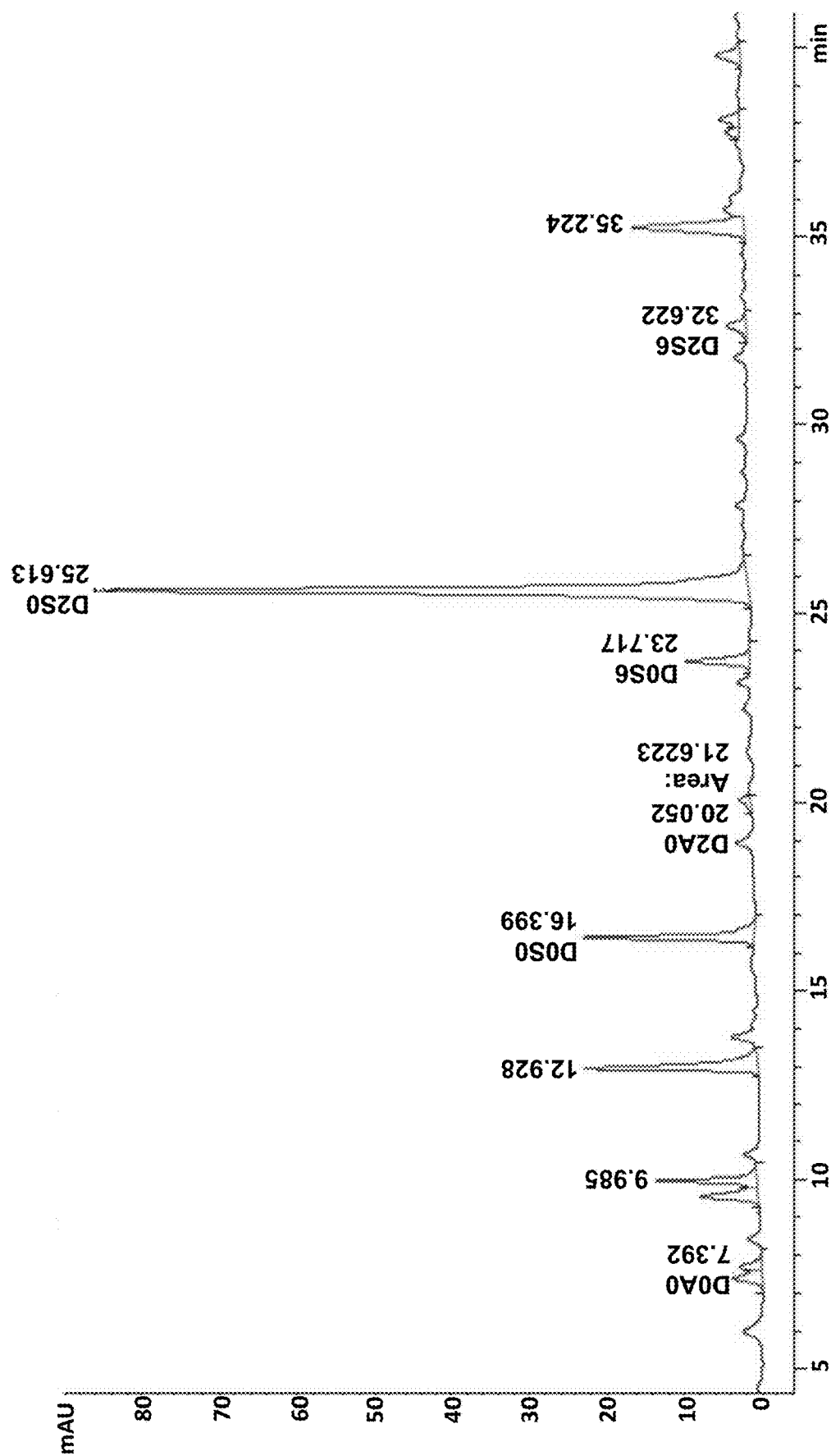

The extracted ion chromatograms corresponding to 6-O sulfated products obtained from reactions with engineered enzymes having the amino acid sequences of SEQ ID NO: 104, SEQ ID NO: 106, or SEQ ID NO: 108 are shown in FIG. 31A, FIG. 31B, and FIG. 31C, respectively. Enzymes having the sequence of SEQ ID NO: 104 and SEQ ID NO: 106 were active when NCS was the sulfo group donor, while the enzyme having the sequence of SEQ ID NO: 108 was active when PNS was the sulfo group donor. Assigned peaks were based on the determined retention times of eight reference disaccharide standards. The eight reference disaccharide standards (D0A0, D0S0, D0A6, D2A0, D0S6, D2S0, D2A6, and D2S6) represent disaccharides that are variably sulfated at the N-, 2-O, and 6-O positions. D0A6, D0S6, D2A6, and D2S6 comprise 6-O sulfated glucosamine residues. S6 indicates an N,6-sulfated glucosamine residue, while A6 indicates a 6-O sulfated N-acetyl glucosamine residue. Each chromatogram indicates two integrable peaks, D0S6 and D2S6, correlating to the synthesis of N,6-sulfated glucosamine residues, adjacent to a hexuronic acid residue that is either non sulfated or sulfated at the 2-O position, respectively. The peak area % of all the labelled disaccharides is in Table 12, below. Since the ionization of each individual disaccharide is different, especially for D0A0 and D2S6, the present percent in EIC chromatograms may not represent their actual abundance. However, the ionization efficiency is identical for each disaccharide from sample to sample. Therefore, it is believed that comparing the peak area percent of the same saccharides from sample to sample can still be achieved.

TABLE 12

| Peak No. | Disaccharides | RT (min) | Peak Area % | | |
|---|---|---|---|---|---|
| | | | SEQ ID NO: 104 | SEQ ID NO: 106 | SEQ ID NO: 108 |
| 1 | D0A0 | 7.7 | 4.6 | 6.0 | 5.4 |
| 2 | D0S0 | 16.4 | 14.2 | 18.4 | 13.0 |
| 3 | D0A6 | ND | ND | ND | ND |
| 4 | D2A0 | 20.0 | 1.1 | 1.8 | 1.3 |

TABLE 12-continued

| Peak No. | Disaccharides | RT (min) | Peak Area % | | |
| --- | --- | --- | --- | --- | --- |
| | | | SEQ ID NO: 104 | SEQ ID NO: 106 | SEQ ID NO: 108 |
| 5 | D0S6 | 23.7 | 4.0 | 3.7 | 5.6 |
| 6 | D2S0 | 25.6 | 73.5 | 68.4 | 72.4 |
| 7 | D2A6 | ND | ND | ND | ND |
| 8 | D2S6 | 32.7 | 2.5 | 1.7 | 2.3 |

Sulfotransferase activity of the engineered enzymes was confirmed by the re-sulfation at the 6-O position of glucosamine residues that had been desulfated by the procedure according to Kariya, Y., et al, above. This is illustrated by the presence of D0S6 and D2S6 disaccharides within the products isolated from the reactions with each enzyme. Among each of the engineered enzymes, it appears that the 6OST having the amino acid sequence of SEQ ID NO: 108 was the most active, based on comparing the peak area percentages of the D0S6 and D2S6 disaccharides. However, while D0A6 and D2A6 polysaccharides were not observed in any of the 6-O sulfated products produced by the engineered enzymes, without being limited by any particular theory, it is believed that these enzymes may nonetheless be able to transfer a sulfo group to N-acetyl glucosamine residues in different reaction conditions, particularly by increasing the concentration of the enzyme and/or polysaccharide where the presence of N-acetyl glucosamine residues is confirmed prior to the reaction, based on the reactivity of natural 6OST enzymes.

Example 6: Mass Spectrometric Characterization of the 3-O Sulfated Polysaccharide Products of Engineered Aryl Sulfate-Dependent 3OST Enzymes A study was conducted in accordance with embodiments of the present disclosure to confirm glucosaminyl 3-O sulfotransferase activity of enzymes comprising the amino acid sequence of SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151 by detecting the presence of 3-O sulfated polysaccharide products as a result of their sulfotransfer reaction, using a reaction, using a similar LCMS procedure as in Example 4, except that the sulfo acceptor polysaccharide was commercially-available UFH (CAS code: 9041-08-1, available from Millipore Sigma). Even though the unmodified UFH contains ~3.5% (w/w) of 3-O sulfated glucosamine residues, about ~60% of the glucosamine residues are N,6-sulfated and are adjacent to a 2-O sulfated hexuronic acid residue, as in Formula X. Consequently, these N,6-sulfated glucosamine residues can still be 3-O sulfated.

Figure 32A:
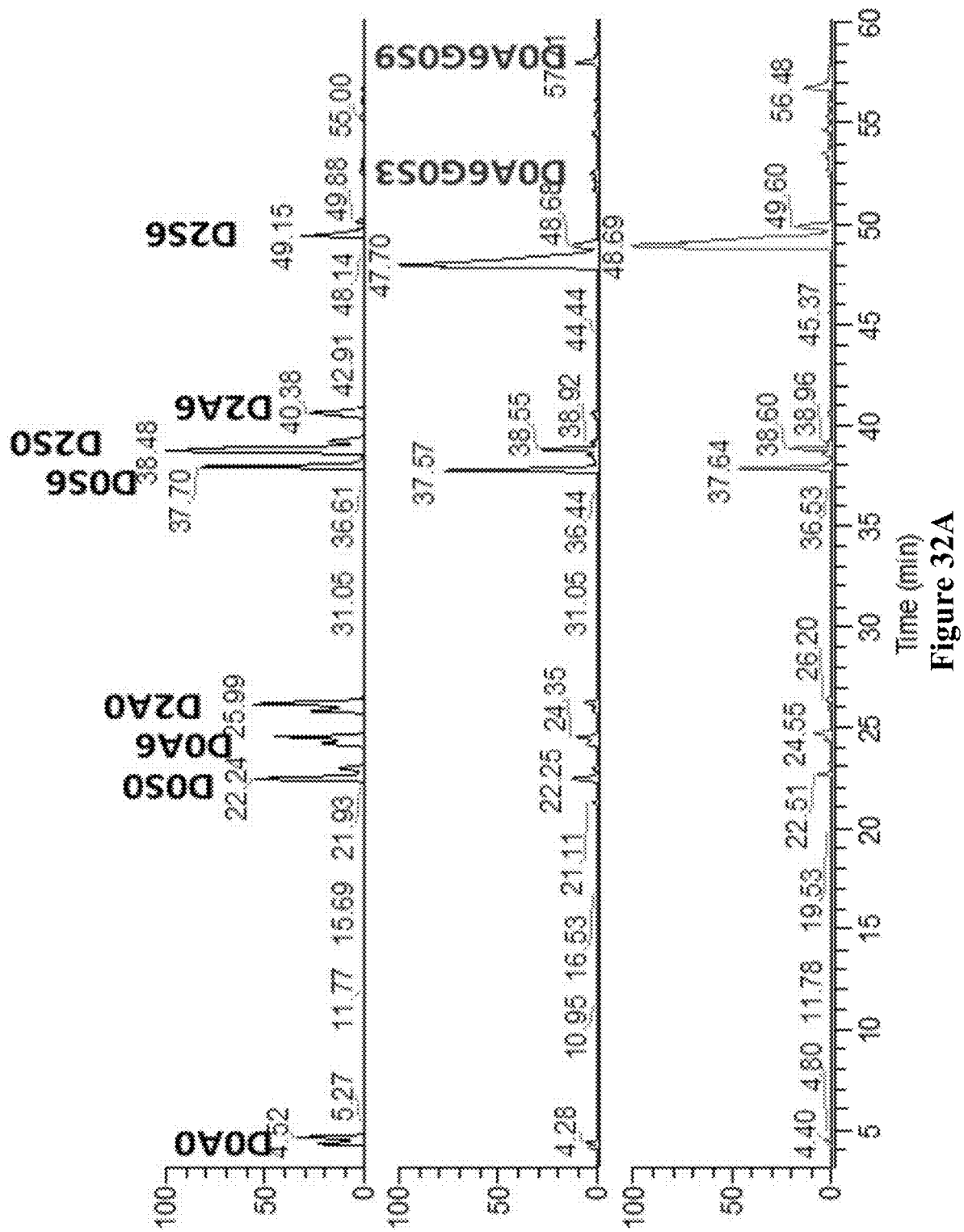
Figure 32B:
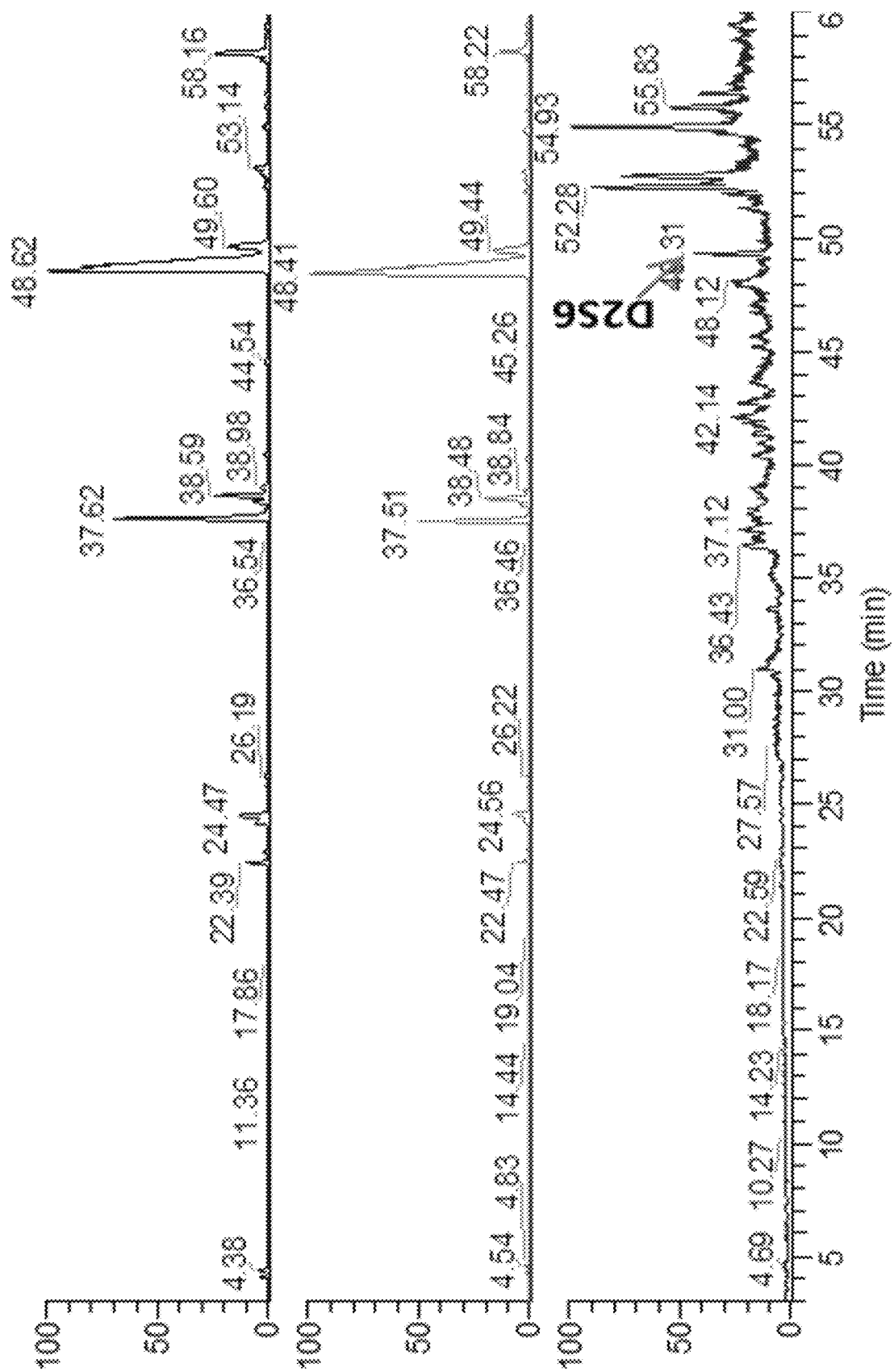

The extracted ion chromatograms are shown in FIG. 32A and FIG. 32B, along with chromatograms of a series of ten reference standards and 100 ng of the commercial polysaccharide, which was also digested using the lyase mixture. The ten reference standards (D0A0, D0S0, D0A6, D2A0, D0S6, D2S0, D2A6, D2S6, D0A6G0S3, and D0A6G0S9) represent di- or tetrasaccharides that are variably sulfated at the N-, 2-O, 3-O, and 6-O positions (FIG. 32A, top). For clarity, reference peaks that include 3-O sulfated glucosamine residues (D0A6G0S3) and (D0A6G0S9) are indicated in the digested commercial polysaccharide spectrum (FIG. 32A, center). Four mass spectra representing the digested sulfated polysaccharide products from reactions with enzymes comprising the amino acid sequence of SEQ ID NO: 147 (PNS, FIG. 32B, center), SEQ ID NO: 149 (PNS, FIG. 32B, bottom) (NCS, FIG. 32A, bottom), and SEQ ID NO: 151 (NCS, FIG. 32A, top) are shown below the digested commercial polysaccharide spectrum. The peak area % of all the labelled disaccharides and tetrasaccharides is in Table 13, below. Since the ionization of each individual disaccharide is different, especially for D0A0 and D2S6, the present percent in EIC chromatograms may not represent their actual abundance. However, the ionization efficiency is identical for each disaccharide or tetrasaccharide from sample to sample. Therefore, it is believed that comparing the peak area percent of the same saccharides from sample to sample can still be achieved.

TABLE 13

| peak No. | Disaccharides | RT (min) | Peak Area % | | | |
| --- | --- | --- | --- | --- | --- | --- |
| | | | Commercial standard | SEQ ID NO: 147 | SEQ ID NO: 149 (NCS) | SEQ ID NO: 151 | SEQ ID NO: 149 (PNS) |
| 1 | D0A0 | 4.5 | 1.9 | 0.6 | 0.8 | 1.4 | N.D. |
| 2 | D0S0 | 22.5 | 3.7 | 1.4 | 1.7 | 2.3 | N.D. |
| 3 | D0A6 | 24.6 | 4.2 | 2.8 | 3.1 | 4.5 | N.D. |
| 4 | D2A0 | 26.2 | 2.2 | 0.5 | 0.8 | 0.5 | N.D. |
| 5 | D0S6 | 37.5 | 16.0 | 10.9 | 10.6 | 13.1 | N.D. |
| 6 | D2S0 | 38.5 | 6.5 | 4.9 | 5.4 | 5.4 | N.D. |
| 7 | D2A6 | 40.3 | 1.6 | 0.8 | 0.8 | 0.9 | N.D. |
| 8 | D2S6 | 48.4 | 60.3 | 73.4 | 71.6 | 64.0 | 100.0 |
| 9 | D0A6G0S3 | 52.9 | 0.6 | 0.8 | 0.9 | 1.4 | N.D. |
| 10 | D0A6G0S9 | 58.2 | 3.0 | 4.0 | 4.1 | 6.5 | N.D. |

Sulfotransferase activity of each of the engineered enzymes was confirmed by the increase in the abundance of the D0A6G0S3 (hexuronic acid-6-O-sulfated N-acetyl glucosamine-glucuronic acid-N,3,6-sulfated glucosamine) and D0A6G0S9 (hexuronic acid-6-O-sulfated N-acetyl glucosamine-glucuronic acid-N,3-sulfated glucosamine) tetrasaccharides relative to the commercial UFH sample. However, the total abundance of disaccharides in the SEQ ID NO: 149 PNS sample was much lower than other samples. Subsequent trials included re-running the experiment with 10 times more injection volume, and a re-digestion of the sample with the lyase mixture. Nonetheless, only the D2S6 disaccharide could ever be found, indicating that the abundance of the SEQ ID NO: 149 PNS sulfated polysaccharide sample isolated initially was extremely low, and/or that the polysaccharide resists lyase digestion, causing the product to potentially elute from the column with a retention time longer than one hour.

Nonetheless, NMR studies (indicated below in Example 7) indicated 3-O sulfotransferase activity with the enzyme comprising the amino acid sequence SEQ ID NO: 149 when PNS is the aryl sulfate compound. Further, the enzyme having the amino acid sequence of SEQ ID NO: 149 was determined to be active as a sulfotransferase when NCS is the aryl sulfate compound. Therefore, it is believed that the observed results for the SEQ ID NO: 149 PNS sulfated polysaccharide sample during the LCMS experiment result from the sample produced for the purpose of the experiment, and not the activity of the enzyme itself. Otherwise, a higher abundance of 3-O sulfation was found in all of the other sulfated polysaccharide products from SEQ ID NO: 147, SEQ ID NO: 149, and SEQ ID NO: 151, relative to the commercial UFH standard.

Example 7: Confirmation of Sulfotransferase Activity of the Engineered 3OSTs Using Nuclear Magnetic Resonance A study was conducted in accordance with embodiments of the present disclosure to confirm the 3-O sulfotransferase activity of the engineered enzymes having the amino acid sequence of SEQ ID NO: 147, SEQ ID NO: 149, and SEQ ID NO: 151, particularly the activity of the enzyme having the amino acid sequence SEQ ID NO: 149 with PNS as the sulfo group donor. Each enzyme was purified according to the procedure of Example 1. To each purified protein solution, 20 mg of an aryl sulfate compound (PNS or NCS) dissolved in 2 mL of reaction buffer (50 mM MES pH 7.0, 2 mM $CaCl_2$)) was added to the protein solution and incubated at 37° C. for 10 min. 2.5 mL of 2 mg/mL solution of the commercial UFH polysaccharide utilized in Example 6 was added to protein/donor solution and incubated overnight at 37° C.

Figure 33:
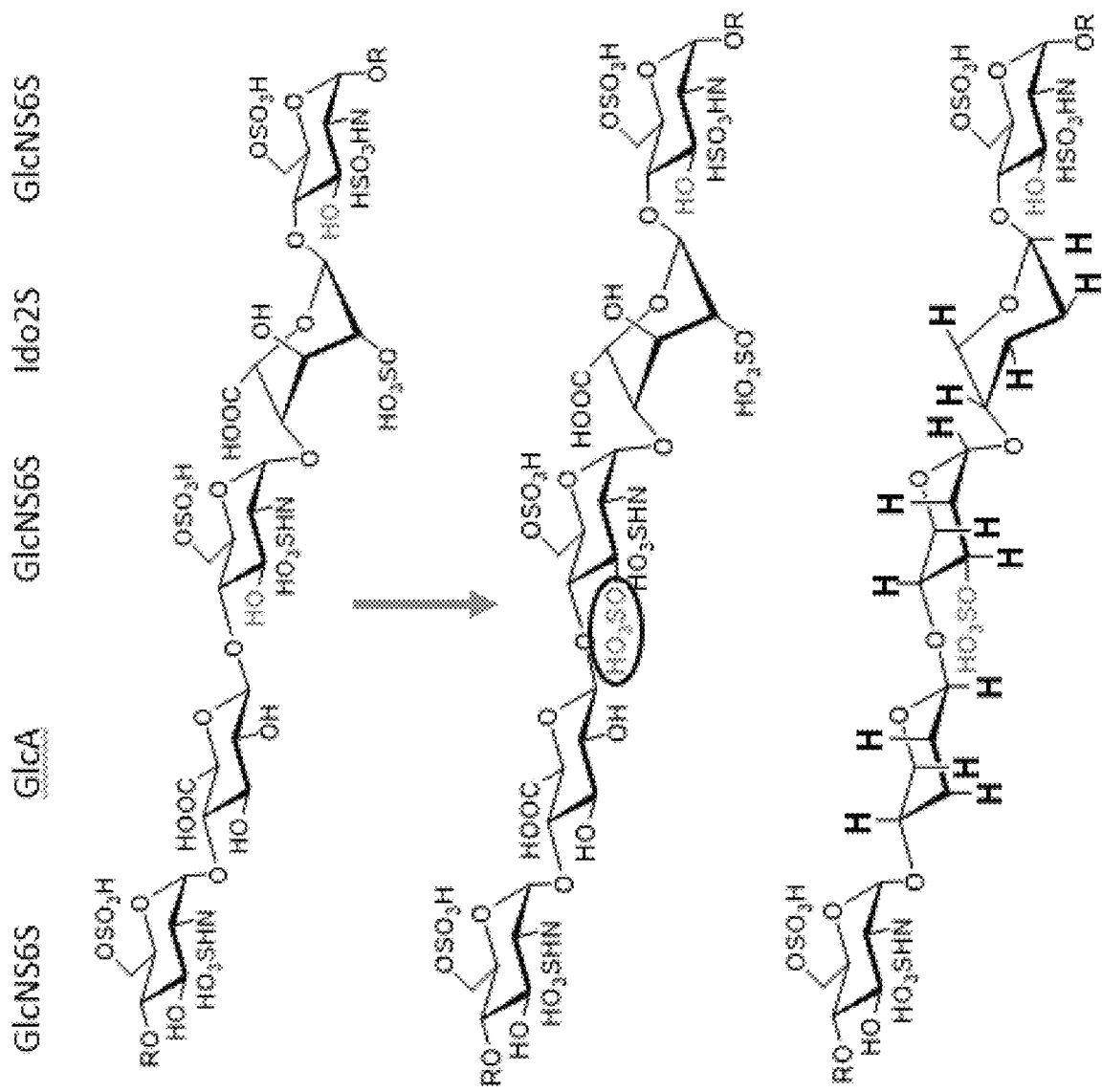

Each reaction was centrifuged at 5,000×g for 10 min, applied to a pre-wetted 30 K MWCO Amicon-15 filter and centrifuged at 5,000×g for 10 min. The filter was washed once with 2 mL water, and centrifuged again. The filtrate was added to a 1 K MWCO Dialysis membrane, dialyzed for 2 days in Milli-Q water, with water changes at 1 h, 2 h, 8 h, 16 h, 32 h, and then lyophilized. The dry, white powder was resuspended in 400 μL $D_2O$, lyophilized to remove exchangeable protons, then resuspended in 600 μL $D_2O$ and transferred to NMR tubes (Wilmad, 0.38 mm×7"). To determine if sulfotransfer took place, $^1$H-NMR spectra were obtained on a Bruker 600 MHz NMR, 32 scans, with water suppression. The overall reaction scheme is shown in FIG. 33. Within FIG. 33, the 3-O positions of any of the glucosamine residues can be sulfated by the 3OST enzyme. The sulfated 3-O position is circled in the central polysaccharide. Exchangeable protons having the ability to exhibit resonance upon deuterium exchange are shown in bold, in the bottom polysaccharide. Crude mixture peaks were integrated to literature-referenced spectra for the sulfo acceptor polysaccharide and associated 3-O sulfated product.

Figure 34:
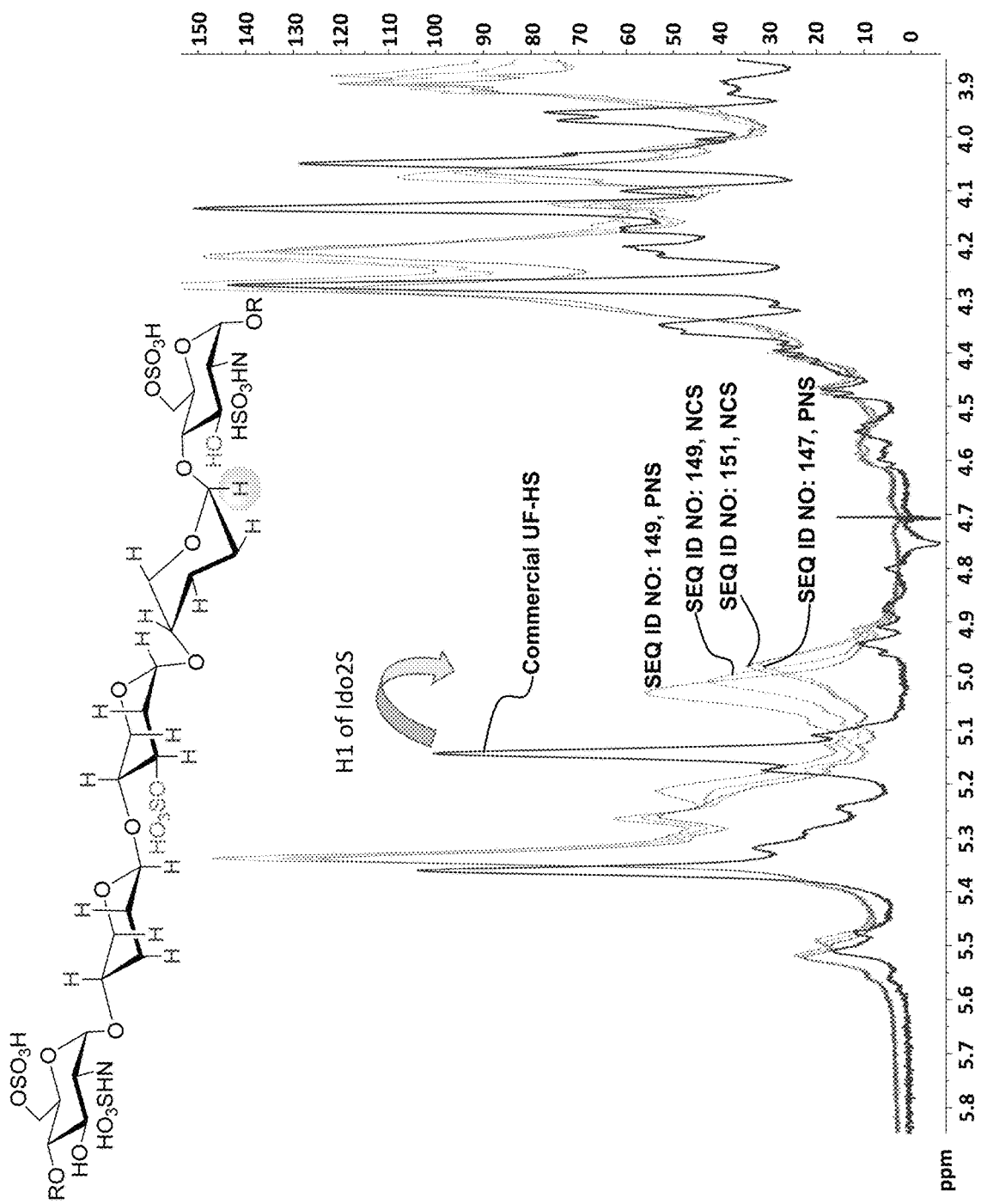

As shown in the overlain spectra in FIG. 34, a sharp peak at 5.15 ppm that correlates to the proton at the C2 carbon of the 2-O sulfated iduronic acid present in the commercial UFH disappears upon reacting with enzymes comprising the amino acid sequence of SEQ ID NO: 147, SEQ ID NO: 149, and SEQ ID NO: 151. The proton of interest is circled in the polysaccharide shown above the spectra. The $^1$H NMR spectra for a 3-O sulfated product synthesized by enzymes comprising the amino acid sequence of SEQ ID NO: 147, SEQ ID NO: 149, or SEQ ID NO: 151 in reaction with either PNS and/or NCS are all illustrated. In each of the product spectra, the $IdoA_{2S}$ peak shifts to between approximately 5.0 and 5.05 ppm. A similar transition is shown when incubating the natural human sulfotransferase enzyme with the same polysaccharide substrate and PAPS (data not shown).

Figure 35:
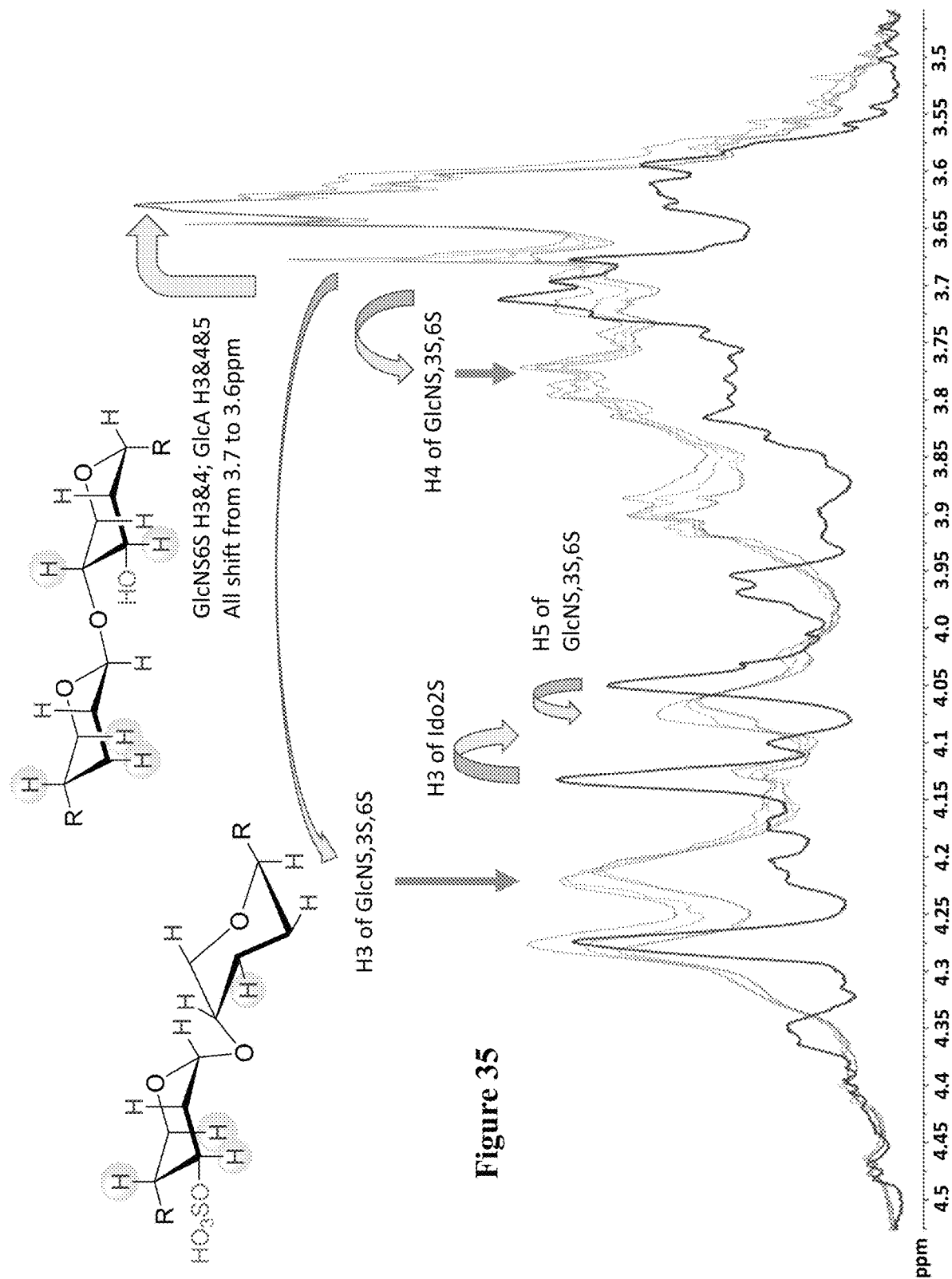

As shown in FIG. 35, the region between 4.5 and 3.5 shows several peaks that similarly shift in response to the addition of the sulfate group to the 3-O position of a glucosamine residue, all of which correlate to the same shifts observed upon incubating the human 3OST1 enzyme with the same commercial UFH substrate and PAPS. Peaks that shift are indicated in curved arrows, and positions of the peaks from 3-O sulfated polysaccharides produced by enzymes having the amino acid sequence of SEQ ID NO: 147, SEQ ID NO: 149, or SEQ ID NO: 151, are shown with straight arrows. The largest shift occurs for H3 of $Gl_{CNS3 6S}$, from 3.7 ppm to 4.2 ppm. This results from being closest to the newly added 3-O sulfate group. Additionally, the H3 proton of $Ido_{2S}$ and H5 of $Gl_{CNS3 6S}$ both converge toward a peak at 4.07 ppm, which shows two overlapping peaks. H4 of $Gl_{CNS3 6S}$ shifts moderately downfield from the 3.7 ppm region to the 3.8 ppm region, and according to references, many peaks such as H3 & H4 from $Gl_{CNS6S}$ and H3, H4, and H5 from GlcA shift from the 3.7 ppm region to the 3.6 ppm region.

Example 8: Chemical Synthesis of N-Sulfated Heparosan for Use with Engineered Sulfotransferases of the Present Invention A study was conducted in accordance with embodiments of the present disclosure to chemically synthesize N-sulfated heparosan for use as sulfo acceptor polysaccharides with any of the engineered aryl sulfate-dependent sulfotransferases of the present invention, particularly the engineered 2OST enzymes. N-deacetylated heparosan was prepared according to the protocol described in Balagurunathan, K. et al., above. Particularly, the heparosan that eluted from the DEAE resin was precipitated overnight in ethanol saturated with sodium acetate, at −30° C., before being resuspended in water and dialyzed within a cellulose dialysis membrane having a 1,000 Da molecular weight cut-off (MWCO).

To N-deacetylate the heparosan, enough sodium hydroxide pellets (~4.0 g) were dissolved to make a 2.5 M solution in a 40 mL aliquot of the dialyzed heparosan in water. The solution was incubated at 55° C. for 16 hours, with shaking at 100 rpm. The sodium hydroxide within the sample was then neutralized with acetic acid until the solution reached a pH of ~7.0, and then dialyzed in water overnight within a 1,000 MWCO dialysis membrane.

Subsequent N-sulfation of the N-deacetylated heparosan was accomplished by adding 100 mg of sodium carbonate and 100 mg of sulfur trioxide-triethylamine complex, and allowing the composition to incubate at 48° C. until all of the solid was dissolved. The pH of the solution was then readjusted to ~9.5, using acetic acid. After incubation at 48° C. overnight with shaking at 100 rpm, an additional 100 mg of sodium carbonate and 100 mg of sulfur trioxide-triethylamine complex was added, before subsequent readjustment of the pH to ~9.5 using acetic acid. The solution was incubated at 48° C. for an additional 24 hours. The sulfated polysaccharide solution was neutralized with acetic acid to a pH of ~7.0, and dialyzed in water overnight within a 1,000 MWCO dialysis membrane. The dialyzed N-sulfated heparosan was then lyophilized prior to further use. The N-sulfated heparosan was then further purified by loading it onto a Zenix SEC-100 column and eluting it isocratically with 0.1 M ammonium acetate, pH 9.0.

Figure 36:
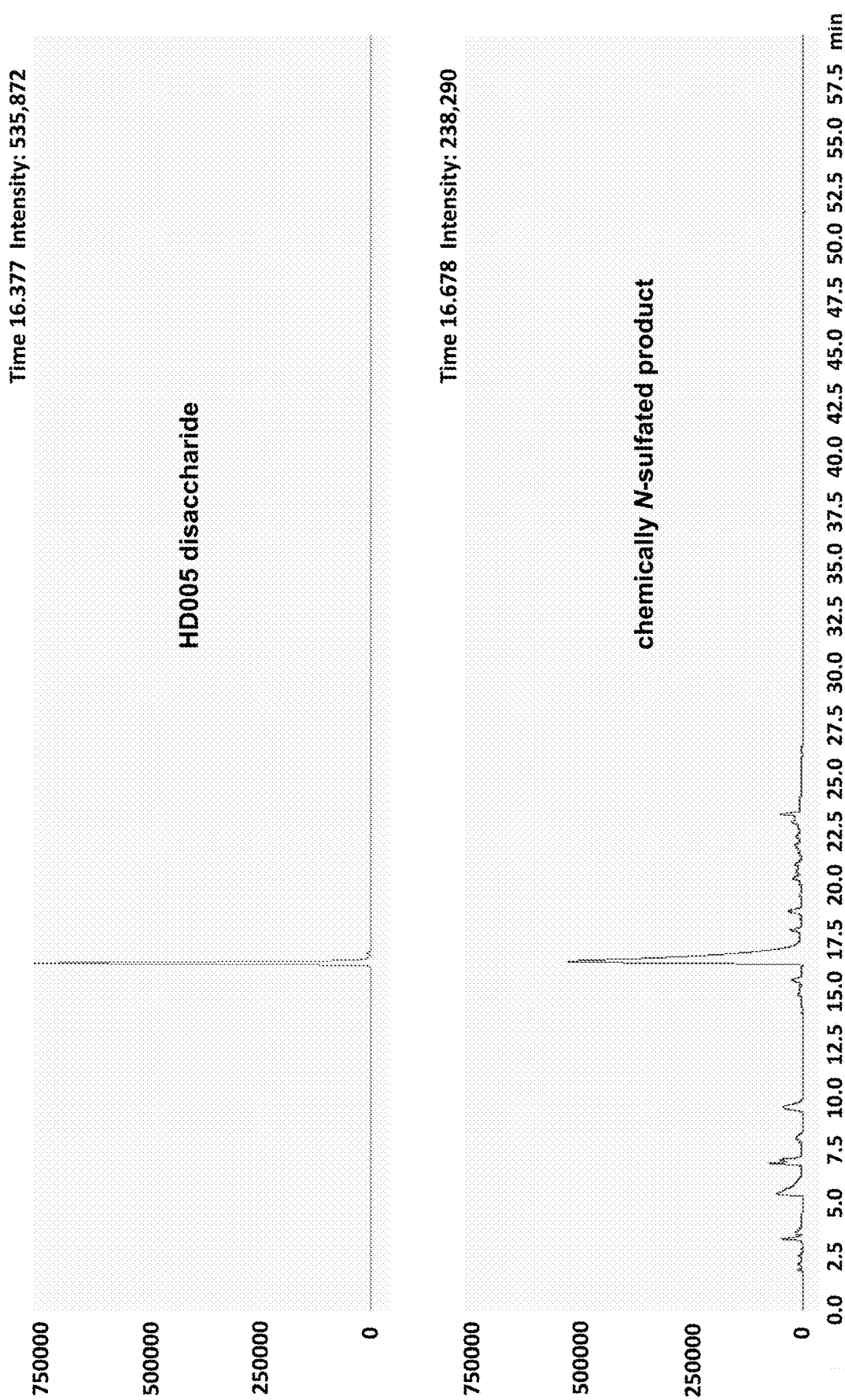

The functionalization of the purified heparosan-based polysaccharide was characterized by digesting it with a mixture of three carbon-oxygen lyases comprising the amino acid sequences of SEQ ID NO: 161, SEQ ID NO: 162, and SEQ ID NO: 163, and analyzing the digested samples using SAX, using a similar procedure described above. As a positive control, the commercial HD005 disaccharide of Example 3, containing N-sulfated glucosamine residues, was also analyzed. Representative chromatograms of both samples are shown in FIG. 36. In both chromatograms, a strong peak is present at about 16.5 minutes, indicating that the synthesized sample contains N-sulfated glucosamine residues.

Example 9: Preparation of an N,2O-HS Polysaccharide Product

A study was conducted in accordance with embodiments of the present disclosure to synthesize an N,2O-HS polysaccharide product comprising the structure of either Formula VI or Formula VII, using an engineered 2OST and the N-sulfated heparosan synthesized in Example 8 as the sulfo acceptor. In a conical-bottom centrifuge tube, 80 mM aliquots of NCS were dissolved in 50 mM MES pH 7.0, 2 mM $CaCl_2$). To each solution, 2 mg of the enzyme having the sequence of SEQ ID NO: 63, based on the absorbance of the enzyme sample at 280 nm, was added (about 4 mL). 5 mg of the lyophilized N-sulfated heparosan synthesized in Example 8 was resuspended in 1 mL of water and added to the reaction mixture containing the enzyme and NCS. The entire reaction mixture was then incubated at 34° C. with shaking at 30 rpm, for 48 hours. A second set of reactions were prepared using the same procedure, except that 2 mg of a $C_5$-hexuronyl epimerase comprising the amino acid sequence of SEQ ID NO: 67 was also added to the reaction mixture, prior to incubation.

The polysaccharide products from both sets of reactions were purified by first precipitating out the proteins from the reaction mixtures by placing the reaction vessels in boiling water for 10 minutes and centrifuging at high speed to form a pellet. The supernatant containing the polysaccharide products was decanted from the pellet and dialyzed in water overnight within a 1,000 MWCO dialysis membrane. The dialyzed products were then lyophilized for future use.

Figure 37:
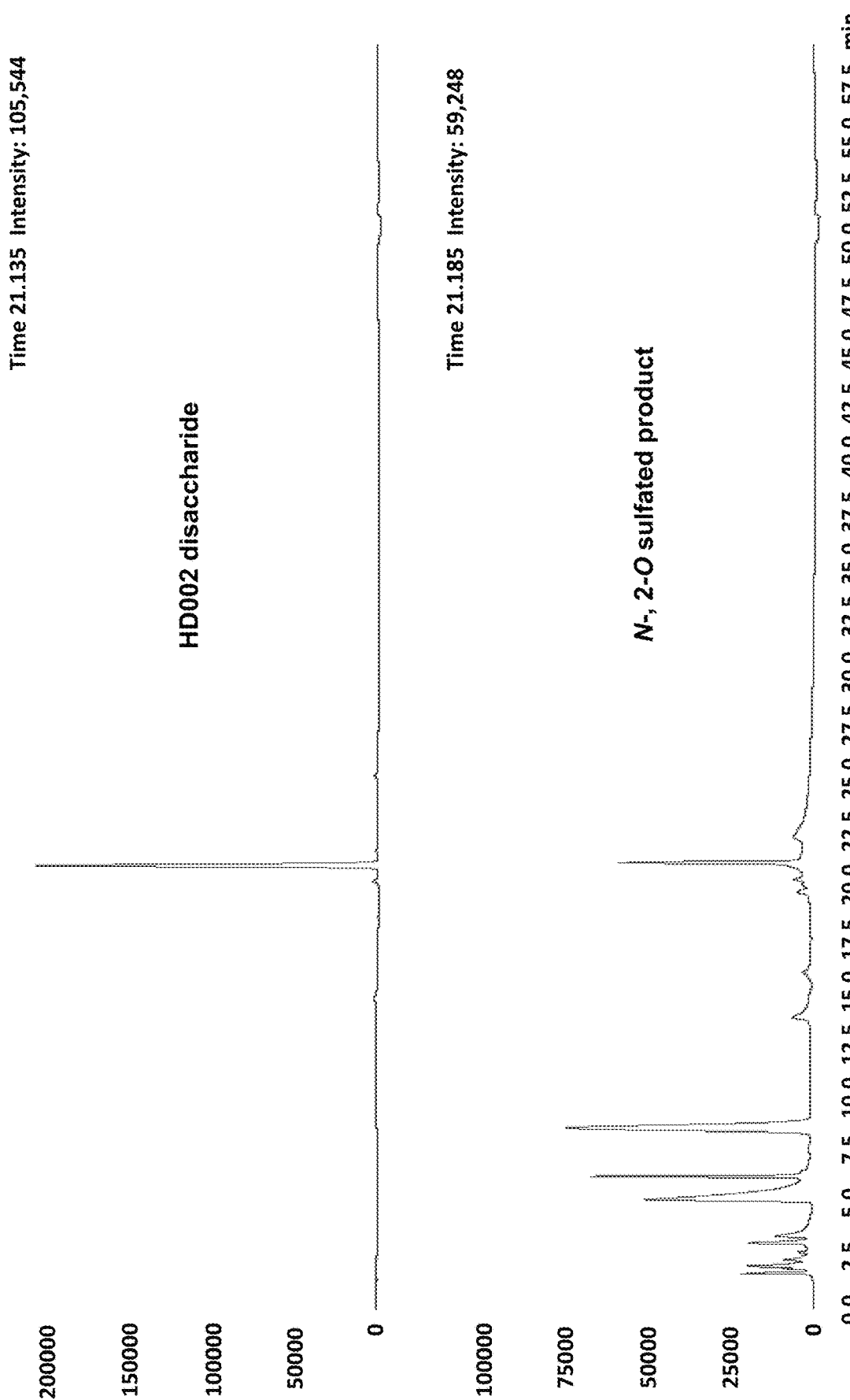
FIG. 37 shows a SAX-HPLC chromatogram of an enzymatically 2-O sulfated polysaccharide product prepared using the chemically N-sulfated polysaccharide product of Example 8 as the sulfo acceptor polysaccharide, compared to a commercial standard.
Figure 38:
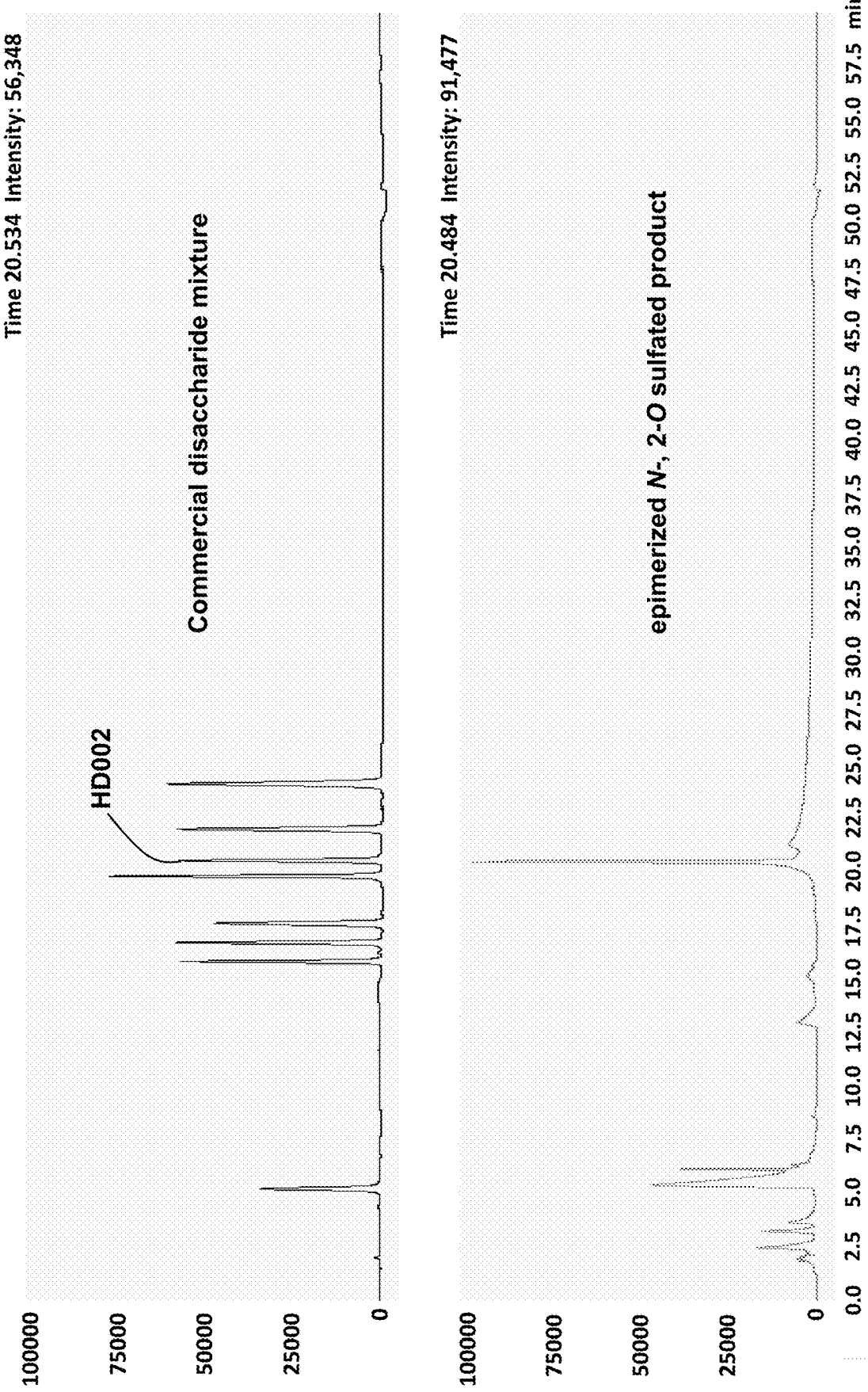
FIG. 38 shows a SAX-HPLC chromatogram of an enzymatically 2-O sulfated polysaccharide product prepared using the chemically N-sulfated polysaccharide product of Example 8 as the sulfo acceptor polysaccharide and with a $C_5$-hexuronyl epimerase included in the reaction mixture, compared to a commercial standard.

To characterize the polysaccharide products, lyophilized samples were resuspended in 400 µL of water, and purified using a Q-Sepharose Fast Flow Column (GE Biosciences). Samples were eluted from the column using a gradient ranging from 0 to 2M NaCl, in 20 mM sodium acetate buffer, pH 5.0. Purified polysaccharides were then digested and analyzed by SAX according to the procedures in Example 3 above, along with a commercial polysaccharide, HD002 (Iduron), which contains disaccharides of 2-O sulfated uronic acid and N-sulfated glucosamine. Representative chromatograms of reactions either without or including the epimerase enzyme are shown in FIG. 37 and FIG. 38, respectively. In FIG. 37, the chromatogram for the HD002 disaccharide has a single, sharp peak at about 21.1 minutes, which correlates to a sharp peak at a nearly identical time in the reaction product, indicating the time that an N,2O-HS product comprising the structure of Formula VI was formed as a result of the reaction. In FIG. 38, the HD002 disaccharide was provided within a mixture containing other disaccharide standards, with the disaccharide corresponding to HD002 eluting at 20.5 minutes, corresponding with the elution time of the HD002 standard in FIG. 37. The epimerized reaction product has a sharp peak at a nearly identical elution time to the HD002 standard, indicating that an N,2O-HS product comprising the structure of Formula VII was formed as a result of the reaction.

Example 10: Preparation of an N,2O,6O-HS Product

A study was conducted in accordance with embodiments of the present disclosure to synthesize an N,2O,6O-HS product comprising the structure of Formula IX, using the procedure of Example 9, except that the epimerized N,2O-HS product of Example 9 was used as the sulfo acceptor polysaccharide, and the engineered 6OST having the amino acid sequence of SEQ ID NO: 104 was used as the enzyme.

Figure 39:
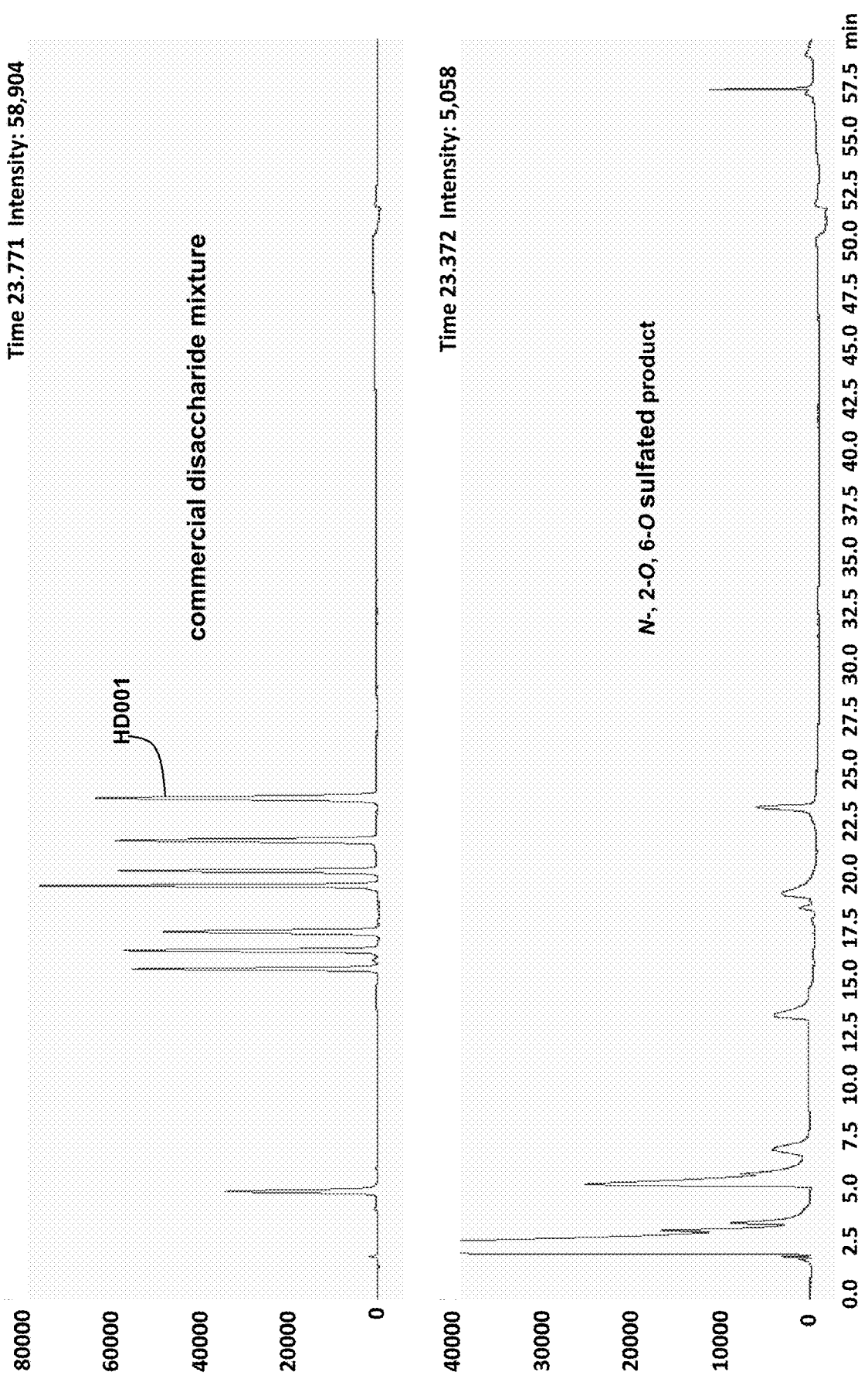
FIG. 39 shows a SAX-HPLC chromatogram of an enzymatically 6-O sulfated polysaccharide product prepared using a 2-O sulfated polysaccharide product of Example 9 as the sulfo group acceptor, compared to a commercial standard.

Representative chromatograms of the sulfated polysaccharide product and a mixture of commercial disaccharides are shown in FIG. 39. The chromatogram of the commercial mixture exhibits a peak at about 23.7 minutes, correlates to disaccharide HD001 (Iduron), which consists of disaccharides of 2-O sulfated uronic acid and N-, 6-O sulfated glucosamine, while the reaction product exhibits a similar peak at 23.4 minutes, indicating that an N,2O,6O-HS product was formed as a result of the reaction. Other peaks present within the N,2O,6O-HS product include undigested polysaccharide (2.5 min), unsubstituted uronic acid and N-acetylated glucosamine (5.5 min), and unsubstituted uronic acid and N-, 6-O sulfated glucosamine.

Example 11: Preparation of an N,2O,3O,6O-HS Product

A study is conducted in accordance with embodiments of the present disclosure to synthesize a sulfated polysaccharide product comprising the structure of Formula I and having N-, 6-O, 3-O sulfated glucosamine and 2-O sulfated hexuronic acid residues, using the procedure of Example 9 except that the chemically synthesized N-, 2-O, 6-O sulfated polysaccharide of Example 10 is used as the sulfo acceptor polysaccharide, and an engineered 3-O sulfotransferase enzyme having the amino acid sequence of SEQ ID NO: 147, SEQ ID NO: 149, or SEQ ID NO: 151 is used as the sulfotransferase. Sulfated polysaccharide products are digested and analyzed according to the procedure of Example 9, using SAX. It is expected that upon comparison to a digested commercial tetrasaccharide comprising a N-, 6-O, 3-O sulfated glucosamine residue, that it will be determined that the sulfated polysaccharide product is 3-O sulfated as a result of the reaction.

Example 12: Confirmation of Anticoagulant Activity of the N,2O,3O,6O-HS Product

A study is conducted in accordance with embodiments of the present disclosure to determine whether N,2O,3O,6O-HS products produced according to procedures of Example 6 or Example 7, using any of the 3OST enzymes described herein, which are expected to have a binding affinity to antithrombin (See Meneghetti, G., et al. (2017) *Org. Biomol. Chem.* 15:6792-6799). A control reaction containing a commercial N,2O,3O,6O-HS product known to have activity with antithrombin, such as the USP reference standard (CAS No: 9041-08-1). Human antithrombin (AT) (1 mg/mL) is incubated with different substrates in the presence of a dye, such as the SyproOrange™ dye (Invitrogen). The dye is diluted in water (1 unit Sypro: 50 units water (v/v)) and 3.5 µL of the diluted dye is added to the mixture reaction in PBS buffer. The SyproOrange™ dye has an excitation wavelength of 300 nm or 470 nm and emits at 570 nm when bound to hydrophobic residues. 25 µg of a N,2O,3O,6O-HS product is included in each reaction mixture. Reactions are incubated at 31° C. for 2 min, before being subjected to a step-wise temperature gradient from 32 to 85° C. in a 0.5° C. steps. Between each temperature step, a 5-second incubation period can be taken to ensure sample equilibrations. Reactions can be developed using a real-time PCR System. It is expected that the melting curves of the control reaction with the USP reference standard, as well as the synthesized N,2O,3O,6O-HS products, will each be shifted to a higher temperature than a standard with the dye and AT alone, indicating that the AT can bind to the N,2O,3O,6O-HS products because the N,2O,3O,6O-HS products contain at least one AT-recognition sequence comprising the structure of Formula I.

Example 13: Determination of Engineered Aryl Sulfate-Dependent Mutants of Other EC 2.8.2.8 Enzymes A study is conducted in accordance with embodiments of the present disclosure to engineer additional aryl sulfate-dependent NST enzymes. As described above, the aryl sulfate-dependent NST enzymes having the amino acid sequences of SEQ ID NO: 5, SEQ ID NO: 7, SEQ ID NO: 9, SEQ ID NO: 11, SEQ ID NO: 13, or SEQ ID NO: 15 have been engineered to be mutants of the N-sulfotransferase domain of the human NDST1 enzyme (see entry sp|P52848|NDST_1_HUMAN, in FIG. 6A, FIG. 6B, and FIG. 6C above), which is a member of enzyme class EC 2.8.2.8. By generating and analyzing a multiple sequence alignment that includes the amino acid sequences of the N-sulfotransferase domain of one or more of the other NDST enzymes as well as the amino acid sequences of aryl sulfate-dependent NST enzymes having the amino acid sequences of SEQ ID NO: 5, SEQ ID NO: 7, SEQ ID NO: 9, SEQ ID NO: 11, SEQ ID NO: 13, and/or SEQ ID NO: 15, mutations in the amino acid sequences in the engineered NST enzymes can be observed relative to the amino acid sequences of the native EC 2.8.2.8 enzymes within the same alignment. Upon selecting the amino acid sequence of the N-sulfotransferase domain of a natural 2.8.2.8 enzyme that is not the human NDST1, mutations that are present within the amino acid sequences of SEQ ID NO: 5, SEQ ID NO: 7, SEQ ID NO: 9, SEQ ID NO: 11, SEQ ID NO: 13, and/or SEQ ID NO: 15 can be engineered into the native sequence in order to form additional mutants that can have aryl sulfate-dependent sulfotransferase activity.

As a non-limiting example, the amino acid sequence encoding for the N-sulfotransferase domain of the pig NDST1 (entry tr|M3V841|M3V841_PIG, as illustrated in the sequence alignment in FIG. 6A, FIG. 6B, and FIG. 6C, above), is aligned with the amino acid sequences of SEQ ID NO: 5, SEQ ID NO: 7, SEQ ID NO: 9, SEQ ID NO: 11, SEQ ID NO: 13, and SEQ ID NO: 15. Amino acid mutations that are present in SEQ ID NO: 5, SEQ ID NO: 7, SEQ ID NO: 9, SEQ ID NO: 11, SEQ ID NO: 13, and SEQ ID NO: 15 are engineered into their equivalent positions within the amino acid sequence of the N-sulfotransferase domain of the pig NDST1 enzyme, in order to generate the mutant amino acid sequences SEQ ID NO: 20, SEQ ID NO: 21, SEQ ID NO: 22, SEQ ID NO: 23, SEQ ID NO: 24, or SEQ ID NO: 25, respectively. Enzymes comprising the amino acid sequences of SEQ ID NO: 20, SEQ ID NO: 21, SEQ ID NO: 22, SEQ ID NO: 23, SEQ ID NO: 24, or SEQ ID NO: 25, respectively, will be utilized in Example 14 and Example 15, below. However, a person skilled in the art would appreciate that the same procedure can be applied to generate mutants of the N-sulfotransferase domain, or the entire enzyme, with respect to any of the other glucosaminyl natural NDST enzymes, and that those are omitted for clarity.

Example 14: Expression and Purification of Engineered Aryl Sulfate-Dependent EC 2.8.2.8 Mutants A study is conducted in accordance with embodiments of the present disclosure to determine whether genes encoding for engineered NST enzymes having the amino acid sequences SEQ ID NO: 20, SEQ ID NO: 21, SEQ ID NO: 22, SEQ ID NO: 23, SEQ ID NO: 24, or SEQ ID NO: 25, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 20, SEQ ID NO: 21, SEQ ID NO: 22, SEQ ID NO: 23, SEQ ID NO: 24, or SEQ ID NO: 25, respectively, based on the desired expression host. Upon synthesizing or inserting those genes within a suitable expression vector, it is expected that genes encoding for each of the amino acid sequences SEQ ID NO: 20, SEQ ID NO: 21, SEQ ID NO: 22, SEQ ID NO: 23, SEQ ID NO: 24, and SEQ ID NO: 25, respectively, will be transformed into host cells, and that enzymes containing those sequences will be subsequently expressed, isolated, and purified in a sufficient quantity and purity to determine aryl sulfate-dependent NST activity.

Example 15: Sulfotransferase Activity of EC 2.8.2.8 Mutants

A study is conducted in accordance with embodiments of the present disclosure to determine whether mutant enzymes comprising the sequences of SEQ ID NO: 20, SEQ ID NO: 21, SEQ ID NO: 22, SEQ ID NO: 23, SEQ ID NO: 24, or SEQ ID NO: 25, respectively, are active sulfotransferases, using the procedures of Example 3. It is expected that SAX studies will confirm the presence of N-sulfated polysaccharide products formed as a result of reacting N-deacetylated heparosan and an aryl sulfate compound with each of the engineered enzymes comprising the sequences of SEQ ID NO: 20, SEQ ID NO: 21, SEQ ID NO: 22, SEQ ID NO: 23, SEQ ID NO: 24, or SEQ ID NO: 25, respectively.

Example 16: Determination of Engineered Aryl Sulfate-Dependent Mutants of Other 2OST Enzymes within EC 2.8.2.-

A study is conducted in accordance with embodiments of the present disclosure to engineer additional aryl sulfate-dependent 2OST enzymes. As described above, the aryl sulfate-dependent 2OST enzymes having the amino acid sequences of SEQ ID NO: 63 and SEQ ID NO: 65 have been engineered to be mutants of the chicken HS 2OST enzyme (see entry sp|Q76KB1|HS2ST_CHICK, in FIG. 17A, FIG. 17B, FIG. 17C, and FIG. 17D, above), which is a member of enzyme class EC 2.8.2.-. By generating and analyzing a multiple sequence alignment that includes the amino acid sequences of one or more of the other 2OST enzymes within EC 2.8.2.-, as well as the amino acid sequences of aryl sulfate-dependent 2OST enzymes having the amino acid sequences of SEQ ID NO: 63 and/or SEQ ID NO: 65, mutations in the amino acid sequences in the engineered 2OST enzymes can be observed relative to the amino acid sequences of the wild-type 2OST enzymes within the same alignment. Upon selecting the amino acid sequence of a wild-type 2OST enzyme that is not the chicken 2OST enzyme, mutations that are present within the amino acid sequences of SEQ ID NO: 63 and/or SEQ ID NO: 65 can be engineered into the wild-type sequence in order to form additional mutants that can have aryl sulfate-dependent sulfotransferase activity.

As a non-limiting example, the amino acid sequence encoding for the human 2OST enzyme (entry sp|Q7LGA3|HS2ST_HUMAN, as illustrated in the sequence alignment in FIG. 17A, FIG. 17B, FIG. 17C, and FIG. 17D, above), is aligned with the amino acid sequences of SEQ ID NO: 63 and SEQ ID NO 65. Amino acid mutations that are present in SEQ ID NO 63 and SEQ ID NO: 65 are engineered into their equivalent positions within the amino acid sequence of the human 2OST enzyme, in order to generate the mutant amino acid sequences SEQ ID NO: 68 or SEQ ID NO: 69, respectively. Enzymes comprising the amino acid sequences of SEQ ID NO: 68 or SEQ ID NO: 69, respectively, will be utilized in Example 17 and Example 18, below. However, a person skilled in the art would appreciate that the same procedure can be applied to generate aryl sulfate-dependent mutants with respect to any of the other 2OST enzymes within the EC 2.8.2.-enzyme class, and that those are omitted for clarity.

Example 17: Expression and Purification of EC 2.8.2.- Mutants Having Hexuronyl 2-O Sulfotransferase Activity A study is conducted in accordance with embodiments of the present disclosure to determine whether genes encoding for engineered 2OST enzymes having the amino acid sequences SEQ ID NO: 68 or SEQ ID NO: 69, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 68 or SEQ ID NO: 69, respectively, based on the desired expression host. Upon synthesizing or inserting those genes within a suitable expression vector, it is expected that genes encoding for each of the amino acid sequences SEQ ID NO: 68 and SEQ ID NO: 69, respectively, will be transformed into host cells, and that enzymes containing those sequences will be subsequently expressed, isolated, and purified in a sufficient quantity and purity to determine aryl sulfate-dependent hexuronyl 2-O sulfotransferase activity.

Example 18: Hexuronyl 2-O Sulfotransferase Activity of EC 2.8.2.- Mutants

A study is conducted in accordance with embodiments of the present disclosure to determine whether mutant enzymes comprising the sequences of SEQ ID NO: 68 or SEQ ID NO: 69, respectively, are active sulfotransferases, using the procedures of Example 4. It is expected that MS studies will confirm the presence of N,2O-HS products formed as a result of reacting an N-sulfated heparosan-based polysaccharide and an aryl sulfate compound with each of the engineered enzymes comprising the sequences of SEQ ID NO: 68 and SEQ ID NO: 69, respectively. It is also expected that both enzymes will be active with heparosan-based polysaccharides comprising either or both of Formula IV or Formula V.

Example 19: Determination of Engineered Aryl Sulfate-Dependent Mutants of Other 6OST Enzymes within EC 2.8.2.-

A study is conducted in accordance with embodiments of the present disclosure to engineer additional aryl sulfate-dependent 6OST enzymes. As described above, the aryl sulfate-dependent 6OST enzymes having the amino acid sequences of SEQ ID NO: 104, SEQ ID NO: 106, or SEQ ID NO: 108 have been engineered to be mutants of the mouse 6OST1 enzyme (see entry Q9QYK5|H6ST1_MOUSE, in FIGS. 21A-21F, above), which is a member of enzyme class EC 2.8.2.-. By generating and analyzing a multiple sequence alignment that includes both the amino acid sequences of one or more of the other 6OST enzymes within EC 2.8.2.-, as well as the amino acid sequences of aryl sulfate-dependent 6OST enzymes having the amino acid sequences of SEQ ID NO: 104, SEQ ID NO: 106, and/or SEQ ID NO: 108, mutations in the amino acid sequences in the engineered 6OST enzymes can be observed relative to the amino acid sequences of the wild-type 6OST enzymes within the same alignment. Upon selecting the amino acid sequence of a wild-type 6OST enzyme that is not the mouse 6OST1 enzyme, mutations that are present within the amino acid sequences of SEQ ID NO: 104, SEQ ID NO: 106, and/or SEQ ID NO: 108 can be engineered into the wild-type sequence in order to form additional mutants that can have aryl sulfate-dependent sulfotransferase activity.

As a non-limiting example, the amino acid sequence encoding for the pig 6OST1 enzyme (entry I3LAM6|I3LAM6_PIG, as illustrated in the sequence alignment in FIGS. 21A-21F, above), is aligned with the amino acid sequences of SEQ ID NO: 104, SEQ ID NO: 106, and SEQ ID NO: 108. Amino acid mutations that are present in SEQ ID NO: 104, SEQ ID NO: 106, and SEQ ID NO: 108 are engineered into their equivalent positions within the amino acid sequence of the pig 6OST enzyme, in order to generate mutant amino acid sequences. Generated mutant amino acid sequences corresponding to residues 67-377 of the pig 6OST1 enzyme, as illustrated in FIGS. 21A-21F, above, are disclosed as SEQ ID NO: 114, SEQ ID NO: 115, and SEQ ID NO: 116, respectively. Generated mutant amino acid sequences corresponding to the full-length amino acid sequence for the pig 6OST1 enzyme (not shown in FIGS. 21A-21F, above) are disclosed as SEQ ID NO: 117, SEQ ID NO: 118, and SEQ ID NO: 119, respectively.

In another non-limiting example, the full-length amino acid sequence encoding for the encoding for the mouse 6OST3 enzyme (entry Q9QYK4|H6HS3_MOUSE, a truncated sequence for which is illustrated in the sequence alignment in FIGS. 21A-21F, above) is aligned with the amino acid sequences of SEQ ID NO: 104, SEQ ID NO: 106, and SEQ ID NO: 108. Amino acid mutations that are present in SEQ ID NO: 104, SEQ ID NO: 106, and SEQ ID NO: 108 are engineered into their equivalent positions within the amino acid sequence of the mouse 6OST3 enzyme, in order to generate mutant amino acid sequences. The generated full-length amino acid sequences are disclosed as SEQ ID NO: 120, SEQ ID NO: 121, and SEQ ID NO: 122, respectively. Enzymes comprising the amino acid sequences of SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122, respectively, will be utilized in Example 20 and Example 21, below. However, a person skilled in the art would appreciate that the same procedure can be applied to generate aryl sulfate-dependent mutants with respect to any of the other natural 6OST enzymes within the EC 2.8.2.- enzyme class, and that those are omitted for clarity.

Example 20: Expression and Purification of EC 2.8.2.- Mutants Having Glucosaminyl 6-O Sulfotransferase Activity A study is conducted in accordance with embodiments of the present disclosure to determine whether genes encoding for engineered 6OST enzymes having the amino acid sequences SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO:

114, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122, respectively, based on the desired expression host. Upon synthesizing or inserting those genes within a suitable expression vector, it is expected that genes encoding for each of the amino acid sequences SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122, respectively, will be transformed into host cells, and that enzymes containing those sequences will be subsequently expressed, isolated, and purified in a sufficient quantity and purity to determine aryl sulfate-dependent glucosaminyl 6-O sulfotransferase activity.

Example 21: Glucosaminyl 6-O Sulfotransferase Activity of EC 2.8.2.- Mutants

A study is conducted in accordance with embodiments of the present disclosure to determine whether mutant enzymes comprising the sequences of SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, or SEQ ID NO: 122, respectively, are active sulfotransferases, using the procedures of Example 5. It is expected that MS studies will confirm the presence of N,2O,6O-HS products formed as a result of reacting an N,2O-HS polysaccharide and an aryl sulfate compound with each of the engineered enzymes comprising the sequences of SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, and SEQ ID NO: 122, respectively.

Example 22: Determination of Engineered Aryl Sulfate-Dependent Mutants of Other 3OST Enzymes within EC 2.8.2.23

A study is conducted in accordance with embodiments of the present disclosure to engineer additional aryl sulfate-dependent 3OST enzymes. As described above, the aryl sulfate-dependent 3OST enzymes having the amino acid sequences of SEQ ID NO: 147, SEQ ID NO: 149, or SEQ ID NO: 151 have been engineered to be mutants of the human 3OST1 enzyme (see entry sp|O14792|HS3S1_HUMAN, in FIGS. 26A-26F, above), which is a member of enzyme class EC 2.8.2.23. By generating and analyzing a multiple sequence alignment that includes both the amino acid sequences of one or more of the other 3OST enzymes within EC 2.8.2.23, as well as the amino acid sequences of aryl sulfate-dependent 3OST enzymes having the amino acid sequences of SEQ ID NO: 147, SEQ ID NO: 149, and/or SEQ ID NO: 151, mutations in the amino acid sequences in the engineered 3OST enzymes can be observed relative to the amino acid sequences of the wild-type 3OST enzymes within the same alignment. Upon selecting the amino acid sequence of a wild-type 3OST enzyme that is not the human 3OST1 enzyme, mutations that are present within the amino acid sequences of SEQ ID NO: 147, SEQ ID NO: 149, and/or SEQ ID NO: 151 can be engineered into the wild-type sequence in order to form additional mutants that can have aryl sulfate-dependent sulfotransferase activity.

As a non-limiting example, the amino acid sequence encoding for the pig 3OST1 enzyme (entry tr|I3LHH5|I3LHH5_PIG, as illustrated in the sequence alignment in FIGS. 26A-26F, above), is aligned with the amino acid sequences of SEQ ID NO: 147, SEQ ID NO: 149, and SEQ ID NO: 151. Amino acid mutations that are present in SEQ ID NO: 147, SEQ ID NO: 149, or SEQ ID NO: 151 are engineered into their equivalent positions within the amino acid sequence of the pig 3OST1 enzyme, in order to the generate mutant amino acid sequences SEQ ID NO: 155, SEQ ID NO: 156, or SEQ ID NO: 157, respectively.

In another non-limiting example, the full-length amino acid sequence encoding for the encoding for the mouse 3OST5 enzyme (not shown in FIGS. 26A-26F, above) is aligned with the amino acid sequences of SEQ ID NO: 147, SEQ ID NO: 149, and SEQ ID NO: 151. Amino acid mutations that are present in SEQ ID NO: 147, SEQ ID NO: 149, and SEQ ID NO: 151 are engineered into their equivalent positions within the amino acid sequence of the mouse 3OST5 enzyme, in order to generate mutant amino acid sequences. The generated full-length amino acid sequences are disclosed as SEQ ID NO: 158, SEQ ID NO: 159, and SEQ ID NO: 160, respectively.

Enzymes comprising the amino acid sequences of SEQ ID NO: 155, SEQ ID NO: 156, SEQ ID NO: 157, SEQ ID NO: 158, SEQ ID NO: 159, or SEQ ID NO: 160 respectively, will be utilized in Example 23 and Example 24, below. However, a person skilled in the art would appreciate that the same procedure can be applied to generate aryl sulfate-dependent mutants with respect to any of the other 3OST enzymes within the EC 2.8.2.23 enzyme class, and that those are omitted for clarity.

Example 23: Expression and Purification of EC 2.8.2.23 Mutants Having Glucosaminyl 3-O Sulfotransferase Activity A study is conducted in accordance with embodiments of the present disclosure to determine whether genes encoding for engineered 3OST enzymes having the amino acid sequences SEQ ID NO: 155, SEQ ID NO: 156, SEQ ID NO: 157, SEQ ID NO: 158, SEQ ID NO: 159, or SEQ ID NO: 160, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 155, SEQ ID NO: 156, SEQ ID NO: 157, SEQ ID NO: 158, SEQ ID NO: 159, or SEQ ID NO: 160, respectively, based on the desired expression host. Upon synthesizing or inserting those genes within a suitable expression vector, it is expected that genes encoding for each of the amino acid sequences SEQ ID NO: 155, SEQ ID NO: 156, SEQ ID NO: 157, SEQ ID NO: 158, SEQ ID NO: 159, and SEQ ID NO: 160, respectively, will be transformed into host cells, and that enzymes containing those sequences will be subsequently expressed, isolated, and purified in a sufficient quantity and purity to determine aryl sulfate-dependent glucosaminyl 3-O sulfotransferase activity.

Example 24: Glucosaminyl 3-O Sulfotransferase Activity of EC 2.8.2.23 Mutants

A study is conducted in accordance with embodiments of the present disclosure to determine whether mutant enzymes comprising the sequences of SEQ ID NO: 155, SEQ ID NO: 156, SEQ ID NO: 157, SEQ ID NO: 158, SEQ ID NO: 159, or SEQ ID NO: 160, respectively, are active sulfotransferases, using the procedures of Example 6 and/or Example 7. It is expected that MS and/or NMR studies will confirm the presence of N,2O,3O,6O-HS products formed as a result of reacting an N,2O,6O-HS polysaccharide and an aryl sulfate compound with each of the engineered enzymes comprising the sequences of SEQ ID NO: 155, SEQ ID NO: 156, SEQ ID NO: 157, SEQ ID NO: 158, SEQ ID NO: 159, and SEQ ID NO: 160, respectively.

I claim:

1. A method of enzymatically forming an N-sulfated heparosan product in the absence of 3'-phosphoadenosine 5'-phosphosulfate (PAPS), the method comprising the following steps:
   a. forming a reaction mixture comprising:
      i. a sulfo group donor, the sulfo group donor consisting of an aryl sulfate compound;
      ii. N-deacetylated heparosan; and
      iii. a non-natural N-sulfotransferase enzyme (NST), engineered to have sulfotransferase activity with an aryl sulfate compound as a sulfo group donor and N-deacetylated heparosan as a sulfo group acceptor, wherein the non-natural NST enzyme comprises an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25;
   b. binding the aryl sulfate compound within the enzyme active site; and c. catalyzing the transfer of the sulfo group from the aryl sulfate compound to N-deacetylated heparosan, thereby forming the N-sulfated heparosan product.

2. The method according to claim 1, wherein the N-deacetylated heparosan comprises N-acetyl glucosamine residues, and the N-acetyl glucosamine residues comprise less than 60% of the total glucosamine residues within the N-deacetylated heparosan.

3. The method according to claim 1, wherein the N-deacetylated heparosan has a weight-average molecular weight in a range between and inclusive of 1,000 Da and 20,000 Da.

4. The method according to claim 3, wherein the N-deacetylated heparosan has a weight-average molecular weight in a range between and inclusive of 9,000 Da and 12,500 Da.

5. A non-natural N-sulfotransferase enzyme (NST) enzyme engineered to have sulfotransferase activity with an aryl sulfate compound as a sulfo group donor and N-deacetylated heparosan as a sulfo group acceptor in the absence of 3'-phosphoadenosine 5'-phosphosulfate (PAPS), wherein the NST enzyme comprises an amino acid sequence selected from the group consisting of SEQ ID NO: 5, SEQ ID NO: 7, SEQ ID NO: 9, SEQ ID NO: 11, SEQ ID NO: 13, SEQ ID NO: 15, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

6. A nucleic acid molecule comprising a nucleotide sequence encoding for the amino acid sequence of the NST enzyme of claim 5.

7. The nucleic acid molecule according to claim 6, wherein the nucleic acid molecule is comprised within an expression vector.

8. The nucleic acid molecule according to claim 7, wherein the expression vector further encodes for a fusion protein comprising the non-natural NST enzyme and one or more additional polypeptides.

9. The nucleic acid molecule according to claim 7, wherein the expression vector is comprised within an isolated host cell, selected from the group consisting of a bacterial cell, a yeast cell, an insect cell, and a mammalian cell.

* * * * *